United States Patent
Kawauchi et al.

(10) Patent No.: US 12,188,098 B2
(45) Date of Patent: Jan. 7, 2025

(54) PANCREATIC CANCER DETECTION KIT OR DEVICE, AND DETECTION METHOD

(71) Applicants: TORAY INDUSTRIES, INC., Tokyo (JP); NATIONAL CANCER CENTER, Tokyo (JP)

(72) Inventors: Junpei Kawauchi, Kamakura (JP); Hitoshi Nobumasa, Kamakura (JP); Satoko Kozono, Kamakura (JP); Satoshi Kondou, Kamakura (JP); Hiroko Sudo, Kamakura (JP); Atsushi Ochiai, Kashiwa (JP); Motohiro Kojima, Kashiwa (JP)

(73) Assignees: Toray Industries, Inc., Tokyo (JP); National Cancer Center, Tokyo (JP)

(*) Notice: Subject to any disclaimer, the term of this patent is extended or adjusted under 35 U.S.C. 154(b) by 0 days.

(21) Appl. No.: 18/463,079

(22) Filed: Sep. 7, 2023

(65) Prior Publication Data
US 2024/0011104 A1 Jan. 11, 2024

Related U.S. Application Data

(60) Division of application No. 17/114,210, filed on Dec. 7, 2020, now Pat. No. 11,788,150, which is a division of application No. 16/452,269, filed on Jun. 25, 2019, now Pat. No. 10,920,282, which is a continuation of application No. 15/314,859, filed as application No. PCT/JP2015/065696 on May 29, 2015, now Pat. No. 10,370,722.

(30) Foreign Application Priority Data

May 30, 2014 (JP) .................................. 2014-113523
Sep. 11, 2014 (JP) .................................. 2014-185730

(51) Int. Cl.
| | | |
|---|---|---|
| C07H 21/02 | (2006.01) |
| C12M 1/00 | (2006.01) |
| C12M 1/34 | (2006.01) |
| C12N 15/09 | (2006.01) |
| C12Q 1/6886 | (2018.01) |
| G01N 33/53 | (2006.01) |
| G01N 33/574 | (2006.01) |
| G01N 37/00 | (2006.01) |

(52) U.S. Cl.
CPC ........... *C12Q 1/6886* (2013.01); *C12M 1/00* (2013.01); *C12M 1/34* (2013.01); *C12N 15/09* (2013.01); *G01N 33/53* (2013.01); *G01N 33/574* (2013.01); *G01N 37/00* (2013.01); *C12Q 2600/158* (2013.01); *C12Q 2600/178* (2013.01)

(58) Field of Classification Search
CPC ............ C12N 2310/141; C12N 15/113
See application file for complete search history.

(56) References Cited

U.S. PATENT DOCUMENTS

| | | |
|---|---|---|
| 9,416,369 B2 | 8/2016 | Ruohola-Baker et al. |
| 2008/0306018 A1 | 12/2008 | Croce et al. |
| 2010/0286232 A1 | 11/2010 | Schmittgen et al. |
| 2013/0072393 A1 | 3/2013 | Zhang et al. |
| 2013/0310276 A1 | 11/2013 | Johansen et al. |
| 2014/0080894 A1 | 3/2014 | Mcelligott |
| 2014/0088170 A1 | 3/2014 | Shi et al. |
| 2015/0011410 A1 | 1/2015 | Ganepola |
| 2015/0011414 A1 | 1/2015 | Johansen et al. |
| 2015/0184248 A1 | 7/2015 | Tsuchiya et al. |
| 2017/0073764 A1 | 3/2017 | Tahara et al. |
| 2017/0121779 A1 | 5/2017 | Kondou et al. |
| 2017/0130273 A1 | 5/2017 | Sudo et al. |
| 2017/0130274 A1 | 5/2017 | Kozono et al. |
| 2017/0130275 A1 | 5/2017 | Kondou et al. |
| 2017/0130276 A1 | 5/2017 | Kozono et al. |
| 2017/0130278 A1 | 5/2017 | Sudo et al. |
| 2017/0166975 A1 | 6/2017 | Kondou et al. |
| 2017/0275699 A1 | 9/2017 | Kawauchi et al. |

FOREIGN PATENT DOCUMENTS

| | | |
|---|---|---|
| EP | 2518158 A1 | 10/2012 |
| EP | 2 522 750 A1 | 11/2012 |
| EP | 3159398 A1 | 4/2017 |
| JP | 2009-528070 A | 8/2009 |
| JP | 2012-507300 A | 3/2012 |
| JP | 2014-509512 A | 4/2014 |
| JP | 2015-502176 A | 1/2015 |
| JP | 2015-107091 A | 6/2015 |
| WO | WO 2007/103808 A2 | 9/2007 |
| WO | WO 2010/062706 A2 | 6/2010 |
| WO | WO 2011/057003 A2 | 5/2011 |

(Continued)

OTHER PUBLICATIONS

"TaqMan® Array MicroRNA Cards, TaqMan® OpenArray® MicroRNA Plates and Megaplex™ Primer Pools: Target List File (TLF); Version 20.1," Internet citation, Mar. 18, 2014, pp. 1-62, XP008185879, URL:https://www.thermofisher.com/order/catalog/product/4398967 [retrieved on Nov. 4, 2020].

Ali et al., "Differentially expressed miRNAs in the plasma may provide a molecular signature for aggressive pancreatic cancer", Am J Transl Res, 2011, vol. 3, (1), p. 28-47.

Anonymous: "miRNA Entry for MI0005563," (Sep. 5, 2006) XP055747207, Retrieved from the Internet: URL:http://www.mirbase.org/cgi-bin/mirna_entry.pl?acc=MI0005563 [retrieved on Nov. 5, 2020].

Author Unknown, "Mature sequence hsa-miR-6836-3p", miRBase, Accession No. MI0022682, http://www.mirbase.org/cgi-bin/mirna_entry.pl?acc=MIMAT0027575, 2 pages.

(Continued)

*Primary Examiner* — Amy Rose Hudson
(74) *Attorney, Agent, or Firm* — Birch, Stewart, Kolasch & Birch, LLP

(57) ABSTRACT

This invention provides a kit or a device for the detection of pancreatic cancer, comprising a nucleic acid(s) capable of specifically binding to a miRNA(s) in a sample from a subject, and a method for detecting pancreatic cancer, comprising measuring the miRNA(s) in vitro.

5 Claims, 4 Drawing Sheets

Specification includes a Sequence Listing.

(56) References Cited

FOREIGN PATENT DOCUMENTS

| | | |
|---|---|---|
| WO | WO 2011/075873 A1 | 6/2011 |
| WO | WO 2013/095941 A1 | 6/2013 |
| WO | WO 2013/107459 A2 | 7/2013 |
| WO | WO 2014/003053 A1 | 1/2014 |
| WO | WO 2015/133477 A1 | 9/2015 |
| WO | WO 2015/153679 A1 | 10/2015 |
| WO | WO 2015/182781 A1 | 12/2015 |
| WO | WO 2015/190584 A1 | 12/2015 |
| WO | WO 2015/190586 A1 | 12/2015 |
| WO | WO 2015/190591 A1 | 12/2015 |
| WO | WO 2015/194535 A1 | 12/2015 |
| WO | WO 2015/194610 A1 | 12/2015 |
| WO | WO 2015/194615 A1 | 12/2015 |
| WO | WO 2015/194627 A1 | 12/2015 |

OTHER PUBLICATIONS

Author Unknown, "Mature sequence hsa-miR-6836-3p," miRBase, Accession No. MIMAT0027575, http://www.mirbase.org/cgi-bin/mature.pl?mature_acc=MIMAT0027575, Sep. 1, 2012, 1 page.

Cheung et al., "Genetics of Quantitative Variation in Human Gene Expression," Col Spring Harbor Symposia on Quantitative Biology (2003), vol. LXVIII, pp. 403-407.

Chinese Office Action and Search Report for Chinese Application No. 202010766419.3, dated Apr. 20, 2023.

Cote et al. "A pilot study to develop a diagnostic test for pancreatic ductal adenocarcinoma based on differential expression of select miRNA in plasma and bile", Am J. Gastroenterol, [online], 109 (12); p. 1942-1952, Epub Oct. 28, 2014, total 11 pages.

Eto et al., "Prospect of microRNA toward laboratory medicine Gastrointestinal Cancer and microRNA", Clinical Chemistry, vol. 43, p. 99-105, 2014.

European Search Report dated Oct. 8, 2019, for European Application No. 17775579.0.

Extended European Search Report issued Feb. 18, 2021, in European Patent Application No. 20174745.8.

Ganepola et al., "Novel blood-based microRNA biomarker panel for early diagnosis of pancreatic cancer", World J Gastrointest Oncol, Jan. 15, 2014, vol. 6(1), p. 22-33.

Hoshikawa et al., "Hypoxia induces different genes in the lungs of rats compared with mice," Physiol. Genomics (2003), vol. 12, pp. 209-219.

Hua et al., "The Expression Level of miRNAs in Pancreatic Cancer Cell Lines and Pancreatic Cancer Tissues", Progress in Modern Biomedicine, vol. 13, No. 17, Jun. 2013, pp. 3238-3242.

International Search Report, issued in PCT/JP2015/065696, PCT/ISA/210, dated Aug. 18, 2015.

International Search Report, issued in PCT/JP2017/013728, PCT/ISA/210, dated Jun. 27, 2017.

Japan Pancreas Society, "2009 Scientific evidence based clinical practice guidelines for pancreatic cancer", http://www.suizou.org/PCMG2009/cq1/cq1-3.html. CQ1 diagnosis methods.

Japanese Office Action for Japanese Application No. 2016-523600, dated Jul. 9, 2019.

Kiyoshi Kurokawa et al. ed., Lab Data, 2013, p. 633, 636-637 (Igaku-Shoin Ltd., Tokyo, Japan), total 6 pages.

Kojima et al., "Micro RNA markers for the diagnosis of pancreatic and bile duct cancers," E-2020, Digital abstract for The 73rd Annual Meeting of the Japanese Cancer Association, published online Sep. 19, 2014, 3 pages.

Kojima et al., "Micro RNA markers for the diagnosis of pancreatic and bile duct cancers;" E-2020, English oral session at The 73rd Annual Meeting of the Japanese Cancer Association, Sep. 26, 2014, 22 pages.

Kojima et al., "MicroRNA Markers for the Diagnosis of Pancreatic and Biliary-Tract Cancers," PLOS One, vol. 10, No. 2, Feb. 23, 2015, pp. 1-22.

Kozomara et al., "miRBase: annotating high confidence microRNAs using deep sequencing data", Nucleic Acids Research, 2013, vol. 42, Database issue, p. D68-D73.

Kozomara et al., "miRBase: integrating microRNA annotation and deep-sequencing data," Nucleic Acids Research, vol. 39, Oct. 30, 2010, pp. D152-D157.

Kurokawa et al. ed., Lab Data, 2013, p. 633, 636 (Igaku-Shoin Ltd., Tokyo, Japan).

Ladewig et al., "Discovery of hundreds of mirtrons in mouse and human small RNA data", PN 163620; Genome Research, 2012, vol. 22, pp. 1634-1645.

Li et al., "MicroRNA Array Analysis Finds Elevated Serum miR-1290 Accurately Distinguishes Patients with Low-Stage Pancreatic Cancer from Healthy and Disease Controls", Clin Cancer Res, 2013, vol. 19, (13), p. 3600-3610.

Liu et al. "Combination of plasma microRNAs with serum CA19-9 for early detection of pancreatic cancer", Int. J. Cancer [online], 131(3), p. 683-691, Epub Nov. 19, 2011, total 9 pages.

Liu et al., "Serum MicroRNA Expression Profile as a Biomarker in the Diagnosis and Prognosis of Pancreatic Cancer", Clinical Chemistry, 2012, vol. 58, No. 3, p. 610-618.

Manavalan et al., "Differential expression of microRNA expression in tamoxifen-sensitive MCF-7 versus tamoxifen-resistant LY2 human breast cancer cells," Cancer Letters, vol. 313, 2011, pp. 26-43.

Miyamae et al. "Plasma microRNA profiles: identification of miR-744 as a novel diagnostic and prognostic biomarker in pancreatic cancer", 2015, British Journal of Cancer, vol. 113, (10), p. 1467-1476, total 10 pages.

Morimura et al. "Novel diagnostic value of circulating miR-18a in plasma of patients with pancreatic cancer", Br. J. Cancer [online], 105(11), p. 1733-1740, Epub Nov. 1, 2011, total 8 pages.

NCBI Database, "*Homo sapiens* microRNA 6836 (MIR6836), microRNA," NCBI Reference Sequence: NR_106895, Apr. 3, 2014, 3 pages.

Office Action issued Aug. 24, 2021, in Japanese Patent Application No. 2020-125426.

Office Action issued in Chinese Application No. 201580028548.X dated Jul. 19, 2018.

Office Action issued in Chinese Application No. 201580028548.X, dated Apr. 1, 2019.

Office Action issued May 21, 2021, in Republic of Korea Patent Application No. 10-2018-7027522.

Partial European Search Report for European Application No. 20174745.8, dated Nov. 18, 2020.

Partial Supplmentary European Search Report issued in European Application No. 15800550.4 on Dec. 15, 2017.

Schultz et al. "MicroRNA Biomarkers in Whole Blood for Detection of Pancreatic Cancer", JAMA [online], 311 (4), p. 392-404, Jan. 22-29, 2014, total 13 pages.

Takizawa et al., "Abstract 5294: The difference of serum RNA profile: RNA extraction and detection method", Cancer Res, Apr. 15, 2013, vol. 73, Abstract No. 5294.

Takizawa et al., "Simultaneous Profiling of Multiple miRNAs in FFPE or Serum Samples Using DNA Chip 3D-Gene®", BIO Clinica, 2013, vol. 28, No. 9, p. 872-873.

Tanaka et al. "International consensus guidelines 2012 for the management of IPMN and MCN of the pancreas", Pancreatology, 12, (2012), p. 183-197, total 15 pages.

Tetsuya Mine, "Suizo (Pancreas), Journal of the Japan Pancreas Society", Japan Pancreas Society, 2007, vol. 22, p. 105-113.

Working Group of the Japan Pancreas Society, International consensus guidelines 2012 for the management of IPMN and MCN of the pancreas, p. 6, 8, total 4 pages.

Written Opinion of the International Searching Authority, issued in PCT/JP2015/065696, PCT/ISA/237, dated Aug. 18, 2015.

Written Opinion of the International Searching Authority, issued in PCT/JP2017/013728, PCT/ISA/237, dated Jun. 27, 2017.

Zhang et al., "Upregulation of miR-194 contributes to tumor growth and ProgresSion in pancreatic ductal adenocarcinoma", Oncology Reports, vol. 31, (3), p. 1157-1164.

British Journal of Cancer (2015), vol. 113, pp. 1467-1476, Supplement.

(56) References Cited

OTHER PUBLICATIONS

Office Action issued Nov. 12. 2024, in Japanese Patent Application No. 2023-185506.

PANCREATIC CANCER DETECTION KIT OR DEVICE, AND DETECTION METHOD

CROSS-REFERENCE TO RELATED APPLICATIONS

This application is a Divisional of U.S. application Ser. No. 17/114,210 filed Dec. 7, 2020, which is a Divisional of U.S. application Ser. No. 16/452,269 filed on Jun. 25, 2019 (issued as U.S. Pat. No. 10,920,282 on Feb. 16, 2021), which is a Continuation of U.S. application Ser. No. 15/314,859 filed Jun. 5, 2017 (issued as U.S. Pat. No. 10,370,722, on Aug. 6, 2019), which is a National Stage of International Application No. PCT/JP2015/065696 filed May 29, 2015, which claims priority based on Japanese Patent Application No. 2014-113523, filed May 30, 2014, and Japanese Patent Application No. 2014-185730, filed Sep. 11, 2014, the contents of all of which are incorporated herein by reference on their entirety.

REFERENCE TO SEQUENCE LISTING SUBMITTED VIA EFS-WEB

This application includes an electronically submitted sequence listing in .XML format. The .XML file contains a sequence listing entitled "14A0475US04(PH-6231-PCT-US-C1-DIV1-DIV1)_Sequence Listing" and is 450,004 bytes in size. The sequence listing contained in this .XML file is part of the specification and is hereby incorporated by reference herein in its entirety.

TECHNICAL FIELD

The present invention relates to a kit or a device for the detection of pancreatic cancer, comprising a nucleic acid capable of specifically binding to a particular miRNA, which is used for examining the presence or absence of pancreatic cancer in a subject, and a method for detecting pancreatic cancer, comprising measuring an expression level of the miRNA using the nucleic acid.

BACKGROUND ART

The pancreas serves as an exocrine gland that secretes pancreatic juice as a digestive juice and sends the juice into the digestive tract through the pancreatic duct, while also functioning as an endocrine gland that secretes hormones such as insulin and glucagon into blood.

Since the pancreas is surrounded by many organs such as the stomach, the duodenum, the small intestine, the liver, and the gallbladder, pancreatic cancer is not only difficult to detect early but has properties such as a lack of subjective symptoms, very rapid progression, and metastasis to other organs and thus has very poor prognosis as compared with other cancers. According to the 2011 statistics of cancer type-specific mortality in Japan disclosed by the Center for Cancer Control and Information Services, National Cancer Center (Tokyo, Japan), the number of pancreatic cancer deaths climbed to 28,829 people, and 5-year relative survival rates by cancer type in 2003 to 2005 were lowest in pancreatic cancer with 7.1% for males and 6.9% for females.

As described in Non-Patent Literature 1, the basic therapy of pancreatic cancer is practiced by surgery, systemic chemotherapy, radiotherapy, or a combination thereof depending on a stage of progression. Although 15 to 20% pancreatic cancer patients undergo surgery for potential cure, the great majority of patients who do not undergo surgery are considered to have local progression or metastasis. The median survival time is reportedly 8 to 12 months for locally advanced cancer and 3 to 6 months for metastatic cancer, which are very poor as compared with other cancers.

The UICC (Unio Internationalis Contra Cancrum) stages of progression of pancreatic cancer are defined in General Rules for the Study of Pancreatic Cancer, the 5th edition (edited by Japan Pancreas Society, KANEHARA & Co., LTD., 2013, p. 55) and classified into stages 0, IA, B, IIA, IIB, III, IVa, and IVb according to the size of primary tumor, lymph node metastasis, distant metastasis, etc. Stages 1 to III occupy half or more of the number of 5-year survivals, and stages IVa and IVb occupy 70% or more of the progressed stages at the time of diagnosis. Also, pancreatic cancer differs in symptoms among sites of origin. Carcinoma of the head of the pancreas often manifests jaundice, whereas carcinoma of the tail of the pancreas has few symptoms. Therefore, the carcinoma of the tail of the pancreas tends to result in delayed diagnosis as compared with the carcinoma of the head of the pancreas.

As described in Non-Patent Literature 2, abdominal ultrasonography is very useful as convenient and limitedly invasive examination in outpatient settings or medical examination for the diagnosis of pancreatic cancer. However, it is often difficult to visualize pancreatic cancer having a small tumor size or a lesion on the pancreatic tail side. In ordinary medical checkup, the prevalence of pancreatic cancer found in pancreatic images by abdominal ultrasonography is approximately 1%, and the detection rate of pancreatic cancer is approximately 0.06% or lower. For example, CA19-9, Span-1, CA50, CA242, Dupan-2, TAG-72, and urinary fucose as carbohydrate antigens, and CEA, POA, and TPS as non-carbohydrate antigens are known as tumor markers for the detection of pancreatic cancer. As for how to use these tumor markers, a subject is suspected of having a cancer when their concentrations in blood are higher or lower than predetermined reference values. For example, as described in Non-Patent Literature 3, the reference value of CEA is set to 5 ng/mL, and the reference value of CA19-9 is set to 37 U/mL. A subject is suspected of having a cancer including pancreatic cancer when their concentrations exhibit these values or higher. However, the evaluation of tumor markers often examines advanced pancreatic cancer and does not show abnormal values for early pancreatic cancer in many cases. Even combinatorial use of tumor markers and abdominal ultrasonography in medical examination results in low rates of detection of pancreatic cancer. The implementation of such medical examinations for the detection of pancreatic cancer is controversial from the viewpoint of cost effectiveness.

As shown in Patent Literatures 1 to 4, there are reports, albeit at a research stage, on the determination of pancreatic cancer using the expression levels of microRNAs (miR-NAs), or combinations of the expression levels of miRNAs and the expression levels of additional protein markers in biological samples including blood.

Patent Literature 1 discloses a method for detecting pancreatic cancer by combining hsa-miR-125a-3p with dozens of other miRNAs in blood.

Patent Literature 2 discloses a method for detecting pancreatic cancer by combining a hsa-miR-204-3p precursor, a hsa-miR-423-5p precursor, or a hsa-miR-328-5p precursor with several hundreds of other miRNAs in blood or tissues.

Patent Literature 3 discloses a method for detecting pancreatic cancer by combining hsa-miR-575, hsa-miR-16-5p, or hsa-miR-24-3p with several hundreds of other miRNAs in blood.

Patent Literature 4 discloses a method for detecting pancreatic cancer by combining hsa-miR-451a with dozens of other miRNAs in blood or tissues.

Patent Literature 5 discloses a method for detecting pancreatic cancer by combining a hsa-miR-150-3p precursor or a hsa-miR-187-5p precursor with several hundreds of other miRNAs in blood or tissues.

Non-Patent Literature 4 discloses hsa-miR-423-5p, hsa-miR-1246, hsa-miR-150-3p, hsa-miR-550a-5p, hsa-miR-371a-5p, hsa-miR-1469, hsa-miR-575, hsa-miR-564, hsa-miR-125a-3p, hsa-miR-451a, hsa-miR-1908-5p and the like in plasma as miRNAs that have significant difference in their expression levels between pancreatic cancer patients and healthy subjects.

Non-Patent Literature 5 discloses miR-3188, miR-16-5p, and the like in plasma as miRNAs that have significant difference in their expression levels between pancreatic cancer patients and healthy subjects.

Non-Patent Literature 6 discloses miR-550a-5p, miR-1290, miR-24-3p, miR-486-3p, miR-423-5p, miR-125a-3p, and the like in serum as miRNAs that have significant difference in their expression levels between pancreatic cancer patients and healthy subjects.

Non-Patent Literature 7 discloses miR-602 in tissues as a miRNA that have significant difference in its expression level between pancreatic cancer patients and healthy subjects.

PRIOR ART LITERATURE

Patent Literature

Patent Literature 1: JP Patent Publication (Kohyo) No. 2012-507300 A (2012)
Patent Literature 2: Published U.S. Patent Application No. 2010/0286232
Patent Literature 3: International Publication No. WO 2013/107459
Patent Literature 4: Published U.S. Patent Application No. 2013/0310276
Patent Literature 5: Published U.S. Patent Application No. 2008/0306018

Non-Patent Literature

Non-Patent Literature 1: Tetsuya Mine, "Suizo (Pancreas), Journal of the Japan Pancreas Society", Japan Pancreas Society, 2007, Vol. 22, p. 10-13
Non-Patent Literature 2: Japan Pancreas Society, "2009 Scientific evidence based clinical practice guidelines for pancreatic cancer" CQ1 diagnosis methods http://wwvw-.suizou.org/PCMG2009/cq1/cq1-3 html
Non-Patent Literature 3: Kiyoshi Kurokawa et al. ed., LAB DATA, 2013, p. 633, 636 (Igaku-Shoin Ltd., Tokyo, Japan)
Non-Patent Literature 4: Ali S. et al. 2011, American Journal of Translational Research, Vol. 3, (1), p. 28-47
Non-Patent Literature 5: Ganepola G A. et al., 2014, World Journal of Gastrointestinal Oncology., Vol. 6, (1), p. 22-33
Non-Patent Literature 6: Li A. et al., 2013, Clinical Cancer Research, Vol. 19, (13), p. 3600-3610

Non-Patent Literature 7: Zhang J. et al., 2014, Oncology Reports, Vol. 31, (3), p. 1157-1164

SUMMARY OF INVENTION

Problem to be Solved by Invention

An object of the present invention is to find novel tumor markers for pancreatic cancer and to provide a method that can effectively detect pancreatic cancer using nucleic acids capable of specifically binding to the markers. As described in Non-Patent Literature 2, for example, CA19-9, Span-1, CA50, CA242, Dupan-2, TAG-72, and urinary fucose as carbohydrate antigens and CEA, POA, and TPS as non-carbohydrate antigens are known as tumor markers for the detection of pancreatic cancer. The pancreatic cancer detection sensitivity of these tumor markers is 70 to 80% for CA19-9, 70 to 80% for Span-1, 50 to 60% for Dupan-2, 30 to 60% for CEA, and 60% for CA50. In addition, their specificity is not much high, and their false positive rates are as high as 20 to 30%. Therefore, there may be the possibility of false detection of other cancers and/or benign tumors and/or benign diseases of the pancreas and/or peripancreatic organs, etc. Particularly, the detection sensitivity of early pancreatic cancer is generally low, and the positive rate of CA19-9 is merely 1/2 (52%) for pancreatic cancer having a tumor size of 2 cm or smaller. Therefore, these tumor markers are not useful for the detection of early pancreatic cancer. Furthermore, the tumor markers based on carbohydrate antigens exhibit false negatives in Lewis blood type negative cases, in which the subjects do not produce the antigens. Therefore, this examination is unsuitable for some subjects.

As described below, there are reports, albeit at a research stage, on the determination of pancreatic cancer using the expression levels of microRNAs (miRNAs) in biological samples including blood, none of which, however, have yet been brought into practical use.

Patent Literature 1 describes a method for diagnosing various cancers including pancreatic cancer by combining hsa-miR-125a-3p with a large number (dozens) of other miRNAs in blood. This literature, however, neither describes specific detection performance thereof such as accuracy, sensitivity, or specificity nor describes a specific method for diagnosing pancreatic cancer using blood.

Patent Literature 2 describes a method for detecting pancreatic cancer by combining a hsa-miR-204-3p precursor, a hsa-miR-423-5p precursor, or a hsa-miR-328-5p precursor with several hundreds of other miRNAs in blood or tissues. This literature, however, neither describes specific detection performance thereof such as accuracy, sensitivity, or specificity nor describes a specific method for diagnosing pancreatic cancer using blood.

The method described in Patent Literature 3 diagnoses pancreatic cancer by combining hsa-miR-575, hsa-miR-16-5p, or hsa-miR-24-3p with several hundreds of other miRNAs and does not state that diagnosis can be conducted by combining several miRNAs.

Patent Literature 4 employs hsa-miR-451a in combination with dozens or more of other miRNAs in pancreatic cancer tissues for the diagnosis of pancreatic cancer. This literature, however, does not describe a specific method for diagnosing pancreatic cancer using blood.

Patent Literature 5 employs a hsa-miR-150-3p precursor or a hsa-miR-187-5p precursor in combination with several hundreds or more of other miRNAs in pancreatic cancer tissues for the diagnosis of pancreatic cancer. This literature, however, neither describes specific detection performance thereof such as accuracy, sensitivity, or specificity nor describes a specific method for diagnosing pancreatic cancer using blood.

In Non-Patent Literature 4, examples of the miRNAs that have significant difference in their expression levels in plasma between pancreatic cancer patients and healthy subjects include miR-423-5p, miR-1246, miR-150-3p, miR-550a-5p, miR-371a-5p, miR-1469, miR-575, miR-564, miR-125a-3p, miR-451a, and miR-1908-5p. This literature, however, does not describe specific detection performance thereof such as accuracy, sensitivity, or specificity.

In Non-Patent Literature 5, examples of the miRNAs that have significant difference in their expression levels in plasma between pancreatic cancer patients and healthy subjects include miR-3188 and miR-16-5p. However, as a result of validation, these miRNAs were excluded from the analytes due to their low reliability.

In Non-Patent Literature 6, examples of the miRNAs that have significant difference in their expression levels in serum between pancreatic cancer patients and healthy subjects include miR-550a-5p, miR-1290, miR-24-3p, miR-486-3p, miR-423-5p, and miR-125a-3p. This literature, however, neither describes the specific detection performance, such as accuracy, sensitivity, or specificity, of miR-550a-5p, miR-24-3p, miR-486-3p, miR-423-5p, and miR-125a-3p nor validated the detection performance of miR-1290 in an independent sample group.

In Non-Patent Literature 7, examples of the miRNA that have significant difference in its expression level in pancreatic tissues between pancreatic cancer patients and healthy subjects include miR-602. This literature, however, neither describes specific detection performance thereof such as accuracy, sensitivity, or specificity nor describes a specific method for diagnosing pancreatic cancer using blood.

As mentioned above, the existing tumor markers exhibit low performance in the detection of pancreatic cancer, or neither performance nor detection methods are specifically shown as to the markers at a research stage. Therefore, use of these markers might require carrying out needless extra examination due to the false detection of healthy subjects as being pancreatic cancer patients, or might waste therapeutic opportunity because of overlooking pancreatic cancer patients. In addition, the measurement of dozens to several hundreds of miRNAs increases examination costs and is therefore difficult to use in large-scale screening such as medical checkup. Furthermore, the collection of pancreatic tissues for measuring the tumor markers is highly invasive to patients and is not favorable. Hence, there is a demand for a highly accurate pancreatic cancer marker that is detectable from blood, which can be collected in less invasive manner, and is capable of correctly determining a pancreatic cancer patient as a pancreatic cancer patient and a healthy subject as a healthy subject. Particularly, a highly sensitive pancreatic cancer marker is desired because tumor resection based on early detection is only radical cure for pancreatic cancer.

Means for Solution of Problem

The present inventors have conducted diligent studies to attain the object and consequently completed the present invention by finding several genes usable as markers for the detection of pancreatic cancer from blood, which can be collected with limited invasiveness, and finding that pancreatic cancer can be significantly detected by using nucleic acids capable of specifically binding to any of these markers.

SUMMARY OF INVENTION

The present invention has the following features:
(1) A kit for the detection of pancreatic cancer, comprising a nucleic acid(s) capable of specifically binding to at least one or more polynucleotides selected from the group consisting of the following pancreatic cancer markers: miR-6893-5p, miR-6075, miR-6820-5p, miR-4294, miR-6729-5p, miR-4476, miR-6836-3p, miR-6765-3p, miR-6799-5p, miR-4530, miR-7641, miR-4454, miR-615-5p, miR-8073, miR-663a, miR-4634, miR-4450, miR-4792, miR-665, miR-7975, miR-7109-5p, miR-6789-5p, miR-4497, miR-6877-5p, miR-6880-5p, miR-7977, miR-4734, miR-6821-5p, miR-8089, miR-5585-3p, miR-6085, miR-6845-5p, miR-4651, miR-4433-3p, miR-1231, miR-4665-5p, miR-7114-5p, miR-1238-5p, miR-8069, miR-4732-5p, miR-619-5p, miR-3622a-5p, miR-1260a, miR-6741-5p, miR-6781-5p, miR-6125, miR-6805-5p, miR-6132, miR-6872-3p, miR-6875-5p, miR-1908-3p, miR-4433b-3p, miR-4736, miR-5100, miR-6724-5p, miR-7107-5p, miR-6726-5p, miR-3185, miR-4638-5p, miR-1273g-3p, miR-6778-5p, miR-328-5p, miR-3679-3p, miR-1228-3p, miR-6779-5p, miR-4723-5p, miR-6850-5p, miR-760, miR-7704, miR-8072, miR-4486, miR-1913, miR-4656, miR-1260b, miR-7106-5p, miR-6889-5p, miR-6780b-5p, miR-6090, miR-4534, miR-4449, miR-5195-3p, miR-1202, miR-4467, miR-6515-3p, miR-4281, miR-4505, miR-4484, miR-6805-3p, miR-3135b, miR-3162-5p, miR-6768-5p, miR-6721-5p, miR-1227-5p, miR-6722-3p, miR-4286, miR-4746-3p, miR-6727-5p, miR-6816-5p, miR-4741, miR-4508, miR-940, miR-4327, miR-4665-3p, miR-718, miR-1203, miR-663b, miR-4258, miR-4649-5p, miR-4516, miR-3619-3p, miR-6826-5p, miR-6757-5p, miR-3131, miR-1343-3p, miR-6775-5p, miR-6813-5p, and miR-3940-5p.
(2) The kit according to (1), wherein miR-6893-5p is hsa-miR-6893-5p, miR-6075 is hsa-miR-6075, miR-6820-5p is hsa-miR-6820-5p, miR-4294 is hsa-miR-4294, miR-6729-5p is hsa-miR-6729-5p, miR-4476 is hsa-miR-4476, miR-6836-3p is hsa-miR-6836-3p, miR-6765-3p is hsa-miR-6765-3p, miR-6799-5p is hsa-miR-6799-5p, miR-4530 is hsa-miR-4530, miR-7641 is hsa-miR-7641, miR-4454 is hsa-miR-4454, miR-615-5p is hsa-miR-615-5p, miR-8073 is hsa-miR-8073, miR-663a is hsa-miR-663a, miR-4634 is hsa-miR-4634, miR-4450 is hsa-miR-4450, miR-4792 is hsa-miR-4792, miR-665 is hsa-miR-665, miR-7975 is hsa-miR-7975, miR-7109-5p is hsa-miR-7109-5p, miR-6789-5p is hsa-miR-6789-5p, miR-4497 is hsa-miR-4497, miR-6877-5p is hsa-miR-6877-5p, miR-6880-5p is hsa-miR-6880-5p, miR-7977 is hsa-miR-7977, miR-4734 is hsa-miR-4734, miR-6821-5p is hsa-miR-6821-5p, miR-8089 is hsa-miR-8089, miR-5585-3p is hsa-miR-5585-3p, miR-6085 is hsa-miR-6085, miR-6845-5p is hsa-miR-6845-5p, miR-4651 is hsa-miR-4651, miR-4433-3p is hsa-miR-4433-3p, miR-1231 is hsa-miR-1231, miR-4665-5p is hsa-miR-4665-5p, miR-7114-5p is hsa-miR-7114-5p, miR-1238-5p is hsa-miR-1238-5p, miR-8069 is hsa-miR-8069, miR-4732-5p is hsa-miR-4732-5p, miR-619-5p is hsa-miR-619-5p, miR-3622a-5p is hsa-miR-3622a-5p, miR-1260a is hsa-miR-1260a, miR-6741-5p is hsa-miR- 6741-5p, miR-6781-5p is hsa-miR-6781-5p, miR-6125 is hsa-miR-6125, miR-6805-5p is hsa-miR-6805-5p, miR-6132 is hsa-miR-6132, miR-6872-3p is hsa-miR-6872-3p, miR-6875-5p is hsa-miR-6875-5p, miR-1908-3p is hsa-miR-1908-3p, miR-4433b-3p is hsa-miR-4433b-3p, miR-4736 is hsa-miR-4736, miR-5100 is hsa-miR-5100, miR-6724-5p is hsa-miR-6724-5p, miR-7107-5p is hsa-miR-7107-5p, miR-6726-5p is hsa-miR-6726-5p, miR-3185 is hsa-miR-3185, miR-4638-5p is hsa-miR-4638-5p, miR-1273g-3p is hsa-miR-1273g-3p, miR-6778-5p is hsa-miR-6778-5p, miR-328-5p is hsa-miR-328-5p, miR-3679-3p is hsa-miR-3679-3p, miR-1228-3p is hsa-miR-1228-3p, miR-6779-5p is hsa-miR-6779-5p, miR-4723-5p is hsa-miR-4723-5p, miR-6850-5p is hsa-miR-6850-5p, miR-760 is hsa-miR-760, miR-7704 is hsa-miR-7704, miR-8072 is hsa-miR-8072, miR-4486 is hsa-miR-4486, miR-1913 is hsa-miR-1913, miR-4656 is hsa-miR-4656, miR-1260b is hsa-miR-1260b, miR-7106-5p is hsa-miR-7106-5p, miR-6889-5p is hsa-miR-6889-5p, miR-6780b-5p is hsa-miR-6780b-5p, miR-6090 is hsa-miR-6090, miR-4534 is hsa-miR-4534, miR-4449 is hsa-miR-4449, miR-5195-3p is hsa-miR-5195-3p, miR-1202 is hsa-miR-1202, miR-4467 is hsa-miR-4467, miR-6515-3p is hsa-miR-6515-3p, miR-4281 is hsa-miR-4281, miR-4505 is hsa-miR-4505, miR-4484 is hsa-miR-4484, miR-6805-3p is hsa-miR-6805-3p, miR-3135b is hsa-miR-3135b, miR-3162-5p is hsa-miR-3162-5p, miR-6768-5p is hsa-miR-6768-5p, miR-6721-5p is hsa-miR-6721-5p, miR-1227-5p is hsa-miR-1227-5p, miR-6722-3p is hsa-miR-6722-3p, miR-4286 is hsa-miR-4286, miR-4746-3p is hsa-miR-4746-3p, miR-6727-5p is hsa-miR-6727-5p, miR-6816-5p is hsa-miR-6816-5p, miR-4741 is hsa-miR-4741, miR-4508 is hsa-miR-4508, miR-940 is hsa-miR-940, miR-4327 is hsa-miR-4327, miR-4665-3p is hsa-miR-4665-3p, miR-718 is hsa-miR-718, miR-1203 is hsa-miR-1203, miR-663b is hsa-miR-663b, miR-4258 is hsa-miR-4258, miR-4649-5p is hsa-miR-4649-5p, miR-4516 is hsa-miR-4516, miR-3619-3p is hsa-miR-3619-3p, miR-6826-5p is hsa-miR-6826-5p, miR-6757-5p is hsa-miR-6757-5p, miR-3131 is hsa-miR-3131, miR-1343-3p is hsa-miR-1343-3p, miR-6775-5p is hsa-miR-6775-5p, miR-6813-5p is hsa-miR-6813-5p, and miR-3940-5p is hsa-miR-3940-5p.

(3) The kit according to (1) or (2), wherein the nucleic acid(s) is a polynucleotide(s) selected from the group consisting of the following polynucleotides (a) to (e):
(a) a polynucleotide consisting of a nucleotide sequence represented by any of SEQ ID NOs: 1 to 104, 464 to 473, and 492 to 494 or a nucleotide sequence derived from the nucleotide sequence by the replacement of u with t, a variant thereof, a derivative thereof, or a fragment thereof comprising 15 or more consecutive nucleotides;
(b) a polynucleotide comprising a nucleotide sequence represented by any of SEQ ID NOs: 1 to 104, 464 to 473, and 492 to 494:
(c) a polynucleotide consisting of a nucleotide sequence complementary to a nucleotide sequence represented by any of SEQ ID NOs: 1 to 104, 464 to 473, and 492 to 494 or a nucleotide sequence derived from the nucleotide sequence by the replacement of u with t, a variant thereof, a derivative thereof, or a fragment thereof comprising 15 or more consecutive nucleotides;
(d) a polynucleotide comprising a nucleotide sequence complementary to a nucleotide sequence represented by any of SEQ ID NOs: 1 to 104, 464 to 473, and 492 to 494 or a nucleotide sequence derived from the nucleotide sequence by the replacement of u with t; and
(e) a polynucleotide hybridizing under stringent conditions to any of the polynucleotides (a) to (d).

(4) The kit according to any of (1) to (3), further comprising, in addition to the nucleic acid(s), a nucleic acid(s) capable of specifically binding to at least one or more polynucleotides selected from the group consisting of miR-125a-3p, miR-204-3p, miR-1469, miR-575, miR-150-3p, miR-423-5p, miR-564, miR-3188, miR-1246, miR-602, miR-1290, miR-16-5p, miR-451a, miR-24-3p, miR-187-5p, miR-1908-5p, miR-371a-5p, and miR-550a-5p.

(5) The kit according to (4), wherein miR-125a-3p is hsa-miR-125a-3p, miR-204-3p is hsa-miR-204-3p, miR-1469 is hsa-miR-1469, miR-575 is hsa-miR-575, miR-150-3p is hsa-miR-150-3p, miR-423-5p is hsa-miR-423-5p, miR-564 is hsa-miR-564, miR-3188 is hsa-miR-3188, miR-1246 is hsa-miR-1246, miR-602 is hsa-miR-602, miR-1290 is hsa-miR-1290, miR-16-5p is hsa-miR-16-5p, miR-451a is hsa-miR-451a, miR-24-3p is hsa-miR-24-3p, miR-187-5p is hsa-miR-187-5p, miR-1908-5p is hsa-miR-1908-5p, miR-371a-5p is hsa-miR-371a-5p, and miR-550a-5p is hsa-miR-550a-5p.

(6) The kit according to (4) or (5), wherein the nucleic acid(s) further comprise a polynucleotide(s) selected from the group consisting of the following polynucleotides (f) to (j):
(f) a polynucleotide consisting of a nucleotide sequence represented by any of SEQ ID NOs: 105 to 122 or a nucleotide sequence derived from the nucleotide sequence by the replacement of u with t, a variant thereof, a derivative thereof, or a fragment thereof comprising 15 or more consecutive nucleotides;
(g) a polynucleotide comprising a nucleotide sequence represented by any of SEQ ID NOs: 105 to 122;
(h) a polynucleotide consisting of a nucleotide sequence complementary to a nucleotide sequence represented by any of SEQ ID NOs: 105 to 122 or a nucleotide sequence derived from the nucleotide sequence by the replacement of u with t, a variant thereof, a derivative thereof, or a fragment thereof comprising 15 or more consecutive nucleotides;
(i) a polynucleotide comprising a nucleotide sequence complementary to a nucleotide sequence represented by any of SEQ ID NOs: 105 to 122 or a nucleotide sequence derived from the nucleotide sequence by the replacement of u with t; and
(j) a polynucleotide hybridizing under stringent conditions to any of the polynucleotides (f) to (i).

(7) The kit according to any of (1) to (6), further comprising, in addition to the nucleic acid(s), a nucleic acid(s) capable of specifically binding to at least one or more polynucleotides selected from the group consisting of miR-4417, miR-4707-5p, miR-7847-3p, miR-2861, miR-4513, miR-7111-5p, miR-6777-5p, miR-7113-3p, miR-4648, miR-3184-5p, miR-4271, miR-6791-5p, miR-642a-3p, miR-7108-5p, miR-128-1-5p, miR-5196-5p, miR-3178, miR-3656, miR-92a-2-5p, miR-6769b-5p, miR-4689, miR-6076, miR-92b-5p, miR-6774-5p, miR-486-3p, miR-6806-5p, miR-6842-5p, miR-6716-5p, miR-557, miR-4673, miR-4674, miR-4442, miR-1915-3p, miR-4687-3p, and miR-92b-3p.

(8) The kit according to claim (7), wherein miR-4417 is hsa-miR-4417, miR-4707-5p is hsa-miR-4707-5p, miR-7847-3p is hsa-miR-7847-3p, miR-2861 is hsa-miR-2861, miR-4513 is hsa-miR-4513, miR-7111-5p is hsa-miR-7111-5p, miR-6777-5p is hsa-miR-6777-5p, miR-7113-3p is hsa-miR-7113-3p, miR-4648 is hsa-miR-4648, miR-3184-5p is hsa-miR-3184-5p, miR-4271 is hsa-miR-4271, miR-6791-5p is hsa-miR-6791-5p, miR-642a-3p is hsa-miR-642a-3p, miR-7108-5p is hsa-miR-7108-5p, miR-128-1-5p is hsa-miR-128-1-5p, miR-5196-5p is hsa-miR-5196-5p, miR-3178 is hsa-miR-3178, miR-3656 is hsa-miR-3656, miR-92a-2-5p is hsa-miR-92a-2-5p, miR-6769b-5p is hsa-miR-6769b-5p, miR-4689 is hsa-miR-4689, miR-6076 is hsa-miR-6076, miR-92b-5p is hsa-miR-92b-5p, miR-6774-5p is hsa-miR-6774-5p, miR-486-3p is hsa-miR-486-3p, miR-6806-5p is hsa-miR-6806-5p, miR-6842-5p is hsa-miR-6842-5p, miR-6716-5p is hsa-miR-6716-5p, miR-557 is hsa-miR-557, miR-4673 is hsa-miR-4673, miR-4674 is hsa-miR-4674, miR-4442 is hsa-miR-4442, miR-1915-3p is hsa-miR-1915-3p, miR-4687-3p is hsa-miR-4687-3p, and miR-92b-3p is hsa-miR-92b-3p.

(9) The kit according to (7) or (8), wherein the nucleic acid(s) is a polynucleotide(s) selected from the group consisting of the following polynucleotides (k) to (o):
(k) a polynucleotide consisting of a nucleotide sequence represented by any of SEQ ID NOs: 349 to 383 or a nucleotide sequence derived from the nucleotide sequence by the replacement of u with t, a variant thereof, a derivative thereof, or a fragment thereof comprising 15 or more consecutive nucleotides;
(l) a polynucleotide comprising a nucleotide sequence represented by any of SEQ ID NOs: 349 to 383;
(m) a polynucleotide consisting of a nucleotide sequence complementary to a nucleotide sequence represented by any of SEQ ID NOs: 349 to 383 or a nucleotide sequence derived from the nucleotide sequence by the replacement of u with t, a variant thereof, a derivative thereof, or a fragment thereof comprising 15 or more consecutive nucleotides:
(n) a polynucleotide comprising a nucleotide sequence complementary to a nucleotide sequence represented by any of SEQ ID NOs: 349 to 383 or a nucleotide sequence derived from the nucleotide sequence by the replacement of u with t; and
(o) a polynucleotide hybridizing under stringent conditions to any of the polynucleotides (k) to (n).

(10) The kit according to any one of (1) to (9), wherein the kit comprises at least two or more nucleic acids capable of specifically binding to at least two or more polynucleotides, respectively, selected from all of the pancreatic cancer markers according to (1) or (2).

(11) A device for the detection of pancreatic cancer, comprising a nucleic acid(s) capable of specifically binding to at least one or more polynucleotides selected from the group consisting of pancreatic cancer markers miR-6893-5p, miR-6075, miR-6820-5p, miR-4294, miR-6729-5p, miR-4476, miR-6836-3p, miR-6765-3p, miR-6799-5p, miR-4530, miR-7641, miR-4454, miR-615-5p, miR-8073, miR-663a, miR-4634, miR-4450, miR-4792, miR-665, miR-7975, miR-7109-5p, miR-6789-5p, miR-4497, miR-6877-5p, miR-6880-5p, miR-7977, miR-4734, miR-6821-5p, miR-8089, miR-5585-3p, miR-6085, miR-6845-5p, miR-4651, miR-4433-3p, miR-1231, miR-4665-5p, miR-7114-5p, miR-1238-5p, miR-8069, miR-4732-5p, miR-619-5p, miR-3622a-5p, miR-1260a, miR-6741-5p, miR-6781-5p, miR-6125, miR-6805-5p, miR-6132, miR-6872-3p, miR-6875-5p, miR-1908-3p, miR-4433b-3p, miR-4736, miR-5100, miR-6724-5p, miR-7107-5p, miR-6726-5p, miR-3185, miR-4638-5p, miR-1273g-3p, miR-6778-5p, miR-328-5p, miR-3679-3p, miR-1228-3p, miR-6779-5p, miR-4723-5p, miR-6850-5p, miR-760, miR-7704, miR-8072, miR-4486, miR-1913, miR-4656, miR-1260b, miR-7106-5p, miR-6889-5p, miR-6780b-5p, miR-6090, miR-4534, miR-4449, miR-5195-3p, miR-1202, miR-4467, miR-6515-3p, miR-4281, miR-4505, miR-4484, miR-6805-3p, miR-3135b, miR-3162-5p, miR-6768-5p, miR-6721-5p, miR-1227-5p, miR-6722-3p, miR-4286, miR-4746-3p, miR-6727-5p, miR-6816-5p, miR-4741, miR-4508, miR-940, miR-4327, miR-4665-3p, miR-718, miR-1203, miR-663b, miR-4258, miR-4649-5p, miR-4516, miR-3619-3p, miR-6826-5p, miR-6757-5p, miR-3131, miR-1343-3p, miR-6775-5p, miR-6813-5p, and miR-3940-5p.

(12) The device according to (11), wherein miR-6893-5p is hsa-miR-6893-5p, miR-6075 is hsa-miR-6075, miR-6820-5p is hsa-miR-6820-5p, miR-4294 is hsa-miR-4294, miR-6729-5p is hsa-miR-6729-5p, miR-4476 is hsa-miR-4476, miR-6836-3p is hsa-miR-6836-3p, miR-6765-3p is hsa-miR-6765-3p, miR-6799-5p is hsa-miR-6799-5p, miR-4530 is hsa-miR-4530, miR-7641 is hsa-miR-7641, miR-4454 is hsa-miR-4454, miR-615-5p is hsa-miR-615-5p, miR-8073 is hsa-miR-8073, miR-663a is hsa-miR-663a, miR-4634 is hsa-miR-4634, miR-4450 is hsa-miR-4450, miR-4792 is hsa-miR-4792, miR-665 is hsa-miR-665, miR-7975 is hsa-miR-7975, miR-7109-5p is hsa-miR-7109-5p, miR-6789-5p is hsa-miR-6789-5p, miR-4497 is hsa-miR-4497, miR-6877-5p is hsa-miR-6877-5p, miR-6880-5p is hsa-miR-6880-5p, miR-7977 is hsa-miR-7977, miR-4734 is hsa-miR-4734, miR-6821-5p is hsa-miR-6821-5p, miR-8089 is hsa-miR-8089, miR-5585-3p is hsa-miR-5585-3p, miR-6085 is hsa-miR-6085, miR-6845-5p is hsa-miR-6845-5p, miR-4651 is hsa-miR-4651, miR-4433-3p is hsa-miR-4433-3p, miR-1231 is hsa-miR-1231, miR-4665-5p is hsa-miR-4665-5p, miR-7114-5p is hsa-miR-7114-5p, miR-1238-5p is hsa-miR-1238-5p, miR-8069 is hsa-miR-8069, miR-4732-5p is hsa-miR-4732-5p, miR-619-5p is hsa-miR-619-5p, miR-3622a-5p is hsa-miR-3622a-5p, miR-1260a is hsa-miR-1260a, miR-6741-5p is hsa-miR-6741-5p, miR-6781-5p is hsa-miR-6781-5p, miR-6125 is hsa-miR-6125, miR-6805-5p is hsa-miR-6805-5p, miR-6132 is hsa-miR-6132, miR-6872-3p is hsa-miR-6872-3p, miR-6875-5p is hsa-miR-6875-5p, miR-1908-3p is hsa-miR-1908-3p, miR-4433b-3p is hsa-miR-4433b-3p, miR-4736 is hsa-miR-4736, miR-5100 is hsa-miR-5100, miR-6724-5p is hsa-miR-6724-5p, miR-7107-5p is hsa-miR-7107-5p, miR-6726-5p is hsa-miR-6726-5p, miR-3185 is hsa-miR-3185, miR-4638-5p is hsa-miR-4638-5p, miR-1273g-3p is hsa-miR-1273g-3p, miR-6778-5p is hsa-miR-6778-5p, miR-328-5p is hsa-miR-328-5p, miR-3679-3p is hsa-miR-3679-3p, miR-1228-3p is hsa-miR-1228-3p, miR-6779-5p is hsa-miR-6779-5p, miR-4723-5p is hsa-miR-4723-5p, miR-6850-5p is hsa-miR-6850-5p, miR-760 is hsa-miR-760, miR-7704 is hsa-miR-7704, miR-8072 is hsa-miR-8072, miR-4486 is hsa-miR-4486, miR-1913 is hsa-miR-1913, miR-4656 is hsa-miR-4656, miR-1260b is hsa-miR-1260b, miR-7106-5p is hsa-miR-7106-5p, miR-6889-5p is hsa-miR-6889-5p, miR-6780b-5p is hsa-miR-6780b-5p, miR-6090 is hsa-miR-6090, miR-4534 is hsa-miR-4534, miR-4449 is hsa-miR-4449, miR-5195-3p is hsa-miR-5195-3p, miR-1202 is hsa-miR-1202, miR-4467 is hsa-miR-4467, miR-6515-3p is hsa-miR-6515-3p, miR-4281 is hsa-miR-4281, miR-4505 is hsa-miR-4505, miR-4484 is hsa-miR-4484, miR-6805-3p is hsa-miR-6805-3p, miR-3135b is hsa-miR-3135b, miR-3162-5p is hsa-miR-3162-5p, miR-6768-5p is hsa-miR-6768-5p, miR-6721-5p is hsa-miR-6721-5p, miR-1227-5p is hsa-miR-1227-5p, miR-6722-3p is hsa-miR-6722-3p, miR-4286 is hsa-miR-4286, miR-4746-3p is hsa-miR-4746-3p, miR-6727-5p is hsa-miR-6727-5p, miR-6816-5p is hsa-miR-6816-5p, miR-4741 is hsa-miR-4741, miR-4508 is hsa-miR-4508, miR-940 is hsa-miR-940, miR-4327 is hsa-miR-4327, miR-4665-3p is hsa-miR-4665-3p, miR-718 is hsa-miR-718, miR-1203 is hsa-miR-1203, miR-663b is hsa-miR-663b, miR-4258 is hsa-miR-4258, miR-4649-5p is hsa-miR-4649-5p, miR-4516 is hsa-miR-4516, miR-3619-3p is hsa-miR-3619-3p, miR-6826-5p is hsa-miR-6826-5p, miR-6757-5p is hsa-miR-6757-5p, miR-3131 is hsa-miR-3131, miR-1343-3p is hsa-miR-1343-3p, miR-6775-5p is hsa-miR-6775-5p, miR-6813-5p is hsa-miR-6813-5p, and miR-3940-5p is hsa-miR-3940-5p.

(13) The device according to (11) or (12), wherein the nucleic acid(s) is a polynucleotide(s) selected from the group consisting of the following polynucleotides (a) to (e):
(a) a polynucleotide consisting of a nucleotide sequence represented by any of SEQ ID NOs: 1 to 104, 464 to 473, and 492 to 494 or a nucleotide sequence derived from the nucleotide sequence by the replacement of u with t, a variant thereof, a derivative thereof, or a fragment thereof comprising 15 or more consecutive nucleotides;
(b) a polynucleotide comprising a nucleotide sequence represented by any of SEQ ID NOs: 1 to 104, 464 to 473, and 492 to 494;
(c) a polynucleotide consisting of a nucleotide sequence complementary to a nucleotide sequence represented by any of SEQ ID NOs: 1 to 104, 464 to 473, and 492 to 494 or a nucleotide sequence derived from the nucleotide sequence by the replacement of u with t, a variant thereof, a derivative thereof, or a fragment thereof comprising 15 or more consecutive nucleotides;
(d) a polynucleotide comprising a nucleotide sequence complementary to a nucleotide sequence represented by any of SEQ ID NOs: 1 to 104, 464 to 473, and 492 to 494 or a nucleotide sequence derived from the nucleotide sequence by the replacement of u with t; and
(e) a polynucleotide hybridizing under stringent conditions to any of the polynucleotides (a) to (d).

(14) The device according to any one of (11) to (13), wherein the device further comprises a nucleic acid(s) capable of specifically binding to at least one or more polynucleotides selected from the group consisting of other pancreatic cancer markers miR-125a-3p, miR-204-3p, miR-1469, miR-575, miR-150-3p, miR-423-5p, miR-564, miR-3188, miR-1246, miR-602, miR-1290, miR-16-5p, miR-451a, miR-24-3p, miR-187-5p, miR-1908-5p, miR-371a-5p, and miR-550a-5p.

(15) The device according to (14), wherein miR-125a-3p is hsa-miR-125a-3p, miR-204-3p is hsa-miR-204-3p, miR-1469 is hsa-miR-1469, miR-575 is hsa-miR-575, miR-150-3p is hsa-miR-150-3p, miR-423-5p is hsa-miR-423-5p, miR-564 is hsa-miR-564, miR-3188 is hsa-miR-3188, miR-1246 is hsa-miR-1246, miR-602 is hsa-miR-602, miR-1290 is hsa-miR-1290, miR-16-5p is hsa-miR-16-5p, miR-451a is hsa-miR-451a, miR-24-3p is hsa-miR-24-3p, miR-187-5p is hsa-miR-187-5p, miR-1908-5p is hsa-miR-1908-5p, miR-371a-5p is hsa-miR-371a-5p, and miR-550a-5p is hsa-miR-550a-5p.

(16) The device according to (14) or (15), wherein the nucleic acid(s) is a polynucleotide(s) selected from the group consisting of the following polynucleotides (f) to (j):
(f) a polynucleotide consisting of a nucleotide sequence represented by any of SEQ ID NOs: 105 to 122 or a nucleotide sequence derived from the nucleotide sequence by the replacement of u with t, a variant thereof, a derivative thereof, or a fragment thereof comprising 15 or more consecutive nucleotides:
(g) a polynucleotide comprising a nucleotide sequence represented by any of SEQ ID NOs: 105 to 122;
(h) a polynucleotide consisting of a nucleotide sequence complementary to a nucleotide sequence represented by any of SEQ ID NOs: 105 to 122 or a nucleotide sequence derived from the nucleotide sequence by the replacement of u with t, a variant thereof, a derivative thereof, or a fragment thereof comprising 15 or more consecutive nucleotides;
(i) a polynucleotide comprising a nucleotide sequence complementary to a nucleotide sequence represented by any of SEQ ID NOs: 105 to 122 or a nucleotide sequence derived from the nucleotide sequence by the replacement of u with t; and
(j) a polynucleotide hybridizing under stringent conditions to any of the polynucleotides (f) to (i).

(17) The device according to any one of (11) to (16), wherein the device further comprises a nucleic acid(s) capable of specifically binding to at least one or more polynucleotides selected from the group consisting of other pancreatic cancer markers miR-4417, miR-4707-5p, miR-7847-3p, miR-2861, miR-4513, miR-7111-5p, miR-6777-5p, miR-7113-3p, miR-4648, miR-3184-5p, miR-4271, miR-6791-5p, miR-642a-3p, miR-7108-5p, miR-128-1-5p, miR-5196-5p, miR-3178, miR-3656, miR-92a-2-5p, miR-6769b-5p, miR-4689, miR-6076, miR-92b-5p, miR-6774-5p, miR-486-3p, miR-6806-5p, miR-6842-5p, miR-6716-5p, miR-557, miR-4673, miR-4674, miR-4442, miR-1915-3p, miR-4687-3p and miR-92b-3p.

(18) The device according to (17), wherein miR-4417 is hsa-miR-4417, miR-4707-5p is hsa-miR-4707-5p, miR-7847-3p is hsa-miR-7847-3p, miR-2861 is hsa-miR-2861, miR-4513 is hsa-miR-4513, miR-7111-5p is hsa-miR-7111-5p, miR-6777-5p is hsa-miR-6777-5p, miR-7113-3p is hsa-miR-7113-3p, miR-4648 is hsa-miR-4648, miR-3184-5p is hsa-miR-3184-5p, miR-4271 is hsa-miR-4271, miR-6791-5p is hsa-miR-6791-5p, miR-642a-3p is hsa-miR-642a-3p, miR-7108-5p is hsa-miR-7108-5p, miR-128-1-5p is hsa-miR-128-1-5p, miR-5196-5p is hsa-miR-5196-5p, miR-3178 is hsa-miR-3178, miR-3656 is hsa-miR-3656, miR-92a-2-5p is hsa-miR-92a-2-5p, miR-6769b-5p is hsa-miR-6769b-5p, miR-4689 is hsa-miR-4689, miR-6076 is hsa-miR-6076, miR-92b-5p is hsa-miR-92b-5p, miR-6774-5p is hsa-miR-6774-5p, miR-486-3p is hsa-miR-486-3p, miR-6806-5p is hsa-miR-6806-5p, miR-6842-5p is hsa-miR-6842-5p, miR-6716-5p is hsa-miR-6716-5p, miR-557 is hsa-miR-557, miR-4673 is hsa-miR-4673, miR-4674 is hsa-miR-4674, miR-4442 is hsa-miR-4442, miR-1915-3p is hsa-miR-1915-3p, miR-4687-3p is hsa-miR-4687-3p, and miR-92b-3p is hsa-miR-92b-3p.

(19) The device according to (17) or (18), wherein the nucleic acid(s) is a polynucleotide(s) selected from the group consisting of the following polynucleotides (k) to (o):

(k) a polynucleotide consisting of a nucleotide sequence represented by any of SEQ ID NOs: 349 to 383 or a nucleotide sequence derived from the nucleotide sequence by the replacement of u with t, a variant thereof, a derivative thereof, or a fragment thereof comprising 15 or more consecutive nucleotides;

(l) a polynucleotide comprising a nucleotide sequence represented by any of SEQ ID NOs: 349 to 383;

(m) a polynucleotide consisting of a nucleotide sequence complementary to a nucleotide sequence represented by any of SEQ ID NOs: 349 to 383 or a nucleotide sequence derived from the nucleotide sequence by the replacement of u with t, a variant thereof, a derivative thereof, or a fragment thereof comprising 15 or more consecutive nucleotides;

(n) a polynucleotide comprising a nucleotide sequence complementary to a nucleotide sequence represented by any of SEQ ID NOs: 349 to 383 or a nucleotide sequence derived from the nucleotide sequence by the replacement of u with t; and (o) a polynucleotide hybridizing under stringent conditions to any of the polynucleotides (k) to (n).

(20) The device according to any one of (11) to (19), wherein the device is for measurement based on a hybridization technique.

(21) The device according to (20), wherein the hybridization technique is a nucleic acid array technique.

(22) The device according to any one of (11) to (21), wherein the device comprises at least two or more nucleic acids capable of specifically binding to at least two or more polynucleotides, respectively, selected from all of the pancreatic cancer markers according to (11) or (12).

(23) A method for detecting pancreatic cancer, comprising: measuring an expression level(s) of a target nucleic acid(s) in a sample from a subject using a kit according to any one of (1) to (10) or a device according to any one of (1) to (22); and evaluating in vitro whether or not the subject has pancreatic cancer using both of the measured expression level(s) and a control expression level(s) in a sample from a healthy subject measured in the same way.

(24) The method according to (23), wherein the subject is a human.

(25) The method according to (23) or (24), wherein the sample is blood, serum, or plasma.

Definition of Terms

The terms used herein are defined as described below.

The term "pancreatic cancer" used herein refers to any malignant tumor formed in the pancreas. Specifically, the "pancreatic cancer" includes serous cystadenoma, mucinous cystadenocarcinoma, intraductal papillary-mucinous carcinoma, invasive ductal carcinoma, acinar cell carcinoma, neuroendocrine cancer, and the like ("General Rules for the Study of Pancreatic Cancer", the 6th edition, revised version, 2013, Japan Pancreas Society, KANEHARA & Co., LTD., p. 21-22).

The term "benign tumors and/or benign diseases of the pancreas and/or peripancreatic organs" used herein refers to diseases with nonmalignant tumors in the pancreas, the liver, and the bile duct.

Abbreviations or terms such as "nucleotide", "polynucleotide", "DNA", and "RNA" used herein abide by "Guidelines for the preparation of specification which contain nucleotide and/or amino acid sequences" (edited by Japan Patent Office) and common use in the art.

The term "polynucleotide" used herein refers to a nucleic acid including any of RNA, DNA, and RNA/DNA (chimera). The DNA includes any of cDNA, genomic DNA, and synthetic DNA The RNA includes any of total RNA, mRNA, rRNA, miRNA, siRNA, snoRNA, snRNA, non-coding RNA and synthetic RNA. Here the "synthetic DNA" and the "synthetic RNA" refer to a DNA and an RNA artificially prepared using, for example, an automatic nucleic acid synthesizer, on the basis of predetermined nucleotide sequences (which may be any of natural and non-natural sequences). The "non-natural sequence" is intended to be used in a broad sense and includes, for example, a sequence comprising substitution, deletion, insertion, and/or addition of one or more nucleotides (i.e., a variant sequence) and a sequence comprising one or more modified nucleotides (i.e., a modified sequence), which are different from the natural sequence. Herein, the term "polynucleotide" is used interchangeably with the term "nucleic acid."

The term "fragment" used herein is a polynucleotide having a nucleotide sequence that consists of a consecutive portion of a polynucleotide and desirably has a length of 15 or more nucleotides, preferably 17 or more nucleotides, more preferably 19 or more nucleotides.

The term "gene" used herein is intended to include not only RNA and double-stranded DNA but also each single-stranded DNA such as a plus(+) strand (or a sense strand) or a complementary strand (or an antisense strand) constituting the duplex. The gene is not particularly limited by its length.

Thus, the "gene" used herein includes any of double-stranded DNA including human genomic DNA, single-stranded DNA (plus strand), single-stranded DNA having a sequence complementary to the plus strand (complementary strand) including cDNA, microRNA (miRNA), and their fragments, and their transcripts, unless otherwise specified. The "gene" includes not only a "gene" represented by a particular nucleotide sequence (or SEQ ID NO) but "nucleic acids" encoding RNAs having biological functions equivalent to RNA encoded by the gene, for example, a congener (i.e., a homolog or an ortholog), a variant (e.g., a genetic polymorph), and a derivative. Specific examples of such a "nucleic acid" encoding a congener, a variant, or a derivative can include a "nucleic acid" having a nucleotide sequence hybridizing under stringent conditions described later to a complementary sequence of a nucleotide sequence represented by any of SEQ ID NOs: 1 to 499 or a nucleotide sequence derived from the nucleotide sequence by the replacement of u with t. Regardless whether or not there is a difference in functional region, the "gene" can comprise, for example, expression control regions, coding region, exons, or introns. The "gene" may be contained in a cell or may exist alone after being released from a cell. Alternatively, the "gene" may be in a state enclosed in a vesicle called exosome.

The term "exosome" used herein is a vesicle that is encapsulated by lipid bilayer and secreted from a cell. The exosome is derived from a multivesicular endosome and may incorporate biomaterials such as "genes" (e.g., RNA or DNA) or proteins when released into an extracellular environment. The exosome is known to be contained in a body fluid such as blood, serum, plasma, or lymph.

The term "transcript" used herein refers to an RNA synthesized from the DNA sequence of a gene as a template. RNA polymerase binds to a site called promoter located upstream of the gene and adds ribonucleotides complementary to the nucleotide sequence of the DNA to the 3' end to synthesize an RNA. This RNA contains not only the gene itself but the whole sequence from a transcription initiation site to the end of a polyA sequence, including expression control regions, coding region, exons, or introns.

Unless otherwise specified, the term "microRNA (miRNA)" used herein is intended to mean a 15- to 25-nucleotide non-coding RNA that is transcribed as an RNA precursor having a hairpin-like structure, cleaved by a dsRNA-cleaving enzyme having RNase III cleavage activity, and integrated into a protein complex called RISC, and that is involved in the suppression of translation of mRNA. The term "miRNA" used herein includes not only a "miRNA" represented by a particular nucleotide sequence (or SEQ ID NO) but a precursor of the "miRNA" (pre-miRNA or pri-miRNA), and miRNAs having biological functions equivalent thereto, for example, a congener (i.e., a homolog or an ortholog), a variant (e.g., a genetic polymorph), and a derivative. Such a precursor, a congener, a variant, or a derivative can be specifically identified using miRBase Release 20 (http://www.mirbase.org/), and examples thereof can include a "miRNA" having a nucleotide sequence hybridizing under stringent conditions described later to a complementary sequence of any particular nucleotide sequence represented by any of SEQ ID NOs: 1 to 499. The term "miRNA" used herein may be a gene product of a miR gene. Such a gene product includes a mature miRNA (e.g., a 15- to 25-nucleotide or 19- to 25-nucleotide non-coding RNA involved in the suppression of translation of mRNA as described above) or a miRNA precursor (e.g., pre-miRNA or pri-miRNA as described above).

The term "probe" used herein includes a polynucleotide that is used for specifically detecting an RNA resulting from the expression of a gene or a polynucleotide derived from the RNA, and/or a polynucleotide complementary thereto.

The term "primer" used herein includes a polynucleotide that specifically recognizes and amplifies an RNA resulting from the expression of a gene or a polynucleotide derived from the RNA, and/or a polynucleotide complementary thereto.

In this context, the complementary polynucleotide (complementary strand or reverse strand) means a polynucleotide in a complementary relationship based on A:T (U) and G:C base pairs with the full-length sequence of a polynucleotide consisting of a nucleotide sequence defined by any of SEQ ID NOs: 1 to 499 or a nucleotide sequence derived from the nucleotide sequence by the replacement of u with t, or a partial sequence thereof (here, this full-length or partial sequence is referred to as a plus strand for the sake of convenience). However, such a complementary strand is not limited to a sequence completely complementary to the nucleotide sequence of the target plus strand and may have a complementary relationship to an extent that permits hybridization under stringent conditions to the target plus strand.

The term "stringent conditions" used herein refers to conditions under which a nucleic acid probe hybridizes to its target sequence to a detectably larger extent (e.g., a measurement value equal to or larger than "(a mean of background measurement values)+(a standard deviation of the background measurement values)×2") than that for other sequences. The stringent conditions are dependent on a sequence and differ depending on an environment where hybridization is performed. A target sequence complementary 100% to the nucleic acid probe can be identified by controlling the stringency of hybridization and/or washing conditions. Specific examples of the "stringent conditions" will be mentioned later.

The term "Tm value" used herein means a temperature at which the double-stranded moiety of a polynucleotide is denatured into single strands so that the double strands and the single strands exist at a ratio of 1:1.

The term "variant" used herein means, in the case of a nucleic acid, a natural variant attributed to polymorphism, mutation, or the like; a variant containing the deletion, substitution, addition, or insertion of 1 or 2 or more nucleotides in a nucleotide sequence represented by any of SEQ ID NOs: 1 to 499 or a nucleotide sequence derived from the nucleotide sequence by the replacement of u with t, or a partial sequence thereof; a variant that exhibits percent (%) identity of approximately 90% or higher, approximately 95% or higher, approximately 97% or higher, approximately 98% or higher, approximately 99% or higher to each of these nucleotide sequences or the partial sequences thereof; or a nucleic acid hybridizing under the stringent conditions defined above to a polynucleotide or an oligonucleotide comprising each of these nucleotide sequences or the partial sequences thereof.

The term "several" used herein means an integer of approximately 10, 9, 8, 7, 6, 5, 4, 3, or 2.

The variant as used herein can be prepared by use of a well-known technique such as site-directed mutagenesis or mutagenesis using PCR.

The term "percent (%) identity" used herein can be determined with or without an introduced gap, using a protein or gene search system based on BLAST or FASTA (Zheng Zhang et al., 2000, J. Comput. Biol., Vol. 7, p. 203-214: Altschul, S. F. et al., 1990, Journal of Molecular Biology, Vol. 215, p. 403-410; and Pearson, W. R. et al., 1988, Proc. Natl. Acad. Sci. U.S.A., Vol. 85, p. 2444-2448).

The term "derivative" used herein is meant to include unlimitedly a modified nucleic acid, for example, a derivative labeled with a fluorophore or the like, a derivative containing a modified nucleotide (e.g., a nucleotide containing a group such as halogen, alkyl such as methyl, alkoxy such as methoxy, thio, or carboxymethyl, and a nucleotide that has undergone base rearrangement, double bond saturation, deamination, replacement of an oxygen molecule with a sulfur atom, etc.), PNA (peptide nucleic acid; Nielsen, P. E. et al., 1991, Science, Vol. 254, p. 1497-500), and LNA (locked nucleic acid; Obika, S. et al., 1998, Tetrahedron Lett., Vol. 39, p. 5401-5404).

As used herein, the "nucleic acid" capable of specifically binding to a polynucleotide selected from the pancreatic cancer marker miRNAs described above is a synthesized or prepared nucleic acid and specifically includes a "nucleic acid probe" or a "primer". The "nucleic acid" is utilized directly or indirectly for detecting the presence or absence of pancreatic cancer in a subject, for diagnosing the presence or absence or the severity of pancreatic cancer, the presence or absence or the degree of amelioration of pancreatic cancer, or the therapeutic sensitivity of pancreatic cancer, or for screening for a candidate substance useful in the prevention, amelioration, or treatment of pancreatic cancer. The "nucleic acid" includes a nucleotide, an oligonucleotide, and a polynucleotide capable of specifically recognizing and binding to a transcript represented by any of SEQ ID NOs: 1 to 499 or a synthetic cDNA nucleic acid thereof in vivo, particularly, in a sample such as a body fluid (e.g., blood or urine), in relation to the development of pancreatic cancer. The nucleotide, the oligonucleotide, and the polynucleotide can be effectively used as probes for detecting the aforementioned gene expressed in vivo, in tissues, in cells, or the like on the basis of the properties described above, or as primers for amplifying the aforementioned gene expressed in vivo.

The term "detection" used herein is interchangeable with the term "examination", "measurement", "detection", or "decision support". As used herein, the term "evaluation" is meant to include diagnosing or evaluation-supporting on the basis of examination results or measurement results.

The term "subject" used herein means a mammal such as a primate including a human and a chimpanzee, a pet animal including a dog and a cat, a livestock animal including cattle, a horse, sheep, and a goat, and a rodent including a mouse and a rat. The term "healthy subject" also means such a mammal without the cancer to be detected.

The term "P" or "P value" used herein refers to a probability at which a more extreme statistic than that actually calculated from data under null hypothesis is observed in a statistical test. Thus, smaller "P" or "P value" is regarded as being a more significant difference between subjects to be compared.

The term "sensitivity" used herein means a value of (the number of true positives)/(the number of true positives+the number of false negatives). High sensitivity allows pancreatic cancer to be detected early, leading to the complete resection of cancer sites and reduction in the rate of recurrence.

The term "specificity" used herein means a value of (the number of true negatives)/(the number of true negatives+the number of false positives). High specificity prevents needless extra examination for healthy subjects misjudged as being pancreatic cancer patients, leading to reduction in burden on patients and reduction in medical expense.

The term "accuracy" used herein means a value of (the number of true positives+the number of true negatives)/(the total number of cases). The accuracy indicates the ratio of samples that are identified correctly to all samples, and serves as a primary index for evaluating detection performance.

As used herein, the "sample" that is subject to determination, detection, or diagnosis refers to a tissue and a biological material in which the expression of the gene of the present invention varies as pancreatic cancer develops, as pancreatic cancer progresses, or as therapeutic effects on pancreatic cancer are exerted. Specifically, the "sample" refers to a pancreatic tissue, a peripancreatic vascular channel, lymph node, and organ, an organ suspected of having metastasis, the skin, a body fluid such as blood, urine, saliva, sweat, or tissue exudates, serum or plasma prepared from blood, feces, hair, and the like. The "sample" further refers to a biological sample extracted therefrom, specifically, a gene such as RNA or miRNA.

The term "hsa-miR-6893-5p gene" or "hsa-miR-6893-5p" used herein includes the hsa-miR-6893-5p gene (miRBase Accession No. MIMAT0027686) described in SEQ ID NO: 1, a homolog or an ortholog of a different organism species, and the like. The hsa-miR-6893-5p gene can be obtained by a method described in Ladewig E et al., 2012, Genome Res., Vol. 22, p. 1634-1645. Also, "hsa-mir-6893" (miRBase Accession No. MI0022740, SEQ ID NO: 123) having a hairpin-like structure is known as a precursor of "hsa-miR-6893-5p".

The term "hsa-miR-6075 gene" or "hsa-miR-6075" used herein includes the hsa-miR-6075 gene (miRBase Accession No. MIMAT0023700) described in SEQ ID NO: 2, a homolog or an ortholog of a different organism species, and the like. The hsa-miR-6075 gene can be obtained by a method described in Voellenkle C et al., 2012, RNA. Vol. 18, p. 472-484. Also, "hsa-mir-6075" (miRBase Accession No. MI0020352, SEQ ID NO: 124) having a hairpin-like structure is known as a precursor of "hsa-miR-6075".

The term "hsa-miR-6820-5p gene" or "hsa-miR-6820-5p" used herein includes the hsa-miR-6820-5p gene (miRBase Accession No. MIMAT0027540) described in SEQ ID NO; 3, a homolog or an ortholog of a different organism species, and the like. The hsa-miR-6820-5p gene can be obtained by a method described in Ladewig E et al., 2012, Genome Res., Vol. 22, p. 1634-1645. Also, "hsa-mir-6820" (miRBase Accession No. MI0022665, SEQ ID NO: 125) having a hairpin-like structure is known as a precursor of "hsa-miR-6820-5p".

The term "hsa-miR-4294 gene" or "hsa-miR-4294" used herein includes the hsa-miR-4294 gene (miRBase Accession No. MIMAT0016849) described in SEQ ID NO: 4, a homolog or an ortholog of a different organism species, and the like. The hsa-miR-4294 gene can be obtained by a method described in Goff L A et al., 2009, PLoS One., Vol. 4, e7192. Also, "hsa-mir-4294" (miRBase Accession No. MI0015827, SEQ ID NO: 126) having a hairpin-like structure is known as a precursor of "hsa-miR-4294".

The term "hsa-miR-6729-5p gene" or "hsa-miR-6729-5p" used herein includes the hsa-miR-6729-5p gene (miRBase Accession No. MIMAT0027359) described in SEQ ID NO: 5, a homolog or an ortholog of a different organism species, and the like. The hsa-miR-6729-5p gene can be obtained by a method described in Ladewig E et al., 2012, Genome Res., Vol. 22, p. 1634-1645. Also, "hsa-mir-6729" (miRBase Accession No. MI0022574, SEQ ID NO: 127) having a hairpin-like structure is known as a precursor of "hsa-miR-6729-5p".

The term "hsa-miR-4476 gene" or "hsa-miR-4476" used herein includes the hsa-miR-4476 gene (miRBase Accession No. MIMAT0019003) described in SEQ ID NO: 6, a homolog or an ortholog of a different organism species, and the like. The hsa-miR-4476 gene can be obtained by a method described in Jima D D et al., 2010, Blood., Vol. 116, e118-e127. Also, "hsa-mir-4476" (miRBase Accession No. MI0016828, SEQ ID NO: 128) having a hairpin-like structure is known as a precursor of "hsa-miR-4476".

The term "hsa-miR-6836-3p gene" or "hsa-miR-6836-3p" used herein includes the hsa-miR-6836-3p gene (miRBase Accession No. MIMAT0027575) described in SEQ ID NO; 7, a homolog or an ortholog of a different organism species, and the like. The hsa-miR-6836-3p gene can be obtained by a method described in Ladewig E et al., 2012, Genome Res., Vol. 22, p. 1634-1645. Also, "hsa-mir-6836" (miRBase Accession No. MI0022682, SEQ ID NO: 129) having a hairpin-like structure is known as a precursor of "hsa-miR-6836-3p".

The term "hsa-miR-6765-3p gene" or "hsa-miR-6765-3p" used herein includes the hsa-miR-6765-3p gene (miRBase Accession No. MIMAT0027431) described in SEQ ID NO; 8, a homolog or an ortholog of a different organism species, and the like. The hsa-miR-6765-3p gene can be obtained by a method described in Ladewig E et al., 2012, Genome Res., Vol. 22, p. 1634-1645. Also, "hsa-mir-6765" (miRBase Accession No. MI0022610, SEQ ID NO: 130) having a hairpin-like structure is known as a precursor of "hsa-miR-6765-3p".

The term "hsa-miR-6799-5p gene" or "hsa-miR-6799-5p" used herein includes the hsa-miR-6799-5p gene (miRBase Accession No. MIMAT0027498) described in SEQ ID NO: 9, a homolog or an ortholog of a different organism species, and the like. The hsa-miR-6799-5p gene can be obtained by a method described in Ladewig E et al., 2012, Genome Res., Vol. 22, p. 1634-1645. Also, "hsa-mir-6799" (miRBase Accession No. MI0022644, SEQ ID NO: 131) having a hairpin-like structure is known as a precursor of "hsa-miR-6799-5p".

The term "hsa-miR-4530 gene" or "hsa-miR-4530" used herein includes the hsa-miR-4530 gene (miRBase Accession No. MIMAT0019069) described in SEQ ID NO: 10, a homolog or an ortholog of a different organism species, and the like. The hsa-miR-4530 gene can be obtained by a method described in n Jima D D et al., 2010, Blood., Vol. 116, e118-e127. Also, "hsa-mir-4530" (miRBase Accession No. MI0016897, SEQ ID NO: 132) having a hairpin-like structure is known as a precursor of "hsa-miR-4530".

The term "hsa-miR-7641 gene" or "hsa-miR-7641" used herein includes the hsa-miR-7641 gene (miRBase Accession No. MIMAT0029782) described in SEQ ID NO: 11, a homolog or an ortholog of a different organism species, and the like. The hsa-miR-7641 gene can be obtained by a method described in Yoo J K et al., 2013, Arch Pharm Res., Vol. 36, p. 353-358. Also, "hsa-mir-7641-1 and hsa-mir-7641-2" (miRBase Accession Nos. MI0024975 and MI0024976, SEQ ID NOs: 133 and 134) having a hairpin-like structure are known as precursors of "hsa-miR-7641".

The term "hsa-miR-4454 gene" or "hsa-miR-4454" used herein includes the hsa-miR-4454 gene (miRBase Accession No. MIMAT0018976) described in SEQ ID NO: 12, a homolog or an ortholog of a different organism species, and the like. The hsa-miR-4454 gene can be obtained by a method described in Jima D D et al., 2010, Blood., Vol. 116, el 18-e127. Also, "hsa-mir-4454" (miRBase Accession No. MI0016800, SEQ ID NO: 135) having a hairpin-like structure is known as a precursor of "hsa-miR-4454".

The term "hsa-miR-615-5p gene" or "hsa-miR-615-5p" used in the present specification includes the hsa-miR-615-5p gene (miRBase Accession No. MIMAT0004804) described in SEQ ID NO: 13, a homolog or an ortholog of a different organism species, and the like. The hsa-miR-615-5p gene can be obtained by a method described in Cummins J M, 2006, Proc Natl Acad Sci, Vol. 103, p. 3687-3692. Also, "hsa-mir-615" (miRBase Accession No. MI0003628, SEQ ID NO: 136) having a hairpin-like structure is known as a precursor of "hsa-miR-615-5p".

The term "hsa-miR-8073 gene" or "hsa-miR-8073" used herein includes the hsa-miR-8073 gene (miRBase Accession No. MIMAT0031000) described in SEQ ID NO: 14, a homolog or an ortholog of a different organism species, and the like. The hsa-miR-8073 gene can be obtained by a method described in Wang H J et al., 2013, Shock., Vol. 39, p. 480487. Also, "hsa-mir-8073" (miRBase Accession No. MI0025909, SEQ ID NO: 137) having a hairpin-like structure is known as a precursor of "hsa-miR-8073".

The term "hsa-miR-663a gene" or "hsa-miR-663a" used herein includes the hsa-miR-663a gene (miRBase Accession No. MIMAT0003326) described in SEQ ID NO: 15, a homolog or an ortholog of a different organism species, and the like. The hsa-miR-663a gene can be obtained by a method described in Cummins J M, 2006, Proc Natl Acad Sci, Vol. 103, p. 3687-3692. Also, "hsa-mir-663a" (miRBase Accession No. MI0003672, SEQ ID NO: 138) having a hairpin-like structure is known as a precursor of "hsa-miR-663a".

The term "hsa-miR-4634 gene" or "hsa-miR-4634" used herein includes the hsa-miR-4634 gene (miRBase Accession No. MIMAT0019691) described in SEQ ID NO: 16, a homolog or an ortholog of a different organism species, and the like. The hsa-miR-4634 gene can be obtained by a method described in Persson H et al., 2011, Cancer Res., Vol. 71, p. 78-86. Also, "hsa-mir-4634" (miRBase Accession No. MI0017261. SEQ ID NO: 139) having a hairpin-like structure is known as a precursor of "hsa-miR-4634".

The term "hsa-miR-4450 gene" or "hsa-miR-4450" used herein includes the hsa-miR-4450 gene (miRBase Accession No. MIMAT0018971) described in SEQ ID NO: 17, a homolog or an ortholog of a different organism species, and the like. The hsa-miR-4450 gene can be obtained by a method described in Jima D D et al., 2010, Blood., Vol. 116, e118-e127. Also, "hsa-mir-4450" (miRBase Accession No. MI0016795. SEQ ID NO: 140) having a hairpin-like structure is known as a precursor of "hsa-miR-4450".

The term "hsa-miR-4792 gene" or "hsa-miR-4792" used herein includes the hsa-miR-4792 gene (miRBase Accession No. MIMAT0019964) described in SEQ ID NO: 18, a homolog or an ortholog of a different organism species, and the like. The hsa-miR-4792 gene can be obtained by a method described in Persson H et al., 2011, Cancer Res., Vol. 71, p. 78-86. Also, "hsa-mir-4792" (miRBase Accession No. MI0017439, SEQ ID NO: 141) having a hairpin-like structure is known as a precursor of "hsa-miR-4792".

The term "hsa-miR-665 gene" or "hsa-miR-665" used herein includes the hsa-miR-665 gene (miRBase Accession No. MIMAT0004952) described in SEQ ID NO: 19, a homolog or an ortholog of a different organism species, and the like. The hsa-miR-665 gene can be obtained by a method described in Berezikov E et al., 2006, Genome Res., Vol. 16, p. 1289-1298. Also, "hsa-mir-665" (miRBase Accession No. MI0005563, SEQ ID NO: 142) having a hairpin-like structure is known as a precursor of "hsa-miR-665".

The term "hsa-miR-7975 gene" or "hsa-miR-7975" used herein includes the hsa-miR-7975 gene (miRBase Accession No. MIMAT0031178) described in SEQ ID NO: 20, a homolog or an ortholog of a different organism species, and the like. The hsa-miR-7975 gene can be obtained by a method described in Velthut-Meikas A et al., 2013, Mol Endocrinol. [Epub prior to print]. Also, "hsa-mir-7975" (miRBase Accession No. MI0025751, SEQ ID NO: 143) having a hairpin-like structure is known as a precursor of "hsa-miR-7975".

The term "hsa-miR-7109-5p gene" or "hsa-miR-7109-5p" used herein includes the hsa-miR-7109-5p gene (miRBase Accession No. MIMAT0028115) described in SEQ ID NO: 21, a homolog or an ortholog of a different organism species, and the like. The hsa-miR-7109-5p gene can be obtained by a method described in Ladewig E et al., 2012, Genome Res., Vol. 22, p. 1634-1645. Also, "hsa-mir-7109" (miRBase Accession No. MI0022960, SEQ ID NO: 144) having a hairpin-like structure is known as a precursor of "hsa-miR-7109-5p".

The term "hsa-miR-6789-5p gene" or "hsa-miR-6789-5p" used herein includes the hsa-miR-6789-5p gene (miRBase Accession No. MIMAT0027478) described in SEQ ID NO: 22, a homolog or an ortholog of a different organism species, and the like. The hsa-miR-6789-5p gene can be obtained by a method described in Ladewig E et al., 2012, Genome Res., Vol. 22, p. 1634-1645. Also, "hsa-mir-6789" (miRBase Accession No. MI0022634, SEQ ID NO: 145) having a hairpin-like structure is known as a precursor of "hsa-miR-6789-5p".

The term "hsa-miR-4497 gene" or "hsa-miR-4497" used herein includes the hsa-miR-4497 gene (miRBase Accession No. MIMAT0019032) described in SEQ ID NO: 23, a homolog or an ortholog of a different organism species, and the like. The hsa-miR-4497 gene can be obtained by a method described in Jima D D et al., 2010, Blood., Vol. 116, el 18-e127. Also, "hsa-mir-4497" (miRBase Accession No. MI0016859, SEQ ID NO: 146) having a hairpin-like structure is known as a precursor of "hsa-miR-4497".

The term "hsa-miR-6877-5p gene" or "hsa-miR-6877-5p" used herein includes the hsa-miR-6877-5p gene (miRBase Accession No. MIMAT0027654) described in SEQ ID NO: 24, a homolog or an ortholog of a different organism species, and the like. The hsa-miR-6877-5p gene can be obtained by a method described in Ladewig E et al., 2012, Genome Res., Vol. 22, p. 1634-1645. Also, "hsa-mir-6877" (miRBase Accession No. MI0022724, SEQ ID NO: 147) having a hairpin-like structure is known as a precursor of "hsa-miR-6877-5p".

The term "hsa-miR-6880-5p gene" or "hsa-miR-6880-5p" used herein includes the hsa-miR-6880-5p gene (miRBase Accession No. MIMAT0027660) described in SEQ ID NO: 25, a homolog or an ortholog of a different organism species, and the like. The hsa-miR-6880-5p gene can be obtained by a method described in Ladewig E et al., 2012, Genome Res., Vol. 22, p. 1634-1645. Also, "hsa-mir-6880" (miRBase Accession No. MI0022727, SEQ ID NO: 148) having a hairpin-like structure is known as a precursor of "hsa-miR-6880-5p".

The term "hsa-miR-7977 gene" or "hsa-miR-7977" used herein includes the hsa-miR-7977 gene (miRBase Accession No. MIMAT0031180) described in SEQ ID NO: 26, a homolog or an ortholog of a different organism species, and the like. The hsa-miR-7977 gene can be obtained by a method described in Velthut-Meikas A et al., 2013, Mol Endocrinol. [Epub prior to print]. Also, "hsa-mir-7977" (miRBase Accession No. MI0025753, SEQ ID NO: 149) having a hairpin-like structure is known as a precursor of "hsa-miR-7977".

The term "hsa-miR-4734 gene" or "hsa-miR-4734" used herein includes the hsa-miR-4734 gene (miRBase Accession No. MIMAT0019859) described in SEQ ID NO: 27, a homolog or an ortholog of a different organism species, and the like. The hsa-miR-4734 gene can be obtained by a method described in Persson H et al., 2011, Cancer Res., Vol. 71, p. 78-86. Also, "hsa-mir-4734" (miRBase Accession No. MI0017371, SEQ ID NO: 150) having a hairpin-like structure is known as a precursor of "hsa-miR-4734".

The term "hsa-miR-6821-5p gene" or "hsa-miR-6821-5p" used herein includes the hsa-miR-6821-5p gene (miRBase Accession No. MIMAT0027542) described in SEQ ID NO: 28, a homolog or an ortholog of a different organism species, and the like. The hsa-miR-6821-5p gene can be obtained by a method described in Ladewig E et al., 2012, Genome Res., Vol. 22, p. 1634-1645. Also, "hsa-mir-6821" (miRBase Accession No. MI0022666, SEQ ID NO: 151) having a hairpin-like structure is known as a precursor of "hsa-miR-6821-5p".

The term "hsa-miR-8089 gene" or "hsa-miR-8089" used herein includes the hsa-miR-8089 gene (miRBase Accession No. MIMAT0031016) described in SEQ ID NO: 29, a homolog or an ortholog of a different organism species, and the like. The hsa-miR-8089 gene can be obtained by a method described in Wang H J et al., 2013, Shock., Vol. 39, p. 480-487. Also, "hsa-mir-8089" (miRBase Accession No. MI0025925, SEQ ID NO: 152) having a hairpin-like structure is known as a precursor of "hsa-miR-8089".

The term "hsa-miR-5585-3p gene" or "hsa-miR-5585-3p" used herein includes the hsa-miR-5585-3p gene (miRBase Accession No. MIMAT0022286) described in SEQ ID NO: 30, a homolog or an ortholog of a different organism species, and the like. The hsa-miR-5585-3p gene can be obtained by a method described in Friedlander M R et al., 2012. Nucleic Acids Res., Vol. 40, p. 37-52. Also, "hsa-mir-5585" (miRBase Accession No. MI0019142, SEQ ID NO: 153) having a hairpin-like structure is known as a precursor of "hsa-miR-5585-3p".

The term "hsa-miR-6085 gene" or "hsa-miR-6085" used herein includes the hsa-miR-6085 gene (miRBase Accession No. MIMAT0023710) described in SEQ ID NO: 31, a homolog or an ortholog of a different organism species, and the like. The hsa-miR-6085 gene can be obtained by a method described in Voellencle C et al., 2012, RNA., Vol. 18, p. 472-484. Also, "hsa-mir-6085" (miRBase Accession No. MI0020362, SEQ ID NO: 154) having a hairpin-like structure is known as a precursor of "hsa-miR-6085".

The term "hsa-miR-6845-5p gene" or "hsa-miR-6845-5p" used herein includes the hsa-miR-6845-5p gene (miRBase Accession No. MIMAT0027590) described in SEQ ID NO: 32, a homolog or an ortholog of a different organism species, and the like. The hsa-miR-6845-5p gene can be obtained by a method described in Ladewig E et al., 2012, Genome Res., Vol. 22, p. 1634-1645. Also, "hsa-mir-6845" (miRBase Accession No. MI0022691, SEQ ID NO: 155) having a hairpin-like structure is known as a precursor of "hsa-miR-6845-5p".

The term "hsa-miR-4651 gene" or "hsa-miR-4651" used herein includes the hsa-miR-4651 gene (miRBase Accession No. MIMAT0019715) described in SEQ ID NO: 33, a homolog or an ortholog of a different organism species, and the like. The hsa-miR-4651 gene can be obtained by a method described in Persson H et al., 2011, Cancer Res., Vol. 71, p. 78-86. Also, "hsa-mir-4651" (miRBase Accession No. MI0017279. SEQ ID NO: 156) having a hairpin-like structure is known as a precursor of "hsa-miR-4651".

The term "hsa-miR-4433-3p gene" or "hsa-miR-4433-3p" used herein includes the hsa-miR-4433-3p gene (miRBase Accession No. MIMAT0018949) described in SEQ ID NO: 34, a homolog or an ortholog of a different organism species, and the like. The hsa-miR-4433-3p gene can be obtained by a method described in Jima D D et al., 2010, Blood., Vol. 116, e118-e127. Also, "hsa-mir-4433" (miRBase Accession No. MI0016773, SEQ ID NO: 157) having a hairpin-like structure is known as a precursor of "hsa-miR-4433-3p".

The term "hsa-miR-1231 gene" or "hsa-miR-1231" used herein includes the hsa-miR-1231 gene (miRBase Accession No. MIMAT0005586) described in SEQ ID NO: 35, a homolog or an ortholog of a different organism species, and the like. The hsa-miR-1231 gene can be obtained by a method described in Berezikov E et al., 2007, Mol Cell., Vol. 28, p. 328-336. Also, "hsa-mir-1231" (miRBase Accession No. MI0006321, SEQ ID NO: 158) having a hairpin-like structure is known as a precursor of "hsa-miR-1231".

The term "hsa-miR-4665-5p gene" or "hsa-miR-4665-5p" used herein includes the hsa-miR-4665-5p gene (miRBase Accession No. MIMAT0019739) described in SEQ ID NO: 36, a homolog or an ortholog of a different organism species, and the like. The hsa-miR-4665-5p gene can be obtained by a method described in Persson H et al., 2011, Cancer Res., Vol. 71, p. 78-86. Also, "hsa-mir-4665" (miRBase Accession No. MI0017295, SEQ ID NO: 159) having a hairpin-like structure is known as a precursor of "hsa-miR-4665-5p".

The term "hsa-miR-7114-5p gene" or "hsa-miR-7114-5p" used herein includes the hsa-miR-7114-5p gene (miRBase Accession No. MIMAT0028125) described in SEQ ID NO: 37, a homolog or an ortholog of a different organism species, and the like. The hsa-miR-7114-5p gene can be obtained by a method described in Ladewig E et al., 2012, Genome Res., Vol. 22, p. 1634-1645. Also, "hsa-mir-7114" (miRBase Accession No. MI0022965, SEQ ID NO: 160) having a hairpin-like structure is known as a precursor of "hsa-miR-7114-5p".

The term "hsa-miR-1238-5p gene" or "hsa-miR-1238-5p" used herein includes the hsa-miR-1238-5p gene (miRBase Accession No. MIMAT0022947) described in SEQ ID NO: 38, a homolog or an ortholog of a different organism species, and the like. The hsa-miR-1238-5p gene can be obtained by a method described in Berezikov E et al., 2007, Mol Cell., Vol. 28, p. 328-336. Also, "hsa-mir-1238" (miRBase Accession No. MI0006328, SEQ ID NO: 161) having a hairpin-like structure is known as a precursor of "hsa-miR-1238-5p".

The term "hsa-miR-8069 gene" or "hsa-miR-8069" used herein includes the hsa-miR-8069 gene (miRBase Accession No. MIMAT0030996) described in SEQ ID NO: 39, a homolog or an ortholog of a different organism species, and the like. The hsa-miR-8069 gene can be obtained by a method described in Wang H J et al., 2013, Shock., Vol. 39, p. 480-487. Also, "hsa-mir-8069" (miRBase Accession No. MI0025905, SEQ ID NO: 162) having a hairpin-like structure is known as a precursor of "hsa-miR-8069".

The term "hsa-miR-4732-5p gene" or "hsa-miR-4732-5p" used herein includes the hsa-miR-4732-5p gene (miRBase Accession No. MIMAT0019855) described in SEQ ID NO: 40, a homolog or an ortholog of a different organism species, and the like. The hsa-miR-4732-5p gene can be obtained by a method described in Persson H et al., 2011, Cancer Res., Vol. 71, p. 78-86. Also, "hsa-mir-4732" (miRBase Accession No. MI0017369, SEQ ID NO: 163) having a hairpin-like structure is known as a precursor of "hsa-miR-4732-5p".

The term "hsa-miR-619-5p gene" or "hsa-miR-619-5p" used herein includes the hsa-miR-619-5p gene (miRBase Accession No. MIMAT0026622) described in SEQ ID NO: 41, a homolog or an ortholog of a different organism species, and the like. The hsa-miR-619-5p gene can be obtained by a method described in Cummins J M, 2006, Proc Natl Acad Sci, Vol. 103, p. 3687-3692. Also, "hsa-mir-619" (miRBase Accession No. MI0003633. SEQ ID NO: 164) having a hairpin-like structure is known as a precursor of "hsa-miR-619-5p".

The term "hsa-miR-3622a-5p gene" or "hsa-miR-3622a-5p" used herein includes the hsa-miR-3622a-5p gene (miRBase Accession No. MIMAT0018003) described in SEQ ID NO: 42, a homolog or an ortholog of a different organism species, and the like. The hsa-miR-3622a-5p gene can be obtained by a method described in Witten D et al., 2010. BMC Biol. Vol. 8, p. 58. Also, "hsa-mir-3622a" (miRBase Accession No. MI0016013, SEQ ID NO: 165) having a hairpin-like structure is known as a precursor of "hsa-miR-3622a-5p".

The term "hsa-miR-1260a gene" or "hsa-miR-1260a" used herein includes the hsa-miR-1260a gene (miRBase Accession No. MIMAT0005911) described in SEQ ID NO: 43, a homolog or an ortholog of a different organism species, and the like. The hsa-miR-1260a gene can be obtained by a method described in Morin R D et al., 2008, Genome Res., Vol. 18, p. 610-621. Also, "hsa-mir-1260a" (miRBase Accession No. MI0006394, SEQ ID NO: 166) having a hairpin-like structure is known as a precursor of "hsa-miR-1260a".

The term "hsa-miR-6741-5p gene" or "hsa-miR-6741-5p" used herein includes the hsa-miR-6741-5p gene (miRBase Accession No. MIMAT0027383) described in SEQ ID NO: 44, a homolog or an ortholog of a different organism species, and the like. The hsa-miR-6741-5p gene can be obtained by a method described in Ladewig E et al., 2012, Genome Res., Vol. 22, p. 1634-1645. Also, "hsa-mir-6741" (miRBase Accession No. MI0022586, SEQ ID NO: 167) having a hairpin-like structure is known as a precursor of "hsa-miR-6741-5p".

The term "hsa-miR-6781-5p gene" or "hsa-miR-6781-5p" used herein includes the hsa-miR-6781-5p gene (miRBase Accession No. MIMAT0027462) described in SEQ ID NO: 45, a homolog or an ortholog of a different organism species, and the like. The hsa-miR-6781-5p gene can be obtained by a method described in Ladewig E et al., 2012, Genome Res., Vol. 22, p. 1634-1645. Also, "hsa-mir-6781" (miRBase Accession No. MI0022626, SEQ ID NO: 168) having a hairpin-like structure is known as a precursor of "hsa-miR-6781-5p".

The term "hsa-miR-6125 gene" or "hsa-miR-6125" used herein includes the hsa-miR-6125 gene (miRBase Accession No. MIMAT0024598) described in SEQ ID NO: 46, a homolog or an ortholog of a different organism species, and the like. The hsa-miR-6125 gene can be obtained by a method described in Smith J L et al., 2012, J Virol., Vol. 86, p. 5278-5287. Also, "hsa-mir-6125" (miRBase Accession No. MI0021259, SEQ ID NO: 169) having a hairpin-like structure is known as a precursor of "hsa-miR-6125".

The term "hsa-miR-6805-5p gene" or "hsa-miR-6805-5p" used herein includes the hsa-miR-6805-5p gene (miRBase Accession No. MIMAT0027510) described in SEQ ID NO: 47, a homolog or an ortholog of a different organism species, and the like. The hsa-miR-6805-5p gene can be obtained by a method described in Ladewig E et al., 2012, Genome Res., Vol. 22, p. 1634-1645. Also, "hsa-mir-6805" (miRBase Accession No. MI0022650, SEQ ID NO: 170) having a hairpin-like structure is known as a precursor of "hsa-miR-6805-5p".

The term "hsa-miR-6132 gene" or "hsa-miR-6132" used herein includes the hsa-miR-6132 gene (miRBase Accession No. MIMAT0024616) described in SEQ ID NO: 48, a homolog or an ortholog of a different organism species, and the like. The hsa-miR-6132 gene can be obtained by a method described in Dannemann M, 2012, Genome Biol Evol., Vol. 4, p. 552-564. Also, "hsa-mir-6132" (miRBase Accession No. MI0021277, SEQ ID NO: 171) having a hairpin-like structure is known as a precursor of "hsa-miR-6132".

The term "hsa-miR-6872-3p gene" or "hsa-miR-6872-3p" used herein includes the hsa-miR-6872-3p gene (miRBase Accession No. MIMAT0027645) described in SEQ ID NO: 49, a homolog or an ortholog of a different organism species, and the like. The hsa-miR-6872-3p gene can be obtained by a method described in Ladewig E et al., 2012, Genome Res., Vol. 22, p. 1634-1645. Also, "hsa-mir-6872" (miRBase Accession No. MI0022719, SEQ ID NO: 172) having a hairpin-like structure is known as a precursor of "hsa-miR-6872-3p".

The term "hsa-miR-6875-5p gene" or "hsa-miR-6875-5p" used herein includes the hsa-miR-6875-5p gene (miRBase Accession No. MIMAT0027650) described in SEQ ID NO: 50, a homolog or an ortholog of a different organism species, and the like. The hsa-miR-6875-5p gene can be obtained by a method described in Ladewig E et al., 2012, Genome Res., Vol. 22, p. 1634-1645. Also, "hsa-mir-6875" (miRBase Accession No. MI0022722, SEQ ID NO: 173) having a hairpin-like structure is known as a precursor of "hsa-miR-6875-5p".

The term "hsa-miR-1908-3p gene" or "hsa-miR-1908-3p" used herein includes the hsa-miR-1908-3p gene (miRBase Accession No. MIMAT0026916) described in SEQ ID NO: 51, a homolog or an ortholog of a different organism species, and the like. The hsa-miR-1908-3p gene can be obtained by a method described in Bar M et al., 2008, Stem Cells., Vol. 26, p. 2496-2505. Also, "hsa-mir-1908" (miRBase Accession No. MI0008329, SEQ ID NO: 174) having a hairpin-like structure is known as a precursor of "hsa-miR-1908-3p".

The term "hsa-miR-4433b-3p gene" or "hsa-miR-4433b-3p" used herein includes the hsa-miR-4433b-3p gene (miRBase Accession No. MIMAT0030414) described in SEQ ID NO: 52, a homolog or an ortholog of a different organism species, and the like. The hsa-miR-4433b-3p gene can be obtained by a method described in Ple H et al., 2012, PLoS One., Vol. 7, e50746. Also, "hsa-mir-4433b" (miRBase Accession No. MI0025511, SEQ ID NO: 175) having a hairpin-like structure is known as a precursor of "hsa-miR-4433b-3p".

The term "hsa-miR-4736 gene" or "hsa-miR-4736" used herein includes the hsa-miR-4736 gene (miRBase Accession No. MIMAT0019862) described in SEQ ID NO: 53, a homolog or an ortholog of a different organism species, and the like. The hsa-miR-4736 gene can be obtained by a method described in Persson H et al., 2011, Cancer Res., Vol. 71, p. 78-86. Also, "hsa-mir-4736" (miRBase Accession No. MI0017373. SEQ ID NO: 176) having a hairpin-like structure is known as a precursor of "hsa-miR-4736".

The term "hsa-miR-5100 gene" or "hsa-miR-5100" used herein includes the hsa-miR-5100 gene (miRBase Accession No. MIMAT0022259) described in SEQ ID NO: 54, a homolog or an ortholog of a different organism species, and the like. The hsa-miR-5100 gene can be obtained by a method described in Tandon M et al., 2012, Oral Dis., Vol. 18, p. 127-131. Also, "hsa-mir-5100" (miRBase Accession No. MI0019116, SEQ ID NO: 177) having a hairpin-like structure is known as a precursor of "hsa-miR-5100".

The term "hsa-miR-6724-5p gene" or "hsa-miR-6724-5p" used herein includes the hsa-miR-6724-5p gene (miRBase Accession No. MIMAT0025856) described in SEQ ID NO: 55 a homolog or an ortholog of a different organism species, and the like. The hsa-miR-6724-5p gene can be obtained by a method described in Li Y et al., 2012, Gene., Vol. 497, p. 330-335. Also, "hsa-mir-6724" (miRBase Accession No. MI0022559, SEQ ID NO: 178) having a hairpin-like structure is known as a precursor of "hsa-miR-6724-5p".

The term "hsa-miR-7107-5p gene" or "hsa-miR-7107-5p" used herein includes the hsa-miR-7107-5p gene (miRBase Accession No. MIMAT0028111) described in SEQ ID NO: 56, a homolog or an ortholog of a different organism species, and the like. The hsa-miR-7107-5p gene can be obtained by a method described in Ladewig E et al., 2012, Genome Res., Vol. 22, p. 1634-1645. Also, "hsa-mir-7107" (miRBase Accession No. MI0022958, SEQ ID NO: 179) having a hairpin-like structure is known as a precursor of "hsa-miR-7107-5p".

The term "hsa-miR-6726-5p gene" or "hsa-miR-6726-5p" used herein includes the hsa-miR-6726-5p gene (miRBase Accession No. MIMAT0027353) described in SEQ ID NO: 57, a homolog or an ortholog of a different organism species, and the like. The hsa-miR-6726-5p gene can be obtained by a method described in Ladewig E et al., 2012, Genome Res., Vol. 22, p. 1634-1645. Also, "hsa-mir-6726" (miRBase Accession No. MI0022571, SEQ ID NO: 180) having a hairpin-like structure is known as a precursor of "hsa-miR-6726-5p".

The term "hsa-miR-3185 gene" or "hsa-miR-3185" used herein includes the hsa-miR-3185 gene (miRBase Accession No. MIMAT0015065) described in SEQ ID NO: 58, a homolog or an ortholog of a different organism species, and the like. The hsa-miR-3185 gene can be obtained by a method described in Stark M S et al., 2010, PLoS One., Vol. 5, e9685. Also, "hsa-mir-3185" (miRBase Accession No. MI0014227, SEQ ID NO: 181) having a hairpin-like structure is known as a precursor of "hsa-miR-3185".

The term "hsa-miR-4638-5p gene" or "hsa-miR-4638-5p" used herein includes the hsa-miR-4638-5p gene (miRBase Accession No. MIMAT0019695) described in SEQ ID NO: 59, a homolog or an ortholog of a different organism species, and the like. The hsa-miR-4638-5p gene can be obtained by a method described in Persson H et al., 2011, Cancer Res., Vol. 71, p. 78-86. Also, "hsa-mir-4638" (miRBase Accession No. MI0017265, SEQ ID NO: 182) having a hairpin-like structure is known as a precursor of "hsa-miR-4638-5p".

The term "hsa-miR-1273g-3p gene" or "hsa-miR-1273g-3p" used herein includes the hsa-miR-1273g-3p gene (miRBase Accession No. MIMAT0022742) described in SEQ ID NO: 60, a homolog or an ortholog of a different organism species, and the like. The hsa-miR-1273g-3p gene can be obtained by a method described in Reshmi G et al., 2011, Genomics., Vol. 97, p. 333-340. Also, "hsa-mir-1273g" (miRBase Accession No. MI0018003, SEQ ID NO: 183) having a hairpin-like structure is known as a precursor of "hsa-miR-1273g-3p".

The term "hsa-miR-6778-5p gene" or "hsa-miR-6778-5p" used herein includes the hsa-miR-6778-5p gene (miRBase Accession No. MIMAT0027456) described in SEQ ID NO: 61, a homolog or an ortholog of a different organism species, and the like. The hsa-miR-6778-5p gene can be obtained by a method described in Ladewig E et al., 2012, Genome Res., Vol. 22, p. 1634-1645. Also, "hsa-mir-6778" (miRBase Accession No. MI0022623, SEQ ID NO: 184) having a hairpin-like structure is known as a precursor of "hsa-miR-6778-5p".

The term "hsa-miR-328-5p gene" or "hsa-miR-328-5p" used herein includes the hsa-miR-328-5p gene (miRBase Accession No. MIMAT0026486) described in SEQ ID NO: 62, a homolog or an ortholog of a different organism species, and the like. The hsa-miR-328-5p gene can be obtained by a method described in Kim J et al., 2004, Proc Natl Acad Sci, Vol. 101, p. 360-365. Also, "hsa-mir-328" (miRBase Accession No. MI0000804, SEQ ID NO: 185) having a hairpin-like structure is known as a precursor of "hsa-miR-328-5p".

The term "hsa-miR-3679-3p gene" or "hsa-miR-3679-3p" used herein includes the hsa-miR-3679-3p gene (miRBase Accession No. MIMAT0018105) described in SEQ ID NO: 63, a homolog or an ortholog of a different organism species, and the like. The hsa-miR-3679-3p gene can be obtained by a method described in Creighton C J et al., 2010, PLoS One., Vol. 5, e9637. Also, "hsa-mir-3679" (miRBase Accession No. MI0016080, SEQ ID NO: 186) having a hairpin-like structure is known as a precursor of "hsa-miR-3679-3p".

The term "hsa-miR-1228-3p gene" or "hsa-miR-1228-3p" used herein includes the hsa-miR-1228-3p gene (miRBase Accession No. MIMAT0005583) described in SEQ ID NO: 64, a homolog or an ortholog of a different organism species, and the like. The hsa-miR-1228-3p gene can be obtained by a method described in Berezikov E et al., 2007, Mol Cell., Vol. 28, p. 328-336. Also, "hsa-mir-1228" (miRBase Accession No. MI0006318, SEQ ID NO: 187) having a hairpin-like structure is known as a precursor of "hsa-miR-1228-3p".

The term "hsa-miR-6779-5p gene" or "hsa-miR-6779-5p" used herein includes the hsa-miR-6779-5p gene (miRBase Accession No. MIMAT0027458) described in SEQ ID NO: 65, a homolog or an ortholog of a different organism species, and the like. The hsa-miR-6779-5p gene can be obtained by a method described in Ladewig E et al., 2012, Genome Res., Vol. 22, p. 1634-1645. Also, "hsa-mir-6779" (miRBase Accession No. MI0022624, SEQ ID NO: 188) having a hairpin-like structure is known as a precursor of "hsa-miR-6779-5p".

The term "hsa-miR-4723-5p gene" or "hsa-miR-4723-5p" used herein includes the hsa-miR-4723-5p gene (miRBase Accession No. MIMAT0019838) described in SEQ ID NO: 66, a homolog or an ortholog of a different organism species, and the like. The hsa-miR-4723-5p gene can be obtained by a method described in Persson H et al., 2011. Cancer Res. Vol. 71, p. 78-86. Also, "hsa-mir-4723" (miRBase Accession No. MI0017359, SEQ ID NO: 189) having a hairpin-like structure is known as a precursor of "hsa-miR-4723-5p".

The term "hsa-miR-6850-5p gene" or "hsa-miR-6850-5p" used herein includes the hsa-miR-6850-5p gene (miRBase Accession No. MIMAT0027600) described in SEQ ID NO: 67, a homolog or an ortholog of a different organism species, and the like. The hsa-miR-6850-5p gene can be obtained by a method described in Ladewig E et al., 2012, Genome Res., Vol. 22, p. 1634-1645. Also, "hsa-mir-6850" (miRBase Accession No. MI00226%, SEQ ID NO: 190) having a hairpin-like structure is known as a precursor of "hsa-miR-6850-5p".

The term "hsa-miR-760 gene" or "hsa-miR-760" used herein includes the hsa-miR-760 gene (miRBase Accession No. MIMAT0004957) described in SEQ ID NO: 68, a homolog or an ortholog of a different organism species, and the like. The hsa-miR-760 gene can be obtained by a method described in Berezikov E et al., 2006, Genome Res., Vol. 16, p. 1289-1298. Also, "hsa-mir-760" (miRBase Accession No. MI0005567, SEQ ID NO: 191) having a hairpin-like structure is known as a precursor of "hsa-miR-760".

The term "hsa-miR-7704 gene" or "hsa-miR-7704" used herein includes the hsa-miR-7704 gene (miRBase Accession No. MIMAT0030019) described in SEQ ID NO: 69, a homolog or an ortholog of a different organism species, and the like. The hsa-miR-7704 gene can be obtained by a method described in Swaminathan S et al., 2013, Biochem Biophys Res Commun., Vol. 434, p. 228-234. Also, "hsa-mir-7704" (miRBase Accession No. MI0025240, SEQ ID NO: 192) having a hairpin-like structure is known as a precursor of "hsa-miR-7704".

The term "hsa-miR-8072 gene" or "hsa-miR-8072" used herein includes the hsa-miR-8072 gene (miRBase Accession No. MIMAT0030999) described in SEQ ID NO: 70, a homolog or an ortholog of a different organism species, and the like. The hsa-miR-8072 gene can be obtained by a method described in Wang H J et al., 2013, Shock., Vol. 39, p. 480-487. Also, "hsa-mir-8072" (miRBase Accession No. MI0025908, SEQ ID NO: 193) having a hairpin-like structure is known as a precursor of "hsa-miR-8072".

The term "hsa-miR-4486 gene" or "hsa-miR-4486" used herein includes the hsa-miR-4486 gene (miRBase Accession No. MIMAT0019020) described in SEQ ID NO: 71, a homolog or an ortholog of a different organism species, and the like. The hsa-miR-4486 gene can be obtained by a method described in Jima D D et al., 2010, Blood., Vol. 116, el 18-e127. Also, "hsa-mir-4486" (miRBase Accession No. MI0016847, SEQ ID NO: 194) having a hairpin-like structure is known as a precursor of "hsa-miR-4486".

The term "hsa-miR-1913 gene" or "hsa-miR-1913" used herein includes the hsa-miR-1913 gene (miRBase Accession No. MIMAT0007888) described in SEQ ID NO: 72, a homolog or an ortholog of a different organism species, and the like. The hsa-miR-1913 gene can be obtained by a method described in Bar M et al., 2008, Stem Cells., Vol. 26, p. 2496-2505. Also, "hsa-mir-1913" (miRBase Accession No. MI0008334, SEQ ID NO: 195) having a hairpin-like structure is known as a precursor of "hsa-miR-1913".

The term "hsa-miR-4656 gene" or "hsa-miR-4656" used herein includes the hsa-miR-4656 gene (miRBase Accession No. MIMAT0019723) described in SEQ ID NO: 73, a homolog or an ortholog of a different organism species, and the like. The hsa-miR-4656 gene can be obtained by a method described in Persson H et al., 2011, Cancer Res., Vol. 71, p. 78-86. Also, "hsa-mir-4656" (miRBase Accession No. MI0017284. SEQ ID NO: 196) having a hairpin-like structure is known as a precursor of "hsa-miR-4656".

The term "hsa-miR-1260b gene" or "hsa-miR-1260b" used herein includes the hsa-miR-1260b gene (miRBase Accession No. MIMAT0015041) described in SEQ ID NO: 74, a homolog or an ortholog of a different organism species, and the like. The hsa-miR-1260b gene can be obtained by a method described in Stark M S et al., 2010, PLoS One., Vol. 5, e9685. Also, "hsa-mir-1260b" (miRBase Accession No. MI0014197, SEQ ID NO: 197) having a hairpin-like structure is known as a precursor of "hsa-miR-1260b".

The term "hsa-miR-7106-5p gene" or "hsa-miR-7106-5p" used herein includes the hsa-miR-7106-5p gene (miRBase Accession No. MIMAT0028109) described in SEQ ID NO: 75, a homolog or an ortholog of a different organism species, and the like. The hsa-miR-7106-5p gene can be obtained by a method described in Ladewig E et al., 2012, Genome Res., Vol. 22, p. 1634-1645. Also, "hsa-mir-7106" (miRBase Accession No. MI0022957, SEQ ID NO: 198) having a hairpin-like structure is known as a precursor of "hsa-miR-7106-5p".

The term "hsa-miR-6889-5p gene" or "hsa-miR-6889-5p" used herein includes the hsa-miR-6889-5p gene (miRBase Accession No. MIMAT0027678) described in SEQ ID NO: 76, a homolog or an ortholog of a different organism species, and the like. The hsa-miR-6889-5p gene can be obtained by a method described in Ladewig E et al., 2012, Genome Res., Vol. 22, p. 1634-1645. Also, "hsa-mir-6889" (miRBase Accession No. MI0022736, SEQ ID NO: 199) having a hairpin-like structure is known as a precursor of "hsa-miR-6889-5p".

The term "hsa-miR-6780b-5p gene" or "hsa-miR-6780b-5p" used herein includes the hsa-miR-6780b-5p gene (miRBase Accession No. MIMAT0027572) described in SEQ ID NO: 77, a homolog or an ortholog of a different organism species, and the like. The hsa-miR-6780b-5p gene can be obtained by a method described in Ladewig E et al., 2012, Genome Res., Vol. 22, p. 1634-1645. Also, "hsa-mir-6780b" (miRBase Accession No. MI0022681, SEQ ID NO: 200) having a hairpin-like structure is known as a precursor of "hsa-miR-6780b-5p".

The term "hsa-miR-6090 gene" or "hsa-miR-6090" used herein includes the hsa-miR-6090 gene (miRBase Accession No. MIMAT0023715) described in SEQ ID NO: 78, a homolog or an ortholog of a different organism species, and the like. The hsa-miR-6090 gene can be obtained by a method described in Yoo J K et al., 2013, Arch Pharm Res. Vol. 36, p. 353-358. Also, "hsa-mir-6090" (miRBase Accession No. MI0020367, SEQ ID NO: 201) having a hairpin-like structure is known as a precursor of "hsa-miR-6090".

The term "hsa-miR-4534 gene" or "hsa-miR-4534" used herein includes the hsa-miR-4534 gene (miRBase Accession No. MIMAT0019073) described in SEQ ID NO: 79, a homolog or an ortholog of a different organism species, and the like. The hsa-miR-4534 gene can be obtained by a method described in Jima D D et al., 2010, Blood., Vol. 116, el 18-e127. Also, "hsa-mir-4534" (miRBase Accession No. MI0016901, SEQ ID NO: 202) having a hairpin-like structure is known as a precursor of "hsa-miR-4534".

The term "hsa-miR-4449 gene" or "hsa-miR-4449" used herein includes the hsa-miR-4449 gene (miRBase Accession No. MIMAT1018968) described in SEQ ID NO: 80, a homolog or an ortholog of a different organism species, and the like. The hsa-miR-4449 gene can be obtained by a method described in Jima D D et al., 2010, Blood., Vol. 116, e118-e127. Also, "hsa-mir-4449" (miRBase Accession No. MI0016792, SEQ ID NO: 203) having a hairpin-like structure is known as a precursor of "hsa-miR-4449".

The term "hsa-miR-5195-3p gene" or "hsa-miR-5195-3p" used herein includes the hsa-miR-5195-3p gene (miRBase Accession No. MIMAT0021127) described in SEQ ID NO: 81, a homolog or an ortholog of a different organism species, and the like. The hsa-miR-5195-3p gene can be obtained by a method described in Schotte D et al., 2011, Leukemia., Vol. 25, p. 1389-1399. Also, "hsa-mir-5195" (miRBase Accession No. MI0018174, SEQ ID NO: 204) having a hairpin-like structure is known as a precursor of "hsa-miR-5195-3p".

The term "hsa-miR-1202 gene" or "hsa-miR-1202" used herein includes the hsa-miR-1202 gene (miRBase Accession No. MIMAT0005865) described in SEQ ID NO: 82, a homolog or an ortholog of a different organism species, and the like. The hsa-miR-1202 gene can be obtained by a method described in Marton S et al., 2008. Leukemia., Vol. 22, p. 330-338. Also, "hsa-mir-1202" (miRBase Accession No. MI0006334, SEQ ID NO: 205) having a hairpin-like structure is known as a precursor of "hsa-miR-1202".

The term "hsa-miR-4467 gene" or "hsa-miR-4467" used herein includes the hsa-miR-4467 gene (miRBase Accession No. MIMAT0018994) described in SEQ ID NO: 83, a homolog or an ortholog of a different organism species, and the like. The hsa-miR-4467 gene can be obtained by a method described in Jima D D et al., 2010, Blood., Vol. 116, el 18-e127. Also, "hsa-mir-4467" (miRBase Accession No. MI0016818, SEQ ID NO: 206) having a hairpin-like structure is known as a precursor of "hsa-miR-4467".

The term "hsa-miR-6515-3p gene" or "hsa-miR-6515-3p" used herein includes the hsa-miR-6515-3p gene (miRBase Accession No. MIMAT0025487) described in SEQ ID NO: 84, a homolog or an ortholog of a different organism species, and the like. The hsa-miR-6515-3p gene can be obtained by a method described in Joyce C E et al., 2011, Hum Mol Genet., Vol. 20, p. 4025-4040. Also, "hsa-mir-6515" (miRBase Accession No. MI0022227, SEQ ID NO: 207) having a hairpin-like structure is known as a precursor of "hsa-miR-6515-3p".

The term "hsa-miR-4281 gene" or "hsa-miR-4281" used herein includes the hsa-miR-4281 gene (miRBase Accession No. MIMAT0016907) described in SEQ ID NO: 85, a homolog or an ortholog of a different organism species, and the like. The hsa-miR-4281 gene can be obtained by a method described in Goff L A et al., 2009, PLoS One., Vol. 4, e7192. Also, "hsa-mir-4281" (miRBase Accession No. MI0015885, SEQ ID NO: 208) having a hairpin-like structure is known as a precursor of "hsa-miR-4281".

The term "hsa-miR-4505 gene" or "hsa-miR-4505" used herein includes the hsa-miR-4505 gene (miRBase Accession No. MIMAT0019041) described in SEQ ID NO: 86, a homolog or an ortholog of a different organism species, and the like. The hsa-miR-4505 gene can be obtained by a method described in Jima D D et al., 2010, Blood., Vol. 116, e118-e127. Also, "hsa-mir-4505" (miRBase Accession No. MI0016868, SEQ ID NO: 209) having a hairpin-like structure is known as a precursor of "hsa-miR-4505".

The term "hsa-miR-4484 gene" or "hsa-miR-4484" used herein includes the hsa-miR-4484 gene (miRBase Accession No. MIMAT0019018) described in SEQ ID NO: 87, a homolog or an ortholog of a different organism species, and the like. The hsa-miR-4484 gene can be obtained by a method described in Jima D D et al., 2010, Blood., Vol. 116, el 18-e127. Also, "hsa-mir-4484" (miRBase Accession No. MI0016845, SEQ ID NO: 210) having a hairpin-like structure is known as a precursor of "hsa-miR-4484".

The term "hsa-miR-6805-3p gene" or "hsa-miR-6805-3p" used herein includes the hsa-miR-6805-3p gene (miRBase Accession No. MIMAT0027511) described in SEQ ID NO: 88, a homolog or an ortholog of a different organism species, and the like. The hsa-miR-6805-3p gene can be obtained by a method described in Ladewig E et al., 2012, Genome Res., Vol. 22, p. 1634-1645. Also, "hsa-mir-6805" (miRBase Accession No. MI0022650, SEQ ID NO: 211) having a hairpin-like structure is known as a precursor of "hsa-miR-6805-3p".

The term "hsa-miR-3135b gene" or "hsa-miR-3135b" used herein includes the hsa-miR-3135b gene (miRBase Accession No. MIMAT0018985) described in SEQ ID NO: 89, a homolog or an ortholog of a different organism species, and the like. The hsa-miR-3135b gene can be obtained by a method described in Jima D D et al., 2010, Blood., Vol. 116, e118-e127. Also, "hsa-mir-3135b" (miRBase Accession No. MI0016809, SEQ ID NO: 212) having a hairpin-like structure is known as a precursor of "hsa-miR-3135b".

The term "hsa-miR-3162-5p gene" or "hsa-miR-3162-5p" used herein includes the hsa-miR-3162-5p gene (miRBase Accession No. MIMAT0015036) described in SEQ ID NO: 90, a homolog or an ortholog of a different organism species, and the like. The hsa-miR-3162-5p gene can be obtained by a method described in Stark M S et al., 2010, PLoS One., Vol. 5, e9685. Also, "hsa-mir-3162" (miRBase Accession No. MI0014192, SEQ ID NO: 213) having a hairpin-like structure is known as a precursor of "hsa-miR-3162-5p".

The term "hsa-miR-6768-5p gene" or "hsa-miR-6768-5p" used herein includes the hsa-miR-6768-5p gene (miRBase Accession No. MIMAT0027436) described in SEQ ID NO: 91, a homolog or an ortholog of a different organism species, and the like. The hsa-miR-6768-5p gene can be obtained by a method described in Ladewig E et al., 2012, Genome Res., Vol. 22, p. 1634-1645. Also, "hsa-mir-6768" (miRBase Accession No. MI0022613, SEQ ID NO: 214) having a hairpin-like structure is known as a precursor of "hsa-miR-6768-5p".

The term "hsa-miR-6721-5p gene" or "hsa-miR-6721-5p" used herein includes the hsa-miR-6721-5p gene (miRBase Accession No. MIMAT0025852) described in SEQ ID NO: 92, a homolog or an ortholog of a different organism species, and the like. The hsa-miR-6721-5p gene can be obtained by a method described in Li Y et al., 2012, Gene., Vol. 497, p. 330-335. Also, "hsa-mir-6721" (miRBase Accession No. MI0022556, SEQ ID NO: 215) having a hairpin-like structure is known as a precursor of "hsa-miR-6721-5p".

The term "hsa-miR-1227-5p gene" or "hsa-miR-1227-5p" used herein includes the hsa-miR-1227-5p gene (miRBase Accession No. MIMAT0022941) described in SEQ ID NO: 93, a homolog or an ortholog of a different organism species, and the like. The hsa-miR-1227-5p gene can be obtained by a method described in Berezikov E et al., 2007, Mol Cell., Vol. 28, p. 328-336. Also, "hsa-mir-1227" (miRBase Accession No. MI0006316, SEQ ID NO: 216) having a hairpin-like structure is known as a precursor of "hsa-miR-1227-5p".

The term "hsa-miR-6722-3p gene" or "hsa-miR-6722-3p" used herein includes the hsa-miR-6722-3p gene (miRBase Accession No. MIMAT0025854) described in SEQ ID NO: 94, a homolog or an ortholog of a different organism species, and the like. The hsa-miR-6722-3p gene can be obtained by a method described in Li Y et al., 2012, Gene. Vol. 497, p. 330-335. Also, "hsa-mir-6722" (miRBase Accession No. MI0022557, SEQ ID NO: 217) having a hairpin-like structure is known as a precursor of "hsa-miR-6722-3p".

The term "hsa-miR-4286 gene" or "hsa-miR-4286" used herein includes the hsa-miR-4286 gene (miRBase Accession No. MIMAT0016916) described in SEQ ID NO: 95, a homolog or an ortholog of a different organism species, and the like. The hsa-miR-4286 gene can be obtained by a method described in Goff L A et al., 2009, PLoS One., Vol. 4, e7192. Also, "hsa-mir-4286" (miRBase Accession No. MI0015894, SEQ ID NO: 218) having a hairpin-like structure is known as a precursor of "hsa-miR-4286".

The term "hsa-miR-4746-3p gene" or "hsa-miR-4746-3p" used herein includes the hsa-miR-4746-3p gene (miRBase Accession No. MIMAT0019881) described in SEQ ID NO: 96, a homolog or an ortholog of a different organism species, and the like. The hsa-miR-4746-3p gene can be obtained by a method described in Persson H et al., 2011, Cancer Res., Vol. 71, p. 78-86. Also, "hsa-mir-4746" (miRBase Accession No. MI0017385, SEQ ID NO: 219) having a hairpin-like structure is known as a precursor of "hsa-miR-4746-3p".

The term "hsa-miR-6727-5p gene" or "hsa-miR-6727-5p" used herein includes the hsa-miR-6727-5p gene (miRBase Accession No. MIMAT0027355) described in SEQ ID NO: 97, a homolog or an ortholog of a different organism species, and the like. The hsa-miR-6727-5p gene can be obtained by a method described in Ladewig E et al., 2012, Genome Res., Vol. 22, p. 1634-1645. Also, "hsa-mir-6727" (miRBase Accession No. MI0022572, SEQ ID NO: 220) having a hairpin-like structure is known as a precursor of "hsa-miR-6727-5p".

The term "hsa-miR-6816-5p gene" or "hsa-miR-6816-5p" used herein includes the hsa-miR-6816-5p gene (miRBase Accession No. MIMAT0027532) described in SEQ ID NO: 98, a homolog or an ortholog of a different organism species, and the like. The hsa-miR-6816-5p gene can be obtained by a method described in Ladewig E et al., 2012, Genome Res., Vol. 22, p. 1634-1645. Also, "hsa-mir-6816" (miRBase Accession No. MI0022661, SEQ ID NO: 221) having a hairpin-like structure is known as a precursor of "hsa-miR-6816-5p".

The term "hsa-miR-4741 gene" or "hsa-miR-4741" used herein includes the hsa-miR-4741 gene (miRBase Accession No. MIMAT0019871) described in SEQ ID NO: 99, a homolog or an ortholog of a different organism species, and the like. The hsa-miR-4741 gene can be obtained by a method described in Persson H et al., 2011, Cancer Res., Vol. 71, p. 78-86. Also, "hsa-mir-4741" (miRBase Accession No. MI0017379, SEQ ID NO: 222) having a hairpin-like structure is known as a precursor of "hsa-miR-4741".

The term "hsa-miR-4508 gene" or "hsa-miR-4508" used herein includes the hsa-miR-4508 gene (miRBase Accession No. MIMAT0019045) described in SEQ ID NO: 100, a homolog or an ortholog of a different organism species, and the like. The hsa-miR-4508 gene can be obtained by a method described in Jima D D et al., 2010, Blood., Vol. 116, el 18-e127. Also, "hsa-mir-4508" (miRBase Accession No. MI0016872, SEQ ID NO: 223) having a hairpin-like structure is known as a precursor of "hsa-miR-4508".

The term "hsa-miR-940 gene" or "hsa-miR-940" used herein includes the hsa-miR-940 gene (miRBase Accession No. MIMAT0004983) described in SEQ ID NO: 101, a homolog or an ortholog of a different organism species, and the like. The hsa-miR-940 gene can be obtained by a method described in Lui W O et al., 2007, A Cancer Res., Vol. 67, p. 6031-6043. Also, "hsa-mir-940" (miRBase Accession No. MI0005762. SEQ ID NO: 224) having a hairpin-like structure is known as a precursor of "hsa-miR-940".

The term "hsa-miR-4327 gene" or "hsa-miR-4327" used herein includes the hsa-miR-4327 gene (miRBase Accession No. MIMAT0016889) described in SEQ ID NO: 102, a homolog or an ortholog of a different organism species, and the like. The hsa-miR-4327 gene can be obtained by a method described in Goff L A et al., 2009, PLoS One. Vol. 4, e7192. Also, "hsa-mir-4327" (miRBase Accession No. MI0015867, SEQ ID NO: 225) having a hairpin-like structure is known as a precursor of "hsa-miR-4327".

The term "hsa-miR-4665-3p gene" or "hsa-miR-4665-3p" used herein includes the hsa-miR-4665-3p gene (miRBase Accession No. MIMAT0019740) described in SEQ ID NO: 103, a homolog or an ortholog of a different organism species, and the like. The hsa-miR-4665-3p gene can be obtained by a method described in Persson H et al., 2011, Cancer Res., Vol. 71, p. 78-86. Also, "hsa-mir-4665" (miRBase Accession No. MI0017295, SEQ ID NO: 159) having a hairpin-like structure is known as a precursor of "hsa-miR-4665-3p".

The term "hsa-miR-718 gene" or "hsa-miR-718" used herein includes the hsa-miR-718 gene (miRBase Accession No. MIMAT0012735) described in SEQ ID NO: 104, a homolog or an ortholog of a different organism species, and the like. The hsa-miR-718 gene can be obtained by a method described in Artzi S et al., 2008, BMC Bioinformatics., Vol. 9, p. 39. Also, "hsa-mir-718" (miRBase Accession No. MI0012489, SEQ ID NO: 226) having a hairpin-like structure is known as a precursor of "hsa-miR-718".

The term "hsa-miR-125a-3p gene" or "hsa-miR-125a-3p" used herein includes the hsa-miR-125a-3p gene (miRBase Accession No. MIMAT0004602) described in SEQ ID NO: 105, a homolog or an ortholog of a different organism species, and the like. The hsa-miR-125a-3p gene can be obtained by a method described in Lagos-Quintana M et al., 2002, Curr Biol., Vol. 12, p. 735-739. Also, "hsa-mir-125a" (miRBase Accession No. MI0000469, SEQ ID NO: 227) having a hairpin-like structure is known as a precursor of "hsa-miR-125a-3p".

The term "hsa-miR-204-3p gene" or "hsa-miR-204-3p" used herein includes the hsa-miR-204-3p gene (miRBase Accession No. MIMAT0022693) described in SEQ ID NO: 106, a homolog or an ortholog of a different organism species, and the like. The hsa-miR-204-3p gene can be obtained by a method described in Lim L P et al., 2003, Science., Vol. 299, p. 1540. Also, "hsa-mir-204" (miRBase Accession No. MI0000284, SEQ ID NO: 228) having a hairpin-like structure is known as a precursor of "hsa-miR-204-3p".

The term "hsa-miR-1469 gene" or "hsa-miR-1469" used herein includes the hsa-miR-1469 gene (miRBase Accession No. MIMAT0007347) described in SEQ ID NO: 107, a homolog or an ortholog of a different organism species, and the like. The hsa-miR-1469 gene can be obtained by a method described in Kawaji H et al., 2008, BMC Genomics, Vol. 9, p. 157. Also, "hsa-mir-1469" (miRBase Accession No. MI0007074, SEQ ID NO: 229) having a hairpin-like structure is known as a precursor of "hsa-miR-1469".

The term "hsa-miR-575 gene" or "hsa-miR-575" used herein includes the hsa-miR-575 gene (miRBase Accession No. MIMAT0003240) described in SEQ ID NO: 108, a homolog or an ortholog of a different organism species, and the like. The hsa-miR-575 gene can be obtained by a method described in Cummins J M, 2006, Proc Natl Acad Sci, Vol. 103, p. 3687-3692. Also, "hsa-mir-575" (miRBase Accession No. MI0003582, SEQ ID NO: 230) having a hairpin-like structure is known as a precursor of "hsa-miR-575".

The term "hsa-miR-150-3p gene" or "hsa-miR-150-3p" used herein includes the hsa-miR-150-3p gene (miRBase Accession No. MIMAT0004610) described in SEQ ID NO: 109, a homolog or an ortholog of a different organism species, and the like. The hsa-miR-150-3p gene can be obtained by a method described in Lagos-Quintana M et al., 2002, Curr Biol., Vol. 12, p. 735-739. Also, "hsa-mir-150" (miRBase Accession No. MI0000479, SEQ ID NO: 231) having a hairpin-like structure is known as a precursor of "hsa-miR-150-3p".

The term "hsa-miR-423-5p gene" or "hsa-miR-423-5p" used herein includes the hsa-miR-423-5p gene (miRBase Accession No. MIMAT0004748) described in SEQ ID NO: 110, a homolog or an ortholog of a different organism species, and the like. The hsa-miR-423-5p gene can be obtained by a method described in Kasashima K et al., 2004, Biochem Biophys Res Commun., Vol. 322, p. 403-410. Also, "hsa-mir-423" (miRBase Accession No. MI0001445, SEQ ID NO: 232) having a hairpin-like structure is known as a precursor of "hsa-miR-423-5p".

The term "hsa-miR-564 gene" or "hsa-miR-564" used herein includes the hsa-miR-564 gene (miRBase Accession No. MIMAT0003228) described in SEQ ID NO: 111, a homolog or an ortholog of a different organism species, and the like. The hsa-miR-564 gene can be obtained by a method described in Cummins J M, 2006, Proc Natl Acad Sci, Vol. 103, p. 3687-3692. Also, "hsa-mir-564" (miRBase Accession No. MI0003570, SEQ ID NO: 233) having a hairpin-like structure is known as a precursor of "hsa-miR-564".

The term "hsa-miR-3188 gene" or "hsa-miR-3188" used herein includes the hsa-miR-3188 gene (miRBase Accession No. MIMAT0015070) described in SEQ ID NO: 112, a homolog or an ortholog of a different organism species, and the like. The hsa-miR-3188 gene can be obtained by a method described in Stark M S et al., 2010, PLoS One., Vol. 5, e9685. Also, "hsa-mir-3188" (miRBase Accession No. MI0014232. SEQ ID NO: 234) having a hairpin-like structure is known as a precursor of "hsa-miR-3188".

The term "hsa-miR-1246 gene" or "hsa-miR-1246" used herein includes the hsa-miR-1246 gene (miRBase Accession No. MIMAT0005898) described in SEQ ID NO: 113, a homolog or an ortholog of a different organism species, and the like. The hsa-miR-1246 gene can be obtained by a method described in Morin R D et al., 2008, Genome Res., Vol. 18, p. 610-621. Also, "hsa-mir-1246" (miRBase Accession No. MI0006381, SEQ ID NO: 235) having a hairpin-like structure is known as a precursor of "hsa-miR-1246".

The term "hsa-miR-602 gene" or "hsa-miR-602" used herein includes the hsa-miR-602 gene (miRBase Accession No. MIMAT0003270) described in SEQ ID NO: 114, a homolog or an ortholog of a different organism species, and the like. The hsa-miR-602 gene can be obtained by a method described in Cummins J M, 2006, Proc Natl Acad Sci, Vol. 103, p. 3687-3692. Also, "hsa-mir-602" (miRBase Accession No. MI0003615, SEQ ID NO: 236) having a hairpin-like structure is known as a precursor of "hsa-miR-602".

The term "hsa-miR-1290 gene" or "hsa-miR-1290" used herein includes the hsa-miR-1290 gene (miRBase Accession No. MIMAT0005880) described in SEQ ID NO: 115, a homolog or an ortholog of a different organism species, and the like. The hsa-miR-1290 gene can be obtained by a method described in Morin R D et al., 2008, Genome Res., Vol. 18, p. 610-621. Also, "hsa-mir-1290" (miRBase Accession No. MI0006352, SEQ ID NO: 237) having a hairpin-like structure is known as a precursor of "hsa-miR-1290".

The term "hsa-miR-16-5p gene" or "hsa-miR-16-5p" used herein includes the hsa-miR-16-5p gene (miRBase Accession No. MIMAT0000069) described in SEQ ID NO: 116, a homolog or an ortholog of a different organism species, and the like. The hsa-miR-16-5p gene can be obtained by a method described in Lagos-Quintana M et al., 2002, Curr Biol., Vol. 12, p. 735-739. Also, "hsa-mir-16-1 and hsa-mir-16-2" (miRBase Accession Nos. MI0000070 and MI0000115, SEQ ID NOs: 238 and 239) having a hairpin-like structure are known as precursors of "hsa-miR-16-5p".

The term "hsa-miR-451a gene" or "hsa-miR-451a" used herein includes the hsa-miR-451a gene (miRBase Accession No. MIMAT0001631) described in SEQ ID NO: 117, a homolog or an ortholog of a different organism species, and the like. The hsa-miR-451a gene can be obtained by a method described in Altuvia Y et al., 2005, Nucleic Acids Res., Vol. 33, p. 2697-2706. Also, "hsa-mir-451a" (miRBase Accession No. MI0001729, SEQ ID NO: 240) having a hairpin-like structure are known as precursors of "hsa-miR-451a".

The term "hsa-miR-24-3p gene" or "hsa-miR-24-3p" used herein includes the hsa-miR-24-3p gene (miRBase Accession No. MIMAT0000080) described in SEQ ID NO: 118, a homolog or an ortholog of a different organism species, and the like. The hsa-miR-24-3p gene can be obtained by a method described in Lagos-Quintana M et al., 2001, Science., Vol. 294, p. 853-858. Also, "hsa-mir-24-1 and hsa-mir-24-2" (miRBase Accession Nos. MI0000080 and MI0000081, SEQ ID NOs: 241 and 242) having a hairpin-like structure are known as precursors of "hsa-miR-24-3p".

The term "hsa-miR-187-5p gene" or "hsa-miR-187-5p" used herein includes the hsa-miR-187-5p gene (miRBase Accession No. MIMAT0004561) described in SEQ ID NO: 119, a homolog or an ortholog of a different organism species, and the like. The hsa-miR-187-5p gene can be obtained by a method described in Lim L P et al., 2003, Science., Vol. 299, p. 1540. Also, "hsa-mir-187" (miRBase Accession No. MI0000274, SEQ ID NO: 243) having a hairpin-like structure are known as precursors of "hsa-miR-187-5p".

The term "hsa-miR-1908-5p gene" or "hsa-miR-1908-5p" used herein includes the hsa-miR-1908-5p gene (miRBase Accession No. MIMAT0007881) described in SEQ ID NO: 120, a homolog or an ortholog of a different organism species, and the like. The hsa-miR-1908-5p gene can be obtained by a method described in Bar M et al., 2008, Stem Cells., Vol. 26, p. 2496-2505. Also, "hsa-mir-1908" (miRBase Accession No. MI0008329, SEQ ID NO: 244) having a hairpin-like structure are known as precursors of "hsa-miR-1908-5p".

The term "hsa-miR-371a-5p gene" or "hsa-miR-371a-5p" used herein includes the hsa-miR-371a-5p gene (miRBase Accession No. MIMAT0004687) described in SEQ ID NO:

121, a homolog or an ortholog of a different organism species, and the like. The hsa-miR-371a-5p gene can be obtained by a method described in Suh M R et al., 2004, Dev Biol., Vol. 270, p. 488-498. Also, "hsa-mir-371a" (miRBase Accession No. MI0000779, SEQ ID NO: 245) having a hairpin-like structure are known as precursors of "hsa-miR-371a-5p".

The term "hsa-miR-550a-5p gene" or "hsa-miR-550a-5p" used herein includes the hsa-miR-550a-5p gene (miRBase Accession No. MIMAT0004800) described in SEQ ID NO: 122, a homolog or an ortholog of a different organism species, and the like. The hsa-miR-550a-5p gene can be obtained by a method described in Cummins J M, 2006, Proc Natl Acad Sci, Vol. 103, p. 3687-3692. Also, "hsa-mir-550a-1 and hsa-mir-550a-2" (miRBase Accession Nos. MI0003600 and MI0003601, SEQ ID NOs: 246 and 247) having a hairpin-like structure are known as precursors of "hsa-miR-550a-5p".

The term "hsa-miR-4417 gene" or "hsa-miR-4417" used herein includes the hsa-miR-4417 gene (miRBase Accession No. MIMAT0018929) described in SEQ ID NO: 349, a homolog or an ortholog of a different organism species, and the like. The hsa-miR-4417 gene can be obtained by a method described in Jima D D et al., 2010, Blood, Vol. 116, e118-e127. Also, "hsa-mir-4417" (miRBase Accession No. MI0016753, SEQ ID NO: 384) having a hairpin-like structure are known as precursors of "hsa-miR-4417".

The term "hsa-miR-4707-5p gene" or "hsa-miR-4707-5p" used herein includes the hsa-miR-4707-5p gene (miRBase Accession No. MIMAT0019807) described in SEQ ID NO: 350, a homolog or an ortholog of a different organism species, and the like. The hsa-miR-4707-5p gene can be obtained by a method described in Persson H et al., 2011, Cancer Res, Vol. 71, p. 78-86. Also, "hsa-mir-4707" (miRBase Accession No. MI0017340, SEQ ID NO: 385) having a hairpin-like structure are known as precursors of "hsa-miR-4707-5p".

The term "hsa-miR-7847-3p gene" or "hsa-miR-7847-3p" used herein includes the hsa-miR-7847-3p gene (miRBase Accession No. MIMAT0030422) described in SEQ ID NO: 351, a homolog or an ortholog of a different organism species, and the like. The hsa-miR-7847-3p gene can be obtained by a method described in Pie H et al., 2012, PLoS One, Vol. 7, e50746. Also, "hsa-mir-7847" (miRBase Accession No. MI0025517, SEQ ID NO: 386) having a hairpin-like structure are known as precursors of "hsa-miR-7847-3p".

The term "hsa-miR-2861 gene" or "hsa-miR-2861" used herein includes the hsa-miR-2861 gene (miRBase Accession No. MIMAT0013802) described in SEQ ID NO: 352, a homolog or an ortholog of a different organism species, and the like. The hsa-miR-2861 gene can be obtained by a method described in Li H et al., 2009, J Clin Invest, Vol. 119, p. 3666-3677. Also, "hsa-mir-2861" (miRBase Accession No. MI0013006, SEQ ID NO: 387) having a hairpin-like structure are known as precursors of "hsa-miR-2861".

The term "hsa-miR-4513 gene" or "hsa-miR-4513" used herein includes the hsa-miR-4513 gene (miRBase Accession No. MIMAT0019050) described in SEQ ID NO: 353, a homolog or an ortholog of a different organism species, and the like. The hsa-miR-4513 gene can be obtained by a method described in Jima D D et al., 2010, Blood, Vol. 116, e118-e127. Also, "hsa-mir-4513" (miRBase Accession No. MI0016879, SEQ ID NO: 388) having a hairpin-like structure are known as precursors of "hsa-miR-4513".

The term "hsa-miR-7111-5p gene" or "hsa-miR-7111-5p" used herein includes the hsa-miR-7111-5p gene (miRBase Accession No. MIMAT0028119) described in SEQ ID NO: 354, a homolog or an ortholog of a different organism species, and the like. The hsa-miR-7111-5p gene can be obtained by a method described in Ladewig E et al., 2012, Genome Res, Vol. 22, p. 1634-1645. Also, "hsa-mir-7111" (miRBase Accession No. MI0022962, SEQ ID NO: 389) having a hairpin-like structure are known as precursors of "hsa-miR-7111-5p".

The term "hsa-miR-6777-5p gene" or "hsa-miR-6777-5p" used herein includes the hsa-miR-6777-5p gene (miRBase Accession No. MIMAT0027454) described in SEQ ID NO: 355, a homolog or an ortholog of a different organism species, and the like. The hsa-miR-6777-5p gene can be obtained by a method described in Ladewig E et al., 2012, Genome Res, Vol. 22, p. 1634-1645. Also, "hsa-mir-6777" (miRBase Accession No. MI0022622, SEQ ID NO: 390) having a hairpin-like structure are known as precursors of "hsa-miR-6777-5p".

The term "hsa-miR-7113-3p gene" or "hsa-miR-7113-3p" used herein includes the hsa-miR-7113-3p gene (miRBase Accession No. MIMAT0028124) described in SEQ ID NO: 356, a homolog or an ortholog of a different organism species, and the like. The hsa-miR-7113-3p gene can be obtained by a method described in Ladewig E et al., 2012, Genome Res, Vol. 22, p. 1634-1645. Also, "hsa-mir-7113" (miRBase Accession No. MI0022964, SEQ ID NO: 391) having a hairpin-like structure are known as precursors of "hsa-miR-7113-3p".

The term "hsa-miR-4648 gene" or "hsa-miR-4648" used herein includes the hsa-miR-4648 gene (miRBase Accession No. MIMAT0019710) described in SEQ ID NO: 357, a homolog or an ortholog of a different organism species, and the like. The hsa-miR-4648 gene can be obtained by a method described in Persson H et al., 2011, Cancer Res, Vol. 71, p. 78-86. Also, "hsa-mir-4648" (miRBase Accession No. MI0017275, SEQ ID NO: 392) having a hairpin-like structure are known as precursors of "hsa-miR-4648".

The term "hsa-miR-3184-5p gene" or "hsa-miR-3184-5p" used herein includes the hsa-miR-3184-5p gene (miRBase Accession No. MIMAT0015064) described in SEQ ID NO: 358, a homolog or an ortholog of a different organism species, and the like. The hsa-miR-3184-5p gene can be obtained by a method described in Stark M S et al., 2010, PLoS One, Vol. 5, e9685. Also, "hsa-mir-3184" (miRBase Accession No. MI0014226, SEQ ID NO: 393) having a hairpin-like structure are known as precursors of "hsa-miR-3184-5p".

The term "hsa-miR-4271 gene" or "hsa-miR-4271" used herein includes the hsa-miR-4271 gene (miRBase Accession No. MIMAT0016901) described in SEQ ID NO: 359, a homolog or an ortholog of a different organism species, and the like. The hsa-miR-4271 gene can be obtained by a method described in Goff L A et al., 2009, PLoS One, Vol. 4, e7192. Also, "hsa-mir-4271" (miRBase Accession No. MI0015879. SEQ ID NO: 394) having a hairpin-like structure are known as precursors of "hsa-miR-4271".

The term "hsa-miR-6791-5p gene" or "hsa-miR-6791-5p" used herein includes the hsa-miR-6791-5p gene (miRBase Accession No. MIMAT0027482) described in SEQ ID NO: 360, a homolog or an ortholog of a different organism species, and the like. The hsa-miR-6791-5p gene can be obtained by a method described in Ladewig E et al., 2012, Genome Res, Vol. 22, p. 1634-1645. Also, "hsa-mir-6791" (miRBase Accession No. MI0022636, SEQ ID NO: 395) having a hairpin-like structure are known as precursors of "hsa-miR-6791-5p".

The term "hsa-miR-642a-3p gene" or "hsa-miR-642a-3p" used herein includes the hsa-miR-642a-3p gene (miRBase Accession No. MIMAT0020924) described in SEQ ID NO: 361, a homolog or an ortholog of a different organism species, and the like. The hsa-miR-642a-3p gene can be obtained by a method described in Cummins J M et al., 2006, Proc Natl Acad Sci USA, Vol. 103, p. 3687-3692, Landgraf P et al., 2007, Cell, Vol. 129, p. 1401-1414, Zaragosi L E et al., 2011, Genome Biol, Vol. 12, R64, etc. Also, "hsa-mir-642a" (miRBase Accession No. MI0003657, SEQ ID NO: 396) having a hairpin-like structure is known as a precursor of "hsa-miR-642a-3p".

The term "hsa-miR-7108-5p gene" or "hsa-miR-7108-5p" used herein includes the hsa-miR-7108-5p gene (miRBase Accession No. MIMAT0028113) described in SEQ ID NO: 362, a homolog or an ortholog of a different organism species, and the like. The hsa-miR-7108-5p gene can be obtained by a method described in Ladewig E et al., 2012, Genome Res, Vol. 22, p. 1634-1645. Also, "hsa-mir-7108" (miRBase Accession No. MI0022959, SEQ ID NO: 397) having a hairpin-like structure is known as a precursor of "hsa-miR-7108-5p".

The term "hsa-miR-128-1-5p gene" or "hsa-miR-128-1-5p" used herein includes the hsa-miR-128-1-5p gene (miRBase Accession No. MIMAT0026477) described in SEQ ID NO: 363, a homolog or an ortholog of a different organism species, and the like. The hsa-miR-128-1-5p gene can be obtained by a method described in Lagos-Quintana M et al., 2002, Curr Biol. Vol. 12, p. 735-739, Kasashima K et al., 2004, Biochem Biophys Res Commun, Vol. 322, p. 403-410, Landgraf P et al., 2007, Cell, Vol. 129, p. 1401-1414, Meunier J et al., 2013, Genome Res, Vol. 23, p. 3445, etc. Also, "hsa-mir-128-1" (miRBase Accession No. MI0000447, SEQ ID NO: 398) having a hairpin-like structure is known as a precursor of "hsa-miR-128-1-5p".

The term "hsa-miR-5196-5p gene" or "hsa-miR-5196-5p" used herein includes the hsa-miR-5196-5p gene (miRBase Accession No. MIMAT0021128) described in SEQ ID NO: 364, a homolog or an ortholog of a different organism species, and the like. The hsa-miR-5196-5p gene can be obtained by a method described in Schotte D et al., 2011, Leukemia. Vol. 25, p. 1389-1399. Also, "hsa-mir-5196" (miRBase Accession No. MI0018175, SEQ ID NO: 399) having a hairpin-like structure is known as a precursor of "hsa-miR-5196-5p".

The term "hsa-miR-3178 gene" or "hsa-miR-3178" used herein includes the hsa-miR-3178 gene (miRBase Accession No. MIMAT0015055) described in SEQ ID NO: 365, a homolog or an ortholog of a different organism species, and the like. The hsa-miR-3178 gene can be obtained by a method described in Stark M S et al., 2010, PLoS One, Vol. 5, e9685. Also, "hsa-mir-3178" (miRBase Accession No. MI0014212, SEQ ID NO: 400) having a hairpin-like structure is known as a precursor of "hsa-miR-3178".

The term "hsa-miR-3656 gene" or "hsa-miR-3656" used herein includes the hsa-miR-3656 gene (miRBase Accession No. MIMAT0018076) described in SEQ ID NO: 366, a homolog or an ortholog of a different organism species, and the like. The hsa-miR-3656 gene can be obtained by a method described in Meiri E et al., 2010, Nucleic Acids Res, Vol. 38, p. 6234-6246. Also, "hsa-mir-3656" (miRBase Accession No. MI0016056, SEQ ID NO: 401) having a hairpin-like structure is known as a precursor of "hsa-miR-3656".

The term "hsa-miR-92a-2-5p gene" or "hsa-miR-92a-2-5p" used herein includes the hsa-miR-92a-2-5p gene (miRBase Accession No. MIMAT0004508) described in SEQ ID NO: 367, a homolog or an ortholog of a different organism species, and the like. The hsa-miR-92a-2-5p gene can be obtained by a method described in Mourelatos Z et al., 2002, Genes Dev, Vol. 16, p. 720-728, Dostie J et al., 2003, RNA, Vol. 9, p. 180-186, Houbaviy H B et al., 2003, Dev Cell, Vol. 5, p. 351-358, Sub M R et al., 2004, Dev Biol, Vol. 270, p. 488-498, Kasashima K et al., 2004, Biochem Biophys Res Commun, Vol. 322, p. 403-410, Fu H et al., 2005, FEBS Lett, Vol. 579, p. 3849-3854, Landgraf P et al., 2007, Cell, Vol. 129, p. 1401-1414. Lui W O et al., 2007. Cancer Res, Vol. 67, p. 6031-6043, etc. Also, "hsa-mir-92a-2" (miRBase Accession No. MI0000094, SEQ ID NO: 402) having a hairpin-like structure is known as a precursor of "hsa-miR-92a-2-5p".

The term "hsa-miR-6769b-5p gene" or "hsa-miR-6769b-5p" used herein includes the hsa-miR-6769b-5p gene (miRBase Accession No. MIMAT0027620) described in SEQ ID NO: 368, a homolog or an ortholog of a different organism species, and the like. The hsa-miR-6769b-5p gene can be obtained by a method described in Ladewig E et al., 2012, Genome Res, Vol. 22, p. 1634-1645. Also, "hsa-mir-6769b" (miRBase Accession No. MI0022706, SEQ ID NO: 403) having a hairpin-like structure is known as a precursor of "hsa-miR-6769b-5p".

The term "hsa-miR-4689 gene" or "hsa-miR-4689" used herein includes the hsa-miR-4689 gene (miRBase Accession No. MIMAT0019778) described in SEQ ID NO: 369, a homolog or an ortholog of a different organism species, and the like. The hsa-miR-4689 gene can be obtained by a method described in Persson H et al., 2011, Cancer Res, Vol. 71, p. 78-86. Also, "hsa-mir-4689" (miRBase Accession No. MI0017322, SEQ ID NO: 404) having a hairpin-like structure is known as a precursor of "hsa-miR-4689".

The term "hsa-miR-6076 gene" or "hsa-miR-6076" used herein includes the hsa-miR-6076 gene (miRBase Accession No. MIMAT0023701) described in SEQ ID NO: 370, a homolog or an ortholog of a different organism species, and the like. The hsa-miR-6076 gene can be obtained by a method described in Voellenkle C et al., 2012, RNA, Vol. 18, p. 472-484. Also, "hsa-mir-6076" (miRBase Accession No. MI0020353, SEQ ID NO: 405) having a hairpin-like structure is known as a precursor of "hsa-miR-6076".

The term "hsa-miR-92b-5p gene" or "hsa-miR-92b-5p" used herein includes the hsa-miR-92b-5p gene (miRBase Accession No. MIMAT0004792) described in SEQ ID NO: 371, a homolog or an ortholog of a different organism species, and the like. The hsa-miR-92b-5p gene can be obtained by a method described in Cummins J M et al., 2006, Proc Natl Acad Sci USA, Vol. 103, p. 3687-3692, Landgraf P et al., 2007, Cell, Vol. 129, p. 1401-1414, L W WO et al., 2007, Cancer Res, Vol. 67, p. 6031-6043, etc. Also, "hsa-mir-92b" (miRBase Accession No. MI0003560, SEQ ID NO: 406) having a hairpin-like structure is known as a precursor of "hsa-miR-92b-5p".

The term "hsa-miR-6774-5p gene" or "hsa-miR-6774-5p" used herein includes the hsa-miR-6774-5p gene (miRBase Accession No. MIMAT0027448) described in SEQ ID NO: 372, a homolog or an ortholog of a different organism species, and the like. The hsa-miR-6774-5p gene can be obtained by a method described in Ladewig E et al., 2012, Genome Res, Vol. 22, p. 1634-1645. Also, "hsa-mir-6774" (miRBase Accession No. MI0022619, SEQ ID NO: 407) having a hairpin-like structure is known as a precursor of "hsa-miR-6774-5p".

The term "hsa-miR-486-3p gene" or "hsa-miR-486-3p" used herein includes the hsa-miR-486-3p gene (miRBase Accession No. MIMAT0004762) described in SEQ ID NO:

373, a homolog or an ortholog of a different organism species, and the like. The hsa-miR-486-3p gene can be obtained by a method described in Fu H et al., 2005, FEBS Lett, Vol. 579, p. 3849-3854, Landgraf P et al., 2007, Cell, Vol. 129, p. 1401-1414, Meunier J et al., 2013, Genome Res, Vol. 23, p. 34-45, etc. Also, "hsa-mir-486 and hsa-mir-486-2" (miRBase Accession Nos. MI0002470 and MI0023622, SEQ ID NOs: 408 and 409) having a hairpin-like structure are known as precursors of "hsa-miR-486-3p".

The term "hsa-miR-6806-5p gene" or "hsa-miR-6806-5p" used herein includes the hsa-miR-6806-5p gene (miRBase Accession No. MIMAT0027512) described in SEQ ID NO: 374, a homolog or an ortholog of a different organism species, and the like. The hsa-miR-6806-5p gene can be obtained by a method described in Ladewig E et al., 2012, Genome Res, Vol. 22, p. 1634-1645. Also, "hsa-mir-6806" (miRBase Accession No. MI0022651, SEQ ID NO: 410) having a hairpin-like structure is known as a precursor of "hsa-miR-6806-5p".

The term "hsa-miR-6842-5p gene" or "hsa-miR-6842-5p" used herein includes the hsa-miR-6842-5p gene (miRBase Accession No. MIMAT0027586) described in SEQ ID NO: 375, a homolog or an ortholog of a different organism species, and the like. The hsa-miR-6842-5p gene can be obtained by a method described in Ladewig E et al., 2012, Genome Res, Vol. 22, p. 1634-1645. Also, "hsa-mir-6842" (miRBase Accession No. MI0022688, SEQ ID NO: 411) having a hairpin-like structure is known as a precursor of "hsa-miR-6842-5p".

The term "hsa-miR-6716-5p gene" or "hsa-miR-6716-5p" used herein includes the hsa-miR-6716-5p gene (miRBase Accession No. MIMAT0025844) described in SEQ ID NO: 376, a homolog or an ortholog of a different organism species, and the like. The hsa-miR-6716-5p gene can be obtained by a method described in Li Y et al., 2012, Gene, Vol. 497, p. 330-335. Also, "hsa-mir-6716" (miRBase Accession No. MI0022550, SEQ ID NO: 412) having a hairpin-like structure is known as a precursor of "hsa-miR-6716-5p".

The term "hsa-miR-557 gene" or "hsa-miR-557" used herein includes the hsa-miR-557 gene (miRBase Accession No. MIMAT0003221) described in SEQ ID NO: 377, a homolog or an ortholog of a different organism species, and the like. The hsa-miR-557 gene can be obtained by a method described in Cummins J M et al., 2006, Proc Natl Acad Sci USA, Vol. 103, p. 3687-3692. Also, "hsa-mir-557" (miRBase Accession No. MI0003563, SEQ ID NO: 413) having a hairpin-like structure is known as a precursor of "hsa-miR-557".

The term "hsa-miR-4673 gene" or "hsa-miR-4673" used herein includes the hsa-miR-4673 gene (miRBase Accession No. MIMAT0019755) described in SEQ ID NO: 378, a homolog or an ortholog of a different organism species, and the like. The hsa-miR-4673 gene can be obtained by a method described in Persson H et al., 2011, Cancer Res, Vol. 71, p. 78-86. Also, "hsa-mir-4673" (miRBase Accession No. MI0017304, SEQ ID NO: 414) having a hairpin-like structure is known as a precursor of "hsa-miR-4673".

The term "hsa-miR-4674 gene" or "hsa-miR-4674" used herein includes the hsa-miR-4674 gene (miRBase Accession No. MIMAT0019756) described in SEQ ID NO: 379, a homolog or an ortholog of a different organism species, and the like. The hsa-miR-4674 gene can be obtained by a method described in Persson H et al., 2011, Cancer Res, Vol. 71, p. 78-86. Also, "hsa-mir-4674" (miRBase Accession No. MI0017305, SEQ ID NO: 415) having a hairpin-like structure is known as a precursor of "hsa-miR-4674".

The term "hsa-miR-4442 gene" or "hsa-miR-4442" used herein includes the hsa-miR-4442 gene (miRBase Accession No. MIMAT0018960) described in SEQ ID NO: 380, a homolog or an ortholog of a different organism species, and the like. The hsa-miR-4442 gene can be obtained by a method described in Jima D D et al., 2010, Blood. Vol. 116, e118-e127. Also, "hsa-mir-4442" (miRBase Accession No. MI0016785, SEQ ID NO: 416) having a hairpin-like structure is known as a precursor of "hsa-miR-4442".

The term "hsa-miR-1915-3p gene" or "hsa-miR-1915-3p" used herein includes the hsa-miR-1915-3p gene (miRBase Accession No. MIMAT0007892) described in SEQ ID NO: 381, a homolog or an ortholog of a different organism species, and the like. The hsa-miR-1915-3p gene can be obtained by a method described in Bar M et al, 2008, Stem Cells, Vol. 26, p. 2496-2505. Also, "hsa-mir-1915" (miRBase Accession No. MI0008336, SEQ ID NO: 417) having a hairpin-like structure is known as a precursor of "hsa-miR-1915-3p".

The term "hsa-miR-4687-3p gene" or "hsa-miR-4687-3p" used herein includes the hsa-miR-4687-3p gene (miRBase Accession No. MIMAT0019775) described in SEQ ID NO: 382, a homolog or an ortholog of a different organism species, and the like. The hsa-miR-4687-3p gene can be obtained by a method described in Persson H et al., 2011, Cancer Res, Vol. 71, p. 78-86. Also, "hsa-mir-4687" (miRBase Accession No. MI0017319, SEQ ID NO: 418) having a hairpin-like structure is known as a precursor of "hsa-miR-4687-3p".

The term "hsa-miR-92b-3p gene" or "hsa-miR-92b-3p" used herein includes the hsa-miR-92b-3p gene (miRBase Accession No. MIMAT0003218) described in SEQ ID NO: 383, a homolog or an ortholog of a different organism species, and the like. The hsa-miR-92b-3p gene can be obtained by a method described in Cummins J M et al., 2006, Proc Natl Acad Sci USA, Vol. 103, p. 3687-3692, Landgraf P et al., 2007, Cell, Vol. 129, p. 1401-1414, Lui W O et al., 2007, Cancer Res, Vol. 67, p. 6031-6043. Also, "hsa-mir-92b" (miRBase Accession No. MI0003560, SEQ ID NO; 419) having a hairpin-like structure is known as a precursor of "hsa-miR-92b-3p".

The term "hsa-miR-1203 gene" or "hsa-miR-1203" used herein includes the hsa-miR-1203 gene (miRBase Accession No. MIMAT0005866) described in SEQ ID NO: 464, a homolog or an ortholog of a different organism species, and the like. The hsa-miR-1203 gene can be obtained by a method described in Marton S et al., 2008, Leukemia., Vol. 22, p. 330-338. Also, "hsa-mir-1203" (miRBase Accession No. MI0006335, SEQ ID NO: 467) having a hairpin-like structure is known as a precursor of "hsa-miR-1203".

The term "hsa-miR-663b gene" or "hsa-miR-663b" used herein includes the hsa-miR-663b gene (miRBase Accession No. MIMAT0005867) described in SEQ ID NO: 465, a homolog or an ortholog of a different organism species, and the like. The hsa-miR-663b gene can be obtained by a method described in Takada S et al., 2008, Leukemia., Vol. 22, p. 1274-1278. Also, "hsa-mir-663b" (miRBase Accession No. MI0006336, SEQ ID NO: 475) having a hairpin-like structure is known as a precursor of "hsa-miR-663b".

The term "hsa-miR-4258 gene" or "hsa-miR-4258" used herein includes the hsa-miR-4258 gene (miRBase Accession No. MIMAT0016879) described in SEQ ID NO: 466, a homolog or an ortholog of a different organism species, and the like. The hsa-miR-4258 gene can be obtained by a method described in Goff L A et al., 2009, PLoS One., Vol. 4, e7192. Also, "hsa-mir-4258" (miRBase Accession No.

MI0015857, SEQ ID NO: 476) having a hairpin-like structure is known as a precursor of "hsa-miR-4258".

The term "hsa-miR-4649-5p gene" or "hsa-miR-4649-5p" used herein includes the hsa-miR-4649-5p gene (miRBase Accession No. MIMAT0019711) described in SEQ ID NO. 467, a homolog or an ortholog of a different organism species, and the like. The hsa-miR-4649-5p gene can be obtained by a method described in Persson H et al., 2011, Cancer Res., Vol. 71, p. 78-86. Also, "hsa-mir-4649" (miRBase Accession No. MI0017276, SEQ ID NO: 477) having a hairpin-like structure is known as a precursor of "hsa-miR-4649-5p".

The term "hsa-miR-4516 gene" or "hsa-miR-4516" used herein includes the hsa-miR-4516 gene (miRBase Accession No. MIMAT0019053) described in SEQ ID NO: 468, a homolog or an ortholog of a different organism species, and the like. The hsa-miR-4516 gene can be obtained by a method described in Jima D D et al., 2010, Blood., Vol. 116, e118-e127. Also, "hsa-mir-4516" (miRBase Accession No. MI0016882, SEQ ID NO: 478) having a hairpin-like structure is known as a precursor of "hsa-miR-4516".

The term "hsa-miR-3619-3p gene" or "hsa-miR-3619-3p" used herein includes the hsa-miR-3619-3p gene (miRBase Accession No. MIMAT0019219) described in SEQ ID NO: 469, a homolog or an ortholog of a different organism species, and the like. The hsa-miR-3619-3p gene can be obtained by a method described in Witten D et al., 2010, BMC Biol., Vol. 8, p. 58. Also, "hsa-mir-3619" (miRBase Accession No. MI0016009, SEQ ID NO: 479) having a hairpin-like structure is known as a precursor of "hsa-miR-3619-3p".

The term "hsa-miR-6826-5p gene" or "hsa-miR-6826-5p" used herein includes the hsa-miR-6826-5p gene (miRBase Accession No. MIMAT0027552) described in SEQ ID NO: 470, a homolog or an ortholog of a different organism species, and the like. The hsa-miR-6826-5p gene can be obtained by a method described in Ladewig E et al., 2012, Genome Res., Vol. 22, p. 1634-1645. Also, "hsa-mir-6826" (miRBase Accession No. MI0022671, SEQ ID NO: 480) having a hairpin-like structure is known as a precursor of "hsa-miR-6826-5p".

The term "hsa-miR-6757-5p gene" or "hsa-miR-6757-5p" used herein includes the hsa-miR-6757-5p gene (miRBase Accession No. MIMAT0027414) described in SEQ ID NO; 471, a homolog or an ortholog of a different organism species, and the like. The hsa-miR-6757-5p gene can be obtained by a method described in Ladewig E et al., 2012, Genome Res., Vol. 22, p. 1634-1645. Also, "hsa-mir-6757" (miRBase Accession No. MI0022602, SEQ ID NO: 481) having a hairpin-like structure is known as a precursor of "hsa-miR-6757-5p".

The term "hsa-miR-3131 gene" or "hsa-miR-3131" used herein includes the hsa-miR-3131 gene (miRBase Accession No. MIMAT0014996) described in SEQ ID NO: 472, a homolog or an ortholog of a different organism species, and the like. The hsa-miR-3131 gene can be obtained by a method described in Stark M S et al., 2010, PLoS One., Vol. 5, e9685. Also, "hsa-mir-3131" (miRBase Accession No. MI0014151, SEQ ID NO: 482) having a hairpin-like structure is known as a precursor of "hsa-miR-3131".

The term "hsa-miR-1343-3p gene" or "hsa-miR-1343-3p" used herein includes the hsa-miR-1343-3p gene (miRBase Accession No. MIMAT0019776) described in SEQ ID NO: 473, a homolog or an ortholog of a different organism species, and the like. The hsa-miR-1343-3p gene can be obtained by a method described in Persson H et al., 2011, Cancer Res., Vol. 71, p. 78-86. Also, "hsa-mir-1343" (miRBase Accession No. MI0017320, SEQ ID NO: 483) having a hairpin-like structure is known as a precursor of "hsa-miR-1343-3p".

The term "hsa-miR-6775-5p gene" or "hsa-miR-6775-5p" used herein includes the hsa-miR-6775-5p gene (miRBase Accession No. MIMAT0027450) described in SEQ ID NO: 492, a homolog or an ortholog of a different organism species, and the like. The hsa-miR-6775-5p gene can be obtained by a method described in Ladewig E et al., 2012, Genome Res, Vol. 22, p. 1634-1645. Also, "hsa-mir-6775" (miRBase Accession No. MI0022620, SEQ ID NO: 495) having a hairpin-like structure is known as a precursor of "hsa-miR-6775-5p".

The term "hsa-miR-6813-5p gene" or "hsa-miR-6813-5p" used herein includes the hsa-miR-6813-5p gene (miRBase Accession No. MIMAT0027526) described in SEQ ID NO: 493, a homolog or an ortholog of a different organism species, and the like. The hsa-miR-6813-5p gene can be obtained by a method described in Ladewig E et al., 2012, Genome Res, Vol. 22, p. 1634-1645. Also, "hsa-mir-6813" (miRBase Accession No. MI0022658, SEQ ID NO: 4%) having a hairpin-like structure is known as a precursor of "hsa-miR-6813-5p".

The term "hsa-miR-3940-5p gene" or "hsa-miR-3940-5p" used herein includes the hsa-miR-3940-5p gene (miRBase Accession No. MIMAT0019229) described in SEQ ID NO: 494, a homolog or an ortholog of a different organism species, and the like. The hsa-miR-3940-5p gene can be obtained by a method described in Liao J Y et al., 2010, PLoS One, Vol. 5, e10563. Also, "hsa-mir-3940" (miRBase Accession No. MI0016597, SEQ ID NO: 497) having a hairpin-like structure is known as a precursor of "hsa-miR-3940-5p".

A mature miRNA may become a variant due to the sequence cleaved shorter or longer by one to several flanking nucleotides, or due to substitution of nucleotides, when cut out as the mature miRNA from its RNA precursor having a hairpin-like structure. This variant is called isomiR (Morin R D. et al., 2008, Genome Res., Vol. 18, p. 610-621). The miRBase Release 20 shows the nucleotide sequences represented by SEQ ID NOs: 1 to 122, 349 to 383, 464 to 473, and 492 to 494 as well as a large number of the nucleotide sequence variants and fragments represented by SEQ ID NOs: 248 to 348,420 to 463, 484 to 491, and 498 to 499, called isomiRs. These variants can also be obtained as miRNAs having a nucleotide sequence represented by any of SEQ ID NOs: 1 to 122, 349 to 383, 464 to 473, and 492 to 494. Specifically, among the variants of polynucleotides consisting of the nucleotide sequence represented by any of SEQ ID NOs: 6, 10, 12, 13, 15, 18, 19, 23, 30, 33, 34, 41, 43, 46, 48, 51, 55, 59, 60, 62, 63, 64, 66, 68, 71, 74, 80, 83, 86, 87, 89, 90, 92, 95, 99, 100, 101, 105, 106, 109, 110, 112, 113, 115, 116, 117, 118, 119, 121, 349, 350, 352, 353, 357, 359, 361, 363, 364, 365, 366, 367, 369, 371, 373, 376, 378, 379, 380, 381, 382, 383, 465, 468, 472, 473, and 492 or a nucleotide sequence derived from the nucleotide sequence by the replacement of u with t according to the present invention, examples of the longest variants registered in miRBase Release 20 include polynucleotides represented by SEQ ID NOs: 248, 250, 251, 253, 255, 257, 259, 262, 265, 267, 268, 272, 275, 277, 278, 279, 282, 285, 287, 289, 291, 292, 294, 296, 298, 300, 302, 305, 306, 307, 309, 310, 312, 314, 316, 318, 320, 322, 324, 326, 328, 330, 332, 334, 336, 337, 339, 341, 342, 344, 346, 420, 422, 424, 426, 428, 430, 432, 434, 436, 438, 440, 442, 444, 446, 448, 450, 452, 454, 456, 458, 460, 462, 484, 486, 488, 490, and 498, respectively. Also, among the variants of polynucleotides consisting of a nucleotide sequence represented by any of SEQ ID NOs: 6, 10, 12, 13, 15, 18, 19, 23, 30, 33, 34, 41, 43, 46, 48, 51, 55, 59, 60, 62, 63, 64, 66, 68, 71, 74, 80, 83, 86, 87, 89, 90, 92, 95, 99, 100, 101, 105, 106, 109, 110, 112, 113, 115, 116, 117, 118, 119, 121, 349, 350, 352, 353, 357, 359, 361, 363, 364, 365, 366, 367, 369, 371, 373, 376, 378, 379, 380, 381, 382, 383, 465, 468, 472, 473 and 492 or a nucleotide sequence derived from the nucleotide sequence by the replacement of u with t according to the present invention, examples of shortest variants registered in the miRBase Release 20 include polynucleotides having sequences represented by SEQ ID NOs: 249, 252, 254, 256, 258, 260, 261, 263, 264, 266, 269, 270, 271, 273, 274, 276, 280, 281, 283, 284, 286, 288, 290, 293, 295, 297, 299, 301, 303, 304, 308, 311, 313, 315, 317, 319, 321, 323, 325, 327, 329, 331, 333, 335, 338, 340, 343, 345, 347, 348, 421, 423, 425, 427, 429, 431, 433, 435, 437, 439, 441, 443, 445, 447, 449, 451, 453, 455, 457, 459, 461, 463, 485, 487, 489, 491, and 499, respectively. In addition to these variants and fragments, examples thereof include a large number of isomiR polynucleotides of SEQ ID NOs: 6, 10, 12, 13, 15, 18, 19, 23, 30, 33, 34, 41, 43, 46, 48, 51, 55, 59, 60, 62, 63, 64, 66, 68, 71, 74, 80, 83, 86, 87, 89, 90, 92, 95, 99, 100, 101, 105, 106, 109, 110, 112, 113, 115, 116, 117, 118, 119, 121, 349, 350, 352, 353, 357, 359, 361, 363, 364, 365, 366, 367, 369, 371, 373, 376, 378, 379, 380, 381, 382, 383, 465, 468, 472, 473 and 492 registered in the miRBase. Examples of the polynucleotide comprising a nucleotide sequence represented by any of SEQ ID NOs: 1 to 122, 349 to 383, 464 to 473 and 492 to 494 include a polynucleotide represented by any of SEQ ID NOs: 123 to 247, 384 to 419, 474 to 483, and 495 to 497, which are their respective precursors.

The names and miRBase Accession Nos. (registration numbers) of the genes represented by SEQ ID NOs: 1 to 499 are shown in Table 1.

As used herein, the term "capable of specifically binding" means that the nucleic acid probe or the primer used in the present invention binds to a particular target nucleic acid and cannot substantially bind to other nucleic acids.

TABLE 1

| SEQ ID NO: | Gene name | miRBase registration No. |
|---|---|---|
| 1 | hsa-miR-6893-5p | MIMAT0027686 |
| 2 | hsa-miR-6075 | MIMAT0023700 |
| 3 | hsa-miR-6820-5p | MIMAT0027540 |
| 4 | hsa-miR-4294 | MIMAT0016849 |
| 5 | hsa-miR-6729-5p | MIMAT0027359 |
| 6 | hsa-miR-4476 | MIMAT0019003 |
| 7 | hsa-miR-6836-3p | MIMAT0027575 |
| 8 | hsa-miR-6765-3p | MIMAT0027431 |
| 9 | hsa-miR-6799-5p | MIMAT0027498 |
| 10 | hsa-miR-4530 | MIMAT0019069 |
| 11 | hsa-miR-7641 | MIMAT0029782 |
| 12 | hsa-miR-4454 | MIMAT0018976 |
| 13 | hsa-miR-615-5p | MIMAT0004804 |
| 14 | hsa-miR-8073 | MIMAT0031000 |
| 15 | hsa-miR-663a | MIMAT0003326 |
| 16 | hsa-miR-4634 | MIMAT0019691 |
| 17 | hsa-miR-4450 | MIMAT0018971 |
| 18 | hsa-miR-4792 | MIMAT0019964 |
| 19 | hsa-miR-665 | MIMAT0004952 |
| 20 | hsa-miR-7975 | MIMAT0031178 |
| 21 | hsa-miR-7109-5p | MIMAT0028115 |
| 22 | hsa-miR-6789-5p | MIMAT0027478 |
| 23 | hsa-miR-4497 | MIMAT0019032 |
| 24 | hsa-miR-6877-5p | MIMAT0027654 |
| 25 | hsa-miR-6880-5p | MIMAT0027660 |
| 26 | hsa-miR-7977 | MIMAT0031180 |
| 27 | hsa-miR-4734 | MIMAT0019859 |
| 28 | hsa-miR-6821-5p | MIMAT0027542 |
| 29 | hsa-miR-8089 | MIMAT0031016 |
| 30 | hsa-miR-5585-3p | MIMAT0022286 |
| 31 | hsa-miR-6085 | MIMAT0023710 |
| 32 | hsa-miR-6845-5p | MIMAT0027590 |
| 33 | hsa-miR-4651 | MIMAT0019715 |
| 34 | hsa-miR-4433-3p | MIMAT0018949 |
| 35 | hsa-miR-1231 | MIMAT0005586 |
| 36 | hsa-miR-4665-5p | MIMAT0019739 |
| 37 | hsa-miR-7114-5p | MIMAT0028125 |
| 38 | hsa-miR-1238-5p | MIMAT0022947 |
| 39 | hsa-miR-8069 | MIMAT0030996 |
| 40 | hsa-miR-4732-5p | MIMAT0019855 |
| 41 | hsa-miR-619-5p | MIMAT0026622 |
| 42 | hsa-miR-3622a-5p | MIMAT0018003 |
| 43 | hsa-miR-1260a | MIMAT0005911 |
| 44 | hsa-miR-6741-5p | MIMAT0027383 |
| 45 | hsa-miR-6781-5p | MIMAT0027462 |
| 46 | hsa-miR-6125 | MIMAT0024598 |
| 47 | hsa-miR-6805-5p | MIMAT0027510 |
| 48 | hsa-miR-6132 | MIMAT0024616 |
| 49 | hsa-miR-6872-3p | MIMAT0027645 |
| 50 | hsa-miR-6875-5p | MIMAT0027650 |
| 51 | hsa-miR-1908-3p | MIMAT0026916 |
| 52 | hsa-miR-4433b-3p | MIMAT0030414 |
| 53 | hsa-miR-4736 | MIMAT0019862 |
| 54 | hsa-miR-5100 | MIMAT0022259 |
| 55 | hsa-miR-6724-5p | MIMAT0025856 |
| 56 | hsa-miR-7107-5p | MIMAT0028111 |
| 57 | hsa-miR-6726-5p | MIMAT0027353 |
| 58 | hsa-miR-3185 | MIMAT0015065 |
| 59 | hsa-miR-4638-5p | MIMAT0019695 |
| 60 | hsa-miR-1273g-3p | MIMAT0022742 |
| 61 | hsa-miR-6778-5p | MIMAT0027456 |
| 62 | hsa-miR-328-5p | MIMAT0026486 |
| 63 | hsa-miR-3679-3p | MIMAT0018105 |
| 64 | hsa-miR-1228-5p | MIMAT0005583 |
| 65 | hsa-miR-6779-5p | MIMAT0027458 |
| 66 | hsa-miR-4723-5p | MIMAT0019838 |
| 67 | hsa-miR-6850-5p | MIMAT0027600 |
| 68 | hsa-miR-760 | MIMAT0004957 |
| 69 | hsa-miR-7704 | MIMAT0030019 |
| 70 | hsa-miR-8072 | MIMAT0030999 |
| 71 | hsa-miR-4486 | MIMAT0019020 |
| 72 | hsa-miR-1913 | MIMAT0007888 |
| 73 | hsa-miR-4656 | MIMAT0019723 |
| 74 | hsa-miR-1260b | MIMAT0015041 |
| 75 | hsa-miR-7106-5p | MIMAT0028109 |
| 76 | hsa-miR-6889-5p | MIMAT0027678 |
| 77 | hsa-miR-6780b-5p | MIMAT0027572 |
| 78 | hsa-miR-6090 | MIMAT0023715 |
| 79 | hsa-miR-4534 | MIMAT0019073 |
| 80 | hsa-miR-4449 | MIMAT0018968 |
| 81 | hsa-miR-5195-3p | MIMAT0021127 |
| 82 | hsa-miR-1202 | MIMAT0005865 |
| 83 | hsa-miR-4467 | MIMAT0018994 |
| 84 | hsa-miR-6515-3p | MIMAT0025487 |
| 85 | hsa-miR-4281 | MIMAT0016907 |
| 86 | hsa-miR-4505 | MIMAT0019041 |
| 87 | hsa-miR-4484 | MIMAT0019018 |
| 88 | hsa-miR-6805-3p | MIMAT0027511 |
| 89 | hsa-miR-3135b | MIMAT0018985 |
| 90 | hsa-miR-3162-5p | MIMAT0015036 |
| 91 | hsa-miR-6768-5p | MIMAT0027436 |
| 92 | hsa-miR-6721-5p | MIMAT0025852 |
| 93 | hsa-miR-1227-5p | MIMAT0022941 |
| 94 | hsa-miR-6722-3p | MIMAT0025854 |
| 95 | hsa-miR-4286 | MIMAT0016916 |
| 96 | hsa-miR-4746-3p | MIMAT0019881 |
| 97 | hsa-miR-6727-5p | MIMAT0027355 |
| 98 | hsa-miR-6816-5p | MIMAT0027532 |
| 99 | hsa-miR-4741 | MIMAT0019871 |
| 100 | hsa-miR-4508 | MIMAT0019045 |
| 101 | hsa-miR-940 | MIMAT0004983 |
| 102 | hsa-miR-4327 | MIMAT0016889 |

TABLE 1-continued

| SEQ ID NO: | Gene name | miRBase registration No. |
|---|---|---|
| 103 | hsa-miR-4665-3p | MIMAT0019740 |
| 104 | hsa-miR-718 | MIMAT0012735 |
| 105 | hsa-miR-125a-3p | MIMAT0004602 |
| 106 | hsa-miR-204-3p | MIMAT0022693 |
| 107 | hsa-miR-1469 | MIMAT0007347 |
| 108 | hsa-miR-575 | MIMAT0003240 |
| 109 | hsa-miR-150-3p | MIMAT0004610 |
| 110 | hsa-miR-423-5p | MIMAT0004748 |
| 111 | hsa-miR-564 | MIMAT0003228 |
| 112 | hsa-miR-3188 | MIMAT0015070 |
| 113 | hsa-miR-1246 | MIMAT0005898 |
| 114 | hsa-miR-602 | MIMAT0003270 |
| 115 | hsa-miR-1290 | MIMAT0005880 |
| 116 | hsa-miR-16-5p | MIMAT0000069 |
| 117 | hsa-miR-451a | MIMAT0001631 |
| 118 | hsa-miR-24-3p | MIMAT0000080 |
| 119 | hsa-miR-187-5p | MIMAT0004561 |
| 120 | hsa-miR-1908-5p | MIMAT0007881 |
| 121 | hsa-miR-371a-5p | MIMAT0004687 |
| 122 | hsa-miR-550a-5p | MIMAT0004800 |
| 123 | hsa-mir-6893 | MI0022740 |
| 124 | hsa-mir-6075 | MI0020352 |
| 125 | hsa-mir-6820 | MI0022665 |
| 126 | hsa-mir-4294 | MI0015827 |
| 127 | hsa-mir-6729 | MI0022574 |
| 128 | hsa-mir-4476 | MI0016828 |
| 129 | hsa-mir-6836 | MI0022682 |
| 130 | hsa-mir-6765 | MI0022610 |
| 131 | hsa-mir-6799 | MI0022644 |
| 132 | hsa-mir-4530 | MI0016897 |
| 133 | hsa-mir-7641-1 | MI0024975 |
| 134 | hsa-mir-7641-2 | MI0024976 |
| 135 | hsa-mir-4454 | MI0016800 |
| 136 | hsa-mir-615 | MI0003628 |
| 137 | hsa-mir-8073 | MI0025909 |
| 138 | hsa-mir-663a | MI0003672 |
| 139 | hsa-mir-4634 | MI0017261 |
| 140 | hsa-mir-4450 | MI0016795 |
| 141 | hsa-mir-4792 | MI0017439 |
| 142 | hsa-mir-665 | MI0005563 |
| 143 | hsa-mir-7975 | MI0025751 |
| 144 | hsa-mir-7109 | MI0022960 |
| 145 | hsa-mir-6789 | MI0022634 |
| 146 | hsa-mir-4497 | MI0016859 |
| 147 | hsa-mir-6877 | MI0022724 |
| 148 | hsa-mir-6880 | MI0022727 |
| 149 | hsa-mir-7977 | MI0025753 |
| 150 | hsa-mir-4734 | MI0017371 |
| 151 | hsa-mir-6821 | MI0022666 |
| 152 | hsa-mir-8089 | MI0025925 |
| 153 | hsa-mir-5585 | MI0019142 |
| 154 | hsa-mir-6085 | MI0020362 |
| 155 | hsa-mir-6845 | MI0022691 |
| 156 | hsa-mir-4651 | MI0017279 |
| 157 | hsa-mir-4433 | MI0016773 |
| 158 | hsa-mir-1231 | MI0006321 |
| 159 | hsa-mir-4665 | MI0017295 |
| 160 | hsa-mir-7114 | MI0022965 |
| 161 | hsa-mir-1238 | MI0006328 |
| 162 | hsa-mir-8069 | MI0025905 |
| 163 | hsa-mir-4732 | MI0017369 |
| 164 | hsa-mir-619 | MI0003633 |
| 165 | hsa-mir-3622a | MI0016013 |
| 166 | hsa-mir-1260a | MI0006394 |
| 167 | hsa-mir-6741 | MI0022586 |
| 168 | hsa-mir-6781 | MI0022626 |
| 169 | hsa-mir-6125 | MI0021259 |
| 170 | hsa-mir-6805 | MI0022650 |
| 171 | hsa-mir-6132 | MI0021277 |
| 172 | hsa-mir-6872 | MI0022719 |
| 173 | hsa-mir-6875 | MI0022722 |
| 174 | hsa-mir-1908 | MI0008329 |
| 175 | hsa-mir-4433b | MI0025511 |
| 176 | hsa-mir-4736 | MI0017373 |
| 177 | hsa-mir-5100 | MI0019116 |
| 178 | hsa-mir-6724 | MI0022559 |
| 179 | hsa-mir-7107 | MI0022958 |
| 180 | hsa-mir-6726 | MI0022571 |
| 181 | hsa-mir-3185 | MI0014227 |
| 182 | hsa-mir-4638 | MI0017265 |
| 183 | hsa-mir-1273g | MI0018003 |
| 184 | hsa-mir-6778 | MI0022623 |
| 185 | hsa-mir-328 | MI0000804 |
| 186 | hsa-mir-3679 | MI0016080 |
| 187 | hsa-mir-1228 | MI0006318 |
| 188 | hsa-mir-6779 | MI0022624 |
| 189 | hsa-mir-4723 | MI0017359 |
| 190 | hsa-mir-6850 | MI0022696 |
| 191 | hsa-mir-760 | MI0005567 |
| 192 | hsa-mir-7704 | MI0025240 |
| 193 | hsa-mir-8072 | MI0025908 |
| 194 | hsa-mir-4486 | MI0016847 |
| 195 | hsa-mir-1913 | MI0008334 |
| 196 | hsa-mir-4656 | MI0017284 |
| 197 | hsa-mir-1260b | MI0014197 |
| 198 | hsa-mir-7106 | MI0022957 |
| 199 | hsa-mir-6889 | MI0022736 |
| 200 | hsa-mir-6780b | MI0022681 |
| 201 | hsa-mir-6090 | MI0020367 |
| 202 | hsa-mir-4534 | MI0016901 |
| 203 | hsa-mir-4449 | MI0016792 |
| 204 | hsa-mir-5195 | MI0018174 |
| 205 | hsa-mir-1202 | MI0006334 |
| 206 | hsa-mir-4467 | MI0016818 |
| 207 | hsa-mir-6515 | MI0022227 |
| 208 | hsa-mir-4281 | MI0015885 |
| 209 | hsa-mir-4505 | MI0016868 |
| 210 | hsa-mir-4484 | MI0016845 |
| 211 | hsa-mir-6805 | MI0022650 |
| 212 | hsa-mir-3135b | MI0016809 |
| 213 | hsa-mir-3162 | MI0014192 |
| 214 | hsa-mir-6768 | MI0022613 |
| 215 | hsa-mir-6721 | MI0022556 |
| 216 | hsa-mir-1227 | MI0006316 |
| 217 | hsa-mir-6722 | MI0022557 |
| 218 | hsa-mir-4286 | MI0015894 |
| 219 | hsa-mir-4746 | MI0017385 |
| 220 | hsa-mir-6727 | MI0022572 |
| 221 | hsa-mir-6816 | MI0022661 |
| 222 | hsa-mir-4741 | MI0017379 |
| 223 | hsa-mir-4508 | MI0016872 |
| 224 | hsa-mir-940 | MI0005762 |
| 225 | hsa-mir-4327 | MI0015867 |
| 226 | hsa-mir-718 | MI0012489 |
| 227 | hsa-mir-125a | MI0000469 |
| 228 | hsa-mir-204 | MI0000284 |
| 229 | hsa-mir-1469 | MI0007074 |
| 230 | hsa-mir-575 | MI0003582 |
| 231 | hsa-mir-150 | MI0000479 |
| 232 | hsa-mir-423 | MI0001445 |
| 233 | hsa-mir-564 | MI0003570 |
| 234 | hsa-mir-3188 | MI0014232 |
| 235 | hsa-mir-1246 | MI0006381 |
| 236 | hsa-mir-602 | MI0003615 |
| 237 | hsa-mir-1290 | MI0006352 |
| 238 | hsa-mir-16-1 | MI0000070 |
| 239 | hsa-mir-16-2 | MI0000115 |
| 240 | hsa-mir-451a | MI0001729 |
| 241 | hsa-mir-24-1 | MI0000080 |
| 242 | hsa-mir-24-2 | MI0000081 |
| 243 | hsa-mir-187 | MI0000274 |
| 244 | hsa-mir-1908 | MI0008329 |
| 245 | hsa-mir-371a | MI0000779 |
| 246 | hsa-mir-550a-1 | MI0003600 |
| 247 | hsa-mir-550a-2 | MI0003601 |
| 248 | isomiR example 1 of SEQ ID NO: 6 | — |
| 249 | isomiR example 2 of SEQ ID NO: 6 | — |
| 250 | isomiR example 1 of SEQ ID NO: 10 | — |
| 251 | isomiR example 1 of SEQ ID NO: 12 | — |
| 252 | isomiR example 2 of SEQ ID NO: 12 | — |
| 253 | isomiR example 1 of SEQ ID NO: 13 | — |
| 254 | isomiR example 2 of SEQ ID NO: 13 | — |

TABLE 1-continued

| SEQ ID NO: | Gene name | miRBase registration No. |
|---|---|---|
| 255 | isomiR example 1 of SEQ ID NO: 15 | — |
| 256 | isomiR example 2 of SEQ ID NO: 15 | — |
| 257 | isomiR example 1 of SEQ ID NO: 18 | — |
| 258 | isomiR example 2 of SEQ ID NO: 18 | — |
| 259 | isomiR example 1 of SEQ ID NO: 19 | — |
| 260 | isomiR example 2 of SEQ ID NO: 19 | — |
| 261 | isomiR example 1 of SEQ ID NO: 20 | — |
| 262 | isomiR example 1 of SEQ ID NO: 23 | — |
| 263 | isomiR example 2 of SEQ ID NO: 23 | — |
| 264 | isomiR example 1 of SEQ ID NO: 27 | — |
| 265 | isomiR example 1 of SEQ ID NO: 30 | — |
| 266 | isomiR example 2 of SEQ ID NO: 30 | — |
| 267 | isomiR example 1 of SEQ ID NO: 33 | — |
| 268 | isomiR example 1 of SEQ ID NO: 34 | — |
| 269 | isomiR example 2 of SEQ ID NO: 34 | — |
| 270 | isomiR example 1 of SEQ ID NO: 36 | — |
| 271 | isomiR example 1 of SEQ ID NO: 40 | — |
| 272 | isomiR example 1 of SEQ ID NO: 41 | — |
| 273 | isomiR example 2 of SEQ ID NO: 41 | — |
| 274 | isomiR example 1 of SEQ ID NO: 42 | — |
| 275 | isomiR example 1 of SEQ ID NO: 43 | — |
| 276 | isomiR example 2 of SEQ ID NO: 43 | — |
| 277 | isomiR example 1 of SEQ ID NO: 46 | — |
| 278 | isomiR example 1 of SEQ ID NO: 48 | — |
| 279 | isomiR example 1 of SEQ ID NO: 51 | — |
| 280 | isomiR example 2 of SEQ ID NO: 51 | — |
| 281 | isomiR example 1 of SEQ ID NO: 54 | — |
| 282 | isomiR example 1 of SEQ ID NO: 55 | — |
| 283 | isomiR example 2 of SEQ ID NO: 55 | — |
| 284 | isomiR example 1 of SEQ ID NO: 58 | — |
| 285 | isomiR example 1 of SEQ ID NO: 59 | — |
| 286 | isomiR example 2 of SEQ ID NO: 59 | — |
| 287 | isomiR example 1 of SEQ ID NO: 60 | — |
| 288 | isomiR example 2 of SEQ ID NO: 60 | — |
| 289 | isomiR example 1 of SEQ ID NO: 62 | — |
| 290 | isomiR example 2 of SEQ ID NO: 62 | — |
| 291 | isomiR example 1 of SEQ ID NO: 63 | — |
| 292 | isomiR example 1 of SEQ ID NO: 64 | — |
| 293 | isomiR example 2 of SEQ ID NO: 64 | — |
| 294 | isomiR example 1 of SEQ ID NO: 66 | — |
| 295 | isomiR example 2 of SEQ ID NO: 66 | — |
| 296 | isomiR example 1 of SEQ ID NO: 68 | — |
| 297 | isomiR example 2 of SEQ ID NO: 68 | — |
| 298 | isomiR example 1 of SEQ ID NO: 71 | — |
| 299 | isomiR example 1 of SEQ ID NO: 72 | — |
| 300 | isomiR example 1 of SEQ ID NO: 74 | — |
| 301 | isomiR example 2 of SEQ ID NO: 74 | — |
| 302 | isomiR example 1 of SEQ ID NO: 80 | — |
| 303 | isomiR example 2 of SEQ ID NO: 80 | — |
| 304 | isomiR example 1 of SEQ ID NO: 82 | — |
| 305 | isomiR example 1 of SEQ ID NO: 83 | — |
| 306 | isomiR example 1 of SEQ ID NO: 86 | — |
| 307 | isomiR example 1 of SEQ ID NO: 87 | — |
| 308 | isomiR example 2 of SEQ ID NO: 87 | — |
| 309 | isomiR example 1 of SEQ ID NO: 89 | — |
| 310 | isomiR example 1 of SEQ ID NO: 90 | — |
| 311 | isomiR example 2 of SEQ ID NO: 90 | — |
| 312 | isomiR example 1 of SEQ ID NO: 92 | — |
| 313 | isomiR example 2 of SEQ ID NO: 92 | — |
| 314 | isomiR example 1 of SEQ ID NO: 95 | — |
| 315 | isomiR example 2 of SEQ ID NO: 95 | — |
| 316 | isomiR example 1 of SEQ ID NO: 99 | — |
| 317 | isomiR example 2 of SEQ ID NO: 99 | — |
| 318 | isomiR example 1 of SEQ ID NO: 100 | — |
| 319 | isomiR example 2 of SEQ ID NO: 100 | — |
| 320 | isomiR example 1 of SEQ ID NO: 101 | — |
| 321 | isomiR example 2 of SEQ ID NO: 101 | — |
| 322 | isomiR example 1 of SEQ ID NO: 105 | — |
| 323 | isomiR example 2 of SEQ ID NO: 105 | — |
| 324 | isomiR example 1 of SEQ ID NO: 106 | — |
| 325 | isomiR example 2 of SEQ ID NO: 106 | — |
| 326 | isomiR example 1 of SEQ ID NO: 109 | — |
| 327 | isomiR example 2 of SEQ ID NO: 109 | — |
| 328 | isomiR example 1 of SEQ ID NO: 110 | — |
| 329 | isomiR example 2 of SEQ ID NO: 110 | — |
| 330 | isomiR example 1 of SEQ ID NO: 112 | — |
| 331 | isomiR example 2 of SEQ ID NO: 112 | — |
| 332 | isomiR example 1 of SEQ ID NO: 113 | — |
| 333 | isomiR example 2 of SEQ ID NO: 113 | — |
| 334 | isomiR example 1 of SEQ ID NO: 115 | — |
| 335 | isomiR example 2 of SEQ ID NO: 115 | — |
| 336 | isomiR example 1 of SEQ ID NO: 116 | — |
| 337 | isomiR example 2 of SEQ ID NO: 116 | — |
| 338 | isomiR example 3 of SEQ ID NO: 116 | — |
| 339 | isomiR example 1 of SEQ ID NO: 117 | — |
| 340 | isomiR example 2 of SEQ ID NO: 117 | — |
| 341 | isomiR example 1 of SEQ ID NO: 118 | — |
| 342 | isomiR example 2 of SEQ ID NO: 118 | — |
| 343 | isomiR example 3 of SEQ ID NO: 118 | — |
| 344 | isomiR example 1 of SEQ ID NO: 119 | — |
| 345 | isomiR example 2 of SEQ ID NO: 119 | — |
| 346 | isomiR example 1 of SEQ ID NO: 121 | — |
| 347 | isomiR example 2 of SEQ ID NO: 121 | — |
| 348 | isomiR example 1 of SEQ ID NO: 122 | — |
| 349 | hsa-miR-4417 | MIMAT0018929 |
| 350 | hsa-miR-4707-5p | MIMAT0019807 |
| 351 | hsa-miR-7847-3p | MIMAT0030422 |
| 352 | hsa-miR-2861 | MIMAT0013802 |
| 353 | hsa-miR-4513 | MIMAT0019050 |
| 354 | hsa-miR-7111-5p | MIMAT0028119 |
| 355 | hsa-miR-6777-5p | MIMAT0027454 |
| 356 | hsa-miR-7113-3p | MIMAT0028124 |
| 357 | hsa-miR-4648 | MIMAT0019710 |
| 358 | hsa-miR-3184-5p | MIMAT0015064 |
| 359 | hsa-miR-4271 | MIMAT0016901 |
| 360 | hsa-miR-6791-5p | MIMAT0027482 |
| 361 | hsa-miR-642a-3p | MIMAT0020924 |
| 362 | hsa-miR-7108-5p | MIMAT0028113 |
| 363 | hsa-miR-128-1-5p | MIMAT0026477 |
| 364 | hsa-miR-5196-5p | MIMAT0021128 |
| 365 | hsa-miR-3178 | MIMAT0015055 |
| 366 | hsa-miR-3656 | MIMAT0018076 |
| 367 | hsa-miR-92a-2-5p | MIMAT0004508 |
| 368 | hsa-miR-6769b-5p | MIMAT0027620 |
| 369 | hsa-miR-4689 | MIMAT0019778 |
| 370 | hsa-miR-6076 | MIMAT0023701 |
| 371 | hsa-miR-92b-5p | MIMAT0004792 |
| 372 | hsa-miR-6774-5p | MIMAT0027448 |
| 373 | hsa-miR-486-3p | MIMAT0004762 |
| 374 | hsa-miR-6806-5p | MIMAT0027512 |
| 375 | hsa-miR-6842-5p | MIMAT0027586 |
| 376 | hsa-miR-6716-5p | MIMAT0025844 |
| 377 | hsa-miR-557 | MIMAT0003221 |
| 378 | hsa-miR-4673 | MIMAT0019755 |
| 379 | hsa-miR-4674 | MIMAT0019756 |

TABLE 1-continued

| SEQ ID NO: | Gene name | miRBase registration No. |
|---|---|---|
| 380 | hsa-miR-4442 | MIMAT0018960 |
| 381 | hsa-miR-1915-3p | MIMAT0007892 |
| 382 | hsa-miR-4687-3p | MIMAT0019775 |
| 383 | hsa-miR-92b-3p | MIMAT0003218 |
| 384 | hsa-mir-4417 | MI0016753 |
| 385 | hsa-mir-4707 | MI0017340 |
| 386 | hsa-mir-7847 | MI0025517 |
| 387 | hsa-mir-2861 | MI0013006 |
| 388 | hsa-mir-4513 | MI0016879 |
| 389 | hsa-mir-7111 | MI0022962 |
| 390 | hsa-mir-6777 | MI0022622 |
| 391 | hsa-mir-7113 | MI0022964 |
| 392 | hsa-mir-4648 | MI0017275 |
| 393 | hsa-mir-3184 | MI0014226 |
| 394 | hsa-mir-4271 | MI0015879 |
| 395 | hsa-mir-6791 | MI0022636 |
| 396 | hsa-mir-642a | MI0003657 |
| 397 | hsa-mir-7108 | MI0022959 |
| 398 | hsa-mir-128-1 | MI0000447 |
| 399 | hsa-mir-5196 | MI0018175 |
| 400 | hsa-mir-3178 | MI0014212 |
| 401 | hsa-mir-3656 | MI0016056 |
| 402 | hsa-mir-92a-2 | MI0000094 |
| 403 | hsa-mir-6769b | MI0022706 |
| 404 | hsa-mir-4689 | MI0017322 |
| 405 | hsa-mir-6076 | MI0020353 |
| 406 | hsa-mir-92b | MI0003560 |
| 407 | hsa-mir-6774 | MI0022619 |
| 408 | hsa-mir-486 | MI0002470 |
| 409 | hsa-mir-486-2 | MI0023622 |
| 410 | hsa-mir-6806 | MI0022651 |
| 411 | hsa-mir-6842 | MI0022688 |
| 412 | hsa-mir-6716 | MI0022550 |
| 413 | hsa-mir-557 | MI0003563 |
| 414 | hsa-mir-4673 | MI0017304 |
| 415 | hsa-mir-4674 | MI0017305 |
| 416 | hsa-mir-4442 | MI0016785 |
| 417 | hsa-mir-1915 | MI0008336 |
| 418 | hsa-mir-4687 | MI0017319 |
| 419 | hsa-mir-92b | MI0003560 |
| 420 | isomiR example 1 of SEQ ID NO: 349 | — |
| 421 | isomiR example 2 of SEQ ID NO: 349 | — |
| 422 | isomiR example 1 of SEQ ID NO: 350 | — |
| 423 | isomiR example 2 of SEQ ID NO: 350 | — |
| 424 | isomiR example 1 of SEQ ID NO: 352 | — |
| 425 | isomiR example 2 of SEQ ID NO: 352 | — |
| 426 | isomiR example 1 of SEQ ID NO: 353 | — |
| 427 | isomiR example 2 of SEQ ID NO: 353 | — |
| 428 | isomiR example 1 of SEQ ID NO: 357 | — |
| 429 | isomiR example 2 of SEQ ID NO: 357 | — |
| 430 | isomiR example 1 of SEQ ID NO: 359 | — |
| 431 | isomiR example 2 of SEQ ID NO: 359 | — |
| 432 | isomiR example 1 of SEQ ID NO: 361 | — |
| 433 | isomiR example 2 of SEQ ID NO: 361 | — |
| 434 | isomiR example 1 of SEQ ID NO: 363 | — |
| 435 | isomiR example 2 of SEQ ID NO: 363 | — |
| 436 | isomiR example 1 of SEQ ID NO: 364 | — |
| 437 | isomiR example 2 of SEQ ID NO: 364 | — |
| 438 | isomiR example 1 of SEQ ID NO: 365 | — |
| 439 | isomiR example 2 of SEQ ID NO: 365 | — |
| 440 | isomiR example 1 of SEQ ID NO: 366 | — |
| 441 | isomiR example 2 of SEQ ID NO: 366 | — |
| 442 | isomiR example 1 of SEQ ID NO: 367 | — |
| 443 | isomiR example 2 of SEQ ID NO: 367 | — |
| 444 | isomiR example 1 of SEQ ID NO: 369 | — |
| 445 | isomiR example 2 of SEQ ID NO: 369 | — |
| 446 | isomiR example 1 of SEQ ID NO: 371 | — |
| 447 | isomiR example 2 of SEQ ID NO: 371 | — |
| 448 | isomiR example 1 of SEQ ID NO: 373 | — |
| 449 | isomiR example 2 of SEQ ID NO: 373 | — |
| 450 | isomiR example 1 of SEQ ID NO: 376 | — |
| 451 | isomiR example 2 of SEQ ID NO: 376 | — |
| 452 | isomiR example 1 of SEQ ID NO: 378 | — |
| 453 | isomiR example 2 of SEQ ID NO: 378 | — |
| 454 | isomiR example 1 of SEQ ID NO: 379 | — |
| 455 | isomiR example 2 of SEQ ID NO: 379 | — |
| 456 | isomiR example 1 of SEQ ID NO: 380 | — |
| 457 | isomiR example 2 of SEQ ID NO: 380 | — |
| 458 | isomiR example 1 of SEQ ID NO: 381 | — |
| 459 | isomiR example 2 of SEQ ID NO: 381 | — |
| 460 | isomiR example 1 of SEQ ID NO: 382 | — |
| 461 | isomiR example 2 of SEQ ID NO: 382 | — |
| 462 | isomiR example 1 of SEQ ID NO: 383 | — |
| 463 | isomiR example 2 of SEQ ID NO: 383 | — |
| 464 | hsa-miR-1203 | MIMAT0005866 |
| 465 | hsa-miR-663b | MIMAT0005867 |
| 466 | hsa-miR-4258 | MIMAT0016879 |
| 467 | hsa-miR-4649-5p | MIMAT0019711 |
| 468 | hsa-miR-4516 | MIMAT0019053 |
| 469 | hsa-miR-3619-3p | MIMAT0019219 |
| 470 | hsa-miR-6826-5p | MIMAT0027552 |
| 471 | hsa-miR-6757-5p | MIMAT0027414 |
| 472 | hsa-miR-3131 | MIMAT0014996 |
| 473 | hsa-miR-1343-3p | MIMAT0019776 |
| 474 | hsa-mir-1203 | MI0006335 |
| 475 | hsa-mir-663b | MI0006336 |
| 476 | hsa-mir-4258 | MI0015857 |
| 477 | hsa-mir-4649 | MI0017276 |
| 478 | hsa-mir-4516 | MI0016882 |
| 479 | hsa-mir-3619 | MI0016009 |
| 480 | hsa-mir-6826 | MI0022671 |
| 481 | hsa-mir-6757 | MI0022602 |
| 482 | hsa-mir-3131 | MI0014151 |
| 483 | hsa-mir-1343 | MI0017320 |
| 484 | isomiR example 1 of SEQ ID NO: 465 | — |
| 485 | isomiR example 2 of SEQ ID NO: 465 | — |
| 486 | isomiR example 1 of SEQ ID NO: 468 | — |
| 487 | isomiR example 2 of SEQ ID NO: 468 | — |
| 488 | isomiR example 1 of SEQ ID NO: 472 | — |

TABLE 1-continued

| SEQ ID NO: | Gene name | miRBase registration No. |
|---|---|---|
| 489 | isomiR example 2 of SEQ ID NO: 472 | — |
| 490 | isomiR example 1 of SEQ ID NO: 473 | — |
| 491 | isomiR example 2 of SEQ ID NO: 473 | — |
| 492 | hsa-miR-6775-5p | MIMAT0027450 |
| 493 | hsa-miR-6813-5p | MIMAT0027526 |
| 494 | hsa-miR-3940-5p | MIMAT0019229 |
| 495 | hsa-mir-6775 | MI0022620 |
| 496 | hsa-mir-6813 | MI0022658 |
| 497 | hsa-mir-3940 | MI0016597 |
| 498 | isomiR example 1 of SEQ ID NO: 494 | — |
| 499 | isomiR example 2 of SEQ ID NO: 494 | — |

The present specification encompasses the contents described in the specifications and/or drawings of Japanese Patent Application No. 2014-113523 and No. 2014-185730 from which the present application claims priorities.

Advantageous Effect of Invention

According to the present invention, pancreatic cancer can be detected easily and in high accuracy.

For example, the presence or absence of pancreatic cancer in patients can be easily detected by using, as indicators, the determined expression levels of several miRNAs in blood, serum, and/or plasma of the patients, which can be collected with limited invasiveness.

MODES FOR CARRYING OUT THE INVENTION

Figure 1:
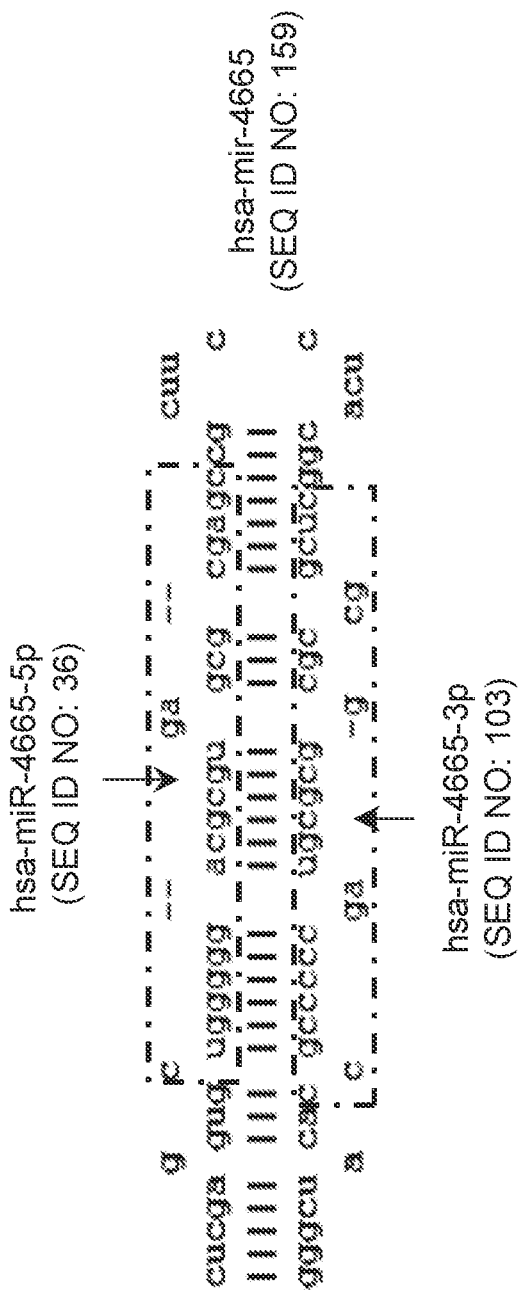
FIG. 1 This figure shows the relationship between the nucleotide sequences of hsa-miR-4665-5p represented by SEQ ID NO: 36 and hsa-miR-4665-3p represented by SEQ ID NO: 103, which are produced from a precursor hsa-mir-4665 represented by SEQ ID NO: 159.

Hereinafter, the present invention will be further described in detail.

1. Target Nucleic Acid for Pancreatic Cancer

Primary target nucleic acids, as pancreatic cancer markers, for detecting the presence and/or absence of pancreatic cancer or pancreatic cancer cells using the nucleic acid probes or the primers for the detection of pancreatic cancer defined above according to the present invention comprise at least one or more miRNAs selected from the group consisting of the following miRNAs: hsa-miR-6893-5p, hsa-miR-6075, hsa-miR-6820-5p, hsa-miR-4294, hsa-miR-6729-5p, hsa-miR-4476, hsa-miR-6836-3p, hsa-miR-6765-3p, hsa-miR-6799-5p, hsa-miR-4530, hsa-miR-7641, hsa-miR-4454, hsa-miR-615-5p, hsa-miR-8073, hsa-miR-663a, hsa-miR-4634, hsa-miR-4450, hsa-miR-4792, hsa-miR-665, hsa-miR-7975, hsa-miR-7109-5p, hsa-miR-6789-5p, hsa-miR-4497, hsa-miR-6877-5p, hsa-miR-6880-5p, hsa-miR-7977, hsa-miR-4734, hsa-miR-6821-5p, hsa-miR-8089, hsa-miR-5585-3p, hsa-miR-6085, hsa-miR-6845-5p, hsa-miR-4651, hsa-miR-4433-3p, hsa-miR-1231, hsa-miR-4665-5p, hsa-miR-7114-5p, hsa-miR-1238-5p, hsa-miR-8069, hsa-miR-4732-5p, hsa-miR-619-5p, hsa-miR-3622a-5p, hsa-miR-1260a, hsa-miR-6741-5p, hsa-miR-6781-5p, hsa-miR-6125, hsa-miR-6805-5p, hsa-miR-6132, hsa-miR-6872-3p, hsa-miR-6875-5p, hsa-miR-1908-3p, hsa-miR-4433b-3p, hsa-miR-4736, hsa-miR-5100, hsa-miR-6724-5p, hsa-miR-7107-5p, hsa-miR-6726-5p, hsa-miR-3185, hsa-miR-4638-5p, hsa-miR-1273g-3p, hsa-miR-6778-5p, hsa-miR-328-5p, hsa-miR-3679-3p, hsa-miR-1228-3p, hsa-miR-6779-5p, hsa-miR-4723-5p, hsa-miR-6850-5p, hsa-miR-760, hsa-miR-7704, hsa-miR-8072, hsa-miR-4486, hsa-miR-1913, hsa-miR-4656, hsa-miR-1260b, hsa-miR-7106-5p, hsa-miR-6889-5p, hsa-miR-6780b-5p, hsa-miR-6090, hsa-miR-4534, hsa-miR-4449, hsa-miR-5195-3p, hsa-miR-1202, hsa-miR-4467, hsa-miR-6515-3p, hsa-miR-4281, hsa-miR-4505, hsa-miR-4484, hsa-miR-6805-3p, hsa-miR-3135b, hsa-miR-3162-5p, hsa-miR-6768-5p, hsa-miR-6721-5p, hsa-miR-1227-5p, hsa-miR-6722-3p, hsa-miR-4286, hsa-miR-4746-3p, hsa-miR-6727-5p, hsa-miR-6816-5p, hsa-miR-4741, hsa-miR-4508, hsa-miR-940, hsa-miR-4327, hsa-miR-4665-3p, hsa-miR-718, hsa-miR-1203, hsa-miR-663b, hsa-miR-4258, hsa-miR-4649-5p, hsa-miR-4516, hsa-miR-3619-3p, hsa-miR-6826-5p, hsa-miR-6757-5p, hsa-miR-3131, hsa-miR-1343-3p, hsa-miR-6775-5p, hsa-miR-6813-5p and hsa-miR-3940-5p. Furthermore, at least one or more miRNAs selected from the group consisting of the following other pancreatic cancer markers that can be combined with these miRNAs, i.e., hsa-miR-125a-3p, hsa-miR-204-3p, hsa-miR-1469, hsa-miR-575, hsa-miR-150-3p, hsa-miR-423-5p, hsa-miR-564, hsa-miR-3188, hsa-miR-1246, hsa-miR-602, hsa-miR-1290, hsa-miR-16-5p, hsa-miR-451a, hsa-miR-24-3p, hsa-miR-187-5p, hsa-miR-1908-5p, hsa-miR-371a-5p and hsa-miR-550a-5p can also be preferably used as target nucleic acids. Moreover, at least one or more miRNAs selected from the group consisting of the following other pancreatic cancer markers that can be combined with these miRNAs, i.e., hsa-miR-4417, hsa-miR-4707-5p, hsa-miR-7847-3p, hsa-miR-2861, hsa-miR-4513, hsa-miR-7111-5p, hsa-miR-6777-5p, hsa-miR-7113-3p, hsa-miR-4648, hsa-miR-3184-5p, hsa-miR-4271, hsa-miR-6791-5p, hsa-miR-642a-3p, hsa-miR-7108-5p, hsa-miR-128-1-5p, hsa-miR-5196-5p, hsa-miR-3178, hsa-miR-3656, hsa-miR-92a-2-5p, hsa-miR-6769b-5p, hsa-miR-4689, hsa-miR-6076, hsa-miR-92b-5p, hsa-miR-6774-5p, hsa-miR-486-3p, hsa-miR-6806-5p, hsa-miR-6842-5p, hsa-miR-6716-5p, hsa-miR-557, hsa-miR-4673, hsa-miR-4674, hsa-miR-4442, hsa-miR-1915-3p, hsa-miR-4687-3p and hsa-miR-92b-3p can also be preferably used as target nucleic acids.

These miRNAs include, for example, a human gene comprising a nucleotide sequence represented by any of SEQ ID NOs: 1 to 122 and 349 to 383, 464 to 473, and 492 to 494 (i.e., hsa-miR-6893-5p, hsa-miR-6075, hsa-miR-6820-5p, hsa-miR-4294, hsa-miR-6729-5p, hsa-miR-4476, hsa-miR-6836-3p, hsa-miR-6765-3p, hsa-miR-6799-5p, hsa-miR-4530, hsa-miR-7641, hsa-miR-4454, hsa-miR-615-5p, hsa-miR-8073, hsa-miR-663a, hsa-miR-4634, hsa-miR-4450, hsa-miR-4792, hsa-miR-665, hsa-miR-7975, hsa-miR-7109-5p, hsa-miR-6789-5p, hsa-miR-4497, hsa-miR-6877-5p, hsa-miR-6880-5p, hsa-miR-7977, hsa-miR-4734, hsa-miR-6821-5p, hsa-miR-8089, hsa-miR-5585-3p, hsa-miR-6085, hsa-miR-6845-5p, hsa-miR-4651, hsa-miR-4433-3p, hsa-miR-1231, hsa-miR-4665-5p, hsa-miR-7114-5p, hsa-miR-1238-5p, hsa-miR-8069, hsa-miR-4732-5p, hsa-miR-619-5p, hsa-miR-3622a-5p, hsa-miR-1260a, hsa-miR-6741-5p, hsa-miR-6781-5p, hsa-miR-6125, hsa-miR-6805-5p, hsa-miR-6132, hsa-miR-6872-3p, hsa-miR-6875-5p, hsa-miR-1908-3p, hsa-miR-4433b-3p, hsa-miR-4736, hsa-miR-5100, hsa-miR-6724-5p, hsa-miR-7107-5p, hsa-miR-6726-5p, hsa-miR-3185, hsa-miR-4638-5p, hsa-miR-1273g-3p, hsa-miR-6778-5p, hsa-miR-328-5p, hsa-miR-3679-3p, hsa-miR-1228-3p, hsa-miR-6779-5p, hsa-miR-4723-5p, hsa-miR-6850-5p, hsa-miR-760, hsa-miR-7704, hsa-miR-8072, hsa-miR-4486, hsa-miR-1913, hsa-miR-4656, hsa-miR-1260b, hsa-miR-7106-5p, hsa-miR-6889-5p, hsa-miR-6780b-5p, hsa-miR-6090, hsa-miR-4534, hsa-miR-4449, hsa-miR-5195-3p, hsa-miR-1202, hsa-miR-4467, hsa-miR-6515-3p, hsa-miR-4281, hsa-miR-4505, hsa-miR-4484, hsa-miR-6805-3p, hsa-miR-3135b, hsa-miR-3162-5p, hsa-miR-6768-5p, hsa-miR-6721-5p, hsa-miR-1227-5p, hsa-miR-6722-3p, hsa-miR-4286, hsa-miR-4746-3p, hsa-miR-6727-5p, hsa-miR-6816-5p, hsa-miR-4741, hsa-miR-4508, hsa-miR-940, hsa-miR-4327, hsa-miR-4665-3p, hsa-miR-718, hsa-miR-125a-3p, hsa-miR-204-3p, hsa-miR-1469, hsa-miR-575, hsa-miR-150-3p, hsa-miR-423-5p, hsa-miR-564, hsa-miR-3188, hsa-miR-1246, hsa-miR-602, hsa-miR-1290, hsa-miR-16-5p, hsa-miR-451a, hsa-miR-24-3p, hsa-miR-187-5p, hsa-miR-1908-5p, hsa-miR-371a-5p, hsa-miR-550a-5p, hsa-miR-4417, hsa-miR-4707-5p, hsa-miR-7847-3p, hsa-miR-2861, hsa-miR-4513, hsa-miR-7111-5p, hsa-miR-6777-5p, hsa-miR-7113-3p, hsa-miR-4648, hsa-miR-3184-5p, hsa-miR-4271, hsa-miR-6791-5p, hsa-miR-642a-3p, hsa-miR-7108-5p, hsa-miR-128-1-5p, hsa-miR-5196-5p, hsa-miR-3178, hsa-miR-3656, hsa-miR-92a-2-5p, hsa-miR-6769b-5p, hsa-miR-4689, hsa-miR-6076, hsa-miR-92b-5p, hsa-miR-6774-5p, hsa-miR-486-3p, hsa-miR-6806-5p, hsa-miR-6842-5p, hsa-miR-6716-5p, hsa-miR-557, hsa-miR-4673, hsa-miR-4674, hsa-miR-4442, hsa-miR-1915-3p, hsa-miR-4687-3p, hsa-miR-92b-3p, hsa-miR-1203, hsa-miR-663b, hsa-miR-4258, hsa-miR-4649-5p, hsa-miR-4516, hsa-miR-3619-3p, hsa-miR-6826-5p, hsa-miR-6757-5p, hsa-miR-3131, hsa-miR-1343-3p, hsa-miR-6775-5p, hsa-miR-6813-5p and hsa-miR-3940-5p, respectively), a congener, a transcript thereof, or/and a variant or a derivative thereof. In this context, the gene, the congener, the transcript, the variant, and the derivative are as defined above.

The target nucleic acid is preferably a human gene comprising a nucleotide sequence represented by any of SEQ ID NOs: 1 to 499 or a transcript thereof, more preferably the transcript, i.e., a miRNA or its precursor RNA (pri-miRNA or pre-miRNA).

The first target gene is the hsa-miR-6893-5p gene, a congener thereof, a transcript thereof, or a variant or a derivative thereof. None of the previously known reports show that change in the expression of the gene or the transcript thereof can serve as a marker for pancreatic cancer.

The second target gene is the hsa-miR-6075 gene, a congener thereof, a transcript thereof, or a variant or a derivative thereof. None of the previously known reports show that change in the expression of the gene or the transcript thereof can serve as a marker for pancreatic cancer.

The third target gene is the hsa-miR-6820-5p gene, a congener thereof, a transcript thereof, or a variant or a derivative thereof. None of the previously known reports show that change in the expression of the gene or the transcript thereof can serve as a marker for pancreatic cancer.

The fourth target gene is the hsa-miR-4294 gene, a congener thereof, a transcript thereof, or a variant or a derivative thereof. None of the previously known reports show that change in the expression of the gene or the transcript thereof can serve as a marker for pancreatic cancer.

The fifth target gene is the hsa-miR-6729-5p gene, a congener thereof, a transcript thereof, or a variant or a derivative thereof. None of the previously known reports show that change in the expression of the gene or the transcript thereof can serve as a marker for pancreatic cancer.

The sixth target gene is the hsa-miR-4476 gene, a congener thereof, a transcript thereof, or a variant or a derivative thereof. None of the previously known reports show that change in the expression of the gene or the transcript thereof can serve as a marker for pancreatic cancer.

The seventh target gene is the hsa-miR-6836-3p gene, a congener thereof, a transcript thereof, or a variant or a derivative thereof. None of the previously known reports show that change in the expression of the gene or the transcript thereof can serve as a marker for pancreatic cancer.

The eighth target gene is the hsa-miR-6765-3p gene, a congener thereof, a transcript thereof, or a variant or a derivative thereof. None of the previously known reports show that change in the expression of the gene or the transcript thereof can serve as a marker for pancreatic cancer.

The ninth target gene is the hsa-miR-6799-5p gene, a congener thereof, a transcript thereof, or a variant or a derivative thereof. None of the previously known reports show that change in the expression of the gene or the transcript thereof can serve as a marker for pancreatic cancer.

The 10th target gene is the hsa-miR-4530 gene, a congener thereof, a transcript thereof, or a variant or a derivative thereof. None of the previously known reports show that change in the expression of the gene or the transcript thereof can serve as a marker for pancreatic cancer.

The 11th target gene is the hsa-miR-7641 gene, a congener thereof, a transcript thereof, or a variant or a derivative thereof. None of the previously known reports show that change in the expression of the gene or the transcript thereof can serve as a marker for pancreatic cancer.

The 12th target gene is the hsa-miR-4454 gene, a congener thereof, a transcript thereof, or a variant or a derivative thereof. None of the previously known reports show that change in the expression of the gene or the transcript thereof can serve as a marker for pancreatic cancer.

The 13th target gene is the hsa-miR-615-5p gene, a congener thereof, a transcript thereof, or a variant or a derivative thereof. None of the previously known reports show that change in the expression of the gene or the transcript thereof can serve as a marker for pancreatic cancer.

The 14th target gene is the hsa-miR-8073 gene, a congener thereof, a transcript thereof, or a variant or a derivative thereof. None of the previously known reports show that change in the expression of the gene or the transcript thereof can serve as a marker for pancreatic cancer.

The 15th target gene is the hsa-miR-663a gene, a congener thereof, a transcript thereof, or a variant or a derivative thereof. None of the previously known reports show that change in the expression of the gene or the transcript thereof can serve as a marker for pancreatic cancer.

The 16th target gene is the hsa-miR-4634 gene, a congener thereof, a transcript thereof, or a variant or a derivative thereof. None of the previously known reports show that change in the expression of the gene or the transcript thereof can serve as a marker for pancreatic cancer.

The 17th target gene is the hsa-miR-4450 gene, a congener thereof, a transcript thereof, or a variant or a derivative thereof. None of the previously known reports show that change in the expression of the gene or the transcript thereof can serve as a marker for pancreatic cancer.

The 18th target gene is the hsa-miR-4792 gene, a congener thereof, a transcript thereof, or a variant or a derivative thereof. None of the previously known reports show that change in the expression of the gene or the transcript thereof can serve as a marker for pancreatic cancer.

The 19th target gene is the hsa-miR-665 gene, a congener thereof, a transcript thereof, or a variant or a derivative thereof. None of the previously known reports show that change in the expression of the gene or the transcript thereof can serve as a marker for pancreatic cancer.

The 20th target gene is the hsa-miR-7975 gene, a congener thereof, a transcript thereof, or a variant or a derivative thereof. None of the previously known reports show that change in the expression of the gene or the transcript thereof can serve as a marker for pancreatic cancer.

The 21st target gene is the hsa-miR-7109-5p gene, a congener thereof, a transcript thereof, or a variant or a derivative thereof. None of the previously known reports show that change in the expression of the gene or the transcript thereof can serve as a marker for pancreatic cancer.

The 22nd target gene is the hsa-miR-6789-5p gene, a congener thereof, a transcript thereof, or a variant or a derivative thereof. None of the previously known reports show that change in the expression of the gene or the transcript thereof can serve as a marker for pancreatic cancer.

The 23rd target gene is the hsa-miR-4497 gene, a congener thereof, a transcript thereof, or a variant or a derivative thereof. None of the previously known reports show that change in the expression of the gene or the transcript thereof can serve as a marker for pancreatic cancer.

The 24th target gene is the hsa-miR-6877-5p gene, a congener thereof, a transcript thereof, or a variant or a derivative thereof. None of the previously known reports show that change in the expression of the gene or the transcript thereof can serve as a marker for pancreatic cancer.

The 25th target gene is the hsa-miR-6880-5p gene, a congener thereof, a transcript thereof, or a variant or a derivative thereof. None of the previously known reports show that change in the expression of the gene or the transcript thereof can serve as a marker for pancreatic cancer.

The 26th target gene is the hsa-miR-7977 gene, a congener thereof, a transcript thereof, or a variant or a derivative thereof. None of the previously known reports show that change in the expression of the gene or the transcript thereof can serve as a marker for pancreatic cancer.

The 27th target gene is the hsa-miR-4734 gene, a congener thereof, a transcript thereof, or a variant or a derivative thereof. None of the previously known reports show that change in the expression of the gene or the transcript thereof can serve as a marker for pancreatic cancer.

The 28th target gene is the hsa-miR-6821-5p gene, a congener thereof, a transcript thereof, or a variant or a derivative thereof. None of the previously known reports show that change in the expression of the gene or the transcript thereof can serve as a marker for pancreatic cancer.

The 29th target gene is the hsa-miR-8089 gene, a congener thereof, a transcript thereof, or a variant or a derivative thereof. None of the previously known reports show that change in the expression of the gene or the transcript thereof can serve as a marker for pancreatic cancer.

The 30th target gene is the hsa-miR-5585-3p gene, a congener thereof, a transcript thereof, or a variant or a derivative thereof. None of the previously known reports show that change in the expression of the gene or the transcript thereof can serve as a marker for pancreatic cancer.

The 31st target gene is the hsa-miR-6085 gene, a congener thereof, a transcript thereof, or a variant or a derivative thereof. None of the previously known reports show that change in the expression of the gene or the transcript thereof can serve as a marker for pancreatic cancer.

The 32nd target gene is the hsa-miR-6845-5p gene, a congener thereof, a transcript thereof, or a variant or a derivative thereof. None of the previously known reports show that change in the expression of the gene or the transcript thereof can serve as a marker for pancreatic cancer.

The 33rd target gene is the hsa-miR-4651 gene, a congener thereof, a transcript thereof, or a variant or a derivative thereof. None of the previously known reports show that change in the expression of the gene or the transcript thereof can serve as a marker for pancreatic cancer.

The 34th target gene is the hsa-miR-4433-3p gene, a congener thereof, a transcript thereof, or a variant or a derivative thereof. None of the previously known reports show that change in the expression of the gene or the transcript thereof can serve as a marker for pancreatic cancer.

The 35th target gene is the hsa-miR-1231 gene, a congener thereof, a transcript thereof, or a variant or a derivative thereof. None of the previously known reports show that change in the expression of the gene or the transcript thereof can serve as a marker for pancreatic cancer.

The 36th target gene is the hsa-miR-4665-5p gene, a congener thereof, a transcript thereof, or a variant or a derivative thereof. None of the previously known reports show that change in the expression of the gene or the transcript thereof can serve as a marker for pancreatic cancer.

The 37th target gene is the hsa-miR-7114-5p gene, a congener thereof, a transcript thereof, or a variant or a derivative thereof. None of the previously known reports show that change in the expression of the gene or the transcript thereof can serve as a marker for pancreatic cancer.

The 38th target gene is the hsa-miR-1238-5p gene, a congener thereof, a transcript thereof, or a variant or a derivative thereof. None of the previously known reports show that change in the expression of the gene or the transcript thereof can serve as a marker for pancreatic cancer.

The 39th target gene is the hsa-miR-8069 gene, a congener thereof, a transcript thereof, or a variant or a derivative thereof. None of the previously known reports show that change in the expression of the gene or the transcript thereof can serve as a marker for pancreatic cancer.

The 40th target gene is the hsa-miR-4732-5p gene, a congener thereof, a transcript thereof, or a variant or a derivative thereof. None of the previously known reports show that change in the expression of the gene or the transcript thereof can serve as a marker for pancreatic cancer.

The 41st target gene is the hsa-miR-619-5p gene, a congener thereof, a transcript thereof, or a variant or a derivative thereof. None of the previously known reports show that change in the expression of the gene or the transcript thereof can serve as a marker for pancreatic cancer.

The 42nd target gene is the hsa-miR-3622a-5p gene, a congener thereof, a transcript thereof, or a variant or a derivative thereof. None of the previously known reports show that change in the expression of the gene or the transcript thereof can serve as a marker for pancreatic cancer.

The 43rd target gene is the hsa-miR-1260a gene, a congener thereof, a transcript thereof, or a variant or a derivative thereof. None of the previously known reports show that change in the expression of the gene or the transcript thereof can serve as a marker for pancreatic cancer.

The 44th target gene is the hsa-miR-6741-5p gene, a congener thereof, a transcript thereof, or a variant or a derivative thereof. None of the previously known reports show that change in the expression of the gene or the transcript thereof can serve as a marker for pancreatic cancer.

The 45th target gene is the hsa-miR-6781-5p gene, a congener thereof, a transcript thereof, or a variant or a derivative thereof. None of the previously known reports show that change in the expression of the gene or the transcript thereof can serve as a marker for pancreatic cancer.

The 46th target gene is the hsa-miR-6125 gene, a congener thereof, a transcript thereof, or a variant or a derivative thereof. None of the previously known reports show that change in the expression of the gene or the transcript thereof can serve as a marker for pancreatic cancer.

The 47th target gene is the hsa-miR-6805-5p gene, a congener thereof, a transcript thereof, or a variant or a derivative thereof. None of the previously known reports show that change in the expression of the gene or the transcript thereof can serve as a marker for pancreatic cancer.

The 48th target gene is the hsa-miR-6132 gene, a congener thereof, a transcript thereof, or a variant or a derivative thereof. None of the previously known reports show that change in the expression of the gene or the transcript thereof can serve as a marker for pancreatic cancer.

The 49th target gene is the hsa-miR-6872-3p gene, a congener thereof, a transcript thereof, or a variant or a derivative thereof. None of the previously known reports show that change in the expression of the gene or the transcript thereof can serve as a marker for pancreatic cancer.

The 50th target gene is the hsa-miR-6875-5p gene, a congener thereof, a transcript thereof, or a variant or a derivative thereof. None of the previously known reports show that change in the expression of the gene or the transcript thereof can serve as a marker for pancreatic cancer.

The 51st target gene is the hsa-miR-1908-3p gene, a congener thereof, a transcript thereof, or a variant or a derivative thereof. None of the previously known reports show that change in the expression of the gene or the transcript thereof can serve as a marker for pancreatic cancer.

The 52nd target gene is the hsa-miR-4433b-3p gene, a congener thereof, a transcript thereof, or a variant or a derivative thereof. None of the previously known reports show that change in the expression of the gene or the transcript thereof can serve as a marker for pancreatic cancer.

The 53rd target gene is the hsa-miR-4736 gene, a congener thereof, a transcript thereof, or a variant or a derivative thereof. None of the previously known reports show that change in the expression of the gene or the transcript thereof can serve as a marker for pancreatic cancer.

The 54th target gene is the hsa-miR-5100 gene, a congener thereof, a transcript thereof, or a variant or a derivative thereof. None of the previously known reports show that change in the expression of the gene or the transcript thereof can serve as a marker for pancreatic cancer.

The 55th target gene is the hsa-miR-6724-5p gene, a congener thereof, a transcript thereof, or a variant or a derivative thereof. None of the previously known reports show that change in the expression of the gene or the transcript thereof can serve as a marker for pancreatic cancer.

The 56th target gene is the hsa-miR-7107-5p gene, a congener thereof, a transcript thereof, or a variant or a derivative thereof. None of the previously known reports show that change in the expression of the gene or the transcript thereof can serve as a marker for pancreatic cancer.

The 57th target gene is the hsa-miR-6726-5p gene, a congener thereof, a transcript thereof, or a variant or a derivative thereof. None of the previously known reports show that change in the expression of the gene or the transcript thereof can serve as a marker for pancreatic cancer.

The 58th target gene is the hsa-miR-3185 gene, a congener thereof, a transcript thereof, or a variant or a derivative thereof. None of the previously known reports show that change in the expression of the gene or the transcript thereof can serve as a marker for pancreatic cancer.

The 59th target gene is the hsa-miR-4638-5p gene, a congener thereof, a transcript thereof, or a variant or a derivative thereof. None of the previously known reports show that change in the expression of the gene or the transcript thereof can serve as a marker for pancreatic cancer.

The 60th target gene is the hsa-miR-1273g-3p gene, a congener thereof, a transcript thereof, or a variant or a derivative thereof. None of the previously known reports show that change in the expression of the gene or the transcript thereof can serve as a marker for pancreatic cancer.

The 61st target gene is the hsa-miR-6778-5p gene, a congener thereof, a transcript thereof, or a variant or a derivative thereof. None of the previously known reports show that change in the expression of the gene or the transcript thereof can serve as a marker for pancreatic cancer.

The 62nd target gene is the hsa-miR-328-5p gene, a congener thereof, a transcript thereof, or a variant or a derivative thereof. None of the previously known reports show that change in the expression of the gene or the transcript thereof can serve as a marker for pancreatic cancer.

The 63rd target gene is the hsa-miR-3679-3p gene, a congener thereof, a transcript thereof, or a variant or a derivative thereof. None of the previously known reports show that change in the expression of the gene or the transcript thereof can serve as a marker for pancreatic cancer.

The 64th target gene is the hsa-miR-1228-3p gene, a congener thereof, a transcript thereof, or a variant or a derivative thereof. None of the previously known reports show that change in the expression of the gene or the transcript thereof can serve as a marker for pancreatic cancer.

The 65th target gene is the hsa-miR-6779-5p gene, a congener thereof, a transcript thereof, or a variant or a derivative thereof. None of the previously known reports show that change in the expression of the gene or the transcript thereof can serve as a marker for pancreatic cancer.

The 66th target gene is the hsa-miR-4723-5p gene, a congener thereof, a transcript thereof, or a variant or a derivative thereof. None of the previously known reports show that change in the expression of the gene or the transcript thereof can serve as a marker for pancreatic cancer.

The 67th target gene is the hsa-miR-6850-5p gene, a congener thereof, a transcript thereof, or a variant or a derivative thereof. None of the previously known reports show that change in the expression of the gene or the transcript thereof can serve as a marker for pancreatic cancer.

The 68th target gene is the hsa-miR-760 gene, a congener thereof, a transcript thereof, or a variant or a derivative thereof. None of the previously known reports show that change in the expression of the gene or the transcript thereof can serve as a marker for pancreatic cancer.

The 69th target gene is the hsa-miR-7704 gene, a congener thereof, a transcript thereof, or a variant or a derivative thereof. None of the previously known reports show that change in the expression of the gene or the transcript thereof can serve as a marker for pancreatic cancer.

The 70th target gene is the hsa-miR-8072 gene, a congener thereof, a transcript thereof, or a variant or a derivative thereof. None of the previously known reports show that change in the expression of the gene or the transcript thereof can serve as a marker for pancreatic cancer.

The 71st target gene is the hsa-miR-4486 gene, a congener thereof, a transcript thereof, or a variant or a derivative thereof. None of the previously known reports show that change in the expression of the gene or the transcript thereof can serve as a marker for pancreatic cancer.

The 72nd target gene is the hsa-miR-1913 gene, a congener thereof, a transcript thereof, or a variant or a derivative thereof. None of the previously known reports show that change in the expression of the gene or the transcript thereof can serve as a marker for pancreatic cancer.

The 73rd target gene is the hsa-miR-4656 gene, a congener thereof, a transcript thereof, or a variant or a derivative thereof. None of the previously known reports show that change in the expression of the gene or the transcript thereof can serve as a marker for pancreatic cancer.

The 74th target gene is the hsa-miR-1260b gene, a congener thereof, a transcript thereof, or a variant or a derivative thereof. None of the previously known reports show that change in the expression of the gene or the transcript thereof can serve as a marker for pancreatic cancer.

The 75th target gene is the hsa-miR-7106-5p gene, a congener thereof, a transcript thereof, or a variant or a derivative thereof. None of the previously known reports show that change in the expression of the gene or the transcript thereof can serve as a marker for pancreatic cancer.

The 76th target gene is the hsa-miR-6889-5p gene, a congener thereof, a transcript thereof, or a variant or a derivative thereof. None of the previously known reports show that change in the expression of the gene or the transcript thereof can serve as a marker for pancreatic cancer.

The 77th target gene is the hsa-miR-6780b-5p gene, a congener thereof, a transcript thereof, or a variant or a derivative thereof. None of the previously known reports show that change in the expression of the gene or the transcript thereof can serve as a marker for pancreatic cancer.

The 78th target gene is the hsa-miR-6090 gene, a congener thereof, a transcript thereof, or a variant or a derivative thereof. None of the previously known reports show that change in the expression of the gene or the transcript thereof can serve as a marker for pancreatic cancer.

The 79th target gene is the hsa-miR-4534 gene, a congener thereof, a transcript thereof, or a variant or a derivative thereof. None of the previously known reports show that change in the expression of the gene or the transcript thereof can serve as a marker for pancreatic cancer.

The 80th target gene is the hsa-miR-4449 gene, a congener thereof, a transcript thereof, or a variant or a derivative thereof. None of the previously known reports show that change in the expression of the gene or the transcript thereof can serve as a marker for pancreatic cancer.

The 81st target gene is the hsa-miR-5195-3p gene, a congener thereof, a transcript thereof, or a variant or a derivative thereof. None of the previously known reports show that change in the expression of the gene or the transcript thereof can serve as a marker for pancreatic cancer.

The 82nd target gene is the hsa-miR-1202 gene, a congener thereof, a transcript thereof, or a variant or a derivative thereof. None of the previously known reports show that change in the expression of the gene or the transcript thereof can serve as a marker for pancreatic cancer.

The 83rd target gene is the hsa-miR-4467 gene, a congener thereof, a transcript thereof, or a variant or a derivative thereof. None of the previously known reports show that change in the expression of the gene or the transcript thereof can serve as a marker for pancreatic cancer.

The 84th target gene is the hsa-miR-6515-3p gene, a congener thereof, a transcript thereof, or a variant or a derivative thereof. None of the previously known reports show that change in the expression of the gene or the transcript thereof can serve as a marker for pancreatic cancer.

The 85th target gene is the hsa-miR-4281 gene, a congener thereof, a transcript thereof, or a variant or a derivative thereof. None of the previously known reports show that change in the expression of the gene or the transcript thereof can serve as a marker for pancreatic cancer.

The 86th target gene is the hsa-miR-4505 gene, a congener thereof, a transcript thereof, or a variant or a derivative thereof. None of the previously known reports show that change in the expression of the gene or the transcript thereof can serve as a marker for pancreatic cancer.

The 87th target gene is the hsa-miR-4484 gene, a congener thereof, a transcript thereof, or a variant or a derivative thereof. None of the previously known reports show that change in the expression of the gene or the transcript thereof can serve as a marker for pancreatic cancer.

The 88th target gene is the hsa-miR-6805-3p gene, a congener thereof, a transcript thereof, or a variant or a derivative thereof. None of the previously known reports show that change in the expression of the gene or the transcript thereof can serve as a marker for pancreatic cancer.

The 89th target gene is the hsa-miR-3135b gene, a congener thereof, a transcript thereof, or a variant or a derivative thereof. None of the previously known reports show that change in the expression of the gene or the transcript thereof can serve as a marker for pancreatic cancer.

The 90th target gene is the hsa-miR-3162-5p gene, a congener thereof, a transcript thereof, or a variant or a derivative thereof. None of the previously known reports show that change in the expression of the gene or the transcript thereof can serve as a marker for pancreatic cancer.

The 91st target gene is the hsa-miR-6768-5p gene, a congener thereof, a transcript thereof, or a variant or a derivative thereof. None of the previously known reports show that change in the expression of the gene or the transcript thereof can serve as a marker for pancreatic cancer.

The 92nd target gene is the hsa-miR-6721-5p gene, a congener thereof, a transcript thereof, or a variant or a derivative thereof. None of the previously known reports show that change in the expression of the gene or the transcript thereof can serve as a marker for pancreatic cancer.

The 93rd target gene is the hsa-miR-1227-5p gene, a congener thereof, a transcript thereof, or a variant or a derivative thereof. None of the previously known reports show that change in the expression of the gene or the transcript thereof can serve as a marker for pancreatic cancer.

The 94th target gene is the hsa-miR-6722-3p gene, a congener thereof, a transcript thereof, or a variant or a derivative thereof. None of the previously known reports show that change in the expression of the gene or the transcript thereof can serve as a marker for pancreatic cancer.

The 95th target gene is the hsa-miR-4286 gene, a congener thereof, a transcript thereof, or a variant or a derivative thereof. None of the previously known reports show that change in the expression of the gene or the transcript thereof can serve as a marker for pancreatic cancer.

The 96th target gene is the hsa-miR-4746-3p gene, a congener thereof, a transcript thereof, or a variant or a derivative thereof. None of the previously known reports show that change in the expression of the gene or the transcript thereof can serve as a marker for pancreatic cancer.

The 97th target gene is the hsa-miR-6727-5p gene, a congener thereof, a transcript thereof, or a variant or a derivative thereof. None of the previously known reports show that change in the expression of the gene or the transcript thereof can serve as a marker for pancreatic cancer.

The 98th target gene is the hsa-miR-6816-5p gene, a congener thereof, a transcript thereof, or a variant or a derivative thereof. None of the previously known reports show that change in the expression of the gene or the transcript thereof can serve as a marker for pancreatic cancer.

The 99th target gene is the hsa-miR-4741 gene, a congener thereof, a transcript thereof, or a variant or a derivative thereof. None of the previously known reports show that change in the expression of the gene or the transcript thereof can serve as a marker for pancreatic cancer.

The 100th target gene is the hsa-miR-4508 gene, a congener thereof, a transcript thereof, or a variant or a derivative thereof. None of the previously known reports show that change in the expression of the gene or the transcript thereof can serve as a marker for pancreatic cancer.

The 101st target gene is the hsa-miR-940 gene, a congener thereof, a transcript thereof, or a variant or a derivative thereof. None of the previously known reports show that change in the expression of the gene or the transcript thereof can serve as a marker for pancreatic cancer.

The 102nd target gene is the hsa-miR-4327 gene, a congener thereof, a transcript thereof, or a variant or a derivative thereof. None of the previously known reports show that change in the expression of the gene or the transcript thereof can serve as a marker for pancreatic cancer.

The 103rd target gene is the hsa-miR-4665-3p gene, a congener thereof, a transcript thereof, or a variant or a derivative thereof. None of the previously known reports show that change in the expression of the gene or the transcript thereof can serve as a marker for pancreatic cancer.

The 104th target gene is the hsa-miR-718 gene, a congener thereof, a transcript thereof, or a variant or a derivative thereof. None of the previously known reports show that change in the expression of the gene or the transcript thereof can serve as a marker for pancreatic cancer.

The 105th target gene is the hsa-miR-125a-3p gene, a congener thereof, a transcript thereof, or a variant or a derivative thereof. The previously known report shows that change in the expression of the gene or the transcript thereof can serve as a marker for pancreatic cancer (Patent Literature 1 described above).

The 106th target gene is the hsa-miR-204-3p gene, a congener thereof, a transcript thereof, or a variant or a derivative thereof. The previously known report shows that change in the expression of the gene or the transcript thereof can serve as a marker for pancreatic cancer (Patent Literature 2 described above).

The 107th target gene is the hsa-miR-1469 gene, a congener thereof, a transcript thereof, or a variant or a derivative thereof. The previously known report shows that change in the expression of the gene or the transcript thereof can serve as a marker for pancreatic cancer (Non-Patent Literature 4 described above).

The 108th target gene is the hsa-miR-575 gene, a congener thereof, a transcript thereof, or a variant or a derivative thereof. The previously known report shows that change in the expression of the gene or the transcript thereof can serve as a marker for pancreatic cancer (Patent Literature 3 described above).

The 109th target gene is the hsa-miR-150-3p gene, a congener thereof, a transcript thereof, or a variant or a derivative thereof. The previously known report shows that change in the expression of the gene or the transcript thereof can serve as a marker for pancreatic cancer (Non-Patent Literature 4 described above).

The 110th target gene is the hsa-miR-423-5p gene, a congener thereof, a transcript thereof, or a variant or a derivative thereof. The previously known report shows that change in the expression of the gene or the transcript thereof can serve as a marker for pancreatic cancer (Patent Literature 2 described above).

The 111th target gene is the hsa-miR-564 gene, a congener thereof, a transcript thereof, or a variant or a derivative thereof. The previously known report shows that change in the expression of the gene or the transcript thereof can serve as a marker for pancreatic cancer (Non-Patent Literature 4 described above).

The 112th target gene is the hsa-miR-3188 gene, a congener thereof, a transcript thereof, or a variant or a derivative thereof. The previously known report shows that change in the expression of the gene or the transcript thereof can serve as a marker for pancreatic cancer (Non-Patent Literature 5 described above).

The 113th target gene is the hsa-miR-1246 gene, a congener thereof, a transcript thereof, or a variant or a derivative thereof. The previously known report shows that change in the expression of the gene or the transcript thereof can serve as a marker for pancreatic cancer (Non-Patent Literature 4 described above).

The 114th target gene is the hsa-miR-602 gene, a congener thereof, a transcript thereof, or a variant or a derivative thereof. The previously known report shows that change in the expression of the gene or the transcript thereof can serve as a marker for pancreatic cancer (Non-Patent Literature 7 described above).

The 115th target gene is the hsa-miR-1290 gene, a congener thereof, a transcript thereof, or a variant or a derivative thereof. The previously known report shows that change in the expression of the gene or the transcript thereof can serve as a marker for pancreatic cancer (Non-Patent Literature 6 described above).

The 116th target gene is the hsa-miR-16-5p gene, a congener thereof, a transcript thereof, or a variant or a derivative thereof. The previously known report shows that change in the expression of the gene or the transcript thereof can serve as a marker for pancreatic cancer (Patent Literature 3 described above).

The 117th target gene is the hsa-miR-451a gene, a congener thereof, a transcript thereof, or a variant or a derivative thereof. The previously known report shows that change in the expression of the gene or the transcript thereof can serve as a marker for pancreatic cancer (Patent Literature 4 described above).

The 118th target gene is the hsa-miR-24-3p gene, a congener thereof, a transcript thereof, or a variant or a derivative thereof. The previously known report shows that change in the expression of the gene or the transcript thereof can serve as a marker for pancreatic cancer (Patent Literature 3 described above).

The 119th target gene is the hsa-miR-187-5p gene, a congener thereof, a transcript thereof, or a variant or a derivative thereof. The previously known report shows that change in the expression of the gene or the transcript thereof can serve as a marker for pancreatic cancer (Patent Literature 5 described above).

The 120th target gene is the hsa-miR-1908-5p gene, a congener thereof, a transcript thereof, or a variant or a derivative thereof. The previously known report shows that change in the expression of the gene or the transcript thereof can serve as a marker for pancreatic cancer (Non-Patent Literature 4 described above).

The 121st target gene is the hsa-miR-371a-5p gene, a congener thereof, a transcript thereof, or a variant or a derivative thereof. The previously known report shows that change in the expression of the gene or the transcript thereof can serve as a marker for pancreatic cancer (Non-Patent Literature 4 described above).

The 122nd target gene is the hsa-miR-550a-5p gene, a congener thereof, a transcript thereof, or a variant or a derivative thereof. The previously known report shows that change in the expression of the gene or the transcript thereof can serve as a marker for pancreatic cancer (Non-Patent Literature 6 described above).

The 123rd target gene is the hsa-miR-4417 gene, a congener thereof, a transcript thereof, or a variant or a derivative thereof. None of the previously known reports show that change in the expression of the gene or the transcript thereof can serve as a marker for pancreatic cancer.

The 124th target gene is the hsa-miR-4707-5p gene, a congener thereof, a transcript thereof, or a variant or a derivative thereof. None of the previously known reports show that change in the expression of the gene or the transcript thereof can serve as a marker for pancreatic cancer.

The 125th target gene is the hsa-miR-7847-3p gene, a congener thereof, a transcript thereof, or a variant or a derivative thereof. None of the previously known reports show that change in the expression of the gene or the transcript thereof can serve as a marker for pancreatic cancer.

The 126th target gene is the hsa-miR-2861 gene, a congener thereof, a transcript thereof, or a variant or a derivative thereof. None of the previously known reports show that change in the expression of the gene or the transcript thereof can serve as a marker for pancreatic cancer.

The 127th target gene is the hsa-miR-4513 gene, a congener thereof, a transcript thereof, or a variant or a derivative thereof. None of the previously known reports show that change in the expression of the gene or the transcript thereof can serve as a marker for pancreatic cancer.

The 128th target gene is the hsa-miR-7111-5p gene, a congener thereof, a transcript thereof, or a variant or a derivative thereof. None of the previously known reports show that change in the expression of the gene or the transcript thereof can serve as a marker for pancreatic cancer.

The 129th target gene is the hsa-miR-6777-5p gene, a congener thereof, a transcript thereof, or a variant or a derivative thereof. None of the previously known reports show that change in the expression of the gene or the transcript thereof can serve as a marker for pancreatic cancer.

The 130th target gene is the hsa-miR-7113-3p gene, a congener thereof, a transcript thereof, or a variant or a derivative thereof. None of the previously known reports show that change in the expression of the gene or the transcript thereof can serve as a marker for pancreatic cancer.

The 131st target gene is the hsa-miR-4648 gene, a congener thereof, a transcript thereof, or a variant or a derivative thereof. None of the previously known reports show that change in the expression of the gene or the transcript thereof can serve as a marker for pancreatic cancer.

The 132nd target gene is the hsa-miR-3184-5p gene, a congener thereof, a transcript thereof, or a variant or a derivative thereof. None of the previously known reports show that change in the expression of the gene or the transcript thereof can serve as a marker for pancreatic cancer.

The 133rd target gene is the hsa-miR-4271 gene, a congener thereof, a transcript thereof, or a variant or a derivative thereof. None of the previously known reports show that change in the expression of the gene or the transcript thereof can serve as a marker for pancreatic cancer.

The 134th target gene is the hsa-miR-6791-5p gene, a congener thereof, a transcript thereof, or a variant or a derivative thereof. None of the previously known reports show that change in the expression of the gene or the transcript thereof can serve as a marker for pancreatic cancer.

The 135th target gene is the hsa-miR-642a-3p gene, a congener thereof, a transcript thereof, or a variant or a derivative thereof. None of the previously known reports show that change in the expression of the gene or the transcript thereof can serve as a marker for pancreatic cancer.

The 136th target gene is the hsa-miR-7108-5p gene, a congener thereof, a transcript thereof, or a variant or a derivative thereof. None of the previously known reports show that change in the expression of the gene or the transcript thereof can serve as a marker for pancreatic cancer.

The 137th target gene is the hsa-miR-128-1-5p gene, a congener thereof, a transcript thereof, or a variant or a derivative thereof. None of the previously known reports show that change in the expression of the gene or the transcript thereof can serve as a marker for pancreatic cancer.

The 138th target gene is the hsa-miR-5196-5p gene, a congener thereof, a transcript thereof, or a variant or a derivative thereof. None of the previously known reports show that change in the expression of the gene or the transcript thereof can serve as a marker for pancreatic cancer.

The 139th target gene is the hsa-miR-3178 gene, a congener thereof, a transcript thereof, or a variant or a derivative thereof. None of the previously known reports show that change in the expression of the gene or the transcript thereof can serve as a marker for pancreatic cancer.

The 140th target gene is the hsa-miR-3656 gene, a congener thereof, a transcript thereof, or a variant or a derivative thereof. None of the previously known reports show that change in the expression of the gene or the transcript thereof can serve as a marker for pancreatic cancer.

The 141st target gene is the hsa-miR-92a-2-5p gene, a congener thereof, a transcript thereof, or a variant or a derivative thereof. None of the previously known reports show that change in the expression of the gene or the transcript thereof can serve as a marker for pancreatic cancer.

The 142nd target gene is the hsa-miR-6769b-5p gene, a congener thereof, a transcript thereof, or a variant or a derivative thereof. None of the previously known reports show that change in the expression of the gene or the transcript thereof can serve as a marker for pancreatic cancer.

The 143rd target gene is the hsa-miR-4689 gene, a congener thereof, a transcript thereof, or a variant or a derivative thereof. None of the previously known reports show that change in the expression of the gene or the transcript thereof can serve as a marker for pancreatic cancer.

The 144th target gene is the hsa-miR-6076 gene, a congener thereof, a transcript thereof, or a variant or a derivative thereof. None of the previously known reports show that change in the expression of the gene or the transcript thereof can serve as a marker for pancreatic cancer.

The 145th target gene is the hsa-miR-92b-5p gene, a congener thereof, a transcript thereof, or a variant or a derivative thereof. None of the previously known reports show that change in the expression of the gene or the transcript thereof can serve as a marker for pancreatic cancer.

The 146th target gene is the hsa-miR-6774-5p gene, a congener thereof, a transcript thereof, or a variant or a derivative thereof. None of the previously known reports show that change in the expression of the gene or the transcript thereof can serve as a marker for pancreatic cancer.

The 147th target gene is the hsa-miR-486-3p gene, a congener thereof, a transcript thereof, or a variant or a derivative thereof. None of the previously known reports show that change in the expression of the gene or the transcript thereof can serve as a marker for pancreatic cancer.

The 148th target gene is the hsa-miR-6806-5p gene, a congener thereof, a transcript thereof, or a variant or a derivative thereof. None of the previously known reports show that change in the expression of the gene or the transcript thereof can serve as a marker for pancreatic cancer.

The 149th target gene is the hsa-miR-6842-5p gene, a congener thereof, a transcript thereof, or a variant or a derivative thereof. None of the previously known reports show that change in the expression of the gene or the transcript thereof can serve as a marker for pancreatic cancer.

The 150th target gene is the hsa-miR-6716-5p gene, a congener thereof, a transcript thereof, or a variant or a derivative thereof. None of the previously known reports show that change in the expression of the gene or the transcript thereof can serve as a marker for pancreatic cancer.

The 151st target gene is the hsa-miR-557 gene, a congener thereof, a transcript thereof, or a variant or a derivative thereof. None of the previously known reports show that change in the expression of the gene or the transcript thereof can serve as a marker for pancreatic cancer.

The 152nd target gene is the hsa-miR-4673 gene, a congener thereof, a transcript thereof, or a variant or a derivative thereof. None of the previously known reports show that change in the expression of the gene or the transcript thereof can serve as a marker for pancreatic cancer.

The 153rd target gene is the hsa-miR-4674 gene, a congener thereof, a transcript thereof, or a variant or a derivative thereof. None of the previously known reports show that change in the expression of the gene or the transcript thereof can serve as a marker for pancreatic cancer.

The 154th target gene is the hsa-miR-4442 gene, a congener thereof, a transcript thereof, or a variant or a derivative thereof. None of the previously known reports show that change in the expression of the gene or the transcript thereof can serve as a marker for pancreatic cancer.

The 155th target gene is the hsa-miR-1915-3p gene, a congener thereof, a transcript thereof, or a variant or a derivative thereof. None of the previously known reports show that change in the expression of the gene or the transcript thereof can serve as a marker for pancreatic cancer.

The 156th target gene is the hsa-miR-4687-3p gene, a congener thereof, a transcript thereof, or a variant or a derivative thereof. None of the previously known reports show that change in the expression of the gene or the transcript thereof can serve as a marker for pancreatic cancer.

The 157th target gene is the hsa-miR-92b-3p gene, a congener thereof, a transcript thereof, or a variant or a derivative thereof. None of the previously known reports show that change in the expression of the gene or the transcript thereof can serve as a marker for pancreatic cancer.

The 158th target gene is the hsa-miR-1203 gene, a congener thereof, a transcript thereof, or a variant or a derivative thereof. None of the previously known reports show that change in the expression of the gene or the transcript thereof can serve as a marker for pancreatic cancer.

The 159th target gene is the hsa-mir-663b gene, a congener thereof, a transcript thereof, or a variant or a derivative thereof. None of the previously known reports show that change in the expression of the gene or the transcript thereof can serve as a marker for pancreatic cancer.

The 160th target gene is the hsa-mir-4258 gene, a congener thereof, a transcript thereof, or a variant or a derivative thereof. None of the previously known reports show that change in the expression of the gene or the transcript thereof can serve as a marker for pancreatic cancer.

The 161st target gene is the hsa-mir-4649 gene, a congener thereof, a transcript thereof, or a variant or a derivative thereof. None of the previously known reports show that change in the expression of the gene or the transcript thereof can serve as a marker for pancreatic cancer.

The 162nd target gene is the hsa-mir-4516 gene, a congener thereof, a transcript thereof, or a variant or a derivative thereof. None of the previously known reports show that change in the expression of the gene or the transcript thereof can serve as a marker for pancreatic cancer.

The 163rd target gene is the hsa-mir-3619 gene, a congener thereof, a transcript thereof, or a variant or a derivative thereof. None of the previously known reports show that change in the expression of the gene or the transcript thereof can serve as a marker for pancreatic cancer.

The 164th target gene is the hsa-mir-6826 gene, a congener thereof, a transcript thereof, or a variant or a derivative thereof. None of the previously known reports show that change in the expression of the gene or the transcript thereof can serve as a marker for pancreatic cancer.

The 165th target gene is the hsa-mir-6757 gene, a congener thereof, a transcript thereof, or a variant or a derivative thereof. None of the previously known reports show that change in the expression of the gene or the transcript thereof can serve as a marker for pancreatic cancer.

The 166th target gene is the hsa-mir-3131 gene, a congener thereof, a transcript thereof, or a variant or a derivative thereof. None of the previously known reports show that change in the expression of the gene or the transcript thereof can serve as a marker for pancreatic cancer.

The 167th target gene is the hsa-mir-1343 gene, a congener thereof, a transcript thereof, or a variant or a derivative thereof. None of the previously known reports show that change in the expression of the gene or the transcript thereof can serve as a marker for pancreatic cancer.

The 168th target gene is the hsa-miR-6775-5p gene, a congener thereof, a transcript thereof, or a variant or a derivative thereof. None of the previously known reports show that change in the expression of the gene or the transcript thereof can serve as a marker for pancreatic cancer.

The 169th target gene is the hsa-miR-6813-5p gene, a congener thereof, a transcript thereof, or a variant or a derivative thereof. None of the previously known reports show that change in the expression of the gene or the transcript thereof can serve as a marker for pancreatic cancer.

The 170th target gene is the hsa-miR-3940-5p gene, a congener thereof, a transcript thereof, or a variant or a derivative thereof. None of the previously known reports show that change in the expression of the gene or the transcript thereof can serve as a marker for pancreatic cancer.

2. Nucleic Acid Probe or Primer for Detection of Pancreatic Cancer

In the present invention, a nucleic acid capable of specifically binding to any of the target nucleic acids as the pancreatic cancer markers described above can be used as a nucleic acid, for example, a nucleic acid probe or a primer, for the detection or diagnosis of pancreatic cancer.

In the present invention, the nucleic acid probes or the primers that can be used for detecting pancreatic cancer or for diagnosing pancreatic cancer enable qualitative and/or quantitative measurement of the presence, expression level, or existing amount (abundance) of: any of human-derived hsa-miR-6893-5p, hsa-miR-6075, hsa-miR-6820-5p, hsa-miR-4294, hsa-miR-6729-5p, hsa-miR-4476, hsa-miR-6836-3p, hsa-miR-6765-3p, hsa-miR-6799-5p, hsa-miR-4530, hsa-miR-7641, hsa-miR-4454, hsa-miR-615-5p, hsa-miR-8073, hsa-miR-663a, hsa-miR-4634, hsa-miR-4450, hsa-miR-4792, hsa-miR-665, hsa-miR-7975, hsa-miR-7109-5p, hsa-miR-6789-5p, hsa-miR-4497, hsa-miR-6877-5p, hsa-miR-6880-5p, hsa-miR-7977, hsa-miR-4734, hsa-miR-6821-5p, hsa-miR-8089, hsa-miR-5585-3p, hsa-miR-6085, hsa-miR-6845-5p, hsa-miR-4651, hsa-miR-4433-3p, hsa-miR-1231, hsa-miR-4665-5p, hsa-miR-7114-5p, hsa-miR-1238-5p, hsa-miR-8069, hsa-miR-4732-5p, hsa-miR-619-5p, hsa-miR-3622a-5p, hsa-miR-1260a, hsa-miR-6741-5p, hsa-miR-6781-5p, hsa-miR-6125, hsa-miR-6805-5p, hsa-miR-6132, hsa-miR-6872-3p, hsa-miR-6875-5p, hsa-miR-1908-3p, hsa-miR-4433b-3p, hsa-miR-4736, hsa-miR-5100, hsa-miR-6724-5p, hsa-miR-7107-5p, hsa-miR-6726-5p, hsa-miR-3185, hsa-miR-4638-5p, hsa-miR-1273g-3p, hsa-miR-6778-5p, hsa-miR-328-5p, hsa-miR-3679-3p, hsa-miR-1228-3p, hsa-miR-6779-5p, hsa-miR-4723-5p, hsa-miR-6850-5p, hsa-miR-760, hsa-miR-7704, hsa-miR-8072, hsa-miR-4486, hsa-miR-1913, hsa-miR-4656, hsa-miR-1260b, hsa-miR-7106-5p, hsa-miR-6889-5p, hsa-miR-6780b-5p, hsa-miR-6090, hsa-miR-4534, hsa-miR-4449, hsa-miR-5195-3p, hsa-miR-1202, hsa-miR-4467, hsa-miR-6515-3p, hsa-miR-4281, hsa-miR-4505, hsa-miR-4484, hsa-miR-6805-3p, hsa-miR-3135b, hsa-miR-3162-5p, hsa-miR-6768-5p, hsa-miR-6721-5p, hsa-miR-1227-5p, hsa-miR-6722-3p, hsa-miR-4286, hsa-miR-4746-3p, hsa-miR-6727-5p, hsa-miR-6816-5p, hsa-miR-4741, hsa-miR-4508, hsa-miR-940, hsa-miR-4327, hsa-miR-4665-3p, hsa-miR-718, hsa-miR-1203, hsa-miR-663b, hsa-miR-4258, hsa-miR-4649-5p, hsa-miR-4516, hsa-miR-3619-3p, hsa-miR-6826-5p, hsa-miR-6757-5p, hsa-miR-3131, hsa-miR-1343-3p, hsa-miR-6775-5p, hsa-miR-6813-5p, and hsa-miR-3940-5p, as target nucleic acids for pancreatic cancer, or a combination thereof, and hsa-miR-125a-3p, hsa-miR-204-3p, hsa-miR-1469, hsa-miR-575, hsa-miR-150-3p, hsa-miR-423-5p, hsa-miR-564, hsa-miR-3188, hsa-miR-1246, hsa-miR-602, hsa-miR-1290, hsa-miR-16-5p, hsa-miR-451a, hsa-miR-24-3p, hsa-miR-187-5p, hsa-miR-1908-5p, hsa-miR-371a-5p, and hsa-miR-550a-5p, that can be further optionally combined therewith or a combination thereof; and hsa-miR-4417, hsa-miR-4707-5p, hsa-miR-7847-3p, hsa-miR-2861, hsa-miR-4513, hsa-miR-7111-5p, hsa-miR-6777-5p, hsa-miR-7113-3p, hsa-miR-4648, hsa-miR-3184-5p, hsa-miR-4271, hsa-miR-6791-5p, hsa-miR-642a-3p, hsa-miR-7108-5p, hsa-miR-128-1-5p, hsa-miR-5196-5p, hsa-miR-3178, hsa-miR-3656, hsa-miR-92a-2-5p, hsa-miR-6769b-5p, hsa-miR-4689, hsa-miR-6076, hsa-miR-92b-5p, hsa-miR-6774-5p, hsa-miR-486-5p, hsa-miR-6806-5p, hsa-miR-6842-5p, hsa-miR-6716-5p, hsa-miR-557, hsa-miR-4673, hsa-miR-4674, hsa-miR-4442, hsa-miR-1915-3p, hsa-miR-4687-3p and hsa-miR-92b-3p, that can be further optionally combined therewith or a combination thereof; congeners thereof: transcripts thereof: or variants or derivatives thereof.

The expression levels of the target nucleic acids described above are increased or decreased (hereinafter, referred to as "increased/decreased") depending on the types of the target nucleic acids in subjects having pancreatic cancer as compared with healthy subjects. Hence, the composition of the present invention can be effectively used for measuring expression levels of the target nucleic acids in body fluids from subjects (e.g., humans) suspected of having pancreatic cancer and body fluids from healthy subjects and thereby detecting pancreatic cancer through the comparison thereof. The composition of the invention can also be effectively used for measuring expression levels of the target nucleic acids in body fluids from subjects (e.g., humans) suspected of having pancreatic cancer and body fluids from colorectal cancer patients, stomach cancer patients, esophageal cancer patients, liver cancer patients, and benign pancreaticobiliary disease patients and thereby specifically detecting pancreatic cancer while distinguished from other cancers, benign diseases or the like, through the comparison thereof.

The nucleic acid probe or the primer that can be used in the present invention is a nucleic acid probe capable of specifically binding to a polynucleotide consisting of a nucleotide sequence represented by at least one of SEQ ID NOs: 1 to 104,464 to 473, and 492 to 494, or a primer for amplifying a polynucleotide consisting of a nucleotide sequence represented by at least one of SEQ ID NOs: 1 to 104, 464 to 473, and 492 to 494.

The nucleic acid probe or the primer that can be used in the present invention may further comprise a nucleic acid probe capable of specifically binding to a polynucleotide consisting of a nucleotide sequence represented by at least one of SEQ ID NOs: 105 to 122, or a primer for amplifying a polynucleotide consisting of a nucleotide sequence represented by at least one of SEQ ID NOs: 105 to 122.

The nucleic acid probe or the primer that can be used in the present invention may further comprise a nucleic acid probe capable of specifically binding to a polynucleotide consisting of a nucleotide sequence represented by at least one of SEQ ID NOs: 349 to 383, or a primer for amplifying a polynucleotide consisting of a nucleotide sequence represented by at least one of SEQ ID NOs: 349 to 383.

Specifically, these nucleic acid probes or primers comprise a combination of one or more polynucleotides selected from: a group of polynucleotides comprising nucleotide sequences represented by any of SEQ ID NOs: 1 to 122, 349 to 383, 464 to 473, and 492 to 494 or nucleotide sequences derived from the nucleotide sequences by the replacement of u with t, and a group of complementary polynucleotides thereof; a group of polynucleotides respectively hybridizing under stringent conditions (mentioned later) to DNAs consisting of nucleotide sequences complementary to these nucleotide sequences, and a group of complementary polynucleotides thereof; and a group of polynucleotides comprising 15 or more, preferably 17 or more consecutive nucleotides and being from the nucleotide sequences of these polynucleotide groups. These polynucleotides can be used as nucleic acid probes and primers for detecting the pancreatic cancer markers as target nucleic acids.

More specifically, examples of the nucleic acid probes or the primers that can be used in the present invention include one or more polynucleotides selected from the group consisting of the following polynucleotides (a) to (e):

(a) a polynucleotide consisting of a nucleotide sequence represented by any of SEQ ID NOs: 1 to 104, 464 to 473, and 492 to 494 or a nucleotide sequence derived from the nucleotide sequence by the replacement of u with t, a variant thereof, a derivative thereof, or a fragment thereof comprising 15 or more consecutive nucleotides;

(b) a polynucleotide comprising a nucleotide sequence represented by any of SEQ ID NOs: 1 to 104, 464 to 473, and 492 to 494:

(c) a polynucleotide consisting of a nucleotide sequence complementary to a nucleotide sequence represented by any of SEQ ID NOs: 1 to 104, 464 to 473, and 492 to 494 or a nucleotide sequence derived from the nucleotide sequence by the replacement of u with t, a variant thereof, a derivative thereof, or a fragment thereof comprising 15 or more consecutive nucleotides;

(d) a polynucleotide comprising a nucleotide sequence complementary to a nucleotide sequence represented by any of SEQ ID NOs: 1 to 104, 464 to 473, and 492 to 494 or a nucleotide sequence derived from the nucleotide sequence by the replacement of u with t; and (e) a polynucleotide hybridizing under stringent conditions to any of the polynucleotides (a) to (d).

In addition to at least one or more polynucleotides selected from any of the polynucleotides (a) to (e), the nucleic acid probes or the primers that can be used in the present invention may further comprise any of the following polynucleotides (f) to (j):

(f) a polynucleotide consisting of a nucleotide sequence represented by any of SEQ ID NOs: 105 to 122 or a nucleotide sequence derived from the nucleotide sequence by the replacement of u with t, a variant thereof, a derivative thereof, or a fragment thereof comprising 15 or more consecutive nucleotides;

(g) a polynucleotide comprising a nucleotide sequence represented by any of SEQ ID NOs: 105 to 122;

(h) a polynucleotide consisting of a nucleotide sequence complementary to a nucleotide sequence represented by any of SEQ ID NOs: 105 to 122 or a nucleotide sequence derived from the nucleotide sequence by the replacement of u with t, a variant thereof, a derivative thereof, or a fragment thereof comprising 15 or more consecutive nucleotides;

(i) a polynucleotide comprising a nucleotide sequence complementary to a nucleotide sequence represented by any of SEQ ID NOs: 105 to 122 or a nucleotide sequence derived from the nucleotide sequence by the replacement of u with t; and (j) a polynucleotide hybridizing under stringent conditions to any of the polynucleotides (f) to (i).

In addition to at least one or more polynucleotides selected from any of the polynucleotides (a) to (j), the nucleic acid probes or the primers that can be used in the present invention may further comprise any of the following polynucleotides (k) to (o):

(k) a polynucleotide consisting of a nucleotide sequence represented by any of SEQ ID NOs: 349 to 383 or a nucleotide sequence derived from the nucleotide sequence by the replacement of u with t, a variant thereof, a derivative thereof, or a fragment thereof comprising 15 or more consecutive nucleotides:

(l) a polynucleotide comprising a nucleotide sequence represented by any of SEQ ID NOs: 349 to 383;

(m) a polynucleotide consisting of a nucleotide sequence complementary to a nucleotide sequence represented by any of SEQ ID NOs: 349 to 383 or a nucleotide sequence derived from the nucleotide sequence by the replacement of u with t, a variant thereof, a derivative thereof, or a fragment thereof comprising 15 or more consecutive nucleotides;

(n) a polynucleotide comprising a nucleotide sequence complementary to a nucleotide sequence represented by any of SEQ ID NOs: 349 to 383 or a nucleotide sequence derived from the nucleotide sequence by the replacement of u with t; and (o) a polynucleotide hybridizing under stringent conditions to any of the polynucleotides (k) to (n).

For the above-mentioned polynucleotides, the "fragment thereof comprising 15 or more consecutive nucleotides" can comprise, but is not limited to, the number of nucleotides in the range of, for example, from 15 consecutive nucleotides to less than the total number of nucleotides of the sequence, from 17 consecutive nucleotides to less than the total number of nucleotides of the sequence, from 19 consecutive nucleotides to less than the total number of nucleotides of the sequence, or the like, and is from the nucleotide sequence of each polynucleotide.

These polynucleotides or fragments thereof used in the present invention may each be DNA or may each be RNA The polynucleotides that can be used in the present invention can be prepared by use of a general technique such as a DNA recombination technique, a PCR method, or a method using an automatic DNA/RNA synthesizer.

The DNA recombination technique and the PCR method may employ techniques described in, for example, Ausubel et al., Current Protocols in Molecular Biology, John Willey & Sons, US (1993); and Sambrook et al., Molecular Cloning—A Laboratory Manual, Cold Spring Harbor Laboratory Press, US (1989).

The human-derived hsa-miR-6893-5p, hsa-miR-6075, hsa-miR-6820-5p, hsa-miR-4294, hsa-miR-6729-5p, hsa-miR-4476, hsa-miR-6836-3p, hsa-miR-6765-3p, hsa-miR-6799-5p, hsa-miR-4530, hsa-miR-7641, hsa-miR-4454, hsa-miR-615-5p, hsa-miR-8073, hsa-miR-663a, hsa-miR-4634, hsa-miR-4450, hsa-miR-4792, hsa-miR-665, hsa-miR-7975, hsa-miR-7109-5p, hsa-miR-6789-5p, hsa-miR-4497, hsa-miR-6877-5p, hsa-miR-6880-5p, hsa-miR-7977, hsa-miR-4734, hsa-miR-6821-5p, hsa-miR-8089, hsa-miR-5585-3p, hsa-miR-6085, hsa-miR-6845-5p, hsa-miR-4651, hsa-miR-4433-3p, hsa-miR-1231, hsa-miR-4665-5p, hsa-miR-7114-5p, hsa-miR-1238-5p, hsa-miR-8069, hsa-miR-4732-5p, hsa-miR-619-5p, hsa-miR-3622a-5p, hsa-miR-1260a, hsa-miR-6741-5p, hsa-miR-6781-5p, hsa-miR-6125, hsa-miR-6805-5p, hsa-miR-6132, hsa-miR-6872-3p, hsa-miR-6875-5p, hsa-miR-1908-3p, hsa-miR-4433b-3p, hsa-miR-4736, hsa-miR-5100, hsa-miR-6724-5p, hsa-miR-7107-5p, hsa-miR-6726-5p, hsa-miR-3185, hsa-miR-4638-5p, hsa-miR-1273g-3p, hsa-miR-6778-5p, hsa-miR-328-5p, hsa-miR-3679-3p, hsa-miR-1228-3p, hsa-miR-6779-5p, hsa-miR-4723-5p, hsa-miR-6850-5p, hsa-miR-760, hsa-miR-7704, hsa-miR-8072, hsa-miR-4486, hsa-miR-1913, hsa-miR-4656, hsa-miR-1260b, hsa-miR-7106-5p, hsa-miR-6889-5p, hsa-miR-6780b-5p, hsa-miR-6090, hsa-miR-4534, hsa-miR-4449, hsa-miR-5195-3p, hsa-miR-1202, hsa-miR-4467, hsa-miR-6515-3p, hsa-miR-4281, hsa-miR-4505, hsa-miR-4484, hsa-miR-6805-3p, hsa-miR-3135b, hsa-miR-3162-5p, hsa-miR-6768-5p, hsa-miR-6721-5p, hsa-miR-1227-5p, hsa-miR-6722-3p, hsa-miR-4286, hsa-miR-4746-3p, hsa-miR-6727-5p, hsa-miR-6816-5p, hsa-miR-4741, hsa-miR-4508, hsa-miR-940, hsa-miR-4327, hsa-miR-4665-3p, hsa-miR-718, hsa-miR-125a-3p, hsa-miR-204-3p, hsa-miR-1469, hsa-miR-575, hsa-miR-150-3p, hsa-miR-423-5p, hsa-miR-564, hsa-miR-3188, hsa-miR-1246, hsa-miR-602, hsa-miR-1290, hsa-miR-16-5p, hsa-miR-451a, hsa-miR-24-3p, hsa-miR-187-5p, hsa-miR-1908-5p, hsa-miR-371a-5p, hsa-miR-550a-5p, hsa-miR-4417, hsa-miR-4707-5p, hsa-miR-7847-3p, hsa-miR-2861, hsa-miR-4513, hsa-miR-7111-5p, hsa-miR-6777-5p, hsa-miR-7113-3p, hsa-miR-4648, hsa-miR-3184-5p, hsa-miR-4271, hsa-miR-6791-5p, hsa-miR-642a-3p, hsa-miR-7108-5p, hsa-miR-128-1-5p, hsa-miR-5196-5p, hsa-miR-3178, hsa-miR-3656, hsa-miR-92a-2-5p, hsa-miR-6769b-5p, hsa-miR-4689, hsa-miR-6076, hsa-miR-92b-5p, hsa-miR-6774-5p, hsa-miR-486-3p, hsa-miR-6806-5p, hsa-miR-6842-5p, hsa-miR-6716-5p, hsa-miR-557, hsa-miR-4673, hsa-miR-4674, hsa-miR-4442, hsa-miR-1915-3p, hsa-miR-4687-3p, hsa-miR-92b-3p, hsa-miR-1203, hsa-miR-663b, hsa-miR-4258, hsa-miR-4649-5p, hsa-miR-4516, hsa-miR-3619-3p, hsa-miR-6826-5p, hsa-miR-6757-5p, hsa-miR-3131, hsa-miR-1343-3p, hsa-miR-6775-5p, hsa-miR-6813-5p and hsa-miR-3940-5p represented by SEQ ID NOs: 1 to 122, 349 to 383, 464 to 473, and 492 to 494 are known in the art, and their obtainment methods are also known as mentioned above. Therefore, each polynucleotide that can be used as a nucleic acid probe or a primer in the present invention can be prepared by cloning the gene.

Such nucleic acid probes or primers can be chemically synthesized using an automatic DNA synthesizer. In general, the phosphoramidite method is used in this synthesis, and single-stranded DNA up to approximately 100 nucleotides can be automatically synthesized by this method. The automatic DNA synthesizer is commercially available from, for example. Polygen GmbH, ABI, or Applied Biosystems, Inc.

Alternatively, the polynucleotides of the present invention can also be prepared by cDNA cloning methods. The cDNA cloning technique may employ, for example, microRNA Cloning Kit Wako.

In this context, the sequences of the nucleic acid probes and the primers for detecting the polynucleotide consisting of a nucleotide sequence represented by any of SEQ ID NOs: 1 to 122, 349 to 383, 464 to 473, and 492 to 494 do not exist as miRNAs or precursors thereof in the living body or in vivo. For example, the nucleotide sequences represented by SEQ ID NO: 36 and SEQ ID NO: 103 are produced from the precursor represented by SEQ ID NO: 159. This precursor has a hairpin-like structure as shown in FIG. 1, and the nucleotide sequences represented by SEQ ID NO: 36 and SEQ ID NO: 103 have mismatch sequences with each other. As such, a nucleotide sequence completely complementary to the nucleotide sequence represented by SEQ ID NO: 36 or SEQ ID NO; 103 does not naturally occur in vivo. Therefore, the nucleic acid probes and the primers for detecting the nucleotide sequence represented by any of SEQ ID NOs: 1 to 122, 349 to 383, 464 to 473, and 492 to 494 have artificial nucleotide sequences that do not exist in the living body or in vivo.

3. Kit or Device for Detection of Pancreatic Cancer

The present invention also provides a kit or a device for the detection of pancreatic cancer, comprising one or more polynucleotides (which may include a variant, a fragment, or a derivative thereof) that can be used as nucleic acid probes or primers in the present invention for measuring target nucleic acids as pancreatic cancer markers.

The target nucleic acids as pancreatic cancer markers according to the present invention are at least one nucleic acid selected from the following group A:
Group A:
miR-6893-5p, miR-6075, miR-6820-5p, miR-4294, miR-6729-5p, miR-4476, miR-6836-3p, miR-6765-3p, miR-6799-5p, miR-4530, miR-7641, miR-4454, miR-615-5p, miR-8073, miR-663a, miR-4634, miR-4450, miR-4792, miR-665, miR-7975, miR-7109-5p, miR-6789-5p, miR-4497, miR-6877-5p, miR-6880-5p, miR-7977, miR-4734, miR-6821-5p, miR-8089, miR-5585-3p, miR-6085, miR-6845-5p, miR-4651, miR-4433-3p, miR-1231, miR-4665-5p, miR-7114-5p, miR-1238-5p, miR-8069, miR-4732-5p, miR-619-5p, miR-3622a-5p, miR-1260a, miR-6741-5p, miR-6781-5p, miR-6125, miR-6805-5p, miR-6132, miR-6872-3p, miR-6875-5p, miR-1908-3p, miR-4433b-3p, miR-4736, miR-5100, miR-6724-5p, miR-7107-5p, miR-6726-5p, miR-3185, miR-4638-5p, miR-1273g-3p, miR-6778-5p, miR-328-5p, miR-3679-3p, miR-1228-3p, miR-6779-5p, miR-4723-5p, miR-6850-5p, miR-760, miR-7704, miR-8072, miR-4486, miR-1913, miR-4656, miR-1260b, miR-7106-5p, miR-6889-5p, miR-6780b-5p, miR-6090, miR-4534, miR-4449, miR-5195-3p, miR-1202, miR-4467, miR-6515-3p, miR-4281, miR-4505, miR-4484, miR-6805-3p, miR-3135b, miR-3162-5p, miR-6768-5p, miR-6721-5p, miR-1227-5p, miR-6722-3p, miR-4286, miR-4746-3p, miR-6727-5p, miR-6816-5p, miR-4741, miR-4508, miR-940, miR-4327, miR-4665-3p, miR-718, miR-1203, miR-663b, miR-4258, miR-4649-5p, miR-4516, miR-3619-3p, miR-6826-5p, miR-6757-5p, miR-3131, miR-1343-3p, miR-6775-5p, miR-6813-5p, and miR-3940-5p.

Additional target nucleic acids that may be optionally used in the measurement are at least one nucleic acid selected from the following group B:
Group B:
miR-125a-3p, miR-204-3p, miR-1469, miR-575, miR-150-3p, miR-423-5p, miR-564, miR-3188, miR-1246, miR-602, miR-1290, miR-16-5p, miR-451a, miR-24-3p, miR-187-5p, miR-1908-5p, miR-371a-5p, and miR-550a-5p.

Additional target nucleic acids that may be further optionally used in the measurement are at least one nucleic acid selected from the following group C:
Group C:
miR-4417, miR-4707-5p, miR-7847-3p, miR-2861, miR-4513, miR-7111-5p, miR-6777-5p, miR-7113-3p, miR-4648, miR-3184-5p, miR-4271, miR-6791-5p, miR-642a-3p, miR-7108-5p, miR-128-1-5p, miR-5196-5p, miR-3178, miR-3656, miR-92a-2-5p, miR-6769b-5p, miR-4689, miR-6076, miR-92b-5p, miR-6774-5p, miR-486-3p, miR-6806-5p, miR-6842-5p, miR-6716-5p, miR-557, miR-4673, miR-4674, miR-4442, miR-1915-3p, miR-4687-3p, and miR-92b-3p.

The kit or the device of the present invention comprises one or more nucleic acids capable of specifically binding to any of the target nucleic acids as the pancreatic cancer markers described above, preferably one or more polynucleotides selected from the polynucleotides described in the preceding Section 2, or variants thereof.

Specifically, the kit or the device of the present invention can comprise at least one or more polynucleotides comprising (or consisting of) a nucleotide sequence represented by any of SEQ ID NOs: 1 to 104, 464 to 473, and 492 to 494 or a nucleotide sequence derived from the nucleotide sequence by the replacement of u with t, polynucleotide(s) comprising (or consisting of) a complementary sequence thereof, a polynucleotide(s) hybridizing under stringent conditions to any of these polynucleotides, or a variant(s) or a fragment(s) comprising 15 or more consecutive nucleotides of any of these polynucleotide sequences.

The kit or the device of the present invention can further comprise one or more polynucleotides comprising (or consisting of) a nucleotide sequence represented by any of SEQ ID NOs: 105 to 122 or a nucleotide sequence derived from the nucleotide sequence by the replacement of u with t, a polynucleotide(s) comprising (or consisting of) a complementary sequence thereof, a polynucleotide(s) hybridizing under stringent conditions to any of these polynucleotides, a variant(s) or a fragment(s) comprising 15 or more consecutive nucleotides of any of these polynucleotide sequences.

The kit or the device of the present invention can further comprise one or more polynucleotides comprising (or consisting of) a nucleotide sequence represented by any of SEQ ID NOs: 349 to 383 or a nucleotide sequence derived from the nucleotide sequence by the replacement of u with t, polynucleotide(s) comprising (or consisting of) a complementary sequence thereof, a polynucleotide(s) hybridizing under stringent conditions to any of these polynucleotides, a variant(s) or a fragment(s) comprising 15 or more consecutive nucleotides of any of these polynucleotide sequences.

The fragment or fragments that can be comprised in the kit or the device of the present invention is/are, for example, one or more polynucleotides, preferably two or more polynucleotides, selected from the group consisting of the following polynucleotides (1) to (3):

(1) a polynucleotide comprising 15 or more consecutive nucleotides that are from a nucleotide sequence derived from a nucleotide sequence represented by any of SEQ ID NOs: 1 to 104, 464 to 473, and 492 to 494 by the replacement of u with t, or a complementary sequence thereof;

(2) a polynucleotide comprising 15 or more consecutive nucleotides that are from a nucleotide sequence derived from a nucleotide sequence represented by any of SEQ ID NOs: 105 to 122 by the replacement of u with t, or a complementary sequence thereof, and (3) a polynucleotide comprising 15 or more consecutive nucleotides that are from a nucleotide sequence derived from a nucleotide sequence represented by any of SEQ ID NOs: 349 to 383 by the replacement of u with t, or a complementary sequence thereof.

In a preferred embodiment, the polynucleotide is a polynucleotide consisting of a nucleotide sequence represented by any of SEQ ID NOs: 1 to 104, 464 to 473, and 492 to 494 or a nucleotide sequence derived from the nucleotide sequence by the replacement of u with t, a polynucleotide consisting of a complementary sequence thereof, a polynucleotide hybridizing under stringent conditions to any of these polynucleotides, or a variant thereof comprising 15 or more, preferably 17 or more, more preferably 19 or more consecutive nucleotides.

In a preferred embodiment, the polynucleotide is a polynucleotide consisting of a nucleotide sequence represented by any of SEQ ID NOs: 105 to 122 or a nucleotide sequence derived from the nucleotide sequence by the replacement of u with t, a polynucleotide consisting of a complementary sequence thereof, a polynucleotide hybridizing under stringent conditions to any of these polynucleotides, or a variant thereof comprising 15 or more, preferably 17 or more, more preferably 19 or more consecutive nucleotides.

In a preferred embodiment, the polynucleotide is a polynucleotide consisting of a nucleotide sequence represented by any of SEQ ID NOs: 349 to 383 or a nucleotide sequence derived from the nucleotide sequence by the replacement of u with t, a polynucleotide consisting of a complementary sequence thereof, a polynucleotide hybridizing under stringent conditions to any of these polynucleotides, or a variant thereof comprising 15 or more, preferably 17 or more, more preferably 19 or more consecutive nucleotides.

In a preferred embodiment, the fragment can be a polynucleotide comprising 15 or more, preferably 17 or more, more preferably 19 or more consecutive nucleotides.

In the present invention, the size of the polynucleotide fragment is the number of nucleotides in the range from, for example, 15 consecutive nucleotides to less than the total number of nucleotides of the sequence, from 17 consecutive nucleotides to less than the total number of nucleotides of the sequence, or from 19 consecutive nucleotides to less than the total number of nucleotides of the sequence, in the nucleotide sequence of each polynucleotide.

Specific examples of the aforementioned combination constituting the kit or the device of the present invention can include the above-mentioned polynucleotides relevant to the combinations of SEQ ID NOs shown in Table 1 (i.e., SEQ ID NOs: 1 to 122, 349 to 383, 464 to 473, and 492 to 494 corresponding to the miRNA markers in Table 1). However, these are given merely for illustrative purposes, and all of various other possible combinations are included in the present invention.

The combination constituting the kit or the device for discriminating a pancreatic cancer patient from a healthy subject according to the present invention is desirably, for example, a combination of two or more polynucleotides consisting of the nucleotide sequences represented by SEQ ID NOs shown in Table 1. Usually, a combination of two of these polynucleotides can produce adequate performance.

The specific combination of two polynucleotides that consist of the above-mentioned nucleotide sequences or the complementary sequences thereof for discriminating a pancreatic cancer patient from a healthy subject is preferably a combination comprising at least one or more polynucleotides of the newly found polynucleotides consisting of the nucleotide sequences represented by SEQ ID NOs: 1 to 104, 349 to 383, 464 to 473, and 492 to 494, among the combinations constituted by two polynucleotides of the polynucleotides consisting of the nucleotide sequences represented by SEQ ID NOs: 1 to 122, 349 to 383, 464 to 473, and 492 to 494.

The combination of two polynucleotides that consist of the above-mentioned nucleotide sequences or the complementary sequences thereof for discriminating a pancreatic cancer patient from a healthy subject is preferably a combination of two polynucleotides comprising at least one polynucleotide selected from the group consisting of polynucleotides consisting of the nucleotide sequences represented by SEQ ID NOs: 1, 2, 4, 7, 15, 24, 105, 107, and 108 or complementary sequences thereof, with any of the polynucleotides of the other SEQ ID NOs.

Non-limiting examples of the combination comprising a polynucleotide consisting of the nucleotide sequence represented by SEQ ID NO: 1 or a complementary sequence thereof among the combinations constituted by two polynucleotides of the polynucleotides consisting of the nucleotide sequences represented by SEQ ID NOs: 1 to 122, 349 to 383, 464 to 473, and 492 to 494 for discriminating a pancreatic cancer patient from a healthy subject are listed below:

(1) a combination of SEQ ID NOs: 1 and 77 (markers: hsa-miR-6893-5p and hsa-miR-6780b-5p);
(2) a combination of SEQ ID NOs: 1 and 119 (markers: hsa-miR-6893-5p and hsa-miR-187-5p); and
(3) a combination of SEQ ID NOs: 1 and 20 (markers: hsa-miR-6893-5p and hsa-miR-7975).

Non-limiting examples of the combination comprising a polynucleotide consisting of the nucleotide sequence represented by SEQ ID NO: 2 or a complementary sequence thereof among the combinations constituted by two polynucleotides of the polynucleotides consisting of the nucleotide sequences represented by SEQ ID NOs: 1 to 122, 349 to 383, 464 to 473, and 492 to 494 for discriminating a pancreatic cancer patient from a healthy subject are further listed below:
(1) a combination of SEQ ID NOs: 2 and 105 (markers: hsa-miR-6075 and hsa-miR-125a-3p):
(2) a combination of SEQ ID NOs: 2 and 16 (markers: hsa-miR-6075 and hsa-miR-4634); and
(3) a combination of SEQ ID NOs: 2 and 10 (markers: hsa-miR-6075 and hsa-miR-4530).

Non-limiting examples of the combination comprising a polynucleotide consisting of the nucleotide sequence represented by SEQ ID NO: 4 or a complementary sequence thereof among the combinations constituted by two polynucleotides of the polynucleotides consisting of the nucleotide sequences represented by SEQ ID NOs: 1 to 122, 349 to 383, 464 to 473, and 492 to 494 for discriminating a pancreatic cancer patient from a healthy subject are further listed below:
(1) a combination of SEQ ID NOs: 4 and 105 (markers: hsa-miR-4294 and hsa-miR-125a-3p);
(2) a combination of SEQ ID NOs: 4 and 119 (markers: hsa-miR-4294 and hsa-miR-187-5p); and
(3) a combination of SEQ ID NOs: 4 and 45 (markers: hsa-miR-4294 and hsa-miR-6781-5p).

Non-limiting examples of the combination comprising a polynucleotide consisting of the nucleotide sequence represented by SEQ ID NO: 7 or a complementary sequence thereof among the combinations constituted by two polynucleotides of the polynucleotides consisting of the nucleotide sequences represented by SEQ ID NOs: 1 to 122, 349 to 383, 464 to 473, and 492 to 494 for discriminating a pancreatic cancer patient from a healthy subject are further listed below:
(1) a combination of SEQ ID NOs: 7 and 105 (markers: hsa-miR-6836-3p and hsa-miR-125a-3p):
(2) a combination of SEQ ID NOs: 7 and 34 (markers: hsa-miR-6836-3p and hsa-miR-4433-3p); and
(3) a combination of SEQ ID NOs: 7 and 12 (markers: hsa-miR-6836-3p and hsa-miR-4454).

Non-limiting examples of the combination comprising a polynucleotide consisting of the nucleotide sequence represented by SEQ ID NO: 105 or a complementary sequence thereof among the combinations constituted by two polynucleotides of the polynucleotides consisting of the nucleotide sequences represented by SEQ ID NOs: 1 to 122, 349 to 383, 464 to 473, and 492 to 494 for discriminating a pancreatic cancer patient from a healthy subject are further listed below:
(1) a combination of SEQ ID NOs: 18 and 105 (markers: hsa-miR-4792 and hsa-miR-125a-3p);
(2) a combination of SEQ ID NOs: 46 and 105 (markers: hsa-miR-6125 and hsa-miR-125a-3p); and
(3) a combination of SEQ ID NOs: 105 and 494 (markers: hsa-miR-125a-3p and hsa-miR-3940-5p).

The combination of polynucleotides with cancer type specificity capable of discriminating a pancreatic cancer patient not only from a healthy subject but also from other cancer patients is preferably, for example, a combination of multiple polynucleotides comprising: at least one polynucleotide selected from the group consisting of polynucleotides consisting of the nucleotide sequences represented by SEQ ID NOs: 2, 4, 6, 7, 9, 10, 25, 28, 30, 31, 38, 48, 82, 103, 105, 108, and 464 or complementary sequences thereof (hereinafter, this group is referred to as "cancer type-specific polynucleotide group 1"); and any of the polynucleotides of the other SEQ ID NOs.

The combination of polynucleotides with cancer type specificity capable of discriminating a pancreatic cancer patient not only from a healthy subject but also from other cancer patients is more preferably a combination of multiple polynucleotides selected from the cancer type-specific polynucleotide group 1.

The combination of polynucleotides with cancer type specificity capable of discriminating a pancreatic cancer patient not only from a healthy subject but also from other cancer patients is more preferably a combination comprising at least one or more polynucleotides selected from the group consisting of polynucleotides consisting of the nucleotide sequences represented by SEQ ID NOs: 2, 4, 7, 10, and 25 or complementary sequences thereof (hereinafter, this group is referred to as "cancer type-specific polynucleotide group 2") included in the cancer type-specific polynucleotide group 1, among the combinations of multiple polynucleotides selected from the cancer type-specific polynucleotide group 1. The number of the polynucleotides with cancer type specificity may be 1, 2, 3, 4, 5, 6, 7, 8, 9, 10 or more in the combination and is more preferably 4 or more in the combination. Usually, the combination of 4 polynucleotides of these polynucleotides can produce adequate performance.

Non-limiting examples of the combination of the polynucleotide consisting of the nucleotide sequence represented by SEQ ID NO: 2 or a complementary sequence thereof, with polynucleotides consisting of nucleotide sequences represented by SEQ ID NOs of three polynucleotides selected from the cancer type-specific polynucleotide group 1 or complementary sequences thereof are listed below:
(1) a combination of SEQ ID NOs: 2, 9, 105, and 7 (markers: hsa-miR-6075, hsa-miR-6799-5p, hsa-miR-125a-3p, and hsa-miR-6836-3p);
(2) a combination of SEQ ID NOs: 2, 7, 108, and 464 (markers: hsa-miR-6075, hsa-miR-6836-3p, hsa-miR-575, and hsa-miR-1203);
(3) a combination of SEQ ID NOs: 2, 31, 48, and 38 (markers: hsa-miR-6075, hsa-miR-6085, hsa-miR-6132, and hsa-miR-1238-5p);
(4) a combination of SEQ ID NOs: 2, 31, 28, and 48 (markers: hsa-miR-6075, hsa-miR-6085, hsa-miR-6821-5p, and hsa-miR-6132); and
(5) a combination of SEQ ID NOs: 2, 25, 105, and 10 (markers: hsa-miR-6075, hsa-miR-6880-5p, hsa-miR-125a-3p, and hsa-miR-4530).

Non-limiting examples of the combination of the polynucleotide consisting of the nucleotide sequence represented by SEQ ID NO: 4 or a complementary sequence thereof, with polynucleotides consisting of nucleotide sequences represented by SEQ ID NOs of three polynucleotides selected from the cancer type-specific polynucleotide group 1 or complementary sequences thereof are further listed below:
(1) a combination of SEQ ID NOs: 4, 31, 7, and 82 (markers: hsa-miR-4294, hsa-miR-6085, hsa-miR-6836-3p, and hsa-miR-1202):
(2) a combination of SEQ ID NOs: 4, 31, 28, and 82 (markers: hsa-miR-4294, hsa-miR-6085, hsa-miR-6821-5p, and hsa-miR-1202);
(3) a combination of SEQ ID NOs: 4, 10, 7, and 82 (markers: hsa-miR-4294, hsa-miR-4530, hsa-miR-6836-3p, and hsa-miR-1202);
(4) a combination of SEQ ID NOs: 4, 7, 82, and 103 (markers: hsa-miR-4294, hsa-miR-6836-3p, hsa-miR-1202, and hsa-miR-4665-3p); and (5) a combination of SEQ ID NOs: 4, 105, 10, and 6 (markers: hsa-miR-4294, hsa-miR-125a-3p, hsa-miR-4530, and hsa-miR-4476).

Non-limiting examples of the combination of the polynucleotide consisting of the nucleotide sequence represented by SEQ ID NO: 7 or a complementary sequence thereof, with polynucleotides consisting of nucleotide sequences represented by SEQ ID NOs of three polynucleotides selected from the cancer type-specific polynucleotide group 1 or complementary sequences thereof are further listed below:

(1) a combination of SEQ ID NOs: 4, 7, 82, and 101 (markers: hsa-miR-4294, hsa-miR-6836-3p, hsa-miR-1202, and hsa-miR-940);
(2) a combination of SEQ ID NOs: 4, 7, 38, and 82 (markers: hsa-miR-4294, hsa-miR-6836-3p, hsa-miR-1238-5p, and hsa-miR-1202):
(3) a combination of SEQ ID NOs: 6, 7, 61, and 68 (markers: hsa-miR-4476, hsa-miR-6836-3p, hsa-miR-6778-5p, and hsa-miR-760):
(4) a combination of SEQ ID NOs: 4, 7, 47, and 82 (markers: hsa-miR-4294, hsa-miR-6836-3p, hsa-miR-6805-5p, and hsa-miR-1202); and
(5) a combination of SEQ ID NOs: 4, 7, 82, and 103 (markers: hsa-miR-4294, hsa-miR-6836-3p, hsa-miR-1202, and hsa-miR-4665-3p).

Non-limiting examples of the combination of the polynucleotide consisting of the nucleotide sequence represented by SEQ ID NO: 10 or a complementary sequence thereof, with polynucleotides consisting of nucleotide sequences represented by SEQ ID NOs of three polynucleotides selected from the cancer type-specific polynucleotide group 1 or complementary sequences thereof are further listed below:

(1) a combination of SEQ ID NOs: 10, 47, 90, and 101 (markers: hsa-miR-4530, hsa-miR-6805-5p, hsa-miR-3162-5p, and hsa-miR-940);
(2) a combination of SEQ ID NOs: 10, 30, 103, and 365 (markers: hsa-miR-4530, hsa-miR-5585-3p, hsa-miR-4665-3p, and hsa-miR-3178);
(3) a combination of SEQ ID NOs: 9, 10, 61, and 68 (markers: hsa-miR-6799-5p, hsa-miR-4530, hsa-miR-6778-5p, and hsa-miR-760);
(4) a combination of SEQ ID NOs: 10, 48, 68, and 90 (markers: hsa-miR-4530, hsa-miR-6132, hsa-miR-760, and hsa-miR-3162-5p); and
(5) a combination of SEQ ID NOs: 10, 30, 68, and 365 (markers: hsa-miR-4530, hsa-miR-5585-3p, hsa-miR-760, and hsa-miR-3178).

Non-limiting examples of the combination of the polynucleotide consisting of the nucleotide sequence represented by SEQ ID NO: 25 or a complementary sequence thereof, with polynucleotides consisting of nucleotide sequences represented by SEQ ID NOs of three polynucleotides selected from the cancer type-specific polynucleotide group 1 or complementary sequences thereof are further listed below:

(1) a combination of SEQ ID NOs: 7, 25, 466, and 47 (markers: hsa-miR-6836-3p, hsa-miR-6880-5p, hsa-miR-4258, and hsa-miR-6805-5p):
(2) a combination of SEQ ID NOs: 7, 25, 48, and 466 (markers: hsa-miR-6836-3p, hsa-miR-6880-5p, hsa-miR-6132, and hsa-miR-4258);
(3) a combination of SEQ ID NOs: 7, 25, 28, and 466 (markers: hsa-miR-6836-3p, hsa-miR-6880-5p, hsa-miR-6821-5p, and hsa-miR-4258);
(4) a combination of SEQ ID NOs: 7, 25, 30, and 466 (markers: hsa-miR-6836-3p, hsa-miR-6880-5p, hsa-miR-5585-3p, and hsa-miR-4258); and
(5) a combination of SEQ ID NOs: 7, 25, 31, and 47 (markers: hsa-miR-6836-3p, hsa-miR-6880-5p, hsa-miR-6085, and hsa-miR-6805-5p).

The kit or the device of the present invention can also comprise a known polynucleotide(s) that enables detection of pancreatic cancer, or a polynucleotide(s) that will be found in the future, in addition to the polynucleotide(s) (which may include a variant(s), a fragment(s), and a derivative(s)) as described above according to the present invention.

The kit of the present invention can also comprise an antibody for measuring a marker or markers for pancreatic cancer examination known in the art, such as CEA, CA19-9, SPan-1, DUPAN-2, CA50, CA242, TAG-72, urinary fucose, POA, and TPS, in addition to the polynucleotide(s) according to the present invention as described above, and a variant or variants thereof or a fragment or fragments thereof.

These polynucleotides and variants thereof or fragments thereof contained in the kit of the present invention may be packaged in different containers either individually or in any combination.

The kit of the present invention may comprise a kit for extracting nucleic acids (e.g., total RNA) from body fluids, cells, or tissues, a fluorescent material for labeling, an enzyme and a medium for nucleic acid amplification, an instruction manual, etc.

The device of the present invention is a device for cancer marker measurement in which nucleic acids such as the polynucleotides according to the present invention described above, variants thereof, derivatives thereof, or fragments thereof are bonded or attached to, for example, a solid phase. Examples of the material for the solid phase include plastics, paper, glass, and silicon. The material for the solid phase is preferably a plastic from the viewpoint of easy processability. The solid phase has any shape and is, for example, square, round, reed-shaped, or film-shaped. The device of the present invention includes, for example, a device for measurement by a hybridization technique. Specific examples thereof include blotting devices and nucleic acid arrays (e.g., microarrays, DNA chips, and RNA chips).

The nucleic acid array technique is a technique which involves bonding or attaching the nucleic acids one by one by use of a method [e.g., a method of spotting the nucleic acids using a high-density dispenser called spotter or arrayer onto the surface of the solid phase surface-treated, if necessary, by coating with L-lysine or the introduction of a functional group such as an amino group or a carboxyl group, a method of spraying the nucleic acids onto the solid phase using an inkjet which injects very small liquid droplets by a piezoelectric element or the like from a nozzle, or a method of sequentially synthesizing nucleotides on the solid phase] to prepare an array such as a chip and measuring target nucleic acids through the use of hybridization using this array.

The kit or the device of the present invention comprises nucleic acids capable of specifically binding to the polynucleotides of at least one or more, preferably at least two or more, more preferably at least three or more, most preferably at least five or more to all of the pancreatic cancer marker miRNAs, respectively, of the group 1 described above. The kit or the device of the present invention can optionally further comprise nucleic acids capable of specifically binding to the polynucleotides of at least one or more, preferably at least two or more, more preferably at least three or more, most preferably at least five or more to all of the pancreatic cancer marker miRNAs, respectively, of the group 2 described above. The kit or the device of the present invention can optionally further comprise nucleic acids capable of specifically binding to the polynucleotides of at least one or more, preferably at least two or more, more preferably at least three or more, most preferably at least five or more to all of the pancreatic cancer marker miRNAs, respectively, of the group 3 described above.

The kit or the device of the present invention can be used for detecting pancreatic cancer as described in Section 4 below.

4. Method for Detecting Pancreatic Cancer

The present invention further provides a method for detecting pancreatic cancer, comprising using the kit or the device of the present invention (comprising the above-mentioned nucleic acid(s) that can be used in the present invention) as described in Section 3 above to measure expression levels of one or more pancreatic cancer-derived genes represented by: an expression level(s) of pancreatic cancer-derived gene(s) selected from the following group of miRNAs, i.e., miR-6893-5p, miR-6075, miR-6820-5p, miR-4294, miR-6729-5p, miR-4476, miR-6836-3p, miR-6765-3p, miR-6799-5p, miR-4530, miR-7641, miR-4454, miR-615-5p, miR-8073, miR-663a, miR-4634, miR-4450, miR-4792, miR-665, miR-7975, miR-7109-5p, miR-6789-5p, miR-4497, miR-6877-5p, miR-6880-5p, miR-7977, miR-4734, miR-6821-5p, miR-8089, miR-5585-3p, miR-6085, miR-6845-5p, miR-4651, miR-4433-3p, miR-1231, miR-4665-5p, miR-7114-5p, miR-1238-5p, miR-8069, miR-4732-5p, miR-619-5p, miR-3622a-5p, miR-1260a, miR-6741-5p, miR-6781-5p, miR-6125, miR-6805-5p, miR-6132, miR-6872-3p, miR-6875-5p, miR-1908-3p, miR-4433b-3p, miR-4736, miR-5100, miR-6724-5p, miR-7107-5p, miR-6726-5p, miR-3185, miR-4638-5p, miR-1273g-3p, miR-6778-5p, miR-328-5p, miR-3679-3p, miR-1228-3p, miR-6779-5p, miR-4723-5p, miR-6850-5p, miR-760, miR-7704, miR-8072, miR-4486, miR-1913, miR-4656, miR-1260b, miR-7106-5p, miR-6889-5p, miR-6780b-5p, miR-6090, miR-4534, miR-4449, miR-5195-3p, miR-1202, miR-4467, miR-6515-3p, miR-4281, miR-4505, miR-4484, miR-6805-3p, miR-3135b, miR-3162-5p, miR-6768-5p, miR-6721-5p, miR-1227-5p, miR-6722-3p, miR-4286, miR-4746-3p, miR-6727-5p, miR-6816-5p, miR-4741, miR-4508, miR-940, miR-4327, miR-4665-3p and miR-718, miR-1203, miR-663b, miR-4258, miR-4649-5p, miR-4516, miR-3619-3p, miR-6826-5p, miR-6757-5p, miR-3131, miR-1343-3p, miR-6775-5p, miR-6813-5p, and miR-3940-5p; and optionally an expression level(s) of pancreatic cancer-derived gene(s) selected from the following group of miRNA: i.e., miR-125a-3p, miR-204-3p, miR-1469, miR-575, miR-150-3p, miR-423-5p, miR-564, miR-3188, miR-1246, miR-602, miR-1290, miR-16-5p, miR-451a, miR-24-3p, miR-187-5p, miR-1908-5p, miR-371a-5p, and miR-550a-5p; and optionally an expression level(s) of pancreatic cancer-derived gene(s) selected from the following group of miRNAs, i.e., miR-4417, miR-4707-5p, miR-7847-3p, miR-2861, miR-4513, miR-7111-5p, miR-6777-5p, miR-7113-3p, miR-4648, miR-3184-5p, miR-4271, miR-6791-5p, miR-642a-3p, miR-7108-5p, miR-128-1-5p, miR-5196-5p, miR-3178, miR-3656, miR-92a-2-5p, miR-6769b-5p, miR-4689, miR-6076, miR-92b-5p, miR-6774-5p, miR-486-3p, miR-6806-5p, miR-6842-5p, miR-6716-5p, miR-557, miR-4673, miR-4674, miR-4442, miR-1915-3p, miR-4687-3p, and miR-92b-3p, in a sample in vitro, further comparing, for example, the expression level(s) of the gene(s) in the sample (e.g., blood, serum, or plasma) collected from a subject suspected of having pancreatic cancer, with a control expression level(s) in the sample(s) collected from a healthy subject(s)(including a non-pancreatic cancer patient(s)), and evaluating the subject as having pancreatic cancer when the expression level(s) of the target nucleic acid(s) is statistically significantly different between the samples.

This method of the present invention enables a limitedly invasive, early diagnosis of the cancer with high sensitivity and high specificity and thereby brings about early treatment and improved prognosis. In addition, exacerbation of the disease or the effectiveness of surgical, radiotherapeutic, and chemotherapeutic treatments can be monitored.

The method for extracting the pancreatic cancer-derived gene(s) from the sample such as blood, serum, or plasma according to the present invention is particularly preferably prepared by the addition of a reagent for RNA extraction in 3D-Gene™ RNA extraction reagent from liquid sample kit (Toray Industries, Inc.). A general acidic phenol method (acid guanidinium-phenol-chloroform (AGPC)) may be used, or Trizol™ (Life Technologies Corp.) may be used. The pancreatic cancer-derived gene(s) may be prepared by the addition of a reagent for RNA extraction containing acidic phenol, such as Trizol (Life Technologies Corp.) or Isogen (Nippon Gene Co., Ltd., Japan). Alternatively, a kit such as miRNeasy™ Mini Kit (Qiagen N.V.) may be used, though the method is not limited thereto.

The present invention also provides use of the kit or the device of the present invention for detecting in vitro an expression product(s) of a pancreatic cancer-derived miRNA gene(s) in a sample derived from a subject.

In the method of the present invention, the kit or the device described above comprises a single polynucleotide or any possible combination of polynucleotides that can be used in the present invention as described above.

In the detection or (genetic) diagnosis of pancreatic cancer according to the present invention, each polynucleotide contained in the kit or the device of the present invention can be used as a probe or a primer. In the case of using the polynucleotide as a primer, TaqMan™ MicroRNA Assays from Life Technologies Corp., miScript PCR System from Qiagen N.V., or the like can be used, though the method is not limited thereto.

The polynucleotide contained in the kit or the device of the present invention can be used as a primer or a probe according to a routine method in a method known in the art for specifically detecting the particular gene, for example, a hybridization technique such as Northern blot, Southern blot, in situ hybridization, Northern hybridization, or Southern hybridization, or a quantitative amplification technique such as quantitative RT-PCR. A body fluid such as blood, serum, plasma, or urine from a subject is collected as a sample to be assayed according to the type of the detection method used. Alternatively, total RNA prepared from such a body fluid by the method described above may be used, and various polynucleotides including cDNA prepared on the basis of the RNA may be used.

The kit or the device of the present invention is useful for the diagnosis of pancreatic cancer or the detection of the presence or absence of pancreatic cancer. Specifically, the detection of pancreatic cancer using the kit or the device can be performed by detecting in vitro an expression level(s) of a gene(s) using the nucleic acid probe(s) or the primer(s) contained in the kit or the device, in a sample such as blood, serum, plasma, or urine from a subject suspected of having pancreatic cancer. The subject suspected of having pancreatic cancer can be evaluated as having pancreatic cancer when the expression level(s) of a target miRNA marker(s)

measured using polynucleotide(s) (including a variant(s), a fragment(s), and a derivative(s) thereof) consisting of a nucleotide sequence(s) represented by at least one or more of SEQ ID NOs: 1 to 104, 464 to 473, and 492 to 494 or a complementary sequence(s) thereof, and optionally a nucleotide sequence(s) represented by one or more of SEQ ID NOs: 105 to 122 or a complementary sequence(s) thereof, and optionally a nucleotide sequence(s) represented by one or more of SEQ ID NOs: 349 to 383 or a complementary sequence(s) thereof, in the sample such as blood, serum, plasma, or urine of the subject, has a statistically significant difference compared to an expression level(s) thereof in the sample such as blood, serum, or plasma, or urine of a healthy subject.

The method of the present invention can be combined with a diagnostic imaging method such as abdominal ultrasonography, CT scanning, endoscopic retrograde cholangiopancreatography, or endoscopic ultrasonography. The method of the present invention is capable of specifically detecting pancreatic cancer and can substantially discriminate pancreatic cancer from the other cancers. Particularly, for bile duct cancer, some miRNA markers for pancreatic cancer can be commonly used. However, pancreatic cancer can be discriminated from bile duct cancer by a way of determining a discriminant boundary according to a discriminant. Alternatively, pancreatic cancer can be discriminated therefrom by combination with an additional diagnostic method such as the diagnostic imaging method as described above.

The method for detecting the absence of an expression product(s) of a pancreatic cancer-derived gene(s) or the presence of the expression product(s) of a pancreatic cancer-derived gene(s) in a sample using the kit or the device of the present invention comprises collecting a body fluid such as blood, serum, plasma, or urine of a subject, and measuring the expression level(s) of the target gene(s) contained therein using one or more polynucleotides (including a variant(s), a fragment(s), or a derivative(s)) selected from the groups of polynucleotides of the present invention, to evaluate the presence or absence of pancreatic cancer or to detect pancreatic cancer. The method for detecting pancreatic cancer according to the present invention can also evaluate or diagnose, for example, the presence or absence of amelioration of the disease or the degree of amelioration thereof in a pancreatic cancer patient in the case that a therapeutic drug is administered to the patient for amelioration of the disease.

The method of the present invention can comprise, for example, the following steps (a), (b), and (c):
  (a) a step of contacting in vitro a sample from a subject with a polynucleotide(s) contained in the kit or the device of the present invention:
  (b) a step of measuring an expression level(s) of the target nucleic acid(s) in the sample using the polynucleotide (s) as a nucleic acid probe(s) or primer(s); and
  (c) a step of evaluating the presence or absence of pancreatic cancer (cells) in the subject on the basis of the measurement results in the step (b).

Specifically, the present invention provides a method for detecting pancreatic cancer, comprising: measuring an expression level(s) of a target nucleic acid(s) in a sample of a subject using a nucleic acid(s) capable of specifically binding to at least one or more (preferably at least two or more) polynucleotides selected from the following miRNAs: miR-6893-5p, miR-6075, miR-6820-5p, miR-4294, miR-6729-5p, miR-4476, miR-6836-3p, miR-6765-3p, miR-6799-5p, miR-4530, miR-7641, miR-4454, miR-615-5p, miR-8073, miR-663a, miR-4634, miR-4450, miR-4792, miR-665, miR-7975, miR-7109-5p, miR-6789-5p, miR-4497, miR-6877-5p, miR-6880-5p, miR-7977, miR-4734, miR-6821-5p, miR-8089, miR-5585-3p, miR-6085, miR-6845-5p, miR-4651, miR-4433-3p, miR-1231, miR-4665-5p, miR-7114-5p, miR-1238-5p, miR-8069, miR-4732-5p, miR-619-5p, miR-3622a-5p, miR-1260a, miR-6741-5p, miR-6781-5p, miR-6125, miR-6805-5p, miR-6132, miR-6872-3p, miR-6875-5p, miR-1908-3p, miR-4433b-3p, miR-4736, miR-5100, miR-6724-5p, miR-7107-5p, miR-6726-5p, miR-3185, miR-4638-5p, miR-1273g-3p, miR-6778-5p, miR-328-5p, miR-3679-3p, miR-1228-3p, miR-6779-5p, miR-4723-5p, miR-6850-5p, miR-760, miR-7704, miR-8072, miR-4486, miR-1913, miR-4656, miR-1260b, miR-7106-5p, miR-6889-5p, miR-6780b-5p, miR-6090, miR-4534, miR-4449, miR-5195-3p, miR-1202, miR-4467, miR-6515-3p, miR-4281, miR-4505, miR-4484, miR-6805-3p, miR-3135b, miR-3162-5p, miR-6768-5p, miR-6721-5p, miR-1227-5p, miR-6722-3p, miR-4286, miR-4746-3p, miR-6727-5p, miR-6816-5p, miR-4741, miR-4508, miR-940, miR-4327, miR-4665-3p and miR-718, miR-1203, miR-663b, miR-4258, miR-4649-5p, miR-4516, miR-3619-3p, miR-6826-5p, miR-6757-5p, miR-3131, miR-1343-3p, miR-6775-5p, miR-6813-5p, and miR-3940-5p; and evaluating in vitro whether or not the subject has pancreatic cancer subject using the above-measured expression levels and control expression levels of a healthy subject(s) measured in the same way as above.

As used herein, the term "evaluation" is evaluation support based on results of in vitro examination, not physician's judgment.

As described above, in the method of the present invention, specifically, miR-6893-5p is hsa-miR-6893-5p, miR-6075 is hsa-miR-6075, miR-6820-5p is hsa-miR-6820-5p, miR-4294 is hsa-miR-4294, miR-6729-5p is hsa-miR-6729-5p, miR-4476 is hsa-miR-4476, miR-6836-3p is hsa-miR-6836-3p, miR-6765-3p is hsa-miR-6765-3p, miR-6799-5p is hsa-miR-6799-5p, miR-4530 is hsa-miR-4530, miR-7641 is hsa-miR-7641, miR-4454 is hsa-miR-4454, miR-615-5p is hsa-miR-615-5p, miR-8073 is hsa-miR-8073, miR-663a is hsa-miR-663a, miR-4634 is hsa-miR-4634, miR-4450 is hsa-miR-4450, miR-4792 is hsa-miR-4792, miR-665 is hsa-miR-665, miR-7975 is hsa-miR-7975, miR-7109-5p is hsa-miR-7109-5p, miR-6789-5p is hsa-miR-6789-5p, miR-4497 is hsa-miR-4497, miR-6877-5p is hsa-miR-6877-5p, miR-6880-5p is hsa-miR-6880-5p, miR-7977 is hsa-miR-7977, miR-4734 is hsa-miR-4734, miR-6821-5p is hsa-miR-6821-5p, miR-8089 is hsa-miR-8089, miR-5585-3p is hsa-miR-5585-3p, miR-6085 is hsa-miR-6085, miR-6845-5p is hsa-miR-6845-5p, miR-4651 is hsa-miR-4651, miR-4433-3p is hsa-miR-4433-3p, miR-1231 is hsa-miR-1231, miR-4665-5p is hsa-miR-4665-5p, miR-7114-5p is hsa-miR-7114-5p, miR-1238-5p is hsa-miR-1238-5p, miR-8069 is hsa-miR-8069, miR-4732-5p is hsa-miR-4732-5p, miR-619-5p is hsa-miR-619-5p, miR-3622a-5p is hsa-miR-3622a-5p, miR-1260a is hsa-miR-1260a, miR-6741-5p is hsa-miR-6741-5p, miR-6781-5p is hsa-miR-6781-5p, miR-6125 is hsa-miR-6125, miR-6805-5p is hsa-miR-6805-5p, miR-6132 is hsa-miR-6132, miR-6872-3p is hsa-miR-6872-3p, miR-6875-5p is hsa-miR-6875-5p, miR-1908-3p is hsa-miR-1908-3p, miR-4433b-3p is hsa-miR-4433b-3p, miR-4736 is hsa-miR-4736, miR-5100 is hsa-miR-5100, miR-6724-5p is hsa-miR-6724-5p, miR-7107-5p is hsa-miR-7107-5p, miR-6726-5p is hsa-miR-6726-5p, miR-3185 is hsa-miR-3185, miR-4638-5p is hsa-miR-4638-5p, miR-1273g-3p is hsa-miR-1273g-3p, miR-6778-5p is hsa-miR-6778-5p, miR-328-5p is hsa-miR-328-5p, miR-3679-3p is hsa-miR-3679-3p, miR-1228-

3p is hsa-miR-1228-3p, miR-6779-5p is hsa-miR-6779-5p, miR-4723-5p is hsa-miR-4723-5p, miR-6850-5p is hsa-miR-6850-5p, miR-760 is hsa-miR-760, miR-7704 is hsa-miR-7704, miR-8072 is hsa-miR-8072, miR-4486 is hsa-miR-4486, miR-1913 is hsa-miR-1913, miR-4656 is hsa-miR-4656, miR-1260b is hsa-miR-1260b, miR-7106-5p is hsa-miR-7106-5p, miR-6889-5p is hsa-miR-6889-5p, miR-6780b-5p is hsa-miR-6780b-5p, miR-6090 is hsa-miR-6090, miR-4534 is hsa-miR-4534, miR-4449 is hsa-miR-4449, miR-5195-3p is hsa-miR-5195-3p, miR-1202 is hsa-miR-1202, miR-4467 is hsa-miR-4467, miR-6515-3p is hsa-miR-6515-3p, miR-4281 is hsa-miR-4281, miR-4505 is hsa-miR-4505, miR-4484 is hsa-miR-4484, miR-6805-3p is hsa-miR-6805-3p, miR-3135b is hsa-miR-3135b, miR-3162-5p is hsa-miR-3162-5p, miR-6768-5p is hsa-miR-6768-5p, miR-6721-5p is hsa-miR-6721-5p, miR-1227-5p is hsa-miR-1227-5p, miR-6722-3p is hsa-miR-6722-3p, miR-4286 is hsa-miR-4286, miR-4746-3p is hsa-miR-4746-3p, miR-6727-5p is hsa-miR-6727-5p, miR-6816-5p is hsa-miR-6816-5p, miR-4741 is hsa-miR-4741, miR-4508 is hsa-miR-4508, miR-940 is hsa-miR-940, miR-4327 is hsa-miR-4327, miR-4665-3p is hsa-miR-4665-3p, miR-718 is hsa-miR-718, miR-1203 is hsa-miR-1203, miR-663b is hsa-miR-663b, miR-4258 is hsa-miR-4258, miR-4649-5p is hsa-miR-4649-5p, miR-4516 is hsa-miR-4516, miR-3619-3p is hsa-miR-3619-3p, miR-6826-5p is hsa-miR-6826-5p, miR-6757-5p is hsa-miR-6757-5p, miR-3131 is hsa-miR-3131, miR-1343-3p is hsa-miR-1343-3p, miR-6775-5p is hsa-miR-6775-5p, miR-6813-5p is hsa-miR-6813-5p, and miR-3940-5p is hsa-miR-3940-5p.

In the method of the present invention, specifically, the nucleic acid(s) (specifically, probe(s) or primer(s)) is selected from the group consisting of the following polynucleotides (a) to (e):
(a) a polynucleotide consisting of a nucleotide sequence represented by any of SEQ ID NOs: 1 to 104, 464 to 473, and 492 to 494 or a nucleotide sequence derived from the nucleotide sequence by the replacement of u with t, a variant thereof, a derivative thereof, or a fragment thereof comprising 15 or more consecutive nucleotides;
(b) a polynucleotide comprising a nucleotide sequence represented by any of SEQ ID NOs: 1 to 104, 464 to 473, and 492 to 494;
(c) a polynucleotide consisting of a nucleotide sequence complementary to a nucleotide sequence represented by any of SEQ ID NOs: 1 to 104, 464 to 473, and 492 to 494 or a nucleotide sequence derived from the nucleotide sequence by the replacement of u with t, a variant thereof, a derivative thereof, or a fragment thereof comprising 15 or more consecutive nucleotides;
(d) a polynucleotide comprising a nucleotide sequence complementary to a nucleotide sequence represented by any of SEQ ID NOs: 1 to 104, 464 to 473, and 492 to 494 or a nucleotide sequence derived from the nucleotide sequence by the replacement of u with t; and
(e) a polynucleotide hybridizing under stringent conditions to any of the polynucleotides (a) to (d).

The nucleic acid(s) further used in the method of the present invention can comprise a nucleic acid(s) capable of specifically binding to at least one or more polynucleotides selected from the following miRNAs: miR-125a-3p, miR-204-3p, miR-1469, miR-575, miR-150-3p, miR-423-5p, miR-564, miR-3188, miR-1246, miR-602, miR-1290, miR-16-5p, miR-451a, miR-24-3p, miR-187-5p, miR-1908-5p, miR-371a-5p, and miR-550a-5p Specifically, miR-125a-3p is hsa-miR-125a-3p, miR-204-3p is hsa-miR-204-3p, miR-1469 is hsa-miR-1469, miR-575 is hsa-miR-575, miR-150-3p is hsa-miR-150-3p, miR-423-5p is hsa-miR-423-5p, miR-564 is hsa-miR-564, miR-3188 is hsa-miR-3188, miR-1246 is hsa-miR-1246, miR-602 is hsa-miR-602, miR-1290 is hsa-miR-1290, miR-16-5p is hsa-miR-16-5p, miR-451a is hsa-miR-451a, miR-24-3p is hsa-miR-24-3p, miR-187-5p is hsa-miR-187-5p, miR-1908-5p is hsa-miR-1908-5p, miR-371a-5p is hsa-miR-371 a-5p, and miR-550a-5p is hsa-miR-550a-5p.

Specifically, the nucleic acid(s) is further selected from the group consisting of the following polynucleotides (f) to (j):
(f) a polynucleotide consisting of a nucleotide sequence represented by any of SEQ ID NOs: 105 to 122 or a nucleotide sequence derived from the nucleotide sequence by the replacement of u with t, a variant thereof, a derivative thereof, or a fragment thereof comprising 15 or more consecutive nucleotides;
(g) a polynucleotide comprising a nucleotide sequence represented by any of SEQ ID NOs: 105 to 122;
(h) a polynucleotide consisting of a nucleotide sequence complementary to a nucleotide sequence represented by any of SEQ ID NOs: 105 to 122 or a nucleotide sequence derived from the nucleotide sequence by the replacement of u with t, a variant thereof, a derivative thereof, or a fragment thereof comprising 15 or more consecutive nucleotides;
(i) a polynucleotide comprising a nucleotide sequence complementary to a nucleotide sequence represented by any of SEQ ID NOs: 105 to 122 or a nucleotide sequence derived from the nucleotide sequence by the replacement of u with t; and
(j) a polynucleotide hybridizing under stringent conditions to any of the polynucleotides (f) to (i).

The nucleic acid(s) further used can comprise a nucleic acid capable of specifically binding to at least one or more polynucleotides selected from the following miRNAs: miR-4417, miR-4707-5p, miR-7847-3p, miR-2861, miR-4513, miR-7111-5p, miR-6777-5p, miR-7113-3p, miR-4648, miR-3184-5p, miR-4271, miR-6791-5p, miR-642a-3p, miR-7108-5p, miR-128-1-5p, miR-5196-5p, miR-3178, miR-3656, miR-92a-2-5p, miR-6769b-5p, miR-4689, miR-6076, miR-92b-5p, miR-6774-5p, miR-486-3p, miR-6806-5p, miR-6842-5p, miR-6716-5p, miR-557, miR-4673, miR-4674, miR-4442, miR-1915-3p, miR-4687-3p, and miR-92b-3p.

Specifically, miR-4417 is hsa-miR-4417, miR-4707-5p is hsa-miR-4707-5p, miR-7847-3p is hsa-miR-7847-3p, miR-2861 is hsa-miR-2861, miR-4513 is hsa-miR-4513, miR-7111-5p is hsa-miR-7111-5p, miR-6777-5p is hsa-miR-6777-5p, miR-7113-3p is hsa-miR-7113-3p, miR-4648 is hsa-miR-4648, miR-3184-5p is hsa-miR-3184-5p, miR-4271 is hsa-miR-4271, miR-6791-5p is hsa-miR-6791-5p, miR-642a-3p is hsa-miR-642a-3p, miR-7108-5p is hsa-miR-7108-5p, miR-128-1-5p is hsa-miR-128-1-5p, miR-5196-5p is hsa-miR-5196-5p, miR-3178 is hsa-miR-3178, miR-3656 is hsa-miR-3656, miR-92a-2-5p is hsa-miR-92a-2-5p, miR-6769b-5p is hsa-miR-6769b-5p, miR-4689 is hsa-miR-4689, miR-6076 is hsa-miR-6076, miR-92b-5p is hsa-miR-92b-5p, miR-6774-5p is hsa-miR-6774-5p, miR-486-3p is hsa-miR-486-3p, miR-6806-5p is hsa-miR-6806-5p, miR-6842-5p is hsa-miR-6842-5p, miR-6716-5p is hsa-miR-6716-5p, miR-557 is hsa-miR-557, miR-4673 is hsa-miR-4673, miR-4674 is hsa-miR-4674, miR-4442 is hsa-miR-4442, miR-1915-3p is hsa-miR-1915-3p, miR-4687-3p is hsa-miR-4687-3p, and miR-92b-3p is hsa-miR-92b-3p.

Specifically, the nucleic acid(s) further used is a polynucleotide(s) selected from the group consisting of the following polynucleotides (k) to (o):
- (k) a polynucleotide consisting of a nucleotide sequence represented by any of SEQ ID NOs: 349 to 383 or a nucleotide sequence derived from the nucleotide sequence by the replacement of u with t, a variant thereof, a derivative thereof, or a fragment thereof comprising 15 or more consecutive nucleotides;
- (l) a polynucleotide comprising a nucleotide sequence represented by any of SEQ ID NOs: 349 to 383;
- (m) a polynucleotide consisting of a nucleotide sequence complementary to a nucleotide sequence represented by any of SEQ ID NOs: 349 to 383 or a nucleotide sequence derived from the nucleotide sequence by the replacement of u with t, a variant thereof, a derivative thereof, or a fragment thereof comprising 15 or more consecutive nucleotides;
- (n) a polynucleotide comprising a nucleotide sequence complementary to a nucleotide sequence represented by any of SEQ ID NOs: 349 to 383 or a nucleotide sequence derived from the nucleotide sequence by the replacement of u with t; and
- (o) a polynucleotide hybridizing under stringent conditions to any of the polynucleotides (k) to (n).

Examples of the sample used in the method of the present invention can include samples prepared from living tissues (preferably pancreatic tissues) or body fluids such as blood, serum, plasma, and urine from subjects. Specifically, for example, an RNA-containing sample prepared from the tissue, a polynucleotide-containing sample further prepared therefrom, a body fluid such as blood, serum, plasma, or urine, a portion or the whole of a living tissue collected from the subject by biopsy or the like, or a living tissue excised by surgery can be used, and the sample for measurement can be prepared therefrom.

As used herein, the subject refers to a mammal, for example, a primate such as a human or a monkey, a rodent such as a mouse or a rat, a pet animal such as a dog or a cat, and an athletic animal such as a horse without any limitation, and is preferably a human.

The steps of the method of the present invention can be changed according to the type of the sample to be assayed.

In the case of using RNA as an analyte, the detection of pancreatic cancer (cells) can comprise, for example, the following steps (a), (b), and (c):
- (a) a step of binding RNA prepared from a sample from a subject or complementary polynucleotides (cDNAs) transcribed from the RNA to a polynucleotide(s) in the kit or the device of the present invention:
- (b) a step of measuring the sample-derived RNA or the cDNAs synthesized from the RNA, which is/are bound to the polynucleotide(s), by hybridization using the polynucleotide(s) as a nucleic acid probe(s) or by quantitative RT-PCR using the polynucleotide(s) as a primer(s); and
- (c) a step of evaluating the presence or absence of pancreatic cancer (or pancreatic cancer-derived gene expression) on the basis of the measurement results of the step (b).

For example, various hybridization methods can be used for detecting, examining, evaluating, or diagnosing pancreatic cancer (or pancreatic cancer-derived gene expression) in vitro according to the present invention. For example, Northern blot, Southern blot, RT-PCR, DNA chip analysis, in situ hybridization, Northern hybridization, or Southern hybridization can be used as such a hybridization method.

In the case of using the Northern blot, the presence or absence of expression of each gene or the expression level thereof in the RNA can be detected or measured by use of the nucleic acid probe(s) that can be used in the present invention. Specific examples thereof can include a method which comprises labeling the nucleic acid probe (or a complementary strand) with a radioisotope ($^{32}$P, $^{33}$P, $^{35}$S, etc.), a fluorescent material, or the like, hybridizing the labeled product with the tissue-derived RNA from a subject, which is transferred to a nylon membrane or the like according to a routine method, and then detecting and measuring a signal derived from the label (radioisotope or fluorescent material) on the formed DNA/RNA duplex using a radiation detector (examples thereof can include BAS-1800 11 (Fujifilm Corp., Japan)) or a fluorescence detector (examples thereof can include STORM 865 (GE Healthcare Japan Corp.)).

In the case of using the quantitative RT-PCR, the presence or absence of expression of each gene or the expression level thereof in the RNA can be detected or measured by use of the primer that can be used in the present invention. Specific examples thereof can include a method which comprises preparing cDNAs from the tissue-derived RNA of a subject according to a routine method, hybridizing a pair of primers (consisting of a plus strand and a reverse strand binding to the cDNA) prepared from the composition for detection of the present invention with the cDNA such that the region of each target gene can be amplified with the cDNA as a template, and performing PCR according to a routine method to detect the obtained double-stranded DNA. The method for detecting the double-stranded DNA can include a method of performing the PCR using the primers labeled in advance with a radioisotope or a fluorescent material, a method of electrophoresing the PCR product on an agarose gel and staining the double-stranded DNA with ethidium bromide or the like for detection, and a method of transferring the produced double-stranded DNA to a nylon membrane or the like according to a routine method and hybridizing the double-stranded DNA to a labeled nucleic acid probe for detection.

In the case of using the nucleic acid array analysis, an RNA chip or a DNA chip in which the composition for detection of the present invention is attached as nucleic acid probes (single-stranded or double-stranded) to a substrate (solid phase) is used. Regions having the attached nucleic acid probes are referred to as probe spots, and regions having no attached nucleic acid probe are referred to as blank spots. A group of genes immobilized on a solid-phase substrate is generally called a nucleic acid chip, a nucleic acid array, a microarray, or the like. The DNA or RNA array includes a DNA or RNA macroarray and a DNA or RNA microarray. In the present specification, the term "chip" includes these arrays, 3D-Gene™ Human miRNA Oligo chip (Toray Industries, Inc.) can be used as the DNA chip, though the DNA chip is not limited thereto.

Examples of the measurement using the DNA chip can include, but are not limited to, a method of detecting and measuring a signal derived from the label on the composition for detection using an image detector (examples thereof can include Typhoon 9410 (GE Healthcare) and 3D-Gene™ scanner (Toray Industries, Inc.)).

The "stringent conditions" used herein are, as mentioned above, conditions under which a nucleic acid probe hybridizes to its target sequence to a detectably larger extent (e.g., a measurement value equal to or larger than "(a mean of background measurement values)+(a standard deviation of the background measurement values)×2") than that for other sequences.

The stringent conditions are defined by hybridization and subsequent washing. Examples of the hybridization conditions include, but not limited to, 30° C. to 60° C. for 1 to 24 hours in a solution containing SSC, a surfactant, formamide, dextran sulfate, a blocking agent(s), etc. In this context, 1×SSC is an aqueous solution (pH 7.0) containing 150 mM sodium chloride and 15 mM sodium citrate. The surfactant includes, for example, SDS (sodium dodecyl sulfate), Triton, or Tween. The hybridization conditions more preferably comprise 3-10×SSC and 0.1-1% SDS. Examples of the conditions for the washing, following the hybridization, which is another condition to define the stringent conditions, can include conditions comprising continuous washing at 30° C. in a solution containing 0.5×SSC and 0.1% SDS, at 30° C. in a solution containing 0.2×SSC and 0.1% SDS, and at 30° C. in a 0.05×SSC solution. It is desirable that the complementary strand should maintain its hybridized state with a target plus strand even by washing under such conditions. Specifically, examples of such a complementary strand can include a strand consisting of a nucleotide sequence in a completely complementary relationship with the nucleotide sequence of the target plus (+) strand, and a strand consisting of a nucleotide sequence having at least 80%, preferably at least 85%, more preferably at least 90% or at least 95%, for example, at least 98% or at least 99% identity to the strand.

Other examples of the "stringent conditions" for the hybridization are described in, for example, Sambrook, J. & Russel, D., Molecular Cloning, A LABORATORY MANUAL, Cold Spring Harbor Laboratory Press, published on Jan. 15, 2001, Vol. 1, 7.42 to 7.45 and Vol. 2, 8.9 to 8.17, and can be used in the present invention.

Examples of the conditions for carrying out PCR using polynucleotide fragments in the kit of the present invention as primers include treatment for approximately 15 seconds to 1 minute at 5 to 10° C. plus a Tm value calculated from the sequences of the primers, using a PCR buffer having composition such as 10 mM Tris-HCL (pH 8.3), 50 mM KCL, and 1 to 2 mM $MgCl_2$. Examples of the method for calculating such a Tm value include Tm value=2×(the number of adenine residues+the number of thymine residues)+4×(the number of guanine residues+the number of cytosine residues).

In the case of using the quantitative RT-PCR, a commercially available kit for measurement specially designed for quantitatively measuring miRNA, such as TaqMan™ MicroRNA Assays (Life Technologies Corp.), LNA™-based MicroRNA PCR (Exiqon), or Ncode™ miRNA qRT-PCT kit (Invitrogen Corp.) may be used.

For the calculation of gene expression levels, statistical treatment described in, for example, Statistical analysis of gene expression microarray data (Speed T., Chapman and Hall/CRC), and A beginner's guide Microarray gene expression data analysis (Causton H. C. et al., Blackwell publishing) can be used in the present invention, though the calculation method is not limited thereto. For example, twice, preferably 3 times, more preferably 6 times the standard deviation of the measurement values of the blank spots are added to the average measurement value of the blank spots on the DNA chip, and probe spots having a signal value equal to or larger than the resulting value can be regarded as detection spots. Alternatively, the average measurement value of the blank spots is regarded as a background and can be subtracted from the measurement values of the probe spots to determine gene expression levels. A missing value for a gene expression level can be excluded from the analyte, preferably replaced with the smallest value of the gene expression level in each DNA chip, or more preferably replaced with a value obtained by subtracting 0.1 from a logarithmic value of the smallest value of the gene expression level. In order to eliminate low-signal genes, only a gene having a gene expression level of 26, preferably $2^8$, more preferably $2^{10}$ or larger in 20% or more, preferably 50% or more, more preferably 80% or more of the number of measurement samples can be selected as the analyte. Examples of the normalization of the gene expression level include, but are not limited to, global normalization and quantile normalization (Bolstad, B. M. et al., 2003, Bioinformatics, Vol. 19, p. 185-193).

The present invention also provides a method comprising measuring target genes or gene expression levels in a sample from a subject using the polynucleotides, the kit, or the device (e.g., chip) for diagnosis of the present invention, or a combination thereof, preparing a discriminant (discriminant function) with gene expression levels in a sample from a pancreatic cancer patient and a sample from a healthy subject as supervising samples, and determining or evaluating the presence and/or absence of the pancreatic cancer-derived genes in the sample.

Specifically, the present invention further provides the method comprising: a first step of measuring in vitro expression levels of target genes in a plurality of samples known to determine or evaluate the presence and/or absence of the pancreatic cancer-derived genes in the samples, using the polynucleotides, the kit, or the device (e.g., chip) for diagnosis of the present invention, or a combination thereof; a second step of preparing a discriminant with the measurement values of the expression levels of the target genes obtained in the first step as supervising samples; a third step of measuring in vitro expression levels of the target genes in a sample derived from a subject in the same way as in the first step; and a fourth step of assigning the measurement values of the expression levels of the target genes obtained in the third step to the discriminant obtained in the second step, and determining or evaluating the presence and/or absence of the pancreatic cancer-derived genes in the sample on the basis of the results obtained from the discriminant, wherein the target genes can be detected using the polynucleotides or using polynucleotides, variants thereof, or fragments thereof contained in the kit or the device (e.g., chip). In this context, the discriminant can be prepared by use of Fisher's discriminant analysis, nonlinear discriminant analysis based on Mahalanobis' distance, neural network, Support Vector Machine (SVM), or the like, though the method is not limited thereto.

When a clustering boundary is a straight line or a hyperplane, the linear discriminant analysis is a method for determining the belonging of a cluster using Formula 1 as a discriminant. In Formula 1, x represents an explanatory variable, w represents a coefficient of the explanatory variable, and wo represents a constant term.

$$f(x) = w_0 + \sum_{i=1}^{n} w_i x_i \qquad \text{Formula 1}$$

Values obtained from the discriminant are referred to as discriminant scores. The measurement values of a newly offered data set can be assigned as explanatory variables to the discriminant to determine clusters by the signs of the discriminant scores.

The Fisher's discriminant analysis, one type of linear discriminant analysis, is a dimensionality reduction method for selecting a dimension suitable for discriminating classes, and constructs a highly discriminating synthetic variable by focusing on the variance of the synthetic variables and minimizing the variance of data having the same label (Venables, W. N. et al., Modern Applied Statistics with S. Fourth edition. Springer, 2002). In the Fishers discriminant analysis, direction w of projection is determined so as to maximize Formula 2. In this formula, µ represents an average input, ng represents the number of data belonging to class g, and µg represents an average input of the data belonging to class g. The numerator and the denominator are the interclass variance and the intraclass variance, respectively, when each data is projected in the direction of the vector w. Discriminant coefficient $w_i$ is determined by maximizing this ratio (Takafumi Kanamori et al., "Pattern Recognition", Kyoritsu Shuppan Co., Ltd., Tokyo, Japan (2009); and Richard O. et al., Pattern Classification Second Edition, Wiley-Interscience, 2000).

$$J(w) = \frac{\sum_{g=1}^{G} n_g (w^T \mu_g - w^T \mu)(w^T \mu_g - w^T \mu)^T}{\sum_{g=1}^{G} \sum_{i, y_i = g} (w^T x_i - w^T \mu_g)(w^T x_i - w^T \mu_g)}$$

$$\text{subject to } \mu = \sum_{i=1}^{n} \frac{x_i}{n}, \mu_g = \sum_{i: u_i = g}^{n} \frac{x_i}{n_g}$$

Formula 2

The Mahalanobis' distance is calculated according to Formula 3 in consideration of data correlation and can be used as nonlinear discriminant analysis for determining a cluster in which a data point belongs to, based on a short Mahalanobis' distance from the data point to that cluster. In Formula 3, p represents a central vector of each cluster, and $S^{-1}$ represents an inverse matrix of the variance-covariance matrix of the cluster. The central vector is calculated from explanatory variable x, and an average vector, a median value vector, or the like can be used.

$$D(x, \mu) = \{(x - \mu)^t S^{-1} (x - \mu)\}^{\frac{1}{2}}$$

Formula 3

SVM is a discriminant analysis method devised by V. Vapnik (The Nature of Statistical Leaning Theory, Springer, 1995). Particular data points of a data set having known classes are defined as explanatory variables, and classes are defined as objective variables. A boundary plane called hyperplane for correctly classifying the data set into the known classes is determined, and a discriminant for data classification is determined using the boundary plane. Then, the measurement values of a newly offered data set can be assigned as explanatory variables to the discriminant to determine classes. In this respect, the result of the discriminant analysis may be classes, may be a probability of being classified into correct classes, or may be the distance from the hyperplane. In SVM, a method of nonlinearly converting a feature vector to a high dimension and performing linear discriminant analysis in the space is known as a method for tackling nonlinear problems. An expression in which an inner product of two factors in a nonlinearly mapped space is expressed only by inputs in their original spaces is called kernel. Examples of the kernel can include a linear kernel, a RBF (Radial Basis Function) kernel, and a Gaussian kernel. While highly dimensional mapping is performed according to the kernel, the optimum discriminant, i.e., a discriminant, can be actually constructed by mere calculation according to the kernel, which avoids calculating features in the mapped space (e.g., Hideki Aso et al., Frontier of Statistical Science 6 "Statistics of pattern recognition and learning—New concepts and approaches", Iwanami Shoten, Publishers, Tokyo, Japan (2004); Nello Cristianini et al., Introduction to SVM, Kyoritsu Shuppan Co., Ltd., Tokyo, Japan (2008)).

C-support vector classification (C-SVC), one type of SVM, comprises preparing a hyperplane by supervising a data set with the explanatory variables of two groups and classifying an unknown data set into either of the groups (C. Cortes et al., 1995, Machine Learning, Vol. 20, p. 273-297).

Exemplary calculation of the C-SVC discriminant that can be used in the method of the present invention will be given below. First, all subjects are divided into two groups, i.e., a pancreatic cancer patient group and a healthy subject group. For example, pancreatic tissue examination can be used for a reference under which each subject is confirmed either as a pancreatic cancer patient or as a healthy subject.

Next, a data set consisting of comprehensive gene expression levels of serum-derived samples of the two divided groups (hereinafter, this data set is referred to as a training cohort) is prepared, and a C-SVC discriminant is determined by using genes found to differ clearly in their gene expression levels between the two groups as explanatory variables and this grouping as objective variables (e.g., −1 and +1). An optimizing objective function is represented by Formula 4 wherein e represents all input vectors, y represents an objective variable, a represents a Lagrange's undetermined multiplier vector, Q represents a positive definite matrix, and C represents a parameter for adjusting constrained conditions.

$$\min_a \frac{1}{2} a^T Q a - e^T a$$

subject to $y^T a = 0, 0 \le a_i \le C, i = 1, \ldots, l,$

Formula 4

Formula 5 is a finally obtained discriminant, and a group in which the data point belongs to can be determined on the basis of the sign of a value obtained according to the discriminant. In this formula, x represents a support vector, y represents a label indicating the belonging of a group, a represents the corresponding coefficient, b represents a constant term, and K represents a kernel function.

$$f(x) = \text{sgn}\left(\sum_{i=1}^{l} y_i a_i K(x_i, x) + b\right)$$

Formula 5

For example, a RBF kernel defined by Formula 6 can be used as the kernel function. In this formula, x represents a support vector, and y represents a kernel parameter for adjusting the complexity of the hyperplane.

$$K(x_i, x_j) = \exp(-r\|x_i - x_j\|^2), r < 0$$

Formula 6

In addition, an approach such as neural network, k-nearest neighbor algorithms, decision trees, or logistic regression analysis can be selected as a method for determining or evaluating the presence and/or absence of expression of a pancreatic cancer-derived target gene(s) in a sample derived from a subject, or for evaluating the expression level thereof by comparison with a control derived from a healthy subject.

The method of the present invention can comprise, for example, the following steps (a), (b), and (c):

(a) a step of measuring an expression level(s) of a target gene(s) in tissues containing pancreatic cancer-derived genes derived from pancreatic cancer patients and/or samples already known to be tissues containing no pancreatic cancer-derived gene(s) derived from healthy subjects, using the polynucleotide(s), the kit, or the device (e.g., DNA chip) for detection according to the present invention;

(b) a step of preparing the discriminants of Formulas 1 to 3, 5, and 6 described above from the measurement values of the expression level measured in the step (a); and (c) a step of measuring an expression level(s) of the target gene(s) in a sample derived from a subject using the polynucleotide(s), the kit, or the device (e.g., DNA chip) for diagnosis (detection) according to the present invention, assigning the obtained measurement value(s) to the discriminants prepared in the step (b), and determining or evaluating the presence and/or absence of expression of the pancreatic cancer-derived target genes in the sample, or evaluating the expression levels thereof by comparison with a healthy subject-derived control, on the basis of the obtained results.

In this context, in the discriminants of Formulas 1 to 3, 5, and 6, x represents an explanatory variable and includes a value obtained by measuring a polynucleotide(s) selected from the polynucleotides described in Section 2 above, or any fragment thereof. Specifically, the explanatory variable for discriminating a pancreatic cancer patient from a healthy subject according to the present invention is a gene expression level(s) selected from, for example, the following expression levels (1) to (3):

(1) a gene expression level(s) in the serum of a pancreatic cancer patient or a healthy subject measured by any RNA or DNA comprising 15 or more consecutive nucleotides in a nucleotide sequence represented by any of SEQ ID NOs: 1 to 104, 464 to 473, and 492 to 494 or a complementary sequence thereof, or nucleotides derived from the nucleotides by the replacement of u with t, (2) a gene expression level(s) in the serum of a pancreatic cancer patient or a healthy subject measured by any RNA or DNA comprising 15 or more consecutive nucleotides in a nucleotide sequence represented by any of SEQ ID NOs: 105 to 122 or a complementary sequence thereof, or nucleotides derived from the nucleotides by the replacement of u with t; and (3) a gene expression level(s) in the serum of a pancreatic cancer patient or a healthy subject measured by any RNA or DNA comprising 15 or more consecutive nucleotides in a nucleotide sequence represented by any of SEQ ID NOs: 349 to 383 or a complementary sequence thereof, or nucleotides derived from the nucleotides by the replacement of u with t.

As described above, for the method for determining or evaluating the presence and/or absence of a pancreatic cancer-derived gene(s) in a sample derived from a subject, the preparation of a discriminant requires a discriminant prepared from a training cohort. For enhancing the accuracy of the discriminant, it is necessary to use genes having clear difference between two groups in the training cohort when preparing the discriminant.

Each gene that is used for an explanatory variable in a discriminant is preferably determined as follows. First, comprehensive gene expression levels of a pancreatic cancer patient group and comprehensive gene expression levels of a healthy subject group, both of which are in a training cohort, are used as a data set, the degree of difference in the expression level of each gene between the two groups is determined through the use of, for example, the P value of t test, which is parametric analysis, or the P value of Mann-Whitney's U test or Wilcoxon test, which is nonparametric analysis.

The gene can be regarded as being statistically significant when the critical rate (significance level) as the P value obtained by the test is smaller than, for example, 5%, 1%, or 0.01%.

In order to correct an increased probability of type I error attributed to the repetition of a test, a method known in the art, for example, Bonferroni or Holm method, can be used for the correction (e.g., Yasushi Nagata et al., "Basics of statistical multiple comparison methods", Scientist Press Co., Ltd. (2007)). As an example of the Bonferroni correction, for example, the P value obtained by a test is multiplied by the number of repetitions of the test, i.e., the number of genes used in the analysis, and the obtained value can be compared with a desired significance level to suppress a probability of causing type I error in the whole test.

Instead of the test, the absolute value (fold change) of an expression ratio of a median value of each gene expression level between gene expression levels of a pancreatic cancer patient group and gene expression levels of a healthy subject group may be calculated to select a gene that is used for an explanatory variable in a discriminant. Alternatively, ROC curves may be prepared using gene expression levels of a pancreatic cancer patient group and a healthy subject group, and a gene that is used for an explanatory variable in a discriminant can be selected on the basis of an AUROC value.

Next, a discriminant that can be calculated by various methods described above is prepared using any number of genes having large difference in their gene expression levels determined here. Examples of the method for constructing a discriminant that produces the largest discrimination accuracy include a method of constructing a discriminant in every combination of genes that satisfy the significance level being P value, and a method of repetitively evaluating the genes for use in the preparation of a discriminant while increasing the number of genes one by one in a descending order of difference in gene expression level (Furey T S. et al., 2000, Bioinformatics., Vol. 16, p. 906-14). A gene expression level of another independent pancreatic cancer patient or healthy subject is assigned as an explanatory variable to this discriminant to calculate discrimination results of the group to which this independent pancreatic cancer patient or healthy subject belongs. Specifically, the found gene set for diagnosis and the discriminant constructed using the gene set for diagnosis can be evaluated in an independent sample cohort to find a more universal gene set for diagnosis capable of detecting pancreatic cancer and a more universal method for discriminating pancreatic cancer.

Split-sample method is preferably used for evaluating the performance (generality) of the discriminant. Specifically, a data set is divided into a training cohort and a validation cohort, and gene selection by a statistical test and discriminant preparation are performed using the training cohort.

Accuracy, sensitivity, and specificity are calculated using a result of discriminating a validation cohort according to the discriminant, and a true group to which the validation cohort belongs, to evaluate the performance of the discriminant. On the other hand, instead of dividing a data set, the gene selection by a statistical test and discriminant preparation may be performed using all of samples, and accuracy, sensitivity, and specificity can be calculated by the discriminate analysis using a newly prepared sample cohort for evaluation of the performance of the discriminant.

The present invention provides polynucleotides for disease diagnosis useful in the diagnosis and treatment of pancreatic cancer, a method for detecting pancreatic cancer using the polynucleotide(s), and a kit and a device for the detection of pancreatic cancer, comprising the polynucleotide(s). Particularly, in order to select a gene(s) for diagnosis and prepare a discriminant so as to exhibit accuracy beyond the pancreatic cancer diagnosis methods using the existing tumor markers CEA and CA19-9, a gene set for diagnosis and a discriminant for the method of the present invention can be constructed, which exhibit accuracy beyond CEA and CA19-9, for example, by comparing expressed genes in serum from a patient confirmed to be negative using CEA and CA19-9 but finally found to have pancreatic cancer by detailed examination such as computed tomography using a contrast medium, with genes expressed in serum from a patient having no pancreatic cancer.

For example, the gene set for diagnosis is set to any combination selected from one or two or more of the polynucleotides based on a nucleotide sequence represented by any of SEQ ID NOs. 1 to 104, 464 to 473, and 492 to 494 or a nucleotide sequence derived from the nucleotide sequence by the replacement of u with t, or a complementary sequence thereof as described above; and optionally one or two or more of the polynucleotides based on a nucleotide sequence represented by any of SEQ ID NOs: 105 to 122 or a nucleotide sequence derived from the nucleotide sequence by the replacement of u with t, or a complementary sequence thereof; and optionally one or two or more of the polynucleotides based on a nucleotide sequence represented by any of SEQ ID NOs: 349 to 383 or a nucleotide sequence derived from the nucleotide sequence by the replacement of u with t, or a complementary sequence thereof. Further, a discriminant is constructed using expression levels of the gene set for diagnosis in samples from class I pancreatic cancer patients as a result of tissue diagnosis and samples from class II healthy subjects as a result of tissue diagnosis. As a result, the presence or absence of pancreatic cancer-derived genes in an unknown sample can be determined with 100% accuracy at the maximum by measuring expression levels of the gene set for diagnosis in an unknown sample.

EXAMPLES

Hereinafter, the present invention will be described further specifically with reference to Examples below. However, the scope of the present invention is not intended to be limited by these Examples.

Reference Example 1

<Collection of Samples of Pancreatic Cancer Patient and Healthy Subject>
Sera were collected using VENOJECT II vacuum blood collecting tube VP-AS109K60 (Terumo Corp., Japan) from 100 healthy subjects and 67 pancreatic cancer patients (1 case with stage IB, 10 cases with stage IIB, 17 cases with stage III, and 39 cases with stage IV) confirmed to have no cancer in organs other than the pancreas after obtainment of informed consent, and used as a training cohort. Likewise, sera were collected using VENOJECT II vacuum blood collecting tube VP-AS109K60 (Terumo Corp.) from 50 healthy subjects and 33 pancreatic cancer patients (1 case with stage IB, 2 cases with stage IIA, 4 cases with stage JIB, 11 cases with stage III, and 15 cases with stage IV) confirmed to have no cancer in organs other than the pancreas after obtainment of informed consent, and used as a validation cohort.
<Extraction of Total RNA>
Total RNA was obtained using a reagent for RNA extraction in 3D-Gene (RNA extraction reagent from liquid sample kit (Toray Industries, Inc., Japan) according to the protocol provided by the manufacturer from 300 µL of the serum sample obtained from each of 250 persons in total of 150 healthy subjects and 100 pancreatic cancer patients included in the training cohort and the validation cohort.
<Measurement of Gene Expression Level>
miRNAs in the total RNA obtained from the serum samples of each of 250 persons in total of 150 healthy subjects and 100 pancreatic cancer patients included in the training cohort and the validation cohort were fluorescently labeled using 3D-Gene™ miRNA Labeling kit (Toray Industries, Inc.) according to the protocol (ver 2.20) provided by the manufacturer. The oligo DNA chip used was 3D-Gene™ Human miRNA Oligo chip (Toray Industries, Inc.) with attached probes having sequences complementary to 2,555 miRNAs among the miRNAs registered in miRBase Release 20. Hybridization under stringent conditions and washing following the hybridization were performed according to the protocol provided by the manufacturer. The DNA chip was scanned using 3D-Gene™ scanner (Toray Industries, Inc.) to obtain images. Fluorescence intensity was digitized using 3D-Gene™ Extraction (Toray Industries, Inc.). The digitized fluorescence intensity was converted to a logarithmic value having a base of 2 and used as a gene expression level, from which a blank value was subtracted. A missing value was replaced with a value obtained by subtracting 0.1 from a logarithmic value of the smallest value of the gene expression level in each DNA chip. As a result, the comprehensive gene expression levels of the miRNAs in the sera were obtained for the 100 pancreatic cancer patients and the 150 healthy subjects. Calculation and statistical analysis using the digitized gene expression levels of the miRNAs were carried out using R language 3.0.2 (R Development Core Team (2013). R: A language and environment for statistical computing. R Foundation for Statistical Computing, URL http://www.R-project.org/.) and MASS package 7.3-30 (Venables, W. N. & Ripley, B. D. (2002) Modern Applied Statistics with S. Fourth Edition. Springer, New York. ISBN 0-387-95457-0).

Reference Example 21

<Collection of Samples of Other Cancers and Benign Diseases>
Sera were collected using VENOJECT II vacuum blood collecting tube VP-AS109K60 (Terumo Corp.) from each of 35 colorectal cancer patients, 37 stomach cancer patients, 32 esophageal cancer patients, 38 liver cancer patients, and 13 benign pancreaticobiliary disease patients confirmed to have no cancer in other organs after obtainment of informed consent, and used as a training cohort together with the samples of 67 pancreatic cancer patients (1 case with stage IIA, 11 cases with stage IIB, 17 cases with stage III, and 38 cases with stage IV) and 93 healthy subjects of Reference Example 1. Likewise, sera were collected using VENOJECT II vacuum blood collecting tube VP-AS109K60 (Terumo Corp.) from each of 15 colorectal cancer patients, 13 stomach cancer patients, 18 esophageal cancer patients, 12 liver cancer patients, and 8 benign pancreaticobiliary disease patients confirmed to have no cancer in other organs after obtainment of informed consent, and used as a validation cohort together with the samples of 33 pancreatic cancer patients (2 cases with stage IB, 1 case with stage IIA, 3 cases with stage IIB, 11 cases with stage III, and 16 cases with stage IV) and 57 healthy subjects of Reference Example 1. Subsequent extraction of total RNA and measurement and analysis of gene expression levels were conducted in the same way as in Reference Example 1.

Example 1

<Selection of Gene Markers Using the Training Cohort, and Method for Evaluating Pancreatic Cancer Discriminant Performance of the Single Gene Marker Using the Validation Cohort>

In this Example, a gene marker for discriminating a pancreatic cancer patient from a healthy subject was selected from the training cohort and studied in the validation cohort independent of the training cohort.

Specifically, first, the miRNA expression levels of the training cohort and the validation cohort obtained in the preceding Reference Examples were combined and normalized by quantile normalization.

Next, genes for diagnosis were selected using the training cohort. Here, in order to acquire diagnostic markers with higher reliability, only genes having the expression level of $2^6$ or higher in 50% or more of the samples in either of the pancreatic cancer patient group of the training cohort or the healthy subject group of the training cohort were selected. In order to further acquire statistically significant genes for discriminating a pancreatic cancer patient group from a healthy subject group, the P value obtained by two-tailed t-test assuming equal variance as to each gene expression level was corrected by the Bonferroni method, and genes that satisfied p<0.01 were acquired as gene markers for use in explanatory variables of a discriminant and described in Table 2.

In this way, hsa-miR-6893-5p, hsa-miR-6075, hsa-miR-6820-5p, hsa-miR-4294, hsa-miR-6729-5p, hsa-miR-4476, hsa-miR-6836-3p, hsa-miR-6765-3p, hsa-miR-6799-5p, hsa-miR-4530, hsa-miR-7641, hsa-miR-4454, hsa-miR-615-5p, hsa-miR-8073, hsa-miR-663a, hsa-miR-4634, hsa-miR-4450, hsa-miR-4792, hsa-miR-665, hsa-miR-7975, hsa-miR-7109-5p, hsa-miR-6789-5p, hsa-miR-4497, hsa-miR-6877-5p, hsa-miR-6880-5p, hsa-miR-7977, hsa-miR-4734, hsa-miR-6821-5p, hsa-miR-8089, hsa-miR-5585-3p, hsa-miR-6085, hsa-miR-6845-5p, hsa-miR-4651, hsa-miR-4433-3p, hsa-miR-1231, hsa-miR-4665-5p, hsa-miR-7114-5p, hsa-miR-1238-5p, hsa-miR-8069, hsa-miR-4732-5p, hsa-miR-619-5p, hsa-miR-3622a-5p, hsa-miR-1260a, hsa-miR-6741-5p, hsa-miR-6781-5p, hsa-miR-6125, hsa-miR-6805-5p, hsa-miR-6132, hsa-miR-6872-3p, hsa-miR-6875-5p, hsa-miR-1908-3p, hsa-miR-4433b-3p, hsa-miR-4736, hsa-miR-5100, hsa-miR-6724-5p, hsa-miR-7107-5p, hsa-miR-6726-5p, hsa-miR-3185, hsa-miR-4638-5p, hsa-miR-1273g-3p, hsa-miR-6778-5p, hsa-miR-328-5p, hsa-miR-3679-3p, hsa-miR-1228-3p, hsa-miR-6779-5p, hsa-miR-4723-5p, hsa-miR-6850-5p, hsa-miR-760, hsa-miR-7704, hsa-miR-8072, hsa-miR-4486, hsa-miR-1913, hsa-miR-4656, hsa-miR-1260b, hsa-miR-7106-5p, hsa-miR-6889-5p, hsa-miR-6780b-5p, hsa-miR-6090, hsa-miR-4534, hsa-miR-4449, hsa-miR-5195-3p, hsa-miR-1202, hsa-miR-4467, hsa-miR-6515-3p, hsa-miR-4281, hsa-miR-4505, hsa-miR-4484, hsa-miR-6805-3p, hsa-miR-3135b, hsa-miR-3162-5p, hsa-miR-6768-5p, hsa-miR-6721-5p, hsa-miR-1227-5p, hsa-miR-6722-3p, hsa-miR-4286, hsa-miR-4746-3p, hsa-miR-6727-5p, hsa-miR-6816-5p, hsa-miR-4741, hsa-miR-4508, hsa-miR-940, hsa-miR-4327, hsa-miR-4665-3p, hsa-miR-718, hsa-miR-125a-3p, hsa-miR-204-3p, hsa-miR-1469, hsa-miR-575, hsa-miR-150-3p, hsa-miR-423-5p, hsa-miR-564, hsa-miR-3188, hsa-miR-1246, hsa-miR-602, hsa-miR-1290, hsa-miR-16-5p, hsa-miR-451a, hsa-miR-24-3p, hsa-miR-187-5p, hsa-miR-1908-5p, hsa-miR-371a-5p, and hsa-miR-550a-5p genes, and the nucleotide sequences of SEQ ID NOs: 1 to 122 related thereto were found.

A discriminant for determining the presence or absence of pancreatic cancer was further prepared by Fishers discriminant analysis with the expression levels of these genes as indicators. Specifically, any newly found polynucleotide consisting of a nucleotide sequence represented by any of SEQ ID NOs: 1 to 104 among the 122 genes selected in the training cohort was input to Formula 2 above to prepare a discriminant. Calculated accuracy, sensitivity, and specificity are shown in Table 3. In this respect, a discriminant coefficient and a constant term are shown in Table 4.

Figure 2:
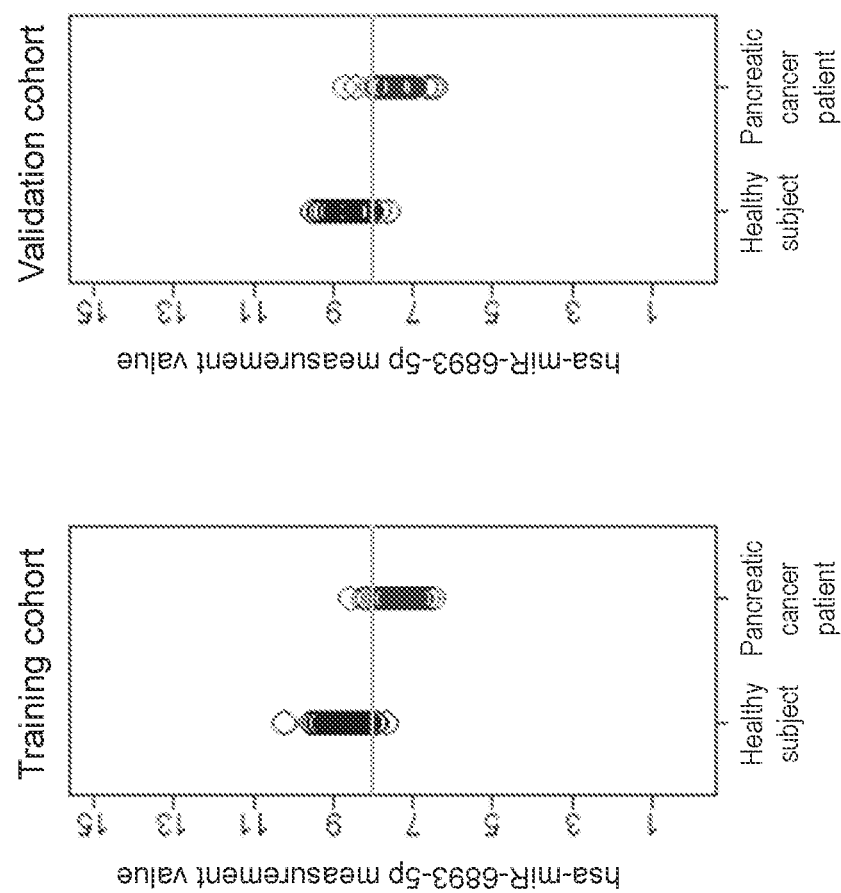
FIG. 2 Left diagram: the expression level measurement values of hsa-miR-6893-5p (SEQ ID NO: 1) in healthy subjects (100 persons) and pancreatic cancer patients (67 persons) selected as a training cohort were each plotted on the ordinate. The horizontal line in the diagram depicts a threshold (8.02) that was optimized by Fisher's discriminant analysis and discriminated between the two groups. Right diagram: the expression level measurement values of hsa-miR-6893-5p (SEQ ID NO: 1) in healthy subjects (50 persons) and pancreatic cancer patients (33 persons) selected as a validation cohort were each plotted on the ordinate. The horizontal line in the diagram depicts the threshold (8.02) that was set in the training cohort and discriminated between the two groups.

Next, accuracy, sensitivity, and specificity in the validation cohort were calculated using the discriminant thus prepared, and the discriminant performance of the selected polynucleotides was validated using independent samples (Table 3). For example, the expression level measurement value of the nucleotide sequence represented by SEQ ID NO: 1 was compared between the healthy subjects (50 persons) and the pancreatic cancer patients (33 persons) in the validation cohort. As a result, the gene expression level measurement values in the training cohort were found to be significantly lower in the pancreatic cancer patient group than in the healthy subject group (see the left diagram of FIG. 2). These results were also reproducible in the validation cohort (see the right diagram of FIG. 2). Likewise, the results obtained about the other polynucleotides shown in SEQ ID NOs: 1 to 122 showed that the gene expression level measurement values were significantly lower (−) or higher (+) in the pancreatic cancer patient group than in the healthy subject group (Table 2). These results were able to be validated in the validation cohort. For example, as for this nucleotide sequence represented by SEQ ID NO: 1, the number of correctly or incorrectly identified samples in the detection of pancreatic cancer was calculated using the threshold (8.02) that was set in the training cohort and discriminated between the two groups. As a result, 30 true positives, 49 true negatives, 1 false positive, and 3 false negatives were obtained. From these values, 95% accuracy, 91% sensitivity, and 98% specificity were obtained as the detection performance. In this way, the detection performance was calculated as to all of the polynucleotides shown in SEQ ID NOs: 1 to 122, and described in Table 3. Among the polynucleotides consisting of the nucleotide sequences represented by SEQ ID NOs: 1 to 104 shown in Table 2, for example, 14 polynucleotides consisting of the nucleotide sequences represented by SEQ ID NOs: 1, 2, 4, 5, 7, 9, 11, 18, 21, 22, 24, 25, 35, and 46 exhibited sensitivity of 87.9%, 90.9%, 87.9%, 81.8%, 90.9%, 78.8%, 78.8%, 78.8%, 84.8%, 78.8%, 81.8%, 81.8%, 93.9%, and 81.8%, respectively, in the validation cohort (Table 3). Also, these polynucleotides were able to correctly identify one stage 1 pancreatic cancer sample contained in the validation cohort as a pancreatic cancer sample. Furthermore, these polynucleotides were able to correctly discriminate pancreatic cancer as to any of the tumors occupying the head, the body, and the tail of the pancreas in the validation cohort, and, particularly, were able to detect tumors even in the tail of the pancreas, which are prone to delayed diagnosis. As seen from Comparative Example mentioned later, the existing markers CEA and CA19-9 had sensitivity of 45.5% and 75.8%, respectively, in the validation cohort (Table 5), demonstrating that, for example, the 14 polynucleotides consisting of the nucleotide sequences represented by SEQ ID Nos: 1, 2, 4, 5, 7, 9, 11, 18, 21, 22, 24, 25, 35, and 46 can discriminate, each alone, pancreatic cancer in the validation cohort with sensitivity beyond CA19-9.

Example 21

<Method a for Evaluating Pancreatic Cancer Discriminant Performance by Combination of Plurality of Gene Markers Using Samples in the Validation Cohort>

In this Example, a method for evaluating pancreatic cancer discriminant performance by a combination of the gene markers selected in Example 1 was studied.

Figure 3:
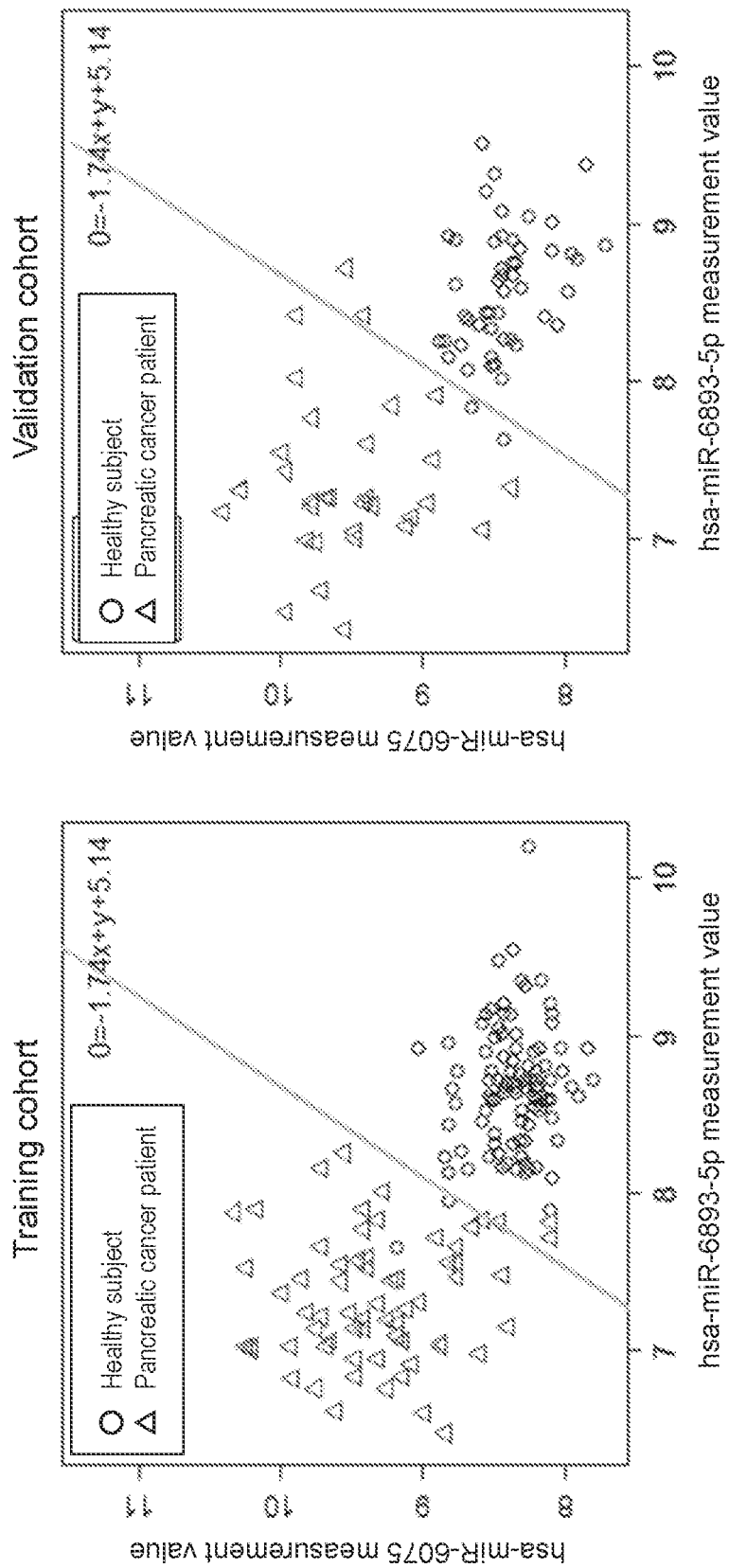
FIG. 3 Left diagram: the expression level measurement values of hsa-miR-6893-5p (SEQ ID NO: 1) in healthy subjects (100 persons, circles) and pancreatic cancer patients (67 persons, triangles) selected as a training cohort were each plotted on the abscissa against their expression level measurement values of hsa-miR-6075 (SEQ ID NO: 2) on the ordinate. The line in the diagram depicts a discriminant function (0=1.74x+y+5.14) that was optimized by Fisher's discriminant analysis and discriminated between the two groups. Right diagram: the expression level measurement values of hsa-miR-6893-5p (SEQ ID NO: 1) in healthy subjects (50 persons, circles) and pancreatic cancer patients (33 persons, triangles) selected as a validation cohort were each plotted on the abscissa against their expression level measurement values of hsa-miR-6075 (SEQ ID NO: 2) on the ordinate. The line in the diagram depicts the threshold (0=1.74x+y+5.14) that was set in the training cohort and discriminated between the two groups.

Specifically. Fisher's discriminant analysis was conducted as to 7,228 combinations of two expression level measurement values comprising at least one or more of the expression level measurement values of the newly found polynucleotides consisting of the nucleotide sequences represented by SEQ ID NOs: 1 to 104 among the polynucleotides consisting of the nucleotide sequences represented by SEQ ID NOs: 1 to 122 selected in Example 1, to construct a discriminant for determining the presence or absence of pancreatic cancer. Next, accuracy, sensitivity, and specificity in the validation cohort were calculated using the discriminant thus prepared, and the discriminant performance of the selected polynucleotides was validated using independent samples. For example, the expression level measurement values of the nucleotide sequences represented by SEQ ID NO: 1 and SEQ ID NO: 2 were compared between the healthy subjects (50 persons) and the pancreatic cancer patients (33 persons) in the validation cohort. As a result, a scatter diagram that significantly separated the expression level measurement values of the pancreatic cancer patient group from those of the healthy subject group was obtained in the training cohort (see the left diagram of FIG. 3). These results were also reproducible in the validation cohort (see the right diagram of FIG. 3). Likewise, a scatter diagram that significantly separated the gene expression level measurement values of the pancreatic cancer patient group from those of the healthy subject group was also obtained as to the other combinations of two expression level measurement values comprising at least one or more of the expression level measurement values of the newly found polynucleotides consisting of the nucleotide sequences represented by SEQ ID NOs: 1 to 104 among the polynucleotides consisting of the nucleotide sequences represented by SEQ ID NOs: 1 to 122. These results were able to be validated in the validation cohort. For example, as for these nucleotide sequences represented by SEQ ID NO: 1 and SEQ ID NO: 2, the number of samples that were correctly or incorrectly identified pancreatic cancer was calculated using the threshold (0=1.74x+y+5.14) that was set in the training cohort and discriminated between the two groups. As a result, 30 true positives, 49 true negatives, 1 false positive, and 3 false negatives were obtained. From these values, 95% accuracy, 91% sensitivity, and 98% specificity were obtained as the detection performance. In this way, the detection performance was calculated for the combinations of two expression level measurement values comprising at least one or more of the expression level measurement values of the newly found polynucleotides consisting of the nucleotide sequences represented by SEQ ID NOs: 1 to 104 among the polynucleotides consisting of the nucleotide sequences represented by SEQ ID NOs: 1 to 122, and the 2,619 combinations that showed sensitivity better than the sensitivity (75.8%) of the existing marker in the validation cohort, were described in Table 6.

The discriminant analysis for pancreatic cancer in the validation cohort was performed using the 7,228 combinations of the expression level measurement values of the polynucleotides. As a result, for example, the combinations of the expression level measurement values of the polynucleotides consisting of the nucleotide sequences represented by SEQ ID NOs: 2 and 105, SEQ ID NOs: 18 and 105, SEQ ID NOs: 46 and 105, and SEQ ID NOs: 55 and 105 exhibited sensitivity of 10/o, 100%, and 100%, respectively, in the validation cohort. In this way, the 2,691 combinations of the expression level measurement values of the polynucleotides having sensitivity beyond the existing marker CA19-9 (Table 5) were obtained in the validation cohort. All of the nucleotide sequences 1 to 122 described in Table 2 obtained in Example 1 were employed at least once in these combinations. These results demonstrated that the combinations of two expression level measurement values comprising at least one or more of the expression level measurement values of the polynucleotides consisting of the nucleotide sequences represented by SEQ ID NOs: 1 to 122 can detect pancreatic cancer with sensitivity beyond CA19-9 in the validation cohort.

Thus, markers capable of detecting pancreatic cancer with excellent sensitivity are obtained even if 3, 4, 5, 6, 7, 8, 9, 10 or more of the expression level measurement values of the polynucleotides consisting of the nucleotide sequences represented by SEQ ID NOs: 1 to 122 are combined. For example, the polynucleotides consisting of the nucleotide sequences represented by SEQ ID NOs: 1 to 122 selected in Example 1 were ranked in the descending order of their P values which indicate statistical significance, and detection performance was calculated using combinations of one or more miRNAs to which the miRNAs were added one by one from the top to the bottom according to the rank. As a result, the sensitivity in the validation cohort was 87.9% for 2 miRNAs, 90.9% for 3 miRNAs, 100% for 5 miRNAs, 100% for 10 miRNAs, 100% for 20 miRNAs, 100% for 50 miRNAs, 100% for 100 miRNAs, and 100% for 122 miRNAs. These values of the sensitivity were higher than the sensitivity of the existing tumor marker in blood, demonstrating that even combinations of a plurality of the miRNAs can serve as excellent markers for the detection of pancreatic cancer. In this context, the combinations of a plurality of the miRNAs are not limited to the combinations of the miRNAs added in the order of statistically significant difference as described above, and any combination of a plurality of the miRNAs can be used in the detection of pancreatic cancer.

From these results, it can be concluded that all of the polynucleotides consisting of the nucleotide sequences represented by SEQ ID NOs: 1 to 122 serve as excellent diagnostic markers.

Tables 2, 3, 4, 5, and 6 mentioned above are as follows.

TABLE 2

| SEQ ID NO: | Gene name | P value after Bonferroni correction | Expression level in pancreatic cancer patient relative to healthy subject |
|---|---|---|---|
| 1 | hsa-miR-6893-5p | 7.19E−46 | − |
| 2 | hsa-miR-6075 | 1.91E−29 | + |
| 3 | hsa-miR-6820-5p | 1.78E−27 | − |
| 4 | hsa-miR-4294 | 3.27E−27 | − |
| 5 | hsa-miR-6729-5p | 6.76E−26 | + |
| 6 | hsa-miR-4476 | 8.49E−25 | − |
| 7 | hsa-miR-6836-3p | 1.97E−22 | + |
| 8 | hsa-miR-6765-3p | 4.75E−22 | − |
| 9 | hsa-miR-6799-5p | 5.00E−19 | − |
| 10 | hsa-miR-4530 | 9.09E−19 | − |
| 11 | hsa-miR-7641 | 7.84E−18 | − |
| 12 | hsa-miR-4454 | 1.29E−17 | − |
| 13 | hsa-miR-615-5p | 3.14E−17 | − |
| 14 | hsa-miR-8073 | 3.61E−17 | + |
| 15 | hsa-miR-663a | 1.72E−16 | + |
| 16 | hsa-miR-4634 | 2.55E−16 | + |
| 17 | hsa-miR-4450 | 3.14E−16 | − |
| 18 | hsa-miR-4792 | 3.80E−16 | + |
| 19 | hsa-miR-665 | 7.86E−16 | + |
| 20 | hsa-miR-7975 | 8.48E−15 | − |
| 21 | hsa-miR-7109-5p | 3.23E−14 | − |
| 22 | hsa-miR-6789-5p | 4.58E−13 | + |
| 23 | hsa-miR-4497 | 5.38E−13 | − |
| 24 | hsa-miR-6877-5p | 5.58E−13 | − |
| 25 | hsa-miR-6880-5p | 6.14E−13 | − |
| 26 | hsa-miR-7977 | 6.28E−13 | − |
| 27 | hsa-miR-4734 | 6.79E−13 | + |
| 28 | hsa-miR-6821-5p | 8.22E−13 | − |
| 29 | hsa-miR-8089 | 9.61E−13 | − |
| 30 | hsa-miR-5585-3p | 1.38E−12 | + |
| 31 | hsa-miR-6085 | 4.32E−12 | − |
| 32 | hsa-miR-6845-5p | 1.41E−11 | + |
| 33 | hsa-miR-4651 | 1.53E−11 | − |
| 34 | hsa-miR-4433-3p | 5.65E−11 | + |
| 35 | hsa-miR-1231 | 1.38E−10 | + |
| 36 | hsa-miR-4665-5p | 2.54E−10 | − |
| 37 | hsa-miR-7114-5p | 5.73E−10 | − |
| 38 | hsa-miR-1238-5p | 6.26E−10 | + |
| 39 | hsa-miR-8069 | 7.39E−10 | + |
| 40 | hsa-miR-4732-5p | 8.03E−10 | + |
| 41 | hsa-miR-619-5p | 2.23E−09 | + |
| 42 | hsa-miR-3622a-5p | 2.53E−09 | − |
| 43 | hsa-miR-1260a | 3.84E−09 | − |
| 44 | hsa-miR-6741-5p | 6.57E−09 | − |
| 45 | hsa-miR-6781-5p | 6.86E−09 | + |
| 46 | hsa-miR-6125 | 7.51E−09 | + |
| 47 | hsa-miR-6805-5p | 8.71E−09 | + |
| 48 | hsa-miR-6132 | 1.71E−08 | − |
| 49 | hsa-miR-6872-3p | 1.74E−08 | − |
| 50 | hsa-miR-6875-5p | 2.76E−08 | + |
| 51 | hsa-miR-1908-3p | 2.77E−08 | + |
| 52 | hsa-miR-4433b-3p | 5.12E−08 | + |
| 53 | hsa-miR-4736 | 5.45E−08 | + |
| 54 | hsa-miR-5100 | 7.94E−08 | − |
| 55 | hsa-miR-6724-5p | 9.14E−08 | + |
| 56 | hsa-miR-7107-5p | 9.80E−08 | − |
| 57 | hsa-miR-6726-5p | 2.49E−07 | − |
| 58 | hsa-miR-3185 | 2.57E−07 | + |
| 59 | hsa-miR-4638-5p | 6.78E−07 | − |
| 60 | hsa-miR-1273g-3p | 6.87E−07 | + |
| 61 | hsa-miR-6778-5p | 6.95E−07 | + |
| 62 | hsa-miR-328-Sp | 7.01E−07 | − |
| 63 | hsa-miR-3679-3p | 7.68E−07 | + |
| 64 | hsa-miR-1228-3p | 9.27E−07 | + |
| 65 | hsa-miR-6779-5p | 1.28E−06 | − |
| 66 | hsa-miR-4723-5p | 1.35E−06 | − |
| 67 | hsa-miR-6850-5p | 1.68E−06 | + |
| 68 | hsa-miR-760 | 1.69E−06 | − |
| 69 | hsa-miR-7704 | 1.82E−06 | − |
| 70 | hsa-miR-8072 | 5.28E−06 | + |
| 71 | hsa-miR-4486 | 8.48E−06 | + |
| 72 | hsa-miR-1913 | 1.02E−05 | + |
| 73 | hsa-miR-4656 | 1.36E−05 | + |
| 74 | hsa-miR-1260b | 3.21E−05 | − |
| 75 | hsa-miR-7106-5p | 3.55E−05 | − |
| 76 | hsa-miR-6889-5p | 4.00E−05 | − |
| 77 | hsa-miR-6780b-5p | 4.32E−05 | + |
| 78 | hsa-miR-6090 | 5.02E−05 | + |
| 79 | hsa-miR-4534 | 1.36E−04 | − |
| 80 | hsa-miR-4449 | 1.63E−04 | + |
| 81 | hsa-miR-5195-3p | 1.70E−04 | − |
| 82 | hsa-miR-1202 | 1.83E−04 | − |
| 83 | hsa-miR-4467 | 7.51E−04 | + |
| 84 | hsa-miR-6515-3p | 8.23E−04 | + |
| 85 | hsa-miR-4281 | 8.83E−04 | − |
| 86 | hsa-miR-4505 | 8.88E−04 | − |
| 87 | hsa-miR-4484 | 9.98E−04 | + |
| 88 | hsa-miR-6805-3p | 1.04E−03 | + |
| 89 | hsa-miR-3135b | 1.11E−03 | − |
| 90 | hsa-miR-3162-5p | 1.26E−03 | − |
| 91 | hsa-miR-6768-5p | 1.45E−03 | − |
| 92 | hsa-miR-6721-5p | 1.57E−03 | + |
| 93 | hsa-miR-1227-5p | 1.65E−03 | + |
| 94 | hsa-miR-6722-3p | 1.66E−03 | + |
| 95 | hsa-miR-4286 | 1.73E−03 | − |
| 96 | hsa-miR-4746-3p | 1.83E−03 | + |
| 97 | hsa-miR-6727-5p | 3.32E−03 | − |
| 98 | hsa-miR-6816-5p | 4.09E−03 | + |
| 99 | hsa-miR-4741 | 4.57E−03 | + |
| 100 | hsa-miR-4508 | 6.50E−03 | + |
| 101 | hsa-miR-940 | 7.02E−03 | − |
| 102 | hsa-miR-4327 | 7.54E−03 | − |
| 103 | hsa-miR-4665-3p | 7.88E−03 | + |
| 104 | hsa-miR-718 | 9.73E−03 | + |
| 105 | hsa-miR-125a-3p | 2.01E−50 | − |
| 106 | hsa-miR-204-3p | 1.58E−30 | − |
| 107 | hsa-miR-1469 | 1.67E−28 | + |
| 108 | hsa-miR-575 | 1.50E−26 | − |
| 109 | hsa-miR-150-3p | 7.09E−23 | − |
| 110 | hsa-miR-423-5p | 4.74E−21 | − |
| 111 | hsa-miR-564 | 2.56E−10 | − |
| 112 | hsa-miR-3188 | 2.93E−09 | + |
| 113 | hsa-miR-1246 | 3.33E−08 | + |
| 114 | hsa-miR-602 | 1.67E−06 | + |
| 115 | hsa-miR-1290 | 3.00E−06 | + |
| 116 | hsa-miR-16-5p | 3.74E−06 | − |
| 117 | hsa-miR-451a | 1.28E−05 | − |
| 118 | hsa-miR-24-3p | 4.71E−05 | − |
| 119 | hsa-miR-187-5p | 1.11E−04 | − |
| 120 | hsa-miR-1908-5p | 4.29E−04 | + |
| 121 | hsa-miR-371a-5p | 1.56E−03 | − |
| 122 | hsa-miR-550a-5p | 8.60E−03 | + |

TABLE 3

| | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 1 | 95.8 | 94 | 97 | 92.8 | 87.9 | 96 |
| 2 | 88.6 | 74.6 | 98 | 96.4 | 90.9 | 100 |

TABLE 3-continued

| | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 3 | 90.4 | 85.1 | 94 | 78.3 | 66.7 | 86 |
| 4 | 86.8 | 74.6 | 95 | 88 | 87.9 | 88 |
| 5 | 88 | 85.1 | 90 | 84.3 | 81.8 | 86 |
| 6 | 86.2 | 73.1 | 95 | 81.9 | 69.7 | 90 |
| 7 | 91.6 | 86.6 | 95 | 92.8 | 90.9 | 94 |
| 8 | 85 | 73.1 | 93 | 84.3 | 69.7 | 94 |
| 9 | 85 | 80.6 | 88 | 83.1 | 78.8 | 86 |
| 10 | 83.2 | 77.6 | 87 | 79.5 | 75.8 | 82 |
| 11 | 79 | 68.7 | 86 | 81.9 | 78.8 | 84 |
| 12 | 81.9 | 71.2 | 89 | 80.7 | 66.7 | 90 |
| 13 | 82 | 77.6 | 85 | 81.9 | 72.7 | 88 |
| 14 | 82 | 65.7 | 93 | 78.3 | 54.5 | 94 |
| 15 | 83.2 | 64.2 | 96 | 85.5 | 66.7 | 98 |
| 16 | 80.8 | 73.1 | 86 | 74.7 | 63.6 | 82 |
| 17 | 83.8 | 65.7 | 96 | 81.9 | 72.7 | 88 |
| 18 | 85 | 77.6 | 90 | 89.2 | 78.8 | 96 |
| 19 | 79.6 | 64.2 | 90 | 81.9 | 63.6 | 94 |
| 20 | 75.4 | 64.2 | 83 | 73.5 | 51.5 | 88 |
| 21 | 76.6 | 70.1 | 81 | 81.9 | 84.8 | 80 |
| 22 | 77.8 | 62.7 | 88 | 83.1 | 78.8 | 86 |
| 23 | 75.4 | 58.2 | 87 | 65.9 | 46.9 | 78 |
| 24 | 76 | 59.7 | 87 | 83.1 | 81.8 | 84 |
| 25 | 80.8 | 67.2 | 90 | 86.7 | 81.8 | 90 |
| 26 | 76.6 | 61.2 | 87 | 73.5 | 48.5 | 90 |
| 27 | 77.2 | 62.7 | 87 | 75.9 | 51.5 | 92 |
| 28 | 76 | 65.7 | 83 | 71.1 | 69.7 | 72 |
| 29 | 76 | 62.7 | 85 | 74.7 | 63.6 | 82 |
| 30 | 79.6 | 68.7 | 87 | 83.1 | 63.6 | 96 |
| 31 | 76 | 62.7 | 85 | 74.7 | 72.7 | 76 |
| 32 | 79 | 64.2 | 89 | 71.1 | 48.5 | 86 |
| 33 | 78.4 | 58.2 | 92 | 80.7 | 60.6 | 94 |
| 34 | 79 | 74.6 | 82 | 75.9 | 66.7 | 82 |
| 35 | 77.8 | 61.2 | 89 | 88 | 93.9 | 84 |
| 36 | 76 | 59.7 | 87 | 69.9 | 51.5 | 82 |
| 37 | 74.9 | 61.2 | 84 | 79.5 | 63.6 | 90 |
| 38 | 77.8 | 52.2 | 95 | 78.3 | 51.5 | 96 |
| 39 | 74.9 | 52.2 | 90 | 83.1 | 66.7 | 94 |
| 40 | 79.6 | 56.7 | 95 | 75.9 | 54.5 | 90 |
| 41 | 76 | 56.7 | 89 | 75.9 | 45.5 | 96 |
| 42 | 78.4 | 53.7 | 95 | 78.3 | 66.7 | 86 |
| 43 | 75.4 | 61.2 | 85 | 68.7 | 36.4 | 90 |
| 44 | 77.8 | 61.2 | 89 | 75.9 | 57.6 | 88 |
| 45 | 71.9 | 59.7 | 80 | 69.9 | 54.5 | 80 |
| 46 | 75.4 | 62.7 | 84 | 84.3 | 81.8 | 86 |
| 47 | 71.3 | 50.7 | 85 | 68.7 | 45.5 | 84 |
| 48 | 75.4 | 56.7 | 88 | 73.5 | 48.5 | 90 |
| 49 | 72.5 | 53.7 | 85 | 66.3 | 39.4 | 84 |
| 50 | 68.9 | 49.3 | 82 | 75.6 | 68.8 | 80 |
| 51 | 77.2 | 62.7 | 87 | 78.3 | 66.7 | 86 |
| 52 | 78.4 | 70.1 | 84 | 72.3 | 63.6 | 78 |
| 53 | 74.9 | 55.2 | 88 | 73.5 | 51.5 | 88 |
| 54 | 74.9 | 53.7 | 89 | 72.3 | 51.5 | 86 |
| 55 | 73.7 | 56.7 | 85 | 74.7 | 63.6 | 82 |
| 56 | 72.5 | 56.7 | 83 | 67.5 | 54.5 | 76 |
| 57 | 74.9 | 47.8 | 93 | 78.3 | 54.5 | 94 |
| 58 | 75.4 | 56.7 | 88 | 81.9 | 72.7 | 88 |
| 59 | 75.4 | 55.2 | 89 | 75.9 | 57.6 | 88 |
| 60 | 74.3 | 46.3 | 93 | 71.1 | 39.4 | 92 |
| 61 | 74.3 | 52.2 | 89 | 72.3 | 42.4 | 92 |
| 62 | 71.3 | 64.2 | 76 | 69.9 | 57.6 | 78 |
| 63 | 67.1 | 47.8 | 80 | 61.4 | 42.4 | 74 |
| 64 | 74.3 | 59.7 | 84 | 74.7 | 66.7 | 80 |
| 65 | 71.9 | 55.2 | 83 | 79.5 | 66.7 | 88 |
| 66 | 77.8 | 64.2 | 87 | 81.9 | 75.8 | 86 |
| 67 | 70.1 | 47.8 | 85 | 75.9 | 69.7 | 80 |
| 68 | 69.5 | 46.3 | 85 | 68.7 | 45.5 | 84 |
| 69 | 74.9 | 62.7 | 83 | 63.9 | 54.5 | 70 |
| 70 | 77.2 | 59.7 | 89 | 71.1 | 60.6 | 78 |
| 71 | 70.7 | 46.3 | 87 | 72.3 | 42.4 | 92 |
| 72 | 70.7 | 50.7 | 84 | 65.9 | 39.4 | 83.7 |
| 73 | 72.5 | 47.8 | 89 | 69.9 | 33.3 | 94 |
| 74 | 71.3 | 44.8 | 89 | 71.1 | 45.5 | 88 |
| 75 | 71.9 | 50.7 | 86 | 78.3 | 69.7 | 84 |
| 76 | 65.3 | 37.3 | 84 | 65.1 | 30.3 | 88 |
| 77 | 71.9 | 50.7 | 86 | 75.3 | 58.1 | 86 |

TABLE 3-continued

| | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 78 | 68.3 | 56.7 | 76 | 68.7 | 66.7 | 70 |
| 79 | 74.9 | 53.7 | 89 | 79.5 | 69.7 | 86 |
| 80 | 70.1 | 43.3 | 88 | 75.9 | 54.5 | 90 |
| 81 | 71.7 | 51.5 | 85 | 75.9 | 57.6 | 88 |
| 82 | 65.3 | 40.3 | 82 | 74.7 | 60.6 | 84 |
| 83 | 65.9 | 38.8 | 84 | 77.1 | 63.6 | 86 |
| 84 | 66.5 | 43.3 | 82 | 60.2 | 36.4 | 76 |
| 85 | 66.5 | 46.3 | 80 | 74.7 | 45.5 | 94 |
| 86 | 71.9 | 44.8 | 90 | 67.5 | 36.4 | 88 |
| 87 | 64.7 | 41.8 | 80 | 65.1 | 36.4 | 84 |
| 88 | 64.7 | 40.3 | 81 | 67.5 | 45.5 | 82 |
| 89 | 71.9 | 47.8 | 88 | 77.1 | 57.6 | 90 |
| 90 | 70.7 | 41.8 | 90 | 72.3 | 45.5 | 90 |
| 91 | 70.7 | 43.3 | 89 | 69.9 | 42.4 | 88 |
| 92 | 68.9 | 50.7 | 81 | 68.7 | 57.6 | 76 |
| 93 | 62.9 | 38.8 | 79 | 69.9 | 51.5 | 82 |
| 94 | 68.3 | 35.8 | 90 | 78.3 | 63.6 | 88 |
| 95 | 66.5 | 41.8 | 83 | 60.2 | 27.3 | 82 |
| 96 | 70.1 | 44.8 | 87 | 79.5 | 60.6 | 78 |
| 97 | 73.7 | 49.3 | 90 | 69.9 | 45.5 | 84 |
| 98 | 75.3 | 57.6 | 87 | 77.1 | 60.6 | 86 |
| 99 | 67.7 | 43.3 | 84 | 73.5 | 54.5 | 82 |
| 100 | 64.1 | 28.4 | 88 | 63.9 | 39.4 | 90 |
| 101 | 62.9 | 31.3 | 84 | 62.7 | 27.3 | 94 |
| 102 | 68.9 | 43.3 | 86 | 66.3 | 24.2 | 84 |
| 103 | 72.5 | 46.3 | 90 | 74.7 | 63.6 | 82 |
| 104 | 70.1 | 44.8 | 87 | 68.7 | 45.5 | 86 |

TABLE 4

| SEQ ID NO: | Discriminant coefficient | Constant term |
|---|---|---|
| 1 | 2.460 | 19.714 |
| 2 | 2.382 | 21.068 |
| 3 | 3.095 | 21.899 |
| 4 | 2.352 | 23.243 |
| 5 | 7.904 | 99.660 |
| 6 | 1.427 | 9.523 |
| 7 | 2.999 | 26.661 |
| 8 | 1.567 | 13.180 |
| 9 | 4.320 | 34.683 |
| 10 | 2.347 | 21.497 |
| 11 | 1.240 | 8.775 |
| 12 | 2.099 | 24.008 |
| 13 | 2.507 | 16.240 |
| 14 | 2.542 | 16.656 |
| 15 | 3.003 | 30.919 |
| 16 | 5.690 | 56.064 |
| 17 | 1.236 | 6.777 |
| 18 | 1.762 | 12.038 |
| 19 | 2.603 | 19.023 |
| 20 | 1.993 | 19.451 |
| 21 | 5.292 | 39.055 |
| 22 | 4.377 | 43.459 |
| 23 | 2.108 | 26.455 |
| 24 | 3.957 | 28.165 |
| 25 | 2.128 | 15.182 |
| 26 | 1.961 | 18.889 |
| 27 | 4.907 | 58.675 |
| 28 | 4.501 | 38.362 |
| 29 | 3.320 | 21.613 |
| 30 | 1.615 | 9.456 |
| 31 | 5.158 | 53.443 |
| 32 | 3.419 | 32.836 |
| 33 | 4.112 | 44.623 |
| 34 | 3.556 | 26.261 |
| 35 | 3.089 | 20.506 |
| 36 | 2.763 | 26.001 |
| 37 | 4.150 | 28.312 |
| 38 | 2.643 | 17.528 |
| 39 | 5.818 | 74.782 |
| 40 | 1.432 | 9.710 |
| 41 | 1.548 | 12.083 |
| 42 | 3.016 | 17.886 |
| 43 | 2.295 | 15.780 |
| 44 | 3.562 | 24.535 |
| 45 | 4.999 | 52.068 |
| 46 | 4.621 | 55.322 |
| 47 | 5.752 | 65.582 |
| 48 | 3.690 | 28.014 |
| 49 | 2.300 | 13.896 |
| 50 | 3.446 | 30.899 |
| 51 | 2.754 | 19.334 |
| 52 | 3.342 | 26.922 |
| 53 | 2.877 | 17.377 |
| 54 | 2.361 | 24.174 |
| 55 | 3.775 | 37.577 |
| 56 | 4.572 | 35.653 |
| 57 | 2.278 | 22.355 |
| 58 | 1.996 | 14.097 |
| 59 | 1.651 | 10.003 |
| 60 | 2.120 | 16.586 |
| 61 | 2.027 | 16.365 |
| 62 | 4.550 | 49.932 |
| 63 | 3.688 | 22.416 |
| 64 | 4.384 | 27.791 |
| 65 | 5.587 | 39.777 |
| 66 | 2.642 | 23.269 |
| 67 | 4.993 | 56.756 |
| 68 | 2.773 | 24.275 |
| 69 | 6.973 | 96.404 |
| 70 | 4.314 | 53.140 |
| 71 | 2.482 | 17.866 |
| 72 | 3.669 | 22.882 |
| 73 | 3.449 | 25.517 |
| 74 | 2.141 | 18.183 |
| 75 | 2.787 | 16.795 |
| 76 | 2.574 | 18.040 |
| 77 | 3.025 | 26.735 |
| 78 | 6.736 | 87.662 |
| 79 | 2.855 | 19.214 |
| 80 | 3.280 | 21.398 |

TABLE 4-continued

| SEQ ID NO: | Discriminant coefficient | Constant term |
|---|---|---|
| 81 | 3.072 | 21.250 |
| 82 | 3.225 | 21.272 |
| 83 | 1.954 | 19.003 |
| 84 | 4.310 | 29.038 |
| 85 | 3.905 | 45.270 |
| 86 | 4.055 | 33.489 |
| 87 | 2.767 | 31.507 |
| 88 | 2.531 | 18.803 |
| 89 | 2.479 | 19.469 |
| 90 | 2.939 | 21.665 |
| 91 | 3.025 | 28.509 |
| 92 | 3.753 | 28.267 |
| 93 | 6.207 | 58.913 |
| 94 | 5.548 | 47.238 |
| 95 | 2.358 | 17.589 |
| 96 | 2.487 | 16.190 |
| 97 | 5.449 | 69.434 |
| 98 | 3.843 | 38.475 |
| 99 | 3.266 | 32.112 |
| 100 | 6.751 | 87.358 |
| 101 | 3.318 | 20.579 |
| 102 | 4.434 | 37.869 |
| 103 | 3.950 | 23.214 |
| 104 | 3.491 | 23.806 |

TABLE 5-1

| Training cohort | | | |
|---|---|---|---|
| Sample name | Cancer stage | CEA(ng/mL) | CA19-9(U/mL) |
| P01 | III | 5.6(+) | 202.7(+) |
| P05 | IV | 7.9(+) | 2535(+) |
| P06 | IV | 5.7(+) | 2381(+) |
| P07 | IB | 0.7(−) | 81.9(+) |
| P09 | IV | 1(−) | 48.6(+) |
| P10 | IIB | 3.3(−) | 85.4(+) |
| P11 | IV | 1.4(−) | 8.4(−) |
| P12 | IV | 23.6(+) | 0.5(−) |
| P13 | IV | 3.8(−) | 21.5(−) |
| P14 | IV | 39.2(+) | 248000(+) |
| P17 | IV | 282.1(+) | 77700(+) |
| P18 | IV | 14.8(+) | 7580(+) |
| P19 | IIB | 6.1(+) | 562(+) |
| P21 | III | 1.4(−) | 4690(+) |
| P25 | IV | 255.7(+) | 302.9(+) |
| P26 | IIB | 3.9(−) | 0.1(−) |
| P27 | III | 1(−) | 1304(+) |
| P29 | III | 5.9(+) | 883(+) |
| P33 | IV | 3.6(−) | 3.7(−) |
| P35 | IV | 3.8(−) | 8600(+) |
| P38 | IV | 26.7(+) | 9080(+) |
| P39 | IV | 31.2(+) | 299000(+) |
| P42 | IV | 4.8(−) | 14.1(−) |
| P43 | IV | 188.2(+) | 119700(+) |
| P44 | IV | 55.3(+) | 38620(+) |
| P46 | IV | 20.7(+) | 10.6(−) |
| P47 | IV | 5.6(+) | 107.9(+) |
| P48 | III | 3.4(−) | 285.6(+) |
| P49 | IIB | 3.6(−) | 338.8(+) |
| P50 | III | 11(+) | 2760(+) |
| P52 | IV | 13.6(+) | 9850(+) |
| P53 | III | 8.8(+) | 891(+) |
| P54 | III | 8.4(+) | 0.5(−) |
| P55 | IV | 8.1(+) | 8799(+) |
| P56 | IV | 202(+) | 337900(+) |
| P57 | IV | 1.8(−) | 110.7(+) |
| P59 | IV | 64.3(+) | 223.9(+) |
| P60 | IIB | 2.8(−) | 270.2(+) |
| P61 | IIB | 1(−) | 29.5(−) |
| P62 | III | 32.2(+) | 1490(+) |
| P66 | IIB | 1.5(−) | 0.1(−) |
| P68 | III | 5.7(+) | 236.9(+) |
| P71 | IB | 6.2(+) | 742(+) |
| P72 | IIB | 3.2(−) | 81.4(+) |

TABLE 5-1-continued

| Training cohort | | | |
|---|---|---|---|
| Sample name | Cancer stage | CEA(ng/mL) | CA19-9(U/mL) |
| P73 | IV | 4.4(−) | 970(+) |
| P75 | III | 1.4(−) | 580(+) |
| P76 | III | 59.9(+) | 1279(+) |
| P79 | IV | 2.6(−) | 1297(+) |
| P80 | IV | 8.4(+) | 0.9(−) |
| P81 | IV | 4.1(−) | 882(+) |
| P83 | IV | 8.6(+) | 2.2(−) |
| P84 | IV | 2(−) | 1375(+) |
| P86 | III | 4.3(−) | 17640(+) |
| P87 | III | 6.6(+) | 374.3(+) |
| P88 | IV | 147.4(+) | 2695(+) |
| P89 | IV | 2.9(−) | 2274(+) |
| P90 | IV | 7.4(+) | 1986(+) |
| P93 | IV | 17.8(+) | 2771(+) |
| P94 | III | 2(−) | 116.1(+) |
| P95 | III | 3.5(−) | 132.9(+) |
| P96 | IV | 1.2(−) | 2.3(−) |
| P97 | IV | 338.1(+) | 42990(+) |
| P98 | IV | 1.5(−) | 57500(+) |
| P99 | IV | 74.1(+) | 89700(+) |
| B38 | IIB | 0.9(−) | 19(−) |
| B87 | III | 5.7(+) | 0.1(−) |
| P101 | IV | 43.2(+) | 91500(+) |
| Sensitivity (%) | | 55.2 | 77.6 |

TABLE 5-2

| Validation cohort | | | |
|---|---|---|---|
| Sample name | Cancer stage | CEA(ng/mL) | CA19-9(U/mL) |
| P02 | IV | 1.5(−) | 569(+) |
| P03 | III | 4(−) | 1116(+) |
| P04 | IV | 4.6(−) | 5.8(−) |
| P08 | III | 3.3(−) | 81.4(+) |
| P15 | IV | 12.8(+) | 47.1(+) |
| P16 | IV | 5.1(+) | 181.4(+) |
| P20 | III | 0.9(−) | 13.6(−) |
| P22 | III | 0.7(−) | 31.4(−) |
| P23 | IV | 7.7(+) | 17080(+) |
| P24 | III | 1.7(−) | 72.9(+) |
| P28 | IV | 25.1(+) | 2995(+) |
| P30 | IV | 4.3(−) | 5.7(−) |
| P31 | IV | 2.9(−) | 3375(+) |
| P32 | III | 12.2(+) | 2955(+) |
| P34 | IIA | 1.3(−) | 66(+) |
| P36 | III | 2.7(−) | 32.2(−) |
| P37 | III | 2(−) | 858(+) |
| P40 | III | 65.6(+) | 9.6(−) |
| P41 | IV | 11.4(+) | 128080(+) |
| P45 | III | 2(−) | 410.8(+) |
| P51 | IV | 26.1(+) | 5880(+) |
| P58 | IV | 80.3(+) | 6510(+) |
| P63 | IIB | 4.4(−) | 5490(+) |
| P65 | IB | 7(+) | 55.3(+) |
| P67 | IIB | 2.5(−) | 28.7(−) |
| P69 | IIB | 4.2(+) | 832(+) |
| P70 | IIB | 1.6(−) | 71.3(+) |
| P74 | IIA | 3.2(−) | 36.8(−) |
| P77 | IV | 9.5(+) | 6110(+) |
| P78 | IV | 417(+) | 971000(+) |
| P82 | III | 6.7(+) | 3730(+) |
| P85 | IV | 5.4(+) | 6960(+) |
| P100 | IV | 240(+) | 68500(+) |
| Sensitivity (%) | | 45.5 | 75.8 |

For CEA, 5 ng/ml or lower was indicated as "−", and, for CA19-9, 37 U/ml or lower was indicated as "−", while values exceeding these were indicated as "+".

TABLE 6

| SEQ ID NO: | Training cohort | | | Validation cohort | | |
| --- | --- | --- | --- | --- | --- | --- |
| | Accuracy (%) | Sensitivity (%) | Specificity (%) | Accuracy (%) | Sensitivity (%) | Specificity (%) |
| 2_105 | 96.4 | 94 | 98 | 100 | 100 | 100 |
| 18_105 | 98.8 | 97 | 100 | 100 | 100 | 100 |
| 46_105 | 97.6 | 95.5 | 99 | 100 | 100 | 100 |
| 55_105 | 98.2 | 97 | 99 | 100 | 100 | 100 |
| 58_105 | 98.2 | 95.5 | 100 | 100 | 100 | 100 |
| 66_105 | 96.4 | 92.5 | 99 | 100 | 100 | 100 |
| 71_105 | 98.2 | 97 | 99 | 100 | 100 | 100 |
| 77_105 | 98.8 | 97 | 100 | 100 | 100 | 100 |
| 83_105 | 97 | 95.5 | 98 | 100 | 100 | 100 |
| 99_105 | 97 | 94 | 99 | 100 | 100 | 100 |
| 10_18 | 96.4 | 91 | 100 | 100 | 100 | 100 |
| 52_105 | 96.4 | 94 | 98 | 98.8 | 100 | 98 |
| 18_109 | 97.6 | 95.5 | 99 | 98.8 | 100 | 98 |
| 18_25 | 88.6 | 79.1 | 95 | 97.6 | 100 | 96 |
| 25_112 | 89.2 | 80.6 | 95 | 97.6 | 100 | 96 |
| 8_109 | 95.8 | 94 | 97 | 96.4 | 100 | 94 |
| 25_58 | 87.4 | 74.6 | 96 | 95.2 | 100 | 92 |
| 5_105 | 98.2 | 97 | 99 | 98.8 | 97 | 100 |
| 8_105 | 97.6 | 95.5 | 99 | 98.8 | 97 | 100 |
| 13_105 | 98.2 | 95.5 | 100 | 98.8 | 97 | 100 |
| 35_105 | 97.6 | 95.5 | 99 | 98.8 | 97 | 100 |
| 70_105 | 97 | 94 | 99 | 98.8 | 97 | 100 |
| 74_105 | 97 | 95.5 | 98 | 98.8 | 97 | 100 |
| 79_105 | 97.6 | 95.5 | 99 | 98.8 | 97 | 100 |
| 89_105 | 97 | 94 | 99 | 98.8 | 97 | 100 |
| 93_105 | 97 | 94 | 99 | 98.8 | 97 | 100 |
| 96_105 | 97 | 94 | 99 | 98.8 | 97 | 100 |
| 97_105 | 97.6 | 94 | 100 | 98.8 | 97 | 100 |
| 18_107 | 97 | 94 | 99 | 98.8 | 97 | 100 |
| 18_108 | 97.6 | 94 | 100 | 98.8 | 97 | 100 |
| 6_18 | 97.6 | 95.5 | 99 | 98.8 | 97 | 100 |
| 4_105 | 97 | 94 | 99 | 97.6 | 97 | 98 |
| 14_105 | 97.6 | 95.5 | 99 | 97.6 | 97 | 98 |
| 21_105 | 97 | 94 | 99 | 97.6 | 97 | 98 |
| 39_105 | 98.2 | 97 | 99 | 97.6 | 97 | 98 |
| 56_105 | 97 | 95.5 | 98 | 97.6 | 97 | 98 |
| 68_105 | 97.6 | 95.5 | 99 | 97.6 | 97 | 98 |
| 94_105 | 97 | 94 | 99 | 97.6 | 97 | 98 |
| 2_16 | 92.2 | 83.6 | 98 | 97.6 | 97 | 98 |
| 4_119 | 88 | 80.6 | 93 | 97.6 | 97 | 98 |
| 12_108 | 93.4 | 89.4 | 96 | 97.6 | 97 | 98 |
| 83_108 | 92.2 | 83.6 | 98 | 97.6 | 97 | 98 |
| 5_33 | 93.4 | 89.6 | 96 | 97.6 | 97 | 98 |
| 13_22 | 91.6 | 88.1 | 94 | 97.6 | 97 | 98 |
| 22_105 | 97 | 94 | 99 | 96.4 | 97 | 96 |
| 2_10 | 92.2 | 83.6 | 98 | 96.4 | 97 | 96 |
| 2_22 | 90.4 | 82.1 | 96 | 96.4 | 97 | 96 |
| 34_108 | 95.2 | 89.6 | 99 | 96.4 | 97 | 96 |
| 4_45 | 89.8 | 83.6 | 94 | 95.2 | 97 | 94 |
| 37_108 | 91.6 | 86.6 | 95 | 95.2 | 97 | 94 |
| 12_109 | 93.4 | 90.9 | 95 | 95.2 | 97 | 94 |
| 13_24 | 91.6 | 92.5 | 91 | 95.2 | 97 | 94 |
| 18_70 | 88 | 77.6 | 95 | 95.2 | 97 | 94 |
| 25_83 | 83.8 | 74.6 | 90 | 95.2 | 97 | 94 |
| 35_113 | 88.6 | 76.1 | 97 | 95.2 | 97 | 94 |
| 35_87 | 80.8 | 73.1 | 86 | 95.2 | 97 | 94 |
| 2_109 | 91.6 | 83.6 | 97 | 94 | 97 | 92 |
| 93_108 | 86.8 | 79.1 | 92 | 94 | 97 | 92 |
| 24_71 | 80.2 | 70.1 | 87 | 94 | 97 | 92 |
| 24_35 | 84.4 | 73.1 | 92 | 92.8 | 97 | 90 |
| 4_98 | 86.7 | 75.8 | 94 | 91.6 | 97 | 88 |
| 13_25 | 91 | 89.6 | 92 | 91.6 | 97 | 88 |
| 35_44 | 83.8 | 73.1 | 91 | 91.6 | 97 | 88 |
| 35_99 | 77.2 | 65.7 | 85 | 91.6 | 97 | 88 |
| 4_58 | 88 | 77.6 | 95 | 90.4 | 97 | 86 |
| 25_35 | 82 | 68.7 | 91 | 89.2 | 97 | 84 |
| 35_63 | 80.8 | 71.6 | 87 | 89.2 | 97 | 84 |
| 35_97 | 79.6 | 68.7 | 87 | 89.2 | 97 | 84 |
| 35_66 | 81.4 | 67.2 | 91 | 88 | 97 | 82 |
| 35_121 | 81.4 | 67.2 | 91 | 88 | 97 | 82 |
| 35_94 | 77.8 | 61.2 | 89 | 86.7 | 97 | 80 |
| 66_109 | 88 | 80.6 | 93 | 85.5 | 97 | 78 |
| 66_100 | 80.2 | 64.2 | 91 | 85.5 | 97 | 78 |
| 50_105 | 97 | 95.5 | 98 | 98.8 | 96.9 | 100 |
| 23_105 | 97 | 94 | 99 | 97.6 | 96.9 | 98 |

TABLE 6-continued

|  | Training cohort | | | Validation cohort | | |
| --- | --- | --- | --- | --- | --- | --- |
| SEQ ID NO: | Accuracy (%) | Sensitivity (%) | Specificity (%) | Accuracy (%) | Sensitivity (%) | Specificity (%) |
| 35_50 | 80.2 | 67.2 | 89 | 89 | 96.9 | 84 |
| 1_77 | 95.8 | 91 | 99 | 96.3 | 96.8 | 96 |
| 6_105 | 96.4 | 94 | 98 | 97.6 | 93.9 | 100 |
| 7_105 | 97 | 94 | 99 | 97.6 | 93.9 | 100 |
| 12_105 | 97.6 | 97 | 98 | 97.6 | 93.9 | 100 |
| 15_105 | 96.4 | 94 | 98 | 97.6 | 93.9 | 100 |
| 17_105 | 97 | 94 | 99 | 97.6 | 93.9 | 100 |
| 20_105 | 97.6 | 97 | 98 | 97.6 | 93.9 | 100 |
| 25_105 | 96.4 | 94 | 98 | 97.6 | 93.9 | 100 |
| 26_105 | 97.6 | 97 | 98 | 97.6 | 93.9 | 100 |
| 27_105 | 97 | 94 | 99 | 97.6 | 93.9 | 100 |
| 31_105 | 96.4 | 92.5 | 99 | 97.6 | 93.9 | 100 |
| 33_105 | 97 | 94 | 99 | 97.6 | 93.9 | 100 |
| 34_105 | 95.8 | 92.5 | 98 | 97.6 | 93.9 | 100 |
| 40_105 | 96.4 | 94 | 98 | 97.6 | 93.9 | 100 |
| 49_105 | 97 | 97 | 97 | 97.6 | 93.9 | 100 |
| 57_105 | 97 | 94 | 99 | 97.6 | 93.9 | 100 |
| 67_105 | 96.4 | 94 | 98 | 97.6 | 93.9 | 100 |
| 81_105 | 97.6 | 95.5 | 99 | 97.6 | 93.9 | 100 |
| 88_105 | 97 | 94 | 99 | 97.6 | 93.9 | 100 |
| 90_105 | 97.6 | 95.5 | 99 | 97.6 | 93.9 | 100 |
| 98_105 | 96.4 | 93.9 | 98 | 97.6 | 93.9 | 100 |
| 1_119 | 97 | 95.5 | 98 | 97.6 | 93.9 | 100 |
| 2_108 | 95.2 | 88.1 | 100 | 97.6 | 93.9 | 100 |
| 2_13 | 91.6 | 82.1 | 98 | 97.6 | 93.9 | 100 |
| 2_18 | 91 | 77.6 | 100 | 97.6 | 93.9 | 100 |
| 2_34 | 90.4 | 79.1 | 98 | 97.6 | 93.9 | 100 |
| 2_35 | 88.6 | 74.6 | 98 | 97.6 | 93.9 | 100 |
| 2_37 | 89.8 | 77.6 | 98 | 97.6 | 93.9 | 100 |
| 2_52 | 89.8 | 77.6 | 98 | 97.6 | 93.9 | 100 |
| 2_58 | 89.2 | 76.1 | 98 | 97.6 | 93.9 | 100 |
| 2_62 | 91 | 80.6 | 98 | 97.6 | 93.9 | 100 |
| 2_65 | 89.8 | 79.1 | 97 | 97.6 | 93.9 | 100 |
| 2_71 | 89.2 | 76.1 | 98 | 97.6 | 93.9 | 100 |
| 2_119 | 90.4 | 80.6 | 97 | 97.6 | 93.9 | 100 |
| 2_120 | 88 | 76.1 | 96 | 97.6 | 93.9 | 100 |
| 2_121 | 88 | 74.6 | 97 | 97.6 | 93.9 | 100 |
| 2_94 | 88.6 | 76.1 | 97 | 97.6 | 93.9 | 100 |
| 2_98 | 89.2 | 77.3 | 97 | 97.6 | 93.9 | 100 |
| 2_99 | 88.6 | 74.6 | 98 | 97.6 | 93.9 | 100 |
| 4_13 | 95.2 | 89.6 | 99 | 97.6 | 93.9 | 100 |
| 58_108 | 95.2 | 88.1 | 100 | 97.6 | 93.9 | 100 |
| 6_8 | 94.6 | 91 | 97 | 97.6 | 93.9 | 100 |
| 9_105 | 97 | 94 | 99 | 96.4 | 93.9 | 98 |
| 24_105 | 97 | 94 | 99 | 96.4 | 93.9 | 98 |
| 28_105 | 97 | 94 | 99 | 96.4 | 93.9 | 98 |
| 29_105 | 97 | 94 | 99 | 96.4 | 93.9 | 98 |
| 36_105 | 97 | 94 | 99 | 96.4 | 93.9 | 98 |
| 37_105 | 97.6 | 95.5 | 99 | 96.4 | 93.9 | 98 |
| 38_105 | 97 | 94 | 99 | 96.4 | 93.9 | 98 |
| 43_105 | 97 | 95.5 | 98 | 96.4 | 93.9 | 98 |
| 45_105 | 97 | 94 | 99 | 96.4 | 93.9 | 98 |
| 47_105 | 96.4 | 94 | 98 | 96.4 | 93.9 | 98 |
| 62_105 | 96.4 | 94 | 98 | 96.4 | 93.9 | 98 |
| 65_105 | 97.6 | 95.5 | 99 | 96.4 | 93.9 | 98 |
| 80_105 | 97 | 94 | 99 | 96.4 | 93.9 | 98 |
| 82_105 | 97 | 94 | 99 | 96.4 | 93.9 | 98 |
| 84_105 | 97 | 94 | 99 | 96.4 | 93.9 | 98 |
| 85_105 | 96.4 | 94 | 98 | 96.4 | 93.9 | 98 |
| 86_105 | 97 | 94 | 99 | 96.4 | 93.9 | 98 |
| 92_105 | 95.8 | 92.5 | 98 | 96.4 | 93.9 | 98 |
| 102_105 | 97 | 94 | 99 | 96.4 | 93.9 | 98 |
| 1_20 | 95.2 | 92.5 | 97 | 96.4 | 93.9 | 98 |
| 2_6 | 93.4 | 88.1 | 97 | 96.4 | 93.9 | 98 |
| 2_112 | 87.4 | 74.6 | 96 | 96.4 | 93.9 | 98 |
| 2_45 | 90.4 | 79.1 | 98 | 96.4 | 93.9 | 98 |
| 2_80 | 88.6 | 74.6 | 98 | 96.4 | 93.9 | 98 |
| 2_81 | 88.6 | 75.8 | 97 | 96.4 | 93.9 | 98 |
| 2_88 | 90.4 | 79.1 | 98 | 96.4 | 93.9 | 98 |
| 13_107 | 96.4 | 91 | 100 | 96.4 | 93.9 | 98 |
| 4_18 | 89.8 | 77.6 | 98 | 96.4 | 93.9 | 98 |
| 5_19 | 92.2 | 85.1 | 97 | 96.4 | 93.9 | 98 |
| 7_34 | 91.6 | 83.6 | 97 | 96.4 | 93.9 | 98 |
| 16_105 | 97.6 | 95.5 | 99 | 95.2 | 93.9 | 96 |
| 51_105 | 97 | 94 | 99 | 95.2 | 93.9 | 96 |

TABLE 6-continued

| | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 75_105 | 97.6 | 95.5 | 99 | 95.2 | 93.9 | 96 |
| 78_105 | 97 | 94 | 99 | 95.2 | 93.9 | 96 |
| 100_105 | 97.6 | 95.5 | 99 | 95.2 | 93.9 | 96 |
| 104_105 | 97 | 94 | 99 | 95.2 | 93.9 | 96 |
| 1_2 | 96.4 | 92.5 | 99 | 95.2 | 93.9 | 96 |
| 1_12 | 95.8 | 92.4 | 98 | 95.2 | 93.9 | 96 |
| 1_37 | 95.2 | 94 | 96 | 95.2 | 93.9 | 96 |
| 2_21 | 90.4 | 77.6 | 99 | 95.2 | 93.9 | 96 |
| 2_67 | 89.2 | 77.6 | 97 | 95.2 | 93.9 | 96 |
| 2_78 | 89.2 | 79.1 | 96 | 95.2 | 93.9 | 96 |
| 2_103 | 89.8 | 77.6 | 98 | 95.2 | 93.9 | 96 |
| 37_107 | 92.2 | 86.6 | 96 | 95.2 | 93.9 | 96 |
| 35_108 | 92.2 | 82.1 | 99 | 95.2 | 93.9 | 96 |
| 71_108 | 94.6 | 89.6 | 98 | 95.2 | 93.9 | 96 |
| 5_44 | 91 | 86.6 | 94 | 95.2 | 93.9 | 96 |
| 5_57 | 91.6 | 83.6 | 97 | 95.2 | 93.9 | 96 |
| 7_12 | 91.6 | 87.9 | 94 | 95.2 | 93.9 | 96 |
| 7_94 | 92.2 | 83.6 | 98 | 95.2 | 93.9 | 96 |
| 18_24 | 88.6 | 80.6 | 94 | 95.2 | 93.9 | 96 |
| 25_98 | 84.3 | 75.8 | 90 | 95.2 | 93.9 | 96 |
| 30_35 | 86.2 | 80.6 | 90 | 95.2 | 93.9 | 96 |
| 3_105 | 95.8 | 94 | 97 | 94 | 93.9 | 94 |
| 2_54 | 89.2 | 77.6 | 97 | 94 | 93.9 | 94 |
| 5_107 | 94 | 91 | 96 | 94 | 93.9 | 94 |
| 4_112 | 88.6 | 76.1 | 97 | 94 | 93.9 | 94 |
| 74_108 | 91.6 | 86.6 | 95 | 94 | 93.9 | 94 |
| 5_18 | 91 | 80.6 | 98 | 94 | 93.9 | 94 |
| 5_30 | 95.8 | 94 | 97 | 94 | 93.9 | 94 |
| 7_18 | 93.4 | 86.6 | 98 | 94 | 93.9 | 94 |
| 7_37 | 90.4 | 83.6 | 95 | 94 | 93.9 | 94 |
| 13_42 | 89.8 | 85.1 | 93 | 94 | 93.9 | 94 |
| 22_24 | 86.8 | 82.1 | 90 | 94 | 93.9 | 94 |
| 35_115 | 82.6 | 70.1 | 91 | 94 | 93.9 | 94 |
| 12_107 | 95.2 | 93.9 | 96 | 92.8 | 93.9 | 92 |
| 4_12 | 91 | 84.8 | 95 | 92.8 | 93.9 | 92 |
| 4_44 | 88 | 76.1 | 96 | 92.8 | 93.9 | 92 |
| 4_75 | 84.4 | 73.1 | 92 | 92.8 | 93.9 | 92 |
| 4_120 | 86.8 | 76.1 | 94 | 92.8 | 93.9 | 92 |
| 4_97 | 89.2 | 82.1 | 94 | 92.8 | 93.9 | 92 |
| 13_108 | 93.4 | 89.6 | 96 | 92.8 | 93.9 | 92 |
| 97_108 | 95.2 | 94 | 96 | 92.8 | 93.9 | 92 |
| 5_31 | 91.6 | 88.1 | 94 | 92.8 | 93.9 | 92 |
| 5_66 | 91 | 86.6 | 94 | 92.8 | 93.9 | 92 |
| 5_80 | 86.8 | 73.1 | 96 | 92.8 | 93.9 | 92 |
| 6_112 | 93.4 | 91 | 95 | 92.8 | 93.9 | 92 |
| 7_119 | 91.6 | 86.6 | 95 | 92.8 | 93.9 | 92 |
| 9_35 | 83.8 | 73.1 | 91 | 92.8 | 93.9 | 92 |
| 10_13 | 90.4 | 88.1 | 92 | 92.8 | 93.9 | 92 |
| 18_35 | 84.4 | 73.1 | 92 | 92.8 | 93.9 | 92 |
| 22_120 | 83.8 | 73.1 | 91 | 92.8 | 93.9 | 92 |
| 25_81 | 81.9 | 71.2 | 89 | 92.8 | 93.9 | 92 |
| 35_112 | 79 | 65.7 | 88 | 92.8 | 93.9 | 92 |
| 4_26 | 88.6 | 79.1 | 95 | 91.6 | 93.9 | 90 |
| 4_49 | 90.4 | 82.1 | 96 | 91.6 | 93.9 | 90 |
| 4_63 | 88.6 | 80.6 | 94 | 91.6 | 93.9 | 90 |
| 4_71 | 88.6 | 79.1 | 95 | 91.6 | 93.9 | 90 |
| 37_109 | 89.2 | 80.6 | 95 | 91.6 | 93.9 | 90 |
| 7_13 | 93.4 | 92.5 | 94 | 91.6 | 93.9 | 90 |
| 10_112 | 94 | 89.6 | 97 | 91.6 | 93.9 | 90 |
| 13_35 | 88.6 | 82.1 | 93 | 91.6 | 93.9 | 90 |
| 18_22 | 87.4 | 82.1 | 91 | 91.6 | 93.9 | 90 |
| 22_98 | 84.9 | 77.3 | 90 | 91.6 | 93.9 | 90 |
| 24_93 | 82 | 73.1 | 88 | 91.6 | 93.9 | 90 |
| 25_120 | 88.6 | 83.6 | 92 | 91.6 | 93.9 | 90 |
| 35_47 | 80.2 | 70.1 | 87 | 91.6 | 93.9 | 90 |
| 35_65 | 80.2 | 70.1 | 87 | 91.6 | 93.9 | 90 |
| 34_107 | 91.6 | 91 | 92 | 90.4 | 93.9 | 88 |
| 4_20 | 91 | 83.6 | 96 | 90.4 | 93.9 | 88 |
| 4_34 | 87.4 | 80.6 | 92 | 90.4 | 93.9 | 88 |
| 4_46 | 88 | 76.1 | 96 | 90.4 | 93.9 | 88 |
| 4_65 | 89.8 | 82.1 | 95 | 90.4 | 93.9 | 88 |
| 4_89 | 89.8 | 80.6 | 96 | 90.4 | 93.9 | 88 |
| 13_66 | 86.8 | 82.1 | 90 | 90.4 | 93.9 | 88 |
| 24_112 | 87.4 | 80.6 | 92 | 90.4 | 93.9 | 88 |
| 24_83 | 80.2 | 67.2 | 89 | 90.4 | 93.9 | 88 |

TABLE 6-continued

| | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 24_96 | 82.6 | 73.1 | 89 | 90.4 | 93.9 | 88 |
| 25_119 | 84.4 | 79.1 | 88 | 90.4 | 93.9 | 88 |
| 25_96 | 82.6 | 68.7 | 92 | 90.4 | 93.9 | 88 |
| 31_119 | 84.4 | 76.1 | 90 | 90.4 | 93.9 | 88 |
| 35_53 | 79.6 | 64.2 | 90 | 90.4 | 93.9 | 88 |
| 35_55 | 79.6 | 59.7 | 93 | 90.4 | 93.9 | 88 |
| 35_119 | 80.8 | 68.7 | 89 | 90.4 | 93.9 | 88 |
| 35_98 | 82.5 | 69.7 | 91 | 90.4 | 93.9 | 88 |
| 4_109 | 88 | 77.6 | 95 | 89.2 | 93.9 | 86 |
| 20_109 | 94.6 | 92.5 | 96 | 89.2 | 93.9 | 86 |
| 22_35 | 83.2 | 74.6 | 89 | 89.2 | 93.9 | 86 |
| 22_58 | 83.2 | 71.6 | 91 | 89.2 | 93.9 | 86 |
| 22_100 | 83.2 | 74.6 | 89 | 89.2 | 93.9 | 86 |
| 35_89 | 82.6 | 70.1 | 91 | 89.2 | 93.9 | 86 |
| 35_92 | 80.8 | 64.2 | 92 | 89.2 | 93.9 | 86 |
| 4_52 | 86.8 | 76.1 | 94 | 88 | 93.9 | 84 |
| 10_35 | 89.8 | 83.6 | 94 | 88 | 93.9 | 84 |
| 25_52 | 88 | 79.1 | 94 | 88 | 93.9 | 84 |
| 35_80 | 80.8 | 65.7 | 91 | 88 | 93.9 | 84 |
| 35_83 | 77.8 | 59.7 | 90 | 88 | 93.9 | 84 |
| 35_72 | 80.2 | 65.7 | 90 | 87.8 | 93.9 | 83.7 |
| 26_109 | 92.8 | 89.6 | 95 | 86.7 | 93.9 | 82 |
| 22_83 | 82 | 70.1 | 90 | 86.7 | 93.9 | 82 |
| 25_99 | 83.2 | 71.6 | 91 | 86.7 | 93.9 | 82 |
| 35_79 | 79 | 64.2 | 89 | 86.7 | 93.9 | 82 |
| 10_52 | 90.4 | 86.6 | 93 | 85.5 | 93.9 | 80 |
| 25_79 | 81.4 | 68.7 | 90 | 85.5 | 93.9 | 80 |
| 1_23 | 97 | 95.5 | 98 | 96.3 | 93.8 | 98 |
| 4_50 | 86.2 | 73.1 | 95 | 90.2 | 93.8 | 88 |
| 3_77 | 92.2 | 83.6 | 98 | 95.1 | 93.5 | 96 |
| 11_105 | 97 | 94 | 99 | 96.4 | 90.9 | 100 |
| 19_105 | 95.8 | 94 | 97 | 96.4 | 90.9 | 100 |
| 30_105 | 97.6 | 95.5 | 99 | 96.4 | 90.9 | 100 |
| 41_105 | 96.4 | 94 | 98 | 96.4 | 90.9 | 100 |
| 44_105 | 97 | 94 | 99 | 96.4 | 90.9 | 100 |
| 48_105 | 97 | 94 | 99 | 96.4 | 90.9 | 100 |
| 60_105 | 97 | 94 | 99 | 96.4 | 90.9 | 100 |
| 73_105 | 96.4 | 94 | 98 | 96.4 | 90.9 | 100 |
| 87_105 | 97 | 94 | 99 | 96.4 | 90.9 | 100 |
| 1_13 | 97 | 94 | 99 | 96.4 | 90.9 | 100 |
| 1_61 | 97 | 95.5 | 98 | 96.4 | 90.9 | 100 |
| 2_7 | 92.8 | 83.6 | 99 | 96.4 | 90.9 | 100 |
| 2_15 | 94 | 86.6 | 99 | 96.4 | 90.9 | 100 |
| 2_19 | 92.2 | 83.6 | 98 | 96.4 | 90.9 | 100 |
| 2_24 | 91 | 82.1 | 97 | 96.4 | 90.9 | 100 |
| 2_25 | 90.4 | 80.6 | 97 | 96.4 | 90.9 | 100 |
| 2_30 | 90.4 | 82.1 | 96 | 96.4 | 90.9 | 100 |
| 2_44 | 89.8 | 79.1 | 97 | 96.4 | 90.9 | 100 |
| 2_46 | 88.6 | 74.6 | 98 | 96.4 | 90.9 | 100 |
| 2_53 | 91.6 | 80.6 | 99 | 96.4 | 90.9 | 100 |
| 2_55 | 88.6 | 74.6 | 98 | 96.4 | 90.9 | 100 |
| 2_63 | 91 | 80.6 | 98 | 96.4 | 90.9 | 100 |
| 2_66 | 88.6 | 74.6 | 98 | 96.4 | 90.9 | 100 |
| 2_70 | 88.6 | 74.6 | 98 | 96.4 | 90.9 | 100 |
| 2_73 | 90.4 | 80.6 | 97 | 96.4 | 90.9 | 100 |
| 2_74 | 89.2 | 77.6 | 97 | 96.4 | 90.9 | 100 |
| 2_118 | 89.2 | 77.6 | 97 | 96.4 | 90.9 | 100 |
| 2_85 | 88 | 74.6 | 97 | 96.4 | 90.9 | 100 |
| 2_87 | 89.8 | 80.6 | 96 | 96.4 | 90.9 | 100 |
| 2_89 | 89.8 | 77.6 | 98 | 96.4 | 90.9 | 100 |
| 2_90 | 89.2 | 76.1 | 98 | 96.4 | 90.9 | 100 |
| 2_92 | 88.6 | 74.6 | 98 | 96.4 | 90.9 | 100 |
| 2_93 | 88.6 | 74.6 | 98 | 96.4 | 90.9 | 100 |
| 2_96 | 88.6 | 76.1 | 97 | 96.4 | 90.9 | 100 |
| 2_100 | 88 | 74.6 | 97 | 96.4 | 90.9 | 100 |
| 32_105 | 95.8 | 92.5 | 98 | 95.2 | 90.9 | 98 |
| 42_105 | 97 | 94 | 99 | 95.2 | 90.9 | 98 |
| 53_105 | 96.4 | 94 | 98 | 95.2 | 90.9 | 98 |
| 54_105 | 96.4 | 94 | 98 | 95.2 | 90.9 | 98 |
| 63_105 | 97 | 94 | 99 | 95.2 | 90.9 | 98 |
| 64_105 | 96.4 | 94 | 98 | 95.2 | 90.9 | 98 |
| 69_105 | 97 | 94 | 99 | 95.2 | 90.9 | 98 |
| 76_105 | 97 | 94 | 99 | 95.2 | 90.9 | 98 |
| 91_105 | 97 | 94 | 99 | 95.2 | 90.9 | 98 |
| 103_105 | 97 | 94 | 99 | 95.2 | 90.9 | 98 |

TABLE 6-continued

| | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 1_108 | 97 | 95.5 | 98 | 95.2 | 90.9 | 98 |
| 1_18 | 97 | 92.5 | 100 | 95.2 | 90.9 | 98 |
| 1_30 | 95.2 | 91 | 98 | 95.2 | 90.9 | 98 |
| 1_36 | 96.4 | 94 | 98 | 95.2 | 90.9 | 98 |
| 1_120 | 96.4 | 94 | 98 | 95.2 | 90.9 | 98 |
| 2_5 | 91 | 80.6 | 98 | 95.2 | 90.9 | 98 |
| 2_14 | 92.8 | 83.6 | 99 | 95.2 | 90.9 | 98 |
| 2_28 | 93.4 | 85.1 | 99 | 95.2 | 90.9 | 98 |
| 2_41 | 91 | 82.1 | 97 | 95.2 | 90.9 | 98 |
| 2_116 | 89.2 | 77.6 | 97 | 95.2 | 90.9 | 98 |
| 2_117 | 89.2 | 77.6 | 97 | 95.2 | 90.9 | 98 |
| 2_82 | 90.4 | 77.6 | 99 | 95.2 | 90.9 | 98 |
| 2_84 | 91 | 80.6 | 98 | 95.2 | 90.9 | 98 |
| 2_104 | 91 | 80.6 | 98 | 95.2 | 90.9 | 98 |
| 4_30 | 88.6 | 77.6 | 96 | 95.2 | 90.9 | 98 |
| 4_87 | 91 | 79.1 | 99 | 95.2 | 90.9 | 98 |
| 8_108 | 96.4 | 92.5 | 99 | 95.2 | 90.9 | 98 |
| 98_108 | 95.2 | 87.9 | 100 | 95.2 | 90.9 | 98 |
| 5_13 | 92.2 | 86.6 | 96 | 95.2 | 90.9 | 98 |
| 7_52 | 91 | 82.1 | 97 | 95.2 | 90.9 | 98 |
| 8_10 | 94.6 | 89.6 | 98 | 95.2 | 90.9 | 98 |
| 18_110 | 95.8 | 94 | 97 | 95.2 | 90.9 | 98 |
| 18_111 | 89.2 | 79.1 | 96 | 95.2 | 90.9 | 98 |
| 19_35 | 86.8 | 77.6 | 93 | 95.2 | 90.9 | 98 |
| 19_58 | 89.8 | 83.6 | 94 | 95.2 | 90.9 | 98 |
| 72_105 | 96.4 | 94 | 98 | 95.1 | 90.9 | 98 |
| 1_4 | 95.8 | 94 | 97 | 94 | 90.9 | 96 |
| 1_8 | 96.4 | 94 | 98 | 94 | 90.9 | 96 |
| 1_110 | 96.4 | 94 | 98 | 94 | 90.9 | 96 |
| 1_14 | 97 | 94 | 99 | 94 | 90.9 | 96 |
| 1_22 | 95.8 | 95.5 | 96 | 94 | 90.9 | 96 |
| 1_25 | 95.8 | 94 | 97 | 94 | 90.9 | 96 |
| 1_26 | 94.6 | 91 | 97 | 94 | 90.9 | 96 |
| 1_35 | 97 | 95.5 | 98 | 94 | 90.9 | 96 |
| 1_40 | 96.4 | 94 | 98 | 94 | 90.9 | 96 |
| 1_112 | 95.8 | 91 | 99 | 94 | 90.9 | 96 |
| 1_43 | 95.2 | 91 | 98 | 94 | 90.9 | 96 |
| 1_49 | 95.8 | 92.5 | 98 | 94 | 90.9 | 96 |
| 1_113 | 95.8 | 92.5 | 98 | 94 | 90.9 | 96 |
| 1_52 | 97 | 94 | 99 | 94 | 90.9 | 96 |
| 1_55 | 96.4 | 94 | 98 | 94 | 90.9 | 96 |
| 1_56 | 96.4 | 95.5 | 97 | 94 | 90.9 | 96 |
| 1_58 | 95.8 | 92.5 | 98 | 94 | 90.9 | 96 |
| 1_65 | 96.4 | 94 | 98 | 94 | 90.9 | 96 |
| 1_66 | 94.6 | 91 | 97 | 94 | 90.9 | 96 |
| 1_69 | 97 | 94 | 99 | 94 | 90.9 | 96 |
| 1_71 | 98.2 | 98.5 | 98 | 94 | 90.9 | 96 |
| 1_74 | 95.8 | 92.5 | 98 | 94 | 90.9 | 96 |
| 1_79 | 96.4 | 95.5 | 97 | 94 | 90.9 | 96 |
| 1_81 | 97 | 93.9 | 99 | 94 | 90.9 | 96 |
| 1_83 | 96.4 | 94 | 98 | 94 | 90.9 | 96 |
| 1_99 | 97 | 94 | 99 | 94 | 90.9 | 96 |
| 1_102 | 97 | 95.5 | 98 | 94 | 90.9 | 96 |
| 8_106 | 94.6 | 88.1 | 99 | 94 | 90.9 | 96 |
| 2_107 | 93.4 | 86.6 | 98 | 94 | 90.9 | 96 |
| 2_4 | 89.2 | 79.1 | 96 | 94 | 90.9 | 96 |
| 2_9 | 92.8 | 85.1 | 98 | 94 | 90.9 | 96 |
| 2_12 | 91.6 | 81.8 | 98 | 94 | 90.9 | 96 |
| 2_111 | 92.2 | 83.6 | 98 | 94 | 90.9 | 96 |
| 2_39 | 88.6 | 74.6 | 98 | 94 | 90.9 | 96 |
| 2_114 | 89.2 | 74.6 | 99 | 94 | 90.9 | 96 |
| 2_69 | 90.4 | 80.6 | 97 | 94 | 90.9 | 96 |
| 2_95 | 89.2 | 77.6 | 97 | 94 | 90.9 | 96 |
| 4_7 | 92.2 | 83.6 | 98 | 94 | 90.9 | 96 |
| 4_41 | 88 | 77.6 | 95 | 94 | 90.9 | 96 |
| 5_108 | 95.2 | 91 | 98 | 94 | 90.9 | 96 |
| 21_108 | 92.2 | 85.1 | 97 | 94 | 90.9 | 96 |
| 49_108 | 92.8 | 86.6 | 97 | 94 | 90.9 | 96 |
| 65_108 | 91.6 | 88.1 | 94 | 94 | 90.9 | 96 |
| 96_108 | 93.4 | 88.1 | 97 | 94 | 90.9 | 96 |
| 99_108 | 94 | 86.6 | 99 | 94 | 90.9 | 96 |
| 13_109 | 94.6 | 89.6 | 98 | 94 | 90.9 | 96 |
| 7_67 | 91 | 83.6 | 96 | 94 | 90.9 | 96 |
| 7_70 | 92.8 | 86.6 | 97 | 94 | 90.9 | 96 |
| 9_119 | 87.4 | 83.6 | 90 | 94 | 90.9 | 96 |

TABLE 6-continued

| | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 10_12 | 91.6 | 89.4 | 93 | 94 | 90.9 | 96 |
| 13_16 | 94.6 | 98.5 | 92 | 94 | 90.9 | 96 |
| 14_18 | 94 | 88.1 | 98 | 94 | 90.9 | 96 |
| 35_41 | 83.2 | 73.1 | 90 | 94 | 90.9 | 96 |
| 66_85 | 83.2 | 68.7 | 93 | 94 | 90.9 | 96 |
| 1_21 | 96.4 | 95.5 | 97 | 92.8 | 90.9 | 94 |
| 1_29 | 96.4 | 94 | 98 | 92.8 | 90.9 | 94 |
| 1_39 | 97.6 | 97 | 98 | 92.8 | 90.9 | 94 |
| 1_70 | 97 | 94 | 99 | 92.8 | 90.9 | 94 |
| 1_75 | 97 | 94 | 99 | 92.8 | 90.9 | 94 |
| 4_107 | 90.4 | 85.1 | 94 | 92.8 | 90.9 | 94 |
| 14_107 | 92.2 | 80.6 | 100 | 92.8 | 90.9 | 94 |
| 58_107 | 92.8 | 88.1 | 96 | 92.8 | 90.9 | 94 |
| 66_107 | 90.4 | 80.6 | 97 | 92.8 | 90.9 | 94 |
| 94_107 | 90.4 | 83.6 | 95 | 92.8 | 90.9 | 94 |
| 99_107 | 89.8 | 80.6 | 96 | 92.8 | 90.9 | 94 |
| 3_119 | 91 | 89.6 | 92 | 92.8 | 90.9 | 94 |
| 4_14 | 90.4 | 82.1 | 96 | 92.8 | 90.9 | 94 |
| 4_113 | 90.4 | 80.6 | 97 | 92.8 | 90.9 | 94 |
| 4_115 | 89.8 | 79.1 | 97 | 92.8 | 90.9 | 94 |
| 43_108 | 93.4 | 91 | 95 | 92.8 | 90.9 | 94 |
| 5_7 | 95.2 | 94 | 96 | 92.8 | 90.9 | 94 |
| 5_12 | 91.6 | 84.8 | 96 | 92.8 | 90.9 | 94 |
| 5_24 | 93.4 | 91 | 95 | 92.8 | 90.9 | 94 |
| 5_112 | 87.4 | 79.1 | 93 | 92.8 | 90.9 | 94 |
| 5_89 | 90.4 | 83.6 | 95 | 92.8 | 90.9 | 94 |
| 7_9 | 90.4 | 89.6 | 91 | 92.8 | 90.9 | 94 |
| 7_16 | 90.4 | 88.1 | 92 | 92.8 | 90.9 | 94 |
| 7_22 | 91 | 83.6 | 96 | 92.8 | 90.9 | 94 |
| 7_51 | 91 | 85.1 | 95 | 92.8 | 90.9 | 94 |
| 7_62 | 91.6 | 85.1 | 96 | 92.8 | 90.9 | 94 |
| 7_114 | 89.8 | 83.6 | 94 | 92.8 | 90.9 | 94 |
| 7_80 | 92.2 | 85.1 | 97 | 92.8 | 90.9 | 94 |
| 7_83 | 91 | 80.6 | 98 | 92.8 | 90.9 | 94 |
| 7_103 | 91.6 | 86.6 | 95 | 92.8 | 90.9 | 94 |
| 10_20 | 89.8 | 85.1 | 93 | 92.8 | 90.9 | 94 |
| 10_58 | 94.6 | 91 | 97 | 92.8 | 90.9 | 94 |
| 13_27 | 91 | 86.6 | 94 | 92.8 | 90.9 | 94 |
| 18_30 | 86.8 | 80.6 | 91 | 92.8 | 90.9 | 94 |
| 18_41 | 85 | 77.6 | 90 | 92.8 | 90.9 | 94 |
| 18_66 | 85 | 74.6 | 92 | 92.8 | 90.9 | 94 |
| 22_85 | 86.2 | 77.6 | 92 | 92.8 | 90.9 | 94 |
| 24_37 | 85 | 74.6 | 92 | 92.8 | 90.9 | 94 |
| 24_119 | 82.6 | 76.1 | 87 | 92.8 | 90.9 | 94 |
| 25_39 | 86.2 | 74.6 | 94 | 92.8 | 90.9 | 94 |
| 25_45 | 88.6 | 76.1 | 97 | 92.8 | 90.9 | 94 |
| 25_46 | 85 | 73.1 | 93 | 92.8 | 90.9 | 94 |
| 1_121 | 98.2 | 97 | 99 | 91.6 | 90.9 | 92 |
| 20_107 | 95.2 | 92.5 | 97 | 91.6 | 90.9 | 92 |
| 26_107 | 95.8 | 94 | 97 | 91.6 | 90.9 | 92 |
| 49_107 | 94 | 91 | 96 | 91.6 | 90.9 | 92 |
| 3_58 | 94.6 | 91 | 97 | 91.6 | 90.9 | 92 |
| 4_5 | 91 | 83.6 | 96 | 91.6 | 90.9 | 92 |
| 4_6 | 90.4 | 80.6 | 97 | 91.6 | 90.9 | 92 |
| 4_10 | 91.6 | 86.6 | 95 | 91.6 | 90.9 | 92 |
| 4_24 | 87.4 | 76.1 | 95 | 91.6 | 90.9 | 92 |
| 4_48 | 89.2 | 79.1 | 96 | 91.6 | 90.9 | 92 |
| 4_55 | 88.6 | 79.1 | 95 | 91.6 | 90.9 | 92 |
| 4_88 | 86.2 | 77.6 | 92 | 91.6 | 90.9 | 92 |
| 4_102 | 89.2 | 80.6 | 95 | 91.6 | 90.9 | 92 |
| 55_108 | 91.6 | 83.6 | 97 | 91.6 | 90.9 | 92 |
| 5_25 | 91 | 86.6 | 94 | 91.6 | 90.9 | 92 |
| 5_42 | 91.6 | 86.6 | 95 | 91.6 | 90.9 | 92 |
| 5_56 | 91.6 | 88.1 | 94 | 91.6 | 90.9 | 92 |
| 7_21 | 90.4 | 85.1 | 94 | 91.6 | 90.9 | 92 |
| 7_35 | 89.8 | 79.1 | 97 | 91.6 | 90.9 | 92 |
| 7_112 | 93.4 | 86.6 | 98 | 91.6 | 90.9 | 92 |
| 7_65 | 91 | 86.6 | 94 | 91.6 | 90.9 | 92 |
| 7_66 | 91 | 85.1 | 95 | 91.6 | 90.9 | 92 |
| 7_79 | 89.8 | 83.6 | 94 | 91.6 | 90.9 | 92 |
| 7_120 | 91 | 83.6 | 96 | 91.6 | 90.9 | 92 |
| 7_87 | 91.6 | 85.1 | 96 | 91.6 | 90.9 | 92 |
| 7_88 | 90.4 | 86.6 | 93 | 91.6 | 90.9 | 92 |
| 7_104 | 91 | 86.6 | 94 | 91.6 | 90.9 | 92 |
| 10_120 | 91.6 | 85.1 | 96 | 91.6 | 90.9 | 92 |

TABLE 6-continued

| SEQ ID NO: | Training cohort | | | Validation cohort | | |
|---|---|---|---|---|---|---|
| | Accuracy (%) | Sensitivity (%) | Specificity (%) | Accuracy (%) | Sensitivity (%) | Specificity (%) |
| 13_21 | 89.8 | 86.6 | 92 | 91.6 | 90.9 | 92 |
| 18_46 | 83.2 | 74.6 | 89 | 91.6 | 90.9 | 92 |
| 22_96 | 80.8 | 70.1 | 88 | 91.6 | 90.9 | 92 |
| 24_79 | 82 | 68.7 | 91 | 91.6 | 90.9 | 92 |
| 25_94 | 82.6 | 68.7 | 92 | 91.6 | 90.9 | 92 |
| 35_90 | 79.6 | 65.7 | 89 | 91.6 | 90.9 | 92 |
| 54_107 | 92.2 | 88.1 | 95 | 90.4 | 90.9 | 90 |
| 3_21 | 91 | 88.1 | 93 | 90.4 | 90.9 | 90 |
| 3_35 | 94.6 | 95.5 | 94 | 90.4 | 90.9 | 90 |
| 4_9 | 88 | 77.6 | 95 | 90.4 | 90.9 | 90 |
| 4_37 | 85.6 | 74.6 | 93 | 90.4 | 90.9 | 90 |
| 4_43 | 86.8 | 74.6 | 95 | 90.4 | 90.9 | 90 |
| 4_47 | 89.2 | 79.1 | 96 | 90.4 | 90.9 | 90 |
| 4_56 | 88.6 | 79.1 | 95 | 90.4 | 90.9 | 90 |
| 4_74 | 86.8 | 74.6 | 95 | 90.4 | 90.9 | 90 |
| 47_108 | 91.6 | 83.6 | 97 | 90.4 | 90.9 | 90 |
| 94_108 | 91.6 | 82.1 | 98 | 90.4 | 90.9 | 90 |
| 5_11 | 91.6 | 86.6 | 95 | 90.4 | 90.9 | 90 |
| 5_21 | 91.6 | 85.1 | 96 | 90.4 | 90.9 | 90 |
| 5_75 | 88.6 | 83.6 | 92 | 90.4 | 90.9 | 90 |
| 7_109 | 93.4 | 86.6 | 98 | 90.4 | 90.9 | 90 |
| 7_44 | 92.2 | 85.1 | 97 | 90.4 | 90.9 | 90 |
| 7_58 | 89.8 | 77.6 | 98 | 90.4 | 90.9 | 90 |
| 7_71 | 89.2 | 82.1 | 94 | 90.4 | 90.9 | 90 |
| 7_121 | 91 | 88.1 | 93 | 90.4 | 90.9 | 90 |
| 7_99 | 88.6 | 80.6 | 94 | 90.4 | 90.9 | 90 |
| 9_24 | 89.2 | 83.6 | 93 | 90.4 | 90.9 | 90 |
| 9_58 | 88 | 80.6 | 93 | 90.4 | 90.9 | 90 |
| 10_34 | 91.6 | 88.1 | 94 | 90.4 | 90.9 | 90 |
| 10_119 | 91 | 88.1 | 93 | 90.4 | 90.9 | 90 |
| 18_67 | 88.6 | 80.6 | 94 | 90.4 | 90.9 | 90 |
| 18_79 | 85.6 | 76.1 | 92 | 90.4 | 90.9 | 90 |
| 21_25 | 84.4 | 73.1 | 92 | 90.4 | 90.9 | 90 |
| 22_46 | 83.2 | 73.1 | 90 | 90.4 | 90.9 | 90 |
| 22_88 | 83.8 | 77.6 | 88 | 90.4 | 90.9 | 90 |
| 24_55 | 85 | 70.1 | 95 | 90.4 | 90.9 | 90 |
| 24_80 | 77.8 | 64.2 | 87 | 90.4 | 90.9 | 90 |
| 24_81 | 84.9 | 77.3 | 90 | 90.4 | 90.9 | 90 |
| 24_90 | 83.2 | 71.6 | 91 | 90.4 | 90.9 | 90 |
| 25_34 | 89.8 | 80.6 | 96 | 90.4 | 90.9 | 90 |
| 35_37 | 79 | 68.7 | 86 | 90.4 | 90.9 | 90 |
| 66_98 | 79.5 | 63.6 | 90 | 90.4 | 90.9 | 90 |
| 52_107 | 92.2 | 89.6 | 94 | 89.2 | 90.9 | 88 |
| 4_25 | 88 | 79.1 | 94 | 89.2 | 90.9 | 88 |
| 4_80 | 86.8 | 74.6 | 95 | 89.2 | 90.9 | 88 |
| 4_81 | 86.7 | 75.8 | 94 | 89.2 | 90.9 | 88 |
| 4_82 | 86.8 | 74.6 | 95 | 89.2 | 90.9 | 88 |
| 4_83 | 86.8 | 74.6 | 95 | 89.2 | 90.9 | 88 |
| 4_85 | 88 | 76.1 | 96 | 89.2 | 90.9 | 88 |
| 4_90 | 87.4 | 76.1 | 95 | 89.2 | 90.9 | 88 |
| 4_91 | 85.6 | 73.1 | 94 | 89.2 | 90.9 | 88 |
| 4_94 | 87.4 | 74.6 | 96 | 89.2 | 90.9 | 88 |
| 49_109 | 89.8 | 89.6 | 90 | 89.2 | 90.9 | 88 |
| 10_81 | 89.2 | 81.8 | 94 | 89.2 | 90.9 | 88 |
| 10_83 | 89.2 | 82.1 | 94 | 89.2 | 90.9 | 88 |
| 10_121 | 89.2 | 83.6 | 93 | 89.2 | 90.9 | 88 |
| 22_80 | 83.2 | 74.6 | 89 | 89.2 | 90.9 | 88 |
| 24_31 | 83.2 | 68.7 | 93 | 89.2 | 90.9 | 88 |
| 24_118 | 83.2 | 74.6 | 89 | 89.2 | 90.9 | 88 |
| 25_66 | 80.8 | 67.2 | 90 | 89.2 | 90.9 | 88 |
| 25_70 | 82.6 | 68.7 | 92 | 89.2 | 90.9 | 88 |
| 25_75 | 82.6 | 73.1 | 89 | 89.2 | 90.9 | 88 |
| 25_80 | 84.4 | 73.1 | 92 | 89.2 | 90.9 | 88 |
| 28_35 | 82 | 71.6 | 89 | 89.2 | 90.9 | 88 |
| 4_11 | 86.8 | 79.1 | 92 | 88 | 90.9 | 86 |
| 4_16 | 88 | 77.6 | 95 | 88 | 90.9 | 86 |
| 4_21 | 87.4 | 76.1 | 95 | 88 | 90.9 | 86 |
| 4_39 | 89.2 | 79.1 | 96 | 88 | 90.9 | 86 |
| 4_76 | 86.8 | 73.1 | 96 | 88 | 90.9 | 86 |
| 4_92 | 85.6 | 73.1 | 94 | 88 | 90.9 | 86 |
| 4_96 | 88 | 76.1 | 96 | 88 | 90.9 | 86 |
| 4_99 | 85.6 | 71.6 | 95 | 88 | 90.9 | 86 |
| 9_109 | 88.6 | 79.1 | 95 | 88 | 90.9 | 86 |
| 54_109 | 88 | 83.6 | 91 | 88 | 90.9 | 86 |
| 9_46 | 88 | 85.1 | 90 | 88 | 90.9 | 86 |

TABLE 6-continued

|  | Training cohort | | | Validation cohort | | |
| --- | --- | --- | --- | --- | --- | --- |
| SEQ ID NO: | Accuracy (%) | Sensitivity (%) | Specificity (%) | Accuracy (%) | Sensitivity (%) | Specificity (%) |
| 13_67 | 83.2 | 74.6 | 89 | 88 | 90.9 | 86 |
| 13_79 | 84.4 | 82.1 | 86 | 88 | 90.9 | 86 |
| 16_83 | 83.8 | 82.1 | 85 | 88 | 90.9 | 86 |
| 22_55 | 81.4 | 73.1 | 87 | 88 | 90.9 | 86 |
| 24_121 | 83.2 | 73.1 | 90 | 88 | 90.9 | 86 |
| 25_92 | 82.6 | 71.6 | 90 | 88 | 90.9 | 86 |
| 35_71 | 78.4 | 62.7 | 89 | 88 | 90.9 | 86 |
| 35_93 | 77.8 | 61.2 | 89 | 88 | 90.9 | 86 |
| 4_84 | 87.4 | 79.1 | 93 | 86.7 | 90.9 | 84 |
| 4_121 | 86.8 | 76.1 | 94 | 86.7 | 90.9 | 84 |
| 81_109 | 84.9 | 80.3 | 88 | 86.7 | 90.9 | 84 |
| 21_35 | 80.8 | 70.1 | 88 | 86.7 | 90.9 | 84 |
| 21_75 | 80.2 | 70.1 | 87 | 86.7 | 90.9 | 84 |
| 21_83 | 80.8 | 74.6 | 85 | 86.7 | 90.9 | 84 |
| 21_89 | 79 | 70.1 | 85 | 86.7 | 90.9 | 84 |
| 21_97 | 81.4 | 71.6 | 88 | 86.7 | 90.9 | 84 |
| 22_66 | 77.2 | 67.2 | 84 | 86.7 | 90.9 | 84 |
| 22_119 | 83.8 | 80.6 | 86 | 86.7 | 90.9 | 84 |
| 24_58 | 81.4 | 71.6 | 88 | 86.7 | 90.9 | 84 |
| 24_120 | 83.2 | 76.1 | 88 | 86.7 | 90.9 | 84 |
| 31_112 | 82.6 | 73.1 | 89 | 86.7 | 90.9 | 84 |
| 35_118 | 81.4 | 67.2 | 91 | 86.7 | 90.9 | 84 |
| 35_120 | 79 | 64.2 | 89 | 86.7 | 90.9 | 84 |
| 35_96 | 78.4 | 62.7 | 89 | 86.7 | 90.9 | 84 |
| 66_70 | 81.4 | 68.7 | 90 | 86.7 | 90.9 | 84 |
| 66_119 | 79 | 70.1 | 85 | 86.7 | 90.9 | 84 |
| 21_109 | 91 | 85.1 | 95 | 85.5 | 90.9 | 82 |
| 21_55 | 79.6 | 65.7 | 89 | 85.5 | 90.9 | 82 |
| 21_56 | 80.8 | 68.7 | 89 | 85.5 | 90.9 | 82 |
| 22_78 | 78.4 | 68.7 | 85 | 85.5 | 90.9 | 82 |
| 35_42 | 82.6 | 65.7 | 94 | 85.5 | 90.9 | 82 |
| 35_81 | 77.1 | 63.6 | 86 | 85.5 | 90.9 | 82 |
| 35_82 | 77.2 | 62.7 | 87 | 85.5 | 90.9 | 82 |
| 35_100 | 77.8 | 64.2 | 87 | 85.5 | 90.9 | 82 |
| 35_103 | 80.8 | 65.7 | 91 | 85.5 | 90.9 | 82 |
| 39_109 | 84.4 | 76.1 | 90 | 84.3 | 90.9 | 80 |
| 31_58 | 82.6 | 73.1 | 89 | 84.3 | 90.9 | 80 |
| 35_75 | 77.8 | 59.7 | 90 | 84.3 | 90.9 | 80 |
| 9_100 | 88.6 | 91 | 87 | 83.1 | 90.9 | 78 |
| 10_94 | 85 | 79.1 | 89 | 83.1 | 90.9 | 78 |
| 21_71 | 80.8 | 71.6 | 87 | 83.1 | 90.9 | 78 |
| 79_109 | 85 | 73.1 | 93 | 81.9 | 90.9 | 76 |
| 99_109 | 85.6 | 80.6 | 89 | 81.9 | 90.9 | 76 |
| 31_109 | 85 | 73.1 | 93 | 80.7 | 90.9 | 74 |
| 2_50 | 91 | 79.1 | 99 | 96.3 | 90.6 | 100 |
| 1_50 | 96.4 | 94 | 98 | 93.9 | 90.6 | 96 |
| 7_50 | 91 | 83.6 | 96 | 93.9 | 90.6 | 96 |
| 2_23 | 91.6 | 82.1 | 98 | 92.7 | 90.6 | 94 |
| 18_23 | 89.8 | 82.1 | 95 | 92.7 | 90.6 | 94 |
| 5_50 | 91 | 83.6 | 96 | 91.5 | 90.6 | 92 |
| 24_50 | 81.4 | 74.6 | 86 | 91.5 | 90.6 | 92 |
| 4_23 | 86.8 | 74.6 | 95 | 87.8 | 90.6 | 86 |
| 22_50 | 83.2 | 76.1 | 88 | 87.8 | 90.6 | 86 |
| 50_109 | 88 | 82.1 | 92 | 80.5 | 90.6 | 74 |
| 2_77 | 88.6 | 74.6 | 98 | 96.3 | 90.3 | 100 |
| 7_77 | 88.6 | 82.1 | 93 | 95.1 | 90.3 | 98 |
| 4_77 | 88 | 76.1 | 96 | 92.6 | 90.3 | 94 |
| 21_77 | 80.8 | 76.1 | 84 | 87.7 | 90.3 | 86 |
| 1_105 | 97 | 94 | 99 | 95.2 | 87.9 | 100 |
| 61_105 | 97 | 94 | 99 | 95.2 | 87.9 | 100 |
| 1_19 | 95.2 | 91 | 98 | 95.2 | 87.9 | 100 |
| 1_87 | 98.2 | 97 | 99 | 95.2 | 87.9 | 100 |
| 13_106 | 94 | 85.1 | 100 | 95.2 | 87.9 | 100 |
| 2_11 | 91 | 82.1 | 97 | 95.2 | 87.9 | 100 |
| 2_17 | 92.2 | 83.6 | 98 | 95.2 | 87.9 | 100 |
| 2_29 | 91.6 | 82.1 | 98 | 95.2 | 87.9 | 100 |
| 2_33 | 92.8 | 85.1 | 98 | 95.2 | 87.9 | 100 |
| 2_38 | 92.8 | 85.1 | 98 | 95.2 | 87.9 | 100 |
| 2_47 | 88.6 | 76.1 | 97 | 95.2 | 87.9 | 100 |
| 2_49 | 88.6 | 77.6 | 96 | 95.2 | 87.9 | 100 |
| 2_113 | 91.6 | 82.1 | 98 | 95.2 | 87.9 | 100 |
| 2_56 | 91 | 82.1 | 97 | 95.2 | 87.9 | 100 |
| 2_57 | 88.6 | 76.1 | 97 | 95.2 | 87.9 | 100 |
| 2_60 | 90.4 | 80.6 | 97 | 95.2 | 87.9 | 100 |
| 2_64 | 91 | 80.6 | 98 | 95.2 | 87.9 | 100 |

TABLE 6-continued

| | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 2_68 | 90.4 | 79.1 | 98 | 95.2 | 87.9 | 100 |
| 2_115 | 91 | 80.6 | 98 | 95.2 | 87.9 | 100 |
| 2_79 | 88.6 | 74.6 | 98 | 95.2 | 87.9 | 100 |
| 2_91 | 89.2 | 76.1 | 98 | 95.2 | 87.9 | 100 |
| 2_101 | 89.2 | 76.1 | 98 | 95.2 | 87.9 | 100 |
| 37_111 | 84.4 | 71.6 | 93 | 95.2 | 87.9 | 100 |
| 2_72 | 89.8 | 80.6 | 96 | 95.1 | 87.9 | 100 |
| 10_105 | 97.6 | 95.5 | 99 | 94 | 87.9 | 98 |
| 95_105 | 97 | 95.5 | 98 | 94 | 87.9 | 98 |
| 1_5 | 97.6 | 97 | 98 | 94 | 87.9 | 98 |
| 1_7 | 97.6 | 94 | 100 | 94 | 87.9 | 98 |
| 1_41 | 95.8 | 92.5 | 98 | 94 | 87.9 | 98 |
| 1_54 | 95.8 | 92.5 | 98 | 94 | 87.9 | 98 |
| 1_97 | 96.4 | 94 | 98 | 94 | 87.9 | 98 |
| 1_101 | 96.4 | 94 | 98 | 94 | 87.9 | 98 |
| 18_106 | 95.8 | 91 | 99 | 94 | 87.9 | 98 |
| 30_106 | 92.8 | 82.1 | 100 | 94 | 87.9 | 98 |
| 2_3 | 96.4 | 91 | 100 | 94 | 87.9 | 98 |
| 2_26 | 88.6 | 76.1 | 97 | 94 | 87.9 | 98 |
| 2_27 | 89.8 | 79.1 | 97 | 94 | 87.9 | 98 |
| 2_31 | 88.6 | 74.6 | 98 | 94 | 87.9 | 98 |
| 2_32 | 92.2 | 82.1 | 99 | 94 | 87.9 | 98 |
| 2_40 | 92.2 | 82.1 | 99 | 94 | 87.9 | 98 |
| 2_51 | 91 | 80.6 | 98 | 94 | 87.9 | 98 |
| 2_83 | 90.4 | 77.6 | 99 | 94 | 87.9 | 98 |
| 3_12 | 92.8 | 89.4 | 95 | 94 | 87.9 | 98 |
| 3_18 | 95.2 | 89.6 | 99 | 94 | 87.9 | 98 |
| 4_19 | 89.2 | 77.6 | 97 | 94 | 87.9 | 98 |
| 7_108 | 92.8 | 85.1 | 98 | 94 | 87.9 | 98 |
| 26_108 | 92.8 | 89.6 | 95 | 94 | 87.9 | 98 |
| 46_108 | 92.2 | 85.1 | 97 | 94 | 87.9 | 98 |
| 89_108 | 89.2 | 82.1 | 94 | 94 | 87.9 | 98 |
| 5_15 | 92.2 | 83.6 | 98 | 94 | 87.9 | 98 |
| 5_38 | 91.6 | 83.6 | 97 | 94 | 87.9 | 98 |
| 6_37 | 89.8 | 82.1 | 95 | 94 | 87.9 | 98 |
| 7_45 | 92.2 | 83.6 | 98 | 94 | 87.9 | 98 |
| 7_74 | 93.4 | 89.6 | 96 | 94 | 87.9 | 98 |
| 7_85 | 92.8 | 85.1 | 98 | 94 | 87.9 | 98 |
| 7_96 | 91 | 80.6 | 98 | 94 | 87.9 | 98 |
| 18_38 | 89.8 | 80.6 | 96 | 94 | 87.9 | 98 |
| 18_59 | 92.2 | 85.1 | 97 | 94 | 87.9 | 98 |
| 19_46 | 90.4 | 85.1 | 94 | 94 | 87.9 | 98 |
| 59_105 | 97 | 95.5 | 98 | 92.8 | 87.9 | 96 |
| 101_105 | 97 | 95.5 | 98 | 92.8 | 87.9 | 96 |
| 1_106 | 95.8 | 94 | 97 | 92.8 | 87.9 | 96 |
| 1_3 | 96.4 | 94 | 98 | 92.8 | 87.9 | 96 |
| 1_6 | 95.8 | 94 | 97 | 92.8 | 87.9 | 96 |
| 1_9 | 96.4 | 94 | 98 | 92.8 | 87.9 | 96 |
| 1_10 | 97 | 94 | 99 | 92.8 | 87.9 | 96 |
| 1_11 | 95.8 | 94 | 97 | 92.8 | 87.9 | 96 |
| 1_16 | 97.6 | 97 | 98 | 92.8 | 87.9 | 96 |
| 1_17 | 95.8 | 94 | 97 | 92.8 | 87.9 | 96 |
| 1_24 | 97 | 95.5 | 98 | 92.8 | 87.9 | 96 |
| 1_28 | 96.4 | 94 | 98 | 92.8 | 87.9 | 96 |
| 1_31 | 97.6 | 95.5 | 99 | 92.8 | 87.9 | 96 |
| 1_32 | 96.4 | 94 | 98 | 92.8 | 87.9 | 96 |
| 1_33 | 95.8 | 94 | 97 | 92.8 | 87.9 | 96 |
| 1_34 | 97 | 94 | 99 | 92.8 | 87.9 | 96 |
| 1_38 | 95.8 | 92.5 | 98 | 92.8 | 87.9 | 96 |
| 1_42 | 95.8 | 94 | 97 | 92.8 | 87.9 | 96 |
| 1_44 | 95.8 | 94 | 97 | 92.8 | 87.9 | 96 |
| 1_45 | 96.4 | 92.5 | 99 | 92.8 | 87.9 | 96 |
| 1_46 | 96.4 | 92.5 | 99 | 92.8 | 87.9 | 96 |
| 1_47 | 97 | 97 | 97 | 92.8 | 87.9 | 96 |
| 1_48 | 97 | 94 | 99 | 92.8 | 87.9 | 96 |
| 1_51 | 95.8 | 94 | 97 | 92.8 | 87.9 | 96 |
| 1_53 | 95.2 | 92.5 | 97 | 92.8 | 87.9 | 96 |
| 1_57 | 95.8 | 94 | 97 | 92.8 | 87.9 | 96 |
| 1_60 | 95.8 | 94 | 97 | 92.8 | 87.9 | 96 |
| 1_62 | 96.4 | 94 | 98 | 92.8 | 87.9 | 96 |
| 1_63 | 95.8 | 94 | 97 | 92.8 | 87.9 | 96 |
| 1_64 | 95.8 | 94 | 97 | 92.8 | 87.9 | 96 |
| 1_114 | 95.2 | 91 | 98 | 92.8 | 87.9 | 96 |
| 1_67 | 96.4 | 94 | 98 | 92.8 | 87.9 | 96 |
| 1_68 | 95.8 | 94 | 97 | 92.8 | 87.9 | 96 |

TABLE 6-continued

| | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 1_115 | 95.8 | 94 | 97 | 92.8 | 87.9 | 96 |
| 1_117 | 95.8 | 92.5 | 98 | 92.8 | 87.9 | 96 |
| 1_73 | 97 | 95.5 | 98 | 92.8 | 87.9 | 96 |
| 1_76 | 95.8 | 94 | 97 | 92.8 | 87.9 | 96 |
| 1_118 | 97.6 | 95.5 | 99 | 92.8 | 87.9 | 96 |
| 1_78 | 95.8 | 94 | 97 | 92.8 | 87.9 | 96 |
| 1_80 | 96.4 | 95.5 | 97 | 92.8 | 87.9 | 96 |
| 1_84 | 95.8 | 94 | 97 | 92.8 | 87.9 | 96 |
| 1_85 | 95.8 | 94 | 97 | 92.8 | 87.9 | 96 |
| 1_86 | 97 | 95.5 | 98 | 92.8 | 87.9 | 96 |
| 1_88 | 95.8 | 92.5 | 98 | 92.8 | 87.9 | 96 |
| 1_89 | 97 | 94 | 99 | 92.8 | 87.9 | 96 |
| 1_90 | 97 | 97 | 97 | 92.8 | 87.9 | 96 |
| 1_91 | 95.8 | 94 | 97 | 92.8 | 87.9 | 96 |
| 1_92 | 95.2 | 92.5 | 97 | 92.8 | 87.9 | 96 |
| 1_94 | 96.4 | 94 | 98 | 92.8 | 87.9 | 96 |
| 1_95 | 96.4 | 94 | 98 | 92.8 | 87.9 | 96 |
| 1_98 | 97 | 93.9 | 99 | 92.8 | 87.9 | 96 |
| 1_100 | 95.8 | 94 | 97 | 92.8 | 87.9 | 96 |
| 1_103 | 96.4 | 95.5 | 97 | 92.8 | 87.9 | 96 |
| 1_104 | 95.8 | 94 | 97 | 92.8 | 87.9 | 96 |
| 2_20 | 90.4 | 79.1 | 98 | 92.8 | 87.9 | 96 |
| 2_36 | 91.6 | 82.1 | 98 | 92.8 | 87.9 | 96 |
| 2_42 | 91.6 | 83.6 | 97 | 92.8 | 87.9 | 96 |
| 2_59 | 91.6 | 82.1 | 98 | 92.8 | 87.9 | 96 |
| 35_107 | 88 | 79.1 | 94 | 92.8 | 87.9 | 96 |
| 98_107 | 90.4 | 81.8 | 96 | 92.8 | 87.9 | 96 |
| 3_13 | 92.8 | 88.1 | 96 | 92.8 | 87.9 | 96 |
| 3_120 | 90.4 | 85.1 | 94 | 92.8 | 87.9 | 96 |
| 3_99 | 92.2 | 86.6 | 96 | 92.8 | 87.9 | 96 |
| 5_17 | 91.6 | 86.6 | 95 | 92.8 | 87.9 | 96 |
| 5_26 | 91 | 85.1 | 95 | 92.8 | 87.9 | 96 |
| 5_115 | 91.6 | 91 | 92 | 92.8 | 87.9 | 96 |
| 5_97 | 91 | 83.6 | 96 | 92.8 | 87.9 | 96 |
| 7_10 | 92.2 | 86.6 | 96 | 92.8 | 87.9 | 96 |
| 7_20 | 91 | 86.6 | 94 | 92.8 | 87.9 | 96 |
| 7_24 | 92.8 | 88.1 | 96 | 92.8 | 87.9 | 96 |
| 7_54 | 88.6 | 82.1 | 93 | 92.8 | 87.9 | 96 |
| 7_76 | 89.8 | 83.6 | 94 | 92.8 | 87.9 | 96 |
| 7_118 | 93.4 | 86.6 | 98 | 92.8 | 87.9 | 96 |
| 7_91 | 91 | 83.6 | 96 | 92.8 | 87.9 | 96 |
| 7_102 | 92.8 | 88.1 | 96 | 92.8 | 87.9 | 96 |
| 9_18 | 91.6 | 85.1 | 96 | 92.8 | 87.9 | 96 |
| 9_120 | 83.2 | 79.1 | 86 | 92.8 | 87.9 | 96 |
| 11_18 | 88 | 83.6 | 91 | 92.8 | 87.9 | 96 |
| 12_24 | 86.1 | 80.3 | 90 | 92.8 | 87.9 | 96 |
| 13_30 | 89.2 | 89.6 | 89 | 92.8 | 87.9 | 96 |
| 13_53 | 85 | 85.1 | 85 | 92.8 | 87.9 | 96 |
| 13_60 | 86.8 | 79.1 | 92 | 92.8 | 87.9 | 96 |
| 14_24 | 88 | 77.6 | 95 | 92.8 | 87.9 | 96 |
| 18_19 | 88 | 80.6 | 93 | 92.8 | 87.9 | 96 |
| 42_119 | 79 | 65.7 | 88 | 92.8 | 87.9 | 96 |
| 1_72 | 95.8 | 94 | 97 | 92.7 | 87.9 | 95.9 |
| 1_109 | 97 | 95.5 | 98 | 91.6 | 87.9 | 94 |
| 1_59 | 95.2 | 91 | 98 | 91.6 | 87.9 | 94 |
| 1_116 | 95.8 | 92.5 | 98 | 91.6 | 87.9 | 94 |
| 1_93 | 97.6 | 95.5 | 99 | 91.6 | 87.9 | 94 |
| 2_106 | 93.4 | 85.1 | 99 | 91.6 | 87.9 | 94 |
| 9_106 | 92.2 | 83.6 | 98 | 91.6 | 87.9 | 94 |
| 9_107 | 93.4 | 86.6 | 98 | 91.6 | 87.9 | 94 |
| 39_107 | 91 | 85.1 | 95 | 91.6 | 87.9 | 94 |
| 44_107 | 95.2 | 91 | 98 | 91.6 | 87.9 | 94 |
| 55_107 | 92.8 | 85.1 | 98 | 91.6 | 87.9 | 94 |
| 3_5 | 97 | 95.5 | 98 | 91.6 | 87.9 | 94 |
| 3_71 | 98.2 | 98.5 | 98 | 91.6 | 87.9 | 94 |
| 4_108 | 93.4 | 88.1 | 97 | 91.6 | 87.9 | 94 |
| 4_8 | 92.8 | 85.1 | 98 | 91.6 | 87.9 | 94 |
| 20_108 | 93.4 | 89.6 | 96 | 91.6 | 87.9 | 94 |
| 70_108 | 90.4 | 79.1 | 98 | 91.6 | 87.9 | 94 |
| 81_108 | 92.2 | 84.8 | 97 | 91.6 | 87.9 | 94 |
| 87_108 | 88 | 83.6 | 91 | 91.6 | 87.9 | 94 |
| 5_20 | 92.2 | 88.1 | 95 | 91.6 | 87.9 | 94 |
| 5_29 | 90.4 | 82.1 | 96 | 91.6 | 87.9 | 94 |
| 5_87 | 89.8 | 83.6 | 94 | 91.6 | 87.9 | 94 |
| 5_90 | 88 | 82.1 | 92 | 91.6 | 87.9 | 94 |

TABLE 6-continued

| SEQ ID NO: | Training cohort | | | Validation cohort | | |
| --- | --- | --- | --- | --- | --- | --- |
| | Accuracy (%) | Sensitivity (%) | Specificity (%) | Accuracy (%) | Sensitivity (%) | Specificity (%) |
| 14_109 | 87.4 | 74.6 | 96 | 91.6 | 87.9 | 94 |
| 7_47 | 86.8 | 80.6 | 91 | 91.6 | 87.9 | 94 |
| 7_55 | 92.2 | 83.6 | 98 | 91.6 | 87.9 | 94 |
| 7_115 | 94 | 88.1 | 98 | 91.6 | 87.9 | 94 |
| 7_75 | 89.8 | 83.6 | 94 | 91.6 | 87.9 | 94 |
| 7_82 | 90.4 | 85.1 | 94 | 91.6 | 87.9 | 94 |
| 7_92 | 90.4 | 83.6 | 95 | 91.6 | 87.9 | 94 |
| 7_93 | 91 | 82.1 | 97 | 91.6 | 87.9 | 94 |
| 7_97 | 91 | 83.6 | 96 | 91.6 | 87.9 | 94 |
| 7_98 | 89.8 | 81.8 | 95 | 91.6 | 87.9 | 94 |
| 11_25 | 88 | 80.6 | 93 | 91.6 | 87.9 | 94 |
| 14_21 | 88.6 | 79.1 | 95 | 91.6 | 87.9 | 94 |
| 18_42 | 89.8 | 79.1 | 97 | 91.6 | 87.9 | 94 |
| 18_51 | 89.2 | 83.6 | 93 | 91.6 | 87.9 | 94 |
| 18_115 | 85.6 | 76.1 | 92 | 91.6 | 87.9 | 94 |
| 19_21 | 87.4 | 76.1 | 95 | 91.6 | 87.9 | 94 |
| 19_34 | 88.6 | 83.6 | 92 | 91.6 | 87.9 | 94 |
| 28_39 | 85.6 | 74.6 | 93 | 91.6 | 87.9 | 94 |
| 30_46 | 85 | 79.1 | 89 | 91.6 | 87.9 | 94 |
| 39_87 | 86.2 | 73.1 | 95 | 91.6 | 87.9 | 94 |
| 58_113 | 87.4 | 79.1 | 93 | 91.6 | 87.9 | 94 |
| 7_72 | 89.2 | 83.6 | 93 | 91.5 | 87.9 | 93.9 |
| 5_106 | 94 | 88.1 | 98 | 90.4 | 87.9 | 92 |
| 16_106 | 93.4 | 86.6 | 98 | 90.4 | 87.9 | 92 |
| 24_107 | 89.2 | 82.1 | 94 | 90.4 | 87.9 | 92 |
| 74_107 | 93.4 | 88.1 | 97 | 90.4 | 87.9 | 92 |
| 96_107 | 89.8 | 82.1 | 95 | 90.4 | 87.9 | 92 |
| 3_55 | 93.4 | 91 | 95 | 90.4 | 87.9 | 92 |
| 3_83 | 93.4 | 92.5 | 94 | 90.4 | 87.9 | 92 |
| 4_22 | 88 | 77.6 | 95 | 90.4 | 87.9 | 92 |
| 4_86 | 91 | 83.6 | 96 | 90.4 | 87.9 | 92 |
| 9_108 | 90.4 | 86.6 | 93 | 90.4 | 87.9 | 92 |
| 31_108 | 91 | 82.1 | 97 | 90.4 | 87.9 | 92 |
| 44_108 | 93.4 | 88.1 | 97 | 90.4 | 87.9 | 92 |
| 52_108 | 95.2 | 88.1 | 100 | 90.4 | 87.9 | 92 |
| 80_108 | 91 | 88.1 | 93 | 90.4 | 87.9 | 92 |
| 7_28 | 92.2 | 91 | 93 | 90.4 | 87.9 | 92 |
| 7_117 | 93.4 | 88.1 | 97 | 90.4 | 87.9 | 92 |
| 7_78 | 92.8 | 86.6 | 97 | 90.4 | 87.9 | 92 |
| 7_81 | 90.4 | 83.3 | 95 | 90.4 | 87.9 | 92 |
| 7_90 | 91 | 85.1 | 95 | 90.4 | 87.9 | 92 |
| 8_21 | 86.2 | 76.1 | 93 | 90.4 | 87.9 | 92 |
| 9_13 | 92.2 | 94 | 91 | 90.4 | 87.9 | 92 |
| 10_37 | 88 | 82.1 | 92 | 90.4 | 87.9 | 92 |
| 10_66 | 87.4 | 76.1 | 95 | 90.4 | 87.9 | 92 |
| 13_31 | 87.4 | 82.1 | 91 | 90.4 | 87.9 | 92 |
| 13_114 | 86.2 | 85.1 | 87 | 90.4 | 87.9 | 92 |
| 13_103 | 85.6 | 82.1 | 88 | 90.4 | 87.9 | 92 |
| 16_119 | 86.2 | 80.6 | 90 | 90.4 | 87.9 | 92 |
| 18_27 | 89.2 | 83.6 | 93 | 90.4 | 87.9 | 92 |
| 18_47 | 83.8 | 76.1 | 89 | 90.4 | 87.9 | 92 |
| 18_113 | 90.4 | 83.6 | 95 | 90.4 | 87.9 | 92 |
| 18_56 | 87.4 | 79.1 | 93 | 90.4 | 87.9 | 92 |
| 22_45 | 87.4 | 79.1 | 93 | 90.4 | 87.9 | 92 |
| 22_97 | 83.2 | 79.1 | 86 | 90.4 | 87.9 | 92 |
| 24_32 | 84.4 | 77.6 | 89 | 90.4 | 87.9 | 92 |
| 24_74 | 80.2 | 76.1 | 83 | 90.4 | 87.9 | 92 |
| 24_99 | 83.2 | 74.6 | 89 | 90.4 | 87.9 | 92 |
| 30_34 | 84.4 | 77.6 | 89 | 90.4 | 87.9 | 92 |
| 35_39 | 78.4 | 61.2 | 90 | 90.4 | 87.9 | 92 |
| 66_112 | 83.8 | 71.6 | 92 | 90.4 | 87.9 | 92 |
| 51_58 | 85.6 | 74.6 | 93 | 90.4 | 87.9 | 92 |
| 65_107 | 92.8 | 85.1 | 98 | 89.2 | 87.9 | 90 |
| 92_107 | 92.8 | 89.6 | 95 | 89.2 | 87.9 | 90 |
| 3_4 | 93.4 | 88.1 | 97 | 89.2 | 87.9 | 90 |
| 4_32 | 90.4 | 83.6 | 95 | 89.2 | 87.9 | 90 |
| 4_53 | 86.2 | 73.1 | 95 | 89.2 | 87.9 | 90 |
| 4_69 | 87.4 | 79.1 | 93 | 89.2 | 87.9 | 90 |
| 4_117 | 88.6 | 77.6 | 96 | 89.2 | 87.9 | 90 |
| 4_79 | 86.8 | 74.6 | 95 | 89.2 | 87.9 | 90 |
| 4_101 | 86.8 | 77.6 | 93 | 89.2 | 87.9 | 90 |
| 42_108 | 89.2 | 80.6 | 95 | 89.2 | 87.9 | 90 |
| 45_108 | 94.6 | 89.6 | 98 | 89.2 | 87.9 | 90 |
| 5_34 | 89.8 | 86.6 | 92 | 89.2 | 87.9 | 90 |
| 5_96 | 87.4 | 77.6 | 94 | 89.2 | 87.9 | 90 |

TABLE 6-continued

| | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 6_58 | 91.6 | 83.6 | 97 | 89.2 | 87.9 | 90 |
| 87_109 | 92.2 | 88.1 | 95 | 89.2 | 87.9 | 90 |
| 7_69 | 89.8 | 83.6 | 94 | 89.2 | 87.9 | 90 |
| 7_100 | 94 | 91 | 96 | 89.2 | 87.9 | 90 |
| 9_20 | 89.8 | 89.6 | 90 | 89.2 | 87.9 | 90 |
| 9_25 | 84.4 | 77.6 | 89 | 89.2 | 87.9 | 90 |
| 9_55 | 86.2 | 77.6 | 92 | 89.2 | 87.9 | 90 |
| 10_98 | 89.8 | 89.4 | 90 | 89.2 | 87.9 | 90 |
| 11_112 | 83.8 | 77.6 | 88 | 89.2 | 87.9 | 90 |
| 12_21 | 85.5 | 77.3 | 91 | 89.2 | 87.9 | 90 |
| 13_18 | 89.8 | 85.1 | 93 | 89.2 | 87.9 | 90 |
| 21_119 | 81.4 | 73.1 | 87 | 89.2 | 87.9 | 90 |
| 21_122 | 77.8 | 68.7 | 84 | 89.2 | 87.9 | 90 |
| 22_115 | 85 | 79.1 | 89 | 89.2 | 87.9 | 90 |
| 24_33 | 82 | 70.1 | 90 | 89.2 | 87.9 | 90 |
| 24_34 | 82.6 | 76.1 | 87 | 89.2 | 87.9 | 90 |
| 24_42 | 77.8 | 59.7 | 90 | 89.2 | 87.9 | 90 |
| 24_66 | 83.2 | 68.7 | 93 | 89.2 | 87.9 | 90 |
| 24_70 | 83.8 | 71.6 | 92 | 89.2 | 87.9 | 90 |
| 24_82 | 81.4 | 71.6 | 88 | 89.2 | 87.9 | 90 |
| 24_97 | 83.2 | 77.6 | 87 | 89.2 | 87.9 | 90 |
| 25_89 | 85 | 74.6 | 92 | 89.2 | 87.9 | 90 |
| 25_121 | 80.8 | 70.1 | 88 | 89.2 | 87.9 | 90 |
| 35_51 | 77.8 | 59.7 | 90 | 89.2 | 87.9 | 90 |
| 35_54 | 80.8 | 70.1 | 88 | 89.2 | 87.9 | 90 |
| 35_61 | 76 | 62.7 | 85 | 89.2 | 87.9 | 90 |
| 35_85 | 77.2 | 62.7 | 87 | 89.2 | 87.9 | 90 |
| 59_112 | 86.8 | 76.1 | 94 | 89.2 | 87.9 | 90 |
| 67_112 | 80.8 | 64.2 | 92 | 89.2 | 87.9 | 90 |
| 46_104 | 84.4 | 71.6 | 93 | 89.2 | 87.9 | 90 |
| 51_52 | 85 | 79.1 | 89 | 89.2 | 87.9 | 90 |
| 55_113 | 89.8 | 80.6 | 96 | 89.2 | 87.9 | 90 |
| 3_67 | 92.2 | 89.6 | 94 | 88 | 87.9 | 88 |
| 3_94 | 91.6 | 86.6 | 95 | 88 | 87.9 | 88 |
| 4_31 | 86.2 | 73.1 | 95 | 88 | 87.9 | 88 |
| 4_35 | 86.8 | 74.6 | 95 | 88 | 87.9 | 88 |
| 4_51 | 86.8 | 74.6 | 95 | 88 | 87.9 | 88 |
| 4_59 | 86.2 | 73.1 | 95 | 88 | 87.9 | 88 |
| 4_62 | 88 | 74.6 | 97 | 88 | 87.9 | 88 |
| 4_114 | 87.4 | 74.6 | 96 | 88 | 87.9 | 88 |
| 4_68 | 86.2 | 73.1 | 95 | 88 | 87.9 | 88 |
| 4_116 | 88.6 | 77.6 | 96 | 88 | 87.9 | 88 |
| 4_78 | 86.2 | 74.6 | 94 | 88 | 87.9 | 88 |
| 4_93 | 86.8 | 76.1 | 94 | 88 | 87.9 | 88 |
| 4_103 | 86.8 | 74.6 | 95 | 88 | 87.9 | 88 |
| 4_104 | 86.8 | 74.6 | 95 | 88 | 87.9 | 88 |
| 75_108 | 91.6 | 82.1 | 98 | 88 | 87.9 | 88 |
| 5_35 | 89.2 | 80.6 | 95 | 88 | 87.9 | 88 |
| 6_21 | 89.8 | 79.1 | 97 | 88 | 87.9 | 88 |
| 9_70 | 86.8 | 79.1 | 92 | 88 | 87.9 | 88 |
| 9_85 | 83.2 | 79.1 | 86 | 88 | 87.9 | 88 |
| 10_79 | 85 | 74.6 | 92 | 88 | 87.9 | 88 |
| 11_55 | 81.4 | 71.6 | 88 | 88 | 87.9 | 88 |
| 16_112 | 88 | 83.6 | 91 | 88 | 87.9 | 88 |
| 18_21 | 86.8 | 77.6 | 93 | 88 | 87.9 | 88 |
| 19_75 | 88.6 | 80.6 | 94 | 88 | 87.9 | 88 |
| 21_22 | 80.2 | 71.6 | 86 | 88 | 87.9 | 88 |
| 21_111 | 83.8 | 73.1 | 91 | 88 | 87.9 | 88 |
| 21_45 | 85.6 | 83.6 | 87 | 88 | 87.9 | 88 |
| 21_115 | 80.2 | 70.1 | 87 | 88 | 87.9 | 88 |
| 22_112 | 87.4 | 76.1 | 95 | 88 | 87.9 | 88 |
| 22_62 | 83.2 | 70.1 | 92 | 88 | 87.9 | 88 |
| 22_118 | 83.2 | 73.1 | 90 | 88 | 87.9 | 88 |
| 24_64 | 77.2 | 62.7 | 87 | 88 | 87.9 | 88 |
| 24_65 | 83.2 | 76.1 | 88 | 88 | 87.9 | 88 |
| 24_75 | 81.4 | 70.1 | 89 | 88 | 87.9 | 88 |
| 25_93 | 83.2 | 73.1 | 90 | 88 | 87.9 | 88 |
| 27_120 | 82.6 | 77.6 | 86 | 88 | 87.9 | 88 |
| 35_46 | 78.4 | 62.7 | 89 | 88 | 87.9 | 88 |
| 35_91 | 80.2 | 67.2 | 89 | 88 | 87.9 | 88 |
| 35_122 | 79 | 67.2 | 87 | 88 | 87.9 | 88 |
| 42_58 | 83.2 | 71.6 | 91 | 88 | 87.9 | 88 |
| 70_112 | 82 | 67.2 | 92 | 88 | 87.9 | 88 |
| 79_112 | 80.8 | 67.2 | 90 | 88 | 87.9 | 88 |
| 4_72 | 89.2 | 82.1 | 94 | 87.8 | 87.9 | 87.8 |

TABLE 6-continued

| | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 21_106 | 93.4 | 85.1 | 99 | 86.7 | 87.9 | 86 |
| 4_64 | 85.6 | 74.6 | 93 | 86.7 | 87.9 | 86 |
| 4_66 | 88 | 77.6 | 95 | 86.7 | 87.9 | 86 |
| 4_118 | 89.8 | 82.1 | 95 | 86.7 | 87.9 | 86 |
| 5_78 | 88.6 | 82.1 | 93 | 86.7 | 87.9 | 86 |
| 5_82 | 89.8 | 85.1 | 93 | 86.7 | 87.9 | 86 |
| 9_56 | 83.2 | 77.6 | 87 | 86.7 | 87.9 | 86 |
| 9_71 | 86.2 | 79.1 | 91 | 86.7 | 87.9 | 86 |
| 9_94 | 85.6 | 77.6 | 91 | 86.7 | 87.9 | 86 |
| 11_35 | 80.8 | 70.1 | 88 | 86.7 | 87.9 | 86 |
| 16_35 | 85.6 | 80.6 | 89 | 86.7 | 87.9 | 86 |
| 21_24 | 85 | 74.6 | 92 | 86.7 | 87.9 | 86 |
| 21_39 | 82.6 | 73.1 | 89 | 86.7 | 87.9 | 86 |
| 21_46 | 82.6 | 71.6 | 90 | 86.7 | 87.9 | 86 |
| 21_49 | 83.2 | 74.6 | 89 | 86.7 | 87.9 | 86 |
| 21_57 | 84.4 | 76.1 | 90 | 86.7 | 87.9 | 86 |
| 21_85 | 80.2 | 68.7 | 88 | 86.7 | 87.9 | 86 |
| 22_52 | 84.4 | 77.6 | 89 | 86.7 | 87.9 | 86 |
| 22_65 | 86.8 | 82.1 | 90 | 86.7 | 87.9 | 86 |
| 22_114 | 82 | 77.6 | 85 | 86.7 | 87.9 | 86 |
| 22_94 | 81.4 | 71.6 | 88 | 86.7 | 87.9 | 86 |
| 22_99 | 83.8 | 74.6 | 90 | 86.7 | 87.9 | 86 |
| 25_44 | 83.2 | 71.6 | 91 | 86.7 | 87.9 | 86 |
| 25_65 | 86.2 | 80.6 | 90 | 86.7 | 87.9 | 86 |
| 25_67 | 80.8 | 70.1 | 88 | 86.7 | 87.9 | 86 |
| 29_31 | 85 | 74.6 | 92 | 86.7 | 87.9 | 86 |
| 35_58 | 82 | 68.7 | 91 | 86.7 | 87.9 | 86 |
| 35_70 | 79.6 | 61.2 | 92 | 86.7 | 87.9 | 86 |
| 35_84 | 79.6 | 67.2 | 88 | 86.7 | 87.9 | 86 |
| 55_115 | 83.2 | 71.6 | 91 | 86.7 | 87.9 | 86 |
| 58_79 | 79 | 64.2 | 89 | 86.7 | 87.9 | 86 |
| 66_83 | 80.8 | 67.2 | 90 | 86.7 | 87.9 | 86 |
| 67_80 | 76.6 | 65.7 | 84 | 86.7 | 87.9 | 86 |
| 79_98 | 77.1 | 60.6 | 88 | 86.7 | 87.9 | 86 |
| 83_104 | 79 | 64.2 | 89 | 86.7 | 87.9 | 86 |
| 4_36 | 87.4 | 76.1 | 95 | 85.5 | 87.9 | 84 |
| 4_100 | 86.8 | 74.6 | 95 | 85.5 | 87.9 | 84 |
| 5_109 | 93.4 | 89.6 | 96 | 85.5 | 87.9 | 84 |
| 16_109 | 90.4 | 86.6 | 93 | 85.5 | 87.9 | 84 |
| 25_109 | 85.6 | 76.1 | 92 | 85.5 | 87.9 | 84 |
| 58_110 | 88 | 83.6 | 91 | 85.5 | 87.9 | 84 |
| 11_71 | 80.8 | 74.6 | 85 | 85.5 | 87.9 | 84 |
| 21_65 | 79.6 | 70.1 | 86 | 85.5 | 87.9 | 84 |
| 21_68 | 81.4 | 70.1 | 89 | 85.5 | 87.9 | 84 |
| 21_74 | 83.2 | 71.6 | 91 | 85.5 | 87.9 | 84 |
| 21_118 | 84.4 | 79.1 | 88 | 85.5 | 87.9 | 84 |
| 21_90 | 77.2 | 71.6 | 81 | 85.5 | 87.9 | 84 |
| 22_104 | 79 | 73.1 | 83 | 85.5 | 87.9 | 84 |
| 24_52 | 81.4 | 71.6 | 88 | 85.5 | 87.9 | 84 |
| 24_67 | 82 | 73.1 | 88 | 85.5 | 87.9 | 84 |
| 24_92 | 80.2 | 70.1 | 87 | 85.5 | 87.9 | 84 |
| 34_75 | 80.2 | 76.1 | 83 | 85.5 | 87.9 | 84 |
| 35_104 | 79 | 62.7 | 90 | 85.5 | 87.9 | 84 |
| 81_104 | 80.1 | 65.2 | 90 | 85.5 | 87.9 | 84 |
| 35_109 | 85 | 73.1 | 93 | 84.3 | 87.9 | 82 |
| 104_109 | 88 | 80.6 | 93 | 84.3 | 87.9 | 82 |
| 10_99 | 88 | 82.1 | 92 | 84.3 | 87.9 | 82 |
| 21_31 | 78.4 | 65.7 | 87 | 84.3 | 87.9 | 82 |
| 21_98 | 78.9 | 69.7 | 85 | 84.3 | 87.9 | 82 |
| 24_98 | 84.9 | 77.3 | 90 | 84.3 | 87.9 | 82 |
| 24_100 | 77.2 | 61.2 | 88 | 84.3 | 87.9 | 82 |
| 25_100 | 82.6 | 71.6 | 90 | 84.3 | 87.9 | 82 |
| 31_34 | 84.4 | 76.1 | 90 | 84.3 | 87.9 | 82 |
| 31_120 | 82.6 | 74.6 | 88 | 84.3 | 87.9 | 82 |
| 35_52 | 79 | 65.7 | 88 | 84.3 | 87.9 | 82 |
| 35_114 | 79.6 | 65.7 | 89 | 84.3 | 87.9 | 82 |
| 35_69 | 83.8 | 73.1 | 91 | 84.3 | 87.9 | 82 |
| 58_67 | 79 | 58.2 | 93 | 84.3 | 87.9 | 82 |
| 65_78 | 74.9 | 65.7 | 81 | 84.3 | 87.9 | 82 |
| 66_94 | 77.8 | 56.7 | 92 | 84.3 | 87.9 | 82 |
| 29_109 | 83.8 | 73.1 | 91 | 83.1 | 87.9 | 80 |
| 90_109 | 88 | 80.6 | 93 | 83.1 | 87.9 | 80 |
| 21_34 | 83.8 | 74.6 | 90 | 83.1 | 87.9 | 80 |
| 21_52 | 80.8 | 71.6 | 87 | 83.1 | 87.9 | 80 |
| 21_121 | 82 | 74.6 | 87 | 83.1 | 87.9 | 80 |

TABLE 6-continued

| | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 21__94 | 79.6 | 70.1 | 86 | 83.1 | 87.9 | 80 |
| 21__102 | 78.4 | 71.6 | 83 | 83.1 | 87.9 | 80 |
| 31__98 | 78.9 | 68.2 | 86 | 83.1 | 87.9 | 80 |
| 66__93 | 77.8 | 59.7 | 90 | 83.1 | 87.9 | 80 |
| 34__109 | 88.6 | 91 | 87 | 81.9 | 87.9 | 78 |
| 80__109 | 87.4 | 80.6 | 92 | 81.9 | 87.9 | 78 |
| 21__100 | 81.4 | 71.6 | 88 | 81.9 | 87.9 | 78 |
| 35__78 | 76.6 | 59.7 | 88 | 81.9 | 87.9 | 78 |
| 42__109 | 85 | 77.6 | 90 | 80.7 | 87.9 | 76 |
| 75__109 | 83.8 | 76.1 | 89 | 80.7 | 87.9 | 76 |
| 96__109 | 85 | 80.6 | 88 | 80.7 | 87.9 | 76 |
| 103__109 | 86.8 | 80.6 | 91 | 80.7 | 87.9 | 76 |
| 10__92 | 89.2 | 86.6 | 91 | 80.7 | 87.9 | 76 |
| 52__109 | 88 | 85.1 | 90 | 79.5 | 87.9 | 74 |
| 50__79 | 74.3 | 56.7 | 86 | 86.6 | 87.5 | 86 |
| 23__35 | 81.4 | 67.2 | 91 | 85.4 | 87.5 | 84 |
| 10__50 | 90.4 | 83.6 | 95 | 84.1 | 87.5 | 82 |
| 50__67 | 74.3 | 61.2 | 83 | 82.9 | 87.5 | 80 |
| 77__108 | 90.4 | 77.6 | 99 | 95.1 | 87.1 | 100 |
| 24__77 | 80.8 | 74.6 | 85 | 88.9 | 87.1 | 90 |
| 9__77 | 83.8 | 76.1 | 89 | 87.7 | 87.1 | 88 |
| 19__106 | 93.4 | 86.6 | 98 | 94 | 84.8 | 100 |
| 87__106 | 92.2 | 83.6 | 98 | 94 | 84.8 | 100 |
| 2__8 | 92.2 | 85.1 | 97 | 94 | 84.8 | 100 |
| 2__75 | 88.6 | 76.1 | 97 | 94 | 84.8 | 100 |
| 2__97 | 88 | 74.6 | 97 | 94 | 84.8 | 100 |
| 2__102 | 92.8 | 82.1 | 100 | 94 | 84.8 | 100 |
| 2__122 | 89.2 | 77.6 | 97 | 94 | 84.8 | 100 |
| 6__119 | 91.6 | 83.6 | 97 | 94 | 84.8 | 100 |
| 7__8 | 93.4 | 85.1 | 99 | 94 | 84.8 | 100 |
| 7__32 | 91 | 82.1 | 97 | 94 | 84.8 | 100 |
| 8__17 | 90.4 | 79.1 | 98 | 94 | 84.8 | 100 |
| 12__15 | 92.8 | 86.4 | 97 | 94 | 84.8 | 100 |
| 17__18 | 91 | 82.1 | 97 | 94 | 84.8 | 100 |
| 1__107 | 95.8 | 92.5 | 98 | 92.8 | 84.8 | 98 |
| 1__122 | 96.4 | 94 | 98 | 92.8 | 84.8 | 98 |
| 2__110 | 92.2 | 85.1 | 97 | 92.8 | 84.8 | 98 |
| 2__48 | 91.6 | 80.6 | 99 | 92.8 | 84.8 | 98 |
| 2__61 | 89.8 | 76.1 | 99 | 92.8 | 84.8 | 98 |
| 2__76 | 91.6 | 80.6 | 99 | 92.8 | 84.8 | 98 |
| 8__107 | 97 | 94 | 99 | 92.8 | 84.8 | 98 |
| 3__66 | 92.8 | 86.6 | 97 | 92.8 | 84.8 | 98 |
| 90__108 | 88 | 80.6 | 93 | 92.8 | 84.8 | 98 |
| 5__113 | 93.4 | 94 | 93 | 92.8 | 84.8 | 98 |
| 5__53 | 91 | 85.1 | 95 | 92.8 | 84.8 | 98 |
| 6__12 | 92.2 | 83.3 | 98 | 92.8 | 84.8 | 98 |
| 6__13 | 94 | 86.6 | 99 | 92.8 | 84.8 | 98 |
| 6__20 | 91.6 | 86.6 | 95 | 92.8 | 84.8 | 98 |
| 6__26 | 91 | 83.6 | 96 | 92.8 | 84.8 | 98 |
| 7__111 | 88.6 | 77.6 | 96 | 92.8 | 84.8 | 98 |
| 7__57 | 89.8 | 79.1 | 97 | 92.8 | 84.8 | 98 |
| 7__101 | 91.6 | 88.1 | 94 | 92.8 | 84.8 | 98 |
| 8__9 | 92.2 | 89.6 | 94 | 92.8 | 84.8 | 98 |
| 13__17 | 89.2 | 79.1 | 96 | 92.8 | 84.8 | 98 |
| 14__55 | 92.8 | 82.1 | 100 | 92.8 | 84.8 | 98 |
| 17__20 | 89.2 | 79.1 | 96 | 92.8 | 84.8 | 98 |
| 18__69 | 86.8 | 76.1 | 94 | 92.8 | 84.8 | 98 |
| 1__15 | 96.4 | 94 | 98 | 91.6 | 84.8 | 96 |
| 1__27 | 97 | 95.5 | 98 | 91.6 | 84.8 | 96 |
| 1__111 | 96.4 | 95.5 | 97 | 91.6 | 84.8 | 96 |
| 1__82 | 96.4 | 95.5 | 97 | 91.6 | 84.8 | 96 |
| 1__96 | 95.8 | 92.5 | 98 | 91.6 | 84.8 | 96 |
| 49__106 | 91.6 | 83.6 | 97 | 91.6 | 84.8 | 96 |
| 7__107 | 94.6 | 88.1 | 99 | 91.6 | 84.8 | 96 |
| 16__107 | 93.4 | 91 | 95 | 91.6 | 84.8 | 96 |
| 22__107 | 89.8 | 83.6 | 94 | 91.6 | 84.8 | 96 |
| 83__107 | 89.2 | 80.6 | 95 | 91.6 | 84.8 | 96 |
| 85__107 | 87.4 | 77.6 | 94 | 91.6 | 84.8 | 96 |
| 87__107 | 93.4 | 88.1 | 97 | 91.6 | 84.8 | 96 |
| 101__107 | 90.4 | 79.1 | 98 | 91.6 | 84.8 | 96 |
| 3__26 | 90.4 | 86.6 | 93 | 91.6 | 84.8 | 96 |
| 4__61 | 89.2 | 80.6 | 95 | 91.6 | 84.8 | 96 |
| 64__108 | 86.8 | 76.1 | 94 | 91.6 | 84.8 | 96 |
| 66__108 | 91.6 | 85.1 | 96 | 91.6 | 84.8 | 96 |
| 5__28 | 91.6 | 89.6 | 93 | 91.6 | 84.8 | 96 |

TABLE 6-continued

| | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 5_37 | 90.4 | 83.6 | 95 | 91.6 | 84.8 | 96 |
| 5_119 | 91 | 82.1 | 97 | 91.6 | 84.8 | 96 |
| 30_109 | 92.8 | 86.6 | 97 | 91.6 | 84.8 | 96 |
| 7_11 | 91.6 | 83.6 | 97 | 91.6 | 84.8 | 96 |
| 7_19 | 92.8 | 88.1 | 96 | 91.6 | 84.8 | 96 |
| 7_26 | 93.4 | 88.1 | 97 | 91.6 | 84.8 | 96 |
| 7_30 | 92.8 | 88.1 | 96 | 91.6 | 84.8 | 96 |
| 7_38 | 93.4 | 86.6 | 98 | 91.6 | 84.8 | 96 |
| 7_46 | 91 | 82.1 | 97 | 91.6 | 84.8 | 96 |
| 7_86 | 89.8 | 83.6 | 94 | 91.6 | 84.8 | 96 |
| 11_13 | 89.2 | 82.1 | 94 | 91.6 | 84.8 | 96 |
| 12_17 | 90.4 | 80.3 | 97 | 91.6 | 84.8 | 96 |
| 12_25 | 92.2 | 89.4 | 94 | 91.6 | 84.8 | 96 |
| 18_55 | 83.2 | 71.6 | 91 | 91.6 | 84.8 | 96 |
| 18_57 | 82.6 | 70.1 | 91 | 91.6 | 84.8 | 96 |
| 22_30 | 85 | 77.6 | 90 | 91.6 | 84.8 | 96 |
| 24_26 | 82.6 | 76.1 | 87 | 91.6 | 84.8 | 96 |
| 24_30 | 87.4 | 77.6 | 94 | 91.6 | 84.8 | 96 |
| 35_60 | 83.8 | 68.7 | 94 | 91.6 | 84.8 | 96 |
| 41_112 | 84.4 | 80.6 | 87 | 91.6 | 84.8 | 96 |
| 46_113 | 86.2 | 79.1 | 91 | 91.6 | 84.8 | 96 |
| 51_120 | 83.2 | 71.6 | 91 | 91.6 | 84.8 | 96 |
| 5_72 | 90.4 | 89.6 | 91 | 91.5 | 84.8 | 95.9 |
| 20_106 | 92.2 | 83.6 | 98 | 90.4 | 84.8 | 94 |
| 25_107 | 90.4 | 83.6 | 95 | 90.4 | 84.8 | 94 |
| 47_107 | 90.4 | 83.6 | 95 | 90.4 | 84.8 | 94 |
| 89_107 | 91 | 80.6 | 98 | 90.4 | 84.8 | 94 |
| 103_107 | 89.2 | 79.1 | 96 | 90.4 | 84.8 | 94 |
| 104_107 | 91 | 83.6 | 96 | 90.4 | 84.8 | 94 |
| 4_33 | 88 | 76.1 | 96 | 90.4 | 84.8 | 94 |
| 4_38 | 86.2 | 74.6 | 94 | 90.4 | 84.8 | 94 |
| 4_40 | 88.6 | 77.6 | 96 | 90.4 | 84.8 | 94 |
| 19_108 | 91.6 | 83.6 | 97 | 90.4 | 84.8 | 94 |
| 24_108 | 89.8 | 83.6 | 94 | 90.4 | 84.8 | 94 |
| 5_49 | 91 | 85.1 | 95 | 90.4 | 84.8 | 94 |
| 5_68 | 89.2 | 83.6 | 93 | 90.4 | 84.8 | 94 |
| 5_74 | 89.2 | 82.1 | 94 | 90.4 | 84.8 | 94 |
| 6_46 | 85.6 | 73.1 | 94 | 90.4 | 84.8 | 94 |
| 7_25 | 91 | 86.6 | 94 | 90.4 | 84.8 | 94 |
| 7_27 | 90.4 | 83.6 | 95 | 90.4 | 84.8 | 94 |
| 7_39 | 91 | 80.6 | 98 | 90.4 | 84.8 | 94 |
| 7_53 | 91 | 86.6 | 94 | 90.4 | 84.8 | 94 |
| 7_64 | 90.4 | 83.6 | 95 | 90.4 | 84.8 | 94 |
| 7_122 | 91.6 | 86.6 | 95 | 90.4 | 84.8 | 94 |
| 9_117 | 85.6 | 79.1 | 90 | 90.4 | 84.8 | 94 |
| 13_40 | 86.2 | 79.1 | 91 | 90.4 | 84.8 | 94 |
| 14_35 | 88 | 79.1 | 94 | 90.4 | 84.8 | 94 |
| 18_40 | 89.2 | 77.6 | 97 | 90.4 | 84.8 | 94 |
| 20_24 | 86.2 | 80.6 | 90 | 90.4 | 84.8 | 94 |
| 22_34 | 87.4 | 82.1 | 91 | 90.4 | 84.8 | 94 |
| 22_44 | 85.6 | 77.6 | 91 | 90.4 | 84.8 | 94 |
| 24_25 | 82 | 67.2 | 92 | 90.4 | 84.8 | 94 |
| 24_40 | 82 | 73.1 | 88 | 90.4 | 84.8 | 94 |
| 25_56 | 81.4 | 73.1 | 87 | 90.4 | 84.8 | 94 |
| 25_85 | 82 | 76.1 | 86 | 90.4 | 84.8 | 94 |
| 27_112 | 86.2 | 80.6 | 90 | 90.4 | 84.8 | 94 |
| 30_58 | 85 | 80.6 | 88 | 90.4 | 84.8 | 94 |
| 30_79 | 85 | 80.6 | 88 | 90.4 | 84.8 | 94 |
| 30_81 | 82.5 | 72.7 | 89 | 90.4 | 84.8 | 94 |
| 33_35 | 82.6 | 67.2 | 93 | 90.4 | 84.8 | 94 |
| 35_40 | 84.4 | 68.7 | 95 | 90.4 | 84.8 | 94 |
| 35_86 | 84.4 | 76.1 | 90 | 90.4 | 84.8 | 94 |
| 37_46 | 79.6 | 71.6 | 85 | 90.4 | 84.8 | 94 |
| 38_112 | 86.8 | 77.6 | 93 | 90.4 | 84.8 | 94 |
| 41_58 | 85.6 | 80.6 | 89 | 90.4 | 84.8 | 94 |
| 46_53 | 84.4 | 74.6 | 91 | 90.4 | 84.8 | 94 |
| 46_115 | 82.6 | 73.1 | 89 | 90.4 | 84.8 | 94 |
| 46_87 | 79.6 | 73.1 | 84 | 90.4 | 84.8 | 94 |
| 53_94 | 82 | 71.6 | 89 | 90.4 | 84.8 | 94 |
| 58_60 | 85 | 77.6 | 90 | 90.4 | 84.8 | 94 |
| 21_107 | 92.8 | 85.1 | 98 | 89.2 | 84.8 | 92 |
| 31_107 | 91 | 80.6 | 98 | 89.2 | 84.8 | 92 |
| 67_107 | 89.8 | 82.1 | 95 | 89.2 | 84.8 | 92 |
| 79_107 | 89.8 | 79.1 | 97 | 89.2 | 84.8 | 92 |
| 95_107 | 92.2 | 85.1 | 97 | 89.2 | 84.8 | 92 |

TABLE 6-continued

| | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 97_107 | 91 | 83.6 | 96 | 89.2 | 84.8 | 92 |
| 100_107 | 89.8 | 79.1 | 97 | 89.2 | 84.8 | 92 |
| 3_112 | 93.4 | 89.6 | 96 | 89.2 | 84.8 | 92 |
| 3_81 | 94.6 | 90.9 | 97 | 89.2 | 84.8 | 92 |
| 4_28 | 88 | 77.6 | 95 | 89.2 | 84.8 | 92 |
| 53_108 | 88 | 76.1 | 96 | 89.2 | 84.8 | 92 |
| 54_108 | 89.2 | 80.6 | 95 | 89.2 | 84.8 | 92 |
| 63_108 | 85.6 | 79.1 | 90 | 89.2 | 84.8 | 92 |
| 85_108 | 89.8 | 83.6 | 94 | 89.2 | 84.8 | 92 |
| 88_108 | 91 | 82.1 | 97 | 89.2 | 84.8 | 92 |
| 103_108 | 88.6 | 82.1 | 93 | 89.2 | 84.8 | 92 |
| 5_9 | 93.4 | 94 | 93 | 89.2 | 84.8 | 92 |
| 5_10 | 94 | 91 | 96 | 89.2 | 84.8 | 92 |
| 5_16 | 92.2 | 91 | 93 | 89.2 | 84.8 | 92 |
| 5_45 | 91 | 86.6 | 94 | 89.2 | 84.8 | 92 |
| 5_51 | 89.8 | 86.6 | 92 | 89.2 | 84.8 | 92 |
| 5_104 | 91 | 83.6 | 96 | 89.2 | 84.8 | 92 |
| 7_31 | 90.4 | 86.6 | 93 | 89.2 | 84.8 | 92 |
| 7_42 | 91 | 83.6 | 96 | 89.2 | 84.8 | 92 |
| 7_84 | 90.4 | 85.1 | 94 | 89.2 | 84.8 | 92 |
| 7_95 | 92.2 | 86.6 | 96 | 89.2 | 84.8 | 92 |
| 9_112 | 91 | 88.1 | 93 | 89.2 | 84.8 | 92 |
| 9_116 | 85 | 79.1 | 89 | 89.2 | 84.8 | 92 |
| 10_26 | 88.6 | 82.1 | 93 | 89.2 | 84.8 | 92 |
| 10_71 | 90.4 | 85.1 | 94 | 89.2 | 84.8 | 92 |
| 13_113 | 88 | 86.6 | 89 | 89.2 | 84.8 | 92 |
| 13_56 | 85.6 | 80.6 | 89 | 89.2 | 84.8 | 92 |
| 15_34 | 88 | 82.1 | 92 | 89.2 | 84.8 | 92 |
| 16_24 | 89.8 | 85.1 | 93 | 89.2 | 84.8 | 92 |
| 17_35 | 85.6 | 70.1 | 96 | 89.2 | 84.8 | 92 |
| 17_112 | 90.4 | 82.1 | 96 | 89.2 | 84.8 | 92 |
| 18_31 | 86.2 | 76.1 | 93 | 89.2 | 84.8 | 92 |
| 18_53 | 87.4 | 79.1 | 93 | 89.2 | 84.8 | 92 |
| 18_68 | 88.6 | 79.1 | 95 | 89.2 | 84.8 | 92 |
| 18_100 | 86.2 | 77.6 | 92 | 89.2 | 84.8 | 92 |
| 21_37 | 81.4 | 70.1 | 89 | 89.2 | 84.8 | 92 |
| 24_103 | 80.2 | 67.2 | 89 | 89.2 | 84.8 | 92 |
| 25_111 | 86.2 | 76.1 | 93 | 89.2 | 84.8 | 92 |
| 25_117 | 85 | 74.6 | 92 | 89.2 | 84.8 | 92 |
| 25_90 | 80.2 | 67.2 | 89 | 89.2 | 84.8 | 92 |
| 29_35 | 86.2 | 73.1 | 95 | 89.2 | 84.8 | 92 |
| 37_55 | 79 | 68.7 | 86 | 89.2 | 84.8 | 92 |
| 38_99 | 86.2 | 76.1 | 93 | 89.2 | 84.8 | 92 |
| 58_115 | 84.4 | 73.1 | 92 | 89.2 | 84.8 | 92 |
| 45_107 | 91 | 83.6 | 96 | 88 | 84.8 | 90 |
| 3_108 | 91.6 | 85.1 | 96 | 88 | 84.8 | 90 |
| 3_39 | 93.4 | 89.6 | 96 | 88 | 84.8 | 90 |
| 4_27 | 88.6 | 77.6 | 96 | 88 | 84.8 | 90 |
| 4_54 | 88.6 | 77.6 | 96 | 88 | 84.8 | 90 |
| 4_95 | 85.6 | 73.1 | 94 | 88 | 84.8 | 90 |
| 4_122 | 85.6 | 71.6 | 95 | 88 | 84.8 | 90 |
| 25_108 | 90.4 | 83.6 | 95 | 88 | 84.8 | 90 |
| 48_108 | 87.4 | 77.6 | 94 | 88 | 84.8 | 90 |
| 59_108 | 88 | 82.1 | 92 | 88 | 84.8 | 90 |
| 62_108 | 89.2 | 80.6 | 95 | 88 | 84.8 | 90 |
| 86_108 | 86.8 | 73.1 | 96 | 88 | 84.8 | 90 |
| 5_22 | 91 | 86.6 | 94 | 88 | 84.8 | 90 |
| 5_36 | 91.6 | 88.1 | 94 | 88 | 84.8 | 90 |
| 5_111 | 91.6 | 86.6 | 95 | 88 | 84.8 | 90 |
| 5_39 | 89.2 | 80.6 | 95 | 88 | 84.8 | 90 |
| 5_52 | 90.4 | 82.1 | 96 | 88 | 84.8 | 90 |
| 5_79 | 88.6 | 83.6 | 92 | 88 | 84.8 | 90 |
| 9_12 | 91 | 87.9 | 93 | 88 | 84.8 | 90 |
| 9_21 | 84.4 | 77.6 | 89 | 88 | 84.8 | 90 |
| 9_22 | 83.8 | 79.1 | 87 | 88 | 84.8 | 90 |
| 9_89 | 87.4 | 82.1 | 91 | 88 | 84.8 | 90 |
| 10_89 | 88 | 80.6 | 93 | 88 | 84.8 | 90 |
| 11_37 | 86.2 | 82.1 | 89 | 88 | 84.8 | 90 |
| 13_46 | 84.4 | 76.1 | 90 | 88 | 84.8 | 90 |
| 13_121 | 83.2 | 77.6 | 87 | 88 | 84.8 | 90 |
| 16_18 | 88 | 83.6 | 91 | 88 | 84.8 | 90 |
| 18_34 | 86.2 | 80.6 | 90 | 88 | 84.8 | 90 |
| 18_75 | 85.6 | 82.1 | 88 | 88 | 84.8 | 90 |
| 18_81 | 85.5 | 78.8 | 90 | 88 | 84.8 | 90 |
| 20_35 | 83.8 | 74.6 | 90 | 88 | 84.8 | 90 |

TABLE 6-continued

| SEQ ID NO: | Training cohort | | | Validation cohort | | |
|---|---|---|---|---|---|---|
| | Accuracy (%) | Sensitivity (%) | Specificity (%) | Accuracy (%) | Sensitivity (%) | Specificity (%) |
| 21_41 | 81.4 | 73.1 | 87 | 88 | 84.8 | 90 |
| 21_113 | 82.6 | 73.1 | 89 | 88 | 84.8 | 90 |
| 24_39 | 82.6 | 70.1 | 91 | 88 | 84.8 | 90 |
| 28_46 | 86.8 | 77.6 | 93 | 88 | 84.8 | 90 |
| 34_41 | 83.2 | 79.1 | 86 | 88 | 84.8 | 90 |
| 34_113 | 85 | 74.6 | 92 | 88 | 84.8 | 90 |
| 35_48 | 86.8 | 79.1 | 92 | 88 | 84.8 | 90 |
| 35_102 | 80.8 | 70.1 | 88 | 88 | 84.8 | 90 |
| 44_111 | 79.6 | 62.7 | 91 | 88 | 84.8 | 90 |
| 46_112 | 76.6 | 62.7 | 86 | 88 | 84.8 | 90 |
| 47_112 | 81.4 | 76.1 | 85 | 88 | 84.8 | 90 |
| 46_70 | 75.4 | 61.2 | 85 | 88 | 84.8 | 90 |
| 46_89 | 78.4 | 65.7 | 87 | 88 | 84.8 | 90 |
| 55_65 | 83.2 | 67.2 | 94 | 88 | 84.8 | 90 |
| 58_70 | 77.8 | 62.7 | 88 | 88 | 84.8 | 90 |
| 66_75 | 78.4 | 62.7 | 89 | 88 | 84.8 | 90 |
| 80_83 | 72.5 | 53.7 | 85 | 88 | 84.8 | 90 |
| 25_106 | 88.6 | 79.1 | 95 | 86.7 | 84.8 | 88 |
| 34_106 | 89.2 | 80.6 | 95 | 86.7 | 84.8 | 88 |
| 3_34 | 91.6 | 86.6 | 95 | 86.7 | 84.8 | 88 |
| 3_121 | 94 | 92.5 | 95 | 86.7 | 84.8 | 88 |
| 3_96 | 93.4 | 89.6 | 96 | 86.7 | 84.8 | 88 |
| 4_42 | 86.8 | 76.1 | 94 | 86.7 | 84.8 | 88 |
| 4_57 | 88.6 | 79.1 | 95 | 86.7 | 84.8 | 88 |
| 4_67 | 86.8 | 74.6 | 95 | 86.7 | 84.8 | 88 |
| 4_70 | 86.8 | 73.1 | 96 | 86.7 | 84.8 | 88 |
| 79_108 | 90.4 | 79.1 | 98 | 86.7 | 84.8 | 88 |
| 6_52 | 87.4 | 80.6 | 92 | 86.7 | 84.8 | 88 |
| 6_99 | 86.8 | 79.1 | 92 | 86.7 | 84.8 | 88 |
| 40_109 | 86.8 | 77.6 | 93 | 86.7 | 84.8 | 88 |
| 9_11 | 88 | 80.6 | 93 | 86.7 | 84.8 | 88 |
| 9_37 | 85 | 79.1 | 89 | 86.7 | 84.8 | 88 |
| 9_45 | 86.8 | 83.6 | 89 | 86.7 | 84.8 | 88 |
| 9_98 | 84.3 | 80.3 | 87 | 86.7 | 84.8 | 88 |
| 10_22 | 84.4 | 77.6 | 89 | 86.7 | 84.8 | 88 |
| 10_55 | 86.8 | 83.6 | 89 | 86.7 | 84.8 | 88 |
| 11_39 | 79.6 | 71.6 | 85 | 86.7 | 84.8 | 88 |
| 11_46 | 79 | 68.7 | 86 | 86.7 | 84.8 | 88 |
| 11_75 | 81.4 | 73.1 | 87 | 86.7 | 84.8 | 88 |
| 13_63 | 88.6 | 91 | 87 | 86.7 | 84.8 | 88 |
| 13_81 | 84.3 | 81.8 | 86 | 86.7 | 84.8 | 88 |
| 16_46 | 84.4 | 82.1 | 86 | 86.7 | 84.8 | 88 |
| 16_58 | 84.4 | 82.1 | 86 | 86.7 | 84.8 | 88 |
| 16_120 | 84.4 | 77.6 | 89 | 86.7 | 84.8 | 88 |
| 17_34 | 84.4 | 73.1 | 92 | 86.7 | 84.8 | 88 |
| 18_78 | 82.6 | 76.1 | 87 | 86.7 | 84.8 | 88 |
| 18_84 | 88.6 | 79.1 | 95 | 86.7 | 84.8 | 88 |
| 21_26 | 83.2 | 70.1 | 92 | 86.7 | 84.8 | 88 |
| 21_33 | 82.6 | 74.6 | 88 | 86.7 | 84.8 | 88 |
| 21_42 | 85 | 71.6 | 94 | 86.7 | 84.8 | 88 |
| 21_43 | 82.6 | 71.6 | 90 | 86.7 | 84.8 | 88 |
| 22_25 | 82 | 76.1 | 86 | 86.7 | 84.8 | 88 |
| 22_75 | 80.2 | 68.7 | 88 | 86.7 | 84.8 | 88 |
| 22_89 | 82.6 | 76.1 | 87 | 86.7 | 84.8 | 88 |
| 22_121 | 82 | 70.1 | 90 | 86.7 | 84.8 | 88 |
| 24_44 | 81.4 | 70.1 | 89 | 86.7 | 84.8 | 88 |
| 24_46 | 82.6 | 74.6 | 88 | 86.7 | 84.8 | 88 |
| 25_118 | 84.4 | 74.6 | 91 | 86.7 | 84.8 | 88 |
| 34_35 | 79.6 | 70.1 | 86 | 86.7 | 84.8 | 88 |
| 35_49 | 84.4 | 77.6 | 89 | 86.7 | 84.8 | 88 |
| 51_83 | 82 | 67.2 | 92 | 86.7 | 84.8 | 88 |
| 56_66 | 83.8 | 74.6 | 90 | 86.7 | 84.8 | 88 |
| 58_66 | 83.8 | 68.7 | 94 | 86.7 | 84.8 | 88 |
| 70_104 | 79.6 | 67.2 | 88 | 86.7 | 84.8 | 88 |
| 24_72 | 79 | 65.7 | 88 | 86.6 | 84.8 | 87.8 |
| 31_106 | 89.8 | 77.6 | 98 | 85.5 | 84.8 | 86 |
| 71_106 | 89.8 | 79.1 | 97 | 85.5 | 84.8 | 86 |
| 99_106 | 89.8 | 77.6 | 98 | 85.5 | 84.8 | 86 |
| 76_108 | 85.6 | 79.1 | 90 | 85.5 | 84.8 | 86 |
| 21_110 | 89.2 | 85.1 | 92 | 85.5 | 84.8 | 86 |
| 9_34 | 86.8 | 80.6 | 91 | 85.5 | 84.8 | 86 |
| 9_83 | 83.8 | 74.6 | 90 | 85.5 | 84.8 | 86 |
| 9_102 | 86.2 | 80.6 | 90 | 85.5 | 84.8 | 86 |
| 10_39 | 91 | 86.6 | 94 | 85.5 | 84.8 | 86 |
| 11_24 | 83.2 | 76.1 | 88 | 85.5 | 84.8 | 86 |

TABLE 6-continued

|  | Training cohort | | | Validation cohort | | |
| --- | --- | --- | --- | --- | --- | --- |
| SEQ ID NO: | Accuracy (%) | Sensitivity (%) | Specificity (%) | Accuracy (%) | Sensitivity (%) | Specificity (%) |
| 11_31 | 83.8 | 73.1 | 91 | 85.5 | 84.8 | 86 |
| 11_66 | 80.8 | 68.7 | 89 | 85.5 | 84.8 | 86 |
| 11_85 | 79.6 | 70.1 | 86 | 85.5 | 84.8 | 86 |
| 11_88 | 77.2 | 71.6 | 81 | 85.5 | 84.8 | 86 |
| 13_47 | 89.8 | 85.1 | 93 | 85.5 | 84.8 | 86 |
| 16_89 | 85 | 79.1 | 89 | 85.5 | 84.8 | 86 |
| 21_48 | 82.6 | 74.6 | 88 | 85.5 | 84.8 | 86 |
| 22_39 | 83.2 | 73.1 | 90 | 85.5 | 84.8 | 86 |
| 22_51 | 82 | 76.1 | 86 | 85.5 | 84.8 | 86 |
| 22_67 | 79 | 64.2 | 89 | 85.5 | 84.8 | 86 |
| 22_71 | 81.4 | 70.1 | 89 | 85.5 | 84.8 | 86 |
| 22_103 | 78.4 | 70.1 | 84 | 85.5 | 84.8 | 86 |
| 24_45 | 84.4 | 74.6 | 91 | 85.5 | 84.8 | 86 |
| 24_85 | 76.6 | 64.2 | 85 | 85.5 | 84.8 | 86 |
| 24_89 | 83.2 | 80.6 | 85 | 85.5 | 84.8 | 86 |
| 25_55 | 85 | 71.6 | 94 | 85.5 | 84.8 | 86 |
| 25_57 | 86.2 | 77.6 | 92 | 85.5 | 84.8 | 86 |
| 25_71 | 83.2 | 70.1 | 92 | 85.5 | 84.8 | 86 |
| 25_104 | 81.4 | 71.6 | 88 | 85.5 | 84.8 | 86 |
| 28_71 | 86.8 | 80.6 | 91 | 85.5 | 84.8 | 86 |
| 31_39 | 82 | 70.1 | 90 | 85.5 | 84.8 | 86 |
| 34_111 | 80.8 | 73.1 | 86 | 85.5 | 84.8 | 86 |
| 35_117 | 77.8 | 58.2 | 91 | 85.5 | 84.8 | 86 |
| 35_76 | 81.4 | 65.7 | 92 | 85.5 | 84.8 | 86 |
| 44_46 | 79 | 68.7 | 86 | 85.5 | 84.8 | 86 |
| 46_80 | 78.4 | 61.2 | 90 | 85.5 | 84.8 | 86 |
| 66_78 | 76 | 61.2 | 86 | 85.5 | 84.8 | 86 |
| 66_88 | 79 | 65.7 | 88 | 85.5 | 84.8 | 86 |
| 70_119 | 75.4 | 62.7 | 84 | 85.5 | 84.8 | 86 |
| 70_98 | 80.7 | 63.6 | 92 | 85.5 | 84.8 | 86 |
| 79_89 | 80.8 | 65.7 | 91 | 85.5 | 84.8 | 86 |
| 103_106 | 89.2 | 79.1 | 96 | 84.3 | 84.8 | 84 |
| 3_78 | 88.6 | 83.6 | 92 | 84.3 | 84.8 | 84 |
| 32_109 | 87.4 | 77.6 | 94 | 84.3 | 84.8 | 84 |
| 35_110 | 85.6 | 74.6 | 93 | 84.3 | 84.8 | 84 |
| 9_75 | 83.8 | 76.1 | 89 | 84.3 | 84.8 | 84 |
| 10_74 | 86.2 | 80.6 | 90 | 84.3 | 84.8 | 84 |
| 11_79 | 80.2 | 70.1 | 87 | 84.3 | 84.8 | 84 |
| 11_98 | 81.9 | 74.2 | 87 | 84.3 | 84.8 | 84 |
| 16_21 | 85 | 77.6 | 90 | 84.3 | 84.8 | 84 |
| 20_67 | 84.4 | 77.6 | 89 | 84.3 | 84.8 | 84 |
| 21_59 | 82 | 74.6 | 87 | 84.3 | 84.8 | 84 |
| 21_120 | 79.6 | 71.6 | 85 | 84.3 | 84.8 | 84 |
| 21_86 | 79.6 | 73.1 | 84 | 84.3 | 84.8 | 84 |
| 21_96 | 77.2 | 68.7 | 83 | 84.3 | 84.8 | 84 |
| 21_99 | 82.6 | 77.6 | 86 | 84.3 | 84.8 | 84 |
| 22_92 | 86.2 | 82.1 | 89 | 84.3 | 84.8 | 84 |
| 22_93 | 82 | 68.7 | 91 | 84.3 | 84.8 | 84 |
| 24_94 | 79 | 62.7 | 90 | 84.3 | 84.8 | 84 |
| 31_35 | 77.2 | 61.2 | 88 | 84.3 | 84.8 | 84 |
| 32_35 | 84.4 | 74.6 | 91 | 84.3 | 84.8 | 84 |
| 34_42 | 79 | 70.1 | 85 | 84.3 | 84.8 | 84 |
| 35_57 | 79 | 58.2 | 93 | 84.3 | 84.8 | 84 |
| 42_94 | 77.8 | 55.2 | 93 | 84.3 | 84.8 | 84 |
| 44_70 | 83.8 | 73.1 | 91 | 84.3 | 84.8 | 84 |
| 55_67 | 81.4 | 64.2 | 93 | 84.3 | 84.8 | 84 |
| 66_99 | 75.4 | 58.2 | 87 | 84.3 | 84.8 | 84 |
| 79_94 | 76.6 | 59.7 | 88 | 84.3 | 84.8 | 84 |
| 82_83 | 72.5 | 52.2 | 86 | 84.3 | 84.8 | 84 |
| 93_106 | 89.2 | 76.1 | 98 | 83.1 | 84.8 | 82 |
| 51_109 | 86.8 | 76.1 | 94 | 83.1 | 84.8 | 82 |
| 53_109 | 91.6 | 88.1 | 94 | 83.1 | 84.8 | 82 |
| 58_109 | 86.2 | 80.6 | 90 | 83.1 | 84.8 | 82 |
| 10_44 | 87.4 | 82.1 | 91 | 83.1 | 84.8 | 82 |
| 10_96 | 90.4 | 88.1 | 92 | 83.1 | 84.8 | 82 |
| 11_21 | 81.4 | 74.6 | 86 | 83.1 | 84.8 | 82 |
| 11_70 | 79.6 | 68.7 | 87 | 83.1 | 84.8 | 82 |
| 11_83 | 79 | 68.7 | 86 | 83.1 | 84.8 | 82 |
| 21_44 | 82 | 71.6 | 89 | 83.1 | 84.8 | 82 |
| 21_58 | 81.4 | 70.1 | 89 | 83.1 | 84.8 | 82 |
| 21_70 | 80.8 | 68.7 | 89 | 83.1 | 84.8 | 82 |
| 24_56 | 81.4 | 77.6 | 84 | 83.1 | 84.8 | 82 |
| 25_31 | 80.8 | 65.7 | 91 | 83.1 | 84.8 | 82 |
| 25_103 | 82 | 70.1 | 90 | 83.1 | 84.8 | 82 |
| 27_34 | 83.8 | 77.6 | 88 | 83.1 | 84.8 | 82 |

TABLE 6-continued

|  | Training cohort | | | Validation cohort | | |
| --- | --- | --- | --- | --- | --- | --- |
| SEQ ID NO: | Accuracy (%) | Sensitivity (%) | Specificity (%) | Accuracy (%) | Sensitivity (%) | Specificity (%) |
| 35_64 | 79 | 65.7 | 88 | 83.1 | 84.8 | 82 |
| 44_79 | 82.6 | 65.7 | 94 | 83.1 | 84.8 | 82 |
| 55_79 | 78.4 | 62.7 | 89 | 83.1 | 84.8 | 82 |
| 55_103 | 77.2 | 64.2 | 86 | 83.1 | 84.8 | 82 |
| 67_89 | 73.1 | 52.2 | 87 | 83.1 | 84.8 | 82 |
| 70_94 | 76 | 61.2 | 86 | 83.1 | 84.8 | 82 |
| 79_119 | 75.4 | 64.2 | 83 | 83.1 | 84.8 | 82 |
| 83_103 | 71.3 | 50.7 | 85 | 83.1 | 84.8 | 82 |
| 3_109 | 92.2 | 89.6 | 94 | 81.9 | 84.8 | 80 |
| 100_108 | 89.8 | 83.6 | 94 | 81.9 | 84.8 | 80 |
| 22_109 | 86.2 | 77.6 | 92 | 81.9 | 84.8 | 80 |
| 24_109 | 84.4 | 79.1 | 88 | 81.9 | 84.8 | 80 |
| 46_109 | 83.8 | 73.1 | 91 | 81.9 | 84.8 | 80 |
| 55_109 | 83.8 | 76.1 | 89 | 81.9 | 84.8 | 80 |
| 85_109 | 83.2 | 77.6 | 87 | 81.9 | 84.8 | 80 |
| 11_16 | 89.2 | 83.6 | 93 | 81.9 | 84.8 | 80 |
| 11_78 | 79.6 | 71.6 | 85 | 81.9 | 84.8 | 80 |
| 11_121 | 80.2 | 70.1 | 87 | 81.9 | 84.8 | 80 |
| 11_92 | 78.4 | 68.7 | 85 | 81.9 | 84.8 | 80 |
| 11_103 | 79.6 | 67.2 | 88 | 81.9 | 84.8 | 80 |
| 21_63 | 83.2 | 74.6 | 89 | 81.9 | 84.8 | 80 |
| 21_67 | 81.4 | 68.7 | 90 | 81.9 | 84.8 | 80 |
| 21_79 | 80.2 | 73.1 | 85 | 81.9 | 84.8 | 80 |
| 21_81 | 80.1 | 72.7 | 85 | 81.9 | 84.8 | 80 |
| 21_84 | 83.2 | 73.1 | 90 | 81.9 | 84.8 | 80 |
| 21_92 | 80.2 | 71.6 | 86 | 81.9 | 84.8 | 80 |
| 21_93 | 78.4 | 71.6 | 83 | 81.9 | 84.8 | 80 |
| 28_75 | 81.4 | 73.1 | 87 | 81.9 | 84.8 | 80 |
| 42_52 | 79 | 59.7 | 92 | 81.9 | 84.8 | 80 |
| 81_94 | 75.9 | 57.6 | 88 | 81.9 | 84.8 | 80 |
| 94_121 | 72.5 | 53.7 | 85 | 81.9 | 84.8 | 80 |
| 21_72 | 79.6 | 70.1 | 86 | 81.7 | 84.8 | 79.6 |
| 47_109 | 85.6 | 79.1 | 90 | 80.7 | 84.8 | 78 |
| 56_109 | 82.6 | 76.1 | 87 | 80.7 | 84.8 | 78 |
| 62_109 | 86.8 | 77.6 | 93 | 80.7 | 84.8 | 78 |
| 82_109 | 85.6 | 76.1 | 92 | 80.7 | 84.8 | 78 |
| 88_109 | 85.6 | 83.6 | 87 | 80.7 | 84.8 | 78 |
| 89_109 | 85 | 77.6 | 90 | 80.7 | 84.8 | 78 |
| 13_104 | 88.6 | 89.6 | 88 | 80.7 | 84.8 | 78 |
| 29_75 | 82 | 74.6 | 87 | 80.7 | 84.8 | 78 |
| 29_79 | 83.2 | 74.6 | 89 | 80.7 | 84.8 | 78 |
| 31_45 | 85.6 | 79.1 | 90 | 80.7 | 84.8 | 78 |
| 79_99 | 74.3 | 55.2 | 87 | 80.7 | 84.8 | 78 |
| 104_121 | 77.8 | 67.2 | 85 | 80.7 | 84.8 | 78 |
| 67_109 | 84.4 | 74.6 | 91 | 79.5 | 84.8 | 76 |
| 94_109 | 82.6 | 76.1 | 87 | 79.5 | 84.8 | 76 |
| 98_109 | 88 | 84.8 | 90 | 79.5 | 84.8 | 76 |
| 31_78 | 80.2 | 67.2 | 89 | 79.5 | 84.8 | 76 |
| 83_109 | 83.8 | 76.1 | 89 | 78.3 | 84.8 | 74 |
| 79_80 | 75.4 | 58.2 | 87 | 78.3 | 84.8 | 74 |
| 92_109 | 85.6 | 83.6 | 87 | 77.1 | 84.8 | 72 |
| 31_100 | 79.6 | 70.1 | 86 | 77.1 | 84.8 | 72 |
| 25_50 | 85.6 | 74.6 | 93 | 91.5 | 84.4 | 96 |
| 23_107 | 88 | 77.6 | 95 | 90.2 | 84.4 | 94 |
| 7_23 | 91 | 85.1 | 95 | 90.2 | 84.4 | 94 |
| 14_50 | 86.2 | 73.1 | 95 | 90.2 | 84.4 | 94 |
| 50_108 | 89.8 | 80.6 | 96 | 87.8 | 84.4 | 90 |
| 50_107 | 89.8 | 80.6 | 96 | 86.6 | 84.4 | 88 |
| 5_23 | 91 | 86.6 | 94 | 85.4 | 84.4 | 86 |
| 50_112 | 76 | 62.7 | 85 | 85.4 | 84.4 | 86 |
| 50_71 | 77.2 | 65.7 | 85 | 85.4 | 84.4 | 86 |
| 16_50 | 84.4 | 79.1 | 88 | 84.1 | 84.4 | 84 |
| 21_50 | 82 | 74.6 | 87 | 84.1 | 84.4 | 84 |
| 50_100 | 74.9 | 59.7 | 85 | 82.9 | 84.4 | 82 |
| 50_70 | 77.2 | 62.7 | 87 | 81.7 | 84.4 | 80 |
| 50_55 | 78.4 | 62.7 | 89 | 80.5 | 84.4 | 78 |
| 10_77 | 89.8 | 79.1 | 97 | 92.6 | 83.9 | 98 |
| 77_106 | 92.2 | 82.1 | 99 | 91.4 | 83.9 | 96 |
| 22_77 | 85.6 | 77.6 | 91 | 90.1 | 83.9 | 94 |
| 25_77 | 85 | 73.1 | 93 | 90.1 | 83.9 | 94 |
| 35_77 | 77.2 | 64.2 | 86 | 88.9 | 83.9 | 92 |
| 77_109 | 86.2 | 82.1 | 89 | 86.4 | 83.9 | 88 |
| 28_77 | 82.6 | 76.1 | 87 | 86.4 | 83.9 | 88 |
| 5_77 | 88 | 85.1 | 90 | 85.2 | 83.9 | 86 |
| 6_7 | 91.6 | 82.1 | 98 | 92.8 | 81.8 | 100 |

TABLE 6-continued

| | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 6_49 | 89.8 | 86.6 | 92 | 92.8 | 81.8 | 100 |
| 7_17 | 89.8 | 77.6 | 98 | 92.8 | 81.8 | 100 |
| 8_111 | 90.4 | 79.1 | 98 | 92.8 | 81.8 | 100 |
| 13_15 | 88.6 | 82.1 | 93 | 92.8 | 81.8 | 100 |
| 15_20 | 88.6 | 83.6 | 92 | 92.8 | 81.8 | 100 |
| 15_112 | 89.8 | 82.1 | 95 | 92.8 | 81.8 | 100 |
| 17_119 | 87.4 | 74.6 | 96 | 92.8 | 81.8 | 100 |
| 17_87 | 86.2 | 71.6 | 96 | 92.8 | 81.8 | 100 |
| 2_43 | 88.6 | 77.6 | 96 | 91.6 | 81.8 | 98 |
| 5_14 | 93.4 | 88.1 | 97 | 91.6 | 81.8 | 98 |
| 7_14 | 93.4 | 88.1 | 97 | 91.6 | 81.8 | 98 |
| 7_33 | 91 | 82.1 | 97 | 91.6 | 81.8 | 98 |
| 7_48 | 90.4 | 85.1 | 94 | 91.6 | 81.8 | 98 |
| 7_59 | 90.4 | 82.1 | 96 | 91.6 | 81.8 | 98 |
| 7_89 | 91.6 | 83.6 | 97 | 91.6 | 81.8 | 98 |
| 8_110 | 93.4 | 89.6 | 96 | 91.6 | 81.8 | 98 |
| 8_14 | 89.8 | 77.6 | 98 | 91.6 | 81.8 | 98 |
| 11_87 | 86.8 | 74.6 | 95 | 91.6 | 81.8 | 98 |
| 13_19 | 90.4 | 88.1 | 92 | 91.6 | 81.8 | 98 |
| 13_96 | 86.2 | 74.6 | 94 | 91.6 | 81.8 | 98 |
| 14_66 | 82.6 | 65.7 | 94 | 91.6 | 81.8 | 98 |
| 14_80 | 85 | 68.7 | 96 | 91.6 | 81.8 | 98 |
| 14_96 | 86.8 | 77.6 | 93 | 91.6 | 81.8 | 98 |
| 15_25 | 87.4 | 73.1 | 97 | 91.6 | 81.8 | 98 |
| 15_65 | 86.2 | 76.1 | 93 | 91.6 | 81.8 | 98 |
| 17_26 | 88.6 | 79.1 | 95 | 91.6 | 81.8 | 98 |
| 18_76 | 92.8 | 91 | 94 | 91.6 | 81.8 | 98 |
| 19_45 | 85 | 71.6 | 94 | 91.6 | 81.8 | 98 |
| 19_70 | 88 | 82.1 | 92 | 91.6 | 81.8 | 98 |
| 19_83 | 86.2 | 82.1 | 89 | 91.6 | 81.8 | 98 |
| 24_117 | 83.8 | 67.2 | 95 | 91.6 | 81.8 | 98 |
| 12_106 | 94 | 86.4 | 99 | 90.4 | 81.8 | 96 |
| 38_106 | 90.4 | 80.6 | 97 | 90.4 | 81.8 | 96 |
| 28_107 | 93.4 | 86.6 | 98 | 90.4 | 81.8 | 96 |
| 36_107 | 88 | 76.1 | 96 | 90.4 | 81.8 | 96 |
| 38_107 | 91.6 | 82.1 | 98 | 90.4 | 81.8 | 96 |
| 41_107 | 91 | 83.6 | 96 | 90.4 | 81.8 | 96 |
| 51_107 | 88.6 | 77.6 | 96 | 90.4 | 81.8 | 96 |
| 59_107 | 88.6 | 77.6 | 96 | 90.4 | 81.8 | 96 |
| 68_107 | 88 | 76.1 | 96 | 90.4 | 81.8 | 96 |
| 70_107 | 88 | 76.1 | 96 | 90.4 | 81.8 | 96 |
| 75_107 | 89.8 | 77.6 | 98 | 90.4 | 81.8 | 96 |
| 82_107 | 89.2 | 79.1 | 96 | 90.4 | 81.8 | 96 |
| 3_8 | 94.6 | 92.5 | 96 | 90.4 | 81.8 | 96 |
| 3_20 | 91 | 86.6 | 94 | 90.4 | 81.8 | 96 |
| 14_108 | 88.6 | 77.6 | 96 | 90.4 | 81.8 | 96 |
| 39_108 | 94 | 89.6 | 97 | 90.4 | 81.8 | 96 |
| 5_40 | 91.6 | 88.1 | 94 | 90.4 | 81.8 | 96 |
| 5_41 | 94 | 89.6 | 97 | 90.4 | 81.8 | 96 |
| 5_60 | 92.2 | 89.6 | 94 | 90.4 | 81.8 | 96 |
| 6_16 | 88.6 | 82.1 | 93 | 90.4 | 81.8 | 96 |
| 6_38 | 88.6 | 74.6 | 98 | 90.4 | 81.8 | 96 |
| 6_74 | 87.4 | 76.1 | 95 | 90.4 | 81.8 | 96 |
| 6_120 | 88 | 79.1 | 94 | 90.4 | 81.8 | 96 |
| 7_29 | 92.8 | 85.1 | 98 | 90.4 | 81.8 | 96 |
| 7_43 | 92.8 | 89.6 | 95 | 90.4 | 81.8 | 96 |
| 7_113 | 94.6 | 89.6 | 98 | 90.4 | 81.8 | 96 |
| 7_73 | 91 | 85.1 | 95 | 90.4 | 81.8 | 96 |
| 8_25 | 92.2 | 83.6 | 98 | 90.4 | 81.8 | 96 |
| 8_59 | 91 | 82.1 | 97 | 90.4 | 81.8 | 96 |
| 10_30 | 87.4 | 76.1 | 95 | 90.4 | 81.8 | 96 |
| 11_30 | 88 | 80.6 | 93 | 90.4 | 81.8 | 96 |
| 11_119 | 82.6 | 73.1 | 89 | 90.4 | 81.8 | 96 |
| 13_111 | 85.6 | 73.1 | 94 | 90.4 | 81.8 | 96 |
| 14_42 | 87.4 | 71.6 | 98 | 90.4 | 81.8 | 96 |
| 14_46 | 86.2 | 73.1 | 95 | 90.4 | 81.8 | 96 |
| 15_31 | 83.8 | 68.7 | 94 | 90.4 | 81.8 | 96 |
| 15_35 | 86.2 | 73.1 | 95 | 90.4 | 81.8 | 96 |
| 15_94 | 85 | 73.1 | 93 | 90.4 | 81.8 | 96 |
| 17_37 | 85.6 | 73.1 | 94 | 90.4 | 81.8 | 96 |
| 18_48 | 88.6 | 79.1 | 95 | 90.4 | 81.8 | 96 |
| 18_89 | 85.6 | 79.1 | 90 | 90.4 | 81.8 | 96 |
| 19_39 | 92.2 | 83.6 | 98 | 90.4 | 81.8 | 96 |
| 19_93 | 85 | 74.6 | 92 | 90.4 | 81.8 | 96 |
| 19_96 | 87.4 | 80.6 | 92 | 90.4 | 81.8 | 96 |

TABLE 6-continued

|  | Training cohort | | | Validation cohort | | |
| --- | --- | --- | --- | --- | --- | --- |
| SEQ ID NO: | Accuracy (%) | Sensitivity (%) | Specificity (%) | Accuracy (%) | Sensitivity (%) | Specificity (%) |
| 24_60 | 79.6 | 62.7 | 91 | 90.4 | 81.8 | 96 |
| 30_120 | 83.2 | 76.1 | 88 | 90.4 | 81.8 | 96 |
| 26_106 | 91.6 | 83.6 | 97 | 89.2 | 81.8 | 94 |
| 40_106 | 90.4 | 77.6 | 99 | 89.2 | 81.8 | 94 |
| 53_106 | 92.2 | 83.6 | 98 | 89.2 | 81.8 | 94 |
| 10_107 | 88.6 | 77.6 | 96 | 89.2 | 81.8 | 94 |
| 15_107 | 90.4 | 77.6 | 99 | 89.2 | 81.8 | 94 |
| 17_107 | 88.6 | 76.1 | 97 | 89.2 | 81.8 | 94 |
| 29_107 | 89.2 | 79.1 | 96 | 89.2 | 81.8 | 94 |
| 40_107 | 91.6 | 80.6 | 99 | 89.2 | 81.8 | 94 |
| 43_107 | 92.8 | 89.6 | 95 | 89.2 | 81.8 | 94 |
| 46_107 | 89.8 | 77.6 | 98 | 89.2 | 81.8 | 94 |
| 56_107 | 89.2 | 79.1 | 96 | 89.2 | 81.8 | 94 |
| 60_107 | 90.4 | 79.1 | 98 | 89.2 | 81.8 | 94 |
| 62_107 | 91.6 | 83.6 | 97 | 89.2 | 81.8 | 94 |
| 64_107 | 91 | 85.1 | 95 | 89.2 | 81.8 | 94 |
| 71_107 | 90.4 | 83.6 | 95 | 89.2 | 81.8 | 94 |
| 76_107 | 88.6 | 77.6 | 96 | 89.2 | 81.8 | 94 |
| 80_107 | 89.2 | 79.1 | 96 | 89.2 | 81.8 | 94 |
| 81_107 | 92.8 | 86.4 | 97 | 89.2 | 81.8 | 94 |
| 84_107 | 89.2 | 80.6 | 95 | 89.2 | 81.8 | 94 |
| 86_107 | 90.4 | 79.1 | 98 | 89.2 | 81.8 | 94 |
| 93_107 | 89.8 | 79.1 | 97 | 89.2 | 81.8 | 94 |
| 11_108 | 90.4 | 77.6 | 99 | 89.2 | 81.8 | 94 |
| 29_108 | 91 | 80.6 | 98 | 89.2 | 81.8 | 94 |
| 38_108 | 86.2 | 71.6 | 96 | 89.2 | 81.8 | 94 |
| 56_108 | 90.4 | 80.6 | 97 | 89.2 | 81.8 | 94 |
| 102_108 | 89.2 | 79.1 | 96 | 89.2 | 81.8 | 94 |
| 5_63 | 91 | 86.6 | 94 | 89.2 | 81.8 | 94 |
| 6_54 | 90.4 | 83.6 | 95 | 89.2 | 81.8 | 94 |
| 6_55 | 86.8 | 74.6 | 95 | 89.2 | 81.8 | 94 |
| 6_71 | 87.4 | 77.6 | 94 | 89.2 | 81.8 | 94 |
| 6_80 | 86.2 | 73.1 | 95 | 89.2 | 81.8 | 94 |
| 7_41 | 91.6 | 89.6 | 93 | 89.2 | 81.8 | 94 |
| 7_49 | 91 | 85.1 | 95 | 89.2 | 81.8 | 94 |
| 7_56 | 91.6 | 86.6 | 95 | 89.2 | 81.8 | 94 |
| 7_63 | 93.4 | 88.1 | 97 | 89.2 | 81.8 | 94 |
| 7_68 | 91.6 | 83.6 | 97 | 89.2 | 81.8 | 94 |
| 9_30 | 87.4 | 82.1 | 91 | 89.2 | 81.8 | 94 |
| 13_38 | 86.2 | 82.1 | 89 | 89.2 | 81.8 | 94 |
| 13_112 | 85.6 | 83.6 | 87 | 89.2 | 81.8 | 94 |
| 13_71 | 88 | 82.1 | 92 | 89.2 | 81.8 | 94 |
| 13_90 | 86.2 | 82.1 | 89 | 89.2 | 81.8 | 94 |
| 14_29 | 90.4 | 76.1 | 100 | 89.2 | 81.8 | 94 |
| 14_83 | 83.8 | 68.7 | 94 | 89.2 | 81.8 | 94 |
| 15_58 | 88 | 79.1 | 94 | 89.2 | 81.8 | 94 |
| 17_25 | 87.4 | 74.6 | 96 | 89.2 | 81.8 | 94 |
| 17_90 | 84.4 | 71.6 | 93 | 89.2 | 81.8 | 94 |
| 18_39 | 84.4 | 71.6 | 93 | 89.2 | 81.8 | 94 |
| 18_60 | 88.6 | 77.6 | 96 | 89.2 | 81.8 | 94 |
| 18_62 | 86.8 | 76.1 | 94 | 89.2 | 81.8 | 94 |
| 18_82 | 86.2 | 82.1 | 89 | 89.2 | 81.8 | 94 |
| 18_91 | 89.2 | 80.6 | 95 | 89.2 | 81.8 | 94 |
| 18_94 | 84.4 | 77.6 | 89 | 89.2 | 81.8 | 94 |
| 18_104 | 83.2 | 73.1 | 90 | 89.2 | 81.8 | 94 |
| 19_79 | 85 | 76.1 | 91 | 89.2 | 81.8 | 94 |
| 24_61 | 83.2 | 71.6 | 91 | 89.2 | 81.8 | 94 |
| 25_30 | 88.6 | 77.6 | 96 | 89.2 | 81.8 | 94 |
| 35_38 | 83.2 | 70.1 | 92 | 89.2 | 81.8 | 94 |
| 37_42 | 84.4 | 74.6 | 91 | 89.2 | 81.8 | 94 |
| 37_67 | 79.6 | 68.7 | 87 | 89.2 | 81.8 | 94 |
| 38_58 | 83.2 | 70.1 | 92 | 89.2 | 81.8 | 94 |
| 55_112 | 80.8 | 65.7 | 91 | 89.2 | 81.8 | 94 |
| 46_60 | 85.6 | 74.6 | 93 | 89.2 | 81.8 | 94 |
| 51_97 | 89.2 | 82.1 | 94 | 89.2 | 81.8 | 94 |
| 83_113 | 85 | 76.1 | 91 | 89.2 | 81.8 | 94 |
| 4_106 | 89.2 | 77.6 | 97 | 88 | 81.8 | 92 |
| 54_106 | 91.6 | 80.6 | 99 | 88 | 81.8 | 92 |
| 32_107 | 91 | 79.1 | 99 | 88 | 81.8 | 92 |
| 42_107 | 86.8 | 74.6 | 95 | 88 | 81.8 | 92 |
| 63_107 | 92.2 | 85.1 | 97 | 88 | 81.8 | 92 |
| 78_107 | 88 | 76.1 | 96 | 88 | 81.8 | 92 |
| 88_107 | 91 | 80.6 | 98 | 88 | 81.8 | 92 |
| 90_107 | 89.8 | 80.6 | 96 | 88 | 81.8 | 92 |
| 3_70 | 94 | 88.1 | 98 | 88 | 81.8 | 92 |

TABLE 6-continued

| SEQ ID NO: | Training cohort ||| Validation cohort |||
| --- | --- | --- | --- | --- | --- | --- |
| | Accuracy (%) | Sensitivity (%) | Specificity (%) | Accuracy (%) | Sensitivity (%) | Specificity (%) |
| 3_75 | 92.8 | 89.6 | 95 | 88 | 81.8 | 92 |
| 4_73 | 87.4 | 77.6 | 94 | 88 | 81.8 | 92 |
| 22_108 | 88 | 80.6 | 93 | 88 | 81.8 | 92 |
| 36_108 | 86.8 | 73.1 | 96 | 88 | 81.8 | 92 |
| 40_108 | 89.8 | 79.1 | 97 | 88 | 81.8 | 92 |
| 5_6 | 95.2 | 94 | 96 | 88 | 81.8 | 92 |
| 5_43 | 87.4 | 82.1 | 91 | 88 | 81.8 | 92 |
| 5_48 | 94 | 89.6 | 97 | 88 | 81.8 | 92 |
| 5_62 | 89.2 | 85.1 | 92 | 88 | 81.8 | 92 |
| 5_64 | 89.8 | 82.1 | 95 | 88 | 81.8 | 92 |
| 5_65 | 88 | 79.1 | 94 | 88 | 81.8 | 92 |
| 5_114 | 89.8 | 82.1 | 95 | 88 | 81.8 | 92 |
| 5_73 | 92.2 | 89.6 | 94 | 88 | 81.8 | 92 |
| 5_88 | 91 | 82.1 | 97 | 88 | 81.8 | 92 |
| 6_96 | 88.6 | 83.6 | 92 | 88 | 81.8 | 92 |
| 7_40 | 95.2 | 89.6 | 99 | 88 | 81.8 | 92 |
| 7_61 | 92.2 | 88.1 | 95 | 88 | 81.8 | 92 |
| 7_116 | 91 | 85.1 | 95 | 88 | 81.8 | 92 |
| 8_11 | 91.6 | 88.1 | 94 | 88 | 81.8 | 92 |
| 37_110 | 88 | 83.6 | 91 | 88 | 81.8 | 92 |
| 9_17 | 83.8 | 73.1 | 91 | 88 | 81.8 | 92 |
| 9_39 | 85 | 76.1 | 91 | 88 | 81.8 | 92 |
| 9_44 | 88 | 82.1 | 92 | 88 | 81.8 | 92 |
| 9_114 | 83.2 | 77.6 | 87 | 88 | 81.8 | 92 |
| 9_87 | 82.6 | 80.6 | 84 | 88 | 81.8 | 92 |
| 10_49 | 91 | 89.6 | 92 | 88 | 81.8 | 92 |
| 10_65 | 88 | 83.6 | 91 | 88 | 81.8 | 92 |
| 10_87 | 86.8 | 82.1 | 90 | 88 | 81.8 | 92 |
| 10_90 | 86.2 | 83.6 | 88 | 88 | 81.8 | 92 |
| 11_38 | 85.6 | 76.1 | 92 | 88 | 81.8 | 92 |
| 13_37 | 90.4 | 89.6 | 91 | 88 | 81.8 | 92 |
| 13_44 | 88 | 86.6 | 89 | 88 | 81.8 | 92 |
| 13_51 | 88.6 | 85.1 | 91 | 88 | 81.8 | 92 |
| 13_59 | 86.8 | 79.1 | 92 | 88 | 81.8 | 92 |
| 14_20 | 91 | 82.1 | 97 | 88 | 81.8 | 92 |
| 14_58 | 89.2 | 82.1 | 94 | 88 | 81.8 | 92 |
| 18_36 | 88.6 | 82.1 | 93 | 88 | 81.8 | 92 |
| 19_25 | 83.8 | 70.1 | 93 | 88 | 81.8 | 92 |
| 19_55 | 89.2 | 82.1 | 94 | 88 | 81.8 | 92 |
| 19_67 | 86.8 | 77.6 | 93 | 88 | 81.8 | 92 |
| 21_38 | 86.8 | 77.6 | 93 | 88 | 81.8 | 92 |
| 22_29 | 88 | 82.1 | 92 | 88 | 81.8 | 92 |
| 22_111 | 83.2 | 67.2 | 94 | 88 | 81.8 | 92 |
| 25_62 | 80.8 | 74.6 | 85 | 88 | 81.8 | 92 |
| 29_55 | 83.2 | 74.6 | 89 | 88 | 81.8 | 92 |
| 29_66 | 82.6 | 70.1 | 91 | 88 | 81.8 | 92 |
| 34_51 | 86.2 | 82.1 | 89 | 88 | 81.8 | 92 |
| 34_60 | 84.4 | 77.6 | 89 | 88 | 81.8 | 92 |
| 35_73 | 81.4 | 71.6 | 88 | 88 | 81.8 | 92 |
| 58_111 | 79 | 64.2 | 89 | 88 | 81.8 | 92 |
| 37_112 | 84.4 | 74.6 | 91 | 88 | 81.8 | 92 |
| 51_112 | 86.8 | 80.6 | 91 | 88 | 81.8 | 92 |
| 46_51 | 84.4 | 73.1 | 92 | 88 | 81.8 | 92 |
| 51_75 | 80.8 | 68.7 | 89 | 88 | 81.8 | 92 |
| 51_119 | 80.8 | 70.1 | 88 | 88 | 81.8 | 92 |
| 51_96 | 82 | 70.1 | 90 | 88 | 81.8 | 92 |
| 98_113 | 86.7 | 75.8 | 94 | 88 | 81.8 | 92 |
| 90_94 | 75.4 | 56.7 | 88 | 88 | 81.8 | 92 |
| 72_108 | 89.2 | 79.1 | 96 | 87.8 | 81.8 | 91.8 |
| 39_106 | 89.8 | 79.1 | 97 | 86.7 | 81.8 | 90 |
| 44_106 | 91 | 80.6 | 98 | 86.7 | 81.8 | 90 |
| 47_106 | 89.2 | 79.1 | 96 | 86.7 | 81.8 | 90 |
| 64_106 | 89.8 | 80.6 | 96 | 86.7 | 81.8 | 90 |
| 66_106 | 89.8 | 76.1 | 99 | 86.7 | 81.8 | 90 |
| 97_106 | 89.8 | 82.1 | 95 | 86.7 | 81.8 | 90 |
| 98_106 | 89.8 | 80.3 | 96 | 86.7 | 81.8 | 90 |
| 91_107 | 90.4 | 79.1 | 98 | 86.7 | 81.8 | 90 |
| 3_93 | 94.6 | 91 | 97 | 86.7 | 81.8 | 90 |
| 4_15 | 89.2 | 82.1 | 94 | 86.7 | 81.8 | 90 |
| 4_17 | 87.4 | 73.1 | 97 | 86.7 | 81.8 | 90 |
| 4_29 | 89.2 | 79.1 | 96 | 86.7 | 81.8 | 90 |
| 4_60 | 86.8 | 73.1 | 96 | 86.7 | 81.8 | 90 |
| 10_108 | 86.2 | 74.6 | 94 | 86.7 | 81.8 | 90 |
| 16_108 | 90.4 | 86.6 | 93 | 86.7 | 81.8 | 90 |
| 28_108 | 87.4 | 80.6 | 92 | 86.7 | 81.8 | 90 |

TABLE 6-continued

| | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 51_108 | 86.8 | 74.6 | 95 | 86.7 | 81.8 | 90 |
| 67_108 | 88.6 | 79.1 | 95 | 86.7 | 81.8 | 90 |
| 69_108 | 86.8 | 77.6 | 93 | 86.7 | 81.8 | 90 |
| 82_108 | 86.8 | 76.1 | 94 | 86.7 | 81.8 | 90 |
| 91_108 | 86.8 | 77.6 | 93 | 86.7 | 81.8 | 90 |
| 5_59 | 91 | 86.6 | 94 | 86.7 | 81.8 | 90 |
| 5_118 | 89.2 | 83.6 | 93 | 86.7 | 81.8 | 90 |
| 5_85 | 87.4 | 83.6 | 90 | 86.7 | 81.8 | 90 |
| 5_86 | 92.8 | 89.6 | 95 | 86.7 | 81.8 | 90 |
| 6_34 | 89.2 | 82.1 | 94 | 86.7 | 81.8 | 90 |
| 6_35 | 88.6 | 76.1 | 97 | 86.7 | 81.8 | 90 |
| 6_66 | 88.6 | 76.1 | 97 | 86.7 | 81.8 | 90 |
| 15_109 | 86.2 | 73.1 | 95 | 86.7 | 81.8 | 90 |
| 9_26 | 89.2 | 86.6 | 91 | 86.7 | 81.8 | 90 |
| 9_54 | 86.8 | 82.1 | 90 | 86.7 | 81.8 | 90 |
| 9_66 | 83.8 | 77.6 | 88 | 86.7 | 81.8 | 90 |
| 9_80 | 84.4 | 80.6 | 87 | 86.7 | 81.8 | 90 |
| 9_97 | 87.4 | 85.1 | 89 | 86.7 | 81.8 | 90 |
| 10_46 | 90.4 | 80.6 | 97 | 86.7 | 81.8 | 90 |
| 10_56 | 83.8 | 74.6 | 90 | 86.7 | 81.8 | 90 |
| 10_117 | 85 | 74.6 | 92 | 86.7 | 81.8 | 90 |
| 10_75 | 86.2 | 76.1 | 93 | 86.7 | 81.8 | 90 |
| 12_42 | 84.9 | 72.7 | 93 | 86.7 | 81.8 | 90 |
| 12_67 | 86.7 | 78.8 | 92 | 86.7 | 81.8 | 90 |
| 13_14 | 86.2 | 79.1 | 91 | 86.7 | 81.8 | 90 |
| 13_65 | 86.8 | 83.6 | 89 | 86.7 | 81.8 | 90 |
| 17_21 | 85.6 | 73.1 | 94 | 86.7 | 81.8 | 90 |
| 17_24 | 83.8 | 73.1 | 91 | 86.7 | 81.8 | 90 |
| 17_31 | 85.6 | 70.1 | 96 | 86.7 | 81.8 | 90 |
| 17_42 | 83.8 | 64.2 | 97 | 86.7 | 81.8 | 90 |
| 17_66 | 85.6 | 67.2 | 98 | 86.7 | 81.8 | 90 |
| 18_73 | 85 | 76.1 | 91 | 86.7 | 81.8 | 90 |
| 18_90 | 83.2 | 71.6 | 91 | 86.7 | 81.8 | 90 |
| 21_62 | 78.4 | 62.7 | 89 | 86.7 | 81.8 | 90 |
| 22_26 | 86.2 | 77.6 | 92 | 86.7 | 81.8 | 90 |
| 22_37 | 81.4 | 73.1 | 87 | 86.7 | 81.8 | 90 |
| 22_56 | 82 | 73.1 | 88 | 86.7 | 81.8 | 90 |
| 24_43 | 83.8 | 80.6 | 86 | 86.7 | 81.8 | 90 |
| 24_114 | 83.2 | 71.6 | 91 | 86.7 | 81.8 | 90 |
| 24_95 | 79.6 | 73.1 | 84 | 86.7 | 81.8 | 90 |
| 25_29 | 86.2 | 74.6 | 94 | 86.7 | 81.8 | 90 |
| 25_97 | 79.6 | 65.7 | 89 | 86.7 | 81.8 | 90 |
| 26_31 | 86.8 | 76.1 | 94 | 86.7 | 81.8 | 90 |
| 26_35 | 86.2 | 77.6 | 92 | 86.7 | 81.8 | 90 |
| 27_119 | 83.2 | 77.6 | 87 | 86.7 | 81.8 | 90 |
| 27_98 | 80.1 | 71.2 | 86 | 86.7 | 81.8 | 90 |
| 28_83 | 84.4 | 77.6 | 89 | 86.7 | 81.8 | 90 |
| 29_71 | 85.6 | 79.1 | 90 | 86.7 | 81.8 | 90 |
| 30_67 | 85.6 | 74.6 | 93 | 86.7 | 81.8 | 90 |
| 35_101 | 77.8 | 67.2 | 85 | 86.7 | 81.8 | 90 |
| 66_111 | 83.2 | 64.2 | 96 | 86.7 | 81.8 | 90 |
| 39_42 | 83.2 | 70.1 | 92 | 86.7 | 81.8 | 90 |
| 39_51 | 86.2 | 77.6 | 92 | 86.7 | 81.8 | 90 |
| 40_55 | 85.6 | 70.1 | 96 | 86.7 | 81.8 | 90 |
| 65_112 | 83.8 | 74.6 | 90 | 86.7 | 81.8 | 90 |
| 44_67 | 80.2 | 71.6 | 86 | 86.7 | 81.8 | 90 |
| 47_66 | 78.4 | 65.7 | 87 | 86.7 | 81.8 | 90 |
| 61_67 | 79 | 67.2 | 87 | 86.7 | 81.8 | 90 |
| 66_118 | 80.8 | 65.7 | 91 | 86.7 | 81.8 | 90 |
| 67_120 | 75.4 | 61.2 | 85 | 86.7 | 81.8 | 90 |
| 79_115 | 80.8 | 67.2 | 90 | 86.7 | 81.8 | 90 |
| 83_99 | 70.7 | 53.7 | 82 | 86.7 | 81.8 | 90 |
| 24_106 | 90.4 | 82.1 | 96 | 85.5 | 81.8 | 88 |
| 29_106 | 89.2 | 79.1 | 96 | 85.5 | 81.8 | 88 |
| 35_106 | 87.4 | 73.1 | 97 | 85.5 | 81.8 | 88 |
| 46_106 | 88.6 | 74.6 | 98 | 85.5 | 81.8 | 88 |
| 58_106 | 90.4 | 79.1 | 98 | 85.5 | 81.8 | 88 |
| 80_106 | 88.6 | 76.1 | 97 | 85.5 | 81.8 | 88 |
| 82_106 | 88.6 | 76.1 | 97 | 85.5 | 81.8 | 88 |
| 83_106 | 88.6 | 74.6 | 98 | 85.5 | 81.8 | 88 |
| 88_106 | 92.2 | 82.1 | 99 | 85.5 | 81.8 | 88 |
| 104_106 | 89.8 | 79.1 | 97 | 85.5 | 81.8 | 88 |
| 3_22 | 94 | 91 | 96 | 85.5 | 81.8 | 88 |
| 3_31 | 95.2 | 91 | 98 | 85.5 | 81.8 | 88 |
| 3_79 | 94 | 91 | 96 | 85.5 | 81.8 | 88 |

TABLE 6-continued

| | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 4_111 | 85.6 | 71.6 | 95 | 85.5 | 81.8 | 88 |
| 32_108 | 88.6 | 82.1 | 93 | 85.5 | 81.8 | 88 |
| 78_108 | 90.4 | 80.6 | 97 | 85.5 | 81.8 | 88 |
| 84_108 | 85.6 | 76.1 | 92 | 85.5 | 81.8 | 88 |
| 92_108 | 89.8 | 85.1 | 93 | 85.5 | 81.8 | 88 |
| 5_55 | 89.8 | 82.1 | 95 | 85.5 | 81.8 | 88 |
| 5_71 | 88 | 83.6 | 91 | 85.5 | 81.8 | 88 |
| 5_91 | 88.6 | 82.1 | 93 | 85.5 | 81.8 | 88 |
| 5_94 | 88.6 | 82.1 | 93 | 85.5 | 81.8 | 88 |
| 5_100 | 88 | 82.1 | 92 | 85.5 | 81.8 | 88 |
| 5_103 | 89.8 | 82.1 | 95 | 85.5 | 81.8 | 88 |
| 6_31 | 85.6 | 71.6 | 95 | 85.5 | 81.8 | 88 |
| 6_89 | 86.8 | 77.6 | 93 | 85.5 | 81.8 | 88 |
| 28_109 | 91 | 86.6 | 94 | 85.5 | 81.8 | 88 |
| 38_109 | 85 | 73.1 | 93 | 85.5 | 81.8 | 88 |
| 9_110 | 89.2 | 82.1 | 94 | 85.5 | 81.8 | 88 |
| 9_42 | 85 | 79.1 | 89 | 85.5 | 81.8 | 88 |
| 9_47 | 82.6 | 77.6 | 86 | 85.5 | 81.8 | 88 |
| 9_62 | 80.2 | 74.6 | 84 | 85.5 | 81.8 | 88 |
| 9_74 | 86.8 | 80.6 | 91 | 85.5 | 81.8 | 88 |
| 10_24 | 88 | 82.1 | 92 | 85.5 | 81.8 | 88 |
| 10_116 | 85.6 | 76.1 | 92 | 85.5 | 81.8 | 88 |
| 10_118 | 86.8 | 80.6 | 91 | 85.5 | 81.8 | 88 |
| 10_80 | 83.8 | 76.1 | 89 | 85.5 | 81.8 | 88 |
| 11_20 | 88 | 83.6 | 91 | 85.5 | 81.8 | 88 |
| 11_56 | 82.6 | 73.1 | 89 | 85.5 | 81.8 | 88 |
| 11_62 | 83.8 | 71.6 | 92 | 85.5 | 81.8 | 88 |
| 11_114 | 82.6 | 68.7 | 92 | 85.5 | 81.8 | 88 |
| 11_102 | 82 | 73.1 | 88 | 85.5 | 81.8 | 88 |
| 12_14 | 92.2 | 84.8 | 97 | 85.5 | 81.8 | 88 |
| 12_35 | 84.9 | 74.2 | 92 | 85.5 | 81.8 | 88 |
| 12_51 | 86.7 | 80.3 | 91 | 85.5 | 81.8 | 88 |
| 13_78 | 84.4 | 79.1 | 88 | 85.5 | 81.8 | 88 |
| 13_82 | 82.6 | 77.6 | 86 | 85.5 | 81.8 | 88 |
| 13_94 | 85.6 | 82.1 | 88 | 85.5 | 81.8 | 88 |
| 13_100 | 83.2 | 80.6 | 85 | 85.5 | 81.8 | 88 |
| 16_45 | 85 | 80.6 | 88 | 85.5 | 81.8 | 88 |
| 16_98 | 84.9 | 81.8 | 87 | 85.5 | 81.8 | 88 |
| 17_96 | 85 | 70.1 | 95 | 85.5 | 81.8 | 88 |
| 18_83 | 82 | 73.1 | 88 | 85.5 | 81.8 | 88 |
| 20_21 | 83.2 | 74.6 | 89 | 85.5 | 81.8 | 88 |
| 20_42 | 83.8 | 71.6 | 92 | 85.5 | 81.8 | 88 |
| 21_30 | 85 | 79.1 | 89 | 85.5 | 81.8 | 88 |
| 21_40 | 83.2 | 65.7 | 95 | 85.5 | 81.8 | 88 |
| 21_51 | 76 | 64.2 | 84 | 85.5 | 81.8 | 88 |
| 21_61 | 81.4 | 71.6 | 88 | 85.5 | 81.8 | 88 |
| 21_117 | 79 | 70.1 | 85 | 85.5 | 81.8 | 88 |
| 21_87 | 80.2 | 71.6 | 86 | 85.5 | 81.8 | 88 |
| 24_57 | 82.6 | 73.1 | 89 | 85.5 | 81.8 | 88 |
| 24_63 | 80.2 | 71.6 | 86 | 85.5 | 81.8 | 88 |
| 25_82 | 83.2 | 74.6 | 89 | 85.5 | 81.8 | 88 |
| 27_58 | 79 | 70.1 | 85 | 85.5 | 81.8 | 88 |
| 31_47 | 78.4 | 67.2 | 86 | 85.5 | 81.8 | 88 |
| 35_36 | 80.2 | 67.2 | 89 | 85.5 | 81.8 | 88 |
| 35_56 | 80.2 | 67.2 | 89 | 85.5 | 81.8 | 88 |
| 35_62 | 80.2 | 70.1 | 87 | 85.5 | 81.8 | 88 |
| 35_74 | 79 | 65.7 | 88 | 85.5 | 81.8 | 88 |
| 40_67 | 80.2 | 65.7 | 90 | 85.5 | 81.8 | 88 |
| 42_55 | 83.8 | 71.6 | 92 | 85.5 | 81.8 | 88 |
| 42_120 | 79 | 68.7 | 86 | 85.5 | 81.8 | 88 |
| 42_98 | 81.3 | 63.6 | 93 | 85.5 | 81.8 | 88 |
| 75_112 | 79.6 | 71.6 | 85 | 85.5 | 81.8 | 88 |
| 44_71 | 77.2 | 64.2 | 86 | 85.5 | 81.8 | 88 |
| 46_119 | 76 | 62.7 | 85 | 85.5 | 81.8 | 88 |
| 46_96 | 74.9 | 62.7 | 83 | 85.5 | 81.8 | 88 |
| 51_93 | 81.4 | 68.7 | 90 | 85.5 | 81.8 | 88 |
| 75_113 | 88 | 82.1 | 92 | 85.5 | 81.8 | 88 |
| 53_58 | 82.6 | 74.6 | 88 | 85.5 | 81.8 | 88 |
| 66_80 | 78.4 | 58.2 | 92 | 85.5 | 81.8 | 88 |
| 66_120 | 77.8 | 61.2 | 89 | 85.5 | 81.8 | 88 |
| 45_106 | 90.4 | 79.1 | 98 | 84.3 | 81.8 | 86 |
| 55_106 | 89.2 | 77.6 | 97 | 84.3 | 81.8 | 86 |
| 59_106 | 88 | 74.6 | 97 | 84.3 | 81.8 | 86 |
| 63_106 | 89.8 | 80.6 | 96 | 84.3 | 81.8 | 86 |
| 67_106 | 88 | 74.6 | 97 | 84.3 | 81.8 | 86 |

TABLE 6-continued

|  | Training cohort | | | Validation cohort | | |
| --- | --- | --- | --- | --- | --- | --- |
| SEQ ID NO: | Accuracy (%) | Sensitivity (%) | Specificity (%) | Accuracy (%) | Sensitivity (%) | Specificity (%) |
| 79_106 | 87.4 | 73.1 | 97 | 84.3 | 81.8 | 86 |
| 89_106 | 88 | 76.1 | 96 | 84.3 | 81.8 | 86 |
| 96_106 | 88 | 76.1 | 96 | 84.3 | 81.8 | 86 |
| 5_46 | 88 | 85.1 | 90 | 84.3 | 81.8 | 86 |
| 5_81 | 87.3 | 83.3 | 90 | 84.3 | 81.8 | 86 |
| 5_120 | 88 | 85.1 | 90 | 84.3 | 81.8 | 86 |
| 5_121 | 88 | 85.1 | 90 | 84.3 | 81.8 | 86 |
| 5_93 | 88 | 85.1 | 90 | 84.3 | 81.8 | 86 |
| 5_98 | 87.3 | 83.3 | 90 | 84.3 | 81.8 | 86 |
| 5_99 | 86.2 | 80.6 | 90 | 84.3 | 81.8 | 86 |
| 6_79 | 88.6 | 77.6 | 96 | 84.3 | 81.8 | 86 |
| 34_110 | 86.2 | 86.6 | 86 | 84.3 | 81.8 | 86 |
| 9_65 | 83.8 | 79.1 | 87 | 84.3 | 81.8 | 86 |
| 9_67 | 82 | 76.1 | 86 | 84.3 | 81.8 | 86 |
| 9_90 | 82.6 | 76.1 | 87 | 84.3 | 81.8 | 86 |
| 9_121 | 83.8 | 77.6 | 88 | 84.3 | 81.8 | 86 |
| 10_47 | 84.4 | 74.6 | 91 | 84.3 | 81.8 | 86 |
| 10_97 | 86.8 | 85.1 | 88 | 84.3 | 81.8 | 86 |
| 11_22 | 85.6 | 76.1 | 92 | 84.3 | 81.8 | 86 |
| 11_44 | 83.8 | 79.1 | 87 | 84.3 | 81.8 | 86 |
| 11_65 | 86.2 | 77.6 | 92 | 84.3 | 81.8 | 86 |
| 11_80 | 80.8 | 67.2 | 90 | 84.3 | 81.8 | 86 |
| 11_81 | 79.5 | 69.7 | 86 | 84.3 | 81.8 | 86 |
| 11_97 | 81.4 | 74.6 | 86 | 84.3 | 81.8 | 86 |
| 11_99 | 82.6 | 77.6 | 86 | 84.3 | 81.8 | 86 |
| 13_69 | 88 | 82.1 | 92 | 84.3 | 81.8 | 86 |
| 13_70 | 85.6 | 79.1 | 90 | 84.3 | 81.8 | 86 |
| 16_93 | 83.2 | 77.6 | 87 | 84.3 | 81.8 | 86 |
| 17_56 | 82.6 | 62.7 | 96 | 84.3 | 81.8 | 86 |
| 18_63 | 86.8 | 77.6 | 93 | 84.3 | 81.8 | 86 |
| 20_31 | 88 | 77.6 | 95 | 84.3 | 81.8 | 86 |
| 21_27 | 82 | 71.6 | 89 | 84.3 | 81.8 | 86 |
| 21_53 | 82 | 76.1 | 86 | 84.3 | 81.8 | 86 |
| 21_116 | 80.2 | 70.1 | 87 | 84.3 | 81.8 | 86 |
| 22_28 | 81.4 | 76.1 | 85 | 84.3 | 81.8 | 86 |
| 22_42 | 82.6 | 68.7 | 92 | 84.3 | 81.8 | 86 |
| 22_47 | 82.6 | 71.6 | 90 | 84.3 | 81.8 | 86 |
| 22_69 | 82 | 74.6 | 87 | 84.3 | 81.8 | 86 |
| 22_70 | 83.2 | 73.1 | 90 | 84.3 | 81.8 | 86 |
| 22_81 | 81.9 | 68.2 | 91 | 84.3 | 81.8 | 86 |
| 24_27 | 84.4 | 73.1 | 92 | 84.3 | 81.8 | 86 |
| 24_36 | 77.2 | 62.7 | 87 | 84.3 | 81.8 | 86 |
| 24_88 | 80.8 | 76.1 | 84 | 84.3 | 81.8 | 86 |
| 25_114 | 83.2 | 70.1 | 92 | 84.3 | 81.8 | 86 |
| 25_78 | 82.6 | 70.1 | 91 | 84.3 | 81.8 | 86 |
| 25_88 | 85 | 77.6 | 90 | 84.3 | 81.8 | 86 |
| 28_98 | 84.3 | 71.2 | 93 | 84.3 | 81.8 | 86 |
| 29_93 | 83.8 | 73.1 | 91 | 84.3 | 81.8 | 86 |
| 30_75 | 87.4 | 80.6 | 92 | 84.3 | 81.8 | 86 |
| 31_89 | 82.6 | 73.1 | 89 | 84.3 | 81.8 | 86 |
| 35_45 | 82.6 | 70.1 | 91 | 84.3 | 81.8 | 86 |
| 40_58 | 86.2 | 73.1 | 95 | 84.3 | 81.8 | 86 |
| 42_83 | 78.4 | 62.7 | 89 | 84.3 | 81.8 | 86 |
| 42_96 | 78.4 | 62.7 | 89 | 84.3 | 81.8 | 86 |
| 56_112 | 83.2 | 74.6 | 89 | 84.3 | 81.8 | 86 |
| 46_66 | 81.4 | 67.2 | 91 | 84.3 | 81.8 | 86 |
| 46_83 | 75.4 | 62.7 | 84 | 84.3 | 81.8 | 86 |
| 46_90 | 76.6 | 65.7 | 84 | 84.3 | 81.8 | 86 |
| 46_92 | 76 | 62.7 | 85 | 84.3 | 81.8 | 86 |
| 46_99 | 73.1 | 62.7 | 80 | 84.3 | 81.8 | 86 |
| 58_100 | 73.7 | 59.7 | 83 | 84.3 | 81.8 | 86 |
| 65_66 | 80.8 | 70.1 | 88 | 84.3 | 81.8 | 86 |
| 65_94 | 78.4 | 65.7 | 87 | 84.3 | 81.8 | 86 |
| 71_114 | 82 | 67.2 | 92 | 84.3 | 81.8 | 86 |
| 70_80 | 79.6 | 62.7 | 91 | 84.3 | 81.8 | 86 |
| 75_98 | 77.1 | 63.6 | 86 | 84.3 | 81.8 | 86 |
| 13_72 | 87.4 | 85.1 | 89 | 84.1 | 81.8 | 85.7 |
| 92_106 | 89.2 | 79.1 | 96 | 83.1 | 81.8 | 84 |
| 94_106 | 88 | 76.1 | 96 | 83.1 | 81.8 | 84 |
| 3_52 | 90.4 | 85.1 | 94 | 83.1 | 81.8 | 84 |
| 33_109 | 86.8 | 77.6 | 93 | 83.1 | 81.8 | 84 |
| 73_109 | 86.8 | 82.1 | 90 | 83.1 | 81.8 | 84 |
| 66_110 | 86.2 | 74.6 | 94 | 83.1 | 81.8 | 84 |
| 9_52 | 85 | 80.6 | 88 | 83.1 | 81.8 | 84 |
| 9_78 | 82.6 | 74.6 | 88 | 83.1 | 81.8 | 84 |

TABLE 6-continued

| | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 9_96 | 85 | 76.1 | 91 | 83.1 | 81.8 | 84 |
| 9_99 | 86.2 | 82.1 | 89 | 83.1 | 81.8 | 84 |
| 11_63 | 81.4 | 73.1 | 87 | 83.1 | 81.8 | 84 |
| 11_64 | 79.6 | 73.1 | 84 | 83.1 | 81.8 | 84 |
| 11_93 | 79 | 70.1 | 85 | 83.1 | 81.8 | 84 |
| 11_96 | 80.2 | 70.1 | 87 | 83.1 | 81.8 | 84 |
| 11_104 | 83.2 | 70.1 | 92 | 83.1 | 81.8 | 84 |
| 13_75 | 86.8 | 85.1 | 88 | 83.1 | 81.8 | 84 |
| 16_25 | 85 | 80.6 | 88 | 83.1 | 81.8 | 84 |
| 16_70 | 83.8 | 80.6 | 86 | 83.1 | 81.8 | 84 |
| 21_112 | 85.6 | 79.1 | 90 | 83.1 | 81.8 | 84 |
| 21_47 | 85 | 76.1 | 91 | 83.1 | 81.8 | 84 |
| 21_91 | 80.8 | 71.6 | 87 | 83.1 | 81.8 | 84 |
| 21_101 | 79 | 70.1 | 85 | 83.1 | 81.8 | 84 |
| 22_82 | 80.8 | 70.1 | 88 | 83.1 | 81.8 | 84 |
| 25_84 | 82 | 73.1 | 88 | 83.1 | 81.8 | 84 |
| 29_47 | 82 | 70.1 | 90 | 83.1 | 81.8 | 84 |
| 29_58 | 80.2 | 71.6 | 86 | 83.1 | 81.8 | 84 |
| 31_44 | 83.8 | 73.1 | 91 | 83.1 | 81.8 | 84 |
| 31_99 | 78.4 | 67.2 | 86 | 83.1 | 81.8 | 84 |
| 34_70 | 82.6 | 77.6 | 86 | 83.1 | 81.8 | 84 |
| 35_88 | 76.6 | 67.2 | 83 | 83.1 | 81.8 | 84 |
| 35_95 | 79 | 65.7 | 88 | 83.1 | 81.8 | 84 |
| 42_46 | 82 | 70.1 | 90 | 83.1 | 81.8 | 84 |
| 42_99 | 79 | 58.2 | 93 | 83.1 | 81.8 | 84 |
| 46_114 | 82 | 71.6 | 89 | 83.1 | 81.8 | 84 |
| 46_79 | 77.2 | 64.2 | 86 | 83.1 | 81.8 | 84 |
| 46_94 | 74.9 | 59.7 | 85 | 83.1 | 81.8 | 84 |
| 46_98 | 75.9 | 62.1 | 85 | 83.1 | 81.8 | 84 |
| 55_66 | 76.6 | 64.2 | 85 | 83.1 | 81.8 | 84 |
| 55_82 | 80.8 | 65.7 | 91 | 83.1 | 81.8 | 84 |
| 65_119 | 77.2 | 68.7 | 83 | 83.1 | 81.8 | 84 |
| 65_80 | 80.2 | 71.6 | 86 | 83.1 | 81.8 | 84 |
| 66_114 | 81.4 | 65.7 | 92 | 83.1 | 81.8 | 84 |
| 66_67 | 77.2 | 56.7 | 91 | 83.1 | 81.8 | 84 |
| 66_79 | 79 | 64.2 | 89 | 83.1 | 81.8 | 84 |
| 93_114 | 77.8 | 62.7 | 88 | 83.1 | 81.8 | 84 |
| 67_119 | 79 | 62.7 | 90 | 83.1 | 81.8 | 84 |
| 79_85 | 74.9 | 58.2 | 86 | 83.1 | 81.8 | 84 |
| 99_104 | 76 | 59.7 | 87 | 83.1 | 81.8 | 84 |
| 52_106 | 89.8 | 80.6 | 96 | 81.9 | 81.8 | 82 |
| 27_109 | 84.4 | 76.1 | 90 | 81.9 | 81.8 | 82 |
| 43_109 | 89.2 | 80.6 | 95 | 81.9 | 81.8 | 82 |
| 44_109 | 89.2 | 85.1 | 92 | 81.9 | 81.8 | 82 |
| 45_109 | 87.4 | 82.1 | 91 | 81.9 | 81.8 | 82 |
| 63_109 | 86.2 | 82.1 | 89 | 81.9 | 81.8 | 82 |
| 31_110 | 88 | 79.1 | 94 | 81.9 | 81.8 | 82 |
| 9_16 | 82.6 | 79.1 | 85 | 81.9 | 81.8 | 82 |
| 9_63 | 84.4 | 79.1 | 88 | 81.9 | 81.8 | 82 |
| 9_92 | 82.6 | 76.1 | 87 | 81.9 | 81.8 | 82 |
| 10_45 | 92.2 | 88.1 | 95 | 81.9 | 81.8 | 82 |
| 11_67 | 80.2 | 70.1 | 87 | 81.9 | 81.8 | 82 |
| 11_118 | 82 | 79.1 | 84 | 81.9 | 81.8 | 82 |
| 16_80 | 82.6 | 77.6 | 86 | 81.9 | 81.8 | 82 |
| 16_94 | 85.6 | 83.6 | 87 | 81.9 | 81.8 | 82 |
| 16_99 | 82 | 79.1 | 84 | 81.9 | 81.8 | 82 |
| 21_64 | 80.2 | 67.2 | 89 | 81.9 | 81.8 | 82 |
| 21_114 | 79.6 | 68.7 | 87 | 81.9 | 81.8 | 82 |
| 22_79 | 81.4 | 71.6 | 88 | 81.9 | 81.8 | 82 |
| 25_69 | 83.8 | 73.1 | 91 | 81.9 | 81.8 | 82 |
| 28_47 | 85 | 80.6 | 88 | 81.9 | 81.8 | 82 |
| 31_92 | 80.8 | 67.2 | 90 | 81.9 | 81.8 | 82 |
| 34_67 | 78.4 | 70.1 | 84 | 81.9 | 81.8 | 82 |
| 35_67 | 78.4 | 64.2 | 88 | 81.9 | 81.8 | 82 |
| 36_99 | 79 | 70.1 | 85 | 81.9 | 81.8 | 82 |
| 42_67 | 79.6 | 64.2 | 90 | 81.9 | 81.8 | 82 |
| 42_79 | 80.8 | 62.7 | 93 | 81.9 | 81.8 | 82 |
| 42_93 | 81.4 | 65.7 | 92 | 81.9 | 81.8 | 82 |
| 46_58 | 76 | 62.7 | 85 | 81.9 | 81.8 | 82 |
| 46_103 | 75.4 | 61.2 | 85 | 81.9 | 81.8 | 82 |
| 55_78 | 74.3 | 65.7 | 80 | 81.9 | 81.8 | 82 |
| 66_87 | 73.7 | 59.7 | 83 | 81.9 | 81.8 | 82 |
| 67_83 | 72.5 | 58.2 | 82 | 81.9 | 81.8 | 82 |
| 75_115 | 79.6 | 67.2 | 88 | 81.9 | 81.8 | 82 |
| 57_109 | 85.6 | 76.1 | 92 | 80.7 | 81.8 | 80 |

TABLE 6-continued

| SEQ ID NO: | Training cohort | | | Validation cohort | | |
| --- | --- | --- | --- | --- | --- | --- |
| | Accuracy (%) | Sensitivity (%) | Specificity (%) | Accuracy (%) | Sensitivity (%) | Specificity (%) |
| 97_109 | 85 | 82.1 | 87 | 80.7 | 81.8 | 80 |
| 11_69 | 81.4 | 71.6 | 88 | 80.7 | 81.8 | 80 |
| 21_66 | 77.8 | 70.1 | 83 | 80.7 | 81.8 | 80 |
| 21_78 | 77.2 | 65.7 | 85 | 80.7 | 81.8 | 80 |
| 21_80 | 77.2 | 67.2 | 84 | 80.7 | 81.8 | 80 |
| 21_82 | 78.4 | 73.1 | 82 | 80.7 | 81.8 | 80 |
| 21_88 | 79 | 70.1 | 85 | 80.7 | 81.8 | 80 |
| 21_103 | 77.8 | 68.7 | 84 | 80.7 | 81.8 | 80 |
| 21_104 | 76 | 68.7 | 81 | 80.7 | 81.8 | 80 |
| 28_93 | 80.8 | 76.1 | 84 | 80.7 | 81.8 | 80 |
| 31_52 | 85 | 73.1 | 93 | 80.7 | 81.8 | 80 |
| 34_79 | 82 | 76.1 | 86 | 80.7 | 81.8 | 80 |
| 35_59 | 80.8 | 65.7 | 91 | 80.7 | 81.8 | 80 |
| 52_111 | 82 | 71.6 | 89 | 80.7 | 81.8 | 80 |
| 66_69 | 83.8 | 70.1 | 93 | 80.7 | 81.8 | 80 |
| 65_109 | 86.2 | 79.1 | 91 | 79.5 | 81.8 | 78 |
| 68_109 | 82.6 | 73.1 | 89 | 79.5 | 81.8 | 78 |
| 71_109 | 84.4 | 77.6 | 89 | 79.5 | 81.8 | 78 |
| 21_69 | 81.4 | 73.1 | 87 | 79.5 | 81.8 | 78 |
| 28_119 | 80.2 | 79.1 | 81 | 79.5 | 81.8 | 78 |
| 67_97 | 74.9 | 59.7 | 85 | 79.5 | 81.8 | 78 |
| 71_78 | 73.1 | 61.2 | 81 | 79.5 | 81.8 | 78 |
| 11_109 | 86.2 | 77.6 | 92 | 78.3 | 81.8 | 76 |
| 17_109 | 83.8 | 74.6 | 90 | 78.3 | 81.8 | 76 |
| 11_94 | 79.6 | 71.6 | 85 | 78.3 | 81.8 | 76 |
| 65_100 | 77.2 | 65.7 | 85 | 78.3 | 81.8 | 76 |
| 79_104 | 73.7 | 59.7 | 83 | 78.3 | 81.8 | 76 |
| 83_100 | 64.7 | 40.3 | 81 | 78.3 | 81.8 | 76 |
| 69_109 | 82.6 | 76.1 | 87 | 77.1 | 81.8 | 74 |
| 78_109 | 84.4 | 77.6 | 89 | 77.1 | 81.8 | 74 |
| 84_109 | 84.4 | 74.6 | 91 | 77.1 | 81.8 | 74 |
| 93_109 | 82.6 | 74.6 | 88 | 77.1 | 81.8 | 74 |
| 31_65 | 81.4 | 76.1 | 85 | 77.1 | 81.8 | 74 |
| 100_109 | 82 | 77.6 | 85 | 75.9 | 81.8 | 72 |
| 28_100 | 80.2 | 73.1 | 85 | 75.9 | 81.8 | 72 |
| 64_79 | 77.8 | 67.2 | 85 | 75.9 | 81.8 | 72 |
| 70_100 | 75.4 | 59.7 | 86 | 75.9 | 81.8 | 72 |
| 10_100 | 86.2 | 80.6 | 90 | 74.7 | 81.8 | 70 |
| 67_69 | 79.6 | 71.6 | 85 | 74.7 | 81.8 | 70 |
| 13_50 | 85 | 79.1 | 89 | 87.8 | 81.2 | 92 |
| 18_50 | 83.8 | 73.1 | 91 | 87.8 | 81.2 | 92 |
| 50_106 | 89.8 | 77.6 | 98 | 85.4 | 81.2 | 88 |
| 40_50 | 81.4 | 67.2 | 91 | 85.4 | 81.2 | 88 |
| 50_114 | 80.2 | 65.7 | 90 | 85.4 | 81.2 | 88 |
| 9_50 | 84.4 | 77.6 | 89 | 84.1 | 81.2 | 86 |
| 50_66 | 74.9 | 56.7 | 87 | 82.9 | 81.2 | 84 |
| 50_81 | 74.1 | 57.6 | 85 | 82.9 | 81.2 | 84 |
| 11_50 | 77.8 | 68.7 | 84 | 81.7 | 81.2 | 82 |
| 50_58 | 76 | 59.7 | 87 | 81.7 | 81.2 | 82 |
| 50_83 | 70.7 | 52.2 | 83 | 81.7 | 81.2 | 82 |
| 23_109 | 83.2 | 71.6 | 91 | 75.6 | 81.2 | 72 |
| 6_77 | 89.2 | 80.6 | 95 | 91.4 | 80.6 | 98 |
| 77_107 | 90.4 | 85.1 | 94 | 88.9 | 80.6 | 94 |
| 19_77 | 82.6 | 71.6 | 90 | 88.9 | 80.6 | 94 |
| 42_77 | 78.4 | 62.7 | 89 | 87.7 | 80.6 | 92 |
| 51_77 | 80.2 | 62.7 | 92 | 87.7 | 80.6 | 92 |
| 6_28 | 91.6 | 85.1 | 96 | 91.6 | 78.8 | 100 |
| 6_43 | 86.2 | 76.1 | 93 | 91.6 | 78.8 | 100 |
| 6_87 | 90.4 | 82.1 | 96 | 91.6 | 78.8 | 100 |
| 7_15 | 91 | 82.1 | 97 | 91.6 | 78.8 | 100 |
| 8_15 | 89.8 | 85.1 | 93 | 91.6 | 78.8 | 100 |
| 10_41 | 86.8 | 74.6 | 95 | 91.6 | 78.8 | 100 |
| 15_18 | 90.4 | 86.6 | 93 | 91.6 | 78.8 | 100 |
| 18_33 | 86.2 | 74.6 | 94 | 91.6 | 78.8 | 100 |
| 14_106 | 91 | 79.1 | 99 | 90.4 | 78.8 | 98 |
| 41_106 | 91.6 | 82.1 | 98 | 90.4 | 78.8 | 98 |
| 2_86 | 91 | 80.6 | 98 | 90.4 | 78.8 | 98 |
| 30_107 | 92.2 | 85.1 | 97 | 90.4 | 78.8 | 98 |
| 6_108 | 89.8 | 80.6 | 96 | 90.4 | 78.8 | 98 |
| 15_108 | 88 | 76.1 | 96 | 90.4 | 78.8 | 98 |
| 30_108 | 92.8 | 85.1 | 98 | 90.4 | 78.8 | 98 |
| 41_108 | 91 | 82.1 | 97 | 90.4 | 78.8 | 98 |
| 68_108 | 87.4 | 76.1 | 95 | 90.4 | 78.8 | 98 |
| 6_14 | 91 | 80.6 | 98 | 90.4 | 78.8 | 98 |
| 7_110 | 91.6 | 82.1 | 98 | 90.4 | 78.8 | 98 |

TABLE 6-continued

| | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 9_19 | 88 | 82.1 | 92 | 90.4 | 78.8 | 98 |
| 13_80 | 85 | 82.1 | 87 | 90.4 | 78.8 | 98 |
| 14_112 | 91.6 | 80.6 | 99 | 90.4 | 78.8 | 98 |
| 15_39 | 89.2 | 79.1 | 96 | 90.4 | 78.8 | 98 |
| 18_32 | 89.2 | 80.6 | 95 | 90.4 | 78.8 | 98 |
| 18_118 | 85.6 | 76.1 | 92 | 90.4 | 78.8 | 98 |
| 24_41 | 82.6 | 68.7 | 92 | 90.4 | 78.8 | 98 |
| 30_31 | 84.4 | 73.1 | 92 | 90.4 | 78.8 | 98 |
| 33_112 | 85.6 | 71.6 | 95 | 90.4 | 78.8 | 98 |
| 87_111 | 83.2 | 67.2 | 94 | 90.4 | 78.8 | 98 |
| 7_106 | 92.2 | 82.1 | 99 | 89.2 | 78.8 | 96 |
| 28_106 | 93.4 | 85.1 | 99 | 89.2 | 78.8 | 96 |
| 61_106 | 91.6 | 80.6 | 99 | 89.2 | 78.8 | 96 |
| 19_107 | 94 | 88.1 | 98 | 89.2 | 78.8 | 96 |
| 3_7 | 95.2 | 89.6 | 99 | 89.2 | 78.8 | 96 |
| 3_30 | 91 | 85.1 | 95 | 89.2 | 78.8 | 96 |
| 17_108 | 87.4 | 71.6 | 98 | 89.2 | 78.8 | 96 |
| 5_8 | 95.2 | 91 | 98 | 89.2 | 78.8 | 96 |
| 5_122 | 90.4 | 85.1 | 94 | 89.2 | 78.8 | 96 |
| 6_22 | 85.6 | 74.6 | 93 | 89.2 | 78.8 | 96 |
| 6_90 | 87.4 | 80.6 | 92 | 89.2 | 78.8 | 96 |
| 7_36 | 91.6 | 82.1 | 98 | 89.2 | 78.8 | 96 |
| 9_41 | 87.4 | 82.1 | 91 | 89.2 | 78.8 | 96 |
| 12_111 | 88 | 78.8 | 94 | 89.2 | 78.8 | 96 |
| 12_56 | 87.3 | 83.3 | 90 | 89.2 | 78.8 | 96 |
| 13_36 | 89.8 | 83.6 | 94 | 89.2 | 78.8 | 96 |
| 13_41 | 85.6 | 85.1 | 86 | 89.2 | 78.8 | 96 |
| 14_34 | 89.8 | 82.1 | 95 | 89.2 | 78.8 | 96 |
| 14_37 | 89.8 | 79.1 | 97 | 89.2 | 78.8 | 96 |
| 14_44 | 89.8 | 76.1 | 99 | 89.2 | 78.8 | 96 |
| 14_75 | 86.2 | 73.1 | 95 | 89.2 | 78.8 | 96 |
| 14_89 | 86.2 | 71.6 | 96 | 89.2 | 78.8 | 96 |
| 15_21 | 84.4 | 71.6 | 93 | 89.2 | 78.8 | 96 |
| 15_44 | 85 | 71.6 | 94 | 89.2 | 78.8 | 96 |
| 18_112 | 84.4 | 76.1 | 90 | 89.2 | 78.8 | 96 |
| 18_44 | 85.6 | 74.6 | 93 | 89.2 | 78.8 | 96 |
| 18_117 | 85 | 73.1 | 93 | 89.2 | 78.8 | 96 |
| 18_119 | 84.4 | 76.1 | 90 | 89.2 | 78.8 | 96 |
| 18_80 | 83.8 | 76.1 | 89 | 89.2 | 78.8 | 96 |
| 18_120 | 84.4 | 76.1 | 90 | 89.2 | 78.8 | 96 |
| 18_98 | 84.3 | 75.8 | 90 | 89.2 | 78.8 | 96 |
| 18_122 | 84.4 | 76.1 | 90 | 89.2 | 78.8 | 96 |
| 19_26 | 83.2 | 73.1 | 90 | 89.2 | 78.8 | 96 |
| 19_31 | 87.4 | 76.1 | 95 | 89.2 | 78.8 | 96 |
| 19_52 | 86.8 | 80.6 | 91 | 89.2 | 78.8 | 96 |
| 20_33 | 88 | 79.1 | 94 | 89.2 | 78.8 | 96 |
| 20_111 | 88.6 | 77.6 | 96 | 89.2 | 78.8 | 96 |
| 24_38 | 84.4 | 71.6 | 93 | 89.2 | 78.8 | 96 |
| 25_38 | 85 | 67.2 | 97 | 89.2 | 78.8 | 96 |
| 30_112 | 85 | 79.1 | 89 | 89.2 | 78.8 | 96 |
| 30_94 | 82.6 | 73.1 | 89 | 89.2 | 78.8 | 96 |
| 33_71 | 82.6 | 73.1 | 89 | 89.2 | 78.8 | 96 |
| 33_99 | 83.8 | 68.7 | 94 | 89.2 | 78.8 | 96 |
| 98_111 | 77.7 | 56.1 | 92 | 89.2 | 78.8 | 96 |
| 37_70 | 79 | 71.6 | 84 | 89.2 | 78.8 | 96 |
| 38_46 | 87.4 | 76.1 | 95 | 89.2 | 78.8 | 96 |
| 40_42 | 82.6 | 61.2 | 97 | 89.2 | 78.8 | 96 |
| 41_120 | 80.8 | 73.1 | 86 | 89.2 | 78.8 | 96 |
| 96_113 | 85 | 74.6 | 92 | 89.2 | 78.8 | 96 |
| 36_106 | 91 | 79.1 | 99 | 88 | 78.8 | 94 |
| 37_106 | 91 | 80.6 | 98 | 88 | 78.8 | 94 |
| 60_106 | 91.6 | 82.1 | 98 | 88 | 78.8 | 94 |
| 62_106 | 91 | 80.6 | 98 | 88 | 78.8 | 94 |
| 74_106 | 91 | 80.6 | 98 | 88 | 78.8 | 94 |
| 90_106 | 89.8 | 77.6 | 98 | 88 | 78.8 | 94 |
| 3_107 | 92.8 | 86.6 | 97 | 88 | 78.8 | 94 |
| 6_107 | 88 | 76.1 | 96 | 88 | 78.8 | 94 |
| 27_107 | 91 | 83.6 | 96 | 88 | 78.8 | 94 |
| 48_107 | 91 | 82.1 | 97 | 88 | 78.8 | 94 |
| 57_107 | 91 | 82.1 | 97 | 88 | 78.8 | 94 |
| 73_107 | 91 | 80.6 | 98 | 88 | 78.8 | 94 |
| 102_107 | 90.4 | 79.1 | 98 | 88 | 78.8 | 94 |
| 3_37 | 91.6 | 88.1 | 94 | 88 | 78.8 | 94 |
| 27_108 | 90.4 | 79.1 | 98 | 88 | 78.8 | 94 |
| 33_108 | 86.8 | 73.1 | 96 | 88 | 78.8 | 94 |

TABLE 6-continued

| | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 57_108 | 87.4 | 71.6 | 98 | 88 | 78.8 | 94 |
| 6_9 | 88.6 | 79.1 | 95 | 88 | 78.8 | 94 |
| 6_25 | 86.2 | 74.6 | 94 | 88 | 78.8 | 94 |
| 6_85 | 86.2 | 79.1 | 91 | 88 | 78.8 | 94 |
| 6_98 | 86.7 | 77.3 | 93 | 88 | 78.8 | 94 |
| 7_60 | 92.8 | 89.6 | 95 | 88 | 78.8 | 94 |
| 8_31 | 89.2 | 82.1 | 94 | 88 | 78.8 | 94 |
| 8_42 | 89.8 | 79.1 | 97 | 88 | 78.8 | 94 |
| 26_110 | 91 | 86.6 | 94 | 88 | 78.8 | 94 |
| 9_38 | 83.2 | 76.1 | 88 | 88 | 78.8 | 94 |
| 10_19 | 88.6 | 79.1 | 95 | 88 | 78.8 | 94 |
| 10_43 | 88 | 83.6 | 91 | 88 | 78.8 | 94 |
| 12_13 | 92.2 | 89.4 | 94 | 88 | 78.8 | 94 |
| 13_29 | 89.2 | 82.1 | 94 | 88 | 78.8 | 94 |
| 13_39 | 86.8 | 74.6 | 95 | 88 | 78.8 | 94 |
| 14_52 | 89.2 | 79.1 | 96 | 88 | 78.8 | 94 |
| 15_119 | 85 | 77.6 | 90 | 88 | 78.8 | 94 |
| 17_54 | 87.4 | 71.6 | 98 | 88 | 78.8 | 94 |
| 17_64 | 85 | 68.7 | 96 | 88 | 78.8 | 94 |
| 17_120 | 84.4 | 68.7 | 95 | 88 | 78.8 | 94 |
| 18_29 | 85 | 74.6 | 92 | 88 | 78.8 | 94 |
| 18_114 | 85 | 74.6 | 92 | 88 | 78.8 | 94 |
| 18_71 | 80.2 | 70.1 | 87 | 88 | 78.8 | 94 |
| 18_86 | 86.2 | 77.6 | 92 | 88 | 78.8 | 94 |
| 18_92 | 84.4 | 76.1 | 90 | 88 | 78.8 | 94 |
| 18_99 | 83.8 | 74.6 | 90 | 88 | 78.8 | 94 |
| 20_25 | 89.8 | 83.6 | 94 | 88 | 78.8 | 94 |
| 24_49 | 83.8 | 79.1 | 87 | 88 | 78.8 | 94 |
| 24_116 | 82.6 | 67.2 | 93 | 88 | 78.8 | 94 |
| 24_87 | 82.6 | 68.7 | 92 | 88 | 78.8 | 94 |
| 30_39 | 89.8 | 82.1 | 95 | 88 | 78.8 | 94 |
| 30_70 | 85.6 | 74.6 | 93 | 88 | 78.8 | 94 |
| 34_38 | 85 | 74.6 | 92 | 88 | 78.8 | 94 |
| 38_98 | 82.5 | 65.2 | 94 | 88 | 78.8 | 94 |
| 39_113 | 87.4 | 76.1 | 95 | 88 | 78.8 | 94 |
| 39_60 | 88 | 74.6 | 97 | 88 | 78.8 | 94 |
| 40_46 | 85 | 74.6 | 92 | 88 | 78.8 | 94 |
| 41_66 | 79.6 | 62.7 | 91 | 88 | 78.8 | 94 |
| 41_83 | 79 | 65.7 | 88 | 88 | 78.8 | 94 |
| 71_112 | 79.6 | 65.7 | 89 | 88 | 78.8 | 94 |
| 83_112 | 77.2 | 64.2 | 86 | 88 | 78.8 | 94 |
| 46_62 | 80.2 | 70.1 | 87 | 88 | 78.8 | 94 |
| 58_73 | 80.8 | 71.6 | 87 | 88 | 78.8 | 94 |
| 59_119 | 82 | 64.2 | 94 | 88 | 78.8 | 94 |
| 67_115 | 78.4 | 68.7 | 85 | 88 | 78.8 | 94 |
| 83_115 | 83.8 | 73.1 | 91 | 88 | 78.8 | 94 |
| 70_120 | 76 | 59.7 | 87 | 88 | 78.8 | 94 |
| 72_107 | 89.2 | 79.1 | 96 | 87.8 | 78.8 | 93.9 |
| 22_106 | 89.2 | 79.1 | 96 | 86.7 | 78.8 | 92 |
| 32_106 | 91 | 77.6 | 100 | 86.7 | 78.8 | 92 |
| 33_106 | 90.4 | 80.6 | 97 | 86.7 | 78.8 | 92 |
| 11_107 | 89.8 | 80.6 | 96 | 86.7 | 78.8 | 92 |
| 3_98 | 90.4 | 86.4 | 93 | 86.7 | 78.8 | 92 |
| 5_61 | 89.8 | 86.6 | 92 | 86.7 | 78.8 | 92 |
| 5_70 | 87.4 | 80.6 | 92 | 86.7 | 78.8 | 92 |
| 5_101 | 87.4 | 80.6 | 92 | 86.7 | 78.8 | 92 |
| 6_83 | 85.6 | 76.1 | 92 | 86.7 | 78.8 | 92 |
| 41_109 | 89.2 | 83.6 | 93 | 86.7 | 78.8 | 92 |
| 9_111 | 83.8 | 71.6 | 92 | 86.7 | 78.8 | 92 |
| 9_43 | 88.6 | 85.1 | 91 | 86.7 | 78.8 | 92 |
| 9_113 | 86.8 | 79.1 | 92 | 86.7 | 78.8 | 92 |
| 9_115 | 85 | 79.1 | 89 | 86.7 | 78.8 | 92 |
| 10_14 | 87.4 | 76.1 | 95 | 86.7 | 78.8 | 92 |
| 10_21 | 89.8 | 82.1 | 95 | 86.7 | 78.8 | 92 |
| 10_33 | 85 | 73.1 | 93 | 86.7 | 78.8 | 92 |
| 11_28 | 86.8 | 76.1 | 94 | 86.7 | 78.8 | 92 |
| 11_113 | 86.8 | 77.6 | 93 | 86.7 | 78.8 | 92 |
| 13_58 | 85 | 76.1 | 91 | 86.7 | 78.8 | 92 |
| 13_68 | 87.4 | 79.1 | 93 | 86.7 | 78.8 | 92 |
| 13_115 | 85.6 | 82.1 | 88 | 86.7 | 78.8 | 92 |
| 14_26 | 89.2 | 76.1 | 98 | 86.7 | 78.8 | 92 |
| 14_31 | 84.4 | 70.1 | 94 | 86.7 | 78.8 | 92 |
| 14_119 | 88 | 76.1 | 96 | 86.7 | 78.8 | 92 |
| 15_42 | 85 | 68.7 | 96 | 86.7 | 78.8 | 92 |
| 17_22 | 85 | 71.6 | 94 | 86.7 | 78.8 | 92 |

TABLE 6-continued

| | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 17_46 | 84.4 | 71.6 | 93 | 86.7 | 78.8 | 92 |
| 17_55 | 88 | 74.6 | 97 | 86.7 | 78.8 | 92 |
| 17_58 | 85 | 73.1 | 93 | 86.7 | 78.8 | 92 |
| 17_65 | 85 | 70.1 | 95 | 86.7 | 78.8 | 92 |
| 17_94 | 83.2 | 68.7 | 93 | 86.7 | 78.8 | 92 |
| 18_28 | 89.8 | 82.1 | 95 | 86.7 | 78.8 | 92 |
| 18_61 | 85.6 | 76.1 | 92 | 86.7 | 78.8 | 92 |
| 18_121 | 83.8 | 77.6 | 88 | 86.7 | 78.8 | 92 |
| 19_81 | 86.1 | 80.3 | 90 | 86.7 | 78.8 | 92 |
| 22_113 | 87.4 | 80.6 | 92 | 86.7 | 78.8 | 92 |
| 24_113 | 83.2 | 73.1 | 90 | 86.7 | 78.8 | 92 |
| 25_40 | 86.2 | 73.1 | 95 | 86.7 | 78.8 | 92 |
| 25_42 | 84.4 | 71.6 | 93 | 86.7 | 78.8 | 92 |
| 25_116 | 84.4 | 74.6 | 91 | 86.7 | 78.8 | 92 |
| 26_29 | 85 | 74.6 | 92 | 86.7 | 78.8 | 92 |
| 29_70 | 82 | 71.6 | 89 | 86.7 | 78.8 | 92 |
| 30_119 | 80.2 | 74.6 | 84 | 86.7 | 78.8 | 92 |
| 33_55 | 83.2 | 67.2 | 94 | 86.7 | 78.8 | 92 |
| 36_119 | 80.8 | 71.6 | 87 | 86.7 | 78.8 | 92 |
| 55_111 | 81.4 | 67.2 | 91 | 86.7 | 78.8 | 92 |
| 37_66 | 79 | 68.7 | 86 | 86.7 | 78.8 | 92 |
| 39_46 | 77.8 | 65.7 | 86 | 86.7 | 78.8 | 92 |
| 39_70 | 78.4 | 64.2 | 88 | 86.7 | 78.8 | 92 |
| 39_75 | 77.8 | 65.7 | 86 | 86.7 | 78.8 | 92 |
| 40_112 | 86.8 | 74.6 | 95 | 86.7 | 78.8 | 92 |
| 41_67 | 80.2 | 64.2 | 91 | 86.7 | 78.8 | 92 |
| 91_112 | 82.6 | 65.7 | 94 | 86.7 | 78.8 | 92 |
| 93_112 | 77.8 | 65.7 | 86 | 86.7 | 78.8 | 92 |
| 46_55 | 79 | 64.2 | 89 | 86.7 | 78.8 | 92 |
| 66_113 | 83.8 | 68.7 | 94 | 86.7 | 78.8 | 92 |
| 79_113 | 84.4 | 73.1 | 92 | 86.7 | 78.8 | 92 |
| 52_53 | 84.4 | 79.1 | 88 | 86.7 | 78.8 | 92 |
| 58_119 | 75.4 | 62.7 | 84 | 86.7 | 78.8 | 92 |
| 58_87 | 82 | 74.6 | 87 | 86.7 | 78.8 | 92 |
| 98_115 | 81.9 | 65.2 | 93 | 86.7 | 78.8 | 92 |
| 15_106 | 89.8 | 77.6 | 98 | 85.5 | 78.8 | 90 |
| 65_106 | 93.4 | 86.6 | 98 | 85.5 | 78.8 | 90 |
| 81_106 | 91 | 80.3 | 98 | 85.5 | 78.8 | 90 |
| 85_106 | 88.6 | 79.1 | 95 | 85.5 | 78.8 | 90 |
| 69_107 | 87.4 | 77.6 | 94 | 85.5 | 78.8 | 90 |
| 3_9 | 93.4 | 88.1 | 97 | 85.5 | 78.8 | 90 |
| 3_45 | 92.8 | 86.6 | 97 | 85.5 | 78.8 | 90 |
| 3_46 | 93.4 | 88.1 | 97 | 85.5 | 78.8 | 90 |
| 61_108 | 91.6 | 86.6 | 95 | 85.5 | 78.8 | 90 |
| 73_108 | 86.2 | 73.1 | 95 | 85.5 | 78.8 | 90 |
| 5_58 | 86.8 | 77.6 | 93 | 85.5 | 78.8 | 90 |
| 5_69 | 90.4 | 83.6 | 95 | 85.5 | 78.8 | 90 |
| 5_76 | 90.4 | 83.6 | 95 | 85.5 | 78.8 | 90 |
| 5_84 | 89.2 | 85.1 | 92 | 85.5 | 78.8 | 90 |
| 5_92 | 88.6 | 85.1 | 91 | 85.5 | 78.8 | 90 |
| 5_95 | 89.8 | 83.6 | 94 | 85.5 | 78.8 | 90 |
| 6_11 | 85.6 | 74.6 | 93 | 85.5 | 78.8 | 90 |
| 8_35 | 89.2 | 82.1 | 94 | 85.5 | 78.8 | 90 |
| 8_40 | 87.4 | 76.1 | 95 | 85.5 | 78.8 | 90 |
| 9_10 | 86.8 | 82.1 | 90 | 85.5 | 78.8 | 90 |
| 9_32 | 84.4 | 79.1 | 88 | 85.5 | 78.8 | 90 |
| 9_48 | 84.4 | 80.6 | 87 | 85.5 | 78.8 | 90 |
| 10_25 | 82.6 | 73.1 | 89 | 85.5 | 78.8 | 90 |
| 10_70 | 88 | 77.6 | 95 | 85.5 | 78.8 | 90 |
| 12_66 | 82.5 | 72.7 | 89 | 85.5 | 78.8 | 90 |
| 12_95 | 85.5 | 78.8 | 90 | 85.5 | 78.8 | 90 |
| 13_34 | 91 | 85.1 | 95 | 85.5 | 78.8 | 90 |
| 13_52 | 89.2 | 82.1 | 94 | 85.5 | 78.8 | 90 |
| 13_99 | 84.4 | 80.6 | 87 | 85.5 | 78.8 | 90 |
| 15_52 | 88 | 82.1 | 92 | 85.5 | 78.8 | 90 |
| 16_55 | 84.4 | 79.1 | 88 | 85.5 | 78.8 | 90 |
| 17_45 | 85.6 | 73.1 | 94 | 85.5 | 78.8 | 90 |
| 17_118 | 83.8 | 70.1 | 93 | 85.5 | 78.8 | 90 |
| 17_83 | 83.2 | 67.2 | 94 | 85.5 | 78.8 | 90 |
| 17_85 | 83.8 | 67.2 | 95 | 85.5 | 78.8 | 90 |
| 17_88 | 82 | 67.2 | 92 | 85.5 | 78.8 | 90 |
| 17_97 | 83.2 | 70.1 | 92 | 85.5 | 78.8 | 90 |
| 18_65 | 86.2 | 76.1 | 93 | 85.5 | 78.8 | 90 |
| 21_32 | 84.4 | 80.6 | 87 | 85.5 | 78.8 | 90 |
| 21_73 | 79.6 | 76.1 | 82 | 85.5 | 78.8 | 90 |

TABLE 6-continued

| | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 22_40 | 87.4 | 76.1 | 95 | 85.5 | 78.8 | 90 |
| 22_57 | 86.8 | 79.1 | 92 | 85.5 | 78.8 | 90 |
| 22_76 | 77.8 | 64.2 | 87 | 85.5 | 78.8 | 90 |
| 24_28 | 85 | 79.1 | 89 | 85.5 | 78.8 | 90 |
| 24_111 | 83.8 | 73.1 | 91 | 85.5 | 78.8 | 90 |
| 24_47 | 77.8 | 65.7 | 86 | 85.5 | 78.8 | 90 |
| 24_62 | 82.6 | 68.7 | 92 | 85.5 | 78.8 | 90 |
| 25_43 | 85 | 76.1 | 91 | 85.5 | 78.8 | 90 |
| 25_51 | 83.2 | 71.6 | 91 | 85.5 | 78.8 | 90 |
| 25_113 | 83.2 | 68.7 | 93 | 85.5 | 78.8 | 90 |
| 25_115 | 82.6 | 68.7 | 92 | 85.5 | 78.8 | 90 |
| 28_55 | 87.4 | 76.1 | 95 | 85.5 | 78.8 | 90 |
| 28_58 | 87.4 | 79.1 | 93 | 85.5 | 78.8 | 90 |
| 29_119 | 83.8 | 80.6 | 86 | 85.5 | 78.8 | 90 |
| 34_115 | 82.6 | 73.1 | 89 | 85.5 | 78.8 | 90 |
| 99_111 | 81.4 | 62.7 | 94 | 85.5 | 78.8 | 90 |
| 38_55 | 88 | 73.1 | 98 | 85.5 | 78.8 | 90 |
| 39_104 | 80.2 | 65.7 | 90 | 85.5 | 78.8 | 90 |
| 40_81 | 80.7 | 68.2 | 89 | 85.5 | 78.8 | 90 |
| 41_79 | 81.4 | 68.7 | 90 | 85.5 | 78.8 | 90 |
| 42_112 | 82 | 67.2 | 92 | 85.5 | 78.8 | 90 |
| 42_56 | 82 | 71.6 | 89 | 85.5 | 78.8 | 90 |
| 68_112 | 82.6 | 70.1 | 91 | 85.5 | 78.8 | 90 |
| 45_66 | 79 | 68.7 | 86 | 85.5 | 78.8 | 90 |
| 51_81 | 77.7 | 66.7 | 85 | 85.5 | 78.8 | 90 |
| 51_98 | 80.7 | 72.7 | 86 | 85.5 | 78.8 | 90 |
| 94_113 | 84.4 | 70.1 | 94 | 85.5 | 78.8 | 90 |
| 58_117 | 78.4 | 61.2 | 90 | 85.5 | 78.8 | 90 |
| 58_80 | 78.4 | 62.7 | 89 | 85.5 | 78.8 | 90 |
| 58_99 | 76.6 | 61.2 | 87 | 85.5 | 78.8 | 90 |
| 62_66 | 79 | 64.2 | 89 | 85.5 | 78.8 | 90 |
| 99_114 | 79 | 67.2 | 87 | 85.5 | 78.8 | 90 |
| 81_115 | 78.3 | 66.7 | 86 | 85.5 | 78.8 | 90 |
| 76_98 | 80.7 | 69.7 | 88 | 85.5 | 78.8 | 90 |
| 27_106 | 89.2 | 76.1 | 98 | 84.3 | 78.8 | 88 |
| 68_106 | 89.8 | 79.1 | 97 | 84.3 | 78.8 | 88 |
| 75_106 | 88 | 74.6 | 97 | 84.3 | 78.8 | 88 |
| 84_106 | 89.2 | 79.1 | 96 | 84.3 | 78.8 | 88 |
| 91_106 | 89.8 | 79.1 | 97 | 84.3 | 78.8 | 88 |
| 3_111 | 88.6 | 79.1 | 95 | 84.3 | 78.8 | 88 |
| 3_103 | 91.6 | 86.6 | 95 | 84.3 | 78.8 | 88 |
| 4_110 | 91 | 86.6 | 94 | 84.3 | 78.8 | 88 |
| 95_108 | 89.8 | 85.1 | 93 | 84.3 | 78.8 | 88 |
| 104_108 | 88 | 79.1 | 94 | 84.3 | 78.8 | 88 |
| 5_110 | 95.2 | 91 | 98 | 84.3 | 78.8 | 88 |
| 5_27 | 88.6 | 83.6 | 92 | 84.3 | 78.8 | 88 |
| 6_39 | 89.8 | 85.1 | 93 | 84.3 | 78.8 | 88 |
| 6_45 | 90.4 | 80.6 | 97 | 84.3 | 78.8 | 88 |
| 6_67 | 87.4 | 74.6 | 96 | 84.3 | 78.8 | 88 |
| 6_93 | 87.4 | 76.1 | 95 | 84.3 | 78.8 | 88 |
| 9_59 | 86.8 | 79.1 | 92 | 84.3 | 78.8 | 88 |
| 9_86 | 85.6 | 80.6 | 89 | 84.3 | 78.8 | 88 |
| 9_88 | 83.8 | 79.1 | 87 | 84.3 | 78.8 | 88 |
| 9_103 | 82.6 | 74.6 | 88 | 84.3 | 78.8 | 88 |
| 9_104 | 81.4 | 76.1 | 85 | 84.3 | 78.8 | 88 |
| 10_60 | 83.8 | 71.6 | 92 | 84.3 | 78.8 | 88 |
| 11_47 | 83.8 | 74.6 | 90 | 84.3 | 78.8 | 88 |
| 11_76 | 82 | 71.6 | 89 | 84.3 | 78.8 | 88 |
| 11_120 | 79.6 | 68.7 | 87 | 84.3 | 78.8 | 88 |
| 12_16 | 88 | 89.4 | 87 | 84.3 | 78.8 | 88 |
| 12_31 | 87.3 | 80.3 | 92 | 84.3 | 78.8 | 88 |
| 12_78 | 85.5 | 80.3 | 89 | 84.3 | 78.8 | 88 |
| 13_62 | 83.2 | 82.1 | 84 | 84.3 | 78.8 | 88 |
| 13_93 | 83.8 | 82.1 | 85 | 84.3 | 78.8 | 88 |
| 14_100 | 85.6 | 71.6 | 95 | 84.3 | 78.8 | 88 |
| 16_34 | 88 | 85.1 | 90 | 84.3 | 78.8 | 88 |
| 16_39 | 89.2 | 86.6 | 91 | 84.3 | 78.8 | 88 |
| 16_97 | 84.4 | 85.1 | 84 | 84.3 | 78.8 | 88 |
| 17_27 | 85 | 70.1 | 95 | 84.3 | 78.8 | 88 |
| 17_39 | 84.4 | 74.6 | 91 | 84.3 | 78.8 | 88 |
| 17_44 | 85 | 70.1 | 95 | 84.3 | 78.8 | 88 |
| 17_121 | 83.2 | 67.2 | 94 | 84.3 | 78.8 | 88 |
| 22_74 | 83.2 | 77.6 | 87 | 84.3 | 78.8 | 88 |
| 24_84 | 79.6 | 68.7 | 87 | 84.3 | 78.8 | 88 |
| 25_32 | 84.4 | 73.1 | 92 | 84.3 | 78.8 | 88 |

TABLE 6-continued

| | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 25_74 | 83.8 | 74.6 | 90 | 84.3 | 78.8 | 88 |
| 25_76 | 80.8 | 67.2 | 90 | 84.3 | 78.8 | 88 |
| 25_91 | 81.4 | 67.2 | 91 | 84.3 | 78.8 | 88 |
| 27_28 | 83.2 | 74.6 | 89 | 84.3 | 78.8 | 88 |
| 28_94 | 82 | 73.1 | 88 | 84.3 | 78.8 | 88 |
| 28_96 | 86.2 | 76.1 | 93 | 84.3 | 78.8 | 88 |
| 29_42 | 80.2 | 64.2 | 91 | 84.3 | 78.8 | 88 |
| 29_96 | 78.4 | 70.1 | 84 | 84.3 | 78.8 | 88 |
| 31_115 | 80.8 | 67.2 | 90 | 84.3 | 78.8 | 88 |
| 32_46 | 85 | 77.6 | 90 | 84.3 | 78.8 | 88 |
| 32_55 | 86.8 | 82.1 | 90 | 84.3 | 78.8 | 88 |
| 35_111 | 82 | 65.7 | 93 | 84.3 | 78.8 | 88 |
| 35_68 | 78.4 | 64.2 | 88 | 84.3 | 78.8 | 88 |
| 37_100 | 79 | 67.2 | 87 | 84.3 | 78.8 | 88 |
| 39_44 | 80.2 | 67.2 | 89 | 84.3 | 78.8 | 88 |
| 40_66 | 81.4 | 61.2 | 95 | 84.3 | 78.8 | 88 |
| 42_66 | 80.2 | 59.7 | 94 | 84.3 | 78.8 | 88 |
| 76_112 | 88 | 80.6 | 93 | 84.3 | 78.8 | 88 |
| 78_112 | 77.2 | 61.2 | 88 | 84.3 | 78.8 | 88 |
| 81_112 | 77.7 | 62.1 | 88 | 84.3 | 78.8 | 88 |
| 44_78 | 79.6 | 68.7 | 87 | 84.3 | 78.8 | 88 |
| 46_75 | 75.4 | 67.2 | 81 | 84.3 | 78.8 | 88 |
| 46_85 | 76.6 | 61.2 | 87 | 84.3 | 78.8 | 88 |
| 46_93 | 74.9 | 59.7 | 85 | 84.3 | 78.8 | 88 |
| 51_55 | 79 | 67.2 | 87 | 84.3 | 78.8 | 88 |
| 53_67 | 77.2 | 67.2 | 84 | 84.3 | 78.8 | 88 |
| 53_75 | 81.4 | 70.1 | 89 | 84.3 | 78.8 | 88 |
| 53_83 | 76.6 | 62.7 | 86 | 84.3 | 78.8 | 88 |
| 55_62 | 83.8 | 70.1 | 93 | 84.3 | 78.8 | 88 |
| 56_58 | 79 | 64.2 | 89 | 84.3 | 78.8 | 88 |
| 56_114 | 79 | 70.1 | 85 | 84.3 | 78.8 | 88 |
| 56_119 | 77.8 | 65.7 | 86 | 84.3 | 78.8 | 88 |
| 62_70 | 80.2 | 64.2 | 91 | 84.3 | 78.8 | 88 |
| 65_70 | 83.2 | 70.1 | 92 | 84.3 | 78.8 | 88 |
| 65_98 | 76.5 | 62.1 | 86 | 84.3 | 78.8 | 88 |
| 66_71 | 80.2 | 67.2 | 89 | 84.3 | 78.8 | 88 |
| 66_74 | 80.8 | 67.2 | 90 | 84.3 | 78.8 | 88 |
| 66_81 | 77.7 | 62.1 | 88 | 84.3 | 78.8 | 88 |
| 66_89 | 80.2 | 68.7 | 88 | 84.3 | 78.8 | 88 |
| 75_114 | 81.4 | 70.1 | 89 | 84.3 | 78.8 | 88 |
| 71_104 | 80.8 | 65.7 | 91 | 84.3 | 78.8 | 88 |
| 81_89 | 77.1 | 62.1 | 87 | 84.3 | 78.8 | 88 |
| 90_98 | 74.1 | 57.6 | 85 | 84.3 | 78.8 | 88 |
| 72_106 | 89.2 | 79.1 | 96 | 84.1 | 78.8 | 87.8 |
| 9_72 | 85 | 79.1 | 89 | 84.1 | 78.8 | 87.8 |
| 18_72 | 87.4 | 80.6 | 92 | 84.1 | 78.8 | 87.8 |
| 6_106 | 89.8 | 79.1 | 97 | 83.1 | 78.8 | 86 |
| 10_106 | 88 | 76.1 | 96 | 83.1 | 78.8 | 86 |
| 11_106 | 89.2 | 77.6 | 97 | 83.1 | 78.8 | 86 |
| 42_106 | 89.2 | 77.6 | 97 | 83.1 | 78.8 | 86 |
| 57_106 | 89.2 | 76.1 | 98 | 83.1 | 78.8 | 86 |
| 69_106 | 89.2 | 77.6 | 97 | 83.1 | 78.8 | 86 |
| 76_106 | 89.2 | 77.6 | 97 | 83.1 | 78.8 | 86 |
| 3_56 | 91.6 | 85.1 | 96 | 83.1 | 78.8 | 86 |
| 5_67 | 87.4 | 82.1 | 91 | 83.1 | 78.8 | 86 |
| 6_121 | 86.8 | 76.1 | 94 | 83.1 | 78.8 | 86 |
| 46_110 | 83.8 | 77.6 | 88 | 83.1 | 78.8 | 86 |
| 9_28 | 86.2 | 86.6 | 86 | 83.1 | 78.8 | 86 |
| 9_64 | 82.6 | 74.6 | 88 | 83.1 | 78.8 | 86 |
| 9_76 | 83.8 | 77.6 | 88 | 83.1 | 78.8 | 86 |
| 9_79 | 85.6 | 79.1 | 90 | 83.1 | 78.8 | 86 |
| 9_82 | 84.4 | 79.1 | 88 | 83.1 | 78.8 | 86 |
| 9_95 | 86.8 | 80.6 | 91 | 83.1 | 78.8 | 86 |
| 9_101 | 85.6 | 83.6 | 87 | 83.1 | 78.8 | 86 |
| 10_11 | 85.6 | 74.6 | 93 | 83.1 | 78.8 | 86 |
| 10_111 | 82 | 68.7 | 91 | 83.1 | 78.8 | 86 |
| 10_40 | 85.6 | 74.6 | 93 | 83.1 | 78.8 | 86 |
| 11_59 | 80.8 | 73.1 | 86 | 83.1 | 78.8 | 86 |
| 11_68 | 79 | 71.6 | 84 | 83.1 | 78.8 | 86 |
| 11_117 | 80.2 | 70.1 | 87 | 83.1 | 78.8 | 86 |
| 11_74 | 81.4 | 74.6 | 86 | 83.1 | 78.8 | 86 |
| 11_90 | 79.6 | 73.1 | 84 | 83.1 | 78.8 | 86 |
| 13_55 | 90.4 | 83.6 | 95 | 83.1 | 78.8 | 86 |
| 16_44 | 82.6 | 76.1 | 87 | 83.1 | 78.8 | 86 |
| 16_65 | 82.6 | 80.6 | 84 | 83.1 | 78.8 | 86 |

TABLE 6-continued

| | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 16_66 | 80.8 | 73.1 | 86 | 83.1 | 78.8 | 86 |
| 16_71 | 83.8 | 77.6 | 88 | 83.1 | 78.8 | 86 |
| 17_52 | 84.4 | 71.6 | 93 | 83.1 | 78.8 | 86 |
| 17_98 | 84.3 | 68.2 | 95 | 83.1 | 78.8 | 86 |
| 21_76 | 79 | 73.1 | 83 | 83.1 | 78.8 | 86 |
| 22_31 | 80.2 | 68.7 | 88 | 83.1 | 78.8 | 86 |
| 22_43 | 86.2 | 76.1 | 93 | 83.1 | 78.8 | 86 |
| 22_90 | 79.6 | 70.1 | 86 | 83.1 | 78.8 | 86 |
| 22_91 | 77.8 | 67.2 | 85 | 83.1 | 78.8 | 86 |
| 26_67 | 83.2 | 74.6 | 89 | 83.1 | 78.8 | 86 |
| 28_34 | 88.6 | 79.1 | 95 | 83.1 | 78.8 | 86 |
| 28_52 | 87.4 | 80.6 | 92 | 83.1 | 78.8 | 86 |
| 29_111 | 80.2 | 65.7 | 90 | 83.1 | 78.8 | 86 |
| 29_112 | 83.8 | 73.1 | 91 | 83.1 | 78.8 | 86 |
| 29_45 | 85 | 79.1 | 89 | 83.1 | 78.8 | 86 |
| 29_46 | 81.4 | 73.1 | 87 | 83.1 | 78.8 | 86 |
| 31_40 | 82 | 67.2 | 92 | 83.1 | 78.8 | 86 |
| 31_46 | 77.8 | 65.7 | 86 | 83.1 | 78.8 | 86 |
| 32_66 | 82.6 | 71.6 | 90 | 83.1 | 78.8 | 86 |
| 32_98 | 86.1 | 80.3 | 90 | 83.1 | 78.8 | 86 |
| 34_66 | 83.2 | 74.6 | 89 | 83.1 | 78.8 | 86 |
| 35_116 | 77.2 | 59.7 | 89 | 83.1 | 78.8 | 86 |
| 39_66 | 78.4 | 64.2 | 88 | 83.1 | 78.8 | 86 |
| 42_71 | 81.4 | 65.7 | 92 | 83.1 | 78.8 | 86 |
| 42_81 | 84.3 | 72.7 | 92 | 83.1 | 78.8 | 86 |
| 44_83 | 76.6 | 61.2 | 87 | 83.1 | 78.8 | 86 |
| 44_93 | 77.8 | 67.2 | 85 | 83.1 | 78.8 | 86 |
| 46_120 | 73.7 | 59.7 | 83 | 83.1 | 78.8 | 86 |
| 51_65 | 82 | 74.6 | 87 | 83.1 | 78.8 | 86 |
| 51_66 | 79.6 | 64.2 | 90 | 83.1 | 78.8 | 86 |
| 51_94 | 80.2 | 67.2 | 89 | 83.1 | 78.8 | 86 |
| 54_56 | 85.6 | 83.6 | 87 | 83.1 | 78.8 | 86 |
| 55_75 | 77.8 | 62.7 | 88 | 83.1 | 78.8 | 86 |
| 55_94 | 75.4 | 59.7 | 86 | 83.1 | 78.8 | 86 |
| 55_98 | 73.5 | 56.1 | 85 | 83.1 | 78.8 | 86 |
| 58_82 | 77.2 | 59.7 | 89 | 83.1 | 78.8 | 86 |
| 58_93 | 74.9 | 58.2 | 86 | 83.1 | 78.8 | 86 |
| 62_81 | 70.5 | 57.6 | 79 | 83.1 | 78.8 | 86 |
| 64_67 | 82.6 | 73.1 | 89 | 83.1 | 78.8 | 86 |
| 66_96 | 77.2 | 61.2 | 88 | 83.1 | 78.8 | 86 |
| 67_98 | 76.5 | 60.6 | 87 | 83.1 | 78.8 | 86 |
| 17_106 | 89.8 | 79.1 | 97 | 81.9 | 78.8 | 84 |
| 70_106 | 88.6 | 74.6 | 98 | 81.9 | 78.8 | 84 |
| 64_109 | 86.2 | 80.6 | 90 | 81.9 | 78.8 | 84 |
| 39_110 | 87.4 | 83.6 | 90 | 81.9 | 78.8 | 84 |
| 9_31 | 83.8 | 76.1 | 89 | 81.9 | 78.8 | 84 |
| 9_81 | 85.5 | 80.3 | 89 | 81.9 | 78.8 | 84 |
| 10_31 | 85.6 | 79.1 | 90 | 81.9 | 78.8 | 84 |
| 10_63 | 83.8 | 79.1 | 87 | 81.9 | 78.8 | 84 |
| 10_114 | 87.4 | 77.6 | 94 | 81.9 | 78.8 | 84 |
| 10_67 | 84.4 | 76.1 | 90 | 81.9 | 78.8 | 84 |
| 10_88 | 88.6 | 79.1 | 95 | 81.9 | 78.8 | 84 |
| 11_36 | 79.6 | 70.1 | 86 | 81.9 | 78.8 | 84 |
| 11_57 | 79 | 68.7 | 86 | 81.9 | 78.8 | 84 |
| 11_58 | 80.8 | 71.6 | 87 | 81.9 | 78.8 | 84 |
| 11_82 | 80.8 | 68.7 | 89 | 81.9 | 78.8 | 84 |
| 11_89 | 80.2 | 70.1 | 87 | 81.9 | 78.8 | 84 |
| 11_91 | 79.6 | 68.7 | 87 | 81.9 | 78.8 | 84 |
| 12_22 | 90.4 | 84.8 | 94 | 81.9 | 78.8 | 84 |
| 16_22 | 82 | 76.1 | 86 | 81.9 | 78.8 | 84 |
| 16_96 | 80.8 | 73.1 | 86 | 81.9 | 78.8 | 84 |
| 17_75 | 83.8 | 67.2 | 95 | 81.9 | 78.8 | 84 |
| 17_100 | 83.2 | 71.6 | 91 | 81.9 | 78.8 | 84 |
| 22_54 | 84.4 | 77.6 | 89 | 81.9 | 78.8 | 84 |
| 27_29 | 83.8 | 74.6 | 90 | 81.9 | 78.8 | 84 |
| 28_66 | 83.2 | 76.1 | 88 | 81.9 | 78.8 | 84 |
| 28_70 | 83.8 | 74.6 | 90 | 81.9 | 78.8 | 84 |
| 28_120 | 85 | 76.1 | 91 | 81.9 | 78.8 | 84 |
| 29_34 | 81.4 | 74.6 | 86 | 81.9 | 78.8 | 84 |
| 31_32 | 86.2 | 79.1 | 91 | 81.9 | 78.8 | 84 |
| 31_66 | 76 | 64.2 | 84 | 81.9 | 78.8 | 84 |
| 31_85 | 77.2 | 67.2 | 84 | 81.9 | 78.8 | 84 |
| 31_87 | 79 | 71.6 | 84 | 81.9 | 78.8 | 84 |
| 31_94 | 79 | 65.7 | 88 | 81.9 | 78.8 | 84 |
| 31_96 | 80.2 | 71.6 | 86 | 81.9 | 78.8 | 84 |

TABLE 6-continued

| SEQ ID NO: | Training cohort | | | Validation cohort | | |
| --- | --- | --- | --- | --- | --- | --- |
| | Accuracy (%) | Sensitivity (%) | Specificity (%) | Accuracy (%) | Sensitivity (%) | Specificity (%) |
| 34_82 | 79 | 74.6 | 82 | 81.9 | 78.8 | 84 |
| 44_99 | 76 | 58.2 | 88 | 81.9 | 78.8 | 84 |
| 44_103 | 81.4 | 64.2 | 93 | 81.9 | 78.8 | 84 |
| 45_46 | 77.2 | 67.2 | 84 | 81.9 | 78.8 | 84 |
| 46_82 | 73.7 | 61.2 | 82 | 81.9 | 78.8 | 84 |
| 47_51 | 80.2 | 67.2 | 89 | 81.9 | 78.8 | 84 |
| 47_120 | 76.6 | 68.7 | 82 | 81.9 | 78.8 | 84 |
| 51_71 | 82.6 | 73.1 | 89 | 81.9 | 78.8 | 84 |
| 55_117 | 78.4 | 59.7 | 91 | 81.9 | 78.8 | 84 |
| 55_99 | 77.8 | 65.7 | 86 | 81.9 | 78.8 | 84 |
| 58_75 | 76 | 64.2 | 84 | 81.9 | 78.8 | 84 |
| 58_94 | 76.6 | 58.2 | 89 | 81.9 | 78.8 | 84 |
| 83_114 | 82.6 | 65.7 | 94 | 81.9 | 78.8 | 84 |
| 94_114 | 78.4 | 64.2 | 88 | 81.9 | 78.8 | 84 |
| 67_118 | 73.7 | 52.2 | 88 | 81.9 | 78.8 | 84 |
| 67_121 | 75.4 | 64.2 | 83 | 81.9 | 78.8 | 84 |
| 78_119 | 73.1 | 56.7 | 84 | 81.9 | 78.8 | 84 |
| 81_98 | 74.5 | 60 | 84 | 81.9 | 78.8 | 84 |
| 93_98 | 74.1 | 56.1 | 86 | 81.9 | 78.8 | 84 |
| 78_106 | 89.2 | 77.6 | 97 | 80.7 | 78.8 | 82 |
| 100_106 | 89.2 | 80.6 | 95 | 80.7 | 78.8 | 82 |
| 10_109 | 86.2 | 77.6 | 92 | 80.7 | 78.8 | 82 |
| 74_109 | 89.2 | 82.1 | 94 | 80.7 | 78.8 | 82 |
| 102_109 | 84.4 | 73.1 | 92 | 80.7 | 78.8 | 82 |
| 79_110 | 86.8 | 76.1 | 94 | 80.7 | 78.8 | 82 |
| 96_110 | 86.2 | 85.1 | 87 | 80.7 | 78.8 | 82 |
| 9_69 | 82.6 | 80.6 | 84 | 80.7 | 78.8 | 82 |
| 9_84 | 82 | 77.6 | 85 | 80.7 | 78.8 | 82 |
| 9_93 | 82.6 | 74.6 | 88 | 80.7 | 78.8 | 82 |
| 10_78 | 85.6 | 77.6 | 91 | 80.7 | 78.8 | 82 |
| 10_93 | 83.8 | 77.6 | 88 | 80.7 | 78.8 | 82 |
| 10_103 | 85 | 77.6 | 90 | 80.7 | 78.8 | 82 |
| 11_42 | 83.2 | 76.1 | 88 | 80.7 | 78.8 | 82 |
| 11_95 | 78.4 | 68.7 | 85 | 80.7 | 78.8 | 82 |
| 11_100 | 78.4 | 68.7 | 85 | 80.7 | 78.8 | 82 |
| 24_78 | 79 | 64.2 | 89 | 80.7 | 78.8 | 82 |
| 25_28 | 82 | 74.6 | 87 | 80.7 | 78.8 | 82 |
| 25_63 | 83.8 | 76.1 | 89 | 80.7 | 78.8 | 82 |
| 28_42 | 82 | 70.1 | 90 | 80.7 | 78.8 | 82 |
| 29_56 | 80.2 | 70.1 | 87 | 80.7 | 78.8 | 82 |
| 31_111 | 81.4 | 65.7 | 92 | 80.7 | 78.8 | 82 |
| 32_79 | 81.4 | 73.1 | 87 | 80.7 | 78.8 | 82 |
| 92_111 | 77.2 | 62.7 | 87 | 80.7 | 78.8 | 82 |
| 39_100 | 74.9 | 61.2 | 84 | 80.7 | 78.8 | 82 |
| 42_57 | 79 | 58.2 | 93 | 80.7 | 78.8 | 82 |
| 42_121 | 81.4 | 70.1 | 89 | 80.7 | 78.8 | 82 |
| 44_100 | 76 | 61.2 | 86 | 80.7 | 78.8 | 82 |
| 100_113 | 84.4 | 74.6 | 91 | 80.7 | 78.8 | 82 |
| 55_118 | 82 | 67.2 | 92 | 80.7 | 78.8 | 82 |
| 55_81 | 76.5 | 54.5 | 91 | 80.7 | 78.8 | 82 |
| 55_87 | 77.2 | 65.7 | 85 | 80.7 | 78.8 | 82 |
| 62_93 | 77.2 | 65.7 | 85 | 80.7 | 78.8 | 82 |
| 78_114 | 77.2 | 65.7 | 85 | 80.7 | 78.8 | 82 |
| 70_96 | 74.3 | 62.7 | 82 | 80.7 | 78.8 | 82 |
| 70_103 | 80.2 | 65.7 | 90 | 80.7 | 78.8 | 82 |
| 78_80 | 74.9 | 59.7 | 85 | 80.7 | 78.8 | 82 |
| 46_72 | 79 | 71.6 | 84 | 80.5 | 78.8 | 81.6 |
| 101_109 | 86.8 | 79.1 | 92 | 79.5 | 78.8 | 80 |
| 10_95 | 82.6 | 74.6 | 88 | 79.5 | 78.8 | 80 |
| 16_78 | 82 | 76.1 | 86 | 79.5 | 78.8 | 80 |
| 21_29 | 82 | 73.1 | 88 | 79.5 | 78.8 | 80 |
| 21_95 | 81.4 | 67.2 | 91 | 79.5 | 78.8 | 80 |
| 27_45 | 83.2 | 80.6 | 85 | 79.5 | 78.8 | 80 |
| 28_45 | 89.2 | 86.6 | 91 | 79.5 | 78.8 | 80 |
| 31_114 | 81.4 | 68.7 | 90 | 79.5 | 78.8 | 80 |
| 31_80 | 79.6 | 62.7 | 91 | 79.5 | 78.8 | 80 |
| 31_88 | 79.6 | 71.6 | 85 | 79.5 | 78.8 | 80 |
| 31_97 | 82 | 73.1 | 88 | 79.5 | 78.8 | 80 |
| 42_100 | 77.8 | 56.7 | 92 | 79.5 | 78.8 | 80 |
| 45_79 | 78.4 | 67.2 | 86 | 79.5 | 78.8 | 80 |
| 46_121 | 75.4 | 61.2 | 85 | 79.5 | 78.8 | 80 |
| 46_100 | 74.9 | 64.2 | 82 | 79.5 | 78.8 | 80 |
| 55_100 | 76.6 | 59.7 | 88 | 79.5 | 78.8 | 80 |
| 56_98 | 74.7 | 60.6 | 84 | 79.5 | 78.8 | 80 |
| 58_78 | 76 | 62.7 | 85 | 79.5 | 78.8 | 80 |

TABLE 6-continued

| SEQ ID NO: | Training cohort | | | Validation cohort | | |
| --- | --- | --- | --- | --- | --- | --- |
| | Accuracy (%) | Sensitivity (%) | Specificity (%) | Accuracy (%) | Sensitivity (%) | Specificity (%) |
| 65_79 | 79 | 62.7 | 90 | 79.5 | 78.8 | 80 |
| 65_104 | 77.8 | 67.2 | 85 | 79.5 | 78.8 | 80 |
| 67_99 | 74.9 | 58.2 | 86 | 79.5 | 78.8 | 80 |
| 78_81 | 72.3 | 59.1 | 81 | 79.5 | 78.8 | 80 |
| 78_90 | 74.3 | 61.2 | 83 | 79.5 | 78.8 | 80 |
| 79_96 | 76 | 62.7 | 85 | 79.5 | 78.8 | 80 |
| 80_121 | 74.9 | 62.7 | 83 | 79.5 | 78.8 | 80 |
| 94_99 | 71.9 | 53.7 | 84 | 79.5 | 78.8 | 80 |
| 3_92 | 92.8 | 89.6 | 95 | 78.3 | 78.8 | 78 |
| 6_109 | 86.2 | 77.6 | 92 | 78.3 | 78.8 | 78 |
| 52_110 | 85.6 | 85.1 | 86 | 78.3 | 78.8 | 78 |
| 10_42 | 84.4 | 76.1 | 90 | 78.3 | 78.8 | 78 |
| 29_67 | 82.6 | 73.1 | 89 | 78.3 | 78.8 | 78 |
| 31_83 | 78.4 | 64.2 | 88 | 78.3 | 78.8 | 78 |
| 46_52 | 79 | 70.1 | 85 | 78.3 | 78.8 | 78 |
| 67_79 | 74.9 | 56.7 | 87 | 78.3 | 78.8 | 78 |
| 67_93 | 73.1 | 53.7 | 86 | 78.3 | 78.8 | 78 |
| 67_103 | 76 | 58.2 | 88 | 78.3 | 78.8 | 78 |
| 70_92 | 75.4 | 62.7 | 84 | 78.3 | 78.8 | 78 |
| 59_109 | 83.8 | 74.6 | 90 | 77.1 | 78.8 | 76 |
| 70_109 | 83.2 | 74.6 | 89 | 77.1 | 78.8 | 76 |
| 76_109 | 82.6 | 73.1 | 89 | 77.1 | 78.8 | 76 |
| 95_109 | 86.2 | 79.1 | 91 | 77.1 | 78.8 | 76 |
| 31_42 | 81.4 | 67.2 | 91 | 77.1 | 78.8 | 76 |
| 31_55 | 83.2 | 70.1 | 92 | 77.1 | 78.8 | 76 |
| 34_55 | 80.2 | 73.1 | 85 | 77.1 | 78.8 | 76 |
| 42_78 | 76 | 59.7 | 87 | 77.1 | 78.8 | 76 |
| 67_85 | 71.3 | 56.7 | 81 | 77.1 | 78.8 | 76 |
| 78_85 | 72.5 | 55.2 | 84 | 77.1 | 78.8 | 76 |
| 79_92 | 72.5 | 52.2 | 86 | 77.1 | 78.8 | 76 |
| 94_103 | 73.7 | 50.7 | 89 | 77.1 | 78.8 | 76 |
| 99_100 | 71.9 | 52.2 | 85 | 77.1 | 78.8 | 76 |
| 36_109 | 83.8 | 74.6 | 90 | 75.9 | 78.8 | 74 |
| 91_109 | 84.4 | 76.1 | 90 | 75.9 | 78.8 | 74 |
| 46_78 | 76 | 62.7 | 85 | 75.9 | 78.8 | 74 |
| 52_67 | 76 | 65.7 | 83 | 75.9 | 78.8 | 74 |
| 63_78 | 78.4 | 74.6 | 81 | 75.9 | 78.8 | 74 |
| 67_70 | 77.8 | 61.2 | 89 | 75.9 | 78.8 | 74 |
| 69_79 | 80.2 | 71.6 | 86 | 75.9 | 78.8 | 74 |
| 31_104 | 77.8 | 65.7 | 86 | 74.7 | 78.8 | 72 |
| 63_79 | 79 | 68.7 | 86 | 74.7 | 78.8 | 72 |
| 67_92 | 73.1 | 56.7 | 84 | 74.7 | 78.8 | 72 |
| 75_78 | 76.6 | 65.7 | 84 | 74.7 | 78.8 | 72 |
| 69_78 | 74.9 | 61.2 | 84 | 73.5 | 78.8 | 70 |
| 79_100 | 74.3 | 59.7 | 84 | 73.5 | 78.8 | 70 |
| 13_23 | 91 | 82.1 | 97 | 90.2 | 78.1 | 98 |
| 23_108 | 89.2 | 80.6 | 95 | 87.8 | 78.1 | 94 |
| 8_23 | 88.6 | 79.1 | 95 | 87.8 | 78.1 | 94 |
| 41_50 | 81.4 | 67.2 | 91 | 86.6 | 78.1 | 92 |
| 50_51 | 79 | 64.2 | 89 | 85.4 | 78.1 | 90 |
| 50_87 | 78.4 | 62.7 | 89 | 85.4 | 78.1 | 90 |
| 37_50 | 82.6 | 71.6 | 90 | 84.1 | 78.1 | 88 |
| 9_23 | 87.4 | 82.1 | 91 | 82.9 | 78.1 | 86 |
| 50_68 | 79.6 | 64.2 | 90 | 82.9 | 78.1 | 86 |
| 23_106 | 89.2 | 76.1 | 98 | 81.7 | 78.1 | 84 |
| 46_50 | 76.6 | 67.2 | 83 | 81.7 | 78.1 | 84 |
| 50_75 | 76 | 64.2 | 84 | 81.7 | 78.1 | 84 |
| 50_111 | 79 | 61.2 | 91 | 80.5 | 78.1 | 82 |
| 31_50 | 82.6 | 70.1 | 91 | 78 | 78.1 | 78 |
| 50_78 | 73.7 | 62.7 | 81 | 74.4 | 78.1 | 72 |
| 77_110 | 84.4 | 76.1 | 90 | 88.9 | 77.4 | 96 |
| 18_77 | 83.2 | 74.6 | 89 | 86.4 | 77.4 | 92 |
| 77_115 | 79 | 67.2 | 87 | 86.4 | 77.4 | 92 |
| 16_77 | 85.6 | 82.1 | 88 | 85.2 | 77.4 | 90 |
| 29_77 | 83.2 | 76.1 | 88 | 85.2 | 77.4 | 90 |
| 58_77 | 74.3 | 56.7 | 86 | 85.2 | 77.4 | 90 |
| 66_77 | 76.6 | 59.7 | 88 | 85.2 | 77.4 | 90 |
| 77_104 | 79.6 | 62.7 | 91 | 84 | 77.4 | 88 |
| 11_77 | 80.2 | 71.6 | 86 | 82.7 | 77.4 | 86 |

Example 3

<Selection of Gene Markers Using all Samples and Method for Evaluating Pancreatic Cancer Discriminant Performance of Acquired Gene Markers>

In this Example, the samples of the training cohort and the validation cohort used in Examples 1 and 2 were integrated, and selection of a gene marker and evaluation of its pancreatic cancer discriminant performance were conducted using all of the samples.

Specifically, the miRNA expression levels in the sera of the 100 pancreatic cancer patients and the 150 healthy subjects obtained in the preceding Reference Examples were normalized by quantile normalization. In order to acquire diagnosis markers with higher reliability, only genes having a gene expression level of $2^6$ or higher in 50% or more of the samples in either of the pancreatic cancer patient group or the healthy subject group were selected in the gene marker selection. In order to further acquire statistical significance for discriminating a pancreatic cancer patient group from a healthy subject group, the P value obtained by two-tailed-test assuming equal variance as to each gene expression level was corrected by the Bonferroni method, and genes that satisfied p<0.01 were selected as gene markers for use in explanatory variables of a discriminant and described in Table 7. In this way, hsa-miR-4417, hsa-miR-4707-5p, hsa-miR-7847-3p, hsa-miR-2861, hsa-miR-4513, hsa-miR-7111-5p, hsa-miR-6777-5p, hsa-miR-7113-3p, hsa-miR-4648, hsa-miR-3184-5p, hsa-miR-4271, hsa-miR-6791-5p, hsa-miR-642a-3p, hsa-miR-7108-5p, hsa-miR-128-1-5p, hsa-miR-5196-5p, hsa-miR-3178, hsa-miR-3656, hsa-miR-92a-2-5p, hsa-miR-6769b-5p, hsa-miR-4689, hsa-miR-6076, hsa-miR-92b-5p, hsa-miR-6774-5p, hsa-miR-486-3p, hsa-miR-6806-5p, hsa-miR-6842-5p, hsa-miR-6716-5p, hsa-miR-557, hsa-miR-4673, hsa-miR-4674, hsa-miR-4442, hsa-miR-1915-3p, hsa-miR-4687-3p, and hsa-miR-92b-3p genes, and the nucleotide sequences of SEQ ID NOs: 349 to 383 related thereto were found in addition to the genes described in Table 2. As with the nucleotide sequences of SEQ ID NOs: 1 to 122, the results obtained about the polynucleotides shown in SEQ ID NOs: 349 to 383 also showed that the measurement values were significantly lower (−) or higher (+) in the pancreatic cancer patient group than in the healthy subject group (Table 7). These results were able to be validated in the validation cohort. Thus, the presence or absence of pancreatic cancer in the newly obtained samples can be determined by the methods described in Examples 1 and 2 by using, alone or in combination, the gene expression level measurement values described in Table 7.

TABLE 7

| SEQ ID NO: | Name | p. value | Expression level in pancreatic cancer patient relative to healthy subject |
|---|---|---|---|
| 105 | hsa-miR-125a-3p | 7.05E−72 | − |
| 1 | hsa-miR-6893-5p | 4.14E−64 | − |
| 2 | hsa-miR-6075 | 1.06E−49 | + |
| 4 | hsa-miR-4294 | 5.56E−43 | − |
| 107 | hsa-miR-1469 | 1.06E−42 | + |
| 106 | hsa-miR-204-3p | 6.17E−42 | − |
| 108 | hsa-miR-575 | 1.26E−39 | − |
| 5 | hsa-miR-6729-5p | 1.24E−38 | + |
| 6 | hsa-miR-4476 | 2.46E−36 | − |
| 3 | hsa-miR-6820-5p | 1.80E−34 | − |
| 8 | hsa-miR-6765-3p | 3.08E−32 | − |
| 109 | hsa-miR-150-3p | 7.57E−31 | − |
| 7 | hsa-miR-6836-3p | 1.12E−29 | + |
| 18 | hsa-miR-4792 | 4.50E−29 | + |
| 9 | hsa-miR-6799-5p | 3.91E−28 | − |
| 10 | hsa-miR-4530 | 6.27E−27 | − |
| 13 | hsa-miR-615-5p | 2.79E−26 | − |
| 12 | hsa-miR-4454 | 4.13E−26 | − |
| 17 | hsa-miR-4450 | 6.27E−26 | − |
| 11 | hsa-miR-7641 | 1.99E−25 | − |
| 110 | hsa-miR-423-5p | 3.69E−25 | − |
| 24 | hsa-miR-6877-5p | 4.17E−25 | − |
| 19 | hsa-miR-665 | 6.54E−25 | + |
| 14 | hsa-miR-8073 | 3.32E−24 | + |
| 35 | hsa-miR-1231 | 4.73E−23 | + |
| 25 | hsa-miR-6880-5p | 4.77E−23 | − |
| 22 | hsa-miR-6789-5p | 1.52E−22 | + |
| 16 | hsa-miR-4634 | 3.85E−22 | + |
| 30 | hsa-miR-5585-3p | 8.16E−22 | + |
| 20 | hsa-miR-7975 | 1.73E−20 | − |
| 33 | hsa-miR-4651 | 3.57E−19 | − |
| 31 | hsa-miR-6085 | 3.92E−19 | − |
| 26 | hsa-miR-7977 | 4.07E−19 | − |
| 29 | hsa-miR-8089 | 2.29E−18 | − |
| 112 | hsa-miR-3188 | 3.55E−18 | + |
| 34 | hsa-miR-4433-3p | 6.97E−18 | + |
| 27 | hsa-miR-4734 | 8.43E−18 | + |
| 111 | hsa-miR-564 | 8.77E−18 | − |
| 46 | hsa-miR-6125 | 4.60E−17 | + |
| 21 | hsa-miR-7109-5p | 4.84E−17 | − |
| 23 | hsa-miR-4497 | 1.63E−16 | − |
| 41 | hsa-miR-619-5p | 2.74E−16 | + |
| 37 | hsa-miR-7114-5p | 2.89E−16 | − |
| 42 | hsa-miR-3622a-5p | 4.11E−16 | − |
| 39 | hsa-miR-8069 | 1.67E−15 | + |
| 58 | hsa-miR-3185 | 2.47E−15 | + |
| 66 | hsa-miR-4723-5p | 2.57E−15 | − |
| 38 | hsa-miR-1238-5p | 2.84E−15 | + |
| 44 | hsa-miR-6741-5p | 3.06E−15 | − |
| 40 | hsa-miR-4732-5p | 4.29E−15 | + |
| 32 | hsa-miR-6845-5p | 1.09E−14 | + |
| 55 | hsa-miR-6724-5p | 1.51E−14 | + |
| 28 | hsa-miR-6821-5p | 2.47E−14 | − |
| 50 | hsa-miR-6875-5p | 7.80E−14 | + |
| 113 | hsa-miR-1246 | 1.34E−13 | + |
| 53 | hsa-miR-4736 | 2.22E−13 | + |
| 47 | hsa-miR-6805-5p | 2.32E−13 | + |
| 36 | hsa-miR-4665-5p | 5.61E−13 | − |
| 114 | hsa-miR-602 | 7.01E−13 | + |
| 45 | hsa-miR-6781-5p | 1.70E−12 | + |
| 15 | hsa-miR-663a | 1.70E−12 | + |
| 57 | hsa-miR-6726-5p | 2.61E−12 | − |
| 67 | hsa-miR-6850-5p | 4.31E−12 | + |
| 56 | hsa-miR-7107-5p | 7.43E−12 | − |
| 52 | hsa-miR-4433b-3p | 7.79E−12 | + |
| 71 | hsa-miR-4486 | 8.29E−12 | + |
| 65 | hsa-miR-6779-5p | 1.76E−11 | − |
| 115 | hsa-miR-1290 | 1.99E−11 | + |
| 51 | hsa-miR-1908-3p | 2.20E−11 | + |
| 70 | hsa-miR-8072 | 2.98E−11 | − |
| 60 | hsa-miR-1273g-3p | 6.69E−11 | + |
| 43 | hsa-miR-1260a | 1.14E−10 | − |
| 79 | hsa-miR-4534 | 2.20E−10 | − |
| 80 | hsa-miR-4449 | 2.54E−10 | + |
| 77 | hsa-miR-6780b-5p | 2.77E−10 | + |
| 49 | hsa-miR-6872-3p | 3.55E−10 | − |
| 119 | hsa-miR-187-5p | 3.74E−10 | − |
| 75 | hsa-miR-7106-5p | 4.23E−10 | − |
| 54 | hsa-miR-5100 | 5.83E−10 | − |
| 83 | hsa-miR-4467 | 6.44E−10 | + |
| 59 | hsa-miR-4638-5p | 9.61E−10 | − |
| 81 | hsa-miR-5195-3p | 1.12E−09 | − |
| 62 | hsa-miR-328-5p | 1.36E−09 | − |
| 68 | hsa-miR-760 | 2.30E−09 | − |
| 78 | hsa-miR-6090 | 2.36E−09 | + |
| 90 | hsa-miR-3162-5p | 3.27E−09 | − |

TABLE 7-continued

| SEQ ID NO: | Name | p. value | Expression level in pancreatic cancer patient relative to healthy subject |
|---|---|---|---|
| 48 | hsa-miR-6132 | 4.46E-09 | - |
| 120 | hsa-miR-1908-5p | 4.47E-09 | + |
| 61 | hsa-miR-6778-5p | 6.12E-09 | + |
| 98 | hsa-miR-6816-Sp | 9.29E-09 | + |
| 94 | hsa-miR-6722-3p | 9.46E-09 | + |
| 82 | hsa-miR-1202 | 1.14E-08 | - |
| 117 | hsa-miR-451a | 2.71E-08 | - |
| 118 | hsa-miR-24-3p | 3.63E-08 | - |
| 74 | hsa-miR-1260b | 6.21E-08 | - |
| 73 | hsa-miR-4656 | 6.81E-08 | + |
| 85 | hsa-miR-4281 | 6.81E-08 | - |
| 99 | hsa-miR-4741 | 9.33E-08 | + |
| 116 | hsa-miR-16-5p | 9.82E-08 | - |
| 121 | hsa-miR-371a-5p | 1.38E-07 | - |
| 93 | hsa-miR-1227-5p | 1.43E-07 | + |
| 63 | hsa-miR-3679-3p | 1.83E-07 | + |
| 72 | hsa-miR-1913 | 3.84E-07 | + |
| 69 | hsa-miR-7704 | 1.35E-06 | - |
| 87 | hsa-miR-4484 | 1.46E-06 | + |
| 89 | hsa-miR-3135b | 1.72E-06 | - |
| 103 | hsa-miR-4665-3p | 3.01E-06 | + |
| 349 | hsa-miR-4417 | 3.10E-06 | + |
| 350 | hsa-miR-4707-5p | 3.58E-06 | + |
| 88 | hsa-miR-6805-3p | 4.95E-06 | + |
| 351 | hsa-miR-7847-3p | 5.06E-06 | - |
| 352 | hsa-miR-2861 | 6.22E-06 | - |
| 104 | hsa-miR-718 | 7.23E-06 | + |
| 353 | hsa-miR-4513 | 7.71E-06 | - |
| 76 | hsa-miR-6889-5p | 1.88E-05 | - |
| 92 | hsa-miR-6721-5p | 2.26E-05 | + |
| 354 | hsa-miR-7111-5p | 2.67E-05 | - |
| 355 | hsa-miR-6777-5p | 3.00E-05 | - |
| 91 | hsa-miR-6768-5p | 3.39E-05 | - |
| 356 | hsa-miR-7113-3p | 3.47E-05 | + |
| 97 | hsa-miR-6727-5p | 3.73E-05 | - |
| 357 | hsa-miR-4648 | 4.03E-05 | + |
| 100 | hsa-miR-4508 | 4.48E-05 | + |
| 358 | hsa-miR-3184-5p | 4.67E-05 | + |
| 359 | hsa-miR-4271 | 4.87E-05 | - |
| 96 | hsa-miR-4746-3p | 4.91E-05 | + |
| 360 | hsa-miR-6791-5p | 7.71E-05 | + |
| 361 | hsa-miR-642a-3p | 2.26E-04 | - |
| 362 | hsa-miR-7108-5p | 2.56E-04 | + |
| 363 | hsa-miR-128-1-5p | 2.70E-04 | + |
| 364 | hsa-miR-5196-5p | 2.85E-04 | - |
| 365 | hsa-miR-3178 | 6.64E-04 | + |
| 366 | hsa-miR-3656 | 7.51E-04 | + |
| 367 | hsa-miR-92a-2-5p | 1.04E-03 | - |
| 368 | hsa-miR-6769b-5p | 1.06E-03 | - |
| 369 | hsa-miR-4689 | 1.17E-03 | - |
| 370 | hsa-miR-6076 | 1.29E-03 | - |
| 371 | hsa-miR-92b-5p | 1.68E-03 | + |
| 122 | hsa-miR-550a-5p | 1.80E-03 | + |
| 372 | hsa-miR-6774-5p | 1.81E-03 | + |
| 373 | hsa-miR-486-3p | 2.00E-03 | + |
| 374 | hsa-miR-6806-5p | 2.02E-03 | + |
| 64 | hsa-miR-1228-3p | 2.28E-03 | + |
| 375 | hsa-miR-6842-5p | 2.35E-03 | + |
| 102 | hsa-miR-4327 | 2.57E-03 | - |
| 376 | hsa-miR-6716-5p | 2.70E-03 | + |
| 377 | hsa-miR-557 | 2.87E-03 | + |
| 378 | hsa-miR-4673 | 3.26E-03 | + |
| 379 | hsa-miR-4674 | 3.91E-03 | + |
| 95 | hsa-miR-4286 | 4.47E-03 | - |
| 86 | hsa-miR-4505 | 5.22E-03 | - |
| 380 | hsa-miR-4442 | 5.97E-03 | - |
| 381 | hsa-miR-1915-3p | 6.28E-03 | + |
| 382 | hsa-miR-4687-3p | 6.36E-03 | - |
| 383 | hsa-miR-92b-3p | 7.44E-03 | + |

Example 4

<Method for Evaluating Pancreatic Cancer-Specific Discriminant Performance by Combination of Plurality of Gene Markers Using Samples of Validation Cohort>

In this Example, gene expression levels of miRNAs in sera were compared between pancreatic cancer patients and a control group consisting of healthy subjects, colorectal cancer patients, stomach cancer patients, esophageal cancer patients, liver cancer patients, and benign pancreaticobiliary disease patients in the same way as the method described in Example 1 with respect to the training cohort as the sample group described in Reference Example 2 to select an additional gene marker for diagnosis. The additional gene marker for diagnosis (at least one of SEQ ID NOs: 464 to 473 and 492 to 494) thus selected was combined with the gene markers selected in Example 1 to study a method for evaluating pancreatic cancer-specific discriminant performance.

Specifically, first, the miRNA expression levels of the training cohort and the validation cohort obtained in Reference Example 2 mentioned above were combined and normalized by quantile normalization. Next, Fisher's discriminant analysis was conducted as to combinations of 1 to 4 expression level measurement values comprising at least one or more of the expression level measurement values of the newly found polynucleotides consisting of the nucleotide sequences represented by SEQ ID NOs: 1 to 104, 349 to 383,464 to 473, and 492 to 494 among the polynucleotides consisting of the nucleotide sequences represented by SEQ ID NOs: 1 to 122, 349 to 383, 464 to 473, and 492 to 494, and the polynucleotides consisting of the nucleotide sequences represented by SEQ ID NOs: 105 and 108, to construct a discriminant for determining the presence or absence of pancreatic cancer. Next, accuracy, sensitivity, and specificity in the validation cohort were calculated using the discriminant thus prepared, with the pancreatic cancer patient group as a positive sample group and the healthy subject group, the colorectal cancer patient group, the stomach cancer patient group, the esophageal cancer patient group, the liver cancer patient group, and the benign pancreaticobiliary disease patient group as negative sample groups. The discriminant performance of the selected polynucleotides was validated using independent samples.

Most of polynucleotides consisting of the nucleotide sequences represented by these SEQ ID NOs (SEQ ID NOs: 1 to 122, 349 to 383, 464 to 473, and 492 to 494 corresponding to the miRNA markers of Table 1) or complementary sequences thereof mentioned above were able to provide relatively high accuracy, sensitivity, and specificity in the determination of the presence or absence of pancreatic cancer, and furthermore, were able to specifically discriminate pancreatic cancer from the other cancers. For example, among the combinations of multiple polynucleotides selected from the group consisting of polynucleotides consisting of the nucleotide sequences represented by SEQ ID NOs: 2, 4, 6, 7, 9, 10, 25, 28, 30, 31, 38, 48, 82, 103, 105, 108, and 464 or complementary sequences thereof (the cancer type-specific polynucleotide group 1) as polynucleotides capable of specifically binding to target markers, combinations comprising at least one or more polynucleotides preferably selected from the group consisting of polynucleotides consisting of the nucleotide sequences represented by SEQ ID NOs: 2, 4, 7, 10, and 25 or complementary sequences thereof (the cancer type-specific polynucleotide group 2) included in the cancer type-specific polynucleotide group 1 were able to specifically discriminate pancreatic cancer from the other cancers with high accuracy.

The number of the polynucleotides with cancer type specificity in the combination mentioned above can be 1, 2, 3, 4, 5, 6, 7, 8, 9, 10 or more for the combination. The combinations of 4 or more of these polynucleotides were able to exhibit discrimination accuracy of 80% or higher.

The probes used in the measurement were the above-defined nucleic acids capable of specifically binding to each polynucleotide as a target marker.

Specifically, the following results were obtained as the discrimination accuracy of the measurement using the polynucleotide consisting of the nucleotide sequence represented by SEQ ID NO: 2 or a complementary sequence thereof as a target marker.

The measurement using one polynucleotide consisting of the nucleotide sequence represented by SEQ ID NO: 2 or a complementary sequence thereof exhibited accuracy of 91.1% in the training cohort and the highest accuracy of 85.3% in the validation cohort (Table 8). Also, for example, the measurement using the combinations of two polynucleotides comprising at least one polynucleotide consisting of the nucleotide sequence represented by SEQ ID NO: 2 or a complementary sequence thereof exhibited the highest accuracy of 93.0% in the training cohort and the highest accuracy of 91.7% in the validation cohort (Table 9). Furthermore, for example, the measurement using the combinations of three polynucleotides comprising at least one polynucleotide consisting of the nucleotide sequence represented by SEQ ID NO: 2 or a complementary sequence thereof exhibited the highest accuracy of 92.7% in the training cohort and the highest accuracy of 93.6% in the validation cohort (Table 10). Furthermore, for example, the measurement using the combinations of four polynucleotides comprising at least one polynucleotide consisting of the nucleotide sequence represented by SEQ ID NO: 2 or a complementary sequence thereof exhibited the highest accuracy of 93.3% in the training cohort and the highest accuracy of 96.2% in the validation cohort (Table 11).

Specifically, the following results were obtained as the discrimination accuracy of the measurement using the polynucleotide consisting of the nucleotide sequence represented by SEQ ID NO: 4 or a complementary sequence thereof as a target marker.

The measurement using one polynucleotide consisting of the nucleotide sequence represented by SEQ ID NO: 4 or a complementary sequence thereof exhibited accuracy of 77.1% in the training cohort and the highest accuracy of 78.8% in the validation cohort (Table 8). Also, for example, the measurement using the combinations of two polynucleotides comprising at least one polynucleotide consisting of the nucleotide sequence represented by SEQ ID NO: 4 or a complementary sequence thereof exhibited the highest accuracy of 89.8% in the training cohort and the highest accuracy of 88.5% in the validation cohort (Table 9). Furthermore, for example, the measurement using the combinations of three polynucleotides comprising at least one polynucleotide consisting of the nucleotide sequence represented by SEQ ID NO: 4 or a complementary sequence thereof exhibited the highest accuracy of 92.7% in the training cohort and the highest accuracy of 91.7% in the validation cohort (Table 10). Furthermore, for example, the measurement using the combinations of four polynucleotides comprising at least one polynucleotide consisting of the nucleotide sequence represented by SEQ ID NO: 4 or a complementary sequence thereof exhibited the highest accuracy of 92.7% in the training cohort and the highest accuracy of 93.6% in the validation cohort (Table 11).

Specifically, the following results were obtained as the discrimination accuracy of the measurement using the polynucleotide consisting of the nucleotide sequence represented by SEQ ID NO: 7 or a complementary sequence thereof as a target marker.

The measurement using one polynucleotide consisting of the nucleotide sequence represented by SEQ ID NO: 7 or a complementary sequence thereof exhibited accuracy of 86.7% in the training cohort and the highest accuracy of 82.1% in the validation cohort (Table 8). Also, for example, the measurement using the combinations of two polynucleotides comprising at least one polynucleotide consisting of the nucleotide sequence represented by SEQ ID NO: 7 or a complementary sequence thereof exhibited the highest accuracy of 90.2% in the training cohort and the highest accuracy of 89.1% in the validation cohort (Table 9). Furthermore, for example, the measurement using the combinations of three polynucleotides comprising at least one polynucleotide consisting of the nucleotide sequence represented by SEQ ID NO: 7 or a complementary sequence thereof exhibited the highest accuracy of 92.7% in the training cohort and the highest accuracy of 93.6% in the validation cohort (Table 10). Furthermore, for example, the measurement using the combinations of four polynucleotides comprising at least one polynucleotide consisting of the nucleotide sequence represented by SEQ ID NO: 7 or a complementary sequence thereof exhibited the highest accuracy of 93.3% in the training cohort and the highest accuracy of 96.2% in the validation cohort (Table 11).

Specifically, the following results were obtained as the discrimination accuracy of the measurement using the polynucleotide consisting of the nucleotide sequence represented by SEQ ID NO: 10 or a complementary sequence thereof as a target marker.

The measurement using one polynucleotide consisting of the nucleotide sequence represented by SEQ ID NO: 10 or a complementary sequence thereof exhibited accuracy of 77.1% in the training cohort and the highest accuracy of 68.6% in the validation cohort (Table 8). Also, for example, the measurement using the combinations of two polynucleotides comprising at least one polynucleotide consisting of the nucleotide sequence represented by SEQ ID NO: 10 or a complementary sequence thereof exhibited the highest accuracy of 90.8% in the training cohort and the highest accuracy of 89.7% in the validation cohort (Table 9). Furthermore, for example, the measurement using the combinations of three polynucleotides comprising at least one polynucleotide consisting of the nucleotide sequence represented by SEQ ID NO: 10 or a complementary sequence thereof exhibited the highest accuracy of 93.0% in the training cohort and the highest accuracy of 91.7% in the validation cohort (Table 10). Furthermore, for example, the measurement using the combinations of four polynucleotides comprising at least one polynucleotide consisting of the nucleotide sequence represented by SEQ ID NO: 10 or a complementary sequence thereof exhibited the highest accuracy of 93.7% in the training cohort and the highest accuracy of 93.6% in the validation cohort (Table 11).

Specifically, the following results were obtained as the discrimination accuracy of the measurement using the polynucleotide consisting of the nucleotide sequence represented by SEQ ID NO: 25 or a complementary sequence thereof as a target marker.

The measurement using one polynucleotide consisting of the nucleotide sequence represented by SEQ ID NO: 25 or a complementary sequence thereof exhibited accuracy of 82.2% in the training cohort and the highest accuracy of 75.6% in the validation cohort (Table 8). Also, for example, the measurement using the combinations of two polynucleotides comprising at least one polynucleotide consisting of the nucleotide sequence represented by SEQ ID NO: 25 or a complementary sequence thereof exhibited the highest accuracy of 90.8% in the training cohort and the highest accuracy of 87.8% in the validation cohort (Table 9). Furthermore, for example, the measurement using the combinations of three polynucleotides comprising at least one polynucleotide consisting of the nucleotide sequence represented by SEQ ID NO: 25 or a complementary sequence thereof exhibited the highest accuracy of 91.1% in the training cohort and the highest accuracy of 91.0% in the validation cohort (Table 10). Furthermore, for example, the measurement using the combinations of four polynucleotides comprising at least one polynucleotide consisting of the nucleotide sequence represented by SEQ ID NO: 25 or a complementary sequence thereof exhibited the highest accuracy of 92.7% in the training cohort and the highest accuracy of 93.6% in the validation cohort (Table 11).

Figure 4:
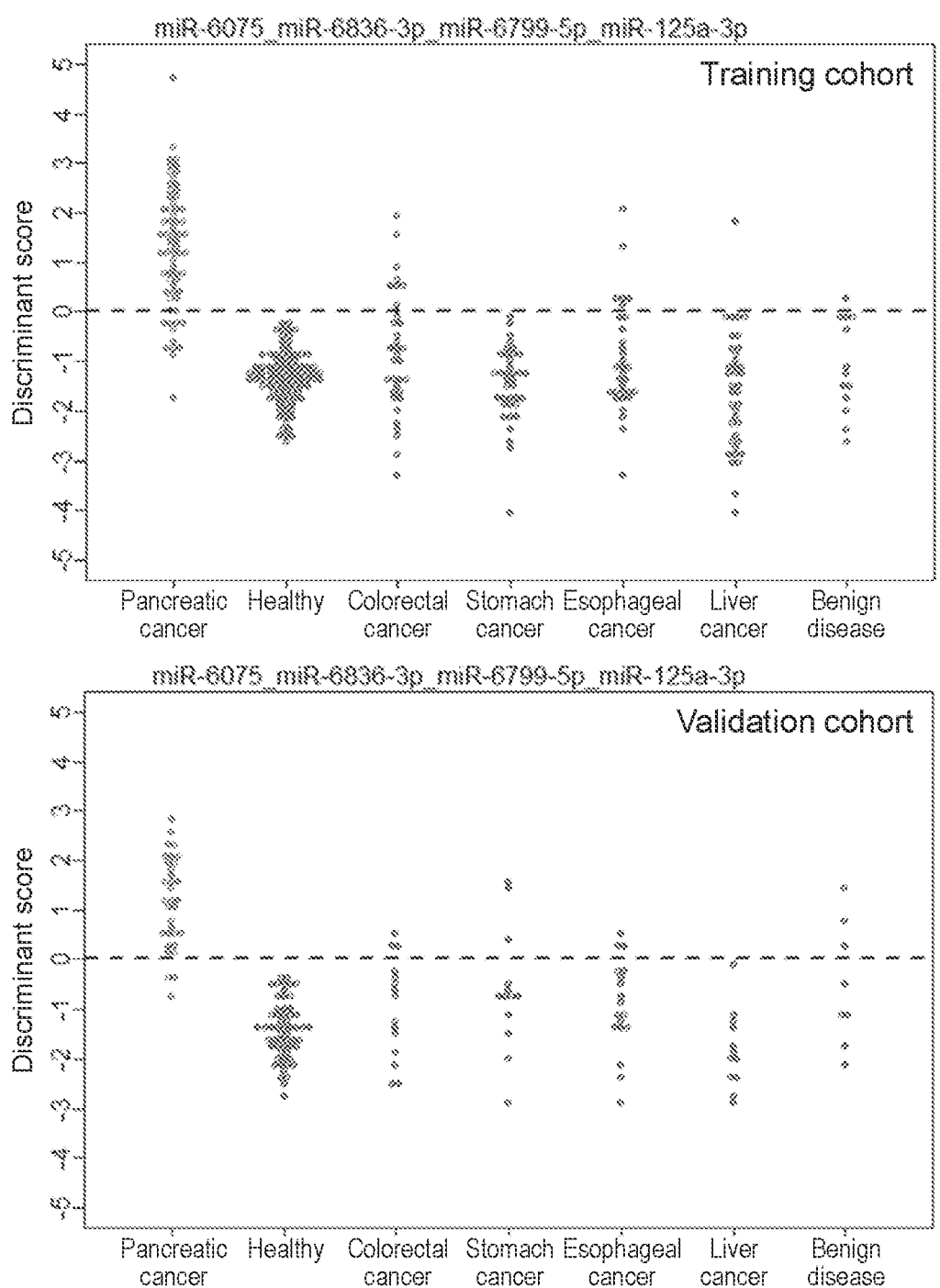
FIG. 4 Upper diagram: a discriminant (1.64×hsa-miR-6075+1.02×hsa-miR-6836-3p −0.35×hsa-miR-6799-5p−0.06×hsa-miR-125a-3p−20.67) was prepared by use of Fisher's discriminant analysis from the expression level measurement values of hsa-miR-6075 (SEQ ID NO: 2), hsa-miR-6836-3p (SEQ ID NO: 7), hsa-miR-6799-5p (SEQ ID NO: 9), and hsa-miR-125a-3p (SEQ ID NO: 105) in 67 pancreatic cancer patients, 93 healthy subjects, 35 colorectal cancer patients, 37 stomach cancer patients, 32 esophageal cancer patients, 38 liver cancer patients, and 13 benign pancreaticobiliary disease patients selected as a training cohort, and discriminant scores obtained from the discriminant were plotted on the ordinate against the sample groups on the abscissa. The dotted line in the diagram depicts a discriminant boundary that offered a discriminant score of 0 and discriminated between the groups. Lower diagram: discriminant scores obtained from the discriminant prepared from the training cohort as to the expression level measurement values of hsa-miR-6075 (SEQ ID NO: 2), hsa-miR-6799-5p (SEQ ID NO: 9), hsa-miR-125a-3p (SEQ ID NO: 105), and hsa-miR-6836-3p (SEQ ID NO: 7) in 33 pancreatic cancer patients, 57 healthy subjects, 15 colorectal cancer patients, 13 stomach cancer patients, 18 esophageal cancer patients, 12 liver cancer patients, and 8 benign pancreaticobiliary disease patients selected as a validation cohort were plotted on the ordinate against the sample groups on the abscissa. The dotted line in the diagram depicts the discriminant boundary that offered a discriminant score of 0 and discriminated between both of the groups.

The expression level measurement values of the nucleotide sequences represented by SEQ ID NOs: 2, 7, 9, and 105 were compared among 67 pancreatic cancer patients, 93 healthy subjects, 35 colorectal cancer patients, 37 stomach cancer patients, 32 esophageal cancer patients, 38 liver cancer patients, and 13 benign pancreaticobiliary disease patients in the training cohort. As a result, a scatter diagram that significantly separated the discriminant score of the pancreatic cancer patient group from the other discriminant scores was obtained in the training cohort (see the upper diagram of FIG. 4). These results were also reproducible in the validation cohort (see the lower diagram of FIG. 4).

Tables 8, 9, 10, and 11 mentioned above are as follows.

TABLE 8

| | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 2 | 91.1 | 83.6 | 93.1 | 85.3 | 69.7 | 89.4 |
| 4 | 77.1 | 77.6 | 77 | 78.8 | 81.8 | 78 |
| 6 | 81 | 76.1 | 82.3 | 75 | 60.6 | 78.9 |
| 7 | 86.7 | 89.6 | 85.9 | 82.1 | 87.9 | 80.5 |
| 9 | 78.4 | 85.1 | 76.6 | 75 | 90.9 | 70.7 |
| 10 | 77.1 | 82.1 | 75.8 | 68.6 | 75.8 | 66.7 |
| 25 | 82.2 | 86.6 | 81 | 75.6 | 72.7 | 76.4 |
| 28 | 68.9 | 74.6 | 67.3 | 67.9 | 69.7 | 67.5 |
| 30 | 70.2 | 70.1 | 70.2 | 76.3 | 72.7 | 77.2 |
| 31 | 75.6 | 68.7 | 77.4 | 74.4 | 69.7 | 75.6 |
| 38 | 77.1 | 67.2 | 79.8 | 73.7 | 63.6 | 76.4 |
| 48 | 74 | 77.6 | 73 | 74.4 | 66.7 | 76.4 |
| 82 | 57.5 | 59.7 | 56.9 | 62.2 | 63.6 | 61.8 |
| 103 | 58.1 | 49.3 | 60.5 | 52.6 | 48.5 | 53.7 |
| 108 | 74.6 | 70.1 | 75.8 | 71.2 | 69.7 | 71.5 |
| 464 | 68.3 | 53.7 | 72.2 | 67.3 | 57.6 | 69.9 |

TABLE 9

| | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 2_48 | 93 | 83.6 | 95.6 | 91.7 | 81.8 | 94.3 |
| 2_10 | 90.8 | 86.6 | 91.9 | 89.7 | 87.9 | 90.2 |
| 2_465 | 89.5 | 83.6 | 91.1 | 89.7 | 87.9 | 90.2 |
| 29 | 90.5 | 85.1 | 91.9 | 89.7 | 84.8 | 91.1 |
| 2_30 | 91.7 | 85.1 | 93.5 | 89.7 | 81.8 | 91.9 |
| 2_61 | 89.8 | 79.1 | 92.7 | 89.7 | 81.8 | 91.9 |
| 2_101 | 90.5 | 82.1 | 92.7 | 89.7 | 78.8 | 92.7 |
| 2_7 | 90.2 | 80.6 | 92.7 | 89.1 | 84.8 | 90.2 |
| 2_28 | 90.5 | 83.6 | 92.3 | 89.1 | 84.8 | 90.2 |
| 2_4 | 89.8 | 83.6 | 91.5 | 88.5 | 81.8 | 90.2 |
| 2_68 | 90.8 | 85.1 | 92.3 | 88.5 | 81.8 | 90.2 |
| 2_25 | 90.8 | 86.6 | 91.9 | 87.8 | 81.8 | 89.4 |

TABLE 10

| | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 2_7_101 | 92.7 | 86.6 | 94.4 | 93.6 | 93.9 | 93.5 |
| 2_48_68 | 93.7 | 83.6 | 96.4 | 93.6 | 78.8 | 97.6 |

TABLE 10-continued

| | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 2_7_82 | 92.7 | 82.1 | 95.6 | 92.9 | 87.9 | 94.3 |
| 2_6_48 | 93.7 | 85.1 | 96 | 92.9 | 87.9 | 94.3 |
| 2_48_17 | 92.7 | 83.6 | 95.2 | 92.9 | 84.8 | 95.1 |
| 2_48_101 | 93.3 | 85.1 | 95.6 | 92.9 | 84.8 | 95.1 |
| 2_465_467 | 90.8 | 82.1 | 93.1 | 92.3 | 93.9 | 91.9 |
| 2_7_48 | 92.4 | 83.6 | 94.8 | 92.3 | 84.8 | 94.3 |
| 2_48_38 | 92.7 | 82.1 | 95.6 | 92.3 | 84.8 | 94.3 |
| 2_48_22 | 92.7 | 85.1 | 94.8 | 92.3 | 84.8 | 94.3 |
| 2_48_30 | 94.3 | 88.1 | 96 | 92.3 | 84.8 | 94.3 |
| 2_48_53 | 93.3 | 83.6 | 96 | 92.3 | 84.8 | 94.3 |
| 2_48_47 | 93 | 85.1 | 95.2 | 92.3 | 84.8 | 94.3 |
| 2_48_365 | 93 | 85.1 | 95.2 | 92.3 | 84.8 | 94.3 |
| 2_38_101 | 91.4 | 85.1 | 93.1 | 92.3 | 84.8 | 94.3 |
| 2_31_101 | 91.7 | 82.1 | 94.4 | 92.3 | 81.8 | 95.1 |
| 2_48_82 | 93 | 83.6 | 95.6 | 92.3 | 81.8 | 95.1 |
| 2_9_103 | 91.4 | 83.6 | 93.5 | 91.7 | 93.9 | 91.1 |
| 2_9_469 | 90.2 | 85.1 | 91.5 | 91.7 | 93.9 | 91.1 |
| 2_38_465 | 91.7 | 85.1 | 93.5 | 91.7 | 87.9 | 92.7 |
| 2_465_373 | 89.8 | 83.6 | 91.5 | 91.7 | 87.9 | 92.7 |
| 2_61_365 | 88.9 | 79.1 | 91.5 | 91.7 | 87.9 | 92.7 |
| 2_31_48 | 93.7 | 86.6 | 95.6 | 91.7 | 84.8 | 93.5 |
| 2_6_101 | 91.7 | 85.1 | 93.5 | 91.7 | 84.8 | 93.5 |
| 2_48_103 | 93.3 | 85.1 | 95.6 | 91.7 | 84.8 | 93.5 |
| 2_68_101 | 91.7 | 85.1 | 93.5 | 91.7 | 84.8 | 93.5 |
| 2_465_101 | 90.8 | 82.1 | 93.1 | 91.7 | 84.8 | 93.5 |
| 2_61_101 | 90.5 | 80.6 | 93.1 | 91.7 | 84.8 | 93.5 |
| 2_4_48 | 92.7 | 82.1 | 95.6 | 91.7 | 81.8 | 94.3 |
| 2_10_48 | 93 | 85.1 | 95.2 | 91.7 | 81.8 | 94.3 |
| 2_9_48 | 93.3 | 85.1 | 95.6 | 91.7 | 81.8 | 94.3 |
| 2_48_51 | 93 | 83.6 | 95.6 | 91.7 | 81.8 | 94.3 |
| 2_48_465 | 93 | 83.6 | 95.6 | 91.7 | 81.8 | 94.3 |
| 2_48_108 | 93 | 82.1 | 96 | 91.7 | 81.8 | 94.3 |
| 2_48_28 | 93 | 83.6 | 95.6 | 91.7 | 81.8 | 94.3 |
| 2_48_373 | 93 | 80.6 | 96.4 | 91.7 | 81.8 | 94.3 |
| 2_48_466 | 92.7 | 82.1 | 95.6 | 91.7 | 81.8 | 94.3 |
| 2_48_61 | 93 | 83.6 | 95.6 | 91.7 | 81.8 | 94.3 |
| 2_48_467 | 93.3 | 82.1 | 96.4 | 91.7 | 81.8 | 94.3 |
| 2_48_464 | 93 | 83.6 | 95.6 | 91.7 | 81.8 | 94.3 |
| 2_48_382 | 92.7 | 83.3 | 95.2 | 91.7 | 81.8 | 94.3 |
| 2_48_370 | 93 | 82.1 | 96 | 91.7 | 81.8 | 94.3 |
| 2_101_365 | 90.5 | 79.1 | 93.5 | 91.7 | 81.8 | 94.3 |
| 2_10_365 | 89.5 | 83.6 | 91.1 | 91 | 93.9 | 90.2 |
| 2_7_465 | 91.1 | 82.1 | 93.5 | 91 | 90.9 | 91.1 |
| 2_7_61 | 90.2 | 82.1 | 92.3 | 91 | 90.9 | 91.3 |
| 2_9_467 | 90.5 | 85.1 | 91.9 | 91 | 90.9 | 91.1 |
| 2_465_469 | 89.2 | 83.6 | 90.7 | 91 | 90.9 | 91.1 |
| 2_25_30 | 91.1 | 86.6 | 92.3 | 91 | 87.9 | 91.9 |
| 2_7_466 | 90.2 | 80.6 | 92.7 | 91 | 87.9 | 91.9 |
| 2_7_47 | 89.8 | 82.1 | 91.9 | 91 | 87.9 | 91.9 |
| 2_10_82 | 90.8 | 88.1 | 91.5 | 91 | 87.9 | 91.9 |
| 2_9_47 | 90.8 | 85.1 | 92.3 | 91 | 87.9 | 91.9 |
| 2_7_68 | 92.4 | 85.1 | 94.4 | 91 | 84.8 | 92.7 |
| 2_7_22 | 91.7 | 83.6 | 94 | 91 | 84.8 | 92.7 |
| 2_7_100 | 90.2 | 80.6 | 92.7 | 91 | 84.8 | 92.7 |
| 2_10_101 | 92.7 | 86.6 | 94.4 | 91 | 84.8 | 92.7 |
| 2_9_101 | 92.4 | 85.1 | 94.4 | 91 | 84.8 | 92.7 |
| 2_48_359 | 93 | 82.1 | 96 | 91 | 84.8 | 92.7 |
| 2_38_103 | 91.4 | 85.1 | 93.1 | 91 | 84.8 | 92.7 |
| 2_465_82 | 90.5 | 85.1 | 91.9 | 91 | 84.8 | 92.7 |
| 2_28_382 | 91.1 | 83.3 | 93.1 | 91 | 84.8 | 92.7 |
| 2_28_82 | 91.7 | 85.1 | 93.5 | 91 | 84.8 | 92.7 |
| 2_30_101 | 92.1 | 83.6 | 94.4 | 91 | 84.8 | 92.7 |
| 2_25_48 | 93 | 85.1 | 95.2 | 91 | 81.8 | 93.5 |
| 2_48_90 | 94 | 88.1 | 95.6 | 91 | 81.8 | 93.5 |
| 2_48_468 | 93 | 83.6 | 95.6 | 91 | 81.8 | 93.5 |
| 2_48_118 | 92.4 | 85.1 | 94.4 | 91 | 81.8 | 93.5 |
| 2_51_101 | 90.8 | 83.6 | 92.7 | 91 | 81.8 | 93.5 |
| 2_38_30 | 90.8 | 82.1 | 93.1 | 91 | 81.8 | 93.5 |
| 2_61_469 | 90.5 | 80.6 | 93.1 | 91 | 81.8 | 93.5 |
| 2_53_101 | 91.1 | 83.6 | 93.1 | 91 | 81.8 | 93.5 |
| 2_101_464 | 90.2 | 80.6 | 92.7 | 91 | 81.8 | 93.5 |
| 2_101_118 | 90.2 | 82.1 | 92.3 | 91 | 81.8 | 93.5 |
| 2_101_469 | 90.5 | 82.1 | 92.7 | 91 | 81.8 | 93.5 |
| 2_101_47 | 91.4 | 83.6 | 93.5 | 91 | 78.8 | 94.3 |
| 2_101_100 | 90.5 | 82.1 | 92.7 | 91 | 78.8 | 94.3 |

TABLE 10-continued

| | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 2_465_365 | 88.9 | 82.1 | 90.7 | 90.4 | 93.9 | 89.4 |
| 2_7_9 | 91.4 | 83.6 | 93.5 | 90.4 | 90.5 | 90.2 |
| 2_7_28 | 91.1 | 82.1 | 93.5 | 90.4 | 90.9 | 90.2 |
| 2_7_53 | 91.1 | 83.6 | 93.1 | 90.4 | 90.9 | 90.2 |
| 2_7_365 | 89.8 | 80.6 | 92.3 | 90.4 | 90.9 | 90.2 |
| 2_10_9 | 91.1 | 86.6 | 92.3 | 90.4 | 90.9 | 90.2 |
| 2_9_365 | 89.5 | 83.6 | 91.1 | 90.4 | 90.9 | 90.2 |
| 2_9_82 | 92.1 | 86.6 | 93.5 | 90.4 | 90.9 | 90.2 |
| 2_465_47 | 89.8 | 83.6 | 91.5 | 90.4 | 90.9 | 90.2 |
| 2_25_61 | 91.1 | 85.1 | 92.7 | 90.4 | 87.9 | 91.1 |
| 2_7_17 | 90.5 | 80.6 | 93.1 | 90.4 | 87.9 | 91.3 |
| 2_7_464 | 89.2 | 79.1 | 91.9 | 90.4 | 87.9 | 91.1 |
| 2_7_103 | 92.4 | 85.1 | 94.4 | 90.4 | 87.9 | 91.1 |
| 2_7_469 | 90.2 | 80.6 | 92.7 | 90.4 | 87.9 | 91.1 |
| 2_10_30 | 91.7 | 88.1 | 92.7 | 90.4 | 87.9 | 91.1 |
| 2_10_61 | 90.5 | 85.1 | 91.9 | 90.4 | 87.9 | 91.1 |
| 2_9_31 | 90.2 | 85.1 | 91.5 | 90.4 | 87.9 | 91.1 |
| 2_9_28 | 91.1 | 83.6 | 93.1 | 90.4 | 87.9 | 91.1 |
| 2_9_468 | 90.2 | 85.1 | 91.5 | 90.4 | 87.9 | 91.1 |
| 2_9_370 | 90.8 | 85.1 | 92.3 | 90.4 | 87.9 | 91.1 |
| 2_9_100 | 89.8 | 85.1 | 91.1 | 90.4 | 87.9 | 91.1 |
| 2_38_61 | 90.8 | 83.6 | 92.7 | 90.4 | 87.9 | 91.1 |
| 2_7_382 | 92 | 81.8 | 94.8 | 90.4 | 84.8 | 91.9 |
| 2_9_61 | 90.5 | 83.6 | 92.3 | 90.4 | 84.8 | 91.9 |
| 2_48_100 | 93.7 | 85.1 | 96 | 90.4 | 84.8 | 91.9 |
| 2_48_469 | 93 | 82.1 | 96 | 90.4 | 84.8 | 91.9 |
| 2_51_30 | 91.7 | 86.6 | 93.1 | 90.4 | 84.8 | 91.9 |
| 2_68_28 | 92.1 | 83.6 | 94.4 | 90.4 | 84.8 | 91.9 |
| 2_465_30 | 91.1 | 85.1 | 92.7 | 90.4 | 84.8 | 91.9 |
| 2_465_61 | 90.8 | 85.1 | 92.3 | 90.4 | 84.8 | 91.9 |
| 2_28_30 | 92.4 | 85.1 | 94.4 | 90.4 | 84.8 | 91.9 |
| 2_28_47 | 90.2 | 83.6 | 91.9 | 90.4 | 84.8 | 91.9 |
| 2_28_370 | 91.1 | 83.6 | 93.1 | 90.4 | 84.8 | 91.9 |
| 2_22_61 | 90.5 | 80.6 | 93.1 | 90.4 | 84.8 | 91.9 |
| 2_30_365 | 90.5 | 82.1 | 92.7 | 90.4 | 84.8 | 91.9 |
| 2_30_100 | 91.4 | 85.1 | 93.1 | 90.4 | 84.8 | 91.9 |
| 2_61_467 | 89.5 | 80.6 | 91.9 | 90.4 | 84.8 | 91.9 |
| 2_61_464 | 89.5 | 77.6 | 92.7 | 90.4 | 84.8 | 91.9 |
| 2_25_101 | 91.1 | 85.1 | 92.7 | 90.4 | 81.8 | 92.7 |
| 2_4_101 | 90.5 | 80.6 | 93.1 | 90.4 | 81.8 | 92.7 |
| 2_28_101 | 91.7 | 83.6 | 94 | 90.4 | 81.8 | 92.7 |
| 2_22_101 | 90.2 | 80.6 | 92.7 | 90.4 | 81.8 | 92.7 |
| 2_30_53 | 90.8 | 82.1 | 93.1 | 90.4 | 81.8 | 92.7 |
| 2_61_47 | 88.9 | 80.6 | 91.1 | 90.4 | 81.8 | 92.7 |
| 2_108_101 | 91.1 | 82.1 | 93.5 | 90.4 | 78.8 | 93.5 |
| 2_28_17 | 92.1 | 85.1 | 94 | 90.4 | 78.8 | 93.5 |
| 2_373_101 | 90.5 | 82.1 | 92.7 | 90.4 | 78.8 | 93.5 |
| 2_466_101 | 90.8 | 82.1 | 93.1 | 90.4 | 78.8 | 93.5 |
| 2_101_468 | 90.5 | 82.1 | 92.7 | 90.4 | 78.8 | 93.5 |
| 2_101_370 | 89.8 | 79.1 | 92.7 | 90.4 | 78.8 | 93.5 |
| 2_101_82 | 91.1 | 82.1 | 93.5 | 90.4 | 78.8 | 93.5 |
| 2_7_10 | 91.7 | 85.1 | 93.5 | 89.7 | 90.9 | 89.4 |
| 2_9_38 | 91.7 | 86.6 | 93.1 | 89.7 | 90.9 | 89.4 |
| 2_25_465 | 89.2 | 85.1 | 90.3 | 89.7 | 87.9 | 90.2 |
| 2_25_28 | 90.8 | 85.1 | 92.3 | 89.7 | 87.9 | 90.2 |
| 2_7_38 | 92.4 | 82.1 | 95.2 | 89.7 | 87.9 | 90.2 |
| 2_7_108 | 90.2 | 80.6 | 92.7 | 89.7 | 87.9 | 90.2 |
| 2_7_118 | 89.5 | 83.6 | 91.1 | 89.7 | 87.9 | 90.2 |
| 2_4_465 | 89.5 | 83.6 | 91.1 | 89.7 | 87.9 | 90.2 |
| 2_10_465 | 91.7 | 86.6 | 93.1 | 89.7 | 87.9 | 90.2 |
| 2_10_28 | 91.1 | 86.6 | 92.3 | 89.7 | 87.9 | 90.2 |
| 2_10_466 | 90.8 | 86.6 | 91.9 | 89.7 | 87.9 | 90.2 |
| 2_10_370 | 91.1 | 86.6 | 92.3 | 89.7 | 87.9 | 90.2 |
| 2_10_359 | 90.8 | 86.6 | 91.9 | 89.7 | 87.9 | 90.2 |
| 2_10_469 | 91.7 | 86.6 | 93.1 | 89.7 | 87.9 | 90.2 |
| 2_9_6 | 89.8 | 86.6 | 90.7 | 89.7 | 87.9 | 90.2 |
| 2_9_465 | 90.5 | 83.6 | 92.3 | 89.7 | 87.9 | 90.2 |
| 2_9_382 | 90.8 | 84.8 | 92.3 | 89.7 | 87.9 | 90.2 |
| 2_6_365 | 89.5 | 83.6 | 91.1 | 89.7 | 87.9 | 90.2 |
| 2_51_465 | 89.5 | 83.6 | 91.1 | 89.7 | 87.9 | 90.2 |
| 2_465_108 | 89.8 | 83.6 | 91.5 | 89.7 | 87.9 | 90.2 |
| 2_465_28 | 90.8 | 85.1 | 92.3 | 89.7 | 87.9 | 90.2 |
| 2_465_22 | 89.2 | 83.6 | 90.7 | 89.7 | 87.9 | 90.2 |
| 2_465_17 | 89.5 | 83.6 | 91.1 | 89.7 | 87.9 | 90.2 |
| 2_465_466 | 89.8 | 83.6 | 91.5 | 89.7 | 87.9 | 90.2 |

TABLE 10-continued

| | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 2_465_464 | 89.8 | 85.1 | 91.1 | 89.7 | 87.9 | 90.2 |
| 2_465_368 | 89.5 | 83.6 | 91.1 | 89.7 | 87.9 | 90.2 |
| 2_465_359 | 89.5 | 83.6 | 91.1 | 89.7 | 87.9 | 90.2 |
| 2_465_100 | 89.8 | 85.1 | 91.1 | 89.7 | 87.9 | 90.2 |
| 2_25_47 | 89.8 | 85.1 | 91.1 | 89.7 | 84.8 | 91.1 |
| 2_7_4 | 90.2 | 80.6 | 92.7 | 89.7 | 84.8 | 91.1 |
| 2_7_31 | 90.2 | 80.6 | 92.7 | 89.7 | 84.8 | 91.1 |
| 2_7_373 | 89.8 | 79.1 | 92.7 | 89.7 | 84.8 | 91.1 |
| 2_7_370 | 90.5 | 80.6 | 93.1 | 89.7 | 84.8 | 91.1 |
| 2_4_61 | 89.8 | 80.6 | 92.3 | 89.7 | 84.8 | 91.1 |
| 2_10_108 | 90.8 | 86.6 | 91.9 | 89.7 | 84.8 | 91.1 |
| 2_10_118 | 90.5 | 86.6 | 91.5 | 89.7 | 84.8 | 91.1 |
| 2_9_108 | 90.5 | 85.1 | 91.9 | 89.7 | 84.8 | 91.1 |
| 2_9_22 | 90.5 | 85.1 | 91.9 | 89.7 | 84.8 | 91.1 |
| 2_9_30 | 91.7 | 85.1 | 93.5 | 89.7 | 84.8 | 91.1 |
| 2_9_466 | 90.5 | 85.1 | 91.9 | 89.7 | 84.8 | 91.1 |
| 2_9_368 | 90.5 | 85.1 | 91.9 | 89.7 | 84.8 | 91.1 |
| 2_51_61 | 90.8 | 83.6 | 92.7 | 89.7 | 84.8 | 91.1 |
| 2_38_382 | 91.1 | 84.8 | 92.7 | 89.7 | 84.8 | 91.1 |
| 2_465_53 | 90.5 | 85.1 | 91.9 | 89.7 | 84.8 | 91.1 |
| 2_108_61 | 89.8 | 82.1 | 91.9 | 89.7 | 84.8 | 91.1 |
| 2_28_467 | 91.4 | 85.1 | 93.1 | 89.7 | 84.8 | 91.1 |
| 2_28_468 | 91.4 | 85.1 | 93.1 | 89.7 | 84.8 | 91.1 |
| 2_28_469 | 91.1 | 83.6 | 93.1 | 89.7 | 84.8 | 91.1 |
| 2_22_103 | 89.8 | 83.6 | 91.5 | 89.7 | 84.8 | 91.1 |
| 2_466_61 | 90.5 | 82.1 | 92.7 | 89.7 | 84.8 | 91.1 |
| 2_7_30 | 92.1 | 88.1 | 93.1 | 89.7 | 81.8 | 91.9 |
| 2_4_30 | 91.1 | 82.1 | 93.5 | 89.7 | 81.8 | 91.9 |
| 2_9_373 | 90.2 | 85.1 | 91.5 | 89.7 | 81.8 | 91.9 |
| 2_9_464 | 90.5 | 85.1 | 91.9 | 89.7 | 81.8 | 91.9 |
| 2_31_465 | 89.8 | 83.6 | 91.5 | 89.7 | 81.8 | 91.9 |
| 2_31_61 | 89.8 | 79.1 | 92.7 | 89.7 | 81.8 | 91.9 |
| 2_68_38 | 92.1 | 85.1 | 94 | 89.7 | 81.8 | 91.9 |
| 2_465_103 | 91.1 | 83.6 | 93.1 | 89.7 | 81.8 | 91.9 |
| 2_28_373 | 91.7 | 85.1 | 93.5 | 89.7 | 81.8 | 91.9 |
| 2_28_61 | 90.8 | 85.1 | 92.3 | 89.7 | 81.8 | 91.9 |
| 2_28_368 | 91.4 | 85.1 | 93.1 | 89.7 | 81.8 | 91.9 |
| 2_28_118 | 90.2 | 85.1 | 91.5 | 89.7 | 81.8 | 91.9 |
| 2_373_61 | 90.2 | 80.6 | 92.7 | 89.7 | 81.8 | 91.9 |
| 2_22_30 | 91.4 | 85.1 | 93.1 | 89.7 | 81.8 | 91.9 |
| 2_30_17 | 91.7 | 85.1 | 93.5 | 89.7 | 81.8 | 91.9 |
| 2_30_61 | 91.7 | 85.1 | 93.5 | 89.7 | 81.8 | 91.9 |
| 2_30_368 | 91.4 | 83.6 | 93.5 | 89.7 | 81.8 | 91.9 |
| 2_30_118 | 92.1 | 85.1 | 94 | 89.7 | 81.8 | 91.9 |
| 2_30_359 | 91.7 | 85.1 | 93.5 | 89.7 | 81.8 | 91.9 |
| 2_30_103 | 92.4 | 83.6 | 94.8 | 89.7 | 81.8 | 91.9 |
| 2_17_61 | 89.8 | 79.1 | 92.7 | 89.7 | 81.8 | 91.9 |
| 2_61_370 | 89.8 | 79.1 | 92.7 | 89.7 | 81.8 | 91.9 |
| 2_61_368 | 89.8 | 77.6 | 93.1 | 89.7 | 81.8 | 91.9 |
| 2_61_118 | 90.2 | 80.6 | 92.7 | 89.7 | 81.8 | 91.9 |
| 2_61_82 | 89.8 | 76.1 | 93.5 | 89.7 | 81.8 | 91.9 |
| 2_17_101 | 90.5 | 82.1 | 92.7 | 89.7 | 78.8 | 92.7 |
| 2_467_101 | 90.5 | 82.1 | 92.7 | 89.7 | 78.8 | 92.7 |
| 2_101_382 | 91.1 | 81.8 | 93.5 | 89.7 | 78.8 | 92.7 |
| 2_101_368 | 90.5 | 82.1 | 92.7 | 89.7 | 78.8 | 92.7 |
| 2_101_359 | 90.5 | 82.1 | 92.7 | 89.7 | 78.8 | 92.7 |
| 2_101_103 | 90.5 | 82.1 | 92.7 | 89.7 | 78.8 | 92.7 |
| 2_90_101 | 90.8 | 82.1 | 93.1 | 89.7 | 75.8 | 93.5 |
| 2_25_9 | 90.2 | 85.1 | 91.5 | 89.1 | 87.9 | 89.4 |
| 2_25_53 | 89.8 | 85.1 | 91.1 | 89.1 | 87.9 | 89.4 |
| 2_7_6 | 90.8 | 85.1 | 92.3 | 89.1 | 87.9 | 89.4 |
| 2_10_22 | 90.8 | 86.6 | 91.9 | 89.1 | 87.9 | 89.4 |
| 2_10_53 | 90.8 | 86.6 | 91.9 | 89.1 | 87.9 | 89.4 |
| 2_10_47 | 89.8 | 86.6 | 90.7 | 89.1 | 87.9 | 89.4 |
| 2_9_51 | 90.5 | 85.1 | 91.9 | 89.1 | 87.9 | 89.4 |
| 2_25_7 | 91.4 | 83.6 | 93.5 | 89.1 | 84.8 | 90.2 |
| 2_25_68 | 91.4 | 86.6 | 92.7 | 89.1 | 84.8 | 90.2 |
| 2_25_17 | 90.5 | 86.6 | 91.5 | 89.1 | 84.8 | 90.2 |
| 2_25_365 | 89.5 | 83.6 | 91.1 | 89.1 | 84.8 | 90.2 |
| 2_7_467 | 90.8 | 80.6 | 93.5 | 89.1 | 84.8 | 90.2 |
| 2_7_468 | 90.5 | 80.6 | 93.1 | 89.1 | 84.8 | 90.2 |
| 2_7_368 | 90.2 | 80.6 | 92.7 | 89.1 | 84.8 | 90.2 |
| 2_7_359 | 90.8 | 83.6 | 92.7 | 89.1 | 84.8 | 90.2 |
| 2_4_10 | 90.8 | 86.6 | 91.9 | 89.1 | 84.8 | 90.2 |
| 2_4_9 | 90.5 | 85.1 | 91.9 | 89.1 | 84.8 | 90.2 |

TABLE 10-continued

| | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 2_4_28 | 90.5 | 83.6 | 92.3 | 89.1 | 84.8 | 90.2 |
| 2_4_90 | 90.5 | 82.1 | 92.7 | 89.1 | 84.8 | 90.2 |
| 2_10_31 | 91.1 | 86.6 | 92.3 | 89.1 | 84.8 | 90.2 |
| 2_10_51 | 90.8 | 86.6 | 91.9 | 89.1 | 84.8 | 90.2 |
| 2_10_382 | 90.4 | 86.4 | 91.5 | 89.1 | 84.8 | 90.2 |
| 2_9_53 | 91.1 | 85.1 | 92.7 | 89.1 | 84.8 | 90.2 |
| 2_9_359 | 90.5 | 85.1 | 91.9 | 89.1 | 84.8 | 90.2 |
| 2_51_28 | 90.8 | 83.6 | 92.7 | 89.1 | 84.8 | 90.2 |
| 2_51_90 | 90.8 | 80.6 | 93.5 | 89.1 | 84.8 | 90.2 |
| 2_68_61 | 91.4 | 82.1 | 94 | 89.1 | 84.8 | 90.2 |
| 2_38_28 | 90.8 | 85.1 | 92.3 | 89.1 | 84.8 | 90.2 |
| 2_108_30 | 91.7 | 88.1 | 92.7 | 89.1 | 84.8 | 90.2 |
| 2_28_466 | 90.5 | 83.6 | 92.3 | 89.1 | 84.8 | 90.2 |
| 2_28_359 | 90.8 | 83.6 | 92.7 | 89.1 | 84.8 | 90.2 |
| 2_28_100 | 90.8 | 85.1 | 92.3 | 89.1 | 84.8 | 90.2 |
| 2_30_464 | 91.4 | 82.1 | 94 | 89.1 | 84.8 | 90.2 |
| 2_468_365 | 88.9 | 80.6 | 91.1 | 89.1 | 84.8 | 90.2 |
| 2_25_82 | 90.8 | 86.6 | 91.9 | 89.1 | 81.8 | 91.1 |
| 2_7_51 | 89.2 | 77.6 | 92.3 | 89.1 | 81.8 | 91.1 |
| 2_4_103 | 91.1 | 82.1 | 93.5 | 89.1 | 81.8 | 91.1 |
| 2_31_68 | 90.2 | 83.6 | 91.9 | 89.1 | 81.8 | 91.1 |
| 2_31_30 | 91.1 | 82.1 | 93.5 | 89.1 | 81.8 | 91.1 |
| 2_6_30 | 91.7 | 88.1 | 92.7 | 89.1 | 81.8 | 91.1 |
| 2_48_368 | 93 | 85.1 | 95.2 | 89.1 | 81.8 | 91.1 |
| 2_51_373 | 89.8 | 83.6 | 91.5 | 89.1 | 81.8 | 91.1 |
| 2_68_47 | 90.5 | 85.1 | 91.9 | 89.1 | 81.8 | 91.1 |
| 2_68_368 | 91.4 | 85.1 | 93.1 | 89.1 | 81.8 | 91.1 |
| 2_68_100 | 91.1 | 85.1 | 92.7 | 89.1 | 81.8 | 91.1 |
| 2_68_103 | 90.8 | 85.1 | 92.3 | 89.1 | 81.8 | 91.3 |
| 2_38_82 | 90.5 | 85.1 | 91.9 | 89.1 | 81.8 | 91.1 |
| 2_108_28 | 91.1 | 83.6 | 93.1 | 89.1 | 81.8 | 91.1 |
| 2_108_17 | 91.4 | 83.6 | 93.5 | 89.1 | 81.8 | 91.1 |
| 2_373_30 | 92.4 | 86.6 | 94 | 89.1 | 81.8 | 91.1 |
| 2_30_466 | 90.8 | 85.1 | 92.3 | 89.1 | 81.8 | 91.1 |
| 2_30_370 | 91.7 | 85.1 | 93.5 | 89.1 | 81.8 | 91.1 |
| 2_30_82 | 91.4 | 85.1 | 93.1 | 89.1 | 81.8 | 91.1 |
| 2_466_103 | 91.4 | 85.1 | 93.1 | 89.1 | 81.8 | 91.1 |
| 2_61_53 | 91.1 | 82.1 | 93.5 | 89.1 | 81.8 | 91.1 |
| 2_61_468 | 89.8 | 79.1 | 92.7 | 89.1 | 81.8 | 91.1 |
| 2_61_359 | 89.8 | 79.1 | 92.7 | 89.1 | 81.8 | 91.1 |
| 2_9_17 | 90.5 | 85.1 | 91.9 | 89.1 | 78.8 | 91.9 |
| 2_28_103 | 91.4 | 83.6 | 93.5 | 89.1 | 78.8 | 91.9 |
| 2_90_100 | 90.5 | 80.6 | 93.1 | 89.1 | 78.8 | 91.9 |
| 2_61_382 | 90.1 | 80.3 | 92.7 | 89.1 | 78.8 | 91.9 |
| 2_100_103 | 90.8 | 83.6 | 92.7 | 89.1 | 75.8 | 92.7 |
| 2_25_10 | 90.2 | 88.1 | 90.7 | 88.5 | 84.8 | 89.4 |
| 2_25_464 | 90.5 | 86.6 | 91.5 | 88.5 | 84.8 | 89.4 |
| 2_4_82 | 90.5 | 85.1 | 91.9 | 88.5 | 84.8 | 89.4 |
| 2_10_467 | 90.8 | 86.6 | 91.9 | 88.5 | 84.8 | 89.4 |
| 2_10_464 | 91.1 | 86.6 | 92.3 | 88.5 | 84.8 | 89.4 |
| 2_10_368 | 90.8 | 86.6 | 91.9 | 88.5 | 84.8 | 89.4 |
| 2_9_68 | 92.1 | 86.6 | 93.5 | 88.5 | 84.8 | 89.4 |
| 2_6_51 | 89.8 | 85.1 | 91.1 | 88.5 | 84.8 | 89.4 |
| 2_6_61 | 88.9 | 83.6 | 90.3 | 88.5 | 84.8 | 89.4 |
| 2_6_464 | 89.5 | 85.1 | 90.7 | 88.5 | 84.8 | 89.4 |
| 2_6_100 | 90.2 | 85.1 | 91.5 | 88.5 | 84.8 | 89.4 |
| 2_51_365 | 89.5 | 83.6 | 91.1 | 88.5 | 84.8 | 89.4 |
| 2_38_90 | 90.8 | 80.6 | 93.5 | 88.5 | 84.8 | 89.4 |
| 2_38_365 | 88.6 | 82.1 | 90.3 | 88.5 | 84.8 | 89.4 |
| 2_108_365 | 89.2 | 83.6 | 90.7 | 88.5 | 84.8 | 89.4 |
| 2_108_82 | 91.1 | 85.1 | 92.7 | 88.5 | 84.8 | 89.4 |
| 2_28_365 | 89.2 | 83.6 | 90.7 | 88.5 | 84.8 | 89.4 |
| 2_22_467 | 89.8 | 85.1 | 91.1 | 88.5 | 84.8 | 89.4 |
| 2_22_382 | 89.8 | 83.3 | 91.5 | 88.5 | 84.8 | 89.4 |
| 2_22_82 | 90.5 | 85.1 | 91.9 | 88.5 | 84.8 | 89.4 |
| 2_466_365 | 89.2 | 83.6 | 90.7 | 88.5 | 84.8 | 89.4 |
| 2_25_38 | 91.4 | 86.6 | 92.7 | 88.5 | 81.8 | 90.2 |
| 2_25_373 | 90.5 | 86.6 | 91.5 | 88.5 | 81.8 | 90.2 |
| 2_25_468 | 90.8 | 85.1 | 92.3 | 88.5 | 81.8 | 90.2 |
| 2_4_464 | 90.2 | 83.6 | 91.9 | 88.5 | 81.8 | 90.2 |
| 2_4_468 | 89.8 | 83.6 | 91.5 | 88.5 | 81.8 | 90.2 |
| 2_4_47 | 90.2 | 83.6 | 91.9 | 88.5 | 81.8 | 90.2 |
| 2_10_373 | 90.2 | 86.6 | 91.1 | 88.5 | 81.8 | 90.2 |
| 2_10_468 | 90.8 | 86.6 | 91.9 | 88.5 | 81.8 | 90.2 |
| 2_9_90 | 90.5 | 82.1 | 92.7 | 88.5 | 81.8 | 90.2 |

TABLE 10-continued

| | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 2_9_118 | 90.5 | 85.1 | 91.9 | 88.5 | 81.8 | 90.2 |
| 2_31_38 | 90.2 | 85.1 | 91.5 | 88.5 | 81.8 | 90.2 |
| 2_6_68 | 91.7 | 85.1 | 93.5 | 88.5 | 81.8 | 90.2 |
| 2_51_82 | 90.2 | 83.6 | 91.9 | 88.5 | 81.8 | 90.2 |
| 2_68_373 | 90.8 | 85.1 | 92.3 | 88.5 | 81.8 | 90.2 |
| 2_68_464 | 89.8 | 83.6 | 91.5 | 88.5 | 81.8 | 90.2 |
| 2_38_464 | 90.2 | 85.1 | 91.5 | 88.5 | 81.8 | 90.2 |
| 2_38_359 | 91.4 | 85.1 | 93.1 | 88.5 | 81.8 | 90.2 |
| 2_465_90 | 90.2 | 80.6 | 92.7 | 88.5 | 81.8 | 90.2 |
| 2_465_468 | 90.2 | 83.6 | 91.9 | 88.5 | 81.8 | 90.2 |
| 2_465_370 | 89.8 | 82.1 | 91.9 | 88.5 | 81.8 | 90.2 |
| 2_465_118 | 90.8 | 86.6 | 91.9 | 88.5 | 81.8 | 90.2 |
| 2_28_464 | 91.1 | 85.1 | 92.7 | 88.5 | 81.8 | 90.2 |
| 2_22_90 | 90.2 | 80.6 | 92.7 | 88.5 | 81.8 | 90.2 |
| 2_22_118 | 90.8 | 83.6 | 92.7 | 88.5 | 81.8 | 90.2 |
| 2_30_467 | 91.7 | 85.1 | 93.5 | 88.5 | 81.8 | 90.2 |
| 2_30_468 | 92.1 | 85.1 | 94 | 88.5 | 81.8 | 90.2 |
| 2_30_47 | 92.1 | 86.6 | 93.5 | 88.5 | 81.8 | 90.2 |
| 2_61_103 | 90.2 | 77.6 | 93.5 | 88.5 | 81.8 | 90.2 |
| 2_467_365 | 87.9 | 80.6 | 89.9 | 88.5 | 81.8 | 90.2 |
| 2_53_365 | 88.9 | 80.6 | 91.1 | 88.5 | 81.8 | 90.2 |
| 2_53_103 | 91.1 | 82.1 | 93.5 | 88.5 | 81.8 | 90.2 |
| 2_31_382 | 89.5 | 80.3 | 91.9 | 88.5 | 78.8 | 91.1 |
| 2_31_103 | 89.5 | 79.1 | 92.3 | 88.5 | 78.8 | 91.1 |
| 2_68_30 | 92.4 | 85.1 | 94.4 | 88.5 | 78.8 | 91.1 |
| 2_68_370 | 90.2 | 83.6 | 91.9 | 88.5 | 78.8 | 91.1 |
| 2_68_82 | 91.4 | 85.1 | 93.1 | 88.5 | 78.8 | 91.1 |
| 2_38_17 | 90.5 | 85.1 | 91.9 | 88.5 | 78.8 | 91.1 |
| 2_38_100 | 90.2 | 85.1 | 91.5 | 88.5 | 78.8 | 91.1 |
| 2_90_61 | 90.5 | 79.1 | 93.5 | 88.5 | 78.8 | 91.1 |
| 2_90_464 | 90.5 | 80.6 | 93.1 | 88.5 | 78.8 | 91.1 |
| 2_90_370 | 90.8 | 80.6 | 93.5 | 88.5 | 78.8 | 91.1 |
| 2_30_382 | 91.1 | 81.8 | 93.5 | 88.5 | 78.8 | 91.1 |
| 2_30_469 | 91.1 | 83.6 | 93.1 | 88.5 | 78.8 | 91.1 |
| 2_61_100 | 89.8 | 80.6 | 92.3 | 88.5 | 78.8 | 91.1 |
| 2_368_82 | 90.8 | 83.6 | 92.7 | 88.5 | 78.8 | 91.1 |
| 2_100_82 | 90.2 | 83.6 | 91.9 | 88.5 | 78.8 | 91.1 |
| 2_90_368 | 90.8 | 80.6 | 93.5 | 88.5 | 75.8 | 91.9 |
| 2_90_118 | 90.2 | 80.6 | 92.7 | 88.5 | 75.8 | 91.9 |
| 7_4_82 | 90.2 | 85.1 | 91.5 | 90.4 | 90.9 | 90.2 |
| 7_68_61 | 89.8 | 88.1 | 90.3 | 89.7 | 87.9 | 90.2 |
| 7_38_101 | 90.2 | 86.6 | 91.1 | 89.7 | 87.9 | 90.2 |
| 7_30_101 | 87.6 | 89.6 | 87.1 | 89.1 | 90.9 | 88.6 |
| 7_30_82 | 87.9 | 89.6 | 87.5 | 89.1 | 87.9 | 89.4 |
| 2_25_7 | 91.4 | 83.6 | 93.5 | 89.1 | 84.8 | 90.2 |
| 7_68_28 | 89.2 | 85.1 | 90.3 | 89.1 | 84.8 | 90.2 |
| 7_4_103 | 88.9 | 88.1 | 89.1 | 88.5 | 87.9 | 88.6 |
| 7_10_31 | 86.3 | 79.1 | 88.3 | 88.5 | 87.9 | 88.6 |
| 7_68_38 | 90.5 | 86.6 | 91.5 | 88.5 | 84.8 | 89.4 |
| 7_68_47 | 88.6 | 85.1 | 89.5 | 88.5 | 84.8 | 89.4 |
| 7_30_103 | 87.9 | 89.6 | 87.5 | 88.5 | 81.8 | 90.2 |
| 25_7_47 | 87.9 | 86.6 | 88.3 | 90.4 | 87.9 | 91.1 |
| 25_7_373 | 89.2 | 91 | 88.7 | 89.1 | 93.9 | 87.8 |
| 25_7_61 | 87.6 | 89.6 | 87.1 | 89.1 | 93.9 | 87.8 |
| 25_7_48 | 89.2 | 88.1 | 89.5 | 89.1 | 87.9 | 89.4 |
| 25_7_467 | 89.2 | 89.6 | 89.1 | 88.5 | 90.9 | 87.8 |
| 25_7_464 | 87.9 | 91 | 87.1 | 88.5 | 90.9 | 87.8 |
| 25_7_118 | 88.9 | 91 | 88.3 | 88.5 | 90.9 | 87.8 |

TABLE 11

| | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 2_7_61_82 | 93.3 | 85.1 | 95.6 | 96.2 | 97 | 95.9 |
| 2_7_82_103 | 93 | 83.6 | 95.6 | 95.5 | 87.9 | 97.6 |
| 2_7_47_82 | 92.4 | 83.6 | 94.8 | 94.9 | 93.9 | 95.1 |
| 2_7_82_101 | 94.6 | 88.1 | 96.4 | 94.9 | 87.9 | 96.7 |
| 2_7_9_101 | 92.7 | 86.6 | 94.4 | 94.2 | 93.9 | 94.3 |
| 2_7_31_101 | 93 | 86.6 | 94.8 | 94.2 | 93.9 | 94.3 |

TABLE 11-continued

| | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 2_7_51_101 | 92.4 | 83.6 | 94.8 | 94.2 | 93.9 | 94.3 |
| 2_38_53_465 | 92.1 | 85.1 | 94 | 94.2 | 93.9 | 94.3 |
| 2_7_9_82 | 93 | 85.1 | 95.2 | 94.2 | 90.9 | 95.1 |
| 2_7_48_103 | 93.7 | 85.1 | 96 | 94.2 | 90.9 | 95.1 |
| 2_7_101_466 | 92.1 | 82.1 | 94.8 | 94.2 | 90.9 | 95.1 |
| 2_7_47_101 | 92.4 | 85.1 | 94.4 | 94.2 | 90.9 | 95.1 |
| 2_7_48_51 | 93 | 86.6 | 94.8 | 94.2 | 87.9 | 95.9 |
| 2_7_48_469 | 92.7 | 83.6 | 95.2 | 94.2 | 87.9 | 95.9 |
| 2_38_82_101 | 91.4 | 83.6 | 93.5 | 94.2 | 87.9 | 95.9 |
| 2_7_48_82 | 94 | 83.6 | 96.8 | 94.2 | 84.8 | 96.7 |
| 2_48_68_467 | 94 | 85.1 | 96.4 | 94.2 | 81.8 | 97.6 |
| 2_48_68_370 | 93.3 | 83.6 | 96 | 94.2 | 81.8 | 97.6 |
| 2_7_25_101 | 92.7 | 86.6 | 94.4 | 93.6 | 93.9 | 93.5 |
| 2_7_101_465 | 92.7 | 86.6 | 94.4 | 93.6 | 93.9 | 93.5 |
| 2_7_61_101 | 92.7 | 86.6 | 94.4 | 93.6 | 93.9 | 93.5 |
| 2_7_61_103 | 92.7 | 83.6 | 95.2 | 93.6 | 93.9 | 93.5 |
| 2_7_101_368 | 92.4 | 85.1 | 94.4 | 93.6 | 93.9 | 93.5 |
| 2_7_101_365 | 92.7 | 85.1 | 94.8 | 93.6 | 93.9 | 93.5 |
| 2_38_51_465 | 91.1 | 85.1 | 92.7 | 93.6 | 93.9 | 93.5 |
| 2_28_465_467 | 92.7 | 86.6 | 94.4 | 93.6 | 93.9 | 93.5 |
| 2_365_373_465 | 90.2 | 83.6 | 91.9 | 93.6 | 93.9 | 93.5 |
| 2_100_465_467 | 91.4 | 85.1 | 93.1 | 93.6 | 93.9 | 93.5 |
| 2_7_10_82 | 93.7 | 83.6 | 96.4 | 93.6 | 90.9 | 94.3 |
| 2_7_38_48 | 93.3 | 83.6 | 96 | 93.6 | 90.9 | 94.3 |
| 2_7_48_359 | 93.3 | 83.6 | 96 | 93.6 | 90.9 | 94.3 |
| 2_7_101_373 | 92.7 | 85.1 | 94.8 | 93.6 | 90.9 | 94.3 |
| 2_7_82_118 | 92.4 | 83.6 | 94.8 | 93.6 | 90.9 | 94.3 |
| 2_7_82_365 | 92.1 | 80.6 | 95.2 | 93.6 | 90.9 | 94.3 |
| 2_6_48_359 | 93.7 | 83.6 | 96.4 | 93.6 | 90.9 | 94.3 |
| 2_38_82_465 | 92.1 | 85.1 | 94 | 93.6 | 90.9 | 94.3 |
| 2_38_101_365 | 92.1 | 83.6 | 94.4 | 93.6 | 90.9 | 94.3 |
| 2_7_25_82 | 93.7 | 85.1 | 96 | 93.6 | 87.9 | 95.1 |
| 2_7_48_466 | 92.4 | 85.1 | 94.4 | 93.6 | 87.9 | 95.1 |
| 2_7_48_467 | 93 | 83.6 | 95.6 | 93.6 | 87.9 | 95.1 |
| 2_7_82_465 | 92.7 | 82.1 | 95.6 | 93.6 | 87.9 | 95.1 |
| 2_7_30_82 | 93 | 85.1 | 95.2 | 93.6 | 87.9 | 95.1 |
| 2_7_101_382 | 93.3 | 84.8 | 95.6 | 93.6 | 87.9 | 95.1 |
| 2_30_31_48 | 94.6 | 89.6 | 96 | 93.6 | 87.9 | 95.1 |
| 2_31_48_53 | 93.7 | 86.6 | 95.6 | 93.6 | 87.9 | 95.1 |
| 2_31_48_82 | 93.3 | 86.6 | 95.2 | 93.6 | 87.9 | 95.1 |
| 2_31_53_101 | 91.4 | 80.6 | 94.4 | 93.6 | 87.9 | 95.1 |
| 2_38_48_101 | 92.7 | 83.6 | 95.2 | 93.6 | 87.9 | 95.1 |
| 2_48_465_467 | 93.3 | 83.6 | 96 | 93.6 | 87.9 | 95.1 |
| 2_17_48_365 | 92.7 | 83.6 | 95.2 | 93.6 | 87.9 | 95.1 |
| 2_28_68_101 | 93.3 | 86.6 | 95.2 | 93.6 | 87.9 | 95.1 |
| 2_30_38_101 | 93 | 86.6 | 94.8 | 93.6 | 87.9 | 95.1 |
| 2_17_25_48 | 92.7 | 83.6 | 95.2 | 93.6 | 84.8 | 95.9 |
| 2_7_47_68 | 91.7 | 83.6 | 94 | 93.6 | 84.8 | 95.9 |
| 2_7_28_82 | 93.7 | 85.1 | 96 | 93.6 | 84.8 | 95.9 |
| 2_7_382_82 | 92.7 | 81.8 | 95.6 | 93.6 | 84.8 | 95.9 |
| 2_4_38_48 | 92.7 | 82.1 | 95.6 | 93.6 | 84.8 | 95.9 |
| 2_48_465_466 | 93 | 83.6 | 95.6 | 93.6 | 84.8 | 95.9 |
| 2_48_101_108 | 93 | 83.6 | 95.6 | 93.6 | 84.8 | 95.9 |
| 2_22_48_82 | 92.4 | 85.1 | 94.4 | 93.6 | 84.8 | 95.9 |
| 2_30_48_467 | 93.3 | 82.1 | 96.4 | 93.6 | 84.8 | 95.9 |
| 2_30_48_82 | 94.6 | 89.6 | 96 | 93.6 | 84.8 | 95.9 |
| 2_17_48_101 | 92.7 | 83.6 | 95.2 | 93.6 | 84.8 | 95.9 |
| 2_48_82_101 | 93.3 | 85.1 | 95.6 | 93.6 | 84.8 | 95.9 |
| 2_38_101_359 | 91.7 | 85.1 | 93.5 | 93.6 | 84.8 | 95.9 |
| 2_82_101_108 | 91.4 | 82.1 | 94 | 93.6 | 84.8 | 95.9 |
| 2_31_48_68 | 94 | 86.6 | 96 | 93.6 | 81.8 | 96.7 |
| 2_6_48_68 | 94.3 | 85.1 | 96.8 | 93.6 | 81.8 | 96.7 |
| 2_38_48_68 | 93.3 | 83.6 | 96 | 93.6 | 81.8 | 96.7 |
| 2_48_68_90 | 94 | 86.6 | 96 | 93.6 | 81.8 | 96.7 |
| 2_25_48_68 | 93.7 | 83.6 | 96.4 | 93.6 | 78.8 | 97.6 |
| 2_4_48_68 | 93.7 | 83.6 | 96.4 | 93.6 | 78.8 | 97.6 |
| 2_48_51_68 | 93.7 | 83.6 | 96.4 | 93.6 | 78.8 | 97.6 |
| 2_48_68_465 | 93.7 | 83.6 | 96.4 | 93.6 | 78.8 | 97.6 |
| 2_48_68_108 | 93.7 | 83.6 | 96.4 | 93.6 | 78.8 | 97.6 |
| 2_48_68_373 | 94 | 83.6 | 96.8 | 93.6 | 78.8 | 97.6 |
| 2_48_68_466 | 93.7 | 83.6 | 96.4 | 93.6 | 78.8 | 97.6 |
| 2_48_68_101 | 94 | 85.1 | 96.4 | 93.6 | 78.8 | 97.6 |
| 2_48_68_103 | 93.7 | 83.6 | 96.4 | 93.6 | 78.8 | 97.6 |
| 2_7_61_365 | 89.8 | 79.1 | 92.7 | 92.9 | 97 | 91.9 |
| 2_10_82_365 | 91.1 | 85.1 | 92.7 | 92.9 | 97 | 91.9 |

TABLE 11-continued

| | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 2_9_82_467 | 92.7 | 88.1 | 94 | 92.9 | 97 | 91.9 |
| 2_7_10_101 | 93.3 | 86.6 | 95.2 | 92.9 | 93.9 | 92.7 |
| 2_7_38_101 | 93.3 | 86.6 | 95.2 | 92.9 | 93.9 | 92.7 |
| 2_7_61_466 | 90.5 | 80.6 | 93.1 | 92.9 | 93.9 | 92.7 |
| 2_51_465_467 | 90.8 | 82.1 | 93.1 | 92.9 | 93.9 | 92.7 |
| 2_38_465_466 | 91.4 | 83.6 | 93.5 | 92.9 | 93.9 | 92.7 |
| 2_38_365_465 | 91.1 | 83.6 | 93.1 | 92.9 | 93.9 | 92.7 |
| 2_47_465_467 | 90.8 | 80.6 | 93.5 | 92.9 | 93.9 | 92.7 |
| 2_368_465_467 | 90.8 | 82.1 | 93.1 | 92.9 | 93.9 | 92.7 |
| 2_25_61_101 | 90.8 | 82.1 | 93.1 | 92.9 | 90.9 | 93.5 |
| 2_7_47_465 | 90.2 | 82.1 | 92.3 | 92.9 | 90.9 | 93.5 |
| 2_7_28_47 | 90.8 | 82.1 | 93.1 | 92.9 | 90.9 | 93.5 |
| 2_7_30_101 | 93.3 | 88.1 | 94.8 | 92.9 | 90.9 | 93.5 |
| 2_7_53_101 | 93 | 88.1 | 94.4 | 92.9 | 90.9 | 93.5 |
| 2_7_101_359 | 92.7 | 85.1 | 94.8 | 92.9 | 90.9 | 93.5 |
| 2_10_82_90 | 94 | 89.6 | 95.2 | 92.9 | 90.9 | 93.5 |
| 2_9_31_101 | 91.4 | 82.1 | 94 | 92.9 | 90.9 | 93.5 |
| 2_31_38_48 | 93 | 85.1 | 95.2 | 92.9 | 84.8 | 95.1 |
| 2_28_31_48 | 93.7 | 86.6 | 95.6 | 92.3 | 87.9 | 93.5 |
| 4_7_82_101 | 92.4 | 91 | 92.7 | 92.3 | 93.9 | 91.9 |
| 4_7_38_82 | 91.1 | 85.1 | 92.7 | 92.3 | 90.9 | 92.7 |
| 6_7_61_68 | 92.1 | 89.6 | 92.7 | 92.3 | 84.8 | 94.3 |
| 7_25_47_466 | 87.3 | 83.6 | 88.3 | 92.3 | 87.9 | 93.5 |
| 7_25_48_466 | 89.8 | 85.1 | 91.1 | 92.3 | 84.8 | 94.3 |
| 4_7_82_103 | 92.4 | 89.6 | 93.1 | 91.7 | 90.9 | 91.9 |
| 4_7_47_82 | 89.2 | 86.6 | 89.9 | 91.7 | 90.9 | 91.9 |
| 7_25_28_466 | 91.7 | 86.6 | 93.1 | 91.7 | 90.9 | 91.9 |
| 7_25_30_466 | 89.2 | 89.6 | 89.1 | 91.7 | 90.9 | 91.9 |
| 7_25_31_47 | 88.9 | 89.6 | 88.7 | 91.7 | 90.9 | 91.9 |
| 4_7_31_82 | 88.6 | 83.6 | 89.9 | 91 | 87.9 | 91.9 |
| 2_7_9_105 | 91.4 | 83.6 | 93.5 | 90.4 | 90.9 | 90.2 |
| 2_7_108_464 | 89.2 | 80.6 | 91.5 | 90.4 | 87.9 | 91.1 |
| 2_10_25_105 | 90.2 | 88.1 | 90.7 | 89.1 | 87.9 | 89.4 |
| 4_28_31_82 | 87.6 | 82.1 | 89.1 | 89.1 | 87.9 | 89.4 |
| 10_47_90_101 | 91.1 | 92.5 | 90.7 | 88.5 | 90.9 | 87.8 |
| 10_30_103_365 | 86.3 | 85.1 | 86.7 | 88.5 | 84.8 | 89.4 |
| 9_10_61_68 | 90.5 | 86.6 | 91.5 | 88.5 | 78.8 | 91.1 |
| 10_48_68_90 | 93.7 | 89.6 | 94.8 | 88.5 | 75.8 | 91.9 |
| 10_30_68_365 | 91.1 | 82.1 | 93.5 | 88.5 | 75.8 | 91.9 |
| 4_7_10_82 | 88.9 | 86.6 | 89.5 | 87.8 | 84.8 | 88.6 |
| 4_6_10_105 | 81 | 83.6 | 80.2 | 78.8 | 78.8 | 78.9 |

Example 51

<Method B for Evaluating Pancreatic Cancer Discriminant Performance by Combination of Multiple Gene Markers Using Samples in the Validation Cohort>

Example 2 showed that discriminant performance was improved by using a combination of the multiple gene markers selected in Example 1, as compared with using one of the gene marker. Thus, in this Example, even the gene markers that were not selected in Example 1 were studied as to whether high pancreatic cancer discriminant performance is obtained by combinations with the gene markers selected in Example 1.

Specifically, among the genes having a gene expression level of $2^6$ or higher in 50% or more of the samples in either of the pancreatic cancer patient group in the training cohort or the healthy subject group in the training cohort, genes that showed statistical significance for discriminating a pancreatic cancer patient group from a healthy subject group with the P value smaller than 0.5 calculated by two-tailed t-test assuming equal variance as to each gene expression level and corrected by the Bonferroni method, were examined. As a result, 161 genes containing the 122 genes selected in Example 1 were found. Fisher's discriminant analysis was conducted as to 13,042 combinations using one or two of these 161 genes, to construct a discriminant for determining the presence or absence of pancreatic cancer. The discriminant performance of the selected combinations of 1 or 2 of the genes was validated in the same way as the method of Example 2.

As a result, some combinations of these genes exhibited accuracy of 85% or higher in both of the training cohort and the validation cohort and are shown in Table 12. For example, the newly found polynucleotide consisting of the nucleotide sequence represented by SEQ ID NO: 492, 493, or 494 discriminated the pancreatic cancer patients from the healthy subjects with high discriminant performance when used in combination of two polynucleotides comprising any of the polynucleotides consisting of the nucleotide sequences represented by SEQ ID NOs: 1 to 122. More specifically, the polynucleotide consisting of the nucleotide sequence represented by SEQ ID NO: 492, 493, or 494 was able to exhibit discrimination accuracy of 85% or higher between the pancreatic cancer patients and the healthy subjects in both of the training cohort and the validation cohort when used in combination of two polynucleotides comprising any of the polynucleotides consisting of the nucleotide sequences represented by SEQ ID NOs: 1, 2, 4, 7, 15, 24, 105, 107, and 108. Examples of such combinations of two genes include combinations of SEQ ID NOs: 105 and 492, SEQ ID NOs: 105 and 493, SEQ ID NOs: 1 and 492, SEQ ID NOs: 105 and 494, SEQ ID NOs: 1 and 493, SEQ ID NOs: 1 and 494, SEQ ID NOs: 107 and 493, SEQ ID NOs: 2 and 493, SEQ ID NOs: 7 and 493, SEQ ID NOs: 4 and 493, SEQ ID NOs: 2 and 492, SEQ ID NOs: 108 and 492, SEQ ID NOs: 2 and 494, SEQ ID NOs: 7 and 492, SEQ ID NOs: 7 and 494, SEQ ID NOs: 108 and 494, SEQ ID NOs: 4 and 492, SEQ ID NOs: 107 and 492, SEQ ID NOs: 107 and 494, SEQ ID NOs: 108 and 493, SEQ ID NOs: 15 and 492, SEQ ID NOs: 24 and 493, and SEQ ID NOs: 15 and 494.

As one example, an attempt was made to discriminate the pancreatic cancer patients from the healthy subjects using the expression level measurement values of the nucleotide sequences represented by SEQ ID NO: 105 and SEQ ID NO: 492. As a result, discriminant performance as high as 97.6% accuracy, 95.5% sensitivity, and 99.0% specificity in the training cohort and 96.4% accuracy, 93.9% sensitivity, and 98.0% specificity in the validation cohort was obtained.

From these results, it can be concluded that all of the polynucleotides consisting of the nucleotide sequences represented by SEQ ID NOs: 492 to 494 are also excellent diagnostic markers.

Table 12 mentioned above is as follows.

firmed for each sample to assess the ability of these tumor markers to detect cancer in pancreatic cancer patients. The sensitivity of each existing marker in the training cohort and the validation cohort was calculated. The results are shown in Table 5. The sensitivity of CEA and CA19-9 was as low as 55.2% and 77.6%, respectively, in the training cohort, and was as low as 45.5% and 75.8%, respectively, in the validation cohort, demonstrating that neither of the markers are useful in the detection of pancreatic cancer (Table 5).

On the other hand, as shown above in Tables 3 and 6 of Examples 1 and 2, it can be concluded that in all of the polynucleotides consisting of the nucleotide sequences represented by SEQ ID NOs: 1 to 122, combinations of 1, 2 or more polynucleotides exhibiting sensitivity beyond the existing pancreatic cancer markers are present, and thus such polynucleotides serve as excellent diagnosis markers.

As shown in these Examples and Comparative Example, the kit and the method of the present invention can detect pancreatic cancer with higher sensitivity than the existing tumor markers and therefore permit early decision to carry out the surgical resection of a cancer site. As a result,

TABLE 12

| | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 105_492 | 97.6 | 95.5 | 99.0 | 96.4 | 93.9 | 98.0 |
| 105_493 | 97.6 | 95.5 | 99.0 | 96.4 | 93.9 | 98.0 |
| 1_492 | 97.6 | 97.0 | 98.0 | 94.0 | 90.9 | 96.0 |
| 105_494 | 96.4 | 94.0 | 98.0 | 96.4 | 93.9 | 98.0 |
| 1_493 | 95.8 | 92.5 | 98.0 | 92.8 | 87.9 | 96.0 |
| 1_494 | 95.8 | 94.0 | 97.0 | 92.8 | 87.9 | 96.0 |
| 107_493 | 94.0 | 88.1 | 98.0 | 89.2 | 84.8 | 92.0 |
| 2_493 | 92.2 | 83.6 | 98.0 | 95.2 | 90.9 | 98.0 |
| 7_493 | 91.0 | 89.6 | 92.0 | 90.4 | 90.9 | 90.0 |
| 4_493 | 91.0 | 85.1 | 95.0 | 88.0 | 87.9 | 88.0 |
| 2_492 | 90.4 | 79.1 | 98.0 | 96.4 | 93.9 | 98.0 |
| 108_492 | 89.8 | 86.6 | 92.0 | 89.2 | 87.9 | 90.0 |
| 2_494 | 89.2 | 79.1 | 96.0 | 95.2 | 93.9 | 96.0 |
| 7_492 | 88.6 | 89.6 | 88.0 | 86.7 | 90.9 | 84.0 |
| 7_494 | 88.6 | 85.1 | 91.0 | 90.4 | 90.9 | 90.0 |
| 108_494 | 88.6 | 83.6 | 92.0 | 88.0 | 87.9 | 88.0 |
| 4_492 | 88.0 | 79.1 | 94.0 | 89.2 | 90.9 | 88.0 |
| 107_492 | 88.0 | 83.6 | 91.0 | 85.5 | 84.8 | 86.0 |
| 107_494 | 87.4 | 83.6 | 90.0 | 86.7 | 84.8 | 88.0 |
| 108_493 | 86.8 | 83.6 | 89.0 | 86.7 | 84.8 | 88.0 |
| 15_492 | 85.6 | 76.1 | 92.0 | 88.0 | 84.8 | 90.0 |
| 24_493 | 85.6 | 83.6 | 87.0 | 86.7 | 84.8 | 88.0 |
| 15_494 | 85.6 | 74.6 | 93.0 | 86.7 | 78.8 | 92.0 |

Comparative Example 1

<Pancreatic Cancer Discriminant Performance of Existing Tumor Markers in Blood>

The concentrations of the existing tumor markers CEA and CA19-9 in blood were measured in the training cohort and the validation cohort obtained in the preceding Reference Examples. When the concentrations of these tumor markers in blood are higher than the reference values described in Non-Patent Literature 3 above (CEA: 5 ng/mL, CA19-9: 37 U/mL), subjects are usually suspected of having cancer. Thus, whether or not the concentrations of CEA and CA19-9 in blood exceeded their reference values was conimprovement in 5-year survival rate and reduction in the rate of recurrence can be achieved.

INDUSTRIAL APPLICABILITY

According to the present invention, pancreatic cancer can be effectively detected by a simple and inexpensive method. This enables early detection, diagnosis and treatment of pancreatic cancer. The method of the present invention can detect pancreatic cancer with limited invasiveness using the blood of a patient and therefore allows pancreatic cancer to be detected conveniently and rapidly.

All publications, patents, and patent applications cited herein are incorporated herein by reference in their entirety.

Sequence Listing

The invention claimed is:

1. A method for detecting pancreatic cancer in a human subject, comprising:
   (a) measuring an expression level of hsa-miR-4665-5p in a blood, serum or plasma sample from the subject:
   (b) comparing the measured expression level of hsa-miR-4665-5p with a control expression level obtained from a healthy subject:
   (c) detecting a decreased expression level of hsa-miR-4665-5p in the sample from the subject as compared to the control expression level,
   wherein the decreased expression level of hsa-miR-4665-5p indicates that the subject has pancreatic cancer; and
   (d) treating the subject for pancreatic cancer or performing a diagnostic procedure on the subject,
   wherein the treatment comprises surgery, radiotherapy, chemotherapy or a combination thereof, and
   wherein the diagnostic procedure comprises abdominal ultrasonography, CT scanning, endoscopic retrograde cholangiopancreatography, or endoscopic ultrasonography, or a combination thereof.

2. The method according to claim 1, wherein the expression level of hsa-miR-4665-5p in the sample is measured by using a kit or device comprising a nucleic acid(s) capable of specifically binding to hsa-miR-4665-5p.

3. The method according to claim 2, wherein the kit or device further comprises one or more nucleic acids capable of specifically binding to one or more other human pancreatic cancer markers selected from the group consisting of: miR-6893-5p, miR-6075, miR-6820-5p, miR-6729-5p, miR-4476, miR-6836-3p, miR-6765-3p, miR-6799-5p, miR-4530, miR-7641, miR-4454, miR-615-5p, miR-8073, miR-663a, miR-4634, miR-4450, miR-4792, miR-7975, miR-7109-5p, miR-6789-5p, miR-4497, miR-6877-5p, miR-6880-5p, miR-7977, miR-4734, miR-6821-5p, miR-8089, miR-5585-3p, miR-6085, miR-6845-5p, miR-4651, miR-4433-3p, miR-1231, miR-7114-5p, miR-1238-5p, miR-8069, miR-4732-5p, miR-619-5p, miR-3622a-5p, miR-1260a, miR-6741-5p, miR-6781-5p, miR-6125, miR-6805-5p, miR-6132, miR-6872-3p, miR-6875-5p, miR-1908-3p, miR-4433b-3p, miR-4736, miR-5100, miR-6724-5p, miR-7107-5p, miR-6726-5p, miR-3185, miR-4638-5p, miR-1273g-3p, miR-6778-5p, miR-328-5p, miR-3679-3p, miR-1228-3p, miR-6779-5p, miR-4723-5p, miR-6850-5p, miR-760, miR-7704, miR-8072, miR-4486, miR-1913, miR-4656, miR-1260b, miR-7106-5p, miR-6889-5p, miR-6780b-5p, miR-6090, miR-4534, miR-4449, miR-5195-3p, miR-1202, miR-4467, miR-6515-3p, miR-4281, miR-4505, miR-4484, miR-6805-3p, miR-3135b, miR-3162-5p, miR-6768-5p, miR-6721-5p, miR-1227-5p, miR-6722-3p, miR-4286, miR-4746-3p, miR-6727-5p, miR-6816-5p, miR-4741, miR-4508, miR-940, miR-4327, miR-4665-3p, miR-718, miR-1203, miR-663b, miR-4258, miR-4649-5p, miR-4516, miR-3619-3p, miR-6826-5p, miR-6757-5p, miR-3131, miR-1343-3p, miR-6775-5p, miR-6813-5p, miR-3940-5p, miR-125a-3p, miR-204-3p, miR-1469, miR-575, miR-150-3p, miR-423-5p, miR-564, miR-3188, miR-1246, miR-602, miR-1290, miR-16-5p, miR-451a, miR-24-3p, miR-187-5p, miR-1908-5p, miR-371a-5p, miR-550a-5p, miR-4417, miR-4707-5p, miR-7847-3p, miR-2861, miR-4513, miR-7111-5p, miR-6777-5p, miR-7113-3p, miR-4648, miR-3184-5p, miR-4271, miR-6791-5p, miR-642a-3p, miR-7108-5p, miR-128-1-5p, miR-5196-5p, miR-3178, miR-3656, miR-92a-2-5p, miR-6769b-5p, miR-4689, miR-6076, miR-92b-5p, miR-6774-5p, miR-486-3p, miR-6806-5p, miR-6842-5p, miR-6716-5p, miR-557, miR-4673, miR-4674, miR-4442, miR-1915-3p, miR-4687-3p, and miR-92b-3p.

4. The method according to claim 1, wherein the step (b) further comprises preparing a discriminant based on a set formula to determine whether or not the subject has pancreatic cancer.

5. The method according to claim 4, wherein the discriminant is compared to a set threshold to determine whether or not the subject has pancreatic cancer.

* * * * *

```
                           SEQUENCE LISTING

Sequence total quantity: 499
SEQ ID NO: 1              moltype = RNA   length = 21
FEATURE                   Location/Qualifiers
source                    1..21
                          mol_type = transcribed RNA
                          organism = Homo sapiens
SEQUENCE: 1
caggcaggtg tagggtggag c                                               21

SEQ ID NO: 2              moltype = RNA   length = 21
FEATURE                   Location/Qualifiers
source                    1..21
                          mol_type = transcribed RNA
                          organism = Homo sapiens
SEQUENCE: 2
acggcccagg cggcattggt g                                               21

SEQ ID NO: 3              moltype = RNA   length = 19
FEATURE                   Location/Qualifiers
source                    1..19
                          mol_type = transcribed RNA
                          organism = Homo sapiens
SEQUENCE: 3
tgcggcagag ctgggtca                                                   19

SEQ ID NO: 4              moltype = RNA   length = 17
FEATURE                   Location/Qualifiers
source                    1..17
                          mol_type = transcribed RNA
                          organism = Homo sapiens
SEQUENCE: 4
gggagtctac agcaggg                                                    17

SEQ ID NO: 5              moltype = RNA   length = 22
FEATURE                   Location/Qualifiers
source                    1..22
                          mol_type = transcribed RNA
                          organism = Homo sapiens
SEQUENCE: 5
tgggcgaggg cggctgagcg gc                                              22

SEQ ID NO: 6              moltype = RNA   length = 22
FEATURE                   Location/Qualifiers
source                    1..22
                          mol_type = transcribed RNA
                          organism = Homo sapiens
SEQUENCE: 6
caggaaggat ttagggacag gc                                              22

SEQ ID NO: 7              moltype = RNA   length = 21
FEATURE                   Location/Qualifiers
source                    1..21
                          mol_type = transcribed RNA
                          organism = Homo sapiens
SEQUENCE: 7
atgcctcccc cggccccgca g                                               21

SEQ ID NO: 8              moltype = RNA   length = 21
FEATURE                   Location/Qualifiers
source                    1..21
                          mol_type = transcribed RNA
                          organism = Homo sapiens
SEQUENCE: 8
tcacctggct ggcccgccca g                                               21

SEQ ID NO: 9              moltype = RNA   length = 20
FEATURE                   Location/Qualifiers
source                    1..20
                          mol_type = transcribed RNA
                          organism = Homo sapiens
SEQUENCE: 9
ggggaggtgt gcagggctgg                                                 20

SEQ ID NO: 10             moltype = RNA   length = 18
FEATURE                   Location/Qualifiers
```

```
source                  1..18
                        mol_type = transcribed RNA
                        organism = Homo sapiens
SEQUENCE: 10
cccagcagga cgggagcg                                                        18

SEQ ID NO: 11           moltype = RNA   length = 19
FEATURE                 Location/Qualifiers
source                  1..19
                        mol_type = transcribed RNA
                        organism = Homo sapiens
SEQUENCE: 11
ttgatctcgg aagctaagc                                                       19

SEQ ID NO: 12           moltype = RNA   length = 20
FEATURE                 Location/Qualifiers
source                  1..20
                        mol_type = transcribed RNA
                        organism = Homo sapiens
SEQUENCE: 12
ggatccgagt cacggcacca                                                      20

SEQ ID NO: 13           moltype = RNA   length = 22
FEATURE                 Location/Qualifiers
source                  1..22
                        mol_type = transcribed RNA
                        organism = Homo sapiens
SEQUENCE: 13
gggggtcccc ggtgctcgga tc                                                   22

SEQ ID NO: 14           moltype = RNA   length = 22
FEATURE                 Location/Qualifiers
source                  1..22
                        mol_type = transcribed RNA
                        organism = Homo sapiens
SEQUENCE: 14
acctggcagc agggagcgtc gt                                                   22

SEQ ID NO: 15           moltype = RNA   length = 22
FEATURE                 Location/Qualifiers
source                  1..22
                        mol_type = transcribed RNA
                        organism = Homo sapiens
SEQUENCE: 15
aggcggggcg ccgcgggacc gc                                                   22

SEQ ID NO: 16           moltype = RNA   length = 19
FEATURE                 Location/Qualifiers
source                  1..19
                        mol_type = transcribed RNA
                        organism = Homo sapiens
SEQUENCE: 16
cggcgcgacc ggcccgggg                                                       19

SEQ ID NO: 17           moltype = RNA   length = 22
FEATURE                 Location/Qualifiers
source                  1..22
                        mol_type = transcribed RNA
                        organism = Homo sapiens
SEQUENCE: 17
tggggatttg gagaagtggt ga                                                   22

SEQ ID NO: 18           moltype = RNA   length = 18
FEATURE                 Location/Qualifiers
source                  1..18
                        mol_type = transcribed RNA
                        organism = Homo sapiens
SEQUENCE: 18
cggtgagcgc tcgctggc                                                        18

SEQ ID NO: 19           moltype = RNA   length = 20
FEATURE                 Location/Qualifiers
source                  1..20
                        mol_type = transcribed RNA
                        organism = Homo sapiens
SEQUENCE: 19
accaggaggc tgaggcccct                                                      20

SEQ ID NO: 20           moltype = RNA   length = 18
```

```
FEATURE              Location/Qualifiers
source               1..18
                     mol_type = transcribed RNA
                     organism = Homo sapiens
SEQUENCE: 20
atcctagtca cggcacca                                                    18

SEQ ID NO: 21        moltype = RNA   length = 21
FEATURE              Location/Qualifiers
source               1..21
                     mol_type = transcribed RNA
                     organism = Homo sapiens
SEQUENCE: 21
ctgggggag gagaccctgc t                                                 21

SEQ ID NO: 22        moltype = RNA   length = 24
FEATURE              Location/Qualifiers
source               1..24
                     mol_type = transcribed RNA
                     organism = Homo sapiens
SEQUENCE: 22
gtagggcgt cccgggcgcg cggg                                              24

SEQ ID NO: 23        moltype = RNA   length = 17
FEATURE              Location/Qualifiers
source               1..17
                     mol_type = transcribed RNA
                     organism = Homo sapiens
SEQUENCE: 23
ctccgggacg gctgggc                                                     17

SEQ ID NO: 24        moltype = RNA   length = 22
FEATURE              Location/Qualifiers
source               1..22
                     mol_type = transcribed RNA
                     organism = Homo sapiens
SEQUENCE: 24
agggccgaag ggtggaagct gc                                               22

SEQ ID NO: 25        moltype = RNA   length = 22
FEATURE              Location/Qualifiers
source               1..22
                     mol_type = transcribed RNA
                     organism = Homo sapiens
SEQUENCE: 25
tggtggagga agagggcagc tc                                               22

SEQ ID NO: 26        moltype = RNA   length = 18
FEATURE              Location/Qualifiers
source               1..18
                     mol_type = transcribed RNA
                     organism = Homo sapiens
SEQUENCE: 26
ttcccagcca acgcacca                                                    18

SEQ ID NO: 27        moltype = RNA   length = 22
FEATURE              Location/Qualifiers
source               1..22
                     mol_type = transcribed RNA
                     organism = Homo sapiens
SEQUENCE: 27
gctgcgggct gcggtcaggg cg                                               22

SEQ ID NO: 28        moltype = RNA   length = 23
FEATURE              Location/Qualifiers
source               1..23
                     mol_type = transcribed RNA
                     organism = Homo sapiens
SEQUENCE: 28
gtgcgtggtg gctcgaggcg ggg                                              23

SEQ ID NO: 29        moltype = RNA   length = 24
FEATURE              Location/Qualifiers
source               1..24
                     mol_type = transcribed RNA
                     organism = Homo sapiens
SEQUENCE: 29
cctggggaca ggggattggg gcag                                             24
```

| | | |
|---|---|---|
| SEQ ID NO: 30<br>FEATURE<br>source | moltype = RNA   length = 22<br>Location/Qualifiers<br>1..22<br>mol_type = transcribed RNA<br>organism = Homo sapiens | |
| SEQUENCE: 30<br>ctgaatagct gggactacag gt | | 22 |
| SEQ ID NO: 31<br>FEATURE<br>source | moltype = RNA   length = 19<br>Location/Qualifiers<br>1..19<br>mol_type = transcribed RNA<br>organism = Homo sapiens | |
| SEQUENCE: 31<br>aaggggctgg gggagcaca | | 19 |
| SEQ ID NO: 32<br>FEATURE<br>source | moltype = RNA   length = 19<br>Location/Qualifiers<br>1..19<br>mol_type = transcribed RNA<br>organism = Homo sapiens | |
| SEQUENCE: 32<br>cggggccaga gcagagagc | | 19 |
| SEQ ID NO: 33<br>FEATURE<br>source | moltype = RNA   length = 20<br>Location/Qualifiers<br>1..20<br>mol_type = transcribed RNA<br>organism = Homo sapiens | |
| SEQUENCE: 33<br>cggggtgggt gaggtcgggc | | 20 |
| SEQ ID NO: 34<br>FEATURE<br>source | moltype = RNA   length = 21<br>Location/Qualifiers<br>1..21<br>mol_type = transcribed RNA<br>organism = Homo sapiens | |
| SEQUENCE: 34<br>acaggagtgg gggtgggaca t | | 21 |
| SEQ ID NO: 35<br>FEATURE<br>source | moltype = RNA   length = 20<br>Location/Qualifiers<br>1..20<br>mol_type = transcribed RNA<br>organism = Homo sapiens | |
| SEQUENCE: 35<br>gtgtctgggc ggacagctgc | | 20 |
| SEQ ID NO: 36<br>FEATURE<br>source | moltype = RNA   length = 23<br>Location/Qualifiers<br>1..23<br>mol_type = transcribed RNA<br>organism = Homo sapiens | |
| SEQUENCE: 36<br>ctggggacg cgtgagcgcg agc | | 23 |
| SEQ ID NO: 37<br>FEATURE<br>source | moltype = RNA   length = 21<br>Location/Qualifiers<br>1..21<br>mol_type = transcribed RNA<br>organism = Homo sapiens | |
| SEQUENCE: 37<br>tctgtggagt ggggtgcctg t | | 21 |
| SEQ ID NO: 38<br>FEATURE<br>source | moltype = RNA   length = 23<br>Location/Qualifiers<br>1..23<br>mol_type = transcribed RNA<br>organism = Homo sapiens | |
| SEQUENCE: 38<br>gtgagtggga gccccagtgt gtg | | 23 |
| SEQ ID NO: 39<br>FEATURE<br>source | moltype = RNA   length = 23<br>Location/Qualifiers<br>1..23<br>mol_type = transcribed RNA<br>organism = Homo sapiens | |
| SEQUENCE: 39<br>ggatggttgg gggcggtcgg cgt | | 23 |

| SEQ ID NO: 40 | moltype = RNA  length = 23 |
| --- | --- |
| FEATURE | Location/Qualifiers |
| source | 1..23 |
| | mol_type = transcribed RNA |
| | organism = Homo sapiens |

SEQUENCE: 40
tgtagagcag ggagcaggaa gct                                              23

| SEQ ID NO: 41 | moltype = RNA  length = 22 |
| --- | --- |
| FEATURE | Location/Qualifiers |
| source | 1..22 |
| | mol_type = transcribed RNA |
| | organism = Homo sapiens |

SEQUENCE: 41
gctgggatta caggcatgag cc                                               22

| SEQ ID NO: 42 | moltype = RNA  length = 22 |
| --- | --- |
| FEATURE | Location/Qualifiers |
| source | 1..22 |
| | mol_type = transcribed RNA |
| | organism = Homo sapiens |

SEQUENCE: 42
caggcacggg agctcaggtg ag                                               22

| SEQ ID NO: 43 | moltype = RNA  length = 18 |
| --- | --- |
| FEATURE | Location/Qualifiers |
| source | 1..18 |
| | mol_type = transcribed RNA |
| | organism = Homo sapiens |

SEQUENCE: 43
atcccacctc tgccacca                                                    18

| SEQ ID NO: 44 | moltype = RNA  length = 22 |
| --- | --- |
| FEATURE | Location/Qualifiers |
| source | 1..22 |
| | mol_type = transcribed RNA |
| | organism = Homo sapiens |

SEQUENCE: 44
gtgggtgctg gtgggagccg tg                                               22

| SEQ ID NO: 45 | moltype = RNA  length = 21 |
| --- | --- |
| FEATURE | Location/Qualifiers |
| source | 1..21 |
| | mol_type = transcribed RNA |
| | organism = Homo sapiens |

SEQUENCE: 45
cgggccggag gtcaagggcg t                                                21

| SEQ ID NO: 46 | moltype = RNA  length = 20 |
| --- | --- |
| FEATURE | Location/Qualifiers |
| source | 1..20 |
| | mol_type = transcribed RNA |
| | organism = Homo sapiens |

SEQUENCE: 46
gcggaaggcg gagcggcgga                                                  20

| SEQ ID NO: 47 | moltype = RNA  length = 22 |
| --- | --- |
| FEATURE | Location/Qualifiers |
| source | 1..22 |
| | mol_type = transcribed RNA |
| | organism = Homo sapiens |

SEQUENCE: 47
taggggcgg cttgtggagt gt                                                22

| SEQ ID NO: 48 | moltype = RNA  length = 19 |
| --- | --- |
| FEATURE | Location/Qualifiers |
| source | 1..19 |
| | mol_type = transcribed RNA |
| | organism = Homo sapiens |

SEQUENCE: 48
agcagggctg gggattgca                                                   19

| SEQ ID NO: 49 | moltype = RNA  length = 21 |
| --- | --- |
| FEATURE | Location/Qualifiers |
| source | 1..21 |
| | mol_type = transcribed RNA |
| | organism = Homo sapiens |

-continued

```
SEQUENCE: 49
cccatgcctc ctgccgcggt c                                              21

SEQ ID NO: 50          moltype = RNA   length = 21
FEATURE                Location/Qualifiers
source                 1..21
                       mol_type = transcribed RNA
                       organism = Homo sapiens
SEQUENCE: 50
tgagggaccc aggacaggag a                                              21

SEQ ID NO: 51          moltype = RNA   length = 21
FEATURE                Location/Qualifiers
source                 1..21
                       mol_type = transcribed RNA
                       organism = Homo sapiens
SEQUENCE: 51
ccggccgccg gctccgcccc g                                              21

SEQ ID NO: 52          moltype = RNA   length = 21
FEATURE                Location/Qualifiers
source                 1..21
                       mol_type = transcribed RNA
                       organism = Homo sapiens
SEQUENCE: 52
caggagtggg gggtgggacg t                                              21

SEQ ID NO: 53          moltype = RNA   length = 19
FEATURE                Location/Qualifiers
source                 1..19
                       mol_type = transcribed RNA
                       organism = Homo sapiens
SEQUENCE: 53
aggcaggtta tctgggctg                                                 19

SEQ ID NO: 54          moltype = RNA   length = 22
FEATURE                Location/Qualifiers
source                 1..22
                       mol_type = transcribed RNA
                       organism = Homo sapiens
SEQUENCE: 54
ttcagatccc agcggtgcct ct                                             22

SEQ ID NO: 55          moltype = RNA   length = 23
FEATURE                Location/Qualifiers
source                 1..23
                       mol_type = transcribed RNA
                       organism = Homo sapiens
SEQUENCE: 55
ctgggcccgc ggcgggcgtg ggg                                            23

SEQ ID NO: 56          moltype = RNA   length = 22
FEATURE                Location/Qualifiers
source                 1..22
                       mol_type = transcribed RNA
                       organism = Homo sapiens
SEQUENCE: 56
tcggcctggg gaggaggaag gg                                             22

SEQ ID NO: 57          moltype = RNA   length = 21
FEATURE                Location/Qualifiers
source                 1..21
                       mol_type = transcribed RNA
                       organism = Homo sapiens
SEQUENCE: 57
cgggagctgg ggtctgcagg t                                              21

SEQ ID NO: 58          moltype = RNA   length = 23
FEATURE                Location/Qualifiers
source                 1..23
                       mol_type = transcribed RNA
                       organism = Homo sapiens
SEQUENCE: 58
agaagaaggc ggtcggtctg cgg                                            23

SEQ ID NO: 59          moltype = RNA   length = 21
FEATURE                Location/Qualifiers
```

```
                        -continued source                  1..21
                        mol_type = transcribed RNA
                        organism = Homo sapiens
SEQUENCE: 59
actcggctgc ggtggacaag t                                          21

SEQ ID NO: 60           moltype = RNA  length = 21
FEATURE                 Location/Qualifiers
source                  1..21
                        mol_type = transcribed RNA
                        organism = Homo sapiens
SEQUENCE: 60
accactgcac tccagcctga g                                          21

SEQ ID NO: 61           moltype = RNA  length = 22
FEATURE                 Location/Qualifiers
source                  1..22
                        mol_type = transcribed RNA
                        organism = Homo sapiens
SEQUENCE: 61
agtgggagga caggaggcag gt                                         22

SEQ ID NO: 62           moltype = RNA  length = 23
FEATURE                 Location/Qualifiers
source                  1..23
                        mol_type = transcribed RNA
                        organism = Homo sapiens
SEQUENCE: 62
ggggggcag gagggctca ggg                                          23

SEQ ID NO: 63           moltype = RNA  length = 22
FEATURE                 Location/Qualifiers
source                  1..22
                        mol_type = transcribed RNA
                        organism = Homo sapiens
SEQUENCE: 63
cttccccca gtaatcttca tc                                          22

SEQ ID NO: 64           moltype = RNA  length = 20
FEATURE                 Location/Qualifiers
source                  1..20
                        mol_type = transcribed RNA
                        organism = Homo sapiens
SEQUENCE: 64
tcacacctgc ctcgccccc                                             20

SEQ ID NO: 65           moltype = RNA  length = 21
FEATURE                 Location/Qualifiers
source                  1..21
                        mol_type = transcribed RNA
                        organism = Homo sapiens
SEQUENCE: 65
ctgggagggg ctgggtttgg c                                          21

SEQ ID NO: 66           moltype = RNA  length = 24
FEATURE                 Location/Qualifiers
source                  1..24
                        mol_type = transcribed RNA
                        organism = Homo sapiens
SEQUENCE: 66
tgggggagcc atgagataag agca                                       24

SEQ ID NO: 67           moltype = RNA  length = 22
FEATURE                 Location/Qualifiers
source                  1..22
                        mol_type = transcribed RNA
                        organism = Homo sapiens
SEQUENCE: 67
gtgcggaacg ctggccgggg cg                                         22

SEQ ID NO: 68           moltype = RNA  length = 20
FEATURE                 Location/Qualifiers
source                  1..20
                        mol_type = transcribed RNA
                        organism = Homo sapiens
SEQUENCE: 68
cggctctggg tctgtgggga                                            20

SEQ ID NO: 69           moltype = RNA  length = 19
```

```
FEATURE            Location/Qualifiers
source             1..19
                   mol_type = transcribed RNA
                   organism = Homo sapiens
SEQUENCE: 69
cggggtcggc ggcgacgtg                                              19

SEQ ID NO: 70      moltype = RNA   length = 20
FEATURE            Location/Qualifiers
source             1..20
                   mol_type = transcribed RNA
                   organism = Homo sapiens
SEQUENCE: 70
ggcggcgggg aggtaggcag                                             20

SEQ ID NO: 71      moltype = RNA   length = 17
FEATURE            Location/Qualifiers
source             1..17
                   mol_type = transcribed RNA
                   organism = Homo sapiens
SEQUENCE: 71
gctgggcgag gctggca                                                17

SEQ ID NO: 72      moltype = RNA   length = 22
FEATURE            Location/Qualifiers
source             1..22
                   mol_type = transcribed RNA
                   organism = Homo sapiens
SEQUENCE: 72
tctgccccct ccgctgctgc ca                                          22

SEQ ID NO: 73      moltype = RNA   length = 23
FEATURE            Location/Qualifiers
source             1..23
                   mol_type = transcribed RNA
                   organism = Homo sapiens
SEQUENCE: 73
tgggctgagg gcaggaggcc tgt                                         23

SEQ ID NO: 74      moltype = RNA   length = 19
FEATURE            Location/Qualifiers
source             1..19
                   mol_type = transcribed RNA
                   organism = Homo sapiens
SEQUENCE: 74
atcccaccac tgccaccat                                              19

SEQ ID NO: 75      moltype = RNA   length = 20
FEATURE            Location/Qualifiers
source             1..20
                   mol_type = transcribed RNA
                   organism = Homo sapiens
SEQUENCE: 75
tgggaggagg ggatcttggg                                             20

SEQ ID NO: 76      moltype = RNA   length = 23
FEATURE            Location/Qualifiers
source             1..23
                   mol_type = transcribed RNA
                   organism = Homo sapiens
SEQUENCE: 76
tcggggagtc tggggtccgg aat                                         23

SEQ ID NO: 77      moltype = RNA   length = 23
FEATURE            Location/Qualifiers
source             1..23
                   mol_type = transcribed RNA
                   organism = Homo sapiens
SEQUENCE: 77
tggggaaggc ttggcaggga aga                                         23

SEQ ID NO: 78      moltype = RNA   length = 19
FEATURE            Location/Qualifiers
source             1..19
                   mol_type = transcribed RNA
                   organism = Homo sapiens
SEQUENCE: 78
ggggagcgag gggcgggc                                               19
```

```
SEQ ID NO: 79           moltype = RNA   length = 17
FEATURE                 Location/Qualifiers
source                  1..17
                        mol_type = transcribed RNA
                        organism = Homo sapiens
SEQUENCE: 79
ggatggagga ggggtct                                                        17

SEQ ID NO: 80           moltype = RNA   length = 22
FEATURE                 Location/Qualifiers
source                  1..22
                        mol_type = transcribed RNA
                        organism = Homo sapiens
SEQUENCE: 80
cgtcccgggg ctgcgcgagg ca                                                  22

SEQ ID NO: 81           moltype = RNA   length = 21
FEATURE                 Location/Qualifiers
source                  1..21
                        mol_type = transcribed RNA
                        organism = Homo sapiens
SEQUENCE: 81
atccagttct ctgaggggc t                                                    21

SEQ ID NO: 82           moltype = RNA   length = 21
FEATURE                 Location/Qualifiers
source                  1..21
                        mol_type = transcribed RNA
                        organism = Homo sapiens
SEQUENCE: 82
gtgccagctg cagtggggga g                                                   21

SEQ ID NO: 83           moltype = RNA   length = 22
FEATURE                 Location/Qualifiers
source                  1..22
                        mol_type = transcribed RNA
                        organism = Homo sapiens
SEQUENCE: 83
tggcggcggt agttatgggc tt                                                  22

SEQ ID NO: 84           moltype = RNA   length = 20
FEATURE                 Location/Qualifiers
source                  1..20
                        mol_type = transcribed RNA
                        organism = Homo sapiens
SEQUENCE: 84
tctcttcatc tacccccag                                                      20

SEQ ID NO: 85           moltype = RNA   length = 18
FEATURE                 Location/Qualifiers
source                  1..18
                        mol_type = transcribed RNA
                        organism = Homo sapiens
SEQUENCE: 85
gggtcccggg gagggggg                                                       18

SEQ ID NO: 86           moltype = RNA   length = 18
FEATURE                 Location/Qualifiers
source                  1..18
                        mol_type = transcribed RNA
                        organism = Homo sapiens
SEQUENCE: 86
aggctgggct gggacgga                                                       18

SEQ ID NO: 87           moltype = RNA   length = 20
FEATURE                 Location/Qualifiers
source                  1..20
                        mol_type = transcribed RNA
                        organism = Homo sapiens
SEQUENCE: 87
aaaaggcggg agaagcccca                                                     20

SEQ ID NO: 88           moltype = RNA   length = 23
FEATURE                 Location/Qualifiers
source                  1..23
                        mol_type = transcribed RNA
                        organism = Homo sapiens
SEQUENCE: 88
ttgctctgct ccccgccc cag                                                   23
```

```
SEQ ID NO: 89            moltype = RNA   length = 22
FEATURE                  Location/Qualifiers
source                   1..22
                         mol_type = transcribed RNA
                         organism = Homo sapiens
SEQUENCE: 89
ggctggagcg agtgcagtgg tg                                              22

SEQ ID NO: 90            moltype = RNA   length = 23
FEATURE                  Location/Qualifiers
source                   1..23
                         mol_type = transcribed RNA
                         organism = Homo sapiens
SEQUENCE: 90
ttagggagta aagggtggg gag                                              23

SEQ ID NO: 91            moltype = RNA   length = 23
FEATURE                  Location/Qualifiers
source                   1..23
                         mol_type = transcribed RNA
                         organism = Homo sapiens
SEQUENCE: 91
cacacaggaa aagcggggcc ctg                                             23

SEQ ID NO: 92            moltype = RNA   length = 23
FEATURE                  Location/Qualifiers
source                   1..23
                         mol_type = transcribed RNA
                         organism = Homo sapiens
SEQUENCE: 92
tgggcagggg cttattgtag gag                                             23

SEQ ID NO: 93            moltype = RNA   length = 17
FEATURE                  Location/Qualifiers
source                   1..17
                         mol_type = transcribed RNA
                         organism = Homo sapiens
SEQUENCE: 93
gtggggccag gcggtgg                                                    17

SEQ ID NO: 94            moltype = RNA   length = 22
FEATURE                  Location/Qualifiers
source                   1..22
                         mol_type = transcribed RNA
                         organism = Homo sapiens
SEQUENCE: 94
tgcaggggtc gggtgggcca gg                                              22

SEQ ID NO: 95            moltype = RNA   length = 17
FEATURE                  Location/Qualifiers
source                   1..17
                         mol_type = transcribed RNA
                         organism = Homo sapiens
SEQUENCE: 95
accccactcc tggtacc                                                    17

SEQ ID NO: 96            moltype = RNA   length = 21
FEATURE                  Location/Qualifiers
source                   1..21
                         mol_type = transcribed RNA
                         organism = Homo sapiens
SEQUENCE: 96
agcggtgctc ctgcgggccg a                                               21

SEQ ID NO: 97            moltype = RNA   length = 23
FEATURE                  Location/Qualifiers
source                   1..23
                         mol_type = transcribed RNA
                         organism = Homo sapiens
SEQUENCE: 97
ctcggggcag gcggctggga gcg                                             23

SEQ ID NO: 98            moltype = RNA   length = 21
FEATURE                  Location/Qualifiers
source                   1..21
                         mol_type = transcribed RNA
                         organism = Homo sapiens
```

-continued

| | | |
|---|---|---|
| SEQUENCE: 98 | | |
| tggggcgggg caggtccctg c | | 21 |
| SEQ ID NO: 99 | moltype = RNA length = 23 | |
| FEATURE | Location/Qualifiers | |
| source | 1..23<br>mol_type = transcribed RNA<br>organism = Homo sapiens | |
| SEQUENCE: 99 | | |
| cgggctgtcc ggaggggtcg gct | | 23 |
| SEQ ID NO: 100 | moltype = RNA length = 17 | |
| FEATURE | Location/Qualifiers | |
| source | 1..17<br>mol_type = transcribed RNA<br>organism = Homo sapiens | |
| SEQUENCE: 100 | | |
| gcggggctgg gcgcgcg | | 17 |
| SEQ ID NO: 101 | moltype = RNA length = 21 | |
| FEATURE | Location/Qualifiers | |
| source | 1..21<br>mol_type = transcribed RNA<br>organism = Homo sapiens | |
| SEQUENCE: 101 | | |
| aaggcagggc ccccgctccc c | | 21 |
| SEQ ID NO: 102 | moltype = RNA length = 19 | |
| FEATURE | Location/Qualifiers | |
| source | 1..19<br>mol_type = transcribed RNA<br>organism = Homo sapiens | |
| SEQUENCE: 102 | | |
| ggcttgcatg ggggactgg | | 19 |
| SEQ ID NO: 103 | moltype = RNA length = 26 | |
| FEATURE | Location/Qualifiers | |
| source | 1..26<br>mol_type = transcribed RNA<br>organism = Homo sapiens | |
| SEQUENCE: 103 | | |
| ctcggccgcg gcgcgtagcc cccgcc | | 26 |
| SEQ ID NO: 104 | moltype = RNA length = 21 | |
| FEATURE | Location/Qualifiers | |
| source | 1..21<br>mol_type = transcribed RNA<br>organism = Homo sapiens | |
| SEQUENCE: 104 | | |
| cttccgcccc gccgggcgtc g | | 21 |
| SEQ ID NO: 105 | moltype = RNA length = 22 | |
| FEATURE | Location/Qualifiers | |
| source | 1..22<br>mol_type = transcribed RNA<br>organism = Homo sapiens | |
| SEQUENCE: 105 | | |
| acaggtgagg ttcttgggag cc | | 22 |
| SEQ ID NO: 106 | moltype = RNA length = 21 | |
| FEATURE | Location/Qualifiers | |
| source | 1..21<br>mol_type = transcribed RNA<br>organism = Homo sapiens | |
| SEQUENCE: 106 | | |
| gctgggaagg caaagggacg t | | 21 |
| SEQ ID NO: 107 | moltype = RNA length = 22 | |
| FEATURE | Location/Qualifiers | |
| source | 1..22<br>mol_type = transcribed RNA<br>organism = Homo sapiens | |
| SEQUENCE: 107 | | |
| ctcggcgcgg ggcgcgggct cc | | 22 |
| SEQ ID NO: 108 | moltype = RNA length = 19 | |
| FEATURE | Location/Qualifiers | |

```
                                source          1..19
                                                mol_type = transcribed RNA
                                                organism = Homo sapiens
                SEQUENCE: 108
                gagccagttg gacaggagc                                                  19

SEQ ID NO: 109  moltype = RNA   length = 22
                FEATURE         Location/Qualifiers
                source          1..22
                                mol_type = transcribed RNA
                                organism = Homo sapiens
                SEQUENCE: 109
                ctggtacagg cctgggggac ag                                              22

SEQ ID NO: 110  moltype = RNA   length = 23
                FEATURE         Location/Qualifiers
                source          1..23
                                mol_type = transcribed RNA
                                organism = Homo sapiens
                SEQUENCE: 110
                tgaggggcag agagcgagac ttt                                             23

SEQ ID NO: 111  moltype = RNA   length = 19
                FEATURE         Location/Qualifiers
                source          1..19
                                mol_type = transcribed RNA
                                organism = Homo sapiens
                SEQUENCE: 111
                aggcacggtg tcagcaggc                                                  19

SEQ ID NO: 112  moltype = RNA   length = 23
                FEATURE         Location/Qualifiers
                source          1..23
                                mol_type = transcribed RNA
                                organism = Homo sapiens
                SEQUENCE: 112
                agaggctttg tgcggatacg ggg                                             23

SEQ ID NO: 113  moltype = RNA   length = 19
                FEATURE         Location/Qualifiers
                source          1..19
                                mol_type = transcribed RNA
                                organism = Homo sapiens
                SEQUENCE: 113
                aatggatttt tggagcagg                                                  19

SEQ ID NO: 114  moltype = RNA   length = 23
                FEATURE         Location/Qualifiers
                source          1..23
                                mol_type = transcribed RNA
                                organism = Homo sapiens
                SEQUENCE: 114
                gacacgggcg acagctgcgg ccc                                             23

SEQ ID NO: 115  moltype = RNA   length = 19
                FEATURE         Location/Qualifiers
                source          1..19
                                mol_type = transcribed RNA
                                organism = Homo sapiens
                SEQUENCE: 115
                tggatttttg gatcaggga                                                  19

SEQ ID NO: 116  moltype = RNA   length = 22
                FEATURE         Location/Qualifiers
                source          1..22
                                mol_type = transcribed RNA
                                organism = Homo sapiens
                SEQUENCE: 116
                tagcagcacg taaatattgg cg                                              22

SEQ ID NO: 117  moltype = RNA   length = 22
                FEATURE         Location/Qualifiers
                source          1..22
                                mol_type = transcribed RNA
                                organism = Homo sapiens
                SEQUENCE: 117
                aaaccgttac cattactgag tt                                              22

SEQ ID NO: 118  moltype = RNA   length = 22
```

```
FEATURE              Location/Qualifiers
source               1..22
                     mol_type = transcribed RNA
                     organism = Homo sapiens
SEQUENCE: 118
tggctcagtt cagcaggaac ag                                              22

SEQ ID NO: 119       moltype = RNA  length = 22
FEATURE              Location/Qualifiers
source               1..22
                     mol_type = transcribed RNA
                     organism = Homo sapiens
SEQUENCE: 119
ggctacaaca caggacccgg gc                                              22

SEQ ID NO: 120       moltype = RNA  length = 21
FEATURE              Location/Qualifiers
source               1..21
                     mol_type = transcribed RNA
                     organism = Homo sapiens
SEQUENCE: 120
cggcggggac ggcgattggt c                                               21

SEQ ID NO: 121       moltype = RNA  length = 20
FEATURE              Location/Qualifiers
source               1..20
                     mol_type = transcribed RNA
                     organism = Homo sapiens
SEQUENCE: 121
actcaaactg tgggggcact                                                 20

SEQ ID NO: 122       moltype = RNA  length = 23
FEATURE              Location/Qualifiers
source               1..23
                     mol_type = transcribed RNA
                     organism = Homo sapiens
SEQUENCE: 122
agtgcctgag ggagtaagag ccc                                             23

SEQ ID NO: 123       moltype = RNA  length = 69
FEATURE              Location/Qualifiers
source               1..69
                     mol_type = transcribed RNA
                     organism = Homo sapiens
SEQUENCE: 123
ccgggcaggc aggtgtaggg tggagcccac tgtggctcct gactcagccc tgctgccttc     60
acctgccag                                                             69

SEQ ID NO: 124       moltype = RNA  length = 95
FEATURE              Location/Qualifiers
source               1..95
                     mol_type = transcribed RNA
                     organism = Homo sapiens
SEQUENCE: 124
gacaccacat gctcctccag gcctgcctgc cctccaggtc atgttccagt gtcccacaga     60
tgcagcacca cggcccaggc ggcattggtg tcacc                                95

SEQ ID NO: 125       moltype = RNA  length = 62
FEATURE              Location/Qualifiers
source               1..62
                     mol_type = transcribed RNA
                     organism = Homo sapiens
SEQUENCE: 125
ccttctgcgg cagagctggg gtcaccagcc ctcatgtact tgtgacttct cccctgccac     60
ag                                                                    62

SEQ ID NO: 126       moltype = RNA  length = 76
FEATURE              Location/Qualifiers
source               1..76
                     mol_type = transcribed RNA
                     organism = Homo sapiens
SEQUENCE: 126
ccgatgcctc gggagtctac agcagggcca tgtctgtgag gcccaaggg tgcatgtgtc      60
tcccaggttt cggtgc                                                     76
```

```
SEQ ID NO: 127          moltype = RNA   length = 65
FEATURE                 Location/Qualifiers
source                  1..65
                        mol_type = transcribed RNA
                        organism = Homo sapiens
SEQUENCE: 127
gagggtgggc gagggcggct gagcggctcc atcccccggc ctgctcatcc ccctcgccct    60
ctcag                                                                65

SEQ ID NO: 128          moltype = RNA   length = 70
FEATURE                 Location/Qualifiers
source                  1..70
                        mol_type = transcribed RNA
                        organism = Homo sapiens
SEQUENCE: 128
aaaagcctgt ccctaagtcc ctcccagcct tccagagttg gtgccaggaa ggatttaggg    60
acaggctttg                                                           70

SEQ ID NO: 129          moltype = RNA   length = 63
FEATURE                 Location/Qualifiers
source                  1..63
                        mol_type = transcribed RNA
                        organism = Homo sapiens
SEQUENCE: 129
ggctccgcag ggcctggcg caggcatcca dacagcgggc gaatgcctcc cccggccccg     60
cag                                                                  63

SEQ ID NO: 130          moltype = RNA   length = 87
FEATURE                 Location/Qualifiers
source                  1..87
                        mol_type = transcribed RNA
                        organism = Homo sapiens
SEQUENCE: 130
gtgaggcggg gccaggaggg tgtgtggcgt gggtgctgcg gggccgtcag ggtgcctgcg    60
ggacgctcac ctggctggcc cgcccag                                        87

SEQ ID NO: 131          moltype = RNA   length = 69
FEATURE                 Location/Qualifiers
source                  1..69
                        mol_type = transcribed RNA
                        organism = Homo sapiens
SEQUENCE: 131
gaggagggga ggtgtgcagg gctggggtca ctgactctgc ttcccctgcc ctgcatggtg    60
tccccacag                                                            69

SEQ ID NO: 132          moltype = RNA   length = 56
FEATURE                 Location/Qualifiers
source                  1..56
                        mol_type = transcribed RNA
                        organism = Homo sapiens
SEQUENCE: 132
cgaccgcacc cgcccgaagc tgggtcaagg agcccagcag gacgggagcg cggcgc        56

SEQ ID NO: 133          moltype = RNA   length = 61
FEATURE                 Location/Qualifiers
source                  1..61
                        mol_type = transcribed RNA
                        organism = Homo sapiens
SEQUENCE: 133
tctcgtttga tctcggaagc taagcagggt tgggcctggt tagtacttgg atgggaaact    60
t                                                                    61

SEQ ID NO: 134          moltype = RNA   length = 53
FEATURE                 Location/Qualifiers
source                  1..53
                        mol_type = transcribed RNA
                        organism = Homo sapiens
SEQUENCE: 134
gtttgatctc ggaagctaag cagggtcggg cctggttagt acttggatgg gag            53

SEQ ID NO: 135          moltype = RNA   length = 55
FEATURE                 Location/Qualifiers
source                  1..55
                        mol_type = transcribed RNA
                        organism = Homo sapiens
SEQUENCE: 135
ccggatccga gtcacggcac caaatttcat gcgtgtccgt gtgaagagac cacca          55
```

```
SEQ ID NO: 136          moltype = RNA   length = 96
FEATURE                 Location/Qualifiers
source                  1..96
                        mol_type = transcribed RNA
                        organism = Homo sapiens
SEQUENCE: 136
ctcgggaggg gcgggagggg ggtccccggt gctcggatct cgagggtgct tattgttcgg    60
tccgagcctg ggtctccctc ttccccccaa cccccc                              96

SEQ ID NO: 137          moltype = RNA   length = 72
FEATURE                 Location/Qualifiers
source                  1..72
                        mol_type = transcribed RNA
                        organism = Homo sapiens
SEQUENCE: 137
gatttcagtg acctggcagc agggagcgtc gtcagtgttt gactgtttat ggtatgtcag    60
ggagctggtt cc                                                        72

SEQ ID NO: 138          moltype = RNA   length = 93
FEATURE                 Location/Qualifiers
source                  1..93
                        mol_type = transcribed RNA
                        organism = Homo sapiens
SEQUENCE: 138
ccttccggcg tcccaggcgg ggcgccgcgg gaccgcccct gtgtctgtgg cggtgggatc    60
ccgcggccgt gttttcctgg tggcccggcc atg                                 93

SEQ ID NO: 139          moltype = RNA   length = 54
FEATURE                 Location/Qualifiers
source                  1..54
                        mol_type = transcribed RNA
                        organism = Homo sapiens
SEQUENCE: 139
ggacaagggc ggcgcgaccg gcccggggct cttgggcggc cgcgtttccc ctcc          54

SEQ ID NO: 140          moltype = RNA   length = 65
FEATURE                 Location/Qualifiers
source                  1..65
                        mol_type = transcribed RNA
                        organism = Homo sapiens
SEQUENCE: 140
tgtctgggga tttggagaag tggtgagcgc aggtctttgg caccatctcc cctggtccct    60
tggct                                                                65

SEQ ID NO: 141          moltype = RNA   length = 74
FEATURE                 Location/Qualifiers
source                  1..74
                        mol_type = transcribed RNA
                        organism = Homo sapiens
SEQUENCE: 141
gcagcccggt gagcgctcgc tggcctggca gtgcgtcgga agaacagggc gggtgggcc     60
gcgcacatct ctgc                                                      74

SEQ ID NO: 142          moltype = RNA   length = 72
FEATURE                 Location/Qualifiers
source                  1..72
                        mol_type = transcribed RNA
                        organism = Homo sapiens
SEQUENCE: 142
tctcctcgag gggtctctgc ctctacccag gactctttca tgaccaggag gctgaggccc    60
ctcacaggcg gc                                                        72

SEQ ID NO: 143          moltype = RNA   length = 68
FEATURE                 Location/Qualifiers
source                  1..68
                        mol_type = transcribed RNA
                        organism = Homo sapiens
SEQUENCE: 143
gtgcaaagag caggaggaca ggggatttat ctcccaaggg aggtcccctg atcctagtca    60
cggcacca                                                             68

SEQ ID NO: 144          moltype = RNA   length = 65
FEATURE                 Location/Qualifiers
source                  1..65
                        mol_type = transcribed RNA
                        organism = Homo sapiens
SEQUENCE: 144
gtctcctggg gggaggagac cctgctctcc ctggcagcaa gcctctcctg cccttccaga    60
ttagc                                                                65
```

```
SEQ ID NO: 145          moltype = RNA   length = 98
FEATURE                 Location/Qualifiers
source                  1..98
                        mol_type = transcribed RNA
                        organism = Homo sapiens
SEQUENCE: 145
cgaggtaggg gcgtcccggg cgcgcgggcg ggtcccaggc tgggcccctc ggaggccggg    60
tgctcactgc cccgtccggg cgcccgtgtc tcctccag                            98

SEQ ID NO: 146          moltype = RNA   length = 89
FEATURE                 Location/Qualifiers
source                  1..89
                        mol_type = transcribed RNA
                        organism = Homo sapiens
SEQUENCE: 146
acctccggga cggctgggcg ccggcggccg ggagatccgc gcttcctgaa tcccggccgg    60
cccgcccggc gcccgtccgc ccgcgggtc                                      89

SEQ ID NO: 147          moltype = RNA   length = 64
FEATURE                 Location/Qualifiers
source                  1..64
                        mol_type = transcribed RNA
                        organism = Homo sapiens
SEQUENCE: 147
agttcagggc cgaagggtgg aagctgctgg tgctcatctc agcctctgcc cttggcctcc    60
ccag                                                                 64

SEQ ID NO: 148          moltype = RNA   length = 62
FEATURE                 Location/Qualifiers
source                  1..62
                        mol_type = transcribed RNA
                        organism = Homo sapiens
SEQUENCE: 148
gagggtggtg gaggaagagg gcagctccca tgactgcctg accgccttct ctcctccccc    60
ag                                                                   62

SEQ ID NO: 149          moltype = RNA   length = 49
FEATURE                 Location/Qualifiers
source                  1..49
                        mol_type = transcribed RNA
                        organism = Homo sapiens
SEQUENCE: 149
ttcccagcca acgcaccaaa aatgatatgg gtctgttgtc tggagaaac                49

SEQ ID NO: 150          moltype = RNA   length = 70
FEATURE                 Location/Qualifiers
source                  1..70
                        mol_type = transcribed RNA
                        organism = Homo sapiens
SEQUENCE: 150
ctcgggcccg accgcgccgg cccgcacctc ccggcccgga gctgcgggct gcggtcaggg    60
cgatcccggg                                                           70

SEQ ID NO: 151          moltype = RNA   length = 74
FEATURE                 Location/Qualifiers
source                  1..74
                        mol_type = transcribed RNA
                        organism = Homo sapiens
SEQUENCE: 151
gtgcgtggtg gctcgaggcg ggggtggggg cctcgccctg cttgggccct ccctgacctc    60
tccgctccgc acag                                                      74

SEQ ID NO: 152          moltype = RNA   length = 82
FEATURE                 Location/Qualifiers
source                  1..82
                        mol_type = transcribed RNA
                        organism = Homo sapiens
SEQUENCE: 152
aaggagcact cactccaatt tccctggact gggggcaggc tgccacctcc tggggacagg    60
ggattggggc aggatgttcc ag                                             82

SEQ ID NO: 153          moltype = RNA   length = 59
FEATURE                 Location/Qualifiers
source                  1..59
                        mol_type = transcribed RNA
                        organism = Homo sapiens
SEQUENCE: 153
tgaagtacca gctactcgag aggtcagagg attgctcctg aatagctggg actacaggt     59
```

```
SEQ ID NO: 154          moltype = RNA   length = 110
FEATURE                 Location/Qualifiers
source                  1..110
                        mol_type = transcribed RNA
                        organism = Homo sapiens
SEQUENCE: 154
gtctaccagg tgtgggccca gctttacata gttcatgctg aggccgggat ttcatgcaga   60
aaactggttg caaaaggtgc tgaaggggct gggggagcac aagggagaag              110

SEQ ID NO: 155          moltype = RNA   length = 61
FEATURE                 Location/Qualifiers
source                  1..61
                        mol_type = transcribed RNA
                        organism = Homo sapiens
SEQUENCE: 155
aactgcgggg ccagagcaga gagcccttgc acaccaccag cctctcctcc ctgtgcccca   60
g                                                                   61

SEQ ID NO: 156          moltype = RNA   length = 73
FEATURE                 Location/Qualifiers
source                  1..73
                        mol_type = transcribed RNA
                        organism = Homo sapiens
SEQUENCE: 156
cggcgacggc ggggtgggtg aggtcgggcc ccaagactcg gggtttgccg ggcgcctcag   60
ttcaccgcgg ccg                                                      73

SEQ ID NO: 157          moltype = RNA   length = 81
FEATURE                 Location/Qualifiers
source                  1..81
                        mol_type = transcribed RNA
                        organism = Homo sapiens
SEQUENCE: 157
catcctcctt acgtcccacc ccccactcct gtttctggtg aaatattcaa acaggagtgg   60
gggtgggaca taaggaggat a                                             81

SEQ ID NO: 158          moltype = RNA   length = 92
FEATURE                 Location/Qualifiers
source                  1..92
                        mol_type = transcribed RNA
                        organism = Homo sapiens
SEQUENCE: 158
gtcagtgtct gggcggacag ctgcaggaaa gggaagacca aggcttgctg tctgtccagt   60
ctgccaccct accctgtctg ttcttgccac ag                                 92

SEQ ID NO: 159          moltype = RNA   length = 79
FEATURE                 Location/Qualifiers
source                  1..79
                        mol_type = transcribed RNA
                        organism = Homo sapiens
SEQUENCE: 159
ctcgaggtgc tgggggacgc gtgagcgcga gccgcttcct cacggctcgg ccgcggcgcg   60
tagcccccgc cacatcggg                                                79

SEQ ID NO: 160          moltype = RNA   length = 61
FEATURE                 Location/Qualifiers
source                  1..61
                        mol_type = transcribed RNA
                        organism = Homo sapiens
SEQUENCE: 160
tccgctctgt ggagtggggt gcctgtcccc tgccactggg tgacccaccc ctctccacca   60
g                                                                   61

SEQ ID NO: 161          moltype = RNA   length = 83
FEATURE                 Location/Qualifiers
source                  1..83
                        mol_type = transcribed RNA
                        organism = Homo sapiens
SEQUENCE: 161
gtgagtggga gccccagtgt gtggttgggg ccatggcggg tgggcagccc agcctctgag   60
ccttcctcgt ctgtctgccc cag                                           83

SEQ ID NO: 162          moltype = RNA   length = 86
FEATURE                 Location/Qualifiers
source                  1..86
                        mol_type = transcribed RNA
                        organism = Homo sapiens
```

```
SEQUENCE: 162
cgcctgagcg tgcagcagga catcttcctg acctggtaat aattaggtga gaaggatggt    60
tgggggcggt cggcgtaact caggga                                         86

SEQ ID NO: 163          moltype = RNA   length = 76
FEATURE                 Location/Qualifiers
source                  1..76
                        mol_type = transcribed RNA
                        organism = Homo sapiens
SEQUENCE: 163
gagggagctg tagagcaggg agcaggaagc tgtgtgtgtc cagccctgac ctgtcctgtt    60
ctgccccag ccctc                                                      76

SEQ ID NO: 164          moltype = RNA   length = 99
FEATURE                 Location/Qualifiers
source                  1..99
                        mol_type = transcribed RNA
                        organism = Homo sapiens
SEQUENCE: 164
cgcccacctc agcctcccaa aatgctggga ttacaggcat gagccactgc ggtcgaccat    60
gacctggaca tgtttgtgcc cagtactgtc agtttgcag                           99

SEQ ID NO: 165          moltype = RNA   length = 83
FEATURE                 Location/Qualifiers
source                  1..83
                        mol_type = transcribed RNA
                        organism = Homo sapiens
SEQUENCE: 165
aatagagggt gcacaggcac gggagctcag gtgaggcagg gagctgagct cacctgacct    60
cccatgcctg tgcaccctct att                                            83

SEQ ID NO: 166          moltype = RNA   length = 73
FEATURE                 Location/Qualifiers
source                  1..73
                        mol_type = transcribed RNA
                        organism = Homo sapiens
SEQUENCE: 166
accttcccag ctcatcccac ctctgccacc aaaacactca tcgcggggtc agagggagtg    60
ccaaaaaagg taa                                                       73

SEQ ID NO: 167          moltype = RNA   length = 63
FEATURE                 Location/Qualifiers
source                  1..63
                        mol_type = transcribed RNA
                        organism = Homo sapiens
SEQUENCE: 167
aatgggtggg tgctggtggg agccgtgccc tggccactca ttcggctctc tccctcaccc    60
tag                                                                  63

SEQ ID NO: 168          moltype = RNA   length = 64
FEATURE                 Location/Qualifiers
source                  1..64
                        mol_type = transcribed RNA
                        organism = Homo sapiens
SEQUENCE: 168
aaccccgggc cggaggtcaa gggcgtcgct tctccctaat gttgcctctt ttccacggcc    60
tcag                                                                 64

SEQ ID NO: 169          moltype = RNA   length = 96
FEATURE                 Location/Qualifiers
source                  1..96
                        mol_type = transcribed RNA
                        organism = Homo sapiens
SEQUENCE: 169
gctctgggc gtgccgccgc cgtcgctgcc acctccccta ccgctagtgg aagaagatgg    60
cggaaggcgg agcggcggat ctggacaccc agcggt                              96

SEQ ID NO: 170          moltype = RNA   length = 62
FEATURE                 Location/Qualifiers
source                  1..62
                        mol_type = transcribed RNA
                        organism = Homo sapiens
SEQUENCE: 170
tggcctaggg ggcggcttgt ggagtgtatg ggctgagcct tgctctgctc cccgccccc    60
ag                                                                   62
```

```
SEQ ID NO: 171          moltype = RNA   length = 109
FEATURE                 Location/Qualifiers
source                  1..109
                        mol_type = transcribed RNA
                        organism = Homo sapiens
SEQUENCE: 171
tgctattgtc ttactgctac agcagggctg gggattgcag tatccgctgt tgctgctgct    60
cccagtcctg ccctgctgc tacctagtcc agcctcaccg catcccaga                109

SEQ ID NO: 172          moltype = RNA   length = 62
FEATURE                 Location/Qualifiers
source                  1..62
                        mol_type = transcribed RNA
                        organism = Homo sapiens
SEQUENCE: 172
gtgggtctcg catcaggagg caaggccagg acccgctgac ccatgcctcc tgccgcggtc    60
ag                                                                  62

SEQ ID NO: 173          moltype = RNA   length = 72
FEATURE                 Location/Qualifiers
source                  1..72
                        mol_type = transcribed RNA
                        organism = Homo sapiens
SEQUENCE: 173
gagtctgagg gacccaggac aggagaaggc ctatggtgat ttgcattctt cctgccctgg    60
ctccatcctc ag                                                       72

SEQ ID NO: 174          moltype = RNA   length = 80
FEATURE                 Location/Qualifiers
source                  1..80
                        mol_type = transcribed RNA
                        organism = Homo sapiens
SEQUENCE: 174
cgggaatgcc gcggcgggga cggcgattgg tccgtatgtg tggtgccacc ggccgccggc    60
tccgccccgg ccccgccccc                                               80

SEQ ID NO: 175          moltype = RNA   length = 102
FEATURE                 Location/Qualifiers
source                  1..102
                        mol_type = transcribed RNA
                        organism = Homo sapiens
SEQUENCE: 175
tgtgttccct atcctcctta tgtcccaccc ccactcctgt ttgaatattt caccagaaac    60
aggagtgggg ggtgggacgt aaggaggatg ggggaaagaa ca                      102

SEQ ID NO: 176          moltype = RNA   length = 47
FEATURE                 Location/Qualifiers
source                  1..47
                        mol_type = transcribed RNA
                        organism = Homo sapiens
SEQUENCE: 176
aggcaggtta tctgggctgc catctcccac tggctgcttg cctgcct                 47

SEQ ID NO: 177          moltype = RNA   length = 119
FEATURE                 Location/Qualifiers
source                  1..119
                        mol_type = transcribed RNA
                        organism = Homo sapiens
SEQUENCE: 177
ccatgaggag ctggcagtgg gatggcctgg gggtaggagc gtggcttctg gagctagacc    60
acatgggttc agatcccagc ggtgcctcta actggcacca ggaccttggg cagtcagct    119

SEQ ID NO: 178          moltype = RNA   length = 92
FEATURE                 Location/Qualifiers
source                  1..92
                        mol_type = transcribed RNA
                        organism = Homo sapiens
SEQUENCE: 178
cgctgcgctt ctgggcccgc ggcgggcgtg gggctgcccg ggccggtcga ccagcgcgcc    60
gtagctcccg aggcccgagc cgcgacccgc gg                                 92

SEQ ID NO: 179          moltype = RNA   length = 80
FEATURE                 Location/Qualifiers
source                  1..80
                        mol_type = transcribed RNA
                        organism = Homo sapiens
```

```
-continued

SEQUENCE: 179
tgccgtcggc ctggggagga ggaagggcaa gtccaaaggt atacagttgg tctgttcatt    60
ctctcttttt ggcctacaag                                                80

SEQ ID NO: 180          moltype = RNA   length = 61
FEATURE                 Location/Qualifiers
source                  1..61
                        mol_type = transcribed RNA
                        organism = Homo sapiens
SEQUENCE: 180
gggggcggga gctgggtct gcaggttcgc actgatgcct gctcgccctg tctcccgcta    60
g                                                                    61

SEQ ID NO: 181          moltype = RNA   length = 68
FEATURE                 Location/Qualifiers
source                  1..68
                        mol_type = transcribed RNA
                        organism = Homo sapiens
SEQUENCE: 181
gaatggaaga agaaggcggt cggtctgcgg gagccaggcc gcagagccat ccgccttctg    60
tccatgtc                                                             68

SEQ ID NO: 182          moltype = RNA   length = 68
FEATURE                 Location/Qualifiers
source                  1..68
                        mol_type = transcribed RNA
                        organism = Homo sapiens
SEQUENCE: 182
gactcggctg cggtggacaa gtccggctcc agaacctgga caccgctcag ccggccgcgg    60
caggggtc                                                             68

SEQ ID NO: 183          moltype = RNA   length = 100
FEATURE                 Location/Qualifiers
source                  1..100
                        mol_type = transcribed RNA
                        organism = Homo sapiens
SEQUENCE: 183
gaggtgggag gattgcttga gtcaggtgg ttgaggctgc agtaagttgt gatcatacca    60
ctgcactcca gcctgagtga cagagcaaga ccttgtctca                          100

SEQ ID NO: 184          moltype = RNA   length = 73
FEATURE                 Location/Qualifiers
source                  1..73
                        mol_type = transcribed RNA
                        organism = Homo sapiens
SEQUENCE: 184
gttcaagtgg gaggacagga ggcaggtgtg gttggaggaa gcagcctgaa cctgcctccc    60
tgacattcca cag                                                       73

SEQ ID NO: 185          moltype = RNA   length = 75
FEATURE                 Location/Qualifiers
source                  1..75
                        mol_type = transcribed RNA
                        organism = Homo sapiens
SEQUENCE: 185
tggagtgggg gggcaggagg ggctcaggga gaaagtgcat acagcccctg gccctctctg    60
cccttccgtc ccctg                                                     75

SEQ ID NO: 186          moltype = RNA   length = 68
FEATURE                 Location/Qualifiers
source                  1..68
                        mol_type = transcribed RNA
                        organism = Homo sapiens
SEQUENCE: 186
cgtggtgagg atatggcagg gaaggggagt ttccctctat tcccttcccc ccagtaatct    60
tcatcatg                                                             68

SEQ ID NO: 187          moltype = RNA   length = 73
FEATURE                 Location/Qualifiers
source                  1..73
                        mol_type = transcribed RNA
                        organism = Homo sapiens
SEQUENCE: 187
gtgggcgggg gcaggtgtgt ggtgggtggt ggcctgcggt gagcagggcc ctcacacctg    60
cctcgccccc cag                                                       73
```

```
SEQ ID NO: 188         moltype = RNA   length = 64
FEATURE                Location/Qualifiers
source                 1..64
                       mol_type = transcribed RNA
                       organism = Homo sapiens
SEQUENCE: 188
gagctctggg aggggctggg tttggcagga cagtttccaa gccctgtctc ctcccatctt   60
ccag                                                                64

SEQ ID NO: 189         moltype = RNA   length = 81
FEATURE                Location/Qualifiers
source                 1..81
                       mol_type = transcribed RNA
                       organism = Homo sapiens
SEQUENCE: 189
agttggtggg ggagccatga gataagagca cctcctagag aatgttgaac taaaggtgcc   60
ctctctggct cctccccaaa g                                             81

SEQ ID NO: 190         moltype = RNA   length = 61
FEATURE                Location/Qualifiers
source                 1..61
                       mol_type = transcribed RNA
                       organism = Homo sapiens
SEQUENCE: 190
gtgcggaacg ctggccgggg cgggagggga agggacgccc ggccggaacg ccgcactcac   60
g                                                                   61

SEQ ID NO: 191         moltype = RNA   length = 80
FEATURE                Location/Qualifiers
source                 1..80
                       mol_type = transcribed RNA
                       organism = Homo sapiens
SEQUENCE: 191
ggcgcgtcgc cccctcagt ccaccagagc ccggatacct cagaaattcg gctctgggtc    60
tgtggggagc gaaatgcaac                                               80

SEQ ID NO: 192         moltype = RNA   length = 59
FEATURE                Location/Qualifiers
source                 1..59
                       mol_type = transcribed RNA
                       organism = Homo sapiens
SEQUENCE: 192
cggggtcggc ggcgacgtgc tcagcttggc acccaagttc tgccgctccg acgcccggc    59

SEQ ID NO: 193         moltype = RNA   length = 80
FEATURE                Location/Qualifiers
source                 1..80
                       mol_type = transcribed RNA
                       organism = Homo sapiens
SEQUENCE: 193
gcgtcaagat ggcggcgggg aggtaggcag agcaggacgc cgctgctgcc gccgccaccg   60
ccgcctccgc tccagtcgcc                                               80

SEQ ID NO: 194         moltype = RNA   length = 63
FEATURE                Location/Qualifiers
source                 1..63
                       mol_type = transcribed RNA
                       organism = Homo sapiens
SEQUENCE: 194
gcatgctggg cgaggctggc atctagcaca ggcggtagat gcttgctctt gccattgcaa   60
tga                                                                 63

SEQ ID NO: 195         moltype = RNA   length = 80
FEATURE                Location/Qualifiers
source                 1..80
                       mol_type = transcribed RNA
                       organism = Homo sapiens
SEQUENCE: 195
acctctacct cccggcagag gaggctgcag aggctggctt tccaaaactc tgcccctcc    60
gctgctgcca agtggctggt                                               80

SEQ ID NO: 196         moltype = RNA   length = 75
FEATURE                Location/Qualifiers
source                 1..75
                       mol_type = transcribed RNA
                       organism = Homo sapiens
```

```
SEQUENCE: 196
aggctggcgt gggctgaggg caggaggcct gtggccggtc ccaggcctcc tgcttcctgg    60
gctcaggctc ggttt                                                    75

SEQ ID NO: 197          moltype = RNA   length = 89
FEATURE                 Location/Qualifiers
source                  1..89
                        mol_type = transcribed RNA
                        organism = Homo sapiens
SEQUENCE: 197
tctccgttta tcccaccact gccaccatta ttgctactgt tcagcaggtg ctgctggtgg    60
tgatggtgat agtctggtgg gggcggtgg                                     89

SEQ ID NO: 198          moltype = RNA   length = 65
FEATURE                 Location/Qualifiers
source                  1..65
                        mol_type = transcribed RNA
                        organism = Homo sapiens
SEQUENCE: 198
gcttctggga ggagggatc ttgggagtga tcccaacagc tgagctccct gaatccctgt     60
cccag                                                               65

SEQ ID NO: 199          moltype = RNA   length = 59
FEATURE                 Location/Qualifiers
source                  1..59
                        mol_type = transcribed RNA
                        organism = Homo sapiens
SEQUENCE: 199
ctgtgtcggg gagtctgggg tccggaattc tccagagcct ctgtgcccct acttcccag    59

SEQ ID NO: 200          moltype = RNA   length = 79
FEATURE                 Location/Qualifiers
source                  1..79
                        mol_type = transcribed RNA
                        organism = Homo sapiens
SEQUENCE: 200
cagcctgggg aaggcttggc agggaagaca catgagcagt gcctccactt cacgcctctc    60
ccttgtctcc tttccctag                                                79

SEQ ID NO: 201          moltype = RNA   length = 60
FEATURE                 Location/Qualifiers
source                  1..60
                        mol_type = transcribed RNA
                        organism = Homo sapiens
SEQUENCE: 201
cgctgggtcc gcgcgccctg ggccgggcga tgtccgcttg ggggagcgag gggcggggcg    60

SEQ ID NO: 202          moltype = RNA   length = 60
FEATURE                 Location/Qualifiers
source                  1..60
                        mol_type = transcribed RNA
                        organism = Homo sapiens
SEQUENCE: 202
tgtgaatgac ccccttccag agccaaaatc accagggatg gaggagggt cttgggtact    60

SEQ ID NO: 203          moltype = RNA   length = 66
FEATURE                 Location/Qualifiers
source                  1..66
                        mol_type = transcribed RNA
                        organism = Homo sapiens
SEQUENCE: 203
agcagccctc ggcggcccgg ggggcgggcg gcggtgcccg tcccggggct gcgcgaggca    60
caggcg                                                              66

SEQ ID NO: 204          moltype = RNA   length = 115
FEATURE                 Location/Qualifiers
source                  1..115
                        mol_type = transcribed RNA
                        organism = Homo sapiens
SEQUENCE: 204
gagcaaaaac cagagaacaa catgggagcg ttcctaaccc ctaaggcaac tggatgggag    60
acctgaccca tccagttctc tgaggggct cttgtgtgtt ctacaaggtt gttca         115

SEQ ID NO: 205          moltype = RNA   length = 83
FEATURE                 Location/Qualifiers
source                  1..83
                        mol_type = transcribed RNA
                        organism = Homo sapiens
```

```
SEQUENCE: 205
cctgctgcag aggtgccagc tgcagtgggg gaggcactgc cagggctgcc cactctgctt    60
agccagcagg tgccaagaac agg                                            83

SEQ ID NO: 206           moltype = RNA   length = 63
FEATURE                  Location/Qualifiers
source                   1..63
                         mol_type = transcribed RNA
                         organism = Homo sapiens
SEQUENCE: 206
tggtggcggc ggtagttatg ggcttctctt tctcaccagc agccctggg ccgccgcctc     60
cct                                                                  63

SEQ ID NO: 207           moltype = RNA   length = 57
FEATURE                  Location/Qualifiers
source                   1..57
                         mol_type = transcribed RNA
                         organism = Homo sapiens
SEQUENCE: 207
cattggaggg tgtggaagac atctgggcca actctgatct cttcatctac cccccag       57

SEQ ID NO: 208           moltype = RNA   length = 62
FEATURE                  Location/Qualifiers
source                   1..62
                         mol_type = transcribed RNA
                         organism = Homo sapiens
SEQUENCE: 208
gctggggtc ccccgacagt gtggagctgg ggccgggtcc cggggagggg ggttctgggc     60
ag                                                                   62

SEQ ID NO: 209           moltype = RNA   length = 73
FEATURE                  Location/Qualifiers
source                   1..73
                         mol_type = transcribed RNA
                         organism = Homo sapiens
SEQUENCE: 209
ggaggctggg ctgggacgga cacccggcct ccactttctg tggcaggtac ctcctccatg    60
tcggcccgcc ttg                                                       73

SEQ ID NO: 210           moltype = RNA   length = 83
FEATURE                  Location/Qualifiers
source                   1..83
                         mol_type = transcribed RNA
                         organism = Homo sapiens
SEQUENCE: 210
gggtttcctc tgccttttt tccaatgaaa ataacgaaac ctgttatttc ccattgaggg     60
ggaaaaaggc gggagaagcc cca                                            83

SEQ ID NO: 211           moltype = RNA   length = 62
FEATURE                  Location/Qualifiers
source                   1..62
                         mol_type = transcribed RNA
                         organism = Homo sapiens
SEQUENCE: 211
tggcctaggg ggcggcttgt ggagtgtatg ggctgagcct tgctctgctc ccccgccccc    60
ag                                                                   62

SEQ ID NO: 212           moltype = RNA   length = 68
FEATURE                  Location/Qualifiers
source                   1..68
                         mol_type = transcribed RNA
                         organism = Homo sapiens
SEQUENCE: 212
tgcccaggct ggagcgagtg cagtggtgca gtcagtccta gctcactgca gcctcgaact    60
cctgggct                                                             68

SEQ ID NO: 213           moltype = RNA   length = 82
FEATURE                  Location/Qualifiers
source                   1..82
                         mol_type = transcribed RNA
                         organism = Homo sapiens
SEQUENCE: 213
ctgactttt tagggagtag aagggtgggg agcatgaaca atgtttctca ctccctaccc     60
ctccactccc caaaaaagtc ag                                             82

SEQ ID NO: 214           moltype = RNA   length = 72
FEATURE                  Location/Qualifiers
```

```
source                          1..72
                                mol_type = transcribed RNA
                                organism = Homo sapiens
SEQUENCE: 214
ccaggcacac aggaaaagcg gggccctggg ttcggctgct accccaaagg ccacattctc    60
ctgtgcacac ag                                                        72

SEQ ID NO: 215                  moltype = RNA   length = 87
FEATURE                         Location/Qualifiers
source                          1..87
                                mol_type = transcribed RNA
                                organism = Homo sapiens
SEQUENCE: 215
ccctcatctc tgggcagggg cttattgtag gagtctctga agagagctgt ggactgacct    60
gctttaaccc ttccccaggt tcccatt                                        87

SEQ ID NO: 216                  moltype = RNA   length = 88
FEATURE                         Location/Qualifiers
source                          1..88
                                mol_type = transcribed RNA
                                organism = Homo sapiens
SEQUENCE: 216
gtggggccag gcggtggtgg gcactgctgg ggtgggcaca gcagccatgc agagcgggca    60
tttgaccccg tgccacccct ttccccag                                       88

SEQ ID NO: 217                  moltype = RNA   length = 78
FEATURE                         Location/Qualifiers
source                          1..78
                                mol_type = transcribed RNA
                                organism = Homo sapiens
SEQUENCE: 217
ggcctcaggc aggcgcaccc gaccacatgc atggctggtg gcggcgtgca ggggtcgggt    60
gggccaggct gtggggcg                                                  78

SEQ ID NO: 218                  moltype = RNA   length = 93
FEATURE                         Location/Qualifiers
source                          1..93
                                mol_type = transcribed RNA
                                organism = Homo sapiens
SEQUENCE: 218
tactatggc accccactcc tggtaccata gtcataagtt aggagatgtt agagctgtga     60
gtaccatgac ttaagtgtgg tggcttaaac atg                                 93

SEQ ID NO: 219                  moltype = RNA   length = 71
FEATURE                         Location/Qualifiers
source                          1..71
                                mol_type = transcribed RNA
                                organism = Homo sapiens
SEQUENCE: 219
gtgtctgtgc cggtcccagg agaacctgca gaggcatcgg gtcagcggtg ctcctgcggg    60
ccgacactca c                                                         71

SEQ ID NO: 220                  moltype = RNA   length = 65
FEATURE                         Location/Qualifiers
source                          1..65
                                mol_type = transcribed RNA
                                organism = Homo sapiens
SEQUENCE: 220
gggtgctcgg ggcaggcggc tgggagcggc cctcacattg atggctcctg ccacctcctc    60
cgcag                                                                65

SEQ ID NO: 221                  moltype = RNA   length = 66
FEATURE                         Location/Qualifiers
source                          1..66
                                mol_type = transcribed RNA
                                organism = Homo sapiens
SEQUENCE: 221
ccgagtgggg cggggcaggt ccctgcaggg actgtgacac tgaaggacct gcaccttcgc    60
ccacag                                                               66

SEQ ID NO: 222                  moltype = RNA   length = 90
FEATURE                         Location/Qualifiers
source                          1..90
                                mol_type = transcribed RNA
                                organism = Homo sapiens
SEQUENCE: 222
cgggcgggc gggtccggcc gcctccgagc ccggccggca gccccgcc ttaaagcgcg       60
ggctgtccgg aggggtcggc tttcccaccg                                     90
```

```
SEQ ID NO: 223            moltype = RNA   length = 70
FEATURE                   Location/Qualifiers
source                    1..70
                          mol_type = transcribed RNA
                          organism = Homo sapiens
SEQUENCE: 223
aggacccagc ggggctgggc gcgcggagca gcgctgggtg cagcgcctgc gccggcagct    60
gcaagggccg                                                          70

SEQ ID NO: 224            moltype = RNA   length = 94
FEATURE                   Location/Qualifiers
source                    1..94
                          mol_type = transcribed RNA
                          organism = Homo sapiens
SEQUENCE: 224
gtgaggtgtg ggcccggccc caggagcggg gcctgggcag ccccgtgtgt tgaggaagga    60
aggcagggcc cccgctcccc gggcctgacc ccac                                94

SEQ ID NO: 225            moltype = RNA   length = 85
FEATURE                   Location/Qualifiers
source                    1..85
                          mol_type = transcribed RNA
                          organism = Homo sapiens
SEQUENCE: 225
ggcctgggta ggcttgcatg ggggactggg aagagaccat gaacaggtta gtccagggag    60
ttctcatcaa gcctttactc agtag                                         85

SEQ ID NO: 226            moltype = RNA   length = 70
FEATURE                   Location/Qualifiers
source                    1..70
                          mol_type = transcribed RNA
                          organism = Homo sapiens
SEQUENCE: 226
ggccgcggcg cgcaagatgg cggcgggccc gggcaccgcc ccttccgccc cgccgggcgt    60
cgcacgaggc                                                          70

SEQ ID NO: 227            moltype = RNA   length = 86
FEATURE                   Location/Qualifiers
source                    1..86
                          mol_type = transcribed RNA
                          organism = Homo sapiens
SEQUENCE: 227
tgccagtctc taggtccctg agacccttta acctgtgagg acatccaggg tcacaggtga    60
ggttcttggg agcctggcgt ctggcc                                        86

SEQ ID NO: 228            moltype = RNA   length = 110
FEATURE                   Location/Qualifiers
source                    1..110
                          mol_type = transcribed RNA
                          organism = Homo sapiens
SEQUENCE: 228
ggctacagtc tttcttcatg tgactcgtgg acttcccttt gtcatcctat gcctgagaat    60
atatgaagga ggctgggaag gcaaagggac gttcaattgt catcactggc               110

SEQ ID NO: 229            moltype = RNA   length = 47
FEATURE                   Location/Qualifiers
source                    1..47
                          mol_type = transcribed RNA
                          organism = Homo sapiens
SEQUENCE: 229
ctcggcgcgg ggcgcgggct ccgggttggg gcgagccaac gccgggg                 47

SEQ ID NO: 230            moltype = RNA   length = 94
FEATURE                   Location/Qualifiers
source                    1..94
                          mol_type = transcribed RNA
                          organism = Homo sapiens
SEQUENCE: 230
aattcagccc tgccactggc ttatgtcatg accttgggct actcaggctg tctgcacaat    60
gagccagttg gacaggagca gtgccactca actc                               94

SEQ ID NO: 231            moltype = RNA   length = 84
FEATURE                   Location/Qualifiers
source                    1..84
                          mol_type = transcribed RNA
                          organism = Homo sapiens
SEQUENCE: 231
ctccccatgg ccctgtctcc caaccccttgt accagtgctg ggctcagacc ctggtacagg    60
cctggggac agggacctgg ggac                                            84
```

```
SEQ ID NO: 232          moltype = RNA    length = 94
FEATURE                 Location/Qualifiers
source                  1..94
                        mol_type = transcribed RNA
                        organism = Homo sapiens
SEQUENCE: 232
ataaaggaag ttaggctgag gggcagagag cgagactttt ctattttcca aaagctcggt    60
ctgaggcccc tcagtcttgc ttcctaaccc gcgc                                94

SEQ ID NO: 233          moltype = RNA    length = 94
FEATURE                 Location/Qualifiers
source                  1..94
                        mol_type = transcribed RNA
                        organism = Homo sapiens
SEQUENCE: 233
cgggcagcgg gtgccaggca cggtgtcagc aggcaacatg gccgagaggc cggggcctcc    60
gggcggcgcc gtgtccgcga ccgcgtaccc tgac                                94

SEQ ID NO: 234          moltype = RNA    length = 85
FEATURE                 Location/Qualifiers
source                  1..85
                        mol_type = transcribed RNA
                        organism = Homo sapiens
SEQUENCE: 234
ggcgcctcct gctctgctgt gccgccaggg cctcccctag cgcgccttct ggagaggctt    60
tgtgcggata cggggctgga ggcct                                          85

SEQ ID NO: 235          moltype = RNA    length = 73
FEATURE                 Location/Qualifiers
source                  1..73
                        mol_type = transcribed RNA
                        organism = Homo sapiens
SEQUENCE: 235
tgtatccttg aatggatttt tggagcagga gtggacacct gacccaaagg aaatcaatcc    60
ataggctagc aat                                                       73

SEQ ID NO: 236          moltype = RNA    length = 98
FEATURE                 Location/Qualifiers
source                  1..98
                        mol_type = transcribed RNA
                        organism = Homo sapiens
SEQUENCE: 236
ttctcacccc cgcctgacac gggcgacagc tgcggcccgc tgtgttcact cgggccgagt    60
gcgtctcctg tcaggcaagg gagagcagag ccccccctg                           98

SEQ ID NO: 237          moltype = RNA    length = 78
FEATURE                 Location/Qualifiers
source                  1..78
                        mol_type = transcribed RNA
                        organism = Homo sapiens
SEQUENCE: 237
gagcgtcacg ttgacactca aaaagtttca gattttggaa catttcggat tttggatttt    60
tggatcaggg atgctcaa                                                  78

SEQ ID NO: 238          moltype = RNA    length = 89
FEATURE                 Location/Qualifiers
source                  1..89
                        mol_type = transcribed RNA
                        organism = Homo sapiens
SEQUENCE: 238
gtcagcagtg ccttagcagc acgtaaatat tggcgttaag attctaaaat tatctccagt    60
attaactgtg ctgctgaagt aaggttgac                                      89

SEQ ID NO: 239          moltype = RNA    length = 81
FEATURE                 Location/Qualifiers
source                  1..81
                        mol_type = transcribed RNA
                        organism = Homo sapiens
SEQUENCE: 239
gttccactct agcagcacgt aaatattggc gtagtgaaat atatattaaa caccaatatt    60
actgtgctgc tttagtgtga c                                              81

SEQ ID NO: 240          moltype = RNA    length = 72
FEATURE                 Location/Qualifiers
source                  1..72
                        mol_type = transcribed RNA
                        organism = Homo sapiens
```

```
SEQUENCE: 240
cttgggaatg gcaaggaaac cgttaccatt actgagttta gtaatggtaa tggttctctt    60
gctataccca ga                                                        72

SEQ ID NO: 241          moltype = RNA   length = 68
FEATURE                 Location/Qualifiers
source                  1..68
                        mol_type = transcribed RNA
                        organism = Homo sapiens
SEQUENCE: 241
ctccggtgcc tactgagctg atatcagttc tcattttaca cactggctca gttcagcagg    60
aacaggag                                                             68

SEQ ID NO: 242          moltype = RNA   length = 73
FEATURE                 Location/Qualifiers
source                  1..73
                        mol_type = transcribed RNA
                        organism = Homo sapiens
SEQUENCE: 242
ctctgcctcc cgtgcctact gagctgaaac acagttggtt tgtgtacact ggctcagttc    60
agcaggaaca ggg                                                       73

SEQ ID NO: 243          moltype = RNA   length = 109
FEATURE                 Location/Qualifiers
source                  1..109
                        mol_type = transcribed RNA
                        organism = Homo sapiens
SEQUENCE: 243
ggtcgggctc accatgacac agtgtgagac ctcgggctac aacacaggac ccgggcgctg    60
ctctgacccc tcgtgtcttg tgttgcagcc ggagggacgc aggtccgca              109

SEQ ID NO: 244          moltype = RNA   length = 80
FEATURE                 Location/Qualifiers
source                  1..80
                        mol_type = transcribed RNA
                        organism = Homo sapiens
SEQUENCE: 244
cgggaatgcc gcggcgggga cggcgattgg tccgtatgtg tggtgccacc ggccgccggc    60
tccgccccgg cccccgcccc                                                80

SEQ ID NO: 245          moltype = RNA   length = 67
FEATURE                 Location/Qualifiers
source                  1..67
                        mol_type = transcribed RNA
                        organism = Homo sapiens
SEQUENCE: 245
gtggcactca aactgtgggg gcactttctg ctctctggtg aaagtgccgc catcttttga    60
gtgttac                                                              67

SEQ ID NO: 246          moltype = RNA   length = 97
FEATURE                 Location/Qualifiers
source                  1..97
                        mol_type = transcribed RNA
                        organism = Homo sapiens
SEQUENCE: 246
tgatgctttg ctggctggtg cagtgcctga gggagtaaga gccctgttgt tgtaagatag    60
tgtcttactc cctcaggcac atctccaaca agtctct                             97

SEQ ID NO: 247          moltype = RNA   length = 97
FEATURE                 Location/Qualifiers
source                  1..97
                        mol_type = transcribed RNA
                        organism = Homo sapiens
SEQUENCE: 247
tgatgctttg ctggctggtg cagtgcctga gggagtaaga gccctgttgt tgtcagatag    60
tgtcttactc cctcaggcac atctccagcg agtctct                             97

SEQ ID NO: 248          moltype = RNA   length = 22
FEATURE                 Location/Qualifiers
source                  1..22
                        mol_type = transcribed RNA
                        organism = Homo sapiens
SEQUENCE: 248
aaggatttag ggacaggctt tg                                             22

SEQ ID NO: 249          moltype = RNA   length = 19
FEATURE                 Location/Qualifiers
```

```
source                  1..19
                        mol_type = transcribed RNA
                        organism = Homo sapiens
SEQUENCE: 249
caggaaggat ttagggaca                                                    19

SEQ ID NO: 250          moltype = RNA   length = 20
FEATURE                 Location/Qualifiers
source                  1..20
                        mol_type = transcribed RNA
                        organism = Homo sapiens
SEQUENCE: 250
cagcaggacg ggagcgcggc                                                   20

SEQ ID NO: 251          moltype = RNA   length = 21
FEATURE                 Location/Qualifiers
source                  1..21
                        mol_type = transcribed RNA
                        organism = Homo sapiens
SEQUENCE: 251
cggatccgag tcacggcacc a                                                 21

SEQ ID NO: 252          moltype = RNA   length = 15
FEATURE                 Location/Qualifiers
source                  1..15
                        mol_type = transcribed RNA
                        organism = Homo sapiens
SEQUENCE: 252
tccgagtcac ggcac                                                        15

SEQ ID NO: 253          moltype = RNA   length = 23
FEATURE                 Location/Qualifiers
source                  1..23
                        mol_type = transcribed RNA
                        organism = Homo sapiens
SEQUENCE: 253
gggggtcccc ggtgctcgga tct                                               23

SEQ ID NO: 254          moltype = RNA   length = 20
FEATURE                 Location/Qualifiers
source                  1..20
                        mol_type = transcribed RNA
                        organism = Homo sapiens
SEQUENCE: 254
gggggtcccc ggtgctcgga                                                   20

SEQ ID NO: 255          moltype = RNA   length = 22
FEATURE                 Location/Qualifiers
source                  1..22
                        mol_type = transcribed RNA
                        organism = Homo sapiens
SEQUENCE: 255
ggcgtcccag gcggggcgcc gc                                                22

SEQ ID NO: 256          moltype = RNA   length = 15
FEATURE                 Location/Qualifiers
source                  1..15
                        mol_type = transcribed RNA
                        organism = Homo sapiens
SEQUENCE: 256
gcgccgcggg accgc                                                        15

SEQ ID NO: 257          moltype = RNA   length = 15
FEATURE                 Location/Qualifiers
source                  1..15
                        mol_type = transcribed RNA
                        organism = Homo sapiens
SEQUENCE: 257
gagcgctcgc tggcc                                                        15

SEQ ID NO: 258          moltype = RNA   length = 15
FEATURE                 Location/Qualifiers
source                  1..15
                        mol_type = transcribed RNA
                        organism = Homo sapiens
SEQUENCE: 258
cggtgagcgc tcgct                                                        15
```

-continued

```
SEQ ID NO: 259            moltype = RNA   length = 22
FEATURE                   Location/Qualifiers
source                    1..22
                          mol_type = transcribed RNA
                          organism = Homo sapiens
SEQUENCE: 259
accaggaggc tgaggcccct ca                                                   22

SEQ ID NO: 260            moltype = RNA   length = 15
FEATURE                   Location/Qualifiers
source                    1..15
                          mol_type = transcribed RNA
                          organism = Homo sapiens
SEQUENCE: 260
accaggaggc tgagg                                                           15

SEQ ID NO: 261            moltype = RNA   length = 17
FEATURE                   Location/Qualifiers
source                    1..17
                          mol_type = transcribed RNA
                          organism = Homo sapiens
SEQUENCE: 261
tcctagtcac ggcacca                                                         17

SEQ ID NO: 262            moltype = RNA   length = 17
FEATURE                   Location/Qualifiers
source                    1..17
                          mol_type = transcribed RNA
                          organism = Homo sapiens
SEQUENCE: 262
cctccgggac ggctggg                                                         17

SEQ ID NO: 263            moltype = RNA   length = 15
FEATURE                   Location/Qualifiers
source                    1..15
                          mol_type = transcribed RNA
                          organism = Homo sapiens
SEQUENCE: 263
ccgggacggc tgggc                                                           15

SEQ ID NO: 264            moltype = RNA   length = 20
FEATURE                   Location/Qualifiers
source                    1..20
                          mol_type = transcribed RNA
                          organism = Homo sapiens
SEQUENCE: 264
gctgcgggct gcggtcaggg                                                      20

SEQ ID NO: 265            moltype = RNA   length = 18
FEATURE                   Location/Qualifiers
source                    1..18
                          mol_type = transcribed RNA
                          organism = Homo sapiens
SEQUENCE: 265
gctcctgaat agctggga                                                        18

SEQ ID NO: 266            moltype = RNA   length = 16
FEATURE                   Location/Qualifiers
source                    1..16
                          mol_type = transcribed RNA
                          organism = Homo sapiens
SEQUENCE: 266
tgaatagctg ggacta                                                          16

SEQ ID NO: 267            moltype = RNA   length = 23
FEATURE                   Location/Qualifiers
source                    1..23
                          mol_type = transcribed RNA
                          organism = Homo sapiens
SEQUENCE: 267
ggtgggtgag gtcgggcccc aag                                                  23

SEQ ID NO: 268            moltype = RNA   length = 23
FEATURE                   Location/Qualifiers
source                    1..23
                          mol_type = transcribed RNA
                          organism = Homo sapiens
```

-continued

```
SEQUENCE: 268
acaggagtgg gggtgggaca taa                                              23

SEQ ID NO: 269         moltype = RNA   length = 20
FEATURE                Location/Qualifiers
source                 1..20
                       mol_type = transcribed RNA
                       organism = Homo sapiens
SEQUENCE: 269
acaggagtgg gggtgggaca                                                  20

SEQ ID NO: 270         moltype = RNA   length = 21
FEATURE                Location/Qualifiers
source                 1..21
                       mol_type = transcribed RNA
                       organism = Homo sapiens
SEQUENCE: 270
ctgggggacg cgtgagcgcg a                                                21

SEQ ID NO: 271         moltype = RNA   length = 15
FEATURE                Location/Qualifiers
source                 1..15
                       mol_type = transcribed RNA
                       organism = Homo sapiens
SEQUENCE: 271
cagggagcag gaagc                                                       15

SEQ ID NO: 272         moltype = RNA   length = 22
FEATURE                Location/Qualifiers
source                 1..22
                       mol_type = transcribed RNA
                       organism = Homo sapiens
SEQUENCE: 272
gctgggatta caggcatgag cc                                               22

SEQ ID NO: 273         moltype = RNA   length = 15
FEATURE                Location/Qualifiers
source                 1..15
                       mol_type = transcribed RNA
                       organism = Homo sapiens
SEQUENCE: 273
gattacaggc atgag                                                       15

SEQ ID NO: 274         moltype = RNA   length = 18
FEATURE                Location/Qualifiers
source                 1..18
                       mol_type = transcribed RNA
                       organism = Homo sapiens
SEQUENCE: 274
gcacgggagc tcaggtga                                                    18

SEQ ID NO: 275         moltype = RNA   length = 20
FEATURE                Location/Qualifiers
source                 1..20
                       mol_type = transcribed RNA
                       organism = Homo sapiens
SEQUENCE: 275
atcccacctc tgccaccaaa                                                  20

SEQ ID NO: 276         moltype = RNA   length = 16
FEATURE                Location/Qualifiers
source                 1..16
                       mol_type = transcribed RNA
                       organism = Homo sapiens
SEQUENCE: 276
tcccacctct gccacc                                                      16

SEQ ID NO: 277         moltype = RNA   length = 16
FEATURE                Location/Qualifiers
source                 1..16
                       mol_type = transcribed RNA
                       organism = Homo sapiens
SEQUENCE: 277
ggagcggcgg atctgg                                                      16

SEQ ID NO: 278         moltype = RNA   length = 23
FEATURE                Location/Qualifiers
```

```
source                  1..23
                        mol_type = transcribed RNA
                        organism = Homo sapiens
SEQUENCE: 278
acagcagggc tggggattgc agt                                              23

SEQ ID NO: 279          moltype = RNA   length = 20
FEATURE                 Location/Qualifiers
source                  1..20
                        mol_type = transcribed RNA
                        organism = Homo sapiens
SEQUENCE: 279
accggccgcc ggctccgccc                                                  20

SEQ ID NO: 280          moltype = RNA   length = 17
FEATURE                 Location/Qualifiers
source                  1..17
                        mol_type = transcribed RNA
                        organism = Homo sapiens
SEQUENCE: 280
ccggccgccg gctccgc                                                     17

SEQ ID NO: 281          moltype = RNA   length = 15
FEATURE                 Location/Qualifiers
source                  1..15
                        mol_type = transcribed RNA
                        organism = Homo sapiens
SEQUENCE: 281
tcccagcggt gcctc                                                       15

SEQ ID NO: 282          moltype = RNA   length = 25
FEATURE                 Location/Qualifiers
source                  1..25
                        mol_type = transcribed RNA
                        organism = Homo sapiens
SEQUENCE: 282
ttctgggccc gcggcgggcg tgggg                                            25

SEQ ID NO: 283          moltype = RNA   length = 15
FEATURE                 Location/Qualifiers
source                  1..15
                        mol_type = transcribed RNA
                        organism = Homo sapiens
SEQUENCE: 283
cgcggcgggc gtggg                                                       15

SEQ ID NO: 284          moltype = RNA   length = 21
FEATURE                 Location/Qualifiers
source                  1..21
                        mol_type = transcribed RNA
                        organism = Homo sapiens
SEQUENCE: 284
aagaaggcgg tcggtctgcg g                                                21

SEQ ID NO: 285          moltype = RNA   length = 22
FEATURE                 Location/Qualifiers
source                  1..22
                        mol_type = transcribed RNA
                        organism = Homo sapiens
SEQUENCE: 285
actcggctgc ggtggacaag tc                                               22

SEQ ID NO: 286          moltype = RNA   length = 20
FEATURE                 Location/Qualifiers
source                  1..20
                        mol_type = transcribed RNA
                        organism = Homo sapiens
SEQUENCE: 286
ctcggctgcg gtggacaagt                                                  20

SEQ ID NO: 287          moltype = RNA   length = 19
FEATURE                 Location/Qualifiers
source                  1..19
                        mol_type = transcribed RNA
                        organism = Homo sapiens
SEQUENCE: 287
ctccagcctg agtgacaga                                                   19

SEQ ID NO: 288          moltype = RNA   length = 15
```

```
FEATURE              Location/Qualifiers
source               1..15
                     mol_type = transcribed RNA
                     organism = Homo sapiens
SEQUENCE: 288
actgcactcc agcct                                                       15

SEQ ID NO: 289       moltype = RNA   length = 16
FEATURE              Location/Qualifiers
source               1..16
                     mol_type = transcribed RNA
                     organism = Homo sapiens
SEQUENCE: 289
gtgggggggc aggagg                                                      16

SEQ ID NO: 290       moltype = RNA   length = 19
FEATURE              Location/Qualifiers
source               1..19
                     mol_type = transcribed RNA
                     organism = Homo sapiens
SEQUENCE: 290
gggggcagg aggggctca                                                    19

SEQ ID NO: 291       moltype = RNA   length = 21
FEATURE              Location/Qualifiers
source               1..21
                     mol_type = transcribed RNA
                     organism = Homo sapiens
SEQUENCE: 291
cttcccccca gtaatcttca t                                                21

SEQ ID NO: 292       moltype = RNA   length = 22
FEATURE              Location/Qualifiers
source               1..22
                     mol_type = transcribed RNA
                     organism = Homo sapiens
SEQUENCE: 292
cctcacacct gcctcgcccc cc                                               22

SEQ ID NO: 293       moltype = RNA   length = 15
FEATURE              Location/Qualifiers
source               1..15
                     mol_type = transcribed RNA
                     organism = Homo sapiens
SEQUENCE: 293
tcacacctgc ctcgc                                                       15

SEQ ID NO: 294       moltype = RNA   length = 22
FEATURE              Location/Qualifiers
source               1..22
                     mol_type = transcribed RNA
                     organism = Homo sapiens
SEQUENCE: 294
gttggtgggg gagccatgag at                                               22

SEQ ID NO: 295       moltype = RNA   length = 22
FEATURE              Location/Qualifiers
source               1..22
                     mol_type = transcribed RNA
                     organism = Homo sapiens
SEQUENCE: 295
ggggagccat gagataagag ca                                               22

SEQ ID NO: 296       moltype = RNA   length = 22
FEATURE              Location/Qualifiers
source               1..22
                     mol_type = transcribed RNA
                     organism = Homo sapiens
SEQUENCE: 296
tcggctctgg gtctgtgggg ag                                               22

SEQ ID NO: 297       moltype = RNA   length = 17
FEATURE              Location/Qualifiers
source               1..17
                     mol_type = transcribed RNA
                     organism = Homo sapiens
SEQUENCE: 297
cggctctggg tctgtgg                                                     17
```

| | | |
|---|---|---|
| SEQ ID NO: 298<br>FEATURE<br>source<br><br>SEQUENCE: 298<br>gctgggcgag gctggcatc | moltype = RNA   length = 19<br>Location/Qualifiers<br>1..19<br>mol_type = transcribed RNA<br>organism = Homo sapiens | <br><br><br><br><br>19 |
| SEQ ID NO: 299<br>FEATURE<br>source<br><br>SEQUENCE: 299<br>tctgccccct ccgctgctgc | moltype = RNA   length = 20<br>Location/Qualifiers<br>1..20<br>mol_type = transcribed RNA<br>organism = Homo sapiens | <br><br><br><br><br>20 |
| SEQ ID NO: 300<br>FEATURE<br>source<br><br>SEQUENCE: 300<br>atcccaccac tgccaccatt | moltype = RNA   length = 20<br>Location/Qualifiers<br>1..20<br>mol_type = transcribed RNA<br>organism = Homo sapiens | <br><br><br><br><br>20 |
| SEQ ID NO: 301<br>FEATURE<br>source<br><br>SEQUENCE: 301<br>ccaccaccca ccactgccac catgccacca | moltype = RNA   length = 30<br>Location/Qualifiers<br>1..30<br>mol_type = transcribed RNA<br>organism = Homo sapiens | <br><br><br><br><br>30 |
| SEQ ID NO: 302<br>FEATURE<br>source<br><br>SEQUENCE: 302<br>gtgcccgtcc cggggctgcg cgag | moltype = RNA   length = 24<br>Location/Qualifiers<br>1..24<br>mol_type = transcribed RNA<br>organism = Homo sapiens | <br><br><br><br><br>24 |
| SEQ ID NO: 303<br>FEATURE<br>source<br><br>SEQUENCE: 303<br>ccggggctgc gcgaggc | moltype = RNA   length = 17<br>Location/Qualifiers<br>1..17<br>mol_type = transcribed RNA<br>organism = Homo sapiens | <br><br><br><br><br>17 |
| SEQ ID NO: 304<br>FEATURE<br>source<br><br>SEQUENCE: 304<br>gctgcagtgg gggag | moltype = RNA   length = 15<br>Location/Qualifiers<br>1..15<br>mol_type = transcribed RNA<br>organism = Homo sapiens | <br><br><br><br><br>15 |
| SEQ ID NO: 305<br>FEATURE<br>source<br><br>SEQUENCE: 305<br>tggcggcggt agttatgggc ttctc | moltype = RNA   length = 25<br>Location/Qualifiers<br>1..25<br>mol_type = transcribed RNA<br>organism = Homo sapiens | <br><br><br><br><br>25 |
| SEQ ID NO: 306<br>FEATURE<br>source<br><br>SEQUENCE: 306<br>gctgggctgg gacggacacc cggcctccac | moltype = RNA   length = 30<br>Location/Qualifiers<br>1..30<br>mol_type = transcribed RNA<br>organism = Homo sapiens | <br><br><br><br><br>30 |
| SEQ ID NO: 307<br>FEATURE<br>source<br><br>SEQUENCE: 307<br>ggaaaaaggc gggagaagcc | moltype = RNA   length = 20<br>Location/Qualifiers<br>1..20<br>mol_type = transcribed RNA<br>organism = Homo sapiens | <br><br><br><br><br>20 |

| | | |
|---|---|---|
| SEQ ID NO: 308 | moltype = RNA length = 15 | |
| FEATURE | Location/Qualifiers | |
| source | 1..15 | |
| | mol_type = transcribed RNA | |
| | organism = Homo sapiens | |
| SEQUENCE: 308 | | |
| ggcgggagaa gcccc | | 15 |
| SEQ ID NO: 309 | moltype = RNA length = 21 | |
| FEATURE | Location/Qualifiers | |
| source | 1..21 | |
| | mol_type = transcribed RNA | |
| | organism = Homo sapiens | |
| SEQUENCE: 309 | | |
| cccaggctgg agcgagtgca g | | 21 |
| SEQ ID NO: 310 | moltype = RNA length = 23 | |
| FEATURE | Location/Qualifiers | |
| source | 1..23 | |
| | mol_type = transcribed RNA | |
| | organism = Homo sapiens | |
| SEQUENCE: 310 | | |
| agggagtaga agggtgggga gca | | 23 |
| SEQ ID NO: 311 | moltype = RNA length = 16 | |
| FEATURE | Location/Qualifiers | |
| source | 1..16 | |
| | mol_type = transcribed RNA | |
| | organism = Homo sapiens | |
| SEQUENCE: 311 | | |
| tagggagtag aagggt | | 16 |
| SEQ ID NO: 312 | moltype = RNA length = 25 | |
| FEATURE | Location/Qualifiers | |
| source | 1..25 | |
| | mol_type = transcribed RNA | |
| | organism = Homo sapiens | |
| SEQUENCE: 312 | | |
| tgggcagggg cttattgtag gagtc | | 25 |
| SEQ ID NO: 313 | moltype = RNA length = 21 | |
| FEATURE | Location/Qualifiers | |
| source | 1..21 | |
| | mol_type = transcribed RNA | |
| | organism = Homo sapiens | |
| SEQUENCE: 313 | | |
| gggcaggggc ttattgtagg a | | 21 |
| SEQ ID NO: 314 | moltype = RNA length = 20 | |
| FEATURE | Location/Qualifiers | |
| source | 1..20 | |
| | mol_type = transcribed RNA | |
| | organism = Homo sapiens | |
| SEQUENCE: 314 | | |
| caccccactc ctggtaccat | | 20 |
| SEQ ID NO: 315 | moltype = RNA length = 15 | |
| FEATURE | Location/Qualifiers | |
| source | 1..15 | |
| | mol_type = transcribed RNA | |
| | organism = Homo sapiens | |
| SEQUENCE: 315 | | |
| ccccactcct ggtac | | 15 |
| SEQ ID NO: 316 | moltype = RNA length = 26 | |
| FEATURE | Location/Qualifiers | |
| source | 1..26 | |
| | mol_type = transcribed RNA | |
| | organism = Homo sapiens | |
| SEQUENCE: 316 | | |
| gcgggctgtc cggaggggtc ggcttt | | 26 |
| SEQ ID NO: 317 | moltype = RNA length = 16 | |
| FEATURE | Location/Qualifiers | |
| source | 1..16 | |
| | mol_type = transcribed RNA | |
| | organism = Homo sapiens | |

```
SEQUENCE: 317
gctgtccgga ggggtc                                                       16

SEQ ID NO: 318          moltype = RNA   length = 18
FEATURE                 Location/Qualifiers
source                  1..18
                        mol_type = transcribed RNA
                        organism = Homo sapiens
SEQUENCE: 318
cagcggggct gggcgcgc                                                     18

SEQ ID NO: 319          moltype = RNA   length = 15
FEATURE                 Location/Qualifiers
source                  1..15
                        mol_type = transcribed RNA
                        organism = Homo sapiens
SEQUENCE: 319
cggggctggg cgcgc                                                        15

SEQ ID NO: 320          moltype = RNA   length = 23
FEATURE                 Location/Qualifiers
source                  1..23
                        mol_type = transcribed RNA
                        organism = Homo sapiens
SEQUENCE: 320
aggaaggaag gcagggcccc cgc                                               23

SEQ ID NO: 321          moltype = RNA   length = 15
FEATURE                 Location/Qualifiers
source                  1..15
                        mol_type = transcribed RNA
                        organism = Homo sapiens
SEQUENCE: 321
gggccccgc tcccc                                                         15

SEQ ID NO: 322          moltype = RNA   length = 23
FEATURE                 Location/Qualifiers
source                  1..23
                        mol_type = transcribed RNA
                        organism = Homo sapiens
SEQUENCE: 322
cacaggtgag gttcttggga gcc                                               23

SEQ ID NO: 323          moltype = RNA   length = 15
FEATURE                 Location/Qualifiers
source                  1..15
                        mol_type = transcribed RNA
                        organism = Homo sapiens
SEQUENCE: 323
gaggttcttg ggagc                                                        15

SEQ ID NO: 324          moltype = RNA   length = 24
FEATURE                 Location/Qualifiers
source                  1..24
                        mol_type = transcribed RNA
                        organism = Homo sapiens
SEQUENCE: 324
gaggctggga aggcaaaggg acgt                                              24

SEQ ID NO: 325          moltype = RNA   length = 15
FEATURE                 Location/Qualifiers
source                  1..15
                        mol_type = transcribed RNA
                        organism = Homo sapiens
SEQUENCE: 325
ctgggaaggc aaagg                                                        15

SEQ ID NO: 326          moltype = RNA   length = 24
FEATURE                 Location/Qualifiers
source                  1..24
                        mol_type = transcribed RNA
                        organism = Homo sapiens
SEQUENCE: 326
tggtacaggc ctgggggaca ggga                                              24

SEQ ID NO: 327          moltype = RNA   length = 19
FEATURE                 Location/Qualifiers
```

```
source                  1..19
                        mol_type = transcribed RNA
                        organism = Homo sapiens
SEQUENCE: 327
ggtacaggcc tgggggaca                                                19

SEQ ID NO: 328          moltype = RNA   length = 30
FEATURE                 Location/Qualifiers
source                  1..30
                        mol_type = transcribed RNA
                        organism = Homo sapiens
SEQUENCE: 328
tgagggcag agagcgagac ttttctattt                                     30

SEQ ID NO: 329          moltype = RNA   length = 15
FEATURE                 Location/Qualifiers
source                  1..15
                        mol_type = transcribed RNA
                        organism = Homo sapiens
SEQUENCE: 329
cagagagcga gactt                                                    15

SEQ ID NO: 330          moltype = RNA   length = 25
FEATURE                 Location/Qualifiers
source                  1..25
                        mol_type = transcribed RNA
                        organism = Homo sapiens
SEQUENCE: 330
ctttgtgcgg atacggggct ggagg                                         25

SEQ ID NO: 331          moltype = RNA   length = 19
FEATURE                 Location/Qualifiers
source                  1..19
                        mol_type = transcribed RNA
                        organism = Homo sapiens
SEQUENCE: 331
agaggctttg tgcggatac                                                19

SEQ ID NO: 332          moltype = RNA   length = 21
FEATURE                 Location/Qualifiers
source                  1..21
                        mol_type = transcribed RNA
                        organism = Homo sapiens
SEQUENCE: 332
gaatggattt ttggagcagg a                                             21

SEQ ID NO: 333          moltype = RNA   length = 15
FEATURE                 Location/Qualifiers
source                  1..15
                        mol_type = transcribed RNA
                        organism = Homo sapiens
SEQUENCE: 333
ggatttttgg agcag                                                    15

SEQ ID NO: 334          moltype = RNA   length = 20
FEATURE                 Location/Qualifiers
source                  1..20
                        mol_type = transcribed RNA
                        organism = Homo sapiens
SEQUENCE: 334
ggatttttgg atcagggatg                                               20

SEQ ID NO: 335          moltype = RNA   length = 15
FEATURE                 Location/Qualifiers
source                  1..15
                        mol_type = transcribed RNA
                        organism = Homo sapiens
SEQUENCE: 335
tttttggatc aggga                                                    15

SEQ ID NO: 336          moltype = RNA   length = 27
FEATURE                 Location/Qualifiers
source                  1..27
                        mol_type = transcribed RNA
                        organism = Homo sapiens
SEQUENCE: 336
tagcagcacg taaatattgg cgttaag                                       27

SEQ ID NO: 337          moltype = RNA   length = 26
```

```
FEATURE                 Location/Qualifiers
source                  1..26
                        mol_type = transcribed RNA
                        organism = Homo sapiens
SEQUENCE: 337
tagcagcacg taaatattgg cgtagt                                        26

SEQ ID NO: 338          moltype = RNA   length = 15
FEATURE                 Location/Qualifiers
source                  1..15
                        mol_type = transcribed RNA
                        organism = Homo sapiens
SEQUENCE: 338
cacgtaaata ttggc                                                    15

SEQ ID NO: 339          moltype = RNA   length = 27
FEATURE                 Location/Qualifiers
source                  1..27
                        mol_type = transcribed RNA
                        organism = Homo sapiens
SEQUENCE: 339
aaaccgttac cattactgag tttagta                                       27

SEQ ID NO: 340          moltype = RNA   length = 15
FEATURE                 Location/Qualifiers
source                  1..15
                        mol_type = transcribed RNA
                        organism = Homo sapiens
SEQUENCE: 340
taccattact gagtt                                                    15

SEQ ID NO: 341          moltype = RNA   length = 24
FEATURE                 Location/Qualifiers
source                  1..24
                        mol_type = transcribed RNA
                        organism = Homo sapiens
SEQUENCE: 341
tggctcagtt cagcaggaac agga                                          24

SEQ ID NO: 342          moltype = RNA   length = 24
FEATURE                 Location/Qualifiers
source                  1..24
                        mol_type = transcribed RNA
                        organism = Homo sapiens
SEQUENCE: 342
ctggctcagt tcagcaggaa cagg                                          24

SEQ ID NO: 343          moltype = RNA   length = 15
FEATURE                 Location/Qualifiers
source                  1..15
                        mol_type = transcribed RNA
                        organism = Homo sapiens
SEQUENCE: 343
agttcagcag gaaca                                                    15

SEQ ID NO: 344          moltype = RNA   length = 22
FEATURE                 Location/Qualifiers
source                  1..22
                        mol_type = transcribed RNA
                        organism = Homo sapiens
SEQUENCE: 344
gggctacaac acaggacccg gg                                            22

SEQ ID NO: 345          moltype = RNA   length = 22
FEATURE                 Location/Qualifiers
source                  1..22
                        mol_type = transcribed RNA
                        organism = Homo sapiens
SEQUENCE: 345
gctacaacac aggacccggg cg                                            22

SEQ ID NO: 346          moltype = RNA   length = 22
FEATURE                 Location/Qualifiers
source                  1..22
                        mol_type = transcribed RNA
                        organism = Homo sapiens
SEQUENCE: 346
actcaaactg tggggcact tt                                             22
```

| | | |
|---|---|---|
| SEQ ID NO: 347 | moltype = RNA length = 19 | |
| FEATURE | Location/Qualifiers | |
| source | 1..19 | |
| | mol_type = transcribed RNA | |
| | organism = Homo sapiens | |
| SEQUENCE: 347 | | |
| actcaaactg tggggcac | | 19 |
| | | |
| SEQ ID NO: 348 | moltype = RNA length = 15 | |
| FEATURE | Location/Qualifiers | |
| source | 1..15 | |
| | mol_type = transcribed RNA | |
| | organism = Homo sapiens | |
| SEQUENCE: 348 | | |
| gagggagtaa gagcc | | 15 |
| | | |
| SEQ ID NO: 349 | moltype = RNA length = 18 | |
| FEATURE | Location/Qualifiers | |
| source | 1..18 | |
| | mol_type = transcribed RNA | |
| | organism = Homo sapiens | |
| SEQUENCE: 349 | | |
| ggtgggcttc ccggaggg | | 18 |
| | | |
| SEQ ID NO: 350 | moltype = RNA length = 23 | |
| FEATURE | Location/Qualifiers | |
| source | 1..23 | |
| | mol_type = transcribed RNA | |
| | organism = Homo sapiens | |
| SEQUENCE: 350 | | |
| gccccggcgc gggcgggttc tgg | | 23 |
| | | |
| SEQ ID NO: 351 | moltype = RNA length = 21 | |
| FEATURE | Location/Qualifiers | |
| source | 1..21 | |
| | mol_type = transcribed RNA | |
| | organism = Homo sapiens | |
| SEQUENCE: 351 | | |
| cgtggaggac gaggaggagg c | | 21 |
| | | |
| SEQ ID NO: 352 | moltype = RNA length = 19 | |
| FEATURE | Location/Qualifiers | |
| source | 1..19 | |
| | mol_type = transcribed RNA | |
| | organism = Homo sapiens | |
| SEQUENCE: 352 | | |
| ggggcctggc ggtgggcgg | | 19 |
| | | |
| SEQ ID NO: 353 | moltype = RNA length = 22 | |
| FEATURE | Location/Qualifiers | |
| source | 1..22 | |
| | mol_type = transcribed RNA | |
| | organism = Homo sapiens | |
| SEQUENCE: 353 | | |
| agactgacgg ctggaggccc at | | 22 |
| | | |
| SEQ ID NO: 354 | moltype = RNA length = 22 | |
| FEATURE | Location/Qualifiers | |
| source | 1..22 | |
| | mol_type = transcribed RNA | |
| | organism = Homo sapiens | |
| SEQUENCE: 354 | | |
| tgggggagga aggacaggcc at | | 22 |
| | | |
| SEQ ID NO: 355 | moltype = RNA length = 23 | |
| FEATURE | Location/Qualifiers | |
| source | 1..23 | |
| | mol_type = transcribed RNA | |
| | organism = Homo sapiens | |
| SEQUENCE: 355 | | |
| acggggagtc aggcagtggt gga | | 23 |
| | | |
| SEQ ID NO: 356 | moltype = RNA length = 23 | |
| FEATURE | Location/Qualifiers | |
| source | 1..23 | |
| | mol_type = transcribed RNA | |
| | organism = Homo sapiens | |
| SEQUENCE: 356 | | |
| cctccctgcc cgcctctctg cag | | 23 |

| | | |
|---|---|---|
| SEQ ID NO: 357<br>FEATURE<br>source | moltype = RNA   length = 20<br>Location/Qualifiers<br>1..20<br>mol_type = transcribed RNA<br>organism = Homo sapiens | |
| SEQUENCE: 357<br>tgtgggactg caaatgggag | | 20 |
| SEQ ID NO: 358<br>FEATURE<br>source | moltype = RNA   length = 24<br>Location/Qualifiers<br>1..24<br>mol_type = transcribed RNA<br>organism = Homo sapiens | |
| SEQUENCE: 358<br>tgagggcct cagaccgagc tttt | | 24 |
| SEQ ID NO: 359<br>FEATURE<br>source | moltype = RNA   length = 19<br>Location/Qualifiers<br>1..19<br>mol_type = transcribed RNA<br>organism = Homo sapiens | |
| SEQUENCE: 359<br>ggggaagaa aaggtgggg | | 19 |
| SEQ ID NO: 360<br>FEATURE<br>source | moltype = RNA   length = 22<br>Location/Qualifiers<br>1..22<br>mol_type = transcribed RNA<br>organism = Homo sapiens | |
| SEQUENCE: 360<br>cccctggggc tgggcaggcg ga | | 22 |
| SEQ ID NO: 361<br>FEATURE<br>source | moltype = RNA   length = 22<br>Location/Qualifiers<br>1..22<br>mol_type = transcribed RNA<br>organism = Homo sapiens | |
| SEQUENCE: 361<br>agacacattt ggagagggaa cc | | 22 |
| SEQ ID NO: 362<br>FEATURE<br>source | moltype = RNA   length = 21<br>Location/Qualifiers<br>1..21<br>mol_type = transcribed RNA<br>organism = Homo sapiens | |
| SEQUENCE: 362<br>gtgtggccgg caggcgggtg g | | 21 |
| SEQ ID NO: 363<br>FEATURE<br>source | moltype = RNA   length = 23<br>Location/Qualifiers<br>1..23<br>mol_type = transcribed RNA<br>organism = Homo sapiens | |
| SEQUENCE: 363<br>cggggccgta gcactgtctg aga | | 23 |
| SEQ ID NO: 364<br>FEATURE<br>source | moltype = RNA   length = 22<br>Location/Qualifiers<br>1..22<br>mol_type = transcribed RNA<br>organism = Homo sapiens | |
| SEQUENCE: 364<br>agggaagggg acgagggttg gg | | 22 |
| SEQ ID NO: 365<br>FEATURE<br>source | moltype = RNA   length = 17<br>Location/Qualifiers<br>1..17<br>mol_type = transcribed RNA<br>organism = Homo sapiens | |
| SEQUENCE: 365<br>ggggcgcggc cggatcg | | 17 |
| SEQ ID NO: 366<br>FEATURE<br>source | moltype = RNA   length = 17<br>Location/Qualifiers<br>1..17<br>mol_type = transcribed RNA<br>organism = Homo sapiens | |

-continued

```
SEQUENCE: 366
ggcgggtgcg ggggtgg                                                    17

SEQ ID NO: 367          moltype = RNA   length = 22
FEATURE                 Location/Qualifiers
source                  1..22
                        mol_type = transcribed RNA
                        organism = Homo sapiens
SEQUENCE: 367
gggtggggat tgttgcatt ac                                               22

SEQ ID NO: 368          moltype = RNA   length = 23
FEATURE                 Location/Qualifiers
source                  1..23
                        mol_type = transcribed RNA
                        organism = Homo sapiens
SEQUENCE: 368
tggtgggtgg ggaggagaag tgc                                             23

SEQ ID NO: 369          moltype = RNA   length = 22
FEATURE                 Location/Qualifiers
source                  1..22
                        mol_type = transcribed RNA
                        organism = Homo sapiens
SEQUENCE: 369
ttgaggagac atggtggggg cc                                              22

SEQ ID NO: 370          moltype = RNA   length = 21
FEATURE                 Location/Qualifiers
source                  1..21
                        mol_type = transcribed RNA
                        organism = Homo sapiens
SEQUENCE: 370
agcatgacag aggagaggtg g                                               21

SEQ ID NO: 371          moltype = RNA   length = 22
FEATURE                 Location/Qualifiers
source                  1..22
                        mol_type = transcribed RNA
                        organism = Homo sapiens
SEQUENCE: 371
agggacggga cgcggtgcag tg                                              22

SEQ ID NO: 372          moltype = RNA   length = 25
FEATURE                 Location/Qualifiers
source                  1..25
                        mol_type = transcribed RNA
                        organism = Homo sapiens
SEQUENCE: 372
acttgggcag gagggaccct gtatg                                           25

SEQ ID NO: 373          moltype = RNA   length = 21
FEATURE                 Location/Qualifiers
source                  1..21
                        mol_type = transcribed RNA
                        organism = Homo sapiens
SEQUENCE: 373
cggggcagct cagtacagga t                                               21

SEQ ID NO: 374          moltype = RNA   length = 24
FEATURE                 Location/Qualifiers
source                  1..24
                        mol_type = transcribed RNA
                        organism = Homo sapiens
SEQUENCE: 374
tgtaggcatg aggcagggcc cagg                                            24

SEQ ID NO: 375          moltype = RNA   length = 22
FEATURE                 Location/Qualifiers
source                  1..22
                        mol_type = transcribed RNA
                        organism = Homo sapiens
SEQUENCE: 375
tgggggtggt ctctagccaa gg                                              22

SEQ ID NO: 376          moltype = RNA   length = 20
FEATURE                 Location/Qualifiers
```

```
source                      1..20
                            mol_type = transcribed RNA
                            organism = Homo sapiens
SEQUENCE: 376
tgggaatggg ggtaagggcc                                              20

SEQ ID NO: 377              moltype = RNA   length = 23
FEATURE                     Location/Qualifiers
source                      1..23
                            mol_type = transcribed RNA
                            organism = Homo sapiens
SEQUENCE: 377
gtttgcacgg gtgggccttg tct                                          23

SEQ ID NO: 378              moltype = RNA   length = 22
FEATURE                     Location/Qualifiers
source                      1..22
                            mol_type = transcribed RNA
                            organism = Homo sapiens
SEQUENCE: 378
tccaggcagg agccggactg ga                                           22

SEQ ID NO: 379              moltype = RNA   length = 21
FEATURE                     Location/Qualifiers
source                      1..21
                            mol_type = transcribed RNA
                            organism = Homo sapiens
SEQUENCE: 379
ctgggctcgg gacgcgcggc t                                            21

SEQ ID NO: 380              moltype = RNA   length = 17
FEATURE                     Location/Qualifiers
source                      1..17
                            mol_type = transcribed RNA
                            organism = Homo sapiens
SEQUENCE: 380
gccggacaag agggagg                                                 17

SEQ ID NO: 381              moltype = RNA   length = 20
FEATURE                     Location/Qualifiers
source                      1..20
                            mol_type = transcribed RNA
                            organism = Homo sapiens
SEQUENCE: 381
ccccagggcg acgcggcggg                                              20

SEQ ID NO: 382              moltype = RNA   length = 21
FEATURE                     Location/Qualifiers
source                      1..21
                            mol_type = transcribed RNA
                            organism = Homo sapiens
SEQUENCE: 382
tggctgttgg aggggggcagg c                                           21

SEQ ID NO: 383              moltype = RNA   length = 22
FEATURE                     Location/Qualifiers
source                      1..22
                            mol_type = transcribed RNA
                            organism = Homo sapiens
SEQUENCE: 383
tattgcactc gtcccggcct cc                                           22

SEQ ID NO: 384              moltype = RNA   length = 73
FEATURE                     Location/Qualifiers
source                      1..73
                            mol_type = transcribed RNA
                            organism = Homo sapiens
SEQUENCE: 384
gaaaacaacc aggtgggctt cccggagggc ggaacaccca gccccagcat ccagggctca  60
cctaccacgt ttg                                                     73

SEQ ID NO: 385              moltype = RNA   length = 80
FEATURE                     Location/Qualifiers
source                      1..80
                            mol_type = transcribed RNA
                            organism = Homo sapiens
SEQUENCE: 385
ggttccggag cccggcgcg gcgggttct ggggtgtaga cgctgctggc cagcccgccc    60
cagccgaggt tctcggcacc                                              80
```

```
SEQ ID NO: 386          moltype = RNA   length = 103
FEATURE                 Location/Qualifiers
source                  1..103
                        mol_type = transcribed RNA
                        organism = Homo sapiens
SEQUENCE: 386
gtgtcggctg tggcgtgact gtccctctgt gtcccccact aggcccactg ctcagtggag    60
cgtggaggac gaggaggagg ccgtccacga gcaatgccag cat                     103

SEQ ID NO: 387          moltype = RNA   length = 90
FEATURE                 Location/Qualifiers
source                  1..90
                        mol_type = transcribed RNA
                        organism = Homo sapiens
SEQUENCE: 387
ggcgcctctg cagctccggc tcccctggc ctctcgggaa ctacaagtcc caggggcct      60
ggcggtgggc ggcgggcgga agaggcgggg                                     90

SEQ ID NO: 388          moltype = RNA   length = 86
FEATURE                 Location/Qualifiers
source                  1..86
                        mol_type = transcribed RNA
                        organism = Homo sapiens
SEQUENCE: 388
attctaggtg gggagactga cggctggagg cccataagct gtctaaaact tcggccccca    60
gatttctggt ctccccactt cagaac                                         86

SEQ ID NO: 389          moltype = RNA   length = 72
FEATURE                 Location/Qualifiers
source                  1..72
                        mol_type = transcribed RNA
                        organism = Homo sapiens
SEQUENCE: 389
ctgggggagg aaggacaggc catctgctat tcgtccacca acctgacttg atcctctctt    60
ccctcctccc ag                                                        72

SEQ ID NO: 390          moltype = RNA   length = 66
FEATURE                 Location/Qualifiers
source                  1..66
                        mol_type = transcribed RNA
                        organism = Homo sapiens
SEQUENCE: 390
tcaagacggg gagtcaggca gtggtggaga tggagagccc tgagcctcca ctctcctggc    60
ccccag                                                               66

SEQ ID NO: 391          moltype = RNA   length = 59
FEATURE                 Location/Qualifiers
source                  1..59
                        mol_type = transcribed RNA
                        organism = Homo sapiens
SEQUENCE: 391
ctccagggag acagtgtgtg aggcctcttg ccatggcctc cctgcccgcc tctctgcag     59

SEQ ID NO: 392          moltype = RNA   length = 72
FEATURE                 Location/Qualifiers
source                  1..72
                        mol_type = transcribed RNA
                        organism = Homo sapiens
SEQUENCE: 392
tgtgggactg caaatgggag ctcagcacct gcctgccacc cacgcagacc agcccctgct    60
ctgttcccac ag                                                        72

SEQ ID NO: 393          moltype = RNA   length = 75
FEATURE                 Location/Qualifiers
source                  1..75
                        mol_type = transcribed RNA
                        organism = Homo sapiens
SEQUENCE: 393
aagcaagact gagggcctc agaccgagct tttggaaaat agaaaagtct cgctctctgc     60
ccctcagcct aactt                                                     75

SEQ ID NO: 394          moltype = RNA   length = 67
FEATURE                 Location/Qualifiers
source                  1..67
                        mol_type = transcribed RNA
                        organism = Homo sapiens
```

```
SEQUENCE: 394
aaatctctct ccatatcttt cctgcagccc ccaggtgggg gggaagaaaa ggtggggaat    60
tagattc                                                             67

SEQ ID NO: 395          moltype = RNA   length = 67
FEATURE                 Location/Qualifiers
source                  1..67
                        mol_type = transcribed RNA
                        organism = Homo sapiens
SEQUENCE: 395
ccagacccct ggggctgggc aggcggaaag aggtctgaac tgcctctgcc tccttggtct    60
ccggcag                                                             67

SEQ ID NO: 396          moltype = RNA   length = 97
FEATURE                 Location/Qualifiers
source                  1..97
                        mol_type = transcribed RNA
                        organism = Homo sapiens
SEQUENCE: 396
atctgagttg ggagggtccc tctccaaatg tgtcttgggg tgggggatca agacacattt    60
ggagagggaa cctcccaact cggcctctgc catcatt                            97

SEQ ID NO: 397          moltype = RNA   length = 87
FEATURE                 Location/Qualifiers
source                  1..87
                        mol_type = transcribed RNA
                        organism = Homo sapiens
SEQUENCE: 397
gtgtggccgg caggcgggtg ggcggggggcg gccggtggga accccgcccc gccccgcgcc    60
cgcactcacc cgcccgtctc cccacag                                       87

SEQ ID NO: 398          moltype = RNA   length = 82
FEATURE                 Location/Qualifiers
source                  1..82
                        mol_type = transcribed RNA
                        organism = Homo sapiens
SEQUENCE: 398
tgagctgttg gattcggggc cgtagcactg tctgagaggt ttacatttct cacagtgaac    60
cggtctcttt ttcagctgct tc                                            82

SEQ ID NO: 399          moltype = RNA   length = 115
FEATURE                 Location/Qualifiers
source                  1..115
                        mol_type = transcribed RNA
                        organism = Homo sapiens
SEQUENCE: 399
tctgaggaga cctgggctgt cagaggccag ggaaggggac gagggttggg gaacaggtgg    60
ttagcacttc atcctcgtct ccctcccagg ttagaagggc cccctctct gaagg         115

SEQ ID NO: 400          moltype = RNA   length = 84
FEATURE                 Location/Qualifiers
source                  1..84
                        mol_type = transcribed RNA
                        organism = Homo sapiens
SEQUENCE: 400
gaggctgggc ggggcgcggc cggatcggtc gagagcgtcc tggctgatga cggtctcccg    60
tgcccacgcc ccaaacgcag tctc                                          84

SEQ ID NO: 401          moltype = RNA   length = 69
FEATURE                 Location/Qualifiers
source                  1..69
                        mol_type = transcribed RNA
                        organism = Homo sapiens
SEQUENCE: 401
ctttcggcca gcgggacggc atccgaggtg ggctaggctc gggcccgtgg cgggtgcggg    60
ggtgggagg                                                           69

SEQ ID NO: 402          moltype = RNA   length = 75
FEATURE                 Location/Qualifiers
source                  1..75
                        mol_type = transcribed RNA
                        organism = Homo sapiens
SEQUENCE: 402
tcatccctgg gtggggattt gttgcattac ttgtgttcta tataaagtat tgcacttgtc    60
ccggcctgtg gaaga                                                    75

SEQ ID NO: 403          moltype = RNA   length = 62
FEATURE                 Location/Qualifiers
```

```
source                  1..62
                        mol_type = transcribed RNA
                        organism = Homo sapiens
SEQUENCE: 403
cttcctggtg ggtggggagg agaagtgccg tcctcatgag cccctctctg tcccacccat        60
ag                                                                      62

SEQ ID NO: 404          moltype = RNA   length = 70
FEATURE                 Location/Qualifiers
source                  1..70
                        mol_type = transcribed RNA
                        organism = Homo sapiens
SEQUENCE: 404
ggtttctcct tgaggagaca tggtgggggc cggtcaggca gcccatgcca tgtgtcctca        60
tggagaggcc                                                              70

SEQ ID NO: 405          moltype = RNA   length = 113
FEATURE                 Location/Qualifiers
source                  1..113
                        mol_type = transcribed RNA
                        organism = Homo sapiens
SEQUENCE: 405
agcatgacag aggagaggtg gaggtaggcg agagtaatat aatttctcca ggagaacatc        60
tgagagggga agttgctttc ctgccctggc cctttcaccc tcctgagttt ggg              113

SEQ ID NO: 406          moltype = RNA   length = 96
FEATURE                 Location/Qualifiers
source                  1..96
                        mol_type = transcribed RNA
                        organism = Homo sapiens
SEQUENCE: 406
cgggccccgg gcgggcggga gggacgggac gcggtgcagt gttgtttttt cccccgccaa        60
tattgcactc gtcccggcct ccggcccccc cggccc                                 96

SEQ ID NO: 407          moltype = RNA   length = 70
FEATURE                 Location/Qualifiers
source                  1..70
                        mol_type = transcribed RNA
                        organism = Homo sapiens
SEQUENCE: 407
tgtgcacttg ggcaggaggg accctgtatg tctccccgca gcaccgtcat cgtgtccctc        60
ttgtccacag                                                              70

SEQ ID NO: 408          moltype = RNA   length = 68
FEATURE                 Location/Qualifiers
source                  1..68
                        mol_type = transcribed RNA
                        organism = Homo sapiens
SEQUENCE: 408
gcatcctgta ctgagctgcc ccgaggccct tcatgctgcc cagctcgggg cagctcagta        60
caggatac                                                                68

SEQ ID NO: 409          moltype = RNA   length = 64
FEATURE                 Location/Qualifiers
source                  1..64
                        mol_type = transcribed RNA
                        organism = Homo sapiens
SEQUENCE: 409
tcctgtactg agctgccccg agctgggcag catgaagggc ctcggggcag ctcagtacag        60
gatg                                                                    64

SEQ ID NO: 410          moltype = RNA   length = 64
FEATURE                 Location/Qualifiers
source                  1..64
                        mol_type = transcribed RNA
                        organism = Homo sapiens
SEQUENCE: 410
tgctctgtag gcatgaggca gggcccaggt tccatgtgat gctgaagctc tgacattcct        60
gcag                                                                    64

SEQ ID NO: 411          moltype = RNA   length = 65
FEATURE                 Location/Qualifiers
source                  1..65
                        mol_type = transcribed RNA
                        organism = Homo sapiens
SEQUENCE: 411
agccctgggg gtggtctcta gccaaggctc tggggtctca cccttggctg gtctctgctc        60
cgcag                                                                   65
```

```
SEQ ID NO: 412           moltype = RNA  length = 80
FEATURE                  Location/Qualifiers
source                   1..80
                         mol_type = transcribed RNA
                         organism = Homo sapiens
SEQUENCE: 412
gagaggccaa gaccttggga atgggggtaa gggccttctg agcccaggtc cgaactctcc    60
attcctctgc agagcgctct                                                80

SEQ ID NO: 413           moltype = RNA  length = 98
FEATURE                  Location/Qualifiers
source                   1..98
                         mol_type = transcribed RNA
                         organism = Homo sapiens
SEQUENCE: 413
agaatgggca aatgaacagt aaatttggag gcctggggcc ctccctgctg ctggagaagt    60
gtttgcacgg gtgggccttg tctttgaaag gaggtgga                            98

SEQ ID NO: 414           moltype = RNA  length = 59
FEATURE                  Location/Qualifiers
source                   1..59
                         mol_type = transcribed RNA
                         organism = Homo sapiens
SEQUENCE: 414
gtccaggcag gagccggact ggacctcagg gaagaggctg accggcccc tcttgcggc      59

SEQ ID NO: 415           moltype = RNA  length = 87
FEATURE                  Location/Qualifiers
source                   1..87
                         mol_type = transcribed RNA
                         organism = Homo sapiens
SEQUENCE: 415
cccaggcgcc cgctcccgac ccacgccgcg ccgccgggtc cctcctcccc ggagaggctg    60
ggctcgggac gcgcggctca gctcggg                                        87

SEQ ID NO: 416           moltype = RNA  length = 67
FEATURE                  Location/Qualifiers
source                   1..67
                         mol_type = transcribed RNA
                         organism = Homo sapiens
SEQUENCE: 416
gcgccctccc tctctccccg gtgtgcaaat gtgtgtgtgc ggtgttatgc cggacaagag    60
ggaggtg                                                              67

SEQ ID NO: 417           moltype = RNA  length = 80
FEATURE                  Location/Qualifiers
source                   1..80
                         mol_type = transcribed RNA
                         organism = Homo sapiens
SEQUENCE: 417
tgagaggccg caccttgcct tgctgcccgg gccgtgcacc cgtgggcccc agggcgacgc    60
ggcggggcg gccctagcga                                                 80

SEQ ID NO: 418           moltype = RNA  length = 80
FEATURE                  Location/Qualifiers
source                   1..80
                         mol_type = transcribed RNA
                         organism = Homo sapiens
SEQUENCE: 418
acctgaggag ccagccctcc tcccgcaccc aaacttggag cacttgacct ttggctgttg    60
gaggggcag gctcgcgggt                                                 80

SEQ ID NO: 419           moltype = RNA  length = 96
FEATURE                  Location/Qualifiers
source                   1..96
                         mol_type = transcribed RNA
                         organism = Homo sapiens
SEQUENCE: 419
cgggccccgg gcgggcggga gggacgggac gcggtgcagt gttgtttttt cccccgccaa    60
tattgcactc gtcccggcct ccggcccccc cggccc                              96

SEQ ID NO: 420           moltype = RNA  length = 18
FEATURE                  Location/Qualifiers
source                   1..18
                         mol_type = transcribed RNA
                         organism = Homo sapiens
SEQUENCE: 420
ggtgggcttc ccggaggg                                                  18
```

```
SEQ ID NO: 421        moltype = RNA    length = 15
FEATURE               Location/Qualifiers
source                1..15
                      mol_type = transcribed RNA
                      organism = Homo sapiens
SEQUENCE: 421
ggtgggcttc ccgga                                                          15

SEQ ID NO: 422        moltype = RNA    length = 23
FEATURE               Location/Qualifiers
source                1..23
                      mol_type = transcribed RNA
                      organism = Homo sapiens
SEQUENCE: 422
gccccggcgc gggcgggttc tgg                                                 23

SEQ ID NO: 423        moltype = RNA    length = 16
FEATURE               Location/Qualifiers
source                1..16
                      mol_type = transcribed RNA
                      organism = Homo sapiens
SEQUENCE: 423
ggagccccgg cgcggg                                                         16

SEQ ID NO: 424        moltype = RNA    length = 16
FEATURE               Location/Qualifiers
source                1..16
                      mol_type = transcribed RNA
                      organism = Homo sapiens
SEQUENCE: 424
ggcggtgggc ggcggg                                                         16

SEQ ID NO: 425        moltype = RNA    length = 15
FEATURE               Location/Qualifiers
source                1..15
                      mol_type = transcribed RNA
                      organism = Homo sapiens
SEQUENCE: 425
ggcctctcgg gaact                                                          15

SEQ ID NO: 426        moltype = RNA    length = 18
FEATURE               Location/Qualifiers
source                1..18
                      mol_type = transcribed RNA
                      organism = Homo sapiens
SEQUENCE: 426
tctaggtggg gagactga                                                       18

SEQ ID NO: 427        moltype = RNA    length = 16
FEATURE               Location/Qualifiers
source                1..16
                      mol_type = transcribed RNA
                      organism = Homo sapiens
SEQUENCE: 427
gtggggagac tgacgg                                                         16

SEQ ID NO: 428        moltype = RNA    length = 22
FEATURE               Location/Qualifiers
source                1..22
                      mol_type = transcribed RNA
                      organism = Homo sapiens
SEQUENCE: 428
tgtgggactg caaatgggag ct                                                  22

SEQ ID NO: 429        moltype = RNA    length = 22
FEATURE               Location/Qualifiers
source                1..22
                      mol_type = transcribed RNA
                      organism = Homo sapiens
SEQUENCE: 429
tgtgggactg caaatgggag ct                                                  22

SEQ ID NO: 430        moltype = RNA    length = 16
FEATURE               Location/Qualifiers
source                1..16
                      mol_type = transcribed RNA
                      organism = Homo sapiens
SEQUENCE: 430
tggggggaa gaaaag                                                          16
```

```
SEQ ID NO: 431           moltype = RNA  length = 16
FEATURE                  Location/Qualifiers
source                   1..16
                         mol_type = transcribed RNA
                         organism = Homo sapiens
SEQUENCE: 431
tgggggggaa gaaaag                                                       16

SEQ ID NO: 432           moltype = RNA  length = 24
FEATURE                  Location/Qualifiers
source                   1..24
                         mol_type = transcribed RNA
                         organism = Homo sapiens
SEQUENCE: 432
agacacattt ggagagggaa cctc                                              24

SEQ ID NO: 433           moltype = RNA  length = 16
FEATURE                  Location/Qualifiers
source                   1..16
                         mol_type = transcribed RNA
                         organism = Homo sapiens
SEQUENCE: 433
agacacattt ggagag                                                       16

SEQ ID NO: 434           moltype = RNA  length = 23
FEATURE                  Location/Qualifiers
source                   1..23
                         mol_type = transcribed RNA
                         organism = Homo sapiens
SEQUENCE: 434
cggggccgta gcactgtctg aga                                               23

SEQ ID NO: 435           moltype = RNA  length = 20
FEATURE                  Location/Qualifiers
source                   1..20
                         mol_type = transcribed RNA
                         organism = Homo sapiens
SEQUENCE: 435
cggggccgta gcactgtctg                                                   20

SEQ ID NO: 436           moltype = RNA  length = 25
FEATURE                  Location/Qualifiers
source                   1..25
                         mol_type = transcribed RNA
                         organism = Homo sapiens
SEQUENCE: 436
gggacgaggg ttggggaaca ggtgg                                             25

SEQ ID NO: 437           moltype = RNA  length = 15
FEATURE                  Location/Qualifiers
source                   1..15
                         mol_type = transcribed RNA
                         organism = Homo sapiens
SEQUENCE: 437
tggggaacag gtggt                                                        15

SEQ ID NO: 438           moltype = RNA  length = 24
FEATURE                  Location/Qualifiers
source                   1..24
                         mol_type = transcribed RNA
                         organism = Homo sapiens
SEQUENCE: 438
gatcggtcga gagcgtcctg gctg                                              24

SEQ ID NO: 439           moltype = RNA  length = 15
FEATURE                  Location/Qualifiers
source                   1..15
                         mol_type = transcribed RNA
                         organism = Homo sapiens
SEQUENCE: 439
gctgggcggg gcgcg                                                        15

SEQ ID NO: 440           moltype = RNA  length = 19
FEATURE                  Location/Qualifiers
source                   1..19
                         mol_type = transcribed RNA
                         organism = Homo sapiens
```

```
SEQUENCE: 440
tgcgggtgc gggggtggg                                                    19

SEQ ID NO: 441          moltype = RNA   length = 15
FEATURE                 Location/Qualifiers
source                  1..15
                        mol_type = transcribed RNA
                        organism = Homo sapiens
SEQUENCE: 441
tggcgggtgc ggggg                                                       15

SEQ ID NO: 442          moltype = RNA   length = 25
FEATURE                 Location/Qualifiers
source                  1..25
                        mol_type = transcribed RNA
                        organism = Homo sapiens
SEQUENCE: 442
gggtggggat tgttgcatt acttg                                             25

SEQ ID NO: 443          moltype = RNA   length = 20
FEATURE                 Location/Qualifiers
source                  1..20
                        mol_type = transcribed RNA
                        organism = Homo sapiens
SEQUENCE: 443
gggtggggat tgttgcatt                                                   20

SEQ ID NO: 444          moltype = RNA   length = 21
FEATURE                 Location/Qualifiers
source                  1..21
                        mol_type = transcribed RNA
                        organism = Homo sapiens
SEQUENCE: 444
ttgaggagac atggtgggg c                                                 21

SEQ ID NO: 445          moltype = RNA   length = 15
FEATURE                 Location/Qualifiers
source                  1..15
                        mol_type = transcribed RNA
                        organism = Homo sapiens
SEQUENCE: 445
ttgaggagac atggt                                                       15

SEQ ID NO: 446          moltype = RNA   length = 26
FEATURE                 Location/Qualifiers
source                  1..26
                        mol_type = transcribed RNA
                        organism = Homo sapiens
SEQUENCE: 446
agggacggga cgcggtgcag tgttgt                                           26

SEQ ID NO: 447          moltype = RNA   length = 15
FEATURE                 Location/Qualifiers
source                  1..15
                        mol_type = transcribed RNA
                        organism = Homo sapiens
SEQUENCE: 447
ggcgggcggg aggga                                                       15

SEQ ID NO: 448          moltype = RNA   length = 23
FEATURE                 Location/Qualifiers
source                  1..23
                        mol_type = transcribed RNA
                        organism = Homo sapiens
SEQUENCE: 448
cggggcagct cagtacagga tac                                              23

SEQ ID NO: 449          moltype = RNA   length = 15
FEATURE                 Location/Qualifiers
source                  1..15
                        mol_type = transcribed RNA
                        organism = Homo sapiens
SEQUENCE: 449
agctcagtac aggat                                                       15

SEQ ID NO: 450          moltype = RNA   length = 21
FEATURE                 Location/Qualifiers
```

```
source                  1..21
                        mol_type = transcribed RNA
                        organism = Homo sapiens
SEQUENCE: 450
tgggaatggg ggtaagggcc t                                                   21

SEQ ID NO: 451          moltype = RNA   length = 15
FEATURE                 Location/Qualifiers
source                  1..15
                        mol_type = transcribed RNA
                        organism = Homo sapiens
SEQUENCE: 451
cttctgagcc caggt                                                          15

SEQ ID NO: 452          moltype = RNA   length = 24
FEATURE                 Location/Qualifiers
source                  1..24
                        mol_type = transcribed RNA
                        organism = Homo sapiens
SEQUENCE: 452
caggcaggag ccggactgga cctc                                                24

SEQ ID NO: 453          moltype = RNA   length = 21
FEATURE                 Location/Qualifiers
source                  1..21
                        mol_type = transcribed RNA
                        organism = Homo sapiens
SEQUENCE: 453
tccaggcagg agccggactg g                                                   21

SEQ ID NO: 454          moltype = RNA   length = 22
FEATURE                 Location/Qualifiers
source                  1..22
                        mol_type = transcribed RNA
                        organism = Homo sapiens
SEQUENCE: 454
ctgggctcgg gacgcgcggc tc                                                  22

SEQ ID NO: 455          moltype = RNA   length = 19
FEATURE                 Location/Qualifiers
source                  1..19
                        mol_type = transcribed RNA
                        organism = Homo sapiens
SEQUENCE: 455
ctgggctcgg gacgcgcgg                                                      19

SEQ ID NO: 456          moltype = RNA   length = 20
FEATURE                 Location/Qualifiers
source                  1..20
                        mol_type = transcribed RNA
                        organism = Homo sapiens
SEQUENCE: 456
ctccccggtg tgcaaatgtg                                                     20

SEQ ID NO: 457          moltype = RNA   length = 15
FEATURE                 Location/Qualifiers
source                  1..15
                        mol_type = transcribed RNA
                        organism = Homo sapiens
SEQUENCE: 457
gtgtgcggtg ttatg                                                          15

SEQ ID NO: 458          moltype = RNA   length = 20
FEATURE                 Location/Qualifiers
source                  1..20
                        mol_type = transcribed RNA
                        organism = Homo sapiens
SEQUENCE: 458
ccccaggcg acgcggcggg                                                      20

SEQ ID NO: 459          moltype = RNA   length = 15
FEATURE                 Location/Qualifiers
source                  1..15
                        mol_type = transcribed RNA
                        organism = Homo sapiens
SEQUENCE: 459
cgcggcgggg gcggc                                                          15

SEQ ID NO: 460          moltype = RNA   length = 20
```

```
                         -continued
FEATURE            Location/Qualifiers
source             1..20
                   mol_type = transcribed RNA
                   organism = Homo sapiens
SEQUENCE: 460
tggctgttgg aggggggcagg                                          20

SEQ ID NO: 461     moltype = RNA   length = 15
FEATURE            Location/Qualifiers
source             1..15
                   mol_type = transcribed RNA
                   organism = Homo sapiens
SEQUENCE: 461
ggaggggggca ggctc                                               15

SEQ ID NO: 462     moltype = RNA   length = 24
FEATURE            Location/Qualifiers
source             1..24
                   mol_type = transcribed RNA
                   organism = Homo sapiens
SEQUENCE: 462
aatattgcac tcgtcccggc ctcc                                      24

SEQ ID NO: 463     moltype = RNA   length = 15
FEATURE            Location/Qualifiers
source             1..15
                   mol_type = transcribed RNA
                   organism = Homo sapiens
SEQUENCE: 463
tattgcactc gtccc                                                15

SEQ ID NO: 464     moltype = RNA   length = 21
FEATURE            Location/Qualifiers
source             1..21
                   mol_type = transcribed RNA
                   organism = Homo sapiens
SEQUENCE: 464
cccggagcca ggatgcagct c                                         21

SEQ ID NO: 465     moltype = RNA   length = 22
FEATURE            Location/Qualifiers
source             1..22
                   mol_type = transcribed RNA
                   organism = Homo sapiens
SEQUENCE: 465
ggtggcccgg ccgtgcctga gg                                        22

SEQ ID NO: 466     moltype = RNA   length = 17
FEATURE            Location/Qualifiers
source             1..17
                   mol_type = transcribed RNA
                   organism = Homo sapiens
SEQUENCE: 466
ccccgccacc gccttgg                                              17

SEQ ID NO: 467     moltype = RNA   length = 24
FEATURE            Location/Qualifiers
source             1..24
                   mol_type = transcribed RNA
                   organism = Homo sapiens
SEQUENCE: 467
tgggcgaggg gtgggctctc agag                                      24

SEQ ID NO: 468     moltype = RNA   length = 17
FEATURE            Location/Qualifiers
source             1..17
                   mol_type = transcribed RNA
                   organism = Homo sapiens
SEQUENCE: 468
gggagaaggg tcgggc                                               17

SEQ ID NO: 469     moltype = RNA   length = 22
FEATURE            Location/Qualifiers
source             1..22
                   mol_type = transcribed RNA
                   organism = Homo sapiens
SEQUENCE: 469
gggaccatcc tgcctgctgt gg                                        22
```

```
SEQ ID NO: 470            moltype = RNA   length = 23
FEATURE                   Location/Qualifiers
source                    1..23
                          mol_type = transcribed RNA
                          organism = Homo sapiens
SEQUENCE: 470
tcaataggaa agaggtggga cct                                                 23

SEQ ID NO: 471            moltype = RNA   length = 22
FEATURE                   Location/Qualifiers
source                    1..22
                          mol_type = transcribed RNA
                          organism = Homo sapiens
SEQUENCE: 471
tagggatggg aggccaggat ga                                                  22

SEQ ID NO: 472            moltype = RNA   length = 23
FEATURE                   Location/Qualifiers
source                    1..23
                          mol_type = transcribed RNA
                          organism = Homo sapiens
SEQUENCE: 472
tcgaggactg gtggaagggc ctt                                                 23

SEQ ID NO: 473            moltype = RNA   length = 22
FEATURE                   Location/Qualifiers
source                    1..22
                          mol_type = transcribed RNA
                          organism = Homo sapiens
SEQUENCE: 473
ctcctggggc ccgcactctc gc                                                  22

SEQ ID NO: 474            moltype = RNA   length = 85
FEATURE                   Location/Qualifiers
source                    1..85
                          mol_type = transcribed RNA
                          organism = Homo sapiens
SEQUENCE: 474
tcctccccgg agccaggatg cagctcaagc cacagcaggg tgtttagcgc tcttcagtgg         60
ctccagattg tggcgctggt gcagg                                               85

SEQ ID NO: 475            moltype = RNA   length = 115
FEATURE                   Location/Qualifiers
source                    1..115
                          mol_type = transcribed RNA
                          organism = Homo sapiens
SEQUENCE: 475
ggtgccgagg gccgtccggc atcctaggcg ggtcgctgcg gtacctccct cctgtctgtg         60
gcggtgggat cccgtggccg tgttttcctg gtggcccggc cgtgcctgag gtttc             115

SEQ ID NO: 476            moltype = RNA   length = 91
FEATURE                   Location/Qualifiers
source                    1..91
                          mol_type = transcribed RNA
                          organism = Homo sapiens
SEQUENCE: 476
acgccccccg ccccgccacc gccttggagg ctgacctctt actttcggtc ggtcttcttc         60
cctgggcttg gtttgggggc gggggagtgt c                                        91

SEQ ID NO: 477            moltype = RNA   length = 64
FEATURE                   Location/Qualifiers
source                    1..64
                          mol_type = transcribed RNA
                          organism = Homo sapiens
SEQUENCE: 477
tctgggcgag gggtgggctc tcagaggggc tggcagtact gctctgaggc ctgcctctcc         60
ccag                                                                      64

SEQ ID NO: 478            moltype = RNA   length = 86
FEATURE                   Location/Qualifiers
source                    1..86
                          mol_type = transcribed RNA
                          organism = Homo sapiens
SEQUENCE: 478
agggagaagg gtcggggcag ggagggcagg gcaggctctg gggtgggggg tctgtgagtc         60
agccacggct ctgcccacgt ctcccc                                              86

SEQ ID NO: 479            moltype = RNA   length = 83
FEATURE                   Location/Qualifiers
```

```
                        source              1..83
                                            mol_type = transcribed RNA
                                            organism = Homo sapiens
SEQUENCE: 479
acggcatctt tgcactcagc aggcaggctg gtgcagcccg tggtggggga ccatcctgcc    60
tgctgtgggg taaggacggc tgt                                           83

SEQ ID NO: 480          moltype = RNA   length = 98
FEATURE                 Location/Qualifiers
source                  1..98
                        mol_type = transcribed RNA
                        organism = Homo sapiens
SEQUENCE: 480
cttggtcaat aggaaagagg tgggacctcc tggcttttcc tctgcagcat ggctcggacc    60
tagtgcaatg tttaagctcc cctctctttc ctgttcag                           98

SEQ ID NO: 481          moltype = RNA   length = 69
FEATURE                 Location/Qualifiers
source                  1..69
                        mol_type = transcribed RNA
                        organism = Homo sapiens
SEQUENCE: 481
gggcttaggg atgggaggcc aggatgaaga ttaatcccta atccccaaca ctggccttgc    60
tatccccag                                                           69

SEQ ID NO: 482          moltype = RNA   length = 63
FEATURE                 Location/Qualifiers
source                  1..63
                        mol_type = transcribed RNA
                        organism = Homo sapiens
SEQUENCE: 482
gagtcgagga ctggtggaag ggcctttccc ctcagaccaa ggccctggcc ccagcttctt    60
ctc                                                                 63

SEQ ID NO: 483          moltype = RNA   length = 84
FEATURE                 Location/Qualifiers
source                  1..84
                        mol_type = transcribed RNA
                        organism = Homo sapiens
SEQUENCE: 483
gctggcgtcg gtgctgggga gcggcccccg ggtgggcctc tgctctggcc cctcctgggg    60
cccgcactct cgctctgggc ccgc                                          84

SEQ ID NO: 484          moltype = RNA   length = 23
FEATURE                 Location/Qualifiers
source                  1..23
                        mol_type = transcribed RNA
                        organism = Homo sapiens
SEQUENCE: 484
ggcccggccg tgcctgaggt ttc                                           23

SEQ ID NO: 485          moltype = RNA   length = 15
FEATURE                 Location/Qualifiers
source                  1..15
                        mol_type = transcribed RNA
                        organism = Homo sapiens
SEQUENCE: 485
tgttttcctg gtggc                                                    15

SEQ ID NO: 486          moltype = RNA   length = 23
FEATURE                 Location/Qualifiers
source                  1..23
                        mol_type = transcribed RNA
                        organism = Homo sapiens
SEQUENCE: 486
agggtcgggg cagggagggc agg                                           23

SEQ ID NO: 487          moltype = RNA   length = 15
FEATURE                 Location/Qualifiers
source                  1..15
                        mol_type = transcribed RNA
                        organism = Homo sapiens
SEQUENCE: 487
ggagaagggt cgggg                                                    15

SEQ ID NO: 488          moltype = RNA   length = 24
FEATURE                 Location/Qualifiers
```

```
source                  1..24
                        mol_type = transcribed RNA
                        organism = Homo sapiens
SEQUENCE: 488
tcgaggactg gtggaagggc cttt                                           24

SEQ ID NO: 489          moltype = RNA   length = 17
FEATURE                 Location/Qualifiers
source                  1..17
                        mol_type = transcribed RNA
                        organism = Homo sapiens
SEQUENCE: 489
actggtggaa gggcctt                                                   17

SEQ ID NO: 490          moltype = RNA   length = 23
FEATURE                 Location/Qualifiers
source                  1..23
                        mol_type = transcribed RNA
                        organism = Homo sapiens
SEQUENCE: 490
ctcctggggc ccgcactctc gct                                            23

SEQ ID NO: 491          moltype = RNA   length = 18
FEATURE                 Location/Qualifiers
source                  1..18
                        mol_type = transcribed RNA
                        organism = Homo sapiens
SEQUENCE: 491
ctcctggggc ccgcactc                                                  18

SEQ ID NO: 492          moltype = RNA   length = 25
FEATURE                 Location/Qualifiers
source                  1..25
                        mol_type = transcribed RNA
                        organism = Homo sapiens
SEQUENCE: 492
tcggggcatg gggagggag gctgg                                           25

SEQ ID NO: 493          moltype = RNA   length = 23
FEATURE                 Location/Qualifiers
source                  1..23
                        mol_type = transcribed RNA
                        organism = Homo sapiens
SEQUENCE: 493
caggggctgg ggtttcaggt tct                                            23

SEQ ID NO: 494          moltype = RNA   length = 20
FEATURE                 Location/Qualifiers
source                  1..20
                        mol_type = transcribed RNA
                        organism = Homo sapiens
SEQUENCE: 494
gtgggttggg gcgggctctg                                                20

SEQ ID NO: 495          moltype = RNA   length = 69
FEATURE                 Location/Qualifiers
source                  1..69
                        mol_type = transcribed RNA
                        organism = Homo sapiens
SEQUENCE: 495
gaacctcggg gcatggggga gggaggctgg acaggagagg gctcacccag gccctgtcct    60
ctgccccag                                                            69

SEQ ID NO: 496          moltype = RNA   length = 56
FEATURE                 Location/Qualifiers
source                  1..56
                        mol_type = transcribed RNA
                        organism = Homo sapiens
SEQUENCE: 496
gtaggcaggg gctggggttt caggttctca gtcagaacct tggcccctct ccccag        56

SEQ ID NO: 497          moltype = RNA   length = 102
FEATURE                 Location/Qualifiers
source                  1..102
                        mol_type = transcribed RNA
                        organism = Homo sapiens
SEQUENCE: 497
gcttatcgag gaaaagatcg aggtgggttg ggcgggctc tggggatttg gtctcacagc     60
ccggatccca gcccacttac cttggttact ctccttcctt ct                       102
```

```
SEQ ID NO: 498           moltype = RNA  length = 19
FEATURE                  Location/Qualifiers
source                   1..19
                         mol_type = transcribed RNA
                         organism = Homo sapiens
SEQUENCE: 498
gtgggttggg gcgggctct                                                    19

SEQ ID NO: 499           moltype = RNA  length = 19
FEATURE                  Location/Qualifiers
source                   1..19
                         mol_type = transcribed RNA
                         organism = Homo sapiens
SEQUENCE: 499
gtgggttggg gcgggctct                                                    19
```